US00RE49700E

(19) United States
(12) Reissued Patent
Yadav et al.

(10) Patent Number: US RE49,700 E
(45) Date of Reissued Patent: *Oct. 17, 2023

(54) SUBSTITUTED NITROGEN CONTAINING COMPOUNDS

(71) Applicant: Bristol-Myers Squibb Company, Princeton, NJ (US)

(72) Inventors: Navnath Dnyanoba Yadav, Bangalore (IN); Rajeev S. Bhide, Princeton Junction, NJ (US); Rajesh Onkardas Bora, Bangalore (IN); Prashantha Gunaga, Bangalore (IN); Manoranjan Panda, Bangalore (IN); Eldon Scott Priestley, Yardley, PA (US); Jeremy Richter, Yardley, PA (US)

(73) Assignee: Bristol-Myers Squibb Company, Princeton, NJ (US)

( * ) Notice: This patent is subject to a terminal disclaimer.

(21) Appl. No.: 17/183,286

(22) Filed: Feb. 23, 2021

Related U.S. Patent Documents

Reissue of:
(64) Patent No.: 10,501,449
Issued: Dec. 10, 2019
Appl. No.: 15/993,683
Filed: May 31, 2018

(30) Foreign Application Priority Data

Jun. 1, 2017 (IN) ..... 201711019293
Feb. 6, 2018 (IN) ..... 201811004486

(51) Int. Cl.
*C07D 405/14* (2006.01)
*C07D 413/14* (2006.01)
*C07D 417/14* (2006.01)
*C07D 487/04* (2006.01)

(52) U.S. Cl.
CPC ..... *C07D 405/14* (2013.01); *C07D 413/14* (2013.01); *C07D 417/14* (2013.01); *C07D 487/04* (2013.01)

(58) Field of Classification Search
CPC .. C07D 405/14; C07D 413/14; C07D 417/14; C07D 487/04; A61P 9/00; A61P 9/04; A61P 9/12; A61K 31/4439; A61K 31/444; A61K 31/496; A61K 31/5377
See application file for complete search history.

(56) References Cited

U.S. PATENT DOCUMENTS 6,642,228 B1 11/2003 Hayashi et al.
9,108,947 B2 8/2015 Walsh et al.
2015/0166505 A1 6/2015 Voss et al.

FOREIGN PATENT DOCUMENTS

CN 105693706 A 6/2016
WO 2003/086279 A2 10/2003
WO 2003/086394 A1 10/2003
WO 2006008260 A1 1/2006
WO 2006/058905 A1 6/2006
WO 2006/068618 A1 6/2006
WO 2010/129379 A1 11/2010
WO 2010/130773 A2 11/2010
WO 2010/136144 A1 12/2010
WO 2011/012896 A2 2/2011
WO 2011/103536 A1 8/2011
WO 2012/037132 A1 3/2012
(Continued)

OTHER PUBLICATIONS

Dajee et al. (2014) "Chronic Diuretics Treatment in Dogs: Novel Diuretic ROMK Inhibitor versus Furosemide", Circulation, 130: 2 pages.

(Continued)

*Primary Examiner* — Alan D Diamond
(74) *Attorney, Agent, or Firm* — Mintz, Levin, Cohn, Ferris, Glovsky and Popeo, P.C.

(57) ABSTRACT

Disclosed are compounds of Formula (I)

(I)

(I)

or a salt thereof,
wherein $R^1$ is:

each W is independently $NR_{1b}$ or O; Z is a bond or $CHR^{1d}$; and $R^1$, $R^2$, $R^d$, $R^{3a}$, $R^{3b}$, $L^1$, B, V, Y, and n are defined herein. Also disclosed are methods of using such compounds as inhibitors of ROMK, and pharmaceutical compositions comprising such compounds. These compounds are useful in treating cardiovascular diseases.

61 Claims, No Drawings

(56) References Cited

FOREIGN PATENT DOCUMENTS

| | | | |
|---|---|---|---|
| WO | 2012/058116 | A1 | 5/2012 |
| WO | 2012/058134 | A1 | 5/2012 |
| WO | 2013/028474 | A1 | 2/2013 |
| WO | 2013/039802 | A1 | 3/2013 |
| WO | 2013/062892 | A1 | 5/2013 |
| WO | 2013/062900 | A1 | 5/2013 |
| WO | 2013/066714 | A1 | 5/2013 |
| WO | 2013/066717 | A1 | 5/2013 |
| WO | 2013/066718 | A2 | 5/2013 |
| WO | 2013/090271 | A1 | 6/2013 |
| WO | 2014/015495 | A1 | 1/2014 |
| WO | 2014/018764 | A1 | 1/2014 |
| WO | 2014/085210 | A1 | 6/2014 |
| WO | 2014/099633 | A2 | 6/2014 |
| WO | 2014/126944 | A2 | 8/2014 |
| WO | 2014/150132 | A1 | 9/2014 |
| WO | 2015/017305 | A1 | 2/2015 |
| WO | 2015/052264 | A1 | 4/2015 |
| WO | 2015/065866 | A1 | 5/2015 |
| WO | 2015/095097 | A2 | 6/2015 |
| WO | 2015/100147 | A1 | 7/2015 |
| WO | 2015/105736 | A1 | 7/2015 |
| WO | 2016/008064 | A1 | 1/2016 |
| WO | 2016/010801 | A1 | 1/2016 |
| WO | 2016/010802 | A1 | 1/2016 |
| WO | 2016/060941 | A1 | 4/2016 |
| WO | 2016/065582 | A1 | 5/2016 |
| WO | 2016/065602 | A1 | 5/2016 |
| WO | 2016/065603 | A1 | 5/2016 |
| WO | 2016/069426 | A1 | 5/2016 |
| WO | 2016/069427 | A1 | 5/2016 |
| WO | 2016/069428 | A1 | 5/2016 |
| WO | 2016/069430 | A1 | 5/2016 |
| WO | 2016/091042 | A1 | 6/2016 |
| WO | 2016/122994 | A1 | 8/2016 |
| WO | 2016/127358 | A1 | 8/2016 |
| WO | 2016/130444 | A1 | 8/2016 |
| WO | 2017/184662 | A1 | 10/2017 |
| WO | 2018/093569 | A1 | 5/2018 |

OTHER PUBLICATIONS

Garcia et al. (Jan. 2014) "Pharmacologic Inhibition of the Renal Outer Medullary Potassium Channel Causes Diuresis and Natriuresis in the Absence of Kaliuresis", The Journal of Pharmacology and Experimental Therapeutics, 348(1):153-164.

Hebert et al. (2005) "Molecular Diversity and Regulation of Renal Potassium Channels", Physiological Reviews, 85:319-371.

Ho et al. (Mar. 1993) "Cloning and Expression of an Inwardly Rectifying ATP-regulated Potassium Channel", Nature, 362(6415):31-38.

Ji et al. (May 2008) "Rare Independent Mutations in Renal Salt Handling Genes Contribute to Blood Pressure Variation", Nature Genetics, 40(5):592-599.

Lee et al. (Jun. 1, 1995) "ROMK Inwardly Rectifying ATP-sensitive K+ Channel. I. Expression in Rat Distal Nephron Segments", American Journal of Physiology-Renal Physiology, 268(6):F1124-F1131.

Lorenz et al. (Jul. 16, 2002) "Impaired Renal NaCI Absorption in Mice Lacking the ROMK Potassium Channel, a Model for Type II Bartter's Syndrome", The Journal of Biological Chemistry, 277(40):37871-37880.

Lu et al. (Oct. 4, 2002) "Absence of Small Conductance K+ Channel (SK) Activity in Apical Membranes of Thick Ascending Limb and Cortical Collecting Duct In ROMK (Bartter's) Knockout Mice", The Journal of Biological Chemistry, 227(40):37881-37887.

McFadden et al. (1991) "Synthesis of (Pyrazol-4-yl)alkanones and Alkylpyrazole-4-Carbonitriles", Australian Journal of Chemistry, 44(9):1263-1273.

Shuck et al. (Sep. 30, 1994) "Cloning and Characterization of Multiple Forms of the Human Kidney ROM-K Potassium Channel", The Journal of Biological Chemistry, 269(39):24261-24270.

Simon et al. (1996) "Genetic Heterogeneity of Barter's Syndrome Revealed by Mutations in the K+ Channel, ROMK", Nature Genetics, Oct. 1, 14:152-156.

Tang et al. (Nov. 1, 2013) "Discovery of a Novel Sub-class of ROMK Channel Inhibitors Typified by 5-(2-(4-(2-4-(1H-Tetrazol-1-yl)phenyl)acetyl)piperazin-1-yl)ethyl)isobenzofuran-1(3H)-one", Bioorganic and Medicinal Chemistry Letter, 23(21):5829-5832.

Walsh et al. (May 7, 2015) "Discovery of a Potent and Selective ROMK Inhibitor with Pharmacokinetic Properties Suitable for Preclinical Evaluation", ACS Medicinal Chemistry Letters, 6(7):747-752.

Welling et al. (May 20, 2009) "A Comprehensive Guide to the ROMK Potassium Channel: Form and Function in Health and Disease", American Journal of Physiology-Renal Physiology, 297(4):F849-F863.

Serpell et al. (Jul. 19, 2010) "Halogen Bond Anion Templated Assembly of an Imidazolium Pseudorotaxane", Angewandte Chemie, 49(31): 5322-5326.

U.S. Appl. No. 17/960,199, filed Oct. 5, 2022, Navnath Dnyanoba Yadav et al.

DeOrazio et al., Synthetic Communications, 41: 3551-3555, 2011.

SUBSTITUTED NITROGEN CONTAINING COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application claims the benefit of Indian Provisional Application No. 201811004486, filed Feb. 6, 2018 and Indian Provisional Application No. 201711019293, filed Jun. 1, 2017, the contents of which are specifically incorporated by reference herein.

The present invention generally relates to substituted nitrogen containing heterocyclic compounds useful as inhibitors of ROMK channel activity. Provided herein are substituted nitrogen containing compounds, compositions comprising such compounds, and methods of their use. The invention further pertains to pharmaceutical compositions containing at least one compound according to the invention that are useful for the treatment of conditions related to ROMK channel activity, including cardiovascular diseases.

BACKGROUND

The renal outer medullary potassium (ROMK, Kir1.1) channel is a weak inward rectifying $K^+$ channe with a key role in renal $K^+$ recycling and secretion (Ho et al., Nature, 1993, 362, 31-38; Shuck et al., The Journal of Biological Chemistry, 1994, 269(39), 24261-24270; Lee and Hebert, American Journal of Physiology-Renal Physiology, 1995, 268(6), F1124-F1131; Lu et al., The Journal of Biological Chemistry, 2002, 277, 37881-37887; and Hebert et al., Physiological Reviews, 2005, 85:319-371). In the thick ascending limb (TAL) of a nephron, ROMK channel activity provides the $K^+$ gradient necessary for Na and Cl reabsorption by the $Na^+$—$K^+$-$2Cl^-$ (NKCC2) co-transporter. In the distal convoluted tubule (DCT) and cortical collecting duct (CCD), ROMK channels form the major secretory pathway for $K^+$ and as a result, play an important role in $K^+$ homeostasis under physiological conditions (Welling and Ho, American Journal of Physiology-Renal Physiology, 2009, 297(4): F849-F863).

Multiple lines of evidence indicate that inhibition of ROMK channel activity results in natriuresis, diuresis and reduced blood pressure. Therefore, ROMK inhibition may offer a novel mechanism of blood pressure regulation and diuresis in patients suffering from hypertension, congestive heart failure or any other edematous disease conditions. The activity of NKCC2 transporter is tightly coupled with ROMK activity in the TAL region and homozygous loss of function mutations in ROMK in humans result in a disease phenotype (renal salt wasting, increased aldosterone levels, metabolic alkalosis, reduction in blood pressure) very similar to that of NKCC2 homozygous mutations but with a milder hypokalemia (Simon et al., Nature Genetics, 1996, 14: 152-156). In addition, humans identified with heterozygous ROMK mutations from the Framingham Heart Study presented with reduced blood pressure (Ji et al., Nature Genetics, 2008, 40(5): 592-599). Similar to human genetics, mouse genetics also support the role of ROMK in $Na^+$ reabsorption in the kidney and overall blood pressure regulation (Lu et al., The Journal of Biological Chemistry, 2002, 277, 37881-37887; and Lorenz et al., The Journal of Biological Chemistry, 2002, 277: 37871-37880). Furthermore, pharmacological blockade of the ROMK channel has been shown to induce natriuresis and diuresis in rats upon acute dosing and in dogs upon both acute and prolonged dosing (Tang et al., Bioorganic and Medicinal Chemistry Letter, 2013, 23: 5829-5832; Garcia et al., The Journal of Pharmacology and Experimental Therapeutics, 2014, 348: 153-164; Walsh et al., ACS Medicinal Chemistry Letters, 2015, 6: 747-752; and Dajee et al., Circulation, 2014, 130: A12397). Since the ROMK channel is also implicated in regulation of net $K^+$ secretion in the distal part of the nephron, it is believed that ROMK inhibition in this region will mitigate the $K^+$ wasting and hypokalemia associated with loop and thiazide diuretics. Acute or prolonged (up to 122 days) ROMK antagonism does not lead to kaliuresis or hypokalemia in dogs (Garcia et al., The Journal of Pharmacology and Experimental Therapeutics, 2014, 348: 153-164; Walsh et al., ACS Medicinal Chemistry Letters, 2015, 6: 747-752; Dajee et al., Circulation, 2014, 130: A12397). Together, these data suggest that inhibition of ROMK may produce diuretic efficacy that is equivalent to or better than currently available loop diuretics and with potentially lower incidence of hypokalemia.

WO 2015/095097 discloses compounds useful as inhibitors of ROMK. Other publications disclosing compounds useful as inhibitors of ROMK include WO 2010/129379, WO 2010/136144, WO 2012/058116, WO 2012/058134, WO 2013/028474, WO 2013/039802, WO 2013/062892, WO 2013/062900, WO 2013/066714, WO 2013/066717, WO 2013/066718, WO 2013/090271, WO 2014/015495, WO 2014/018764, WO 2014/085210, WO 2014/099633, WO 2014/126944, WO 2014/150132, WO 2015/017305, WO 2015/065866, WO 2015/095097, WO 2015/100147, WO 2015/105736, WO 2016/008064, WO 2016/010801, WO 2016/010802, WO2016/060941, WO2016/065582, WO2016/065602, WO2016/065603, WO2016/069426, WO2016/069427, WO2016/069428, WO2016/069430, WO2016/091042, WO2016/122994, WO2016/127358, WO2016/130444, CN105693706, and WO2016/091042.

In view of the numerous conditions that are contemplated to benefit by treatment involving inhibition of ROMK, it is immediately apparent that new compounds capable of inhibiting ROMK and methods of using these compounds should provide substantial therapeutic benefits to a wide variety of patients.

The present invention relates to a new class of compounds found to be effective inhibitors of ROMK.

SUMMARY OF THE INVENTION

The present invention provides compounds of Formula (I) that are useful as inhibitors of ROMK, and are useful for the treatment of cardiovascular diseases and promotion of diuresis or natriuresis.

The present invention also provides pharmaceutical compositions comprising a pharmaceutically acceptable carrier and at least one of the compounds of Formula (I) or stereoisomers, tautomers, salts, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The present invention also provides a method for inhibiting ROMK comprising administering to a host in need of such treatment a therapeutically effective amount of at least one of the compounds of Formula (I) or stereoisomers, tautomers, salts, pharmaceutically acceptable salts, solvates, or prodrugs thereof.

The present invention also provides a method for treating cardiovascular disease comprising administering to a host in need of such treatment a therapeutically effective amount of at least one of the compounds of Formula (I) or stereoisomers, tautomers, salts, pharmaceutically acceptable salts, solvates, or prodrugs thereof.

The present invention also provides a method for treating cardiovascular disease comprising administering to a host in need of such treatment a therapeutically effective amount of at least one of the compounds of Formula (I) or stereoisomers, tautomers, salts, pharmaceutically acceptable salts, solvates, or prodrugs thereof, either alone or in combination with other compounds of the present invention, or in combination with one or more other agent(s). One embodiment provides a method for treating cardiovascular disease. Particular, cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypetension, pulmonary arterial hypertension, cardiac insufficiency, nephrotic syndrome, and acute kidney insufficiency.

One embodiment provides a method for promotion of diuresis or natriuresis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cardiovascular disease or promotion of diuresis or natriuresis. The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth further below.

DETAILED DESCRIPTION

The first aspect of the present invention provides at least one compound of Formula (I):

(I)

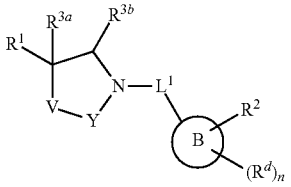

or stereoisomer, tautomer, salt, pharmaceutically acceptable salt, solvate, or prodrug thereof, wherein:

R is:

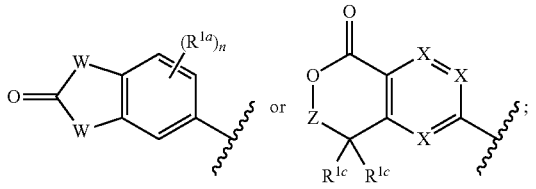

each W is independently $NR^{1b}$ or O;

Z is a bond or $CHR^{1d}$;

X is independently N or $CR^{1a}$, wherein X is N at only 0, 1, or 2 positions;

each $R^{1a}$ is independently H, F, Cl, —OH, —CN, $C_{1-3}$ alkyl, $C_{1-3}$ fluoroalkyl, $C_{3-6}$ cycloalkyl, $C_{1-3}$ alkoxy, or $C_{1-3}$ fluoroalkoxy;

each $R^{1b}$ is independently H, $C_{1-3}$ alkyl, $C_{2-3}$ fluoroalkyl, $C_{3-6}$ cycloalkyl $R^{1c}$ is independently H, deuterium, $C_{1-4}$ alkyl, $C_{1-4}$ fluoroalkyl, or $C_{3-6}$ cycloalkyl;

$R^{1d}$ is H, $C_{1-3}$ alkyl, $C_{1-4}$ fluoroalkyl, or $C_{3-6}$ cycloalkyl;

Y is $—C(R^6)_2—$, $—C(R^6)_2—C(R^6)_2—$, C(═O)—, —C(═O)—$C(R^6)_2$—, —$C(R^6)_2$—C(═O) , or —$SO_2$—;

V is —O—, —$NR^4$—, —$CR^5R^5$—, —S—, —S(O)—, —$SO_2$—, or —C(═O) ; wherein if V is —O—, —S—. —S(O)—, —$SO_2$—, or —C(═O) , then Y is not —$SO_2$—, and wherein if V is 13 O—, —S—, or $NR^4$, then Y is not $C(R^6)_2$, and wherein if V is —S(O)—, —$SO_2$—, or C(═O , then Y is not —C(═O)—, —C(═O —C $(R^6)_2$—;

$L^1$ is—$C(R)_2$—, —C(═O)—, or —$C(R)_2$—$C(R)_2$—; wherein R is independently H, F, OH, $C_{1-3}$ alkyl, $C_{1-3}$ hydroxyalkyl, $C_{1-3}$ alkoxyalkyl, or $C_{1-3}$ fluoroalkyl; wherein R is not —OH or F if it is attached to a carbon atom that is adjacent to a nitrogen atom:

Ring B is phenyl, pyridinyl, pyrimidinyl, pyrrazolyl, thiazolyl, imidazolyl, triazolyl, tetrazolyl, oxadiazolyl, thiadiazolyl, isoxazolyl, isothiazolyl, pyrrolyl, pyrazinyl, oxazolyl, pyridazinyl, pyrrolidinyl, or imidazolidinyl, $R^2$ is a $C_{6-10}$ aryl, or a 5 to 10 membered heterocycle ring containing 1 to 4 heteroatoms selected from N, O, and S, the heterocycle optionally containing an oxo substitution, the aryl or heterocycle are substituted with 0-3 $R^{2a}$;

$R^{2a}$ is independently OH, ═O, CN, halo, $C_{1-4}$ alkyl, $C_{1-4}$ deuteroalkyl, $C_{1-4}$ fluoroalkyl, $C_{1-4}$ alkoxy, $C_{1-4}$ deuteroalkoxy, $C_{1-4}$ fluoroalkoxy, $C_{3-6}$ cycloalkyl, $C_{3-6}$ cycloalkoxy, $C(═O)N(R^{4b}R^{4b})$, $C(═O)C_{1-4}$ alkyl, $SO_2R^e$, $NR^{4b}SO_2R^{4b}$, or a 4 to 6 membered heterocycle having 1, 2, 3, or 4 heteroatoms selected from O, S, and N, the heterocycle optionally containing an oxo substitution and is substituted with 0-3 $R^{2b}$;

$R^{2b}$ is independently $C_{1-3}$ alkyl $C_{1-3}$ fluoralkyl, $C_{1-3}$ hydroxyalkyl, $C_{3-6}$ cycloalkyl, $C_{3-6}$ fluorocycloalkyl;

$R^{3a}$ is H, halo, OH, CN, $C_{1-3}$ alkyl, $C_{1-3}$ hydroxyalkyl, $C_{1-3}$ fluoroalkyl, $C_{1-3}$ alkoxy, or $C_{3-6}$ cycloalkyl, wherein if V is —O—, —$NR^4$—, —S—, —S(O)—, —$SO_2$—, or —C(═O)—, then $R^{3a}$ is not halo, wherein if V is —O—, —$NR^4$—, —S—, then $R^{3a}$ is not OH, CN;

$R^{3b}$ is H, ═O, $C_{1-3}$ alkyl, $C_{1-3}$ hydroxyalkyl, $C_{1-3}$ fluoroalkyl, $C_{1-3}$ alkoxy, or $C_{3-6}$ cycloalkyl;

$R^4$ is H, $C_{1-3}$ alkyl, $C_{2-3}$ fluoroalkyl, $C_{2-3}$ hydroxyalkyl, $CO_2R^{4a}$, $C(=O)R^{4a}$, $SO_2R^{4a}$, $C(=O)N(R^{4b}R^{4b})$, $SO_2N(R^{4b}R^{4b})$, or OH;

$R^{4a}$ is $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4 to 10 membered heterocycle having 1, 2, 3 or 4 heteroatoms selected from O, S, and N, the aryl or heterocycle being substituted with 0-3 $R^{4c}$;

$R^{4b}$ is independently H, $C_{1-3}$ alkyl, $C_{2-3}$ fluoroalkyl, $C_{3-6}$ cycloalkyl, $C_{3-6}$ fluorocycloalkyl, $C_{6-10}$ aryl or a 4 to 10 membered heterocycle having 1, 2 3 or 4 heteroatoms selected from O, S, N;

alternatively, 2 $R^{4b}$'s, along with the atom to which they are attached, join to form a 3 to 6 membered saturated ring containing an additional 0-2 heteroatoms selected from O, S, and N;

$R^{4c}$ is independently H, F, Cl, or $C_{1-3}$ alkyl;

$R^5$ is independently H, F, OH, $C_{1-3}$ alkoxy, $C_{1-3}$ fluoroalkoxy, $C_{1-3}$ alkyl, $C_{1-3}$ fluoroalkyl, $C_{1-3}$ hydroxyalkyl, $C_{3-6}$ cycloalkyl, $C_{3-6}$ fluorocycloalkyl, $NR^{5b}R^{5b}$, or $O—R^{5c}$, or 2 $R^5$s are =O; wherein if one $R^5$ is F, OH or $NR^{5b}R^{5b}$, then the other $R^5$ is not OH, or $NR^{5b}R^{5b}$.

$R^{5b}$ is independently H, $C_{1-3}$ alkyl, $C_{3-6}$ cycloalkyl, $C(O)R^a$, $SO_2R^a$, or $C(O)NR^bR^b$;

alternatively, 2 $R^{5b}$'s, along with the atom to which they are attached, join to form a 3 to 6 membered saturated ring containing 0-2 heteroatoms selected from O, S, or N;

$R^{5c}$ is independently H, $C_{1-3}$ alkyl, $C_{3-6}$ cycloalkyl, or $C(O)NR^bR^b$;

$R^6$ is independently H, OH, F, $C_{1-3}$ alkyl, $C_{1-3}$ deuteroalkyl, $C_{1-3}$ fluoroalkyl, $C_{3-6}$ cycloalkyl, $C_{3-6}$ fluorocycloalkyl, $C_{1-3}$ alkoxy, $C_{1-3}$ hydroxyalkyl, $C_{1-3}$ hydroxydeuteroalkyl, $C_{1-3}$ alkoxyalkyl, or $C_{1-3}$ fluoroalkoxyalkyl, or $NR^{6b}R^{6b}$; wherein if one $R^6$ on one carbon atom is F, OH or $NR^{6b}R^{6b}$, then the other $R^6$ on the same carbon atom is not OH or $NR^{6b}R^{6b}$.

$R^{6b}$ is independently H, $C_{1-3}$ alkyl, $C_{3-6}$ cycloalkyl, $C(O)R^a$, $SO_2R^a$, or $C(O)NR^bR^b$; alternatively, 2 $R^6$s along with the same atom to which they are attached can form a 3 to 6 membered saturated ring containing 0-2 heteroatoms selected from O, S, and N;

$R^a$ is independently H, $C_{1-3}$ alkyl, $C_{2-3}$ fluoroalkyl, $C_{3-6}$ cycloalkyl, $C_{3-6}$ fluorocycloalkyl, $C_{6-10}$ aryl or a 4-10 membered heterocycle having 1, 2, 3, or 4 heteroatoms selected from O, S, and N;

$R^b$ is independently H, $C_{1-3}$ alkyl, $C_{2-3}$ fluoroalkyl, $C_{3-6}$ cycloalkyl, $C_{3-6}$ fluorocycloalkyl, $C_{6-10}$ aryl or a 4 to 10 membered heterocycle having 1, 2 3 or 4 heteroatoms selected from O, S, and N;

alternatively, 2 $R^b$'s along with the atom to which they are attached, join to form a 3-6 membered saturated ring, containing 0-2 heteroatoms selected from O, S, and N;

each $R^d$ is independently H, F, $C_{1-3}$ alkyl, $C_{1-3}$ fluoroalkyl, $C_{1-3}$ alkoxy, $C_{1-3}$ fluoroalkoxy, $C_{1-3}$ hydroxyalkyl, $C_{3-6}$ cycloalkyl, halo, OH, =O, CN, $OCF_3$, $OCHF_2$, $CHF_2CF_3$, or $C(O)NR^eR^e$;

each $R^e$ is independently H, $C_{1-3}$ alkyl, $C_{2-3}$ fluoroalkyl, $C_{3-6}$ cycloalkyl, $C_{2-3}$ hydroxyalkyl, $C_{2-3}$ alkoxyalkyl, $C_{6-10}$ aryl, or a 5 to 10 membered heteroaryl having 1, 2, 3, or 4 heteroatoms selected from O, S, and N;

alternatively, 2 $R^e$'s along with the atom to which they are attached, join to form a 3 to 6 membered saturated ring, containing 0-2 heteroatoms selected from O, S, and N; and n is 0, 1, or 2.

The another aspect of the present invention provides at least one compound of Formula (I):

(I)

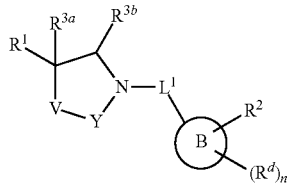

or stereoisomer, tautomer, salt, pharmaceutically acceptable salt, solvate, or prodrug thereof, wherein:

$R^1$ is:

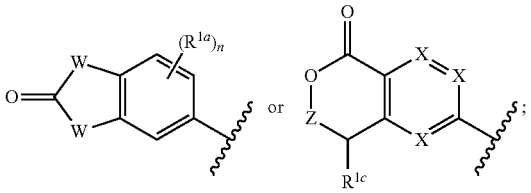

each W is independently $NR^{1b}$ or O;

Z is a bond or $CHR^{1d}$;

X is N or $CR^{1a}$, wherein X is N at only 0, 1, or 2 positions;

each $R^{1a}$ is independently H, F, Cl, —OH, —CN, $C_{1-3}$ alkyl, $C_{1-3}$ fluoroalkyl, $C_{3-6}$ cycloalkyl, $C_{1-3}$ alkoxy, or $C_{1-3}$ fluoroalkoxy;

each $R^{1b}$ is independently H, $C_{1-3}$ alkyl, $C_{1-3}$ fluoroalkyl, or $C_{3-6}$ cycloalkyl;

$R^{1c}$ is H, $C_{1-4}$ alkyl, $C_{1-4}$ fluoroalkyl, or $C_{3-6}$ cycloalkyl;

$R^{1d}$ is H, $C_{1-3}$ alkyl, $C_{1-4}$ fluoroalkyl, or $C_{3-6}$ cycloalkyl;

V is —O—, $—NR^4—$, $—CR^5R^5—$, —S—, —S(O)—, $—SO_2—$, or —C(=O) ; wherein if V is —O—, —S—, —S(O)—, $—SO_2—$, or —C(=O)—, then Y is not $—SO_2$, and wherein if V is —O—, —S—, or $NR^4$, then Y is not $C(R^6)_2$;

Y is $—C(R^6)_2—$, $—C(R^6)_2—C(R^6)_2—$, —C(=O)—, $—C(=O)—C(R^6)_2—$, $—C(R^6)_2—C(=O)—$, or $—SO_2—$;

$L^1$ is $—C(R)_2—$, =C(=O)—, $—C(R)_2—CH_2—$, $—CH_2—C(R)_2—$, or $—C(R)_2—C(R)_2$; wherein R is independently hydrogen, F, OH, $C_{1-3}$alkyl, $C_{1-3}$ hydroxyalkyl, $C_{1-3}$ alkoxyalkyl, or $C_{1-3}$fluoroalkyl; wherein R is not —OH or F if it is attached to a carbon atom which is adjacent to a nitrogen atom:

Ring B is phenyl, pyridinyl, pyrimidinyl, pyrrazolyl, indolyl, indazolyl, thiazolyl, imidazolyl, triazolyl, tetrazolyl, oxadiazolyl, thiadiazolyl, isothiazolyl, isoxazolyl, pyrazinyl, oxazolyl, pyridazinyl, furanyl, thiophenyl, pyrrolyl, triazinyl, azaindolyl, benzimidazolyl, benzoxazolyl, benzothiazolyl, benzofuranyl, or benzothiophenyl.

$R^2$ is a $C_{6-10}$ aryl, or a 5 to 10 membered heterocycle ring containing 1 to 4 heteroatoms selected from N, O, and S, the heterocycle optionally containing an oxo substitution, the aryl or heterocycle are substituted with 0-3 $R^{2a}$;

$R^{2a}$ is independently OH, =O, CN, halo, $C_{1-4}$ alkyl, $C_{1-4}$ fluoroalkyl, $C_{1-4}$ alkoxy, $C_{1-4}$ fluoroalkoxy, $C_{3-6}$ cycloalkyl, $C_{3-6}$ cycloalkoxy, $C(=O)N(R^{4b}R^{4b})$, C(=O) $C_{1-4}$ alkyl, $SO_2R^e$, or a 4 to 6 membered heterocyclyl having 1, 2, 3, or 4 heteroatoms selected from O, S, and N, wherein the heterocycle is substituted with 0-3 $R^{2b}$;

$R^{2b}$ is independently $C_{1-3}$ alkyl $C_{1-3}$ fluoralkyl, $C_{1-3}$ hydroxyalkyl, $C_{3-6}$ cycloalkyl, $C_{3-6}$ fluorocycloalkyl;

$R^{3a}$ is H, halo, OH, CN, $C_{1-3}$alkyl, $C_{1-3}$hydroxyalkyl, $C_{1-3}$fluoroalkyl, $C_{1-3}$alkoxy, $C_{3-6}$cycloalkyl, wherein if V is —O—, —$NR^4$—, —S—, —S(O)—, —$SO_2$—, or —C(=CO)—, then $R^{3a}$ is not halo;

$R^{3b}$ is H, OH, CN, $C_{1-3}$alkyl, $C_{1-3}$hydroxyalkyl, $C_{1-3}$fluoroalkyl, $C_{1-3}$alkoxy, $C_{3-6}$cycloalkyl $R^4$ is H, $C_{1-3}$ alkyl, $C_{2-3}$ fluoroalkyl, $C_{2-3}$ hydroxyalkyl, $CO_2R^{4a}$, $C(=O)R^{4a}$, $SO_2R^{4a}$, $C(=O)N(R^{4b}R^{4b})$, or $SO_2N(R^{4b}R^{4b}R^{4b})$;

$R^{4a}$ is $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4-10 membered heterocycle having 1, 2, 3 or 4 heteroatoms selected from O, S, N, the aryl or heterocycle being substituted with 0-3 $R^{4c}$;

$R^{4b}$ is independently H, $C_{1-3}$ alkyl, $C_{1-3}$ fluoroalkyl, $C_{3-6}$ cycloalkyl, $C_{3-6}$-fluorocycloalkyl, $C_{6-10}$ aryl or a 4-10 membered heterocycle having 1, 2 3 or 4 heteroatoms selected from O, S, N, alternatively, 2 $R^{4b}$'s, along with the atom to which they are attached, join to form a 3-6 membered saturated ring containing and additional 0-2 heteroatoms selected from O, S, or N;

$R^{43}$ is independently H, F, Cl, or $C_{1-3}$ alkyl;

$R^5$ is independently H, F, OH, $C_{1-3}$ alkoxy, $C_{1-3}$ fluoroalkoxy, $C_{1-3}$ alkyl, $C_{1-3}$ fluoroalkyl, $C_{1-3}$ hydroxyalkyl, $C_{3-6}$ cycloalkyl, $C_{3-6}$ fluorocycloalkyl, or $NR^{5b}R^{5b}$;

$R^{5b}$ is independently H, $C_{1-3}$ alkyl, $C_{3-6}$ cycloalkyl, $C(O)R^a$, $SO_2R^a$, or $C(O)NR^bR^b$;

alternatively, 2 $R^{5b}$'s, along with the atom to which they are attached, join to form a 3-6 membered saturated ring containing 0-2 heteroatoms selected from O, S, or N;

$R^6$ is independently H, $C_{1-3}$ alkyl, $C_{1-3}$ deuteroalkyl, $C_{1-3}$ fluoroalkyl, $C_{3-6}$ cycloalkyl, $C_{3-6}$ fluorocycloalkyl, $C_{1-3}$ hydroxylalkyl, $C_{1-3}$ hydroxydeuteroalkyl, $C_{1-3}$ alkoxyalkyl, or $C_{1-3}$ fluoroalkoxyalkyl;

alternatively, 2 $R^6$s attached to the same atom can form a 3-6 membered saturated ring containing 0-2 heteroatoms selected from O, S, or N;

$R^a$ is H, $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4-10 membered heterocycle having 1, 2 3 or 4 heteroatoms selected from O, S, N;

$R^b$ is H, $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4-10 membered heterocycle having 1, 2 3 or 4 heteroatoms selected from O, S, N;

each $R^d$ is independently H, $C_{1-3}$ alkyl, $C_{1-3}$ fluoroalkyl, $C_{1-3}$ alkoxy, $C_{1-3}$ fluoroalkoxy, $C_{2-3}$ hydroxyalkyl, halo, OH, =O, CN $OCF_3$, $OCHF_2$, $CHF_2$ and $CF_3$; each $R^e$ is independently H, $C_{1-3}$ alkyl, $C_{1-3}$ fluoroalkyl, $C_{3-6}$ cycloalkyl, $C_{1-3}$ hydroxyalkyl, $C_{1-3}$ alkoxyalkyl, $C_{6-10}$ aryl, or a 5 to 10 membered heteroaryl having 1, 2, 3, or 4 heteroatoms selected from O, S, and N; and n is 0, 1, or 2.

In another aspect of the present invention provides at least one compound of Formula (I):

(I)

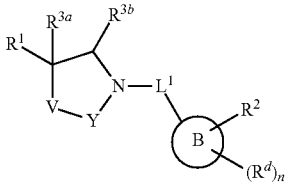

or stereoisomer, tautomer, salt, pharmaceutically acceptable salt, solvate, or prodrug thereof, wherein:

$R^1$ is:

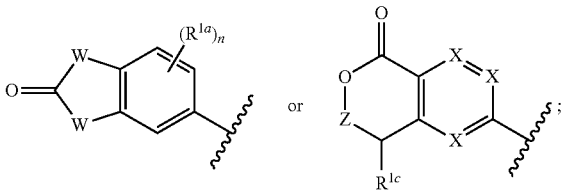

each W is independently $NR^{12b}$ or O;

Z is a bond or $CHR^{1d}$;

X is N or $CR^{1a}$, wherein X is N at only 0, 1, or 2 positions;

each $R^{1a}$ is independently H, F, Cl, —OH, —CN, $C_{1-3}$ alkyl, $C_{1-3}$ fluoroalkyl, $C_{3-6}$ cycloalkyl, $C_{1-3}$ alkoxy, or $C_{1-3}$ fluoroalkoxy;

each $R^{1b}$ is independently H, $C_{1-3}$ alkyl, $C_{1-3}$ fluoroalkyl, or $C_{3-6}$ cycloalkyl;

$R^{1c}$ is H, $C_{1-4}$ alkyl, $C_{1-4}$ fluoroalkyl, or $C_{3-6}$ cycloalkyl;

$R^{1d}$ is H, $C_{1-3}$ alkyl, $C_{1-4}$ fluoroalkyl, or $C_{3-6}$ cycloalkyl;

V is —O—, —$NR^4$—, —$CR^5R^5$—, —S—, —S(O)—, —$SO_2$—, or —C(=O)—; wherein if V is —O—, —S—, —S(O)—, —$SO_2$—, or —C(=O)—, then Y is not —$SO_2$, and wherein if V is —O—, —S—, or $NR^4$, then Y is not $C(R^6)_2$;

Y is —$C(R^6)_2$—, —$C(R^6)_2$—$C(R^6)_2$—, —C(=O)—, —C(=O)—$C(R^6)_2$—, —$C(R^6)_2$—C(=O)—, or —$SO_2$—;

$L^1$ is —C(R)$_2$—, —C(=O)—, —C(R)$_2$—$CH_2$—, —$CH_2$—C(R)$_2$—, or —C(R)$_2$—(R)$_2$; wherein R is independently hydrogen, F, OH, $C_{1-3}$alkyl, $C_{1-3}$ hydroxyalkyl, $C_{1-3}$ alkoxyalkyl, or $C_{1-3}$fluoroalkyl; wherein R is not —OH or F if it is attached to a carbon atom which is adjacent to a nitrogen atom:

Ring B is phenyl, pyridinyl, pyrimidinyl, pyrrazolyl, indolyl, ndazolyl, thiazolyl, imidazolyl, triazolyl, tetrazolyl, oxadiazolyl, thiadiazolyl, isothiazolyl, isoxazolyl, pyrazinyl, oxazolyl, pyridazinyl, furanyl, thiophenyl, pyrrolyl, triazinyl, azaindolyl, benzimidazolyl, benzoxazolyl, benzothiazolyl, benzofuranyl, or benzothiophenyl.

$R^2$ is a $C_{6-10}$ aryl, or a 5 to 10 membered heterocycle ring containing 1 to 4 heteroatoms selected from N, O, and S, the heterocycle optionally containing an oxo substitution, the aryl or heterocycle are substituted with 0-3 $R^{2a}$;

$R^{2a}$ is independently OH, =O, CN, halo, $C_{1-4}$alkyl, $C_{1-4}$ fluoroalkyl, $C_{1-4}$ alkoxy, $C_{1-4}$ fluoroalkoxy, $C_{3-6}$ cycloalkyl, $C_{3-6}$ cycloalkoxy, $C(=O)N(R^{4b}R^{4b})$, C(=O) $C_{1-4}$ alkyl, $SO_2R^e$, or a 4 to 6 membered heterocyclyl having 1, 2, 3, or 4 heteroatoms selected from O, S, and N, wherein the heterocycle is substituted with 0-3 $R^{2b}$;

$R^{2b}$ is independently $C_{1-3}$ alkyl $C_{1-3}$ fluoralkyl, $C_{1-3}$ hydroxyalkyl, $C_{3-6}$ cycloalkyl, $C_{3-6}$ fluorocycloalkyl;

$R^{3a}$ is H, halo, OH, CN, $C_{1-3}$alkyl, $C_{1-3}$hydroxyalkyl, $C_{1-3}$fluoroalkyl, $C_{1-3}$alkoxy, $C_{3-6}$cycloalkyl, wherein if V is —O—, —$NR^4$—, —S—, —S(O)—, —$SO_2$—, or —C(50 O)—, then $R^{3a}$ is not halo;

$R^{3b}$ is H, OH, CN, $C_{1-3}$alkyl, $C_{1-3}$hydroxyalkyl, $C_{1-3}$fluoroalkyl, $C_{1-3}$alkoxy, $C_{3-6}$cycloalkyl $R^4$ is H, $C_{1-3}$ alkyl, $C_{2-3}$ fluoroalkyl, $C_{2-3}$ hydroxyalkyl, $CO_2R^{4a}$, $C(=O)R^{4a}$, $SO_2R^{4a}$, $C(=O)N(R^{4b}R^{4b})$, or $SO_2N(R^{4b}R^{4b}R^{4b})$;

$R^{4a}$ is $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4-10 membered heterocycle having 1, 2, 3 or 4 heteroatoms selected from O, S, N, the aryl or heterocycle being substituted with 0-3 $R^{4c}$;

$R^{4b}$ is independently H, $C_{1-3}$ alkyl, $C_{1-3}$ fluoroalkyl, $C_{3-6}$ cycloalkyl, $C_{3-6}$-fluorocycloalkyl, $C_{6-10}$ aryl or a 4-10 membered heterocycle having 1, 2 3 or 4 heteroatoms selected from O, S, N, alternatively, 2 $R^{4b}$'s, along with the atom to which they are attached, join to form a 3-6 membered saturated ring containing and additional 0-2 heteroatoms selected from O, S, or N;

$R^{4c}$ is independently H, F, Cl, or $C_{1-3}$ alkyl;

$R^5$ is independently H, F, OH, $C_{1-3}$ alkoxy, $C_{1-3}$ fluoroalkoxy, $C_{1-3}$ alkyl, $C_{1-3}$ fluoroalkyl, $C_{1-3}$ hydroxyalkyl, $C_{3-6}$ cycloalkyl, $C_{3-6}$ fluorocycloalkyl, or $NR^{5b}R^{5b}$;

$R^{5b}$ is independently H, $C_{1-3}$ alkyl, $C_{3-6}$ cycloalkyl, $C(O)R^a$, $SO_2R^a$, or $C(O)NR^bR^b$;

alternatively, 2 $R^{5b}$'s, along with the atom to which they are attached, join to form a 3-6 membered saturated ring containing 0-2 heteroatoms selected from O, S, or N;

$R^6$ is independently H, $C_{1-3}$ alkyl, $C_{1-3}$ fluoroalkyl, $C_{3-6}$ cycloalkyl, $C_{3-6}$ fluorocycloalkyl, $C_{1-3}$ hydroxylalkyl, $C_{1-3}$ alkoxyalkyl, or $C_{1-3}$ fluoroalkoxyalkyl;

alternatively, 2 $R^6$s attached to the same atom can form a 3-6 membered saturated ring containing 0-2 heteroatoms selected from O, S, or N;

$R^a$ is H, $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4-10 membered heterocycle having 1, 2 3 or 4 heteroatoms selected from O, S, N;

$R^b$ is H, $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4-10 membered heterocycle having 1, 2 3 or 4 heteroatoms selected from O, S, N;

each $R^d$ is independently H, $C_{1-3}$ alkyl, $C_{1-3}$ fluoroalkyl, $C_{1-3}$ alkoxy, $C_{1-3}$ fluoroalkoxy, $C_{2-3}$ hydroxyalkyl, halo, OH, =O, CN $OCF_3$, $OCHF_2$, $CHF_2$ and $CF_3$; each $R^e$ is independently H, $C_{1-3}$ alkyl, $C_{1-3}$ fluoroalkyl, $C_{3-6}$ cycloalkyl, $C_{1-3}$ hydroxyalkyl, $C_{1-3}$ alkoxyalkyl, $C_{6-10}$ aryl, or a 5 to 10 membered heteroaryl having 1, 2, 3, or 4 heteroatoms selected from O, S, and N; and n is 0, 1, or 2.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^1$ is:

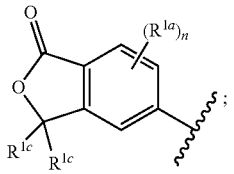

each $R^{1a}$ is independently selected from F, Cl, $C_{1-3}$ alkyl, $C_{1-3}$ fluoroalkyl, and $C_{3-6}$ cycloalkyl;

$R^{1c}$ is H, deuterium, $C_{1-2}$ alkyl, or $C_{3-6}$ cycloalkyl;

n is zero, 1, or 2

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazolonyl, pyrazolo[4,3-b]pyridinyl, pyridin-2-onyl, pyrazolyl, [1,2,4]triazolo[1,5-a]pyridinyl, imidazo[1,2-b]pyridazinyl, pyrazinyl, pyrazolo[1,5-a]pyrimidinyl, thiazolyl, thiophenyl, 1,2,3-triazolyl, benzo[d][1,2,3]triazolyl, [1,2,4]triazolo[4,3-b]pyridazinyl, benzo[d]imidazolyl, imidazolyl, pyrazolo[3,4-b]pyridinyl, pyrazolo[3,4-c]pyridinyl, pyrazolo[4,3-c]pyridinyl, pyrrolyl, pyrrolo[2,3-b]pyridinyl, pyrrolo[2,3-c]pyridinyl, pyrrolo[3,2-b]pyridinyl, pyrrolo[3,2-c]pyridinyl, pyrazolo[1,5-a]pyrimidinyl, tetrazolyl, 1,2,4-triazolyl, isothiazolyl, isoxazolyl, oxazolyl, pyridazinyl, pyrimidinyl, or benzo[d]oxazol-2-onyl, triazolyl, oxadiazolyl, pyrrolopyridinyl, each being substituted with 0-3 $R^{2a}$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is pyridinyl, pyrimidinyl, pyrrazolyl, thiazolyl, imidazolyl, triazolyl, tetrazolyl, oxadiazolyl, thiadiazolyl, isoxazolyl, pyrazinyl, oxazolyl, or pyridazinyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

V is —O—, —$NR^4$—, —$CR^5R^5$—, or —C(=O)—;

wherein if V is —O—, or $NR^4$, then Y is not $C(R^6)_2$;

Y is —$C(R^6)_2$—, —$C(R^6)_2$—$C(R^6)_2$—, —C(=O)—, —C(=O)—$C(R^6)_2$—, or —$C(R^6)_2$—C(=O)—;

$L^l$ is —$C(R)_2$—, —C(=O)—, or —$CH_2$—$C(R)_2$—;

wherein R is independently from hydrogen, F, OH, $C_{1-3}$ alkyl, $C_{1-3}$ hydroxyalkyl, $C_{1-3}$ alkoxyalkyl, or $C_{1-3}$fluoroalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazol-2(3H)-onyl, pyrazolo[4,3-b]pyridinyl, pyridin-2(1H)-onyl, pyrazolyl, pyrimidinyl, imidazolyl, pyrazolyl, triazolyl, oxadiazolyl, thiadiazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]yridazinyl, pyrazolo[1,5-a]pyrimidinyl, or benzo[d]oxazol-2(3H)-only, each being substituted with 0-3 $R^{2a}$; and $R^{2a}$ is OH, =O, CN, halo, $SO_2C_{1-4}$ alkyl, oxazolidin-2-one substituted with 0-1 $R^{2b}$;

$R^{2b}$ is $C_{1-3}$alkyl, $C_{1-3}$ fluoroalkyl, $C_{1-3}$ alkoxy, or $C_{1-3}$ fluoroalkoxy.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^1$ is

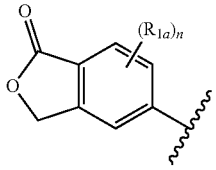

$R^{a1}$ is H or —$CH_3$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is pyridinyl, triazolyl, thiazolyl, oxadiazolyl, imidazolyl, or pyrrazolyl; and $R^2$ is phenyl, pyridinyl, pyrimidinyl, benzo[d]oxazol-2(3H)-onyl, imidazolyl, pyrrazolyl, triazolyl, or oxadiazolyl, each being substituted with 0-3 $R^{2a}$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

V is —O—, —$NR^4$—, or —$CR^5R^5$—;

Y is —$C(R^6)_2$—$C(R^6)_2$— or —$C(R^6)_2$—;

$L^1$ is —$C(R)_2$—; wherein R is independently from hydrogen, F, OH, $C_{1-3}$alkyl, $C_{1-3}$ hydroxyalkyl, $C_{1-3}$ alkoxyalkyl, or $C_{1-3}$fluoroalkyl; and $R^6$ is independently H, $C_{1-3}$-alkyl, $C_{1-3}$-fluoroalkyl, or $C_{3-6}$-cycloalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^1$ is:

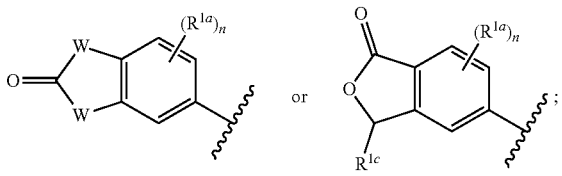

one W is $NR^{1b}$ and the other W is O;

each $R^{1a}$ is independently selected from F, Cl, $C_{1-3}$ alkyl, $C_{1-3}$ fluoroalkyl, and $C_{3-6}$ cycloalkyl;

$R^{1b}$ is H, $C_{1-3}$ alkyl, or $C_{1-3}$ fluoroalkyl;

$R^{1c}$ is H, $C_{1-2}$ alkyl, or $C_{3-6}$ cycloalkyl;

n is zero, 1, or 2.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazolonyl, pyrazolo[4,3-b]pyridinyl, pyridin-2-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiazolyl, thiophenyl, 1,2,3-triazolyl, benzo[d][1,2,3]triazolyl, [1,2,4]triazolo[4,3-b]pyridazinyl, benzo[d]imidazolyl, imidazolyl, pyrazolo[3,4-b]pyridinyl, pyrazolo[3,4-c]pyridinyl, pyrazolo[4,3-c]pyridinyl, pyrrolyl, pyrrolo[2,3-b]pyridinyl, pyrrolo[2,3-c]pyridinyl, pyrrolo[3,2-b]pyridinyl, pyrrolo[3,2-c]pyridinyl, pyrazolo[1,5-a]pyrimidinyl, tetrazolyl, 1,2,4-triazolyl, isothiazolyl, isoxazolyl, oxazolyl, pyridazinyl, pyrimidinyl, or benzo[d]oxazol-2-onyl, each being substituted with 0-3 $R^{2a}$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is phenyl, pyridinyl, pyrimidinyl, pyrrazolyl, indolyl, indazolyl, thiazolyl, imidazolyl, pyridinoyl, 1,2-dihydro-3H pyrazol-3-onyl, 1H-1,2,3-triazolyl, pyrazinyl or pyridazinyl, or oxazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is phenyl, pyridinyl, pyrimidinyl, pyrrazolyl, indolyl, indazolyl, thiazolyl, imidazolyl, pyridinoyl, 1,2-dihydro-3H pyrazol-3-onyl, 1H-1,2,3-triazolyl, 2H-1,2,3-triazolyl, pyrazinyl or pyridazinyl, or oxazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is phenyl, pyridinyl, pyrimidinyl, pyrrazolyl, thiazolyl, imidazolyl, triazolyl, tetrazolyl, oxadiazolyl, thiadiazolyl, isoxazolyl, isothiazolyl, pyrrolyl, pyrazinyl, oxazolyl, pyridazinyl, pyrrolidinyl, oxazolonyl, oxazolidinonyl, pyrazolinonyl, imidazolidinyl, imidazolonyl, pyrrolidinonyl, pyrimidinonyl, pyridazinonyl, or pyridinoyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is pyrazolyl, triazolyl, oxadiazolyl, isoxazolyl, imidazolyl, or imidazolonyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

V is —O—, —$NR^4$—, —$CR^5R^5$—, or —C(=O)—;

wherein if V is —O—, or $NR^4$, then Y is not $C(R^6)_2$;

Y is —$C(R^6)_2$—, —$C(R^6)_2$—$C(R^6)_2$—, —C(=O)—, —C(=O)—$C(R^6)_2$—, or —$C(R^6)_2$—C(=O)—;

$L^1$ is —$C(R)_2$—, —C(=O)—, or —$CH_2$—$C(R)_2$—; wherein R is independently from hydrogen, F, OH, $C_{1-3}$alkyl, $C_{1-3}$ hydroxyalkyl, $C_{1-3}$ alkoxyalkyl, or $C_{1-3}$fluoroalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, pyrazolo[1,5-a]pyrimidinyl, or benzo[d]oxazol-2(3H)-only, each being substituted with 0-3 $R^{2a}$; and $R^{2a}$ is OH, =O, CN, halo, $SO_2C_{1-4}$ alkyl, oxazolidin-2-one substituted with 0-1 $R^{2b}$;

$R^{2b}$ is $C_{1-3}$alkyl, $C_{1-3}$ fluoroalkyl, $C_{1-3}$ alkoxy, or $C_{1-3}$ fluoroalkoxy.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, pyrazolo[1,5-a]pyrimidinyl, or benzo[d]oxazol-2(3H)-only, each being substituted with 0-3 $R^{2a}$; and $R^{2a}$ is OH, =O, CN, halo, $C_{1-4}$ alkyl, $SO_2C_{1-4}$ alkyl, oxazolidin-2-one substituted with 0-1 $R^{2b}$;

$R^{2b}$ is $C_{1-3}$alkyl, $C_{1-3}$ fluoroalkyl, $C_{1-3}$ alkoxy, or $C_{1-3}$ fluoroalkoxy.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^1$ is

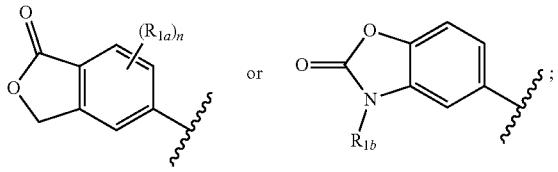

and $R^{1a}$ is H or —$CH_3$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is phenyl, pyridinyl, pyrimidinyl, indolyl, or pyrrazolyl, indazolyl; and $R^2$ is phenyl, indolyl, pyridinyl, benzo[d]oxazol-2(3H)-onyl, pyridin-2(1H)-onyl, or indazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazol-2(3H)-onyl, pyrazolo[4,3-b]pyridinyl, pyridin-2(1H)-onyl, pyrazolyl, pyrimidinyl, imidazolyl, pyrazolyl, triazolyl, oxadiazolyl, thiadiazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, pyrazolo[1,5-a]pyrimidinyl, or benzo[d]oxazol-2(3H)-only, each being substituted with 0-3 $R^{2a}$; and $R^{2a}$ is OH, =O, CN, halo, $SO_2C_{1-4}$ alkyl, oxazolidin-2-one substituted with 0-1 $R^{2b}$;

$R^{2b}$ is $C_{1-3}$alkyl, $C_{1-3}$ fluoroalkyl, $C_{1-3}$ alkoxy, or $C_{1-3}$ fluoroalkoxy.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

V is —O—, —$NR^4$—, or —$CR^5R^5$—;

Y is —$C(R^6)_2$—$C(R^6)_2$—, —C(=O)—, —C(=O)—$C(R^6)_2$—, or —$C(R^6)_2$—C(=O)—;

$L^1$ is —$C(R)_2$—, —C(=O)—, or —$CH_2$—CH(R)—; wherein R is independently from hydrogen, F, OH, $C_{1-3}$alkyl, $C_{1-3}$ hydroxyalkyl, $C_{1-3}$ alkoxyalkyl, or $C_{1-3}$ fluoroalkyl;

$R^6$ $i_s$ independently H, $C_{1-3}$-alkyl, $C_{1-3}$-fluoroalkyl, or $C_{3-6}$-cycloalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

V is —O—, —$NR^4$—, or —$CR^5R^5$—;

Y is —$C(R^6)_2$—$C(R^6)_2$—, or —$C(R^6)_2$—;

$L^1$ is —$C(R)_2$—; wherein R is independently from hydrogen, F, OH, $C_{1-3}$alkyl, $C_{1-3}$ hydroxyalkyl, $C_{1-3}$ alkoxyalkyl, or $C_{1-3}$fluoroalkyl; and $R^6$ is independently H, $C_{1-3}$-alkyl, $C_{1-3}$-fluoroalkyl, or $C_{3-6}$-cycloalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^6$ is independently H or $C_{1-3}$ alkyl; or $R^6$ is independently H or methyl; or $R^6$ is methyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^{2a}$ is OH, =O, CN, halo, $C_{1-4}$alkyl, $C_{1-4}$ fluoroalkyl, $C_{1-4}$ alkoxy, or $C_{1-4}$ fluoroalkoxy. Alternatively, $R^{2a}$ s OH, =O, CN, halo, $SO_2C_{1-4}$ alkyl, oxazolidin-2-one substituted with 0-1 $R^{2b}$;

$R^{2b}$ is $C_{1-3}$alkyl, $C_{1-3}$ fluoroalkyl, $C_{1-3}$ alkoxy, or $C_{1-3}$ fluoroalkoxy.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^4$ is H, $C_{1-3}$-alkyl, $CO_2R^{4a}$, $C(=O)R^{4a}$, $SO_2R^{4a}$, $C(=O)N(R^{4b}R^{4b})$, $SO_2N(R^{4b}R^{4b})$;

$R^{4a}$ is $C_{1-3}$-alkyl, $C_{1-3}$-fluoroalkyl, $C_{3-6}$-cycloalkyl;

$R^{4b}$ is independently H, $C_{1-3}$-alkyl, $C_{3-6}$-cycloalkyl, $R^5$ is independently H, F, OH, $C_{1-3}$-alkoxy, $C_{1-3}$-alkyl, $C_{3-6}$-cycloalkyl, $NR^{5b}R^{5b}$;

$R^{5b}$ is independently H, $C_{1-3}$-alkyl, $C_{3-6}$-cycloalkyl, $C(O)R^a$, $SO_2R^a$, or $C(O)NR^bR^b$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^4$ is H, $C_{1-3}$-alkyl, $CO_2R^{4a}$, $C(=O)R^{4a}$, $SO_2R^{4a}$, $C(=O)N(R^{4b}R^{4b})$, $SO_2N(R^{4b}R^{4b})$;

$R^{4a}$ is $C_{1-3}$-alkyl, $C_{1-3}$-fluoroalkyl, $C_{3-6}$-cycloalkyl;

$R^{4b}$ is independently H, $C_{1-3}$-alkyl, $C_{3-6}$-cycloalkyl, $R^5$ is independently H, F, OH, $C_{1-3}$-alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the compound of Formula (I) is

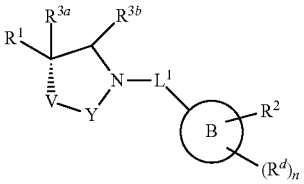

or

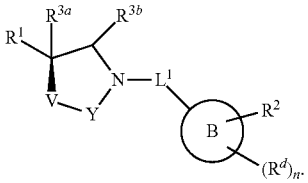

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^1$ is

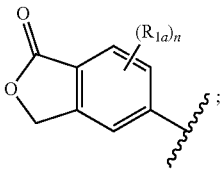

and $R^{1a}$ is H or —$CH_3$; or $R^1$ is

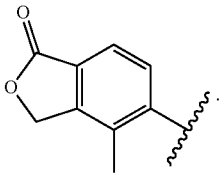

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^1$ is

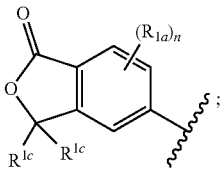

and $R^{1a}$ is H or —$CH_3$; and $R^{1c}$ is independently H or deuterium; or $R^1$ is

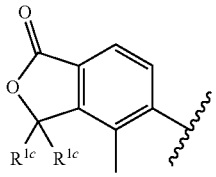

$R^{1c}$ is independently H or deuterium.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{3a}$ and $R^{3b}$ are H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R_1$ is

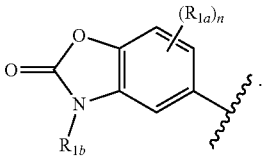

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R_1$ is

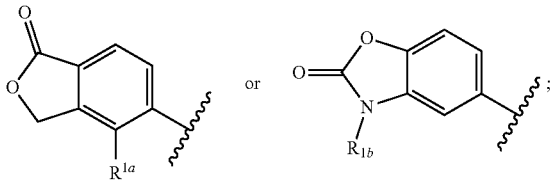

$R^{1a}$ is H or —$CH_3$; Rib is H or —$CH_3$; $L_1$ is a bond, —$CH_2$—, —$CH_2CH_2$—, —$CH(CH_2OH)$—, or —$CH(OH)CH_2$—.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{1a}$ is H, F, $C_{1-3}$ alkyl, or $CF_3$; or $R^{1a}$ is H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: each $R^{1b}$ is independently H, or $C_{1-3}$ alkyl; or each $R^{1b}$ is H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is

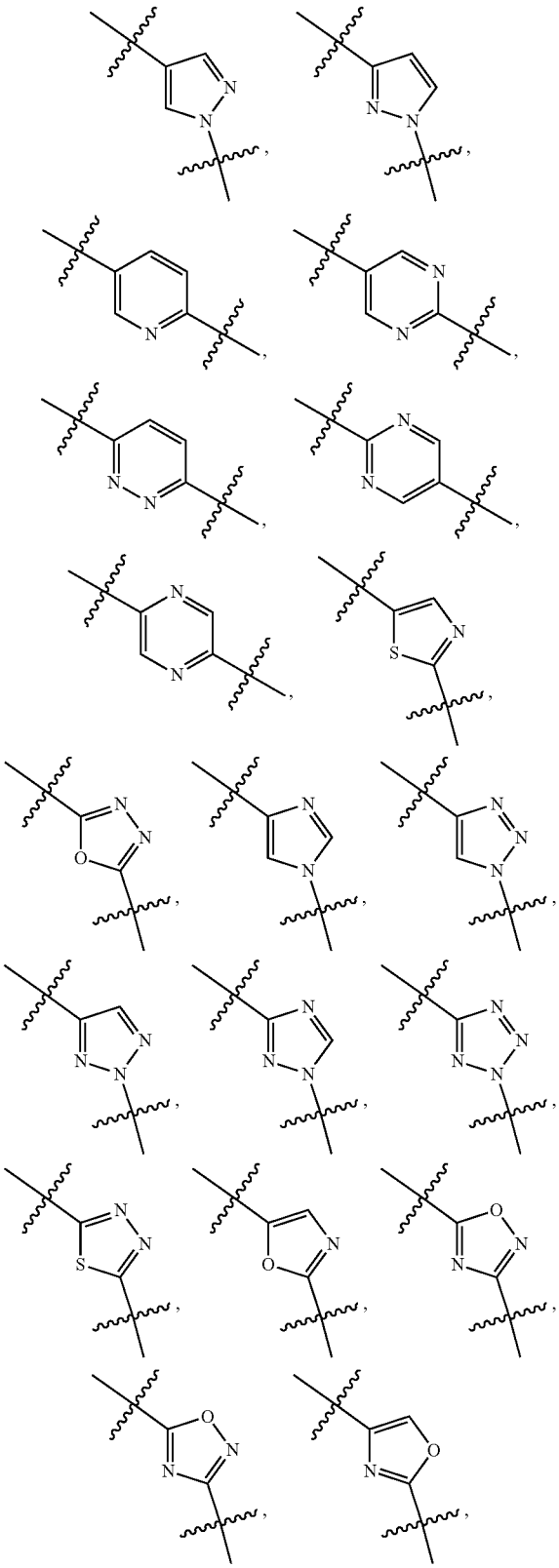

-continued

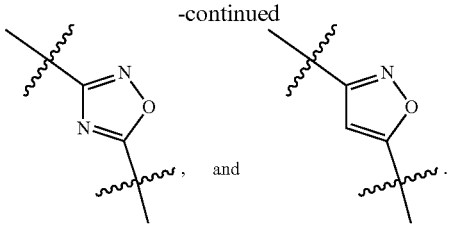

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is

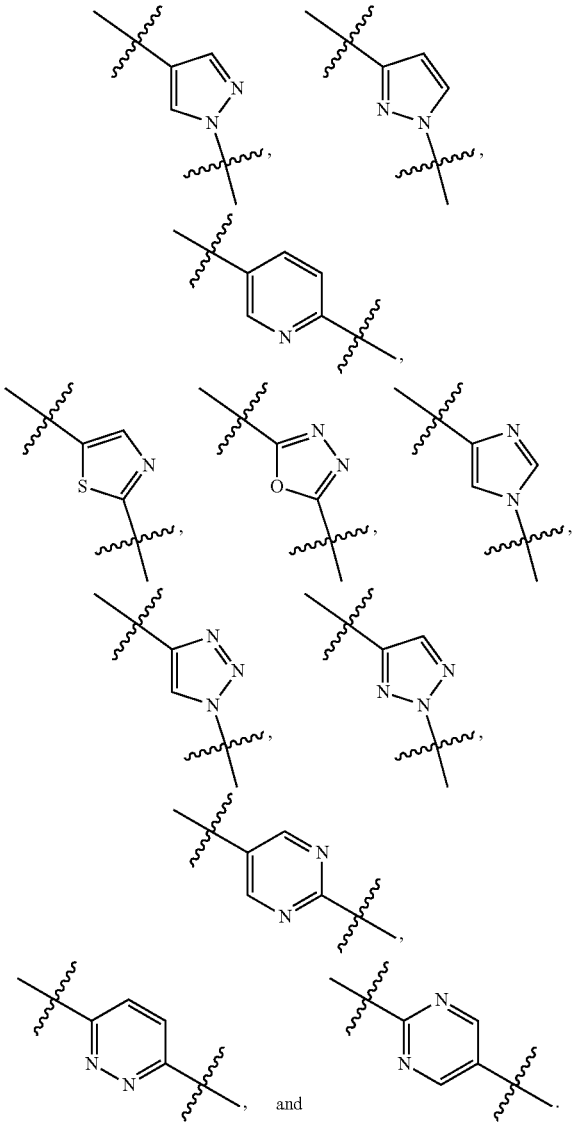

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is

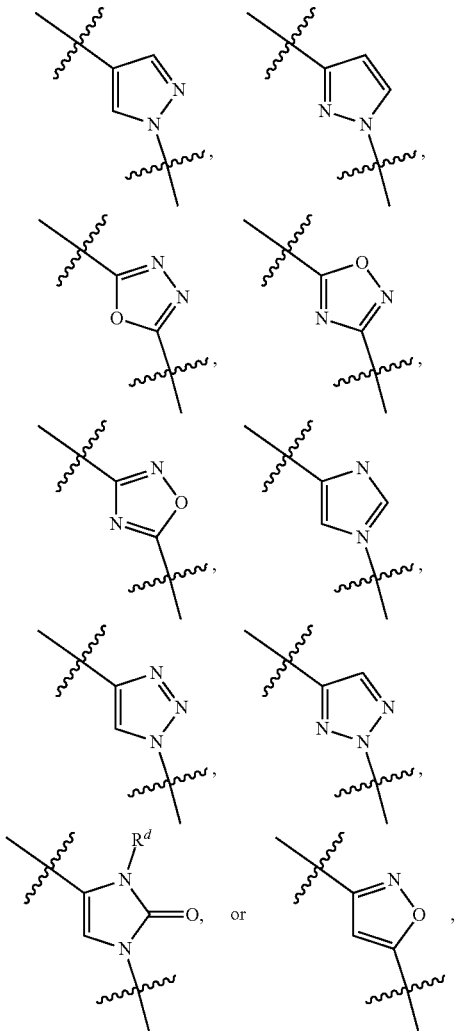

any of which are substituted with 0-1 $R^d$.

In a ninth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

Ring B is phenyl, pyridinyl, pyrimidinyl, indolyl, pyrrazolyl, or indazolyl; and $R^2$ is phenyl, indolyl, pyridinyl, benzo[d]oxazol-2(3H)-onyl, pyridin-2(1H)-onyl, or indazolyl.

In a ninth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

Ring B is phenyl, pyridinyl, pyrimidinyl, indolyl, pyrrazolyl, triazolyl or indazolyl; and $R^2$ is phenyl, indolyl, pyridinyl, benzo[d]oxazol-2(3H)-onyl, pyridin-2(1H)-onyl, or indazolyl.

In another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

Ring B is phenyl, pyridinyl, pyrimidinyl, imidazolyl, oxadiazolyl, pyrrazolyl, or triazolyl.

In another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

$R^2$ is phenyl, imidazolyl, pyridinyl, benzo[d]oxazol-2(3H)-onyl, pyridin-2(1H)-onyl, pyrazinyl, pyrrazolyl, pyrazolopyrimidinyl, pyrimidinyl, thiazolyl, thiophenyl, or triazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{2a}$ is CN, halo, or $C_{1-4}$alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^{2a}$ is OH, =O, CN, halo, $C_{1-4}$alkyl, $C_{1-4}$ fluoroalkyl, $C_{1-4}$ alkoxy, $C_{1-4}$ fluoroalkoxy, $SO_2R^e$, or oxazolidin-2-one substituted with 0-1 $R^{2b}$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^{2a}$ is independently OH, =O, CN, halo, $C_{1-4}$ alkyl, $C_{1-4}$ deuteroalkyl, $C_{1-4}$ fluoroalkyl, $C_{1-4}$ alkoxy, $C_{1-4}$ deuteroalkoxy, $C_{1-4}$ fluoroalkoxy, $C_{3-6}$ cycloalkyl, $C_{3-6}$ cycloalkoxy, $C(=O)N(R^{4b}R^{4b})$, $C(=O)C_{1-4}$ alkyl, $SO_2R^e$, $NR^{4b}SO_2R^{4b}$, or a 4 to 6 membered heterocycle having 1, 2, 3, or 4 heteroatoms selected from O, S, and N, wherein the heterocycle optionally containing an oxo substitution and is substituted with 0-3 $R^{2b}$;

alternatively, two $R^{2a}$ on adjacent atoms join to form —O—$CH_2$—O—, or —O—$CF_2$—O—;

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$L^1$ is —$CH_2$—, —C(=O)—, or $CH_2$~CH(R)—; wherein R is independently from hydrogen, F, OH, $C_{1-3}$ alkyl, $C_{1-3}$ hydroxyalkyl,$C_{1-3}$alkoxyalkyl, or $C_{1-3}$fluoroalkyl; or $L^1$ is —$CH_2$—, —C(=O)—, or —$CH_2$~CH(R)—; wherein R is independently from hydrogen, or OH; or $L^1$ is —$CH_2$—, or —$CH_2$—$CH_2$—.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the compound of Formula (I) is:

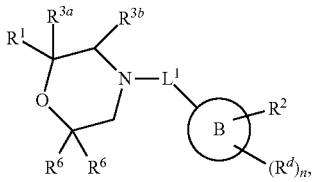

-continued

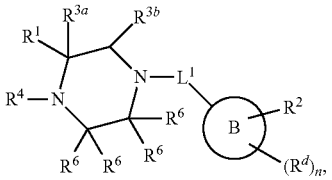

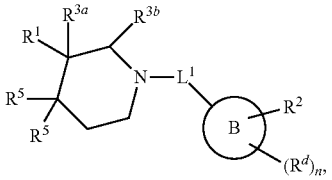

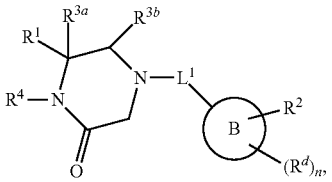

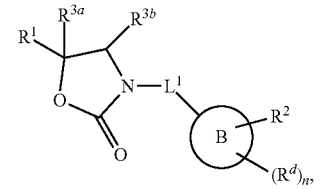

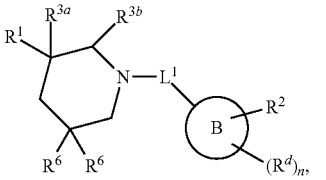

or

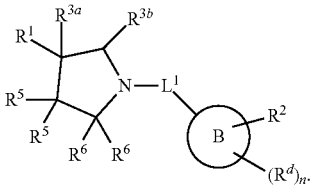

In another aspect, there are disclosed compounds of Formula (I), or compounds f Formula (I) as described by any of the other embodiments or aspects, including salts, enantiomers, diastereomers, tautomers, pharmaceutically-acceptable salts, hydrates, or solvates thereof, wherein the compound of Formula (I) is:

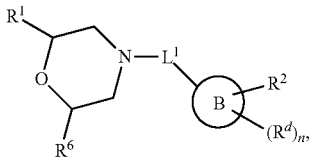

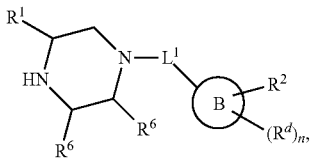

-continued

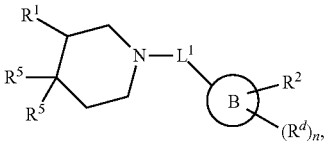

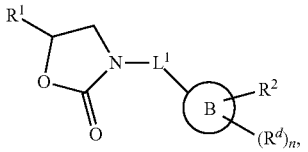

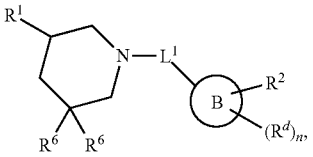

and

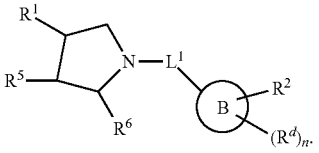

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the compound of formula (I) is:

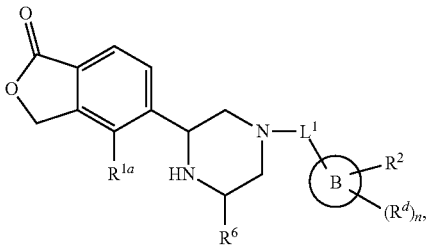

or

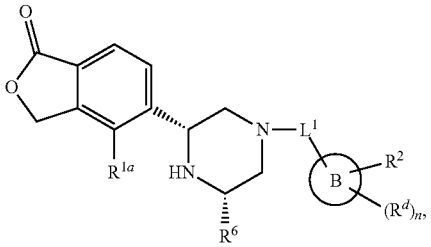

or

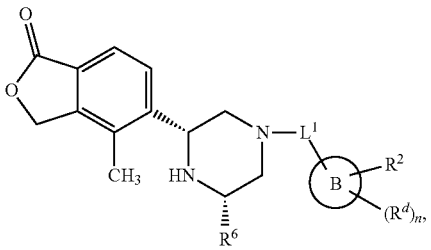

or

-continued

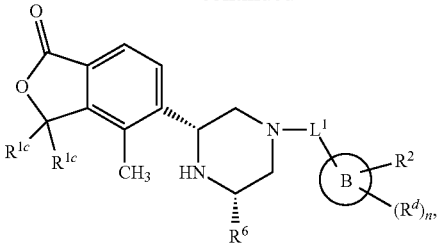

or

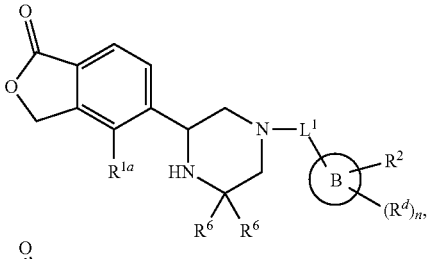

or

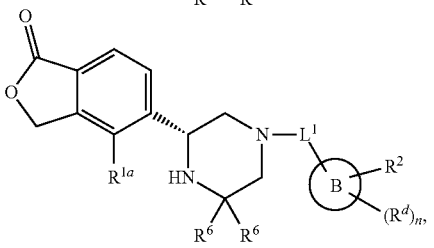

or

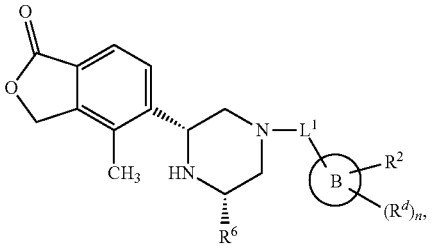

or

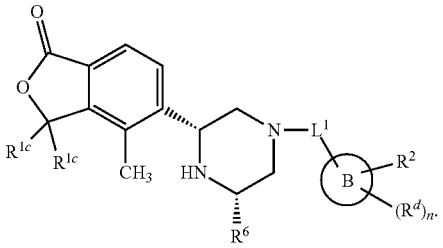

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the compound of formula (I) is:

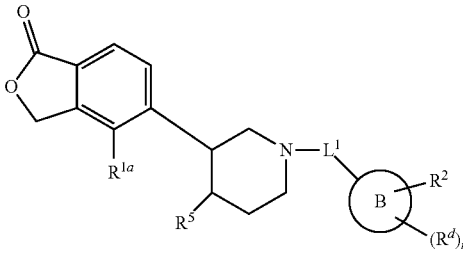

or

-continued

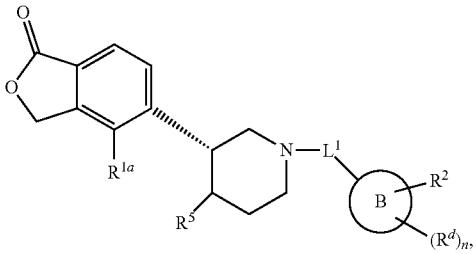

or

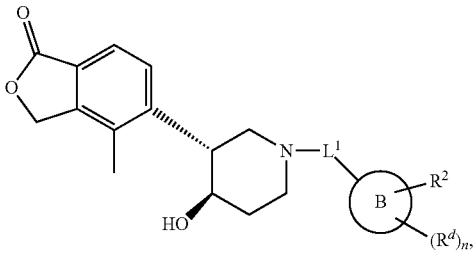

or

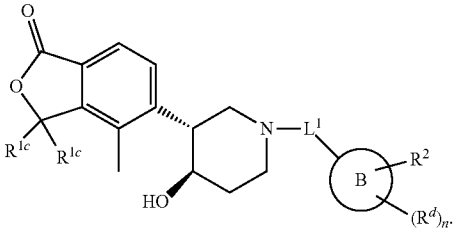

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiazolyl, thiophenyl, 1H-1,2,3-triazolyl, 1H-benzo[d][1,2,3]triazolyl, [1,2,4]triazolo[4,3-b]pyridazinyl, 1H-benzo[d]imidazolyl, 1H-imidazolyl, 1H-pyrazolo[3,4-b]pyridinyl, 1H-pyrazolo[3,4-c]pyridinyl, 1H-pyrazolo[4,3-c]pyridinyl, 1H-pyrrolyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, pyrazolo[1,5-a]pyrimidinyl, 1H-tetrazolyl, 4H-1,2,4-triazolyl, isothiazolyl, isoxazolyl, oxazolyl, pyridazinyl, pyrimidinyl, or benzo[d]oxazol-2(3H)-only, each being substituted with 0-3 $R^{2a}$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^2$ is phenyl,

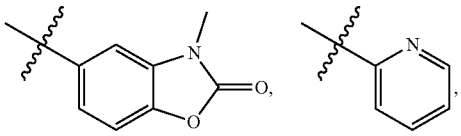

-continued

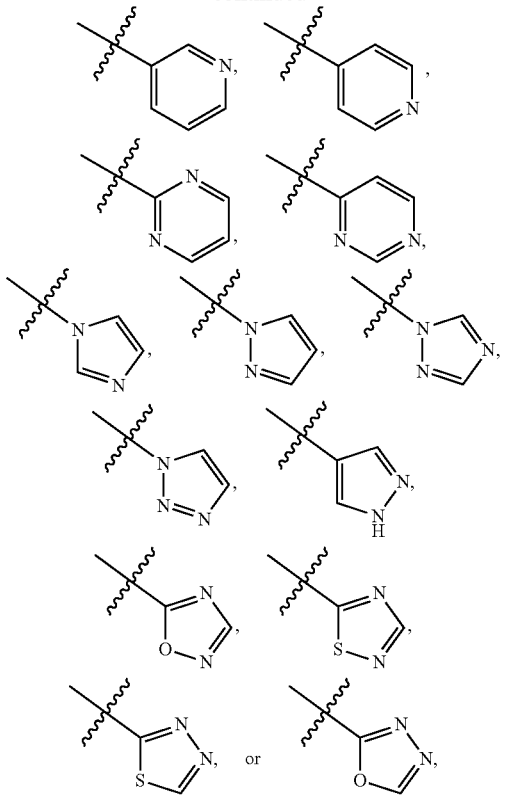

each being substituted with 0-3 $R^{2a}$ (as valance allows).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^2$ is phenyl,

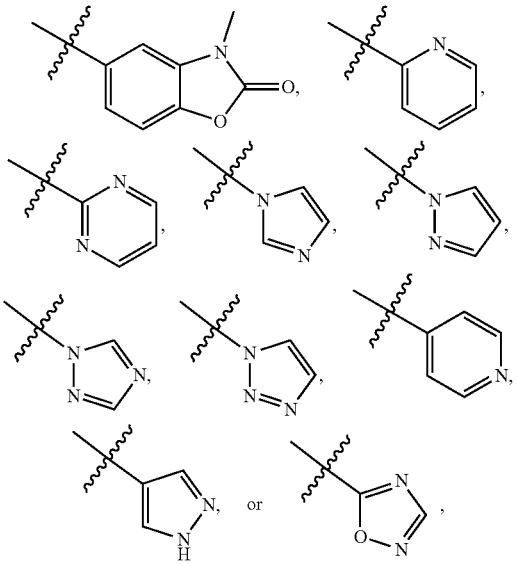

each being substituted with 0-3 $R^{2a}$ (as valance allows).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^2$ is phenyl,

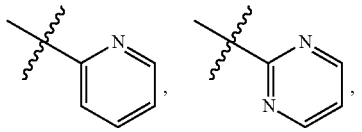

each being substituted with 0-3 $R^{2a}$ (as valence allows).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^2$ is phenyl,

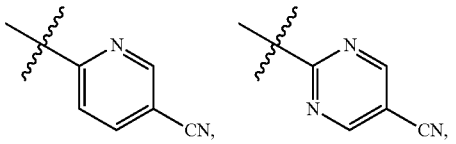

each being substituted with 0-2 $R^{2a}$ (as valance allows).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: the compounds are selected from the Examples.

In another aspect, there is disclosed a pharmaceutical composition, comprising a pharmaceutically acceptable carrier and any one or more compounds of Formula (I), or compounds of Formula (I) as described by any of the other embodiments or aspects or examples, or a pharmaceutically acceptable salt thereof.

In another aspect, there is disclosed a method for the treatment of one or more diseases or disorders which can be modulated by inhibition of ROMK, comprising administering to a patient in need of such treatment or prophylaxis a therapeutically effective amount of at least one of the compounds of Formula (I), or compounds of Formula (I) as described by any of the other embodiments or aspects or examples, wherein the disease or disorder is treated by promotion of diuresis or natriuresis.

In another aspect, there is disclosed a method for the treatment or prophylaxis of one or more diseases or disorders which can be modulated by ROMK inhibition, wherein the compound of any of the embodiments is administered in combination with at least one other type of therapeutic agent.

In another aspect, there is disclosed a method for the treatment or prophylaxis of multiple diseases or disorders, comprising administering to a patient in need of such treatment or prophylaxis a therapeutically effective amount of at least one of the compounds of Formula (I), or compounds of Formula (I) as described by any of the other embodiments or aspects, wherein the disease or disorder is treated by the promotion of diuresis or natriuresis, or for ROMK associated disorders.

In another aspect, there is disclosed a method for the treatment or prophylaxis of diseases or disorders, wherein the compound of any of the embodiments is administered in combination with at least one other type of therapeutic agent. In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the examples.

In another aspect, the present invention provides treatment of hypertension or heart failure for patients in need of diuresis or natriuresis.

In another aspect, the present invention provides for the treatment of hypertension.

In another aspect, the present invention provides for the treatment of hypertension, idiopathic hypertension, refractory hypertension, and/or pulmonary hypertension.

In another aspect, the present invention provides for the treatment of heart failure.

In another aspect, the present invention provides for the treatment of edema, cardiac insufficiency, systolic heart failure, diastolic heart failure, diabetic heart failure, and/or acute-decompensated heart failure.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds. Where a substituent definition represents more than one substituent, each substituent is independently selected from the other substituent(s).

In accordance with a convention used in the art,

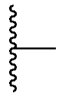

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group $—NH_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms, and is intended to include $C_1$, $C_2$, $C_3$, and $C_4$ alkyl groups. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, $—CF_3$, $—CCl_3$, $—CFCl_2$, and $—CH_2CF_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, $—CF_3$ and $—CH_2CF_3$.

The term "hydroxyalkyl" includes both branched and straight-chain saturated alkyl groups substituted with one or more hydroxyl groups. For example, "hydroxyalkyl" includes $—CH_2OH$, $—CH_2CH_2OH$, and $C_{1-4}$ hydroxyalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group —($OCH_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "aryl" as used herein, refers to a group of atoms derived from a molecule containing aromatic ring(s) by removing one hydrogen that is bonded to the aromatic ring(s), containing 4 to 10, or 6 to 10 carbon atoms. Aryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclyl" or "heterocycle" as used herein, refers to substituted and unsubstituted saturated, partially saturated, and aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring having 1, 2, 3, or 4 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain other heteroatoms or only carbon atoms; and may be saturated, partially saturated, or aromatic. The heterocyclo group may be attached at any available nitrogen or carbon atom in the heterocyclo group. The term "heterocyclyl" includes "heteroaryl" groups. As valence allows, if said further ring is cycloalkyl or heterocyclo it is additionally optionally substituted with =O (oxo).

The term "heteroaryl" refers to substituted and unsubstituted aromatic 5- or 6-membered monocyclic groups, 9- or 10-membered bicyclic groups, and 11- to 14-membered tricyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain other heteroatoms or only carbon atoms. The nitrogen and sulfur atoms may optionally be oxidized and the nitrogen atoms may optionally be quaternized. Bicyclic and tricyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) The Practice of Medicinal Chemistry, Camille G. Wermuth et al., Ch 31, (Academic Press, 1996);
b) Design of Prodrugs, edited by H. Bundgaard, (Elsevier, 1985);
c) A Textbook of Drug Design and Development, P. Krogsgaard-Larson and H. Bundgaard, eds. Ch 5, pgs 113-191 (Harwood Academic Publishers, 1991); and
d) Hydrolysis in Drug and Prodrug Metabolism, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Compounds of the formula I and/or the Examples herein may in some cases form salts which are also within the scope of this invention. Reference to a compound of the formula I and/or Examples herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

"Base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. In one aspect, inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, ethylglucamine, theobromine, purines, piperazine, piperidine, N-ethylpiperidine, polyamine resins and the like. In another aspect, organic bases are isopropylamine, diethylamine, ethanolamine, trimethylamine, dicyclohexylamine, choline and caffeine.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds. Combinations of substituents and/or variables are permissible only if such combinations result in stable compounds.

"Therapeutically effective amount" is intended to include an amount of a compound of the present invention alone or an amount of the combination of compounds claimed or an amount of a compound of the present invention in combination with other active ingredients effective to act as an inhibitor to ROMK, or effective to treat or prevent cardiovascular disease.

In another aspect, there is disclosed a method for the treatment or prophylaxis of one or more disease or disorder which can be modulated by ROMK inhibition, comprising administering to a patient in need of such treatment or prophylaxis a therapeutically effective amount of at least one of the compounds of Formula (I), or compounds of Formula (I) as described by any of the other embodiments or aspects, wherein the disease or disorder is treated by the promotion of diuresis or natriuresis.

In another aspect, there is disclosed a method for the treatment of one or more disease or disorder which can be treated by promotion of diuresis or natriuresis, wherein the cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, refractory hypertension cardiac insufficiency, nephrotic syndrome and acute kidney insufficiency.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds, whether those isotopes occur in their natural abundancy, or are enriched to a level greater than its natural abundancy. Isotopes include those atoms having the same atomic number but different mass numbers. By way of general example and without limitation, isotopes of hydrogen include deuterium (D) and tritium (T). Isotopes of carbon include $^{13}C$ and $^{14}C$. For example, methyl (—$CH_3$) also includes deuterated methyl groups such as —$CD_3$, —$CHD_2$, or —$CH_2D$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alphatocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, and flavors) according to techniques such as those well known in the art of pharmaceutical formulation.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

UTILITY

The compounds of the invention inhibit the activity of ROMK. Accordingly, compounds of Formula (I) have utility in treating conditions associated with the inhibition of ROMK.

The compounds described herein are intended for the treatment and/or prophylaxis of any disorders that benefit from increased excretion of water and sodium from the body, or for any patient in need of diuresis or natriuresis. Specific disorders would include any form of hypertension or heart failure (acute-decompensated and chronic, diastolic and systolic). For heart failure treatment, the compounds would be used to treat acute-decompensated heart failure to reduce edema and other symptoms and/or to overcome resistance to other classes of diuretics, or to shorten hospital stay. The compounds could also be used in heart failure after discharge from hospital or during chronic therapy to treat symptoms and reduce recurrences of acute-decompensations and hospital admissions. Other disorders for which a diuretic or natriuretic or both would have therapeutic or prophylactic benefit include post-operative volume overload, any edematous states including idiopathic edema, pulmonary hypertension including pulmonary arterial hypertension, cardiac insufficiency, nephrotic syndrome and acute kidney insufficiency.

The compounds in accordance with the present invention are beneficial in the treatment and/or prevention of various human ailments. The compounds in accordance with the present invention can be beneficial either as a stand alone therapy or in combination with other therapies that therapeutically could provide greater benefit. The ailments for which the compounds in the present invention could be of benefit include cardiovascular disease; and promotion of diuresis or natriuresis.

One embodiment provides a method for treating cardiovascular disease. Particular, cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome and acute kidney insufficiency. For example, a therapeutically effective amount for treating a disorder may be administered in the method of the present embodiment.

One embodiment provides a method for the promotion of diuresis or natriuresis.

One or more additional pharmacologically active agents may be administered in combination with the compounds described herein including any other diuretic from any other diuretic class (thiazides, loops, potassium-sparing, osmotic, carbonic anhydrase inhibitors, mineralocorticoid receptor antagonists), acetylcholinesterase inhibitors, angiotensin receptor blockers, neutral endopeptidase inhibitors, dual angiotensin receptor antagonists and neutral endopeptidase inhibitors, aldosterone antagonists, natriuretic peptides, calcium channel blockers, relaxin or relaxin mimetics, inotropic agents, peripheral vasodilators, or mineralocorticoid receptor antagonists. One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment of cardiovascular disease. In the present embodiment, the use for the manufacture of a medicament may include the administration of a therapeutically-effective amount of a compound of Formula (I) for the treatment of cardiovascular disease.

The present invention also provides the use of the compounds of Formula (I) for the manufacture of a medicament for promotion of diuresis or natriuresis.

In one embodiment, the compounds of Formula (I) inhibit ROMK activity with $IC_{50}$ values of less than 10 μM, for example, from 0.001 to less than 10 μM, as measured by the Thallium Flux assay. Preferably, the compounds of Formula (I) inhibit ROMK activity with $IC_{50}$ values of less than 1 μM, for example, from 0.001 to less than 1 μM. Other compounds inhibit ROMK activity with $IC_{50}$ values of 100 nM and less, for example, from 1 to 100 nM.

Examples of compounds of Formula (I) as specified in the "Examples" section below, have been tested in one or more of the assays described below.

METHODS OF PREPARATION

The following are the definitions of symbols used.

Ar Aryl
ACN Acetonitrile
$BF_3.OEt_2$ Boron trifluoride etherate
$CH_2Cl_2$ Dichloromethane
$CHCl_3$ Chloroform
$CDCl_3$ Deuterated chloroform
$CD_3OD$ Deuterated methanol
DCM Dichloromethane
DMAP 4-Dimethylaminopyridine
DMF N,N-dimethyl formamide
DMSO Dimethyl sulfoxide
DMSO-$d_6$ Deuterated dimethyl sulfoxide
Et Ethyl
EtOAc Ethyl acetate
EtOH Ethanol
HATU (O(7-azabenzotriazol-1-yl)-N,N,N',N'-tetramethyl uronium hexafluorophosphate)
HCl Hydrochloric acid
HCOOH Formic acid
$HCOONH_4$ Ammonium formate
KI Potassium iodide
$K_2CO_3$ Potassium carbonate
KOAc Potassium acetate
$K_3PO_4$ Potassium phosphate
LiOH Lithium hydroxide
Me Methyl
MeOH Methanol
NaH Sodium hydride
$NaHCO_3$ Sodium bicarbonate
$NaNO_2$ Sodium nitrite
$Na_2SO_4$ Sodium sulfate
$Na_2S_2O_3$ Sodium thiosulfate
$NH_3$ Ammonia
$NH_4OAc$ Ammonium acetate
Pd/C Palladium on carbon
$Pd_2(dba)_3$ Tris(dibenzylideneacetone)dipalladium (0)
$Pd(dppf)_2Cl_2:CH_2Cl_2$ [1,1'Bis(diphenylphosphino)ferrocene]dichloropalladium(II), complex with dichloromethane
$POCl_3$ Phosphorus oxychloride
THF Tetrahydrofuran
TFA Trifluoroacetic acid
XANTPHOS 4,5-Bis(diphenylphosphino)-9,9-dimethylxanthene
IPA Isopropyl alcohol
DEA Diethylamine
STAB Sodium triacetoxyborohydride Synthesis:

A particularly useful compendium of synthetic methods which may be applicable to the preparation of compounds of the present invention may be found in Larock, R. C., Comprehensive Organic Transformations, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituent's that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (Protective Groups in Organic Synthesis, Wiley and Sons (1991)).

Scheme 1:

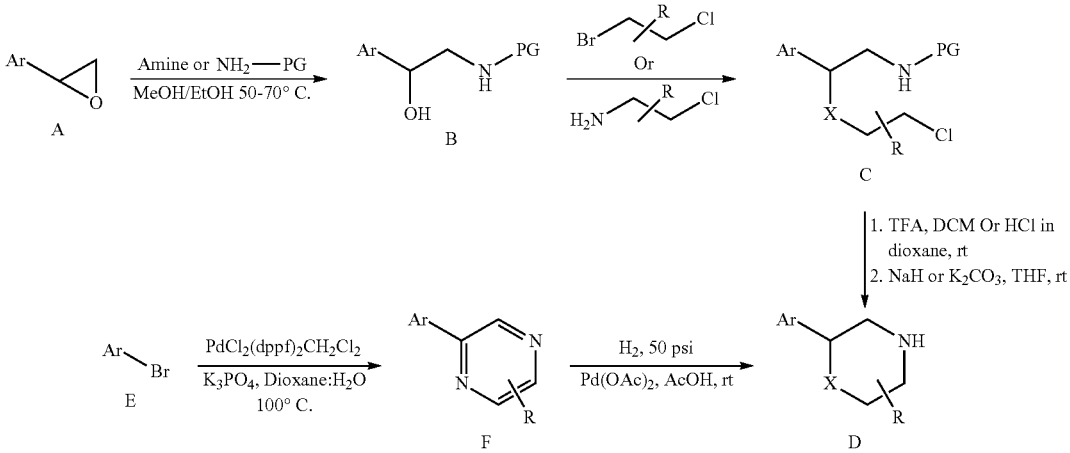

X = O, NH

Intermediates of general formula D may be synthesized according to Scheme 1.

Substituted epoxides (A) were converted to (B) by reaction with appropriate amine. B was subjected to alkylation, acylation or mitsunobu inversion reactions with appropriately substituted alkyl amines or alkyl/acylhalides to generate (C). Compound C was deprotected using choroethylchloroformate, TFA or hydrogenation in the presence of Pd/C followed by cyclization to generate intermediate (D). Intermediate D (X=N) was also synthesized by an alternative route using appropriately substituted aryl halides (E), were E was converted to (F) using Suzuki coupling of appropriately substituted halo pyrazines followed by reduction of F under hydrogen pressure in the presence of Palladium(II) acetate to generate intermediate (D).

Scheme 2:

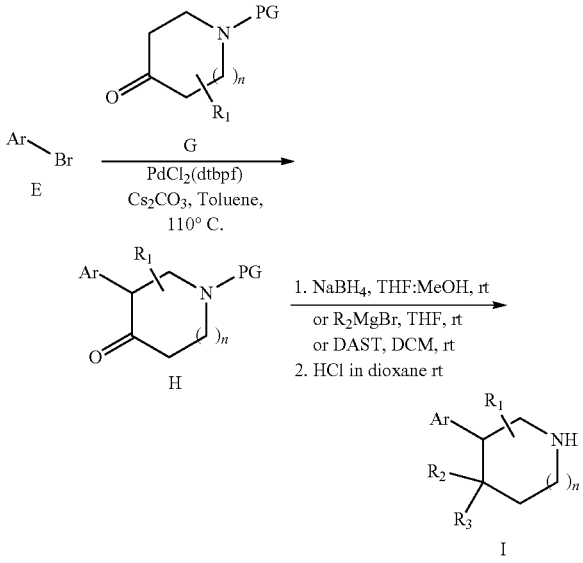

Intermediates of general formula I may be synthesized according to Scheme 2.

Appropriately substituted aryl halides (E) were subjected to the C—H activation reaction in presences of N-protected and appropriately substituted piperidinone/pyrrolidinone to generate H. Compound H was subjected to reduction and/or fluorination followed by N-deprotection to generate intermediates of the general formula (I).

Scheme 3:

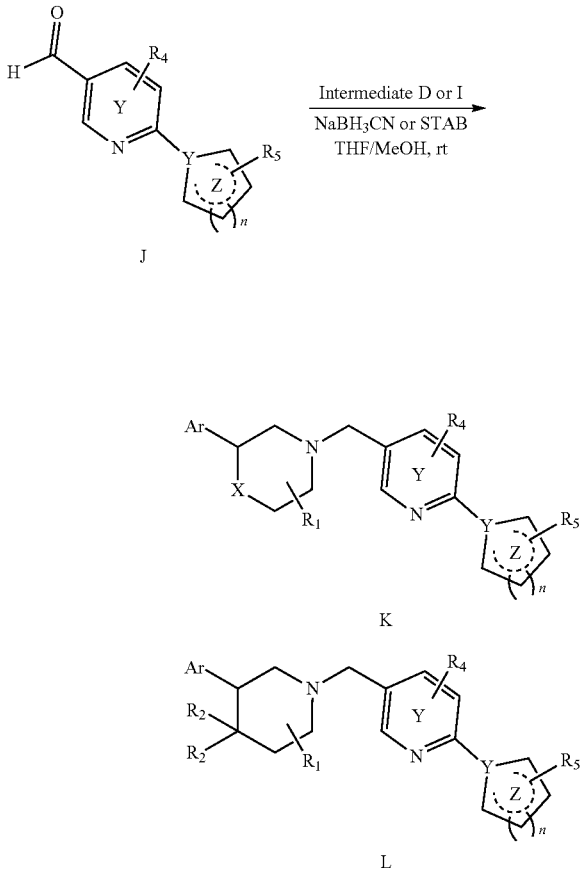

-continued

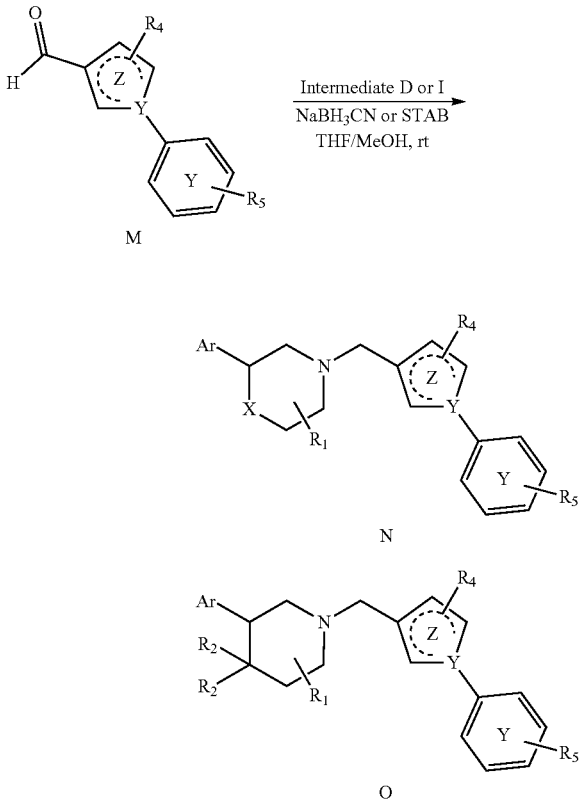

Y = N OR CH etc
Z = N, O, S etc

Compounds of general formula K, L, N and O may be synthesized according to Scheme 3.

Aldehydes J and M were synthesized according to literature procedures and J and M were subjected to reductive amination with borane reagents like sodium triacetoxyborohydride and appropriately substituted intermediates (D or I) to generate compounds of the general formula K, L, N and O.

Scheme 4:

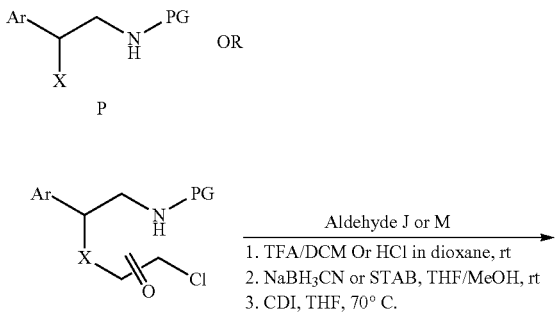

-continued

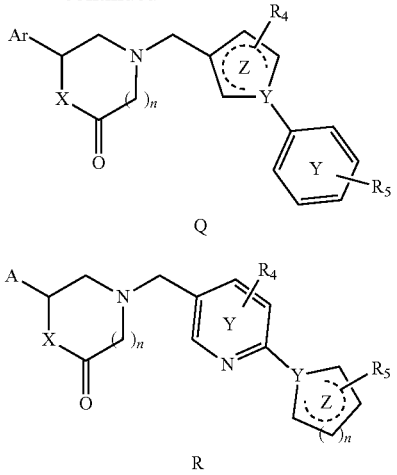

X = OH, NH or O

Compounds of general formula Q and R may be synthesized according to Scheme 4.

Intermediates P and C was synthesized according to literature procedures. Intermediates P and C were subjected to deprotection, and reductive amination of deprotected amine with appropriately substituted aldehydes (J or M) in presence of borane reagents like sodium cyanoborohydride followed by cyclization generate compounds of the general formula Q and R.

General Methods:

The following methods were used in the working Examples, except where noted otherwise.

Analytical HPLC and HPLC/MS methods employed in characterization of examples:

Reverse phase analytical HPLC/MS was performed on Shimadzu LC10AS systems coupled with Waters ZMD Mass Spectrometers or Waters Aquity system coupled with a Waters Micromass ZQ Mass Spectrometer. Chiral analytical LC was performed on a Berger Analytical SFC instrument.

Method A:

Ascentis Express C18 (2.1×50 mm) 2.7 micron; Solvent A: 95% water, 5% acetonitrile, 0.1% TFA; Solvent B: 95% acetonitrile, 5% water, 0.1% TFA; Temperature: 50° C.; Gradient: 0-100% B over 3 minutes, then 1 minute hold at 100% B; Flow: 1.1 mL/min, UV 220 nm.

Method B:

Ascentis Express C18 (2.1×50 mm) 2.7 micron; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then 1 minute hold at 100% B; Flow: 1.1 mL/min, UV 220 nm.

Method C:

SunFire C18 (4.6×150 mm) 5.0 micron; Solvent A: 95% water, 5% acetonitrile, 0.05% TFA; Solvent B: 5% water, 95% acetonitrile, 0.05% TFA; Gradient: 50-100% B over 15 minutes, then 5 minute hold at 100% B; Flow: 1.1 mL/min, UV 220 nm.

Method D:

Kinetex, XB C18 (2.6 μm×75.3 mm); Solvent A: 10 mM $NH_4CO_2H$ in 98% water, 2% acetonitrile; Solvent B: 10 mM $NH_4CO_2H$ in 2% water, 98% acetonitrile, Gradient: 20-100% B over 4 minutes, then 0.6 minute hold at 100% B; Flow: 1.1 mL/min, UV 220 nm.

Method E:

Sunfire C18 (4.6×150 mm) 3.5 micron; Solvent A: 95% water, 5% acetonitrile, 0.05% TFA; Solvent B: 5% water, 95% acetonitrile, 0.05% TFA; Gradient: 10-100% B over 25 minutes, then 5 minutes hold at 100% B; Flow: 1.1 mL/min, UV 254 nm.

Method F:

Sunfire C18 (4.6×150 mm) 3.5 micron; Solvent A: 95% water, 5% acetonitrile, 0.05% TFA; Solvent B: 5% water, 95% acetonitrile, 0.05% TFA; Gradient: 10-100% Solvent B over 18 minutes, then 5 minutes hold at 100% B; Flow: 1.1 mL/min, UV 220 nm.

Method G:

XBridge Phenyl (4.6×150 mm) 3.5 micron; Solvent A: 95% water, 5% acetonitrile, 0.05% TFA; Solvent B: 5% water, 95% acetonitrile, 0.05% TFA; Gradient: 10-100% Solvent B over 18 minutes, then 5 minutes hold at 100% B; Flow: 1.1 mL/min, UV 220 nm.

Method H:

ZORBAX SB C18 (4.6×50 mm) 5.0 micron; Solvent A: 10 mM $NH_4CO_2H$ in 98% water, 2% acetonitrile; Solvent B: 10 mM $NH_4CO_2H$ in 2% water, 98% acetonitrile, Gradient: 30-100% B over 4 minutes, then 0.6 minute hold at 100% B; Flow: 1.0 mL/min, UV 220 nm.

Method I:

Acquity BEH C8 (2.1×50 mm) 1.7 micron; Solvent A: 10 mM ammonium acetate in 95% water, 5% acetonitrile; Solvent B: 10 mM ammonium acetate in 5% water, 95% acetonitrile, Gradient: 20-90% B over 1.1 minutes, then 0.7 minute hold at 90% B; Flow: 0.5 mL/min, UV 220 nm.

Method J:

Kinetex XB-C18 (3×75 mm) 2.6 micron; Solvent A: 0.1% HCOOH in water; Solvent B: Acetonitrile, Gradient: 20-90% B over 1.1 minutes, then 0.7 minute hold at 90% B; Flow: 0.5 mL/min, UV 220 nm.

Method K:

Kinetex C18 (2.1×50 mm) 2.6 micron; Solvent A: 5 mM ammonium acetate in 95% water, 5% acetonitrile; Solvent B: 5 mM ammonium acetate in 5% water, 95% acetonitrile, Gradient: 20-90% B over 1.1 minutes, then 0.6 minute hold at 90% B; Flow: 0.7 mL/min, UV 220 nm.

Method L:

Acquity BEH C18 (3×50 mm) 1.7 micron; Solvent A: 0.1% TFA in water, Solvent B: 0.1% TFA in ACN, Gradient: 20-90% B over 1.0 minutes, then 0.6 minute hold at 90% B; Flow: 0.7 mL/min, UV 220 nm.

Method M:

Xbridge Phenyl (21.2×250 ID) 5 micron; Solvent A: 0.1% TFA in water, Solvent B: Acetonitrile, Gradient: 5-25% B over 1.0 minutes, then 0.6 minute hold at 90% B Flow: 0.7 mL/min, UV 220 nm.

Method N:

ZORBAX SB C18 (4.6×50 mm) 5.0 micron; Solvent A: 0.1% TFA in 95% water, 5% acetonitrile; Solvent B: 0.1% TFA in 5% water, 95% acetonitrile, Gradient: 0-100% B over 3 minutes; Flow: 1.1 mL/min, UV 220 nm.

Method O:

Acquity UPLC BEH C18 (3×50 mm) 1.7 micron; Solvent A: 5 mM ammonium acetate in 95% water, 5% acetonitrile; Solvent B: 5 mM ammonium acetate in 5% water, 95% acetonitrile, Gradient: 20-90% B over 1.1 minutes, then 0.6 minute hold at 90% B; Flow: 0.7 mL/min, UV 220 nm.

Method P:

Kinetex EVO C18 (4.6×100 mm) 2.6 micron; Solvent A: 95% water, 5% acetonitrile, 0.05% TFA; Solvent B: 5% water, 95% acetonitrile, 0.05% TFA; Gradient: 20-100% B over 11 minutes, then 1.5 minute hold at 100% B; Flow: 1.0 mL/min, UV 300 nm.

Method Q:

Kinetex Biphenyl (4.6×11 mm) 2.6 micron; Solvent A: 0.05% TFA in water; Solvent B: Acetonitrile, Gradient: 20-100% B over 11 minutes, then 1.5 minute hold at 100% B; Flow: 1.0 mL/min, UV 300 nm.

Method R:

XBridge BEH XP C18 (2.1×50 mm) 2.5 micron; Solvent A: 0.1% TFA in 95% water, 5% acetonitrile; Solvent B: 0.1% TFA in 5% water, 95% acetonitrile, Gradient: 0-100% B over 3 minutes; Flow: 1.1 mL/min, UV 220 nm.

Method S:

XBridge BEH XP C18 (2.1×50 mm) 2.5 micron; Solvent A: 10 mM ammonium acetate in 95% water, 5% acetonitrile; Solvent B: 10 mM ammonium acetate in 5% water, 95% acetonitrile, Gradient: 0-100% B over 3 minutes; Flow: 1.1 mL/min, UV 220 nm.

Method T:

DAD-1 Kinetix biphenyl (4.6×100 mm) 2.6 micron; Solvent A: 95% water, 5% acetonitrile, 0.05% TFA; Solvent B: 5% water, 95% acetonitrile, 0.05% TFA; Gradient: 0-100% B over 12.5 minutes, then 1.5 minutes hold at 100% B; Flow: 1.0 mL/min, UV 300 nm.

Method U:

DAD-1 Kinetex EVO C18 (4.6×100 mm) 2.6 micron; Solvent A: 95% water, 5% acetonitrile, 0.05% TFA; Solvent B: 5% water, 95% acetonitrile, 0.05% TFA; Gradient: 0-100% B over 12.5 minutes, then 1.5 minutes hold at 100% B; Flow: 1.0 mL/min, UV 300 nm.

SFC and Chiral Purity Methods:

Method I:

Lux Amylose 2 (250×4.6 mm) 5 micron; 0.2% DEA in n-hexane:EtOH: 5:95, Flow: 2.0 mL/min, Temperature: 25° C., UV: 270 nm.

Method II:

Chiralpak AS-H (250×4.6 mm) 5 micron; 0.2% DEA in n-hexane:EtOH: 5:95, Flow: 2.0 mL/min, Temperature: 25° C., UV: 270 nm.

Method III:

Chiralpak IE (250×4.6 mm) 5.0 micron; 0.2% DEA in EtOH, Flow: 1.0 mL/min, Temperature: 25° C., UV: 220 nm.

Method IV:

Chiralcel IE (250×4.6 mm) 5 micron; 0.2% DEA in n-hexane:EtOH: 50:50, Flow: 1.0 mL/min, Temperature: 25° C., UV: 260 nm.

Method V:

Chiralpak IB (250×4.6 mm) 5 micron; 0.1% DEA in EtOH, Flow: 1.0 mL/min, Temperature: 25° C., UV: 270 nm.

Method VI:

Chiralpak ID (250×4.6 mm) 5 micron; 0.1% DEA in EtOH, Flow: 1.0 mL/min. Temperature: 25° C., UV: 254 nm.

Method VII:

Chiralpak IF (250×4.6 mm) 5 micron; 0.2% DEA in EtOH, Flow: 1.0 mL/min, Temperature: 25° C., UV: 254 nm.

Method VIII:

Chiralpak IA (250×4.6 mm) 5 micron; 0.2% DEA in MeOH, Flow: 4.0 mL/min, Temperature: 25° C., UV: 280 nm.

Method IX:

Chiralpak ID (250×4.6 mm) 5 micron; 0.2% TEA in n-hexane: EtOH (10:90) Flow: 1.0 mL/min, Temperature: 25° C., UV: 254 nm.

Method X:

Chiralcel OJ-H (250×4.6 mm) 5 micron; 0.2% DEA in MeOH, Flow: 4.0 mL/min, Temperature: 30° C., UV: 296 nm.

Method XI:

Chiralpak IC (250×4.6 mm) 5 micron; 0.1% DEA in MeOH, Flow: 1.0 mL/min, Temperature: 25° C., UV: 254 nm.

Method XII:

Chiralpak ADH (250×4.6 mm) 5 micron; 0.2% DEA in MeOH+IPA (1:1), Flow: 1.2 mL/min, Temperature: 25° C., UV: 233 nm.

Method XIII:

Chiralpak AS-H (250×4.6 mm) 5 micron; 0.2% DEA in MeOH, Flow: 1.2 mL/min, Temperature: 23.3° C., UV: 271 nm.

Method XIV:

Chiralpak IB (250×4.6 mm) 5 micron; 0.2% DEA in MeOH, Flow: 1.0 mL/min, Temperature: 25° C., UV: 254 nm.

Method XV: Chiralpak ID (250×4.6 mm) 5 micron; 0.2% DEA in MeOH, Flow: 1.0 mL/min. Temperature: 25° C., UV: 254 nm.

Method XVI:

Lux Amylose 2 (250×4.6 mm) 5 micron; 0.1% DEA in MeOH, Flow: 1.0 mL/min, Temperature: 25° C., UV: 254 nm.

Method XVII:

Chiralpak IF (250×4.6 mm) 5 micron; 0.2% DEA in MeOH, Flow: 1.0 mL/min, Temperature: 25° C., UV: 254 nm.

Method XVIII:

Chiralpak IE (250×4.6 mm) 5.0 micron; 0.2% DEA in MeOH, Flow: 1.0 mL/min, Temperature: 25° C., UV: 220 nm.

Method XIX:

Lux Cellulose 4 (250×4.6 mm) 5.0 micron; 0.1% DEA in EtOH, Flow: 1.0 mL/min, Temperature: 25° C., UV: 220 nm.

Method XX:

Chiralcel OD-H (250×4.6 mm) 5 micron; 0.2% DEA in MeOH, Flow: 1.0 mL/min, Temperature: 25° C., UV: 220 nm.

Method XXI:

Chiralcel OD-H (250×4.6 mm) 5 micron; 0.2% $NH_4OH$ in MeOH and ACN (1:1), Flow: 4.0 mL/min, Temperature: 30° C., UV: 290 nm.

Method XXII:

Lux Cellulose C2 (250×4.6 mm) 5.0 micron; 0.2% DEA in MeOH, Flow: 1.0 mL/min, Temperature: 25° C., UV: 220 nm.

Method XXIII:

Phenomenex IC (250×4.6 mm) 5 micron; 0.2% DEA in EtOH, Flow: 1.0 mL/min, Temperature: 25° C., UV: 254 nm.

Method XXIV:

Whelk-1(R,R) (250×4.6 mm) 5 micron; 0.1% DEA in MeOH, Flow: 1.0 mL/min, Temperature: 25° C., UV: 220 mn.

Method XXV:

Cellulose-4 (250×4.6 mm) 5.0 micron; 0.1% DEA in ACN, Flow: 1.0 mL/min, Temperature: 25° C., UV: 254 nm.

Method XXVI:

Chiralpak IC (250×4.6 mm) 5.0 micron; 0.2% ammonia in ACN:MeOH (1:1) Flow: 1.0 mL/min, Temperature: 25° C., UV: 220 nm Method XXVII:

Chiralpak IC (250×4.6 mm) 5 micron; 0.2% $NH_4OH$ in MeOH+ACN (1:1), Flow: 1.2 mL/min. Temperature: 30° C., UV: 235 nm Method XXVIII: Lux cellulose-2 (250×4.6 mm) 5 micron; 0.2% $NH_4OH$ in MeOH, Flow: 1.2 mL/min. Temperature: 30° C., UV: 240 nm NMR Employed in Characterization of Examples:

NMR spectra were obtained with Bruker or JEOL Fourier transform spectrometers operating at frequencies as follows: $^1H$ NMR: 400 MHz or 300 MHz (Bruker). $^{13}C$ NMR: 100 MHz or 75 MHz (Bruker). Spectral data are reported in the format: chemical shift (multiplicity, coupling constants, and number of hydrogens). Chemical shifts are specified in ppm downfield of a tetramethylsilane internal standard (6 units, tetramethylsilane=0 ppm) and/or referenced to solvent peaks, which in $^1H$ NMR spectra appear at 2.49 ppm for $CD_2HSOCD_3$, 3.30 ppm for $CD_2HOD$, and 7.24 ppm for $CHCl_3$, and which in $^{13}C$ NMR spectra appear at 39.7 ppm for $CD_3SOCD_3$, 49.0 ppm for $CD_3OD$, and 77.0 ppm for $CDCl_3$. All $^{13}C$ NMR spectra were proton decoupled.

Intermediate 1-I: (R)-4-methyl-5-(oxiran-2-yl) isobenzofuran-1(3H)-one

Intermediate 1-II: (S)-4-methyl-5-(oxiran-2-yl) isobenzofuran-1(3H)-one

Enantiomer-I (1-I)

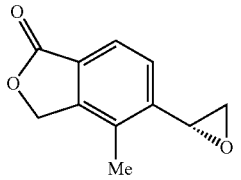

Enantiomer-II (1-II)

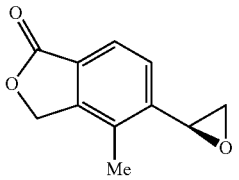

Both enantiomers were synthesized according to literature procedures (WO 2010/129379).

Intermediate 2-I: (R)-4-methyl-5-(piperazin-2-yl) isobenzofuran-1(3H)-one

Intermediate 2II: (S)-4-methyl-5-(piperazin-2-yl) isobenzofuran-1(3H)-one

Enantiomer-I (2-I)

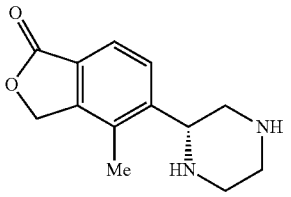

-continued

Enantiomer-II (2-II)

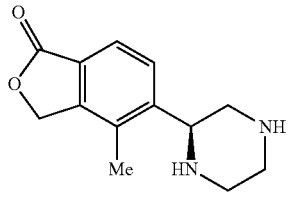

Intermediate 2A:
5-bromo-4-methylisobenzofuran-1(3H)-one

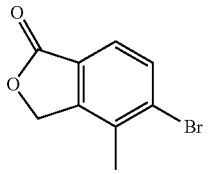

Synthesized according to literature procedures (PCT Int. Appl., 2015095097).

Intermediate 2B: 4-methyl-5-(4,4,5,5-tetramethyl-1,3,2-dioxaborolan-2-yl)isobenzofuran-1(3H)-one

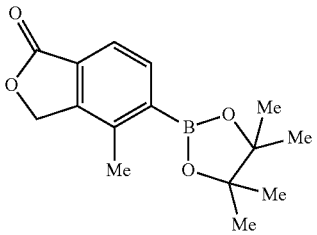

A solution of Intermediate 2A (12.50 g, 55.10 mmol), bispinacolatodiboron (20.97 g, 83.00 mmol) and potassium acetate (16.21 g, 165.00 mmol) in dioxane (200 mL) was degassed with nitrogen for 20 minutes. $PdCl_2(dppf)_2CH_2Cl_2$ (4.50 g, 5.51 mmol) was added and the resulting mixture was degassed again for 10 minutes then was heated at 100° C. for 12 h. The reaction was cooled to ambient temperature, filtered through Celite® and the filtrate was concentrated under reduced pressure. The resultant residue was washed with n-hexane to obtain Intermediate 2B (8.55 g, 56.70%) as a black solid. The compound was taken directly to the subsequent step without further purification. $^1$H NMR (300 MHz, DMSO-$d_6$) δ ppm 1.28-1.43 (m, 12H), 2.46 (s, 3H), 5.41 (s, 2H), 7.65 (d, J=7.9 Hz, 1H), 7.72-7.87 (m, 1H). LCMS (Method-I): retention time 1.43 min, [M+H] 275.1.

Intermediate 2C: 4-methyl-5-(pyrazin-2-yl)isobenzofuran-1(3H)-one

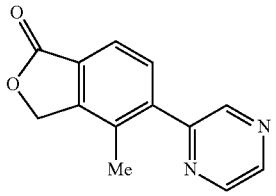

A solution of 2-chloropyrazine (7.94 g, 69.30 mmol), Intermediate 2B (19.00 g, 69.30 mmol), and potassium phosphate tribasic (36.80 g, 173.00 mmol) in a mixture of 1,4-dioxane (100 mL) and $H_2O$ (20 mL) was degassed with nitrogen for 10 minutes. $PdCl_2(dppf)_2CH_2Cl_2$ (2.83 g, 3.47 mmol) was added and the resulting mixture was degassed again for 10 minutes then was heated at 100° C. for 12 h. The reaction mixture was cooled to ambient temperature, filtered through the Celite® and the filtrate was concentrated under reduced pressure. The residue was purified by silica gel column chromatography (Redisep—330 g, 40% EtOAc/n-hexane) to obtain Intermediate 2C (13.00 g, 83.00%) as an off-white solid. $^1$H NMR (400 MHz, DMSO-$d_6$) δ ppm 2.32 (s, 3H), 5.50 (s, 2H), 7.72 (d, J=7.5 Hz, 1H), 7.82 (d, J=8.0 Hz, 1H), 8.73 (d, J=2.5 Hz, 1H), 8.77-8.87 (m, 1H), 8.91 (d, J=2.0 Hz, 1H). LCMS (Method-H): retention time 1.06 min, [M+H] 227.0.

Intermediate 2-I and 2H

To a stirred solution of Intermediate 2C (13.00 g, 57.50 mmol) in acetic acid (150 mL) was added palladium(II) acetate (1.94 g, 8.62 mmol). The reaction mixture was stirred under $H_2$ gas pressure (50 psi) at ambient temperature for 14 h. The reaction mixture was filtered through Celite® and washed with MeOH. The filtrate was evaporated under reduced pressure and the racemate was separated into two individual enantiomers by supercritical fluid chromatography (SFC) [Chiralpak ADH (250×4.6 mm) 5 micron; 0.2% DEA in MeOH+IPA (1:1), Flow: 1.2 mL/min. Temperature: 23.8° C., UV: 235 nm]. First eluted compound (retention time 2.98 min), designated as Intermediate 2-I, was obtained (4.00 g, 30.00%) as yellow semi solid. $^1$H NMR (400 MHz, DMSO-$d_6$) δ ppm 2.32 (s, 3H), 2.37-2.39 (m, 1H), 2.57-2.68 (m, 2H), 2.71-2.85 (m, 4H), 2.91 (d, J=11.55 Hz, 1H), 3.94 (dd, J=9.79, 2.76 Hz, 1H), 5.38 (s, 2H), 7.64 (d, J=8.03 Hz, 1H), 7.79 (d, J=8.03 Hz, 1H). LCMS (Method-H) retention time 0.74 min, [M+H] 233.0. Chiral purity (Method-XI): retention time 3.00 min, 99.0% ee. SOR: $[\alpha]^{25}_D$=−52.00 (c 0.05, MeOH). Second eluted compound (retention time 3.90 min), designated as Intermediate 2-II, was obtained (4.00 g, 30.00%) as a yellow solid. $^1$H NMR (400 MHz, DMSO-$d_6$) δ ppm 2.32 (s, 3H), 2.37-2.39 (m, 1H), 2.57-2.68 (m, 2H), 2.71-2.85 (m, 4H), 2.91 (d, J=11.55 Hz, 1H), 3.94 (dd, J=9.79, 2.76 Hz, 1H), 5.38 (s, 2H), 7.64 (d, J=8.03 Hz, 1H), 7.79 (d, J=8.03 Hz, 1H). LCMS (Method-H) retention time 3.73 min, [M+H] 233.0. Chiral purity (Method-XII): retention time 3.73 min, 100% ee. SOR: $[\alpha]^{25}_D$=+62.00 (c 0.05, MeOH).

Intermediate 3-I: (R)-4-methyl-5-(morpholin-2-yl) isobenzofuran-1(3H)-one

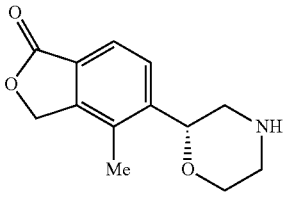

Intermediate 3A-I: (R)-5-(2-(benzyl(2-hydroxyethyl)amino)-1-hydroxyethyl)-4-methylisobenzofuran-1(3H)-one

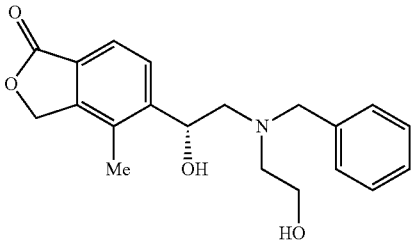

To a stirred solution of Intermediate 1-I (1.00 g, 5.26 mmol) in ethanol (5 mL) was added 2-(benzylamino)ethanol (0.75 mL, 5.26 mmol) and the resulting reaction mixture was stirred at 85° C. for 48 h. The reaction mixture was cooled to ambient temperature and concentrated under reduced pressure, diluted with water (30 mL) and extracted with ethyl acetate (2×50 mL). The combined organic layers were washed with brine (50 mL), dried over anhydrous sodium sulfate and evaporated under reduced pressure. The residue was washed with n-hexane (50 mL) to obtain Intermediate 3A-I (1.20 g, 66.90%). $^1$H NMR (400 MHz, DMSO-$d_6$) δ ppm 2.11 (s, 3H), 2.56-2.72 (m, 4H), 3.40-3.53 (m, 3H), 3.72 (s, 2H), 4.45-4.51 (m, 1H), 4.98 (dd, J=7.53, 4.52 Hz, 1H), 5.27-5.37 (m, 2H), 5.75 (s, 3H), 7.18-7.34 (m, 3H), 7.62 (s, 1H). LCMS (Method-H): retention time 1.48 min, [M+H] 342.2.

Intermediate 3B-I: (R)-5-(4-benzylmorpholin-2-yl)-4-methylisobenzofuran-1(3H)-one

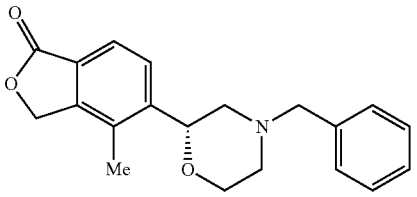

To a solution of Intermediate 3A-I (1.20 g, 3.51 mmol) in THF (25 mL) was added tri-N-butylphosphine (1.42 g, 7.03 mmol) followed by DIAD (0.82 mL, 4.22 mmol) and the resulting reaction mixture was stirred at ambient temperature for 2 h. The reaction mixture was diluted with water (30 mL) and extracted with ethyl acetate (2×40 mL). The combined organic layers were washed with brine (40 mL), dried over anhydrous sodium sulfate and evaporated under reduced pressure. The residue was purified by silica gel column chromatography (Redisep—40 g, 55% EtOAc/n-Hexanes) to afford Intermediate 3B-I (0.75 g, 66.00%). $^1$H NMR (400 MHz, DMSO-$d_6$) δ ppm 2.18-2.22 (m, 3H), 2.23-2.28 (m, 1H), 2.51-2.56 (m, 1H), 2.75 (d, J=12.55 Hz, 1H), 2.85 (d, J=11.55 Hz, 1H), 3.55 (d, J=5.52 Hz, 2H), 3.73-3.80 (m, 1H), 3.99 (dd, J=11.55, 2.01 Hz, 1H), 4.82 (dd, J=10.04, 2.51 Hz, 1H), 5.38 (d, J=2.01 Hz, 2H), 7.24-7.29 (m, 1H), 7.34 (d, J=4.52 Hz, 4H), 7.58-7.70 (m, 2H). LCMS (Method-D): retention time 2.74 min, [M+H] 324.2.

Intermediate 3-I

A solution of Intermediate 3B-I (0.75 g, 2.32 mmol) in ethanol (50 mL) was purged with nitrogen for 2 min. 10% Pd/C (0.25 g, 2.32 mmol) was added and the reaction mixture was stirred at ambient temperature for 3 h under $H_2$ atmosphere. The resulting reaction mixture was concentrated under reduced pressure, diluted with water, neutralzed by aq. $NaHCO_3$ and extracted with ethyl acetate (2×25 mL). The combined organic layers were washed with brine (10 mL), dried over anhydrous sodium sulfate and evaporated under reduced pressure. The residue was purified by column chromatography (Alumina-24 g, 5% MeOH/DCM) to obtain Intermediate 3-I (0.25 g, 46.20%). $^1$H NMR (400 MHz, DMSO-$d_6$) δ ppm 2.27 (s, 3H), 2.45 (d, J=2.51 Hz, 1H), 2.77-2.81 (m, 2H), 2.93 (dd, J=12.55, 2.51 Hz, 1H), 3.63-3.70 (m, 1H), 3.90-3.95 (m, 1H), 4.71 (dd, J=10.04, 2.51 Hz, 1H), 5.39 (d, J=3.01 Hz, 2H), 7.60-7.63 (m, 1H), 7.66-7.69 (m, 1H), (Exchangeable proton not observed). LCMS (Method-H): retention time 0.89 min, [M+H] 234.2.

Intermediate 4: 5-(1-((1H-pyrazol-4-yl)methyl)-4,4-difluoropiperidin-3-yl)-4-methylisobenzofuran-1(3H)-one

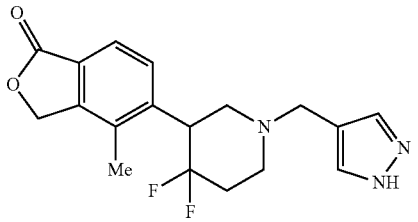

Intermediate 4A: tert-butyl3-(4-methyl-1-oxo-1,3-dihydroisobenzofuran-5-yl)-4-oxopiperidine-1-carboxylate

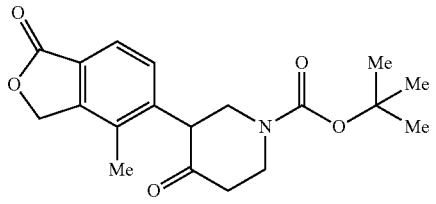

A solution of 5-bromo-4-methylisobenzofuran-1(3H)-one (1.70 g, 7.53 mmol), tert-butyl 4-oxopiperidine-1-carboxylate (2.50 g, 12.55 mmol) and $Cs_2CO_3$ (4.91 g, 15.06 mmol) in toluene (50 mL) was degassed with nitrogen for 20 minutes. $PdCl_2$(dtbpf) (0.81 g, 1.25 mmol) was added and the resulting mixture was degassed again for 10 minutes and then heated at 110° C. for 12 h. The reaction mixture was cooled to ambient temperature, filtered through Celite® and the filtrate was concentrated under reduced pressure. The residue was purified by column chromatography (Redisep—24 g, 60% EtOAc/n-hexanes) to obtain Intermediate 4A (0.90 g, 20.77%). $^1$H NMR (400 MHz, DMSO-$d_6$) δ ppm 1.41-1.47 (m, 9H), 2.21 (s, 3H), 2.39-2.48 (m, 1H), 2.65-2.76 (m, 1H), 3.47 (br. s., 2H), 4.04-4.21 (m, 3H), 5.41 (d, J=3.01 Hz, 2H), 7.39 (d, J=8.03 Hz, 1H), 7.65 (d, J=8.03 Hz, 1H). LCMS (Method-H): retention time 1.92 min, [M+$H_2O$] 363.2

Intermediate 4B: tert-butyl 4,4-difluoro-3-(4-methy-1-oxo-1,3-dihydroisobenzofuran-5-yl)piperidine-1-carboxylate

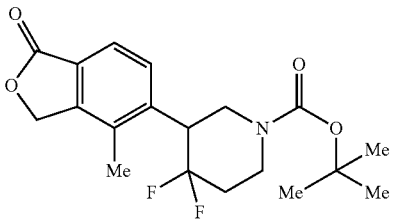

To a stirred solution of Intermediate 4A (0.05 g, 0.14 mmol) in DCM (5 mL) at 0° C. was added DAST (0.19 mL, 1.44 mmol) and the reaction mixture was stirred at ambient temperature for 2 h. The resulting reaction mixture was concentrated under reduced pressure, diluted with water (10 mL), neutralized by aq. $NaHCO_3$ (10 mL) and extracted with DCM (3×20 mL). The combined organic layer was washed with brine (10 mL), dried over anhydrous sodium sulfate and evaporated under reduced pressure. The residue was purified by column chromatography (Redisep—12 g, 35% EtOAc/n-hexanes) to obtain Intermediate 4B (0.02 g, 37.60%). $^1$H NMR (400 MHz, DMSO-$d_6$) δ ppm 1.42 (s, 9H), 2.12-2.19 (m, 2H), 2.22 (s, 3H), 3.09 (br. s., 1H), 3.37-3.44 (m, 1H), 3.60 (d, J=9.54 Hz, 1H), 3.98 (d, J=17.07 Hz, 1H), 4.13 (br. s., 1H), 5.43 (d, J=5.52 Hz, 2H), 7.58 (d, J=7.03 Hz, 1H), 7.70 (d, J=8.03 Hz, 1H). $^{19}$F NMR (400 MHz, DMSO-$d_6$) δ ppm −93.57, −111.02. LCMS (Method-H): retention time 2.45 min, [M+H] 368.2.

Intermediate 4C: 5-(4,4-difluoropiperidin-3-yl)-4-methylisobenzofuran-1(3H)-one

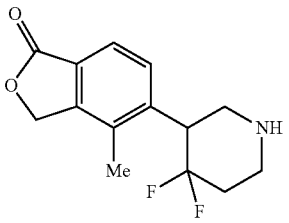

To a solution of Intermediate 4B (0.24 g, 0.65 mmol) in DCM (25 mL) at 0° C. was added 4N HCl in dioxane (5 mL, 1.14 mmol). The resulting mixture was stirred at ambient temperature for 2 h. The reaction mixture was concentrated to dryness and diluted with water (10 mL). The aqueous layer was washed with ethyl acetate (2×20 mL), basified with 10% $NaHCO_3$ solution and extracted with DCM (3×50 mL). The combined organic layers were washed with brine (10 mL), dried over anhydrous sodium sulfate and evaporated under reduced pressure to obtain Intermediate 4C (0.12 g, 68.70%). $^1$H NMR (400 MHz, DMSO-$d_6$) δ ppm 1.94-2.12 (m, 2H), 2.29 (s, 3H), 2.76 (td, J=12.93, 3.26 Hz, 1H), 2.96-3.06 (m, 2H), 3.14 (d, J=12.05 Hz, 1H), 3.51-3.63 (m, 1H), 5.38-5.43 (m, 2H), 7.52-7.57 (m, 1H), 7.67 (d, J=8.03 Hz, 1H) (Exchangeable proton not observed). $^{19}$F NMR (400 MHz, DMSO-$d_6$) δ ppm −88.62, −110.24. LCMS (Method-H): retention time 1.34 min, [M+H] 268.0.

Intermediate 4

To a solution of Intermediate 4C (0.10 g, 0.37 mmol) in MeOH (2 mL) was added 1H-pyrazole-4-carbaldehyde (0.030 g, 0.37 mmol) and the reaction mixture was stirred at ambient temperature for 15 min. To this mixture was added $NaCNBH_3$ (0.071 g, 1.12 mmol) and stirring was continued for 12 h. The reaction mixture was diluted with water (15 mL) and extracted with DCM (3×20 mL). The combined organic layer was washed with brine (20 mL), dried over anhydrous sodium sulfate and evaporated under reduced pressure. The resulting residue was washed with diethyl ether (20 mL) to obtain Intermediate 4 (0.08 g, 61.60%). $^1$H NMR (400 MHz, DMSO-$d_6$) δ ppm 2.08-2.18 (m, 2H) 2.23 (s, 3H) 2.76 (d, J=11.04 Hz, 1H) 2.86 (d, J=11.55 Hz, 1H) 3.45 (s, 2H) 3.65-3.80 (m, 2H) 4.78 (d, J=8.03 Hz, 1H) 5.33-5.43 (m, 2H) 7.41 (br. s., 1H) 7.52-7.71 (m, 3H) 12.64 (br. s., 1H). LCMS (Method-H): retention time 1.121 min, [M+H] 348.2.

Intermediate 5-I: (R)-5-(4-((6-bromopyridin-3-yl)methyl)morpholin-2-yl)-4-methylisobenzofuran-1(3H)-one

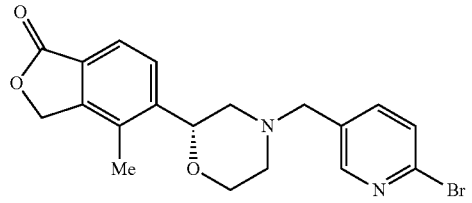

Intermediate 5-I was prepared (0.25 g, 72.30%), by using a similar synthetic protocol as that of Intermediate 4 and starting from 6-bromonicotinaldehyde (0.15 g, 0.85 mmol) and Intermediate 3-I LCMS (Method-I): retention time 0.68 min, [M+H] 403.0. The compound was taken directly to the subsequent step without further purification or characterization.

Intermediate 6: 6-(4-formyl-1H-pyrazol-1-yl)nicotinonitrile

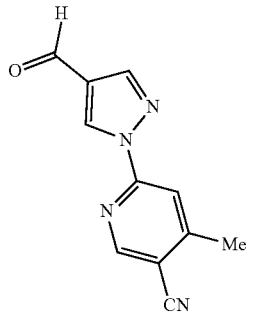

To a stirred solution of 1H-pyrazole-4-carbaldehyde (1.00 g, 10.40 mmol) and 6-bromo-4-methylnicotinonitrile (2.05 g, 10.40 mmol) in dioxane (15 mL) were added $K_2CO_3$ (4.31 g, 31.20 mmol). The resulting reaction mixture was degassed with nitrogen for 5 minutes then copper (I) iodide (0.59 g, 3.12 mmol) was added, followed by trans-N,N'-dimethylcyclohexane-1,2-diamine (2.59 mL, 16.4 mmol). The resulting mixture was degassed again for 10 minutes and heated at 110° C. for 1 h under microwave irradiation. The reaction mixture was cooled to ambient temperature, filtered through Celite® and the organic layer was concentrated under reduced pressure. The residue was purified by column chromatography (Redisep—24 g, 20-40% EtOAc/n-hexane) to obtain Intermediate 6 (1.15 g, 52.10%) as pale yellow solid. $^1$H NMR (300 MHz, DMSO-$d_6$) δ ppm 2.62 (s, 3H), 8.10 (s, 1H), 8.38 (s, 1H), 8.95 (s, 1H), 9.37 (s, 1H), 9.98 (s, 1H). LCMS (method-D), retention time 1.68 min, [M+H] 213.2.

Intermediate 7: 5-bromo-3-methylbenzo[d]oxazol-2(3H)-one

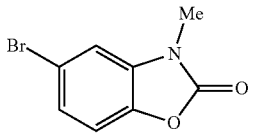

Synthesized according to literature procedures (PCT Int. Appl. 2010130773).

Intermediate 8: 3-methyl-5-(4,4,5,5-tetramethyl-1,3,2-dioxaborolan-2-yl)benzo[d]oxazol-2(3H)-one

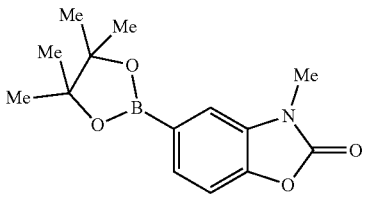

Intermediate 8 was prepared (1.30 g, 59.80%) as a yellow solid, by using Intermediate 7 (1.50 g, 6.44 mmol) in a manner similar to that described for Intermediate 2A. $^1$H NMR (300 MHz, DMSO-$d_6$) δ ppm 1.31 (s, 12H), 3.37 (s, 3H), 7.34 (d, J=7.93 Hz, 1H), 7.41-7.54 (m, 2H). LCMS (Method-D): retention time 2.79 min, [M−H] 292.2 (water adduct).

Intermediate 9: 6-(4-formyl-5-methoxy-1H-pyrazol-1-yl)-4-methylnicotinonitrile

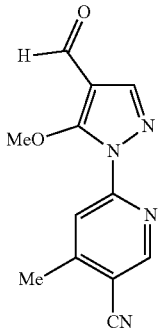

Intermediate 9A: dimethyl 2-((dimethylamino)methylene)malonate

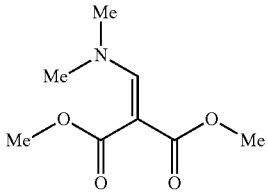

To a solution of dimethyl malonate (10.00 g, 76.00 mmol) in toluene (100 mL) was added DMF-DMA (20.27 mL, 151.00 mmol) at ambient temperature under a nitrogen atmosphere. The resulting reaction mixture was heated at 100° C. for 5 h. The reaction mixture was cooled to ambient temperature and concentrated under reduced pressure to obtain Intermediate 9A (13.00 g, 84.00%) as a yellow solid. $^1$H NMR (400 MHz, $CDCl_3$) δ ppm 2.92-3.07 (m, 6H), 3.66-3.72 (br.s., 3H), 3.74-3.79 (br.s., 3H), 7.53 (s, 1H). LCMS (Method-D): retention time 0.63 min, [M+H] 188.2. The compound was taken directly to the subsequent step without further purification or characterization.

Intermediate 9B: methyl 5-methoxy-1H-pyrazole-4-carboxylate

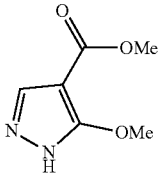

To a solution of Intermediate 9A (13.00 g, 69.40 mmol) in EtOH (50 mL) was added $NH_2NH_2$.2HCl (7.29 g, 69.40 mmol) at ambient temperature under a nitrogen atmosphere. The resulting reaction mixture was heated at 70° C. for 5 h. The reaction mixture was cooled to ambient temperature and concentrated under reduced pressure. The residue was dissolved in DCM (250 mL) and basified with saturated $NaHCO_3$ solution (0.5 L). The organic layer was separated, washed with brine (20 mL), dried over anhydrous sodium sulfate and evaporated under reduced pressure. The residue was purified by column chromatography (Redisep—120 g, 45-50% EtOAc/n-hexanes) to obtain Intermediate 9B (2.50 g, 13.14%) as a pale yellow solid. $^1$H NMR (300 MHz, DMSO-$d_6$) δ ppm 3.67 (s, 3H), 3.84 (s, 3H), 8.11 (d, J=2.27 Hz, 1H), 12.56 (br. s., 1H). LCMS (Method-D): retention time 0.48 min, [M+H] 157.0.

Intermediate 9C: methyl 1-(5-cyano-4-methylpyridin-2-yl)-5-methoxy-1H-pyrazole-4-carboxylate

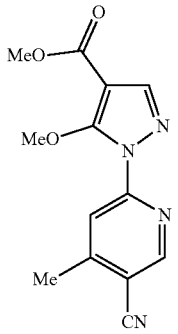

Intermediate 9C was prepared (0.80 g, 15.42%) as a beige solid, using a similar synthetic protocol to that of Intermediate 6 and starting from Intermediate 9B (2.50 g, 16.01 mmol). $^1$H NMR (400 MHz, $CDCl_3$) δ ppm 2.64 (s, 3H), 3.87 (s, 3H), 4.11 (s, 3H), 7.81 (d, J=1.00 Hz, 1H), 8.57 (s, 1H), 8.89 (s, 1H). LCMS (Method-H): retention time 1.81 min, [M+H] 273.

Intermediate 9D: 1-(5-cyano-4-methylpyridin-2-yl)-5-methoxy-1H-pyrazole-4-carboxylic acid

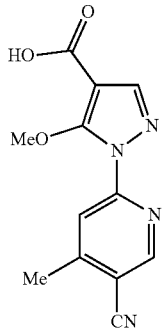

To a solution of Intermediate 9C (0.80 g, 2.94 mmol) in THF (25 mL) was added $(CH_3)_3SiOK$ (1.50 g, 11.75 mmol) and stirring was continued at ambient temperature for 16 h. The reaction mixture was diluted with water (80 mL), neutralized with solid citric acid and extracted with ethyl acetate (2×80 mL). The combined organic layers were washed with brine (30 mL), dried over anhydrous sodium sulfate and evaporated under reduced pressure to obtain Intermediate 9D (0.75 g, 61.30%) as beige solid. $^1$H NMR (300 MHz, DMSO-$d_6$) δ ppm 2.59 (s, 3H), 4.00 (s, 3H), 7.86 (s, 1H), 8.78 (s, 1H), 8.85 (s, 1H), 12.37-12.91 (br. s, 1H). LCMS (Method-H): retention time 0.40 min, [M+H] 259.5.

Intermediate 9E: 6-(4-(hydroxymethyl)-5-methoxy-1H-pyrazol-1-yl)-4-methylnicotinonitrile

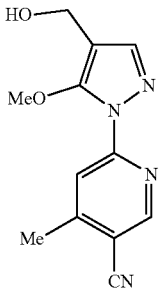

To a solution of Intermediate 9D (0.75 g, 2.90 mmol) in THF (15 mL) was added TEA (1.21 mL, 8.71 mmol) followed by isobutyl chloroformate (0.76 mL, 5.81 mmol) at 0° C. under a nitrogen atmosphere. The reaction mixture was stirred at ambient temperature for 16 h. The reaction mixture was filtered through a scintered glass funnel and the filtrate was cooled to 0° C. and treated with a solution of $NaBH_4$ (0.22 g, 5.81 mmol) in water (2 mL) for 10 minutes. The resultant mixture was allowed to reach ambient temperature and stir for 16 h. The reaction mixture was diluted with saturated $NH_4Cl$ (40 mL) and extracted with ethyl acetate (2×100 mL). The combined organic layers were washed with 10% $NaHCO_3$ solution (30 mL), dried over anhydrous sodium sulfate and evaporated under reduced pressure to obtain Intermediate 9E (0.43 g, 53.30%) as beige solid. $^1$H NMR (400 MHz, DMSO-$d_6$) δ ppm 2.54 (s, 3H), 3.96 (s, 3H), 4.30 (d, J=5.02 Hz, 2H), 4.97 (t, J=5.52 Hz, 1H), 7.72 (s, 1H), 8.37 (s, 1H), 8.75 (s, 1H). LCMS (Method-D): retention time 1.681 min, [M+H] 245.0.

Intermediate 9

To a solution of Intermediate 9E (0.40 g, 1.64 mmol) in DCM (30 mL) was added Dess-Martin periodinane (1.39 g, 3.28 mmol) at ambient temperature under a nitrogen atmosphere and stirring was continued for 20 h. The reaction mixture was diluted with DCM (50 mL) and 10% $NaHCO_3$ (50 mL) was added. The organic layer was separated and washed with brine (30 mL), dried over anhydrous sodium sulfate and evaporated under reduced pressure to obtain Intermediate 9 (0.30 g, 68.10%) as beige solid. $^1$H NMR (400 MHz, DMSO-$d_6$) δ ppm 2.61 (s, 3H), 4.05 (s, 3H), 7.91 (s, 1H), 8.90 (s, 1H), 9.18 (s, 1H), 9.85 (s, 1H). LCMS (Method-H): retention time 2.13 min, [M+H] 243.0.

Intermediate 10:
6-bromo-4-cyclopropylnicotinonitrile

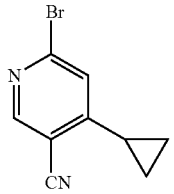

Intermediate 10A: 6-bromo-4-iodonicotinonitrile

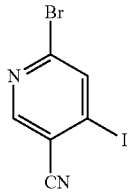

To a solution of diisopropylamine (7.79 mL, 54.60 mmol) in THF (100 mL) was added n-BuLi (21.86 mL, 54.60 mmol) at −78° C. under a nitrogen atmosphere. After 30 minutes, 6-bromonicotinonitrile (10.00 g, 54.6 mmol) in THF (20 mL) followed by Iodine (15.26 g, 60.10 mmol) in THF (10 mL) was added and stirring was continued for 2 h. The resulting reaction mixture was diluted with saturated $NH_4Cl$ (40 mL) and extracted with ethyl acetate (2×200 mL). The combined organic layer was washed with brine solution (30 mL), dried over anhydrous sodium sulfate, and evaporated under reduced pressure. The residue was purified by column chromatography (Redisep—80 g, 10-15% EtOAc/n-Hexanes) to obtain Intermediate 10A (6.50 g, 38.50%) as brown solid. $^1$H NMR (400 MHz, DMSO-$d_6$) δ ppm 8.51 (s, 1H), 8.76 (s, 1H). LCMS: The compound did not ionize well.

Intermediate 10

To a solution of Intermediate 10A (0.60 g, 1.94 mmol) in a mixture of toluene (10 mL) and water (2 mL) was added cyclopropylboronic acid (0.20 g, 2.33 mmol) followed by $K_3PO_4$ (0.82 g, 3.88 mmol) and the resulting mixture was degassed for 15 minutes. Palladium(II) acetate (0.05 g, 0.19 mmol) and tricyclohexylphosphine (0.11 g, 0.39 mmol) ware added. The resulting mixture was degassed again for 10 minutes and heated at 140° C. for 1 h in the microwave. The reaction mixture was cooled to ambient temperature and filtered through Celite®. The filtrate was concentrated under reduced pressure. The residue was purified by column chromatography (Redisep—12 g, 15-20% EtOAc/n-Hexanes) to obtain Intermediate 10 (0.10 g, 23.08%) as a yellow solid. $^1$H NMR (400 MHz, DMSO-$d_6$) δ ppm 0.93-1.02 (m, 1H), 1.04-1.13 (m, 1H), 1.19-1.35 (m, 2H), 2.05-2.21 (m, 1H), 8.51 (s, 1H), 8.75 (s, 1H). LCMS (Method-D): retention time 2.25 min, [M+2H] 223.0.

Intermediate 11: 6-(4-formyl-1H-imidazol-1-yl)-4-methoxynicotinonitrile

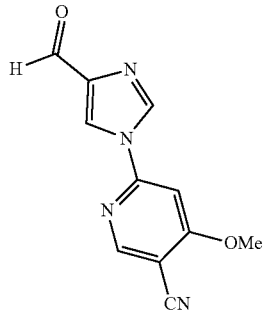

To a solution of 1H-imidazole-4-carbaldehyde (0.50 g, 5.20 mmol) and 6-chloro-4-methoxynicotinonitrile (1.05 g, 6.24 mmol) in DMF (10 mL) was added $K_2CO_3$ (1.08 g, 7.81 mmol) at ambient temperature under a nitrogen atmosphere. The resulting reaction mixture was heated at 90° C. for 1 h. The reaction mixture was cooled to ambient temperature and diluted with ice water (30 mL). The resulting precipitate was filtered and was washed with ethanol (2 mL) to obtained Intermediate 11 (0.30 g, 25.00%). $^1$H NMR (400 MHz, DMSO-$d_6$) δ ppm 4.13 (s, 3H), 7.81 (s, 1H), 8.83 (s, 2H), 8.95 (d, J=1.19 Hz, 1H), 9.87 (s, 1H). LCMS (Method-L): retention time 0.75 min, [M+H] 229.1.

Intermediate 12-I: (R)-6-(4-(((2-hydroxy-2-(4-methyl-1-oxo-1,3-dihydroisobenzofuran-5-yl)ethyl) amino) methyl)-1H-pyrazol-1-yl)-4-methylnicotino-nitrile

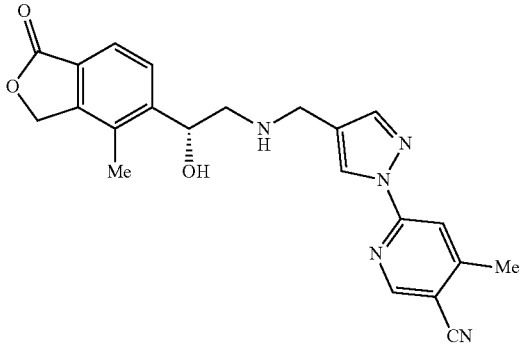

Intermediate 12A-I: (R)-5-(2-amino-1-hydroxy-ethyl)-4-methylisobenzofuran-1(3H)-one

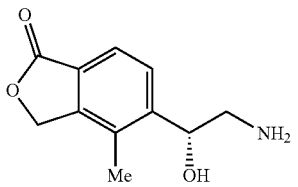

To a solution of Intermediate 1-I (1.00 g, 5.26 mmol) in MeO H (40 mL) at −10° C. was purged excess of ammonia gas and the resulting reaction mixture was stirred at 50° C. for 16 h in a sealed tube. The reaction mixture was concentrated under reduced pressure and the residue was washed with ether (30 mL) to obtain Intermediate 12A-I (0.75 g, 68.80%). $^1$H NMR (400 MHz, DMSO-$d_6$) δ ppm 2.26 (s, 3H), 2.52-2.56 (m, 1H), 2.69 (dd, J=13.05, 4.02 Hz, 1H), 4.80 (dd, J=8.03, 3.51 Hz, 1H), 5.38 (d, J=1.51 Hz, 3H), 7.65 (s, 2H), (2 Exchangeable protons not observed). LCMS (Method-H): retention time 0.54 min, [M+H] 208.2.

Intermediate 12-I

To a solution of Intermediate-6 (0.20 g, 0.94 mmol) in MeOH (5 mL) was added acetic acid (0.08 mL, 1.42 mmol) followed by Intermediate 12A-I (0.23 g, 1.13 mmol) and the reaction mixture was stirred at ambient temperature for 10 minutes. To the reaction was added $NaCNBH_3$ (0.18 g, 2.83 mmol) and stirring was continued for 12 h. The reaction mixture was diluted with water (20 mL), basified with 10% $NaHCO_3$ solution and extracted with ethyl acetate (2×30 mL). The combined organic layers were washed with brine (20 mL), dried over anhydrous sodium sulfate and evaporated under reduced pressure. The residue was purified by HPLC [Luna C18 (250×301D) 5 micron; Solvent A: 0.1% TFA in $H_2O$, Solvent B: Acetonitrile, Gradient: 20-100 over 14 min, Flow: 25 mL/min, retention time 11.16 min, UV 220 nm] to obtain Intermediate 12-I (0.09 g, 22.86%). $^1$H NMR (400 MHz, $CDCl_3$) δ ppm 2.28 (s, 3H), 2.63 (s, 3H), 2.77-2.67 (m, 1H), 3.03-2.93 (m, 1H), 3.62 (m, 2H), 3.86 (d, J=6.00 Hz, 2H), 5.10-5.03 (m, 1H), 5.25 (s, 2H), 7.80-7.74 (m, 3H), 7.95 (d, J=0.80 Hz, 1H), 8.49 (d, J=0.80 Hz, 1H), 8.59 (s, 1H). LCMS/HPLC (Method-H): retention time 1.80 min, [M+H] 404.2, purity: 99.7%. (Method-C): retention time 10.54 min, purity: 99.70%. Chiral purity (Method-VI): retention time 9.44 min, 100% ee.

Intermediate 13-I: (R) N-((1-(5-cyano-4-methylpyridin-2-yl)-1H-pyrazol-4-yl)methyl)-2-hydroxy-N-(2-hydroxy-2-(4-methyl-1-oxo-1,3-dihydroisobenzofuran-5-yl)ethyl)acetamide

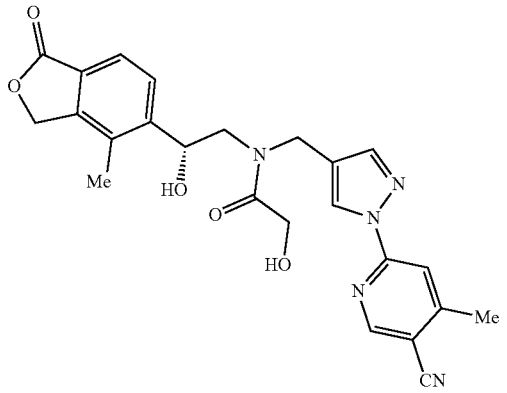

To a stirred solution of Intermediate 12-I (0.23 g, 0.57 mmol) and 2-hydroxyacetic acid (0.05 g, 0.57 mmol) in DCM (10 mL) was added HATU (0.43 g, 1.14 mmol) followed by DIPEA (0.29 mL, 1.71 mmol). The resultant mixture was stirred at ambient temperature overnight. Water (30 mL) was added to the reaction mixture, which was then extracted with DCM (3×20 mL). The combined organic layers were washed with brine (20 mL), dried over sodium sulfate and evaporated under reduced pressure. The residue was purified by column chromatography (Redisep—12 g, 10-12% MeOH in DCM), to obtain Intermediate 13-I (0.15 g, 57.00%) as an off-white solid. $^1$H NMR (400 MHz, DMSO-$d_6$) δ ppm 2.21-2.35 (m, 3H), 2.58 (s, 3H), 3.14-3.29 (m, 1H), 3.37-3.68 (m, 1H), 4.10-4.36 (m, 2H), 4.41-4.78 (m, 3H), 5.08-5.30 (m, 1H), 5.31-5.45 (m, 2H), 5.66-5.92 (m, 1H), 7.61-7.77 (m, 2H), 7.84 (s, 1H), 7.94-8.02 (m, 1H), 8.57 (s, 1H), 8.84 (s, 1H). LCMS/HPLC (Method-A): retention time 1.382 min, [M+H] 462.1, purity: 98.52%. (Method-B): retention time 1.372 min, [M+H] 462.1, purity: 99.62%.

Intermediate 14-I: (R)-5-(4-((1H-pyrazol-4-yl)methyl)morpholin-2-yl)-4-methylisobenzofuran-1(3H)-one

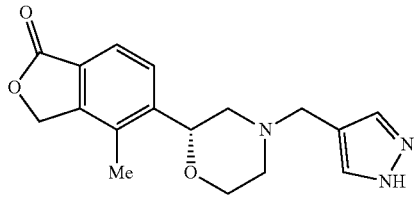

Intermediate 14-I was prepared (0.15 g, 27.90%), by using a similar synthetic protocol as that of Intermediate 4 and starting from Intermediate 3-I (2.00 g, 8.57 mmol). $^1$H NMR (400 MHz, DMSO-$d_6$) δ ppm 1.78-1.87 (m, 1H), 2.11-2.20 (m, 1H), 2.23 (s, 3H), 2.76 (d, J=11.04 Hz, 1H), 2.86 (d, J=11.55 Hz, 1H), 3.45 (s, 2H), 3.67-3.79 (m, 1H), 3.97 (d, J=9.54 Hz, 1H), 4.78 (d, J=8.03 Hz, 1H), 5.38 (d, J=2.01 Hz, 2H), 7.41 (br. s., 1H), 7.57-7.62 (m, 2H), 7.64-7.69 (m, 1H), 12.64 (br. s., 1H). LCMS/HPLC (Method-H): retention time 0.767 min, [M+H] 314.2.

Intermediate 15: 4-methoxy-6-(4-(2-oxoethyl)-1H-pyrazol-1-yl)nicotinonitrile

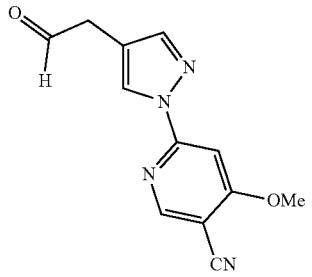

Intermediate 15A:
3-(diethoxymethyl)-2-ethoxytetrahydrofuran

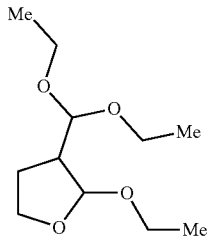

$FeCl_3$ (0.02 g, 0.14 mmol) was added to a flask containing triethoxymethane (23.26 g, 157.00 mmol) and cooled to 10° C. The resulting reaction mixture was stirred at the same temperature for 30 minutes and 2,3-dihydrofuran (10.00 g, 143.00 mmol) was added dropwise over 30 minutes. The reaction mixture was stirred at 10° C. for 1 h, diluted with DCM (100 mL) and filtered through Celite®. The filtrate was concentrated under reduced pressure to obtain Intermediate 15A (30.00 g, 96.00%) as brown oil. $^1$H NMR (400 MHz, $CDCl_3$) δ ppm 1.09-1.29 (m, 9H), 1.76 (dd, J=12.55, 5.52 Hz, 1H), 1.84-2.13 (m, 1H), 2.29-2.57 (m, 1H), 3.38-3.81 (m, 6H), 3.82-4.14 (m, 2H), 4.33 (d, J=8.53 Hz, 1H), 4.88-5.09 (m, 1H).

Intermediate 15B: 2-(1H-pyrazol-4-yl)ethanol

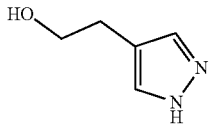

To a solution of $NH_2NH_2.2HCl$ (18.75 g, 179.00 mmol) in a mixture of water (50 mL) and ethanol (25 mL) was added Intermediate 15A (30.00 g, 137.00 mmol) at 0° C. The reaction mixture was stirred at 0° C. for 1 h and at ambient temperature for 1 h. Sodium carbonate (30.00 g) was added to the reaction mixture and evaporated to dryness under reduced pressure. The residue was washed with ethanol (100 mL) and evaporated to obtain Intermediate 15B (15.00 g, 92.00%) as a brown oil. $^1$H NMR (400 MHz, $CDCl_3$) δ ppm 2.78 (t, J=6.38 Hz, 2H), 3.72 (d, J=7.25 Hz, 1H), 3.77-3.88 (m, 2H), 7.49 (s, 2H), 9.52-10.74 (m, 1H). LCMS (Method-I): retention time 0.40 min, [M+H] 113.0.

Intermediate 15C: 6-(4-(2-hydroxyethyl)-1H-pyrazol-1-yl)-4-methoxynicotinonitrile

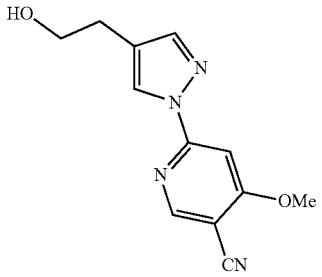

To a solution of Intermediate 15B (0.50 g, 4.46 mmol) and 6-bromo-4-methoxynicotinonitrile (0.95 g, 4.46 mmol) in dioxane (20 mL) was added $K_2CO_3$ (1.54 g, 11.15 mmol) and XANTPHOS (0.52 g, 0.89 mmol) and the resulting reaction mixture was degassed with nitrogen for 5 minutes. $Pd_2(dba)_3$(0.41 g, 0.45 mmol) was added and the resulting mixture was degassed again for 5 minutes then heated at 100° C. for 16 h. The reaction mixture was cooled to ambient temperature, filtered through Celite® and the filtrate was concentrated under reduced pressure. The residue was purified by column chromatography (Redisep—24 g, 2-2.5% MeOH in DCM), to obtain Intermediate 15C (0.40 g, 36.70%) as a pale yellow solid. $^1$H NMR (400 MHz, DMSO-$d_6$) δ ppm 2.65 (t, J=6.78 Hz, 2H), 3.61 (td, J=6.78, 5.02 Hz, 2H), 4.10 (s, 3H), 4.62-4.76 (m, 1H), 7.58 (s, 1H), 7.81 (s, 1H), 8.47 (s, 1H), 8.73 (s, 1H). LCMS (Method-I): retention time 0.83 min, [M+H] 245.3.

Intermediate 15

To a stirred solution of Intermediate 15C (0.20 g, 0.82 mmol) in DCM (10 mL) was added Dess-Martin periodinane (0.52 g, 1.23 mmol) and the reaction mixture was stirred at ambient temperature for 10 minutes. The reaction mixture was diluted with 10% $NaHCO_3$ (30 mL) and extracted with DCM (3×25 mL). The combined extracts were washed with brine (20 mL), dried over sodium sulfate and evaporated under reduced pressure to obtain Intermediate 15 (0.20 g, 45.32%). LCMS (Method-I): retention time 0.95 min, [M+H] 243.0. The compound was taken directly to the subsequent step without further purification or characterization.

Intermediate 16: 6-(5-(chloromethyl)-1,3,4-oxadiazol-2-yl)nicotinonitrile

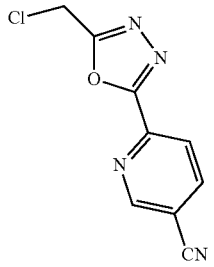

Intermediate 16A: methyl 5-cyanopicolinate

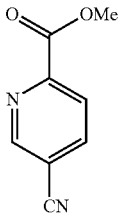

To a stirred solution of 6-bromonicotinonitrile (3.00 g, 16.39 mmol) in MeOH (80 mL) and DMF (80 mL) was added $PdCl_2$(dppf)-$CH_2Cl_2$ (2.68 g, 3.28 mmol) and TEA (5.71 mL, 41.00 mmol). The resultant mixture was heated at 60° C. under an atmosphere of CO (50 psi pressure) for 14 h. The reaction mixture was cooled to ambient temperature and filtered through Celite®. The filtrate was concentrated under reduced pressure. The residue obtained was purified by column chromatography (Redisep—40.00 g, 60% EtOAc/n-Hexanes) to obtain Intermediate 16A (2.25 g, 85.00%) as an off white solid. $^1$H NMR (400 MHz, DMSO-$d_6$) δ ppm 3.93 (s, 3H), 8.20 (dd, J=8.03, 1.00 Hz, 1H), 8.54 (dd, J=8.03, 2.01 Hz, 1H), 9.09-9.25 (m, 1H). LCMS (Method-L): retention time 0.70 min, [M+H] 163.1.

Intermediate 16B: 5-cyanopicolinohydrazide

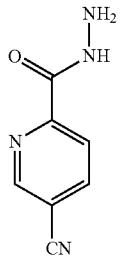

To a stirred solution of Intermediate 16A (2.25 g, 13.88 mmol) in EtOH (50 mL) was added hydrazine hydrate (3.39 mL, 69.40 mmol). The reaction mixture was stirred at 80° C. for 14 h then cooled to ambient temperature. The resultant precipitate was filtered and washed with EtOH (30 mL) to obtain Intermediate 16B (1.90 g, 84.00%) as a white solid. $^1$H NMR (400 MHz, DMSO-$d_6$) δ ppm 4.68 (d, J=4.02 Hz, 2H), 7.91-8.23 (m, 1H), 8.42-8.61 (m, 1H), 8.92-9.24 (m, 1H), 10.21 (br. s., 1H). LCMS (Method-L): retention time 0.45 min, [M+H] 163.1.

Intermediate 16

To a stirred solution of Intermediate 16B (1.00 g, 6.17 mmol) in $POCl_3$ (15 mL) was added 2-chloroacetic acid (0.58 g, 6.17 mmol). The resulting reaction mixture was refluxed at 100° C. for 14 h then was cooled to ambient temperature. $POCl_3$ was evaporated under reduced pressure and the mixture was diluted with ice water (100 mL). The acidic solution was basified by slow addition of solid $NaHCO_3$ and extracted with ethyl acetate (3×50 mL). The combined organic extracts were washed with brine (50 mL), dried over sodium sulfate and evaporated under reduced pressure. The residue was purified by column chromatography (Redisep—40 g, 20% EtOAc/n-Hexane) to obtain Intermediate 16 (0.25 g, 18.37%) as an yellow solid. $^1$H NMR (400 MHz, DMSO-$d_6$) δ ppm 5.20 (s, 2H), 8.38 (dd, J=8.53, 1.00 Hz, 1H), 8.55-8.64 (m, 1H), 9.24 (dd, J=2.01, 1.00 Hz, 1H). (Method-I): retention time 0.84 min, [M+H] 221.4.

Intermediate 17: 6-(5-(chloromethyl)-1,3,4-oxadiazol-2-yl)-4-methylnicotinonitrile

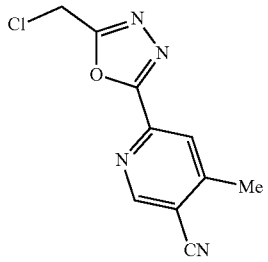

Intermediate 17A: methyl 5-cyano-4-methylpicolinate

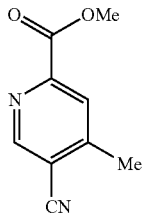

Intermediate 17A was prepared (1.05 g, 39.10%) as an off white solid, by using a similar synthetic protocol as that of Intermediate 16A and starting from 6-bromo-4-methylnicotinonitrile (3.00 g, 15.23 mmol). $^1$H NMR (400 MHz, DMSO-$d_6$) δ ppm 2.60 (s, 3H), 3.92 (s, 3H), 7.85-8.33 (m, 1H), 9.04 (s, 1H). (Method-I): retention time 0.76 min, [M+H] 177.2.

Intermediate 17B: 5-cyano-4-methylpicolinohydrazide

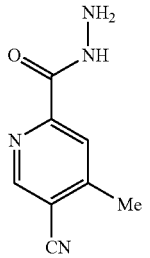

Intermediate 17B was prepared (0.45 g, 82.00%) as white solid, by using a similar synthetic protocol as that of Intermediate 16B and starting from Intermediate 17A (0.55 g, 3.12 mmol). $^1$H NMR (300 MHz, DMSO-$d_6$) δ ppm 2.59 (s, 3H), 4.67 (br. s., 2H), 8.07 (s, 1H), 8.74-9.05 (m, 1H), 10.15 (br. s., 1H). (Method-I): retention time 0.51 min, [M+H] 177.2.

Intermediate 17

Intermediate 17 was prepared (0.20 g, 25.03%) as yellow solid, by using a similar synthetic protocol as that of Intermediate 16 and starting from Intermediate 17B (0.60 g, 3.41 mmol).

$^1$H NMR (400 MHz, DMSO-$d_6$) δ ppm 2.64 (s, 3H), 5.20 (s, 2H), 8.36 (s, 1H), 9.13 (s, 1H). (Method-f): retention time 0.93 min, [M−H] 232.9.

Intermediate 18-I: tert-butyl (R)-(2-amino-2-(4-methyl-1-oxo-1,3-dihydroisobenzofuran-5-yl)ethyl) carbamate

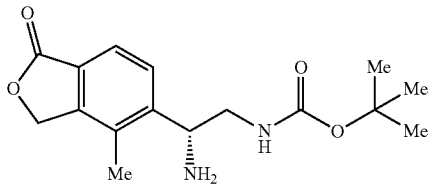

Intermediate 18A-II: (S)-5-(2-amino-1-hydroxy-ethyl)-4-methylisobenzofuran-1(3H)-one

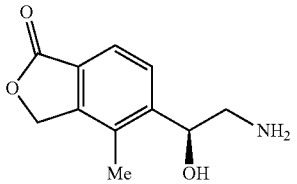

Intermediate 18A-II was prepared (40.00 g, 68.80%) as a brown solid, by using a similar synthetic protocol as that of Intermediate 12A-I and starting from Intermediate 1-II (40.00 g, 210.00 mmol). $^1$H NMR (400 MHz, DMSO-$d_6$) δ ppm 2.26 (s, 3H), 2.52-2.56 (m, 1H), 2.69 (dd, J=13.05, 4.02 Hz, 1H), 4.80 (dd, J=8.03, 3.51 Hz, 1H), 5.38 (d, J=1.51 Hz, 3H), 7.65 (s, 2H). (2 Exchangeable protons not observed). LCMS (Method-H): retention time 0.54 min, [M+H] 208.2.

Intermediate 18B-II: tert-butyl (S)-(2-hydroxy-2-(4-methyl-1-oxo-1,3-dihydroisobenzofuran-5-yl)ethyl) carbamate

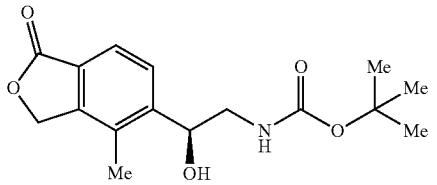

A stirred solution of Intermediate 18A-II (40.00 g, 145.00 mmol) in DCM (400 mL) was cooled to 0° C. TEA (60.50 mL, 434.00 mmol) followed by $BOC_2O$ (40.30 mL, 174.00 mmol) were added. The resulting reaction mixture was stirred at ambient temperature overnight, diluted with water (200 mL) and extracted with DCM (3×200 mL). The combined organic layers were washed with brine (150 mL), dried over sodium sulfate and evaporated under reduced pressure. The residue was purified by column chromatography (Redisep—750 g, 2% MeOH in chloroform) to obtain Intermediate 18B-II: (48.00 g, 80.00%) as a colorless oil. $^1$H NMR (400 MHz, DMSO-$d_6$) δ ppm 1.35 (s, 9H), 2.29 (s, 3H), 2.96 (ddd, J=13.70, 7.90, 6.00 Hz, 1H), 3.20-3.06 (m, 1H), 4.89-5.02 (m, 1H), 5.38 (s, 2H), 5.54 (d, J=4.50 Hz, 1H), 6.89 (t, J=5.80 Hz, 1H), 7.66 (s, 2H). LCMS (Method-I): retention time 0.93 min, [M+H] 308.4.

Intermediate 18C-I: tert-butyl (R)-(2-(1,3-dioxoi-soindolin-2-yl)-2-(4-methyl-1-oxo-1,3-dihy-droisobenzofuran-5-yl)ethyl)carbamate

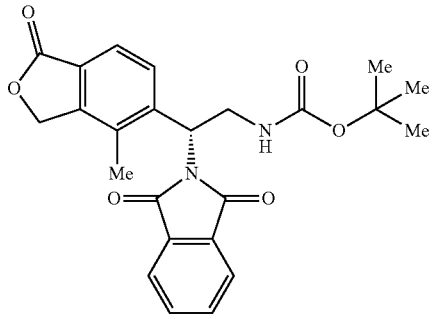

To a stirred solution of Intermediate 18B-II (47.00 g, 113.00 mmol) in THF (800 mL) were added triphenylphosphine (65.30 g, 249.00 mmol) followed by DIAD (39.60 mL, 204.00 mmol). The resulting reaction mixture was stirred at ambient temperature for 2 h, diluted with water (1.5 L) and extracted with ethyl acetate (3×500 mL). The combined organic layers were washed with brine (300 mL), dried over anhydrous sodium sulfate and evaporated under reduced pressure. The residue was purified by silica gel column chromatography (Redisep—1.5 kg, 40% EtOAc/n-hexane) to obtain Intermediate 18C-I (50.00 g, 91.00%) as a colorless oil. $^1$H NMR (300 MHz, DMSO-$d_6$) δ ppm 1.19-1.33 (m, 9H), 2.28 (s, 3H), 3.63 (dt, J=13.79, 5.57 Hz, 1H), 3.94-4.15 (m, 1H), 5.26-5.46 (m, 2H), 5.65 (dd, J=9.44, 4.15 Hz, 1H), 7.23 (s, 1H), 7.71 (d, J=8.31 Hz, 1H), 7.78-7.94 (m, 5H). LCMS (Method-I): retention time 1.23 min, [M+H] 437.2.

Intermediate 18-I

To a stirred solution of Intermediate 18C-I (40.00 g, 92.00 mmol) in MeOH (500 mL) was added hydrazine hydrate (44.80 mL, 916.00 mmol). The resulting reaction mixture was heated at 60° C. for 14 h, cooled to ambient temperature and diluted with ethyl acetate (200 mL). The resultant solid was filtered and the filtrate was evaporated under reduced pressure. The residue was purified by silica gel column chromatography (Redisep—330 g, 2% MeOH/chloroform) to obtain Intermediate 18-I (28.50 g, 91.00%) as a greenish oil. $^1$H NMR (400 MHz, DMSO-$d_6$) δ ppm 1.35 (s, 9H), 1.87-2.01 (m, 2H), 2.29 (s, 3H), 2.85-2.97 (m, 1H), 3.10 (dd, J=12.30, 6.27 Hz, 1H), 4.24-4.34 (m, 1H), 5.37 (s, 2H), 6.87-6.98 (m, 1H), 7.64 (d, J=8.03 Hz, 1H), 7.75 (d, J=8.03 Hz, 1H). LCMS (Method-I): retention time 0.84 min, [M+H] 307.1.

Intermediate 19-I: (R)—N-(2-amino-1-(4-methyl-1-oxo-1,3-dihydroisobenzofuran-5-yl)ethyl)-2-chloroacetamide

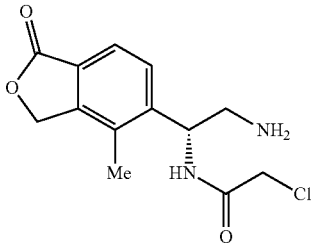

Intermediate 19A-I: tert-butyl (R)-(2-(2-chloroacetamido)-2-(4-methyl-1-oxo-1,3-dihydroisobenzofuran-5-yl)ethyl)carbamate

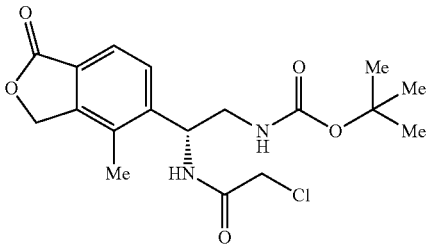

To a stirred solution of Intermediate 18-I (0.50 g, 1.63 mmol) in DCM (20 mL) at 0° C. was added TEA (0.68 mL, 4.90 mmol) followed by chloroacetyl chloride (0.13 mL, 1.63 mmol). The resulting reaction mixture was stirred at ambient temperature for 14 h, diluted with water (30 mL) and extracted with DCM (3×30 mL). The combined organic extracts were washed with brine (30 mL), dried over sodium sulfate and evaporated under reduced pressure. The residue was purified by column chromatography (Redisep—12 g, 2% MeOH in chloroform) to obtain Intermediate 19A-I (0.40 g, 64.00%) as an off-white solid. $^1$H NMR (400 MHz, DMSO-$d_6$) δ ppm 1.34 (s, 9H), 2.34 (s, 3H), 3.15-3.26 (m, 2H), 4.08 (s, 2H), 5.25 (q, J=7.36 Hz, 1H), 5.34-5.45 (m, 2H), 7.00 (t, J=5.77 Hz, 1H), 7.54 (d, J=8.03 Hz, 1H), 7.68 (d, J=8.03 Hz, 1H), 8.76 (d, J=7.53 Hz, 1H). (Method-H): retention time 1.53 min, [M+H)] 383.0.

Intermediate 19-I

To a stirred solution of Intermediate 19A-I (0.05 g, 0.13 mmol) in DCM (10 mL) was added TFA (1.00 ml, 12.98 mmol) and reaction mixture was stirred at ambient temperature for 30 minutes. The reaction mixture was concentrated to dryness under reduced pressure. The residue was dissolved in MeCN (10 mL), water (0.3 mL) and $Na_2CO3$ (0.07 g, 0.65 mmol) was added and the reaction mixture was heated at 80° C. for 1 h. The reaction mixture was cooled to ambient temperature and excess solid sodium carbonate was filtered off. The filtrate was dried over sodium sulfate and concentrated under reduced pressure to obtain Intermediate 19-I (0.04 g, 95.00%) as colorless oil. $^1$H NMR (400 MHz, DMSO-$d_6$) δ ppm 2.36 (s, 3H), 3.04-3.27 (m, 2H), 4.04-4.23 (m, 2H), 5.37-5.53 (m, 3H), 7.61 (d, J=8.03 Hz, 1H), 7.76 (d, J=8.03 Hz, 1H), 8.01 (br. s., 2H), 8.91 (d, J=8.53 Hz, 1H). (Method-I): retention time 0.53 min, [M−1] 281.3.

Intermediate 20: 6-(4-methyl-1H-imidazol-1-yl)nicotinaldehyde

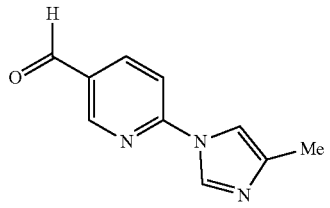

To a stirring solution of 6-bromonicotinaldehyde (1.25 g, 6.72 mmol) in DMF (10 mL) was added $K_2CO_3$ (2.32 g, 16.80 mmol) and 4-methyl-1H-imidazole (0.55 g, 6.72 mmol). The resulting mixture was heated at 100° C. for 1 h then cooled to ambient temperature. The reaction was poured into ice water (30 mL) and extracted with ethyl acetate (2×75 mL). The combined organic layers were washed with brine (50 mL), dried over sodium sulfate and evaporated under reduced pressure. The residue was purified by flash chromatography (Redisep—40 g, 0-100% EtOAc/n-Hexane)) to obtain Intermediate 20 (0.50 g, 39.70%) as light brown solid. $^1$H NMR (300 MHz, DMSO-$d_6$) δ ppm 2.50 (s, 3H), 7.76 (s, 1H), 7.95 (dd, J=6.00, 1.20 Hz, 1H), 8.39 (dd, J=6.60, 1.80 Hz, 1H), 8.55 (d, 1.20 Hz, 1H), 8.99 (s, 1H), 10.08 (s, 1H), LCMS: (Method-H) retention time: 1.03 min, [M+1]: 188.0.

Intermediate 21: 1-(5-formylpyridin-2-yl)-1H-imidazole-4-carbonitrile

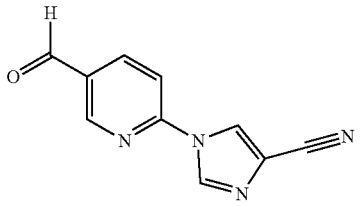

Intermediate 21 was prepared (0.40 g, 37.50%) as an off-white solid, by using a similar synthetic protocol as that of Intermediate 20 and starting from 6-bromonicotinaldehyde (1.00 g, 5.38 mmol) and 1H-imidazole-4-carbonitrile. $^1$H NMR (400 MHz, DMSO-$d_6$) δ ppm 8.11 (d, J=8.53 Hz, 1H), 8.53 (dd, J=8.28, 2.26 Hz, 1H), 8.89 (d, J=1.51 Hz, 1H), 9.03 (d, J=1.51 Hz, 1H), 9.05-9.10 (m, 1H), 10.14 (s, 1H). LCMS/HPLC: (Method-H) retention time 0.85 min, [M+1]: 199.2.

Intermediate 22:
6-(3-methyl-1H-1,2,4-triazol-1-yl)nicotinaldehyde

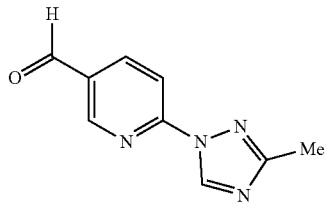

Intermediate 22 was prepared (0.30 g, 59.30%) as an off-white solid, by using a similar synthetic protocol as that of Intermediate 20 and starting from 6-bromonicotinaldehyde (0.50 g, 2.69 mmol) and 3-methyl-1H-1,2,4-triazole (0.33 g, 4.03 mmol). $^1$H NMR (400 MHz, DMSO-$d_6$) δ ppm 2.42 (s, 3H), 7.99 (d, J=8.53 Hz, 1H), 8.47 (dd, J=8.53, 2.01 Hz, 1H), 9.02-9.04 (m, 1H), 9.37 (s, 1H), 10.12 (s, 1H). LCMS/HPLC: (Method-H) retention time 0.88 min, [M+1]: 189.0.

Intermediate 23-I: (R)-5'-((2-hydroxy-2-(4-methyl-1-oxo-1,3-dihydroisobenzofuran-5-yl)ethyl)amino)methyl)-4-methoxy-[2,2'-bipyridine]-5-carbonitrile

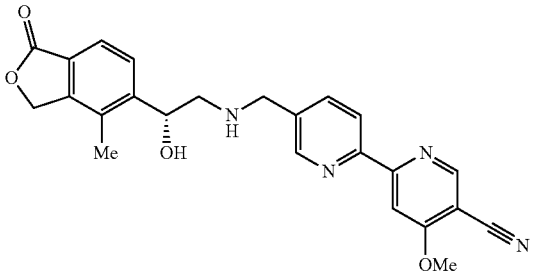

Intermediate 23A:
4-methoxy-6-(trimethylstannyl)nicotinonitrile

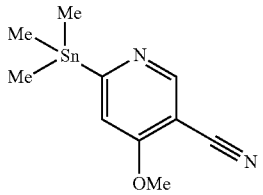

A solution of 6-chloro-4-methoxynicotinonitrile (2.00 g, 11.86 mmol) in dioxane (10 mL) was degassed with nitrogen for 20 minutes. Hexamethylditin (2.71 mL, 13.05 mmol) and 1,1'-bis(di-tert-butylphosphino)ferrocene palladium (II) chloride (0.77 g, 1.19 mmol) were added. The resulting reaction mixture was degassed again for 10 minutes, heated at 100° C. for 12 h and was cooled to ambient temperature. The reaction mixture was filtered through Celite® and the filtrate was concentrated under reduced pressure to obtain Intermediate 23A: (5.00 g, 39.50%) as a dark oil. LCMS (Method-I): retention time 1.26 min, [M+H] 299.1. The compound was taken directly to the subsequent step without further purification or characterization.

Intermediate 23B: 5'-formyl-4-methoxy-[2,2'-bipyridine]-5-carbonitrile

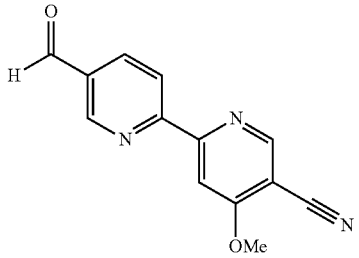

A solution of 6-bromonicotinaldehyde (1.10 g, 5.91 mmol) and Intermediate 23A (4.83 g, 6.51 mmol) in dioxane (20 mL) was degassed with nitrogen for 20 minutes. To the stirring solution was added tetrakistriphenylphosphine palladium (0.68 g, 0.59 mmol) followed by copper (I) iodide (0.11 g, 0.59 mmol) and the resulting mixture was degassed again for 10 minutes. The resulting reaction mixture was heated at 100° C. for 16 h then cooled to ambient temperature and filtered through Celite®. The filtrate was concentrated under reduced pressure. The residue was purified by column chromatography (Redisep—40 g, 0-40% EtOAc/n-Hexane) to obtain Intermediate 23B (1.60 g, 79.00%) as off-white solid. $^1$H NMR (300 MHz, DMSO-$d_6$) δ ppm 4.16 (s, 3H), 8.22 (d, J=14.35 Hz, 1H), 8.46 (d, J=8.31 Hz, 1H), 8.55-8.72 (m, 1H), 8.99 (d, J=1.51 Hz, 1H), 9.24 (s, 1H), 10.20 (s, 1H). LCMS/HPLC: (Method H) retention time: 1.63 min, [M+1]: 240.0.

Intermediate 23-I

To a solution of Intermediate 23B (0.60 g, 1.75 mmol) in a mixture of DCM (20 mL) and MeOH (6 mL) were added 12A-I (0.36 g, 1.75 mmol) followed by AcOH (0.40 mL, 7.02 mmol). The resulting reaction mixture was stirred at ambient temperature for 2 h followed by the addition of $NaBH(CH_3CO_2)_3$ (0.37 g, 1.75 mmol). Stirring was continued for 12 h. The reaction was then diluted with water (15 mL) and extracted with DCM (2×100 mL). The combined organic layer was washed with brine (50 mL), dried over anhydrous sodium sulfate and evaporated under reduced pressure. The residue was purified by prep HPLC [Symmetry C8 (300×19 ID) 9 micron; Solvent A: 10 mM ammonium acetate, Solvent B: Acetonitrile, Gradient: 0-100% B over 21 min, Flow: 18 mL/min, retention time 12.50 min, UV 220 nm] to obtain Intermediate 23-I (0.10 g, 13.76%) as a white solid. $^1$H NMR (400 MHz, DMSO-$d_6$) δ ppm 2.22 (s, 3H), 2.58-2.71 (m, 2H), 3.89 (s, 2H), 4.12 (s, 3H), 5.04 (br. s., 1H), 5.30-5.42 (m, 2H), 5.52 (br. s., 1H), 7.59-7.71 (m, 2H), 7.94 (dd, J=8.19, 2.32 Hz, 1H), 8.15 (s, 1H), 8.38 (d, J=8.31 Hz, 1H), 8.67 (s, 1H), 8.91 (s, 1H), (Exchangeable proton not observed). LCMS/HPLC: (Method-D) retention time: 1.70 min, [M+1]: 431.0.

Intermediate 24: 4-methyl-6-(4-(oxiran-2-yl)-1H-pyrazol-1-yl)nicotinonitrile

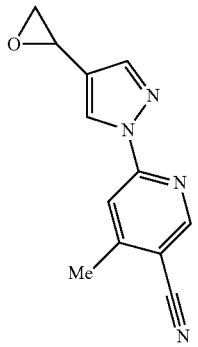

Intermediate 24A: 4-methyl-6-(1H-pyrazol-1-yl)nicotinonitrile

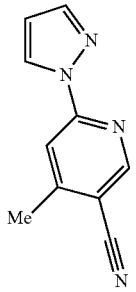

Intermediate 24A was prepared (0.85 g, 60.60%) as an off-white solid, by using a similar synthetic protocol as that of Intermediate 6 and starting from 1H-pyrazole (0.52 g, 7.61 mmol). $^1$H NMR (400 MHz, DMSO-d6) δ ppm 2.50 (s, 3H), 6.65 (s, 1H), 7.93 (s, 1H), 8.02 (s, 1H), 8.66 (s, 1H), 8.85 (s, 1H). LCMS/HPLC: (Method-H) retention time: 1.63 min, [M+1]: 185.0.

Intermediate 24B: 6-(4-bromo-1H-pyrazol-1-yl)-4-methylnicotinonitrile

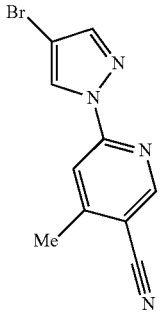

To a solution of Intermediate 24A (0.85 g, 4.61 mmol) in AcOH (20 mL) was added bromine (0.59 mL, 11.54 mmol) in AcOH (3 mL) drop wise. The resulting mixture was stirred at ambient temperature for 16 h. The reaction mixture was poured into ice water followed by the addition of saturated ammonium thiosulfate (10 mL). The precipitate obtained was filtered and dried under reduced pressure to afford Intermediate 24B (1.12 g, 92.00%) as an off-white solid. $^1$H NMR (400 MHz, DMSO-d6) δ ppm 2.60 (s, 3H), 8.02 (s, 1H), 8.08 (s, 1H), 8.88 (s, 2H). LCMS/HPLC: (Method-D) retention time: 2.89 min, [M+2]: 265.0.

Intermediate 24C: 4-methyl-6-(4-vinyl-1H-pyrazol-1-yl)nicotinonitrile

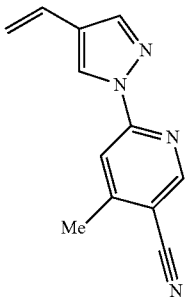

To a stirring solution of Intermediate 24B (1.12 g, 4.37 mmol) in THF (25 mL) was added tributylvinyltin (1.66 g, 5.25 mmol) and the resulting mixture was degassed with nitrogen for 15 minutes. Triphenylphosphine (0.34 g, 1.31 mmol) followed by palladium(II) acetate (0.15 g, 0.66 mmol) were added and the mixture was degassed again for 10 minutes. The resulting reaction mixture was heated at 80° C. for 48 h then cooled to ambient temperature. The reaction was filtered through Celite® and the filtrate was concentrated under reduced pressure. The residue was purified by column chromatography (Redisep—40 g, 0-10% EtOAc/n-Hexane) to obtain Intermediate 24C (0.80 g, 87.00%) as an off-white solid. $^1$H NMR (300 MHz, DMSO-d6) δ ppm 2.58 (s, 3H), 5.76 (d, J=17.70 Hz, 1H), 5.23 (d, J=11.10 Hz, 1H), 6.61-6.71 (m, 1H), 8.02 (s, 1H), 8.17 (s, 1H), 8.73 (s, 1H), 8.85 (s, 1H). LCMS/HPLC: (Method-H) retention time: 2.06 min, [M+1]: 211.2.

Intermediate 24

To a stirring solution of Intermediate 24C (0.40 g, 1.90 mmol) in tert-butanol (10 mL) and water (20 mL) was added NBS (0.40 g, 2.28 mmol) and the reaction mixture was heated at 40° C. for 1 h. The reaction mixture was cooled to 0° C. and NaOH (0.23 g, 5.71 mmol) in water (5 mL) was added. The reaction mixture was stirred at ambient temperature 2 h, diluted with water (20 mL) and extracted with ethyl acetate (3×50 mL). The combined organic layers were washed with brine (20 mL), dried over sodium sulfate and evaporated under reduced pressure to obtain Intermediate 24 (0.30 g). LCMS: (Method-I) retention time: 1.06 min, [M+1]: 227.0. The compound was taken directly to the subsequent step without further purification or characterization.

Intermediate 25-I: (R)-5-(4-((2-bromothiazol-5-yl)methyl)morpholin-2-yl)-4-methylisobenzofuran-1(3H)-one

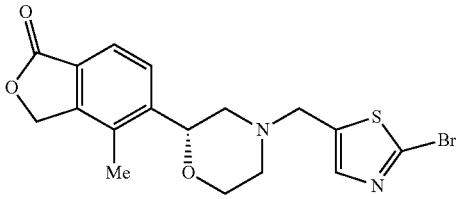

Intermediate 25A: (2-bromothiazol-5-yl)methanol

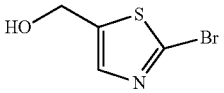

To a stirring solution of methyl 2-bromothiazole-5-carboxylate (2.00 g, 9.01 mmol) in THF (40 mL) was added $LiBH_4$ (1.96 g, 90 mmol) and stirring was continued at ambient temperature for 48 h. The reaction mixture was evaporated under reduced pressure and the residue was diluted with water (50 mL) and extracted with DCM (3×75 mL). The combined organic layer was washed with brine (50 mL), dried over anhydrous sodium sulfate and evaporated under reduced pressure. The residue was purified by column chromatography (Redisep—40 g, 0-35% EtOAc/n-Hexane) to obtain Intermediate 25A (0.65 g, 37.20%) as yellow solid. $^1$H NMR (400 MHz, DMSO-$d_6$) δ ppm 4.63 (d, J=5.60 Hz, 2H), 5.67 (d, J=5.60 Hz, 1H), 7.53 (s, 1H). LCMS: (Method-D) retention time: 0.68 min, [M+2]: 196.0.

Intermediate 25B: 2-bromothiazole-5-carbaldehyde

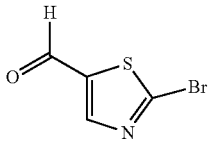

Intermediate 25B was prepared (0.38 g, 64.00%) from Intermediate 25A (0.60 g, 3.09 mmol) as a white solid, by using a similar suynthetic protocol as that of preparation of Intermediate 9 from 9E. $^1$H NMR (400 MHz, DMSO-$d_6$) δ ppm 8.55 (s, 1H), 10.00 (s, 1H). LCMS: The compound did not ionize well.

Intermediate 25-I

Intermediate 25-I was prepared (0.35 g, 45.60%) as an off-white solid, by using a similar synthetic protocol as that of Intermediate 23-I and starting from Intermediate 25B (0.18 g, 0.93 mmol) and intermediate 3-I (0.22 g, 0.94 mmol). $^1$H NMR (400 MHz, DMSO-$d_6$) δ ppm 2.24 (s, 3H), 2.27-2.36 (m, 1H), 2.76-2.85 (m, 1H), 2.89-2.95 (m, 1H), 3.68-3.77 (m, 1H), 3.78 (br. s., 2H), 3.95-4.05 (m, 1H), 4.64 (d, J=5.02 Hz, 1H), 4.76-4.85 (m, 1H), 5.39 (d, J=2.01 Hz, 2H), 7.56 (s, 1H) 7.59-7.63 (m, 1H), 7.64-7.70 (m, 1H). LCMS: (Method-I) retention time: 1.23 minutes, [M+2]: 411.0.

Intermediate 26-I: (R)-5-(4-(2-bromothiazole-5-carbonyl)morpholin-2-yl)-4-methylisobenzofuran-1(3H)-one

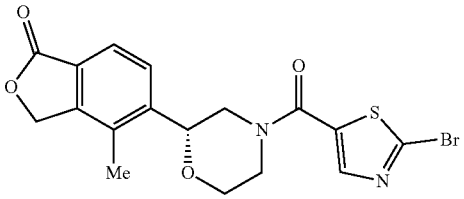

Intermediate 26A: 2-bromothiazole-5-carboxylic acid

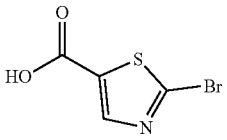

To a stirring solution of methyl 2-bromothiazole-5-carboxylate (1.50 g, 6.75 mmol) in THF (10 mL), MeOH (4 mL) and water (2 mL) was added LiOH (0.81 g, 33.80 mmol) and stirring was continued at ambient temperature for 2 h. The reaction mixture was concentrated under reduced pressure, diluted with water (10 mL) and acidified with 2N HCl. The solid precipitate was filtered and dried under reduced pressure to obtain Intermediate 26A (0.70 g, 49.80%) as an off-white solid. $^1$H NMR (400 MHz, DMSO-d6) δ ppm 8.21 (s, 1H), 13.83 (br.s., 1H). LCMS: (Method-D) retention time: 0.38 min, [M+2]: 208.0.

Intermediate 26-I

To a stirring solution of Intermediate 26A (0.40 g, 1.92 mmol) and Intermediate 3-I (0.45 g, 1.92 mmol) in DCM (10 mL) was added TEA (0.80 mL, 5.77 mmol) followed by Propylphosphonic anhydride (1.22 g, 3.85 mmol) and stirring was continued at ambient temp for 3 h. The reaction mixture was diluted with water (20 mL) and extracted with DCM (3×30 mL). The combined organic layers were washed with brine (20 mL), dried over anhydrous sodium sulfate and concentrated under reduced pressure. The residue was triturated with DCM/n-Hexane to obtain Intermediate 26-I (0.80 g, 67.80%) as an off-white solid. LCMS: (Method-D) retention Time: 2.06 min, [M+2]: 425.0. The compound was taken directly to the subsequent step without further purification or characterization.

Intermediate 27: 1-(5-formylthiazol-2-yl)-1H-imidazole-4-carbonitrile

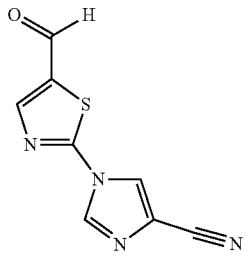

Intermediate 27 was prepared (0.12 g, 37.80%) as a light brown solid, by using a similar synthetic protocol as that of Intermediate 11 and starting from Intermediate 25B (0.20 g, 1.04 mmol). $^1$H NMR (400 MHz, DMSO-d6) δ ppm 8.65 (s, 1H), 8.80 (s, 1H), 9.00 (s, 1H), 10.06 (s, 1H). LCMS: (Method-D) retention time: 0.96 min, [M+1]: 205.0.

Intermediate 28: 6-(4-formyl-2H-1,2,3-triazol-2-yl)-4-methylnicotinonitrile

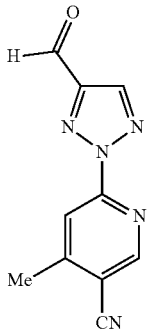

Intermediate 28A: (1H-1,2,3-triazol-4-yl)methanol

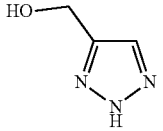

To a solon of prop-2-yn-1-ol (2.00 g, 35.70 mmol) in a mixture of DMF (18 mL) and MeOH (0.50 mL) in a sealed tube was added TMS-$N_3$ (7.10 mL, 53.50 mmol) and copper (I) iodide (0.34 g, 1.78 mmol) at ambient temperature. The resulting reaction mixture was heated at 95° C. for 12 h, cooled to ambient temperature, diluted with DCM (100 mL) and filtered through Celite®. The filtrate was evaporated under reduced pressure to obtain Intermediate 28A (3.30 g 93.00%) as a brown liquid. $^1$H NMR (400 MHz, DMSO-$d_6$) δ ppm 4.55 (d, J=3.51 Hz, 2H), 5.12-5.27 (m, 1H), 7.70 (br. s., 1H), 14.58-15.07 (br. s., 1H). GCMS: retention time 9.36 min, [M] 99.0. The compound was taken directly to the subsequent step without further purification.

Intermediate 28B: 6-(4-(hydroxymethyl)-2H-1,2,3-triazol-2-yl)-4-methylnicotinonitrile

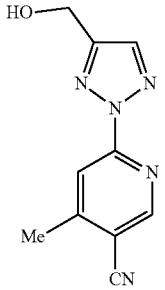

Intermediate 28B was prepared (0.50 g, 20.95%) as a light brown solid, by using a similar synthetic protocol as that of Intermediate 6 and starting from Intermediate 28A (1.00 g, 10.09 mmol). $^1$H NMR (400 MHz, DMSO-$d_6$) δ ppm 2.62 (s, 3H), 4.67 (d, J=5.52 Hz, 2H), 5.49-5.54 (m, 1H), 8.12 (d, J=1.00 Hz, 1H), 8.18 (s, 1H), 8.94 (s, 1H). LCMS (Method-D): retention time 0.951 min, [M+H] 216.2.

Intermediate 28

Intermediate 28 was prepared (0.90 g, 64.20%) as a yellow solid, by using a similar synthetic protocol as that of Intermediate 9 and starting from Intermediate 28B (1.40 g, 6.51 mmol). $^1$HNMR (400 MHz, DMSO-$d_6$) δ ppm 2.67 (s, 3H), 8.29 (s, 1H), 8.79 (s, 1H), 9.03 (s, 1H), 10.21 (s, 1H). LCMS (Method-D): retention time 1.32 min, [M+H] 214.2.

Intermediate 29: 2-(3-methyl-2-oxo-2,3-dihydrobenzo[d]oxazol-5-yl)-2H-1,2,3-triazole-4-carbaldehyde

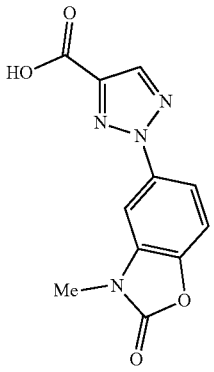

Intermediate 29A: 5-(4-(hydroxymethyl)-2H-1,2,3-triazol-2-yl)-3-methylbenzo[d]oxazol-2(3H)-one

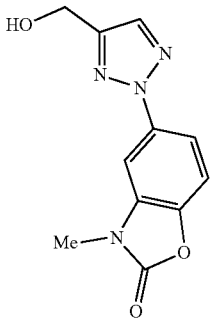

Intermediate 29A was prepared (0.65 g, 13.78%) as a brown solid, by using a similar synthetic protocol as that of Intermediate 6 and starting from Intermediate 28A (1.50 g, 15.14 mmol). $^1$H NMR (400 MHz, DMSO-$d_6$) δ ppm 3.42 (s, 3H), 4.65 (d, J=5.52 Hz, 2H), 5.43 (t, J=5.77 Hz, 1H), 7.49 (d, J=8.53 Hz, 1H), 7.75 (dd, J=8.78, 2.26 Hz, 1H), 7.85 (d, J=2.26 Hz, 1H), 8.02 (s, 1H). LCMS (Method-D): retention time 1.04 min, [M+H] 247.2.

Intermediate 29

Intermediate 29 was prepared (0.12 g, 79.00%) as an off-white solid, by using a similar synthetic protocol as that of Intermediate 9 and starting from Intermediate 29A (0.15 g, 0.60 mmol). $^1$H NMR (400 MHz, DMSO-d6) δ ppm 3.44 (s, 3H), 7.57 (d, J=8.78 Hz, 1H), 7.88 (dd, J=8.78, 2.26 Hz, 1H), 7.99 (d, J=2.26 Hz, 1H), 8.70 (s, 1H), 10.18 (s, 1H). LCMS (Method-D): retention time 1.687 min, [M+H] 245.2.

Intermediate 30: 6-(4-formyl-1H-1,2,3-triazol-1-yl)-4-methylnicotinonitrile

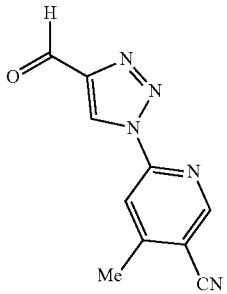

Intermediate 30A: 6-azido-4-methylnicotinonitrile

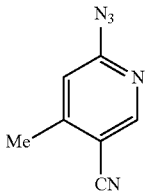

To a stirring solution of 6-bromo-4-methylnicotinonitrile (2.00 g, 10.15 mmol) in DMF (10 mL) was added sodium azide (1.32 g, 20.30 mmol) and stirring was continued for 12 h at ambient temperature. The reaction mixture was diluted with water (300 mL) and extracted with ethyl acetate (3×200 mL). The combined organic layer was dried over anhydrous $Na_2SO_4$ and evaporated under reduced pressure. The residue was purified by column chromatography (Redisep—40 g, 20-35% EtOAc/n-Hexane) to obtain Intermediate 30A (0.87 g, 54.00%). $^1$H NMR (400 MHz, DMSO-$d_6$) δ ppm 2.62 (d, J=1.00 Hz, 3H), 8.28 (t, J=1.00 Hz, 1H), 10.21 (s, 1H). LCMS (Method-D): retention time 0.88 min, [M+H] 160.2.

Intermediate 30B: 6-(4-(hydroxymethyl)-1H-1,2,3-triazol-1-yl)-4-methylnicotinonitrile

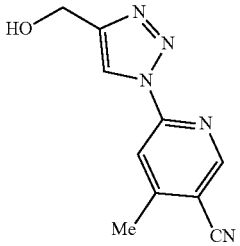

Intermediate 30B was prepared (0.21 g, 31.00%), by using a similar synthetic protocol as that of Intermediate 28A and starting from Intermediate 30A (0.50 g, 3.14 mmol). $^1$H NMR (400 MHz, DMSO-$d_6$) δ ppm 2.65 (s, 3H), 4.63 (d, J=6.53 Hz, 2H), 5.33-5.39 (m, 1H), 8.30 (d, J=1.00 Hz, 1H), 8.71 (s, 1H), 9.00 (s, 1H). LCMS (Method-D): retention time 0.87 min, [M+H] 216.2.

Intermediate 30

Intermediate 30 was prepared (0.13 g, 65.60%) from Intermediate 30B, by using a similar synthetic protocol as that of preparation of Intermediate 9 from Intermediate 9E. $^1$H NMR (300 MHz, DMSO-$d_6$) δ ppm 2.64-2.70 (m, 3H), 8.39 (s, 1H), 9.06 (s, 1H), 9.58 (s, 1H), 10.13 (s, 1H). LCMS (Method-D): retention time 1.42 min, [M+H] 214.2.

Intermediate 31: 6-(4-formyl-1H-1,2,3-triazol-1-yl)-4-methoxynicotinonitrile

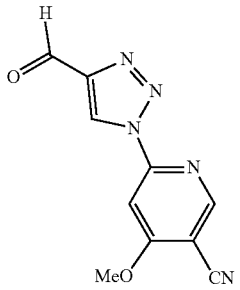

Intermediate 31A: 6-azido-4-methoxynicotinonitrile

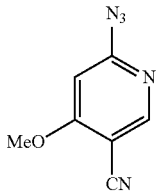

Intermediate 31A was prepared (1.40 g, 67.00%), by using a similar synthetic protocol as that of Intermediate 30A and starting from 6-chloro-4-methoxynicotinonitrile (2.00 g, 11.86 mmol). $^1$H NMR (400 MHz, DMSO-$d_6$) δ ppm 4.10 (s, 3H), 7.81 (s, 1H), 7.89 (s, 1H). LCMS (Method-D): retention time 0.79 min, [M+H] 176.0.

Intermediate 31B: 6-(4-(hydroxymethyl)-1H-1,2,3-triazol-1-yl)-4-methoxynicotinonitrile

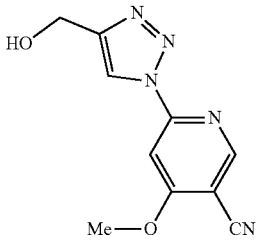

Intermediate 31B was prepared (0.23 g, 13.40%), by using a similar synthetic protocol as that of Intermediate 28A and starting from Intermediate 31A (1.30 g, 7.42 mmol). $^1$H NMR (400 MHz, DMSO-$d_6$) δ ppm 4.15-4.19 (m, 3H), 4.64 (s, 2H), 7.89 (s, 1H), 8.71 (s, 1H), 8.89 (s, 1H), (Exchangeable proton not observed). LCMS (Method-D): retention time 1.01 min, [M+H] 232.2.

Intermediate 31

Intermediate 31 was prepared (0.12 g, 60.50%) from Intermediate 31B (0.20 g, 0.86 mmol) by using a similar synthetic protocol as that of preparation of Intermediate 9 from Intermediate 9E. $^1$H NMR (300 MHz, DMSO-$d_6$) δ ppm 4.19 (s, 3H), 7.99 (s, 1H), 8.96 (s, 1H), 9.59 (s, 1H), 10.14 (s, 1H). LCMS (Method-D): retention time 1.1.42 min, [M+H] 230.2.

Intermediate 32: 1-(3-methyl-2-oxo-2,3-dihydrobenzo[d]oxazol-5-yl)-1H-1,2,3-triazole-4-carbaldehyde

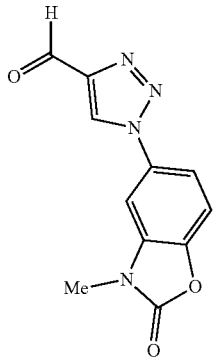

Intermediate 32A: 5-nitrobenzo[d]oxazol-2(3H)-one

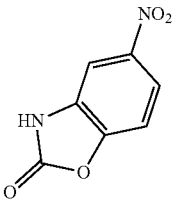

To a stirred solution of 2-amino-4-nitrophenol (5.00 g, 32.40 mmol) in THF (50 mL) was added CDI (6.84 g, 42.20 mmol) at 70° C. and stirring was continued at ambient temperature for 3 h. The reaction mixture was concentrated under reduced pressure, diluted with water (200 mL) and extracted with ethyl acetate (2×100 mL). The combined organic layers were washed with brine (80 mL), dried over anhydrous sodium sulfate and evaporated under reduced pressure to obtain Intermediate 32A (5.50 g, 94.00%) as a yellow solid. $^1$H NMR (300 MHz, DMSO-$d_6$) δ ppm 7.49 (d, J=8.69 Hz, 1H), 7.82 (d, J=2.27 Hz, 1H), 8.02 (dd, J=8.69, 2.27 Hz, 1H). (Exchangeable proton not observed). LCMS (Method-H): retention time 0.69 min, [M−H] 179.0.

Intermediate 32B: 3-methyl-5-nitrobenzo[d]oxazol-2(3H)-one

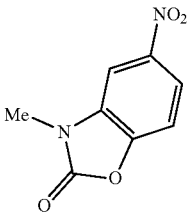

To a stirring solution of Intermediate 32A (5.00 g, 27.80 mmol) in DMSO (55 mL) was added $K_2CO_3$ (4.22 g, 30.50 mmol), followed by methyl iodide (5.21 mL, 83.00 mmol) and stirring was continued at ambient temperature for 12 h.

The reaction mixture was cooled to 0° C. and diluted with ice water (150 mL). The resulting suspension was stirred at ambient temperature for 1 h. The solid that formed was filtered, dried under reduced pressure, to obtain Intermediate 32B (4.50 g, 83.00%) as a yellow solid. $^1$H NMR (300 MHz, DMSO-$d_6$) δ ppm 7.57 (d, J=8.69 Hz, 1H), 8.09 (dd, J=8.69, 2.27 Hz, 1H), 8.21 (d, J=2.64 Hz, 1H), 3.43 (s, 3H). LCMS (Method-H): retention time 1.23 min, [M+H] 195.2.

Intermediate 32C: 5-amino-3-methylbenzo[d]oxazol-2(3H)-one

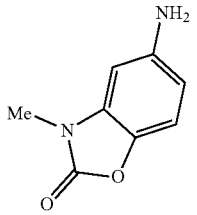

To a solution of Intermediate 32B (1.80 g, 9.27 mmol) in acetic acid (50 mL) was added 10% Pd/C (0.10 g, 0.93 mmol) and the reaction mixture was stirred at ambient temperature under an hydrogen atmosphere for 14 h. The reaction mixture was filtered through Celite® then washed with 10% MeOH in DCM (20 mL). Filtrate was evaporated under reduced pressure to obtain Intermediate 32C (1.20 g, 80.00%). $^1$H NMR (400 MHz, DMSO-$d_6$) δ ppm 3.23 (s, 3H), 5.06 (br. s., 2H), 6.28 (dd, J=8.53, 2.51 Hz, 1H), 6.37 (d, J=2.01 Hz, 1H), 6.95 (d, J=8.53 Hz, 1H). LCMS (Method-D): retention time 0.59 min, [M+H] 165.2.

Intermediate 32D: 5-azido-3-methylbenzo[d]oxazol-2(3H)-one

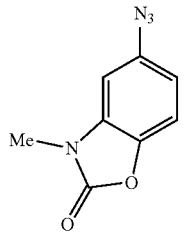

To a solution of Intermediate 32C (1.50 g, 9.14 mmol) in ACN (20 mL) at 0° C. was added tert-butyl nitrite (3.26 mL, 27.40 mmol) followed by azidotrimethylsilane (3.61 mL, 27.40 mmol). The resultant reaction mixture was stirred at ambient temperature for 2 h. It was diluted with water (100 mL) and extracted with ethyl acetate (3×100 mL). The combined organic layer was dried over anhydrous $Na_2SO_4$ and evaporated under reduced pressure to obtain Intermediate 32D (1.00 g, 57.20%). $^1$H NMR (400 MHz, DMSO-$d_6$) δ ppm 3.34 (s, 3H), 6.85 (dd, J=8.53, 2.01 Hz, 1H), 7.14 (d, J=2.51 Hz, 1H), 7.35 (d, J=8.53 Hz, 1H). LCMS (Method-H): retention time 2.30 min, [M+H] 191.2.

Intermediate 32E: 5-(4-(hydroxymethyl)-1H-1,2,3-triazol-1-yl)-3-methylbenzo[d]oxazol-2(3H)-one

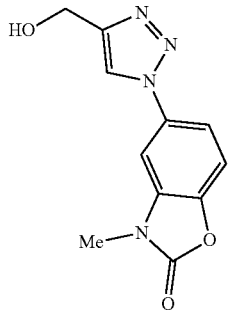

To a stirring solution of Intermediate 32D (1.30 g, 6.84 mmol) and prop-2-yn-1-ol (0.83 g, 6.84 mmol) in a mixture of t-butanol (8 mL) and water (8 mL) was added a freshly prepared 1 M solution of sodium ascorbate (0.55 mL, 0.55 mmol), followed by copper(II) sulfate pentahydrate (0.014 g, 0.055 mmol). The resulting reaction mixture was stirred at ambient temperature for 8 h, diluted with DCM (200 mL), and washed with water (100 mL). The organic layer was dried over anhydrous sodium sulfate and concentrated under reduced pressure. The residue was purified by column chromatography (Redisep—24 g, 20-35% EtOAc/n-Hexane) to obtain Intermediate 32E (1.40 g, 83.00%). $^1$H NMR (300 MHz, DMSO-$d_6$) δ ppm 3.32 (s, 3H), 4.62 (d, J=5.67 Hz, 2H), 5.35 (t, J=5.67 Hz, 1H), 7.52 (d, J=8.69 Hz, 1H), 7.65 (dd, J=8.50, 2.08 Hz, 1H), 7.89 (d, J=2.27 Hz, 1H), 8.67 (s, 1H). LCMS (Method-H): retention time 0.62 min, [M+H] 247.0.

Intermediate 32

Intermediate 32 was prepared (1.00 g, 78.00%), by using a similar synthetic protocol as that of Intermediate 9 and starting from Intermediate 32E (1.30 g, 5.28 mmol). $^1$H NMR (300 MHz, DMSO-$d_6$) δ ppm 3.41 (s, 3H), 7.58 (d, J=8.31 Hz, 1H), 7.69-7.80 (m, 1H), 7.98 (d, J=2.27 Hz, 1H), 9.55 (s, 1H), 10.13 (s, 1H). LCMS (Method-D): retention time 2.55 min, [M+H] 245.0.

Intermediate 33: 1-(7-fluoro-3-methyl-2-oxo-2,3-dihydrobenzo[d]oxazol-5-yl)-1H-pyrazole-4-carbaldehyde

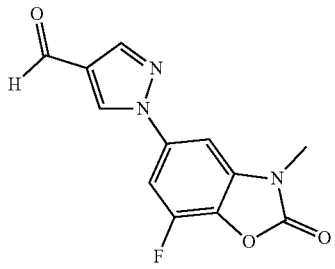

Intermediate 33A: 5-bromo-7-fluorobenzo[d]oxazol-2(3H)-one

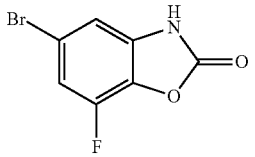

A solution of 2-amino-4-bromo-6-fluorophenol (2.00 g, 9.71 mmol) and CDI (1.73 g, 10.68 mmol) in THF (20 mL) was heated at 70° C. for 2 h. The reaction mixture was concentrated to dryness and diluted with water (30 mL). The precipitated solid was filtered and dried under reduced pressure to obtain Intermediate 33A (2.00 g, 89.00%) as an off-white solid. $^1$H NMR (400 MHz, DMSO-$d_6$) δ 8 7.13 (d, J=1.50 Hz, 1H), 7.34 (dd, J=10.00, 2.0 Hz, 1H), 7.82 (br.s, 1H). LCMS: (Method-I) retention time: 1.17 min, [M+2]: 232.0.

Intermediate 33B: 5-bromo-7-fluoro-3-methylbenzo[d]oxazol-2(3H)-one

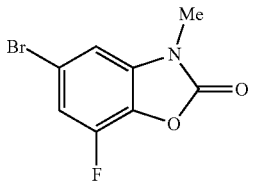

Intermediate 33B was prepared (1.90 g, 90.00%) as a black solid, by using a similar synthetic protocol as that of Intermediate 32B and starting from Intermediate 33A (2.00 g, 8.62 mmol).

$^1$H NMR (400 MHz, $CDCl_3$) δ 3.40 (s, 3H), 6.94 (dd, J=1.60, 0.90 Hz, 1H), 7.10 (dd, J=9.3, 1.8 Hz, 1H). LCMS: (Method-I) retention time: 1.17 min, [M+2]: 248.0.

Intermediate 33

Intermediate 33 was prepared (0.06 g, 11.30%) as a brown solid, by using a similar synthetic protocol as that of Intermediate 6 and starting from Intermediate 33B (0.50 g, 2.03 mmol) and pyrazole-4-carbaldehyde (0.49 g, 5.08 mmol). $^1$H NMR (400 MHz, DMSO-$d_6$) δ ppm 3.41 (s, 3H), 7.73 (dd, J=11.55, 2.01 Hz, 1H), 7.79 (d, J=2.01 Hz, 1H), 8.32 (s, 1H) 9.26 (s, 1H), 9.93 (s, 1H). LCMS: (Method-L) retention time: 0.95 min, [M+1]: 262.0.

Intermediate 34: 1-(3,7-dimethyl-2-oxo-2,3-dihydrobenzo[d]oxazol-5-yl)-1H-pyrazole-4-carbaldehyde

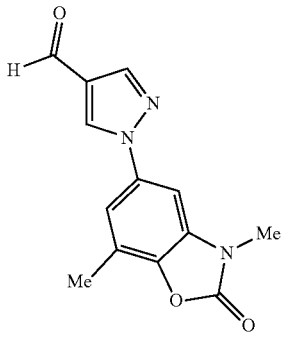

Intermediate 34A: 4-bromo-2-methyl-6-nitrophenol

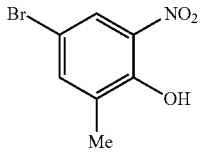

To a suspension of 4-bromo-2-methylphenol (3.00 g, 16.04 mmol) in water (25 mL) was added AcOH (1.84 mL, 32.10 mmol) followed by nitric acid (3.58 mL, 80.00 mmol) at 0° C. and the resultant reaction mixture was stirred at ambient temperature for 30 minutes. The reaction mixture was diluted with water (50 mL) and extracted with ethyl acetate (2×100 mL). The combined organic layers were washed with brine (50 mL), dried over anhydrous sodium sulfate and evaporated under reduced pressure. The residue was purified by column chromatography (Redisep—40 g, 0-15% EtOAc/n-Hexane) to obtain Intermediate 34A (1.20 g, 30.00%) as a yellow solid. $^1$H NMR (300 MHz, DMSO-$d_6$) δ ppm 2.34 (s, 3H), 8.38 (dd, J=3.02, 0.76 Hz, 1H), 8.59 (d, J=3.02 Hz, 1H), (Exchangeable proton not observed). LCMS (Method-D) retention time: 2.93 min, [M+2]: 234.0

Intermediate 34B: 2-amino-4-bromo-6-methylphenol

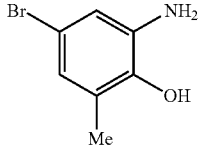

To a solution of tin (II) chloride (5.31 g, 28.00 mmol) and conc. HCl (6.00 mL, 197.00 mmol) in MeOH (25 mL) at 0° C. was added Intermediate 34A (1.30 g, 5.60 mmol). The reaction mixture was stirred at ambient temperature for 14 h, concentrated under reduced pressure and diluted with water (100 mL). The mixture was basified using saturated $NaHCO_3$, filtered through Celite® and the filtrate was extracted with DCM (2×75 ml). The combined organic extracts were dried over anhydrous sodium sulfate and concentrated under reduced pressure to obtain Intermediate 34B (0.90 g, 80.00%) as a brown solid. $^1$H NMR (300 MHz, DMSO-$d_6$) δ ppm 2.15 (s, 3H), 4.83 (br. s., 2H), 6.44 (d, J=2.64 Hz, 1H), 6.61 (d, J=2.27 Hz, 1H), 8.06 (br. s., 1H). LCMS: (Method-D) retention time: 2.93 min, [M+2]: 204.0

Intermediate 34C: 5-bromo-7-methylbenzo[d]oxazol-2(3H)-one

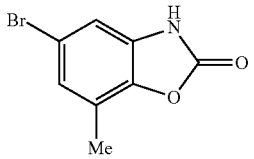

Intermediate 34C was prepared (0.85 g, 84.00%) as a light brown solid, by using a similar synthetic protocol as that of Intermediate 33A and starting from Intermediate 34B (0.90 g, 4.45 mmol). $^1$H NMR (400 MHz, DMSO-$d_6$) δ ppm 2.28 (s, 3H) 7.08 (d, J=1.51 Hz, 1H) 7.14 (s, 1H), 11.80 (br.s., 1H). LCMS: (Method-D) retention time: 2.93 min, [M+2]: 230.0.

Intermediate 34D: 5-bromo-3,7-dimethylbenzo[d]oxazol-2(3H)-one

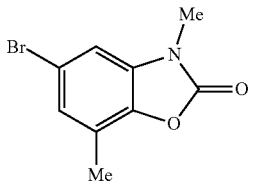

Intermediate 34D was prepared (0.90 g, 89.00%) as a light brown solid, by using a similar synthetic protocol as that of Intermediate 32B and starting from Intermediate 34C (0.95 g, 4.17 mmol). $^1$H NMR (400 MHz, $CDCl_3$) δ ppm 2.35 (s, 3H), 3.37 (s, 3H), 6.94 (d, J=1.51 Hz, 1H), 7.08-7.10 (m, 1H). LCMS: (Method-H) retention time: 2.09 min, [M+$H_2O$]: 260.0.

Intermediate 34

Intermediate 34 was prepared (0.08 g, 15.06%) as an off-white solid, by using a similar synthetic protocol as that of Intermediate 6 and starting from Intermediate 34D (0.50 g, 2.07 mmol). $^1$H NMR (400 MHz, DMSO-$d_6$) δ ppm 2.39 (s, 3H), 3.38 (s, 3H), 7.58 (s, 1H), 7.70 (d, J=2.01 Hz, 1H), 8.28 (s, 1H), 9.19 (s, 1H), 9.92 (s, 1H). LCMS: (Method-L) retention time: 0.94 min, [M+1]: 258.4.

Intermediate 35: 1-(7-methoxy-3-methyl-2-oxo-2,3-dihydrobenzo[d]oxazol-5-yl)-1H-pyrazole-4-carbaldehyde

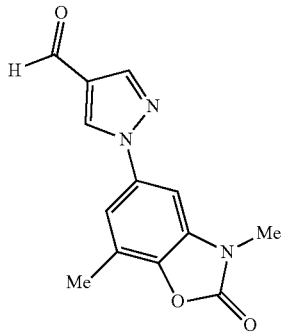

Intermediate 35A: 4-bromo-2-methoxy-6-nitrophenol

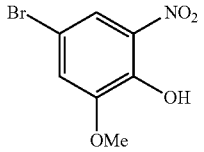

To a stirred solution of 4-bromo-2-methoxyphenol (4.50 g, 22.16 mmol) in a mixture of diethyl ether (30 mL) and water (10 mL), was added nitric acid (1.19 mL, 26.6 mmol) over 5 minutes. The resulting reaction mixture was stirred at ambient temperature for 30 minutes, diluted with water (50 mL) and extracted with ethyl acetate (2×100 mL). The combined organic layer was washed with brine (50 mL), dried over anhydrous sodium sulfate and evaporated under reduced pressure. The residue was purified by column chromatography (Redisep—40 g, 0-20% EtOAc/n-Hexane) to obtain Intermediate 35A (2.50 g, 45.50%) as a yellow solid. $^1$H NMR (400 MHz, DMSO-$d_6$) δ ppm 3.90 (s, 3H), 7.43 (d, J=2.51 Hz, 1H), 7.60-7.64 (m, 1H), 10.70 (br. s., 1H). LCMS: (Method I) retention time: 0.94 min, [M+2]: 250.2.

Intermediate 35B: 2-amino-4-bromo-6-methoxyphenol

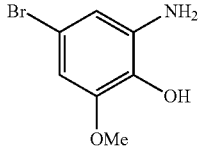

Intermediate 35B was prepared (1.50 g, 68.30%) as off-white solid, by using a similar synthetic protocol as that of Intermediate 34B and starting from Intermediate 35A (2.50 g, 10.08 mmol). $^1$H NMR (400 MHz, DMSO-$d_6$) δ ppm 3.73 (s, 3H), 4.79 (br. s., 2H), 6.36 (d, J=2.01 Hz, 1H), 6.43-6.47 (m, 1H), 8.34 (br. s., 1H). LCMS: (Method-D) retention time: 1.51 min, [M+2]: 220.0.

Intermediate 35C: 5-bromo-7-methoxybenzo[d]oxazol-2(3H)-one

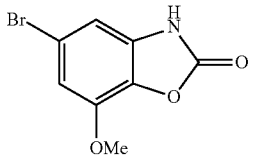

Intermediate 35C was prepared (1.50 g, 82.00%) as an off-white solid, by using a similar synthetic protocol as that of Intermediate 33A and starting from Intermediate 35B (1.63 g, 7.48 mmol). $^1$H NMR (300 MHz, DMSO-$d_6$) δ ppm 3.90 (s, 3H), 6.89 (d, J=1.13 Hz, 1H), 7.01 (d, J=1.51 Hz, 1H), 11.80 (br. s., 1H). LCMS: (Method-D) retention time: 1.79 min, [M+2]: 246.0.

Intermediate 35D: 5-bromo-7-methoxy-3-methylbenzo[d]oxazol-2(3H)-one

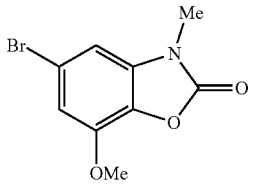

Intermediate 35D was prepared (1.40 g, 88.00%) as an off-white solid, by using a similar synthetic protocol as that of Intermediate 32B and starting from Intermediate 35C (1.50 g, 6.15 mmol). $^1$H NMR (300 MHz, DMSO-$d_6$) δ ppm 3.31 (s, 3H), 3.91 (s, 3H), 7.06 (d, J=1.51 Hz, 1H), 7.19 (d, J=1.13 Hz, 1H). LCMS: (Method-H) retention time 1.84 min, [M+$H_2O$]: 275.0.

Intermediate 35

Intermediate 35 was prepared (0.24 g, 45.30%) as an off-white solid, by using a similar synthetic protocol as that of Intermediate 6 and starting from Intermediate 35D (0.50 g, 1.94 mmol). $^1$H NMR (300 MHz, DMSO-$d_6$) δ ppm 3.34 (s, 3H), 4.00 (s, 3H), 7.42 (d, J=1.89 Hz, 1H), 7.51 (d, J=1.89 Hz, 1H), 8.30 (s, 1H), 9.28 (s, 1H), 9.93 (s, 1H). LCMS: (Method-L) retention time: 0.90 min, [M+1]: 274.1.

Intermediate 36: 6-(4-formyl-3-methyl-1H-pyrazol-1-yl)-4-methylnicotinonitrile

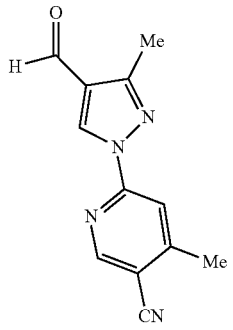

Intermediate 36 was prepared (0.21 g, 25.60%) as a beige solid, by using a similar synthetic protocol as that of Intermediate 6 and starting from 3-methyl-1H-pyrazole-4-carbaldehyde (0.40 g, 3.63 mmol) and 6-bromo-4-methylnicotinonitrile. $^1$H NMR (400 MHz, DMSO-$d_6$) δ ppm 2.52 (s, 3H), 2.6 (s, 3H), 8.01 (s, 1H), 8.90 (s, 1H), 9.28 (s, 1H), 10.00 (s, 1H). LCMS: (method-H) retention time 1.85 min, [M+H] 227.0.

Intermediate 37: 6-(3-formyl-1H-pyrazol-1-yl)-4-methylnicotinonitrile

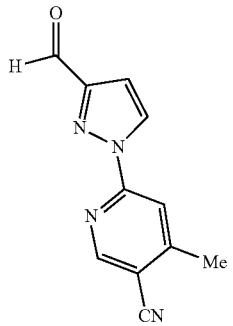

Intermediate 37 was prepared (0.27 g, 30.50%), by using a similar synthetic protocol as that of Intermediate 6 and starting from 1H-pyrazole-3-carbaldehyde (0.40 g, 4.16 mmol) and 6-bromo-4-methylnicotinonitrile. $^1$H NMR (400 MHz, DMSO-$d_6$) δ ppm 2.50-2.68 (s, 3H), 7.20-7.22 (s, 1H), 8.03 (s, 1H), 8.09-8.17 (s, 1H), 8.95-8.99 (s, 1H), 10.48 (s, 1H). LCMS: (method-I) retention time 1.00 min, [M+H] 213.0.

Intermediate 38-I: 5-((2R,6R)-6-(hydroxymethyl) piperazin-2-yl)-4-methylisobenzofuran-1(3H)-one

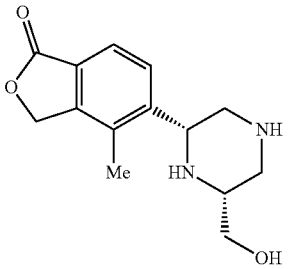

Intermediate 38A: methyl 6-(4-methyl-1-oxo-1,3-dihydroisobenzofuran-5-yl)pyrazine-2-carboxylate

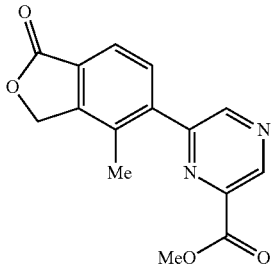

Intermediate 38A was prepared (6.20 g, 75.00%) as an off-white solid, by using a similar synthetic protocol as that of Intermediate 2C and starting from Intermediate 2B (8.74 g, 31.90 mmol) and 6-chloropyrazine-2-carboxylate (5.00 g, 29.00 mmol). $^1$H NMR (400 MHz, DMSO-$d_6$) δ ppm 2.34 (s, 3H), 3.96 (s, 3H), 5.52 (s, 2H), 7.76 (d, J=8.03 Hz, 1H), 7.85 (d, J=7.53 Hz, 1H), 9.16 (s, 1H), 9.26 (s, 1H). LCMS (Method-J): retention time 1.15 min, [M+H] 285.2.

Intermediate 38B: methyl 6-(4-methyl-1-oxo-1,3-dihydroisobenzofuran-5-yl)piperazine-2-carboxylate

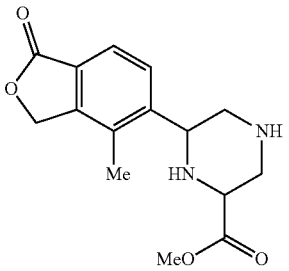

Intermediate 38B was prepared (4.00 g, 97.00%), by using a similar synthetic protocol as that of Intermediate 2-I and starting from Intermediate 38A (4.00 g, 14.07 mmol). $^1$H NMR (400 MHz, DMSO-$d_6$) δ ppm 2.25-2.32 (m, 4H), 2.54-2.62 (m, 1H), 2.82 (d, J=12.55 Hz, 1H), 3.10 (d, J=12.05 Hz, 1H), 3.54-3.60 (m, 1H), 3.70 (s, 3H), 4.06 (d, J=8.03 Hz, 1H), 5.32-5.43 (m, 2H), 7.62-7.71 (m, 1H), 7.76-7.83 (m, 1H), (2 Exchangeable protons not observed). LCMS (Method-I): retention time 0.49 min, [M+H] 291.5.

Intermediate 38C: 1-(tert-butyl) 3-methyl 5-(4-methyl-1-oxo-1,3-dihydroisobenzofuran-5-yl)piperazine-1,3-dicarboxylate

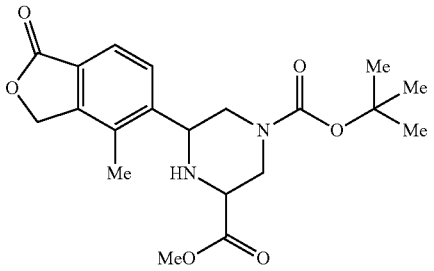

Intermediate 38C was prepared (4.50 g, 95.00%), by using a similar synthetic protocol as that of Intermediate 18B-II and starting from Intermediate 38B (3.50 g, 12.06 mmol). $^1$H NMR (400 MHz, DMSO-$d_6$) δ ppm 1.31-1.51 (m, 9H), 2.26-2.39 (m, 3H), 2.74-2.95 (m, 1H), 3.06 (br. s., 1H), 3.58 (d, J=8.03 Hz, 1H), 3.72 (s, 3H), 3.82-3.94 (m, 1H), 4.03 (d, J=8.53 Hz, 1H), 4.13-4.28 (m, 1H), 5.38-5.46 (m, 2H), 7.64-7.76 (m, 1H), 7.82 (d, J=7.53 Hz, 1H), (1 Exchangeable proton not observed). LCMS (Method-I): retention time 1.17 min, [M+H] 391.6.

Intermediate 38D-I, II, III and IV: tert-butyl 3-(hydroxymethyl)-5-(4-methyl-1-oxo-1,3-dihydroisobenzofuran-5-yl)piperazine-1-carboxylate

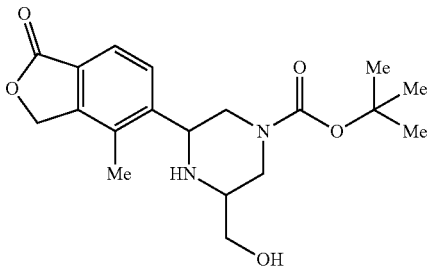

To a solution of Intermediate 38C (6.20 g, 11.12 mmol) in a mixture of THF (50 mL) and EtOH (50 mL) was added LiCl (0.94 g, 22.23 mmol) and $NaBH_4$ (0.84 g, 22.23 mmol) under a nitrogen atmosphere and the reaction mixture was stirred at ambient temperature for 14 h. The reaction mixture was quenched with 10% aqueous solution of sodium bicarbonate (150 mL) and extracted with ethyl acetate (3×150 mL). The combined organic layers were washed with brine (100 mL), dried over anhydrous sodium sulfate and evaporated under reduced pressure. The residue was purified by preparative HPLC [Sunfire OBD (250×30 ID) 5 micron; Solvent A: 10 mM Ammonium acetate in water, Solvent B: Acetonitrile, Gradient: 30-100% B over 16 min, Flow: 25 mL/min] to obtain diastereomer-I and II. The diastereomer-I was separated into two individual enantiomers by supercritical fluid chromatography (SFC) [Chiralpak ADH (250×4.6 mm) 5 micron; 0.2% $NH_4OH$ in MeOH, Flow: 3.0 mL/min. Temperature: 30° C., UV: 210 nm]. First eluted compound (retention time 2.67 min), designated as Intermediate 38D-I, was obtained (1.10 g, 27.30%) as white solid. $^1$H NMR (400 MHz, DMSO-$d_6$) δ ppm 1.42 (s, 9H), 2.32 (s, 3H), 2.78 (dd, J=10.79, 3.26 Hz, 1H), 3.37-3.43 (m, 3H), 3.79-4.11 (m, 4H), 4.73 (br. s., 1H), 5.41 (s, 2H), 7.69 (d, J=8.03 Hz, 1H), 7.81 (d, J=8.03 Hz, 1H), (1 Exchangeable proton not observed). LCMS (Method-I): retention time 0.97 min, [M+H] 363.2. Chiral purity (Method-XII): retention time 2.69 min, 100% ee. SOR: $[\alpha]^{25}$ D=−26.00 (c 0.1, MeO H).

Second eluted compound (retention time 3.72 min), designated as Intermediate 38D-II, was obtained (1.10 g, 27.30%) as white solid. $^1$H NMR (400 MHz, DMSO-$d_6$) δ ppm 1.42 (s, 9H), 2.32 (s, 3H), 2.78 (dq, J=13.62, 2.99 Hz, 1H), 3.38-3.44 (m, 3H), 3.82-4.12 (m, 4H), 4.74 (br. s., 1H), 5.41 (s, 2H), 7.69 (d, J=8.03 Hz, 1H), 7.81 (d, J=8.03 Hz, 1H), (1 Exchangeable proton not observed). LCMS (Method-I): retention time 0.97 min, [M+H] 363.2. Chiral purity (Method-XII): retention time 3.81 min, 100% ee.

The diastereomer-II was separated into two individual enantiomers by SFC [Luxcellulose-2 (250×21.5 mm) 5 micron; 0.2% $NH_4OH$ in MeOH+ACN (1:1) Flow: 3.0 g/min. Temperature: 30° C., UV: 235 nm]. First eluted compound (retention time 6.64 min), designated as Intermediate 38D-III, was obtained (0.25 g, 6.21%) as an off-white solid. $^1$NMR (400 MHz, DMSO-$d_6$) δ ppm 1.41 (s, 9H), 2.26-2.37 (m, 3H), 2.96 (br. s., 1H), 3.39 (br. s., 2H), 3.57 (d, J=10.54 Hz, 2H), 3.70-3.92 (m, 3H), 4.67 (br. s., 1H), 5.40 (s, 2H), 7.68 (d, J=8.03 Hz, 1H), 7.84 (d, J=8.03 Hz, 1H), (1 Exchangeable proton not observed). LCMS (Method-I): retention time 0.92 min, [M+H] 363.2. Chiral purity (Method-XIX): retention time 6.69 min, 100% ee. SOR: $[\alpha]^{25}$ D=+26.00 (c 0.1, MeO H). Second eluted compound (retention time 8.49 min), designated as Intermediate 38D-IV, was obtained as a white solid (0.25 g, 6.21%). $^1$H NMR (400 MHz, DMSO-$d_6$) δ ppm 1.41 (s, 9H), 2.28-2.36 (m, 3H), 2.96 (br. s., 1H), 3.35-3.46 (m, 2H), 3.58 (br. s., 3H), 3.75 (d, J=14.05 Hz, 1H), 4.67 (t, J=5.27 Hz, 2H), 5.40 (s, 2H), 7.68 (d, J=8.03 Hz, 1H), 7.84 (d, J=8.03 Hz, 1H), (1 Exchangeable proton not observed). LCMS (Method-I): retention time 0.92 min, [M+H] 363.2. Chiral purity (Method-XIX): retention time 8.62 min, 100% ee.

Intermediate 38-I

To a solution of Intermediate 38D-I (1.50 g, 4.14 mmol) in MeOH (50 mL) was added 4 N HCl in dioxane (20 mL, 80 mmol). The reaction mixture was stirred at ambient temperature for 1 h and was concentrated to dryness. The residue was diluted with MeOH (100 mL), cooled to 0° C. and ammonia was purged through it for 5 min. The resulting clear solution was concentrated under reduced pressure to obtain Intermediate 38-I (1.00 g, 92.00%). The compound 55 was taken directly to the subsequent step without further purification. $^1$H NMR (400 MHz, DMSO-$d_6$) δ ppm 2.31 (s, 3H), 2.59-2.77 (m, 2H), 2.82-2.95 (m, 2H), 3.38-3.44 (m, 2H), 3.73 (br. s., 1H), 3.87 (d, J=11.04 Hz, 1H), 4.04-4.23 (m, 1H), 5.41 (s, 2H), 7.70 (d, J=7.53 Hz, 1H), 7.85 (d, J=8.03 Hz, 1H), (2 Exchangeable protons not observed). LCMS (Method-I): retention time 0.40 min, [M+H] 263.2. To determine stereochemistry of Intermediate 38-I, 5-((2R, 6R)-4-(4-bromobenzoyl)-6-(hydroxymethyl)piperazin-2yl)-4-methylisobenzofuran-1(3H)-one was prepared according to literature procedure (US2002/156081A1, 2002), and absolute configuration was determined by single-crystal X-ray diffraction method.

Intermediate 39-I: 5-(6-(hydroxymethyl-$d_2$)piperazin-2-yl)-4-methylisobenzofuran-1(3H)-one

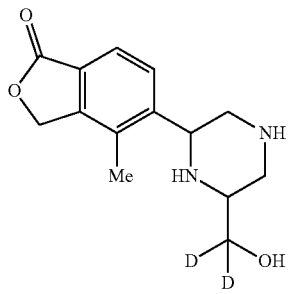

Intermediate 39A-I, II, III and IV: tert-butyl 3-(hydroxymethyl-$d_2$)-5-(4-methyl-1-oxo-1,3-dihydroisobenzofuran-5-yl)piperazine-1-carboxylate

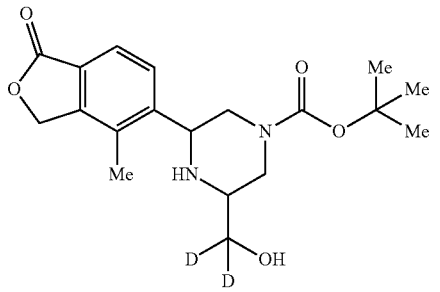

Intermediate 39A-I, II, III and IV was prepared, by using a similar synthetic protocol as that of Intermediate 38A-I, II, III and IV and starting from Intermediate 38C (1.40 gm, 2.51 mmol and $NaBD_4$ (0.21 g, 5.02 mmol). The crude residue was purified by preparative HPLC [Sunfire OBD (250×30 ID) 5 micron; Solvent A: 10 mM Ammonium acetate in water, Solvent B: Acetonitrile, Gradient: 30-100% B over 16 min, Flow: 25 mL/min] to obtain diastereomer-I and II. The diastereomer-I was separated into two individual enantiomers by SFC [Chiralpak ADH (250×4.6 mm) 5 micron; 0.2% $NH_4OH$ in MeOH, Flow: 3.0 g/min. Temperature: 30° C., UV: 210 nm]. First eluted compound (retention time 2.67 min), designated as Intermediate 39A-I, was obtained (0.20 g, 21.80%) as white solid. $^1$H NMR (400 MHz, DMSO-$d_6$) δ ppm 1.43 (s, 9H), 2.33 (s, 3H), 2.39-2.47 (m, 2H), 2.65-2.81 (m, 2H), 3.86-4.14 (m, 3H), 4.72 (s, 1H), 5.42 (s, 2H), 7.70 (d, J=8.03 Hz, 1H), 7.82 (d, J=8.03 Hz, 1H). LCMS (Method-I): retention time 0.97 min, [M+H] 365.3. Chiral purity (Method-XII): retention time 2.27 min, 100% ee. Second eluted compound (retention time 3.72 min), designated as Intermediate 39A-II, was obtained (0.20 g, 21.80%) as white solid. $^1$H NMR (400 MHz, DMSO-$d_6$) δ ppm 1.43 (s, 9H), 2.33 (s, 3H), 2.38-2.47 (m, 2H), 2.67-2.83 (m, 2H), 3.84-4.08 (m, 3H), 4.69-4.75 (m, 1H), 5.42 (s, 2H), 7.70 (d, J=8.03 Hz, 1H), 7.82 (d, J=8.03 Hz, 1H). LCMS (Method-I): retention time 0.97 min, [M+H] 365.3. Chiral purity (Method-XII): retention time 2.97 min, 95.40% ee.

The diastereomer-II was separated into two individual enantiomers by SFC [Luxcellulose-2 (250×21.5 mm) 5 micron; 0.2% $NH_4OH$ in MeOH+ACN (1:1) Flow: 70.0 g/min. Temperature: 30+ C., UV: 235 nm]. First eluted compound (retention time 6.59 min), designated as Intermediate 39A-III, was obtained (0.05 g, 5.47%) as white solid. $^1$H NMR (400 MHz, DMSO-$d_6$) δ ppm 1.42 (s, 9H), 2.28-2.36 (m, 3H), 2.64-2.74 (m, 2H), 2.87-3.02 (m, 1H), 3.18 (s, 2H), 3.70-3.94 (m, 2H), 4.26 (d, J=9.54 Hz, 1H), 5.42 (s, 2H), 7.69 (d, J=8.03 Hz, 1H), 7.85 (d, J=8.03 Hz, 1H). LCMS (Method-I): retention time 0.93 min, [M+H] 365.3. Chiral purity (Method-XIX): retention time 6.56 min, 100% ee. Second eluted compound (retention time 8.32 min), designated as Intermediate 39A-IV, was obtained (0.05 g, 5.47%) as white solid. $^1$H NMR (400 MHz, DMSO-$d_6$) δ ppm 1.42 (s, 9H), 2.28-2.37 (m, 3H), 2.66-2.72 (m, 2H), 2.87-3.02 (m, 1H), 3.18 (s, 2H), 3.70-3.94 (m, 2H), 4.26 (d, J=10.54 Hz, 1H), 5.42 (s, 2H), 7.69 (d, J=8.03 Hz, 1H), 7.85 (d, J=7.53 Hz, 1H). LCMS (Method-I): retention time 0.93 min, [M+H] 365.3. Chiral purity (Method-XIX): retention time 8.32 min, 98% ee.

Intermediate 39-I

Intermediate 39-I was prepared (0.13 g, 93.00%) as an off-white solid, by using a similar synthetic protocol as that of Intermediate 38-I and starting from Intermediate 39A-I (0.20 g, 0.55 mmol). $^1$H NMR (400 MHz, DMSO-$d_6$) δ ppm 2.34 (s, 3H), 2.57-2.69 (m, 2H), 3.17 (d, J=10.54 Hz, 1H), 3.21-3.31 (m, 2H), 4.59 (d, J=9.54 Hz, 1H), 4.96 (br. s., 1H), 5.33-5.48 (m, 2H), 7.70 (d, J=8.03 Hz, 1H), 7.80 (d, J=8.03 Hz, 1H), (2 Exchangeable proton not observed). LCMS (Method-I): retention time 0.39 min, [M+H] 265.2.

Intermediate 40-I: 5-(6,6-dimethylpiperazin-2-yl)-4-methylisobenzofuran-1(3H)-one

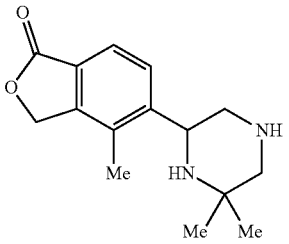

Intermediate 40A: 5-(2-bromoacetyl)-4-methylisobenzofuran-1(3H)-one

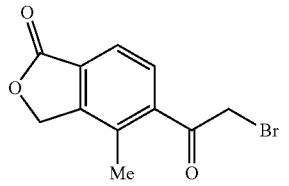

Synthesized according to similar literature procedure (WO2010/129379, A1 , 2010)

Intermediate 40B: 2-(4-methyl-1-oxo-1,3-dihydroisobenzofuran-5-yl)-2-oxoacetaldehyde

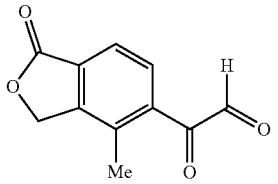

To a solution of Intermediate 40A (2.65 g, 7.88 mmol) in a mixture of DMSO (15 mL) and water (0.142 mL) was added 48% HBr in water (0.018 mL, 0.158 mmol) and the reaction mixture was heated at 80° C. for 5 h. The reaction mixture was cooled to room temperature, diluted with water (50 mL), basified by 10% aqueous solution of sodium bicarbonate (50 mL) and extracted with ethyl acetate (3×50 mL). The combined organic layers were washed with brine (30 mL), dried over anhydrous sodium sulfate and evaporated under reduced pressure to obtain Intermediate 40B (1.00 g, 43.50%) as an off-white solid. The compound was taken directly to the subsequent step without further purification. $^1$H NMR (400 MHz, DMSO-$d_6$) δ ppm 2.29 (s, 3H), 5.54 (br. s., 2H), 7.20 (dd, J=8.07, 0.98 Hz, 1H), 7.74-7.88 (m, 1H), 7.95 (d, J=8.31 Hz, 1H). LCMS (Method-I): retention time 0.82 min, [M−H] 203.0.

Intermediate 40C: tert-butyl 3,3-dimethyl-5-(4-methyl-1-oxo-1,3-dihydroisobenzofuran-5-yl)piperazine-1-carboxylate

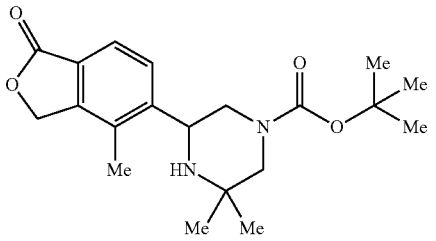

To a solution of Intermediate 40B (0.95 g, 3.72 mmol) in a mixture of THF (24 mL) and MeOH (6 mL) was added 2-methylpropane-1,2-diamine (0.33 g, 3.72 mmol) and the reaction mixture was stirred at ambient temperature for 1 h. $NaBH_4$ (0.28 g, 7.44 mmol) was added and the resulting mixture was stirred for 30 min. TEA (1.556 mL, 11.17 mmol) followed by $BOC_2O$ (0.864 mL, 3.72 mmol) were added and the reaction mixture was stirred at ambient temperature for 14 h, diluted with water (100 mL) and extracted with DCM (3×50 mL). The combined organic layers were washed with brine (50 mL), dried over anhydrous sodium sulfate and evaporated under reduced pressure. The residue was purified by column chromatography (Redisep—40 g, 50% EtOAc/n-hexane) to obtain racemate (1.10 g). The racemate was separated into two individual enantiomers by SFC [Chiralpak ADH (250×21.5 mm) 5 micron; 0.2% $NH_4OH$ in MeOH+ACN (1:1), Flow; 3.0 g/min. Temperature: 30° C., UV: 235 nm]. First eluted compound (retention time 3.02 min), designated as Intermediate 40C-I, was obtained (0.40 g, 29.80%) as white solid. $^1$H NMR (400 MHz, DMSO-$d_6$) δ ppm 1.13 (d, J=16.56 Hz, 6H), 1.37-1.48 (m, 9H), 2.34 (s, 3H), 2.64-2.77 (m, 2H), 3.71 (br. s., 1H), 3.97 (br. s., 1H), 4.26 (d, J=8.03 Hz, 1H), 5.33-5.48 (m, 2H), 7.70 (d, J=8.03 Hz, 1H), 7.83 (d, J=8.03 Hz, 1H), (1 Exchangeable proton not observed). LCMS (Method-I): retention time 1.61 min, [M+H] 361.4. Chiral purity (Method-XII): retention time 3.04 min, 100% ee. Second eluted compound (retention time 4.42 min), designated as Intermediate 40C-II, was obtained (0.40 g, 29.80%) as white solid. $^1$H NMR (400 MHz, DMSO-$d_6$) δ ppm 1.13 (d, J=16.56 Hz, 6H), 1.44 (s, 9H), 2.30-2.40 (m, 3H), 2.68 (d, J=2.01 Hz, 2H), 3.73 (br. s., 1H), 3.94 (s, 1H), 4.26 (d, J=9.54 Hz, 1H), 5.42 (s, 2H), 7.70 (d, J=8.03 Hz, 1H), 7.83 (d, J=8.03 Hz, 1H) (1 Exchangeable proton not observed). LCMS (Method-I): retention time 1.61 min, [M+H] 361.4. Chiral purity (Method-XII): retention time 4.44 min, 100% ee.

Intermediate 40-I

Intermediate 40-I was prepared (0.26 g, 90.00%) as a pale yellow solid, by using a similar synthetic protocol as that of Intermediate 38-I and starting from Intermediate 40C-I (0.40 g, 1.11 mmol). $^1$H NMR (400 MHz, $CDCl_3$) δ ppm 1.06 (s, 3H), 1.28 (s, 3H), 2.42 (s, 3H), 2.46 (dd, J=12.01, 10.51 Hz, 1H), 2.54-2.60 (m, 1H), 2.64-2.71 (m, 1H), 2.95 (dt, J=12.01, 1.50 Hz, 1H), 4.31 (dd, J=10.51, 2.75 Hz, 1H), 5.12-5.20 (m, 2H), 7.63-7.70 (m, 1H), 7.71-7.78 (m, 1H), (2 Exchangeable protons not observed). LCMS (Method-I): retention time 0.47 min, [M−H] 261.3.

Intermediate 41: 6-(4-formyl-1H-pyrazol-1-yl)-2-methoxynicotinonitrile

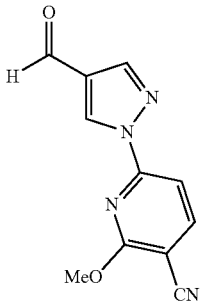

Intermediate 41A: 6-chloro-2-methoxynicotinonitrile and Intermediate 41B: 2-chloro-6-methoxynicotinonitrile

41A

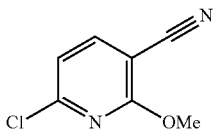

41B

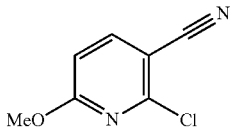

To a solution of 2,6-dichloronicotinonitrile (0.50 g, 2.89 mmol) in MeOH (10 mL) was added sodium methoxide (0.62 g, 2.89 mmol) at ambient temperature and the resulting mixture was stirred at 60° C. for 12 h. The reaction mixture was cooled to ambient temperature, concentrated to dryness under reduced pressure. The residue was diluted with water (50 mL) and extracted with ethyl acetate (3×50 mL). The combined organic layers were washed with brine (30 mL), dried over anhydrous sodium sulfate and evaporated under reduced pressure. The residue was purified by preparative HPLC [Xbridge Phenyl (250×21.2 ID) 5 micron; Solvent A: 0.1% TFA in water, Solvent B: Acetonitrile, Gradient: 0-100% B over 20 min, Flow: 20 mL/min, UV 220 nm]. First eluted compound (retention time 15.34 min), designated as Intermediate 41A, was obtained (0.10 g, 19.70%) as white solid, $^1$H NMR (400 MHz, $CDCl_3$) δ ppm 4.08 (s, 3H), 7.02 (d, J=7.83 Hz, 1H), 7.82 (d, J=7.83 Hz, 1H). LCMS (Method-D): retention time 1.94 min, [M+1H] 169.2. Second eluted compound (retention time 16.74 min), designated as Intermediate 41B, was obtained (0.04 g, 1.64%) as an off-white solid. $^1$H NMR (400 MHz, DMSO-d6) b ppm 3.95 (s, 3H), 7.07 (s, 1H), 8.29 (d, J=8.53 Hz, 1H). LCMS (Method-D): retention time 1.89 min, [M+1H] 169.2. Structure of Intermediate 41A and 41B was determined by single-crystal X-ray diffraction method.

Intermediate 41

Intermediate 41 was prepared (0.15 g, 62.20%) as pale yellow solid, by using a similar synthetic protocol as that of Intermediate 11 and starting from Intermediate 41A (0.16 g, 0.98 mmol). $^1$H NMR (400 MHz, DMSO-d6) δ ppm 4.15 (s, 3H), 7.65-7.67 (d, J=6 Hz, 1H), 8.38 (s, 1H), 8.45-8.47 (d, J=6 Hz, 1H), 9.44 (s, 1H), 9.99 (s, 1H). LCMS: The compound did not ionize well.

Intermediate 42: 2-(4-formyl-1H-imidazol-1-yl)-4,6-dimethylpyrimidine-5-carbonitrile

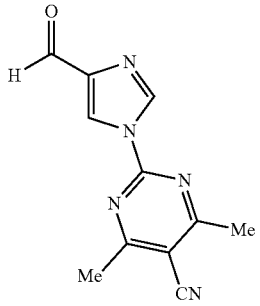

Intermediate 42A: 5-bromo-4,6-dimethylpyrimidin-2-amine

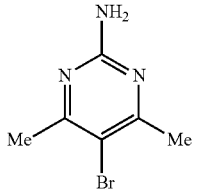

Synthesized according to literature procedures (WO2011/103536 A1, 2011).

Intermediate 42B:
2-amino-4,6-dimethylpyrimidine-5-carbonitrile

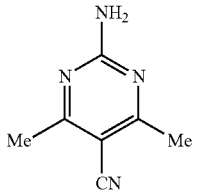

To a solution of Intermediate 42A (6.00 g, 29.70 mmol) in DMF (50 mL) was added copper (I) cyanide (3.99 g, 44.55 mmol) and the resulting mixture was heated at 180° C. for 16 h. The reaction mixture was cooled to ambient temperature, diluted with water (50 mL) and ethyl acetate (100 mL). The resulting mixture was filtered through Celite® and the filtrate was concentrated under reduced pressure to obtain Intermediate 42B (3.00 g, 54.00%). The compound was taken directly to the subsequent step without further purification. $^1$H NMR (400 MHz, DMSO-$d_6$) δ ppm 2.32-2.41 (m, 6H), 7.533 (s, 2H). LCMS (Method-D): retention time 0.72 min, [M+H] 149.1.

Intermediate 42C:
2-bromo-4,6-dimethylpyrimidine-5-carbonitrile

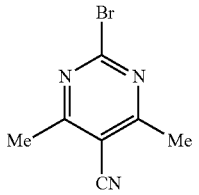

To a solution of isoamyl nitrite (4.91 mL, 36.4 mmol) in acetonitrile (50 mL) at 0° C. was added copper(II)bromide (8.14 g, 36.40 mmol). The resulting reaction mixture was stirred at ambient temperature for 10 minutes and Intermediate 42B (2.70 g, 18.22 mmol) in acetonitrile (10 mL) was added and the stirring was continued for 3 h. The reaction mixture was diluted with water (30 mL) and extracted with ethyl acetate (3×50 mL). The combined organic layers were washed with brine (30 mL), dried over anhydrous sodium sulfate and evaporated under reduced pressure. The residue was purified by column chromatography (Redisep—40 g, 10-20% EtOAc/n-hexane) to obtain Intermediate 42C (0.90 g, 23.90%). $^1$H NMR (400 MHz, DMSO-$d_6$) δ ppm 2.50-2.63 (m, 6H). LCMS (Method-D): retention time 1.692 min, [M+H] 211.9.

Intermediate 42

To a solution of 1H-imidazole-4-carbaldehyde (0.50 g, 5.20 mmol) and Intermediate 42C (1.10 g, 5.20 mmol) in DMF (15 mL) was added triethylamine (2.18 mL, 15.61 mmol). The resulting reaction mixture was stirred at ambient temperature for 1.5 h. The reaction mixture was concentrated to dryness under reduced pressure. The residue was purified by column chromatography (Redisep—24 g, 40% EtOAc/n-hexane) to obtain Intermediate 42 (0.25 g, 21.14%) as white solid. $^1$H NMR (400 MHz, DMSO-$d_6$) δ ppm 2.89-2.73 (s, 6H), 8.80 (s, 2H), 9.88 (s, 1H). LCMS (method-D): retention time 1.41 min, [M+H] 228.2.

Intermediate 43: 2-(4-formyl-1H-pyrazol-1-yl)-4-methylpyrimidine-5-carbonitrile

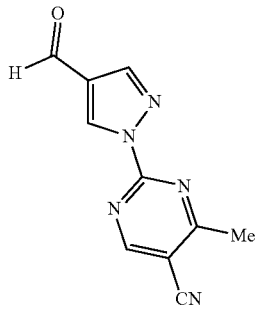

Intermediate 43A: (E)-2-((dimethylamino)methylene)-3-oxobutanenitrile

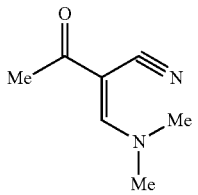

To a solution of 3-oxobutanenitrile (10.00 g, 120.00 mmol) in DMF (30 mL) was added DMF-DMA (19.34 mL, 144.00 mmol) and the resulting mixture was stirred at 80° C. for 16 h. The reaction was cooled to ambient temperature, concentrated to dryness under reduced pressure, diluted with n-hexane (200 mL). The solid precipitate was filtered and dried under vacuum to obtain Intermediate 43A (13.00 g, 78.00%). $^1$H NMR (400 MHz, DMSO-$d_6$) δ ppm 2.17 (s, 3H), 3.25 (s, 3H), 3.29 (s, 3H), 7.83 (s, 1H). LCMS (Method-L): retention time 0.54 min, [M+H] 139.2.

Intermediate 43B:
2-amino-4-methylpyrimidine-5-carbonitrile

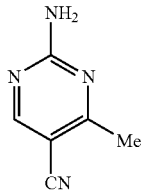

To a stirred solution of Intermediate 43A (12.00 g, 87.00 mmol) in EtOH (25 mL) was added guanidine carbonate (31.30 g, 174.00 mmol) and sodium acetate (21.37 g, 261.00 mmol) and the reaction was stirred at 80° C. for 5 h. The reaction mixture was cooled to ambient temperature, concentrated to dryness and diluted with n-hexane (200 mL).

The solid precipitate was filtered, washed with EtOH (30 mL) and dried under vacuum to obtain Intermediate 43B (9.50 g, 82.00%). $^1$H NMR (400 MHz, DMSO-$d_6$) δ ppm 2.38 (s, 3H), 7.62 (s, 2H), 8.53 (s, 1H). LCMS (Method-L): retention time 0.54 min, [M+H] 135.1.

Intermediate 43C: 2-bromo-4-methylpyrimidine-5-carbonitrile

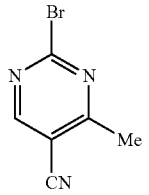

To a solution of Intermediate 43B (5.00 g, 37.30 mmol) in a mixture of THF (75 mL) and DMF (15 mL) was added copper(II)bromide (16.65 g, 74.50 mmol), isoamyl nitrite (7.53 ml, 55.9 mmol) at ambient temperature and the reaction mixture was refluxed for 1 h. The reaction mixture was cooled to ambient temperature, concentrated to dryness under reduced pressure, diluted with DCM (200 mL), solid precipitate was filtered and washed with THF (200 mL). The combined organic filtrate were washed with 10% aqueous solution of sodium bicarbonate (150 mL) and brine (50 mL), dried over anhydrous sodium sulfate and evaporated under reduced pressure. The residue was purified by column chromatography (Redisep—120 g, 0-15% EtOAc/n-Hexane) to obtain Intermediate 43C (0.75 g, 10.00%). $^1$H NMR (400 MHz, DMSO-$d_6$) δ ppm 2.65 (s, 3H), 9.08 (s, 1H). LCMS (Method-L): retention time 0.92 min, [M+2H] 199.1.

Intermediate 43

Intermediate 43 was prepared (0.04 g, 14.00%), by using a similar synthetic protocol as that of Intermediate 15C and starting from Intermediate 43C (0.30 g, 1.56 mmol) and 1H-pyrazole-4-carbaldehyde (0.18 g, 1.89 mmol). $^1$H NMR (400 MHz, DMSO-$d_6$) δ ppm 2.66 (s, 3H), 8.37 (s, 1H), 9.31 (s, 1H), 9.44 (s, 1H), 10.00 (s, 1H). LCMS (Method-L): retention time 0.74 min, [M+H] 214.1.

Intermediate 44: 2-(4-formyl-2H-1,2,3-triazol-2-yl)-4-methylpyrimidine-5-carbonitrile

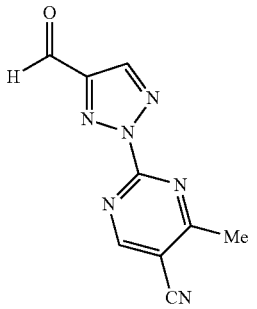

Intermediate 44A: 2-(4-(hydroxymethyl)-2H-1,2,3-triazol-2-yl)-4-methylpyrimidine-5-carbonitrile

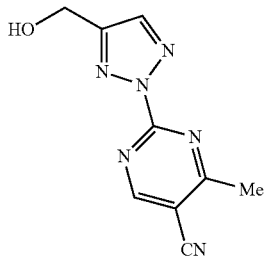

To a solution of (2H-1,2,3-triazol-4-yl)methanol (0.75 g, 0.76 mmol) in DMF (10 mL) was added $K_2CO_3$ (1.08 g, 7.81 mmol), Intermediate 43C (0.10 g, 0.50 mmol) and the reaction mixture was stirred at ambient temperature for 1 h. The reaction mixture was concentrated to dryness under reduced pressure, diluted with water (50 mL) and extracted with ethyl acetate (3×50 mL). The combined organic layers were washed with brine (30 mL), dried over anhydrous sodium sulfate and evaporated under reduced pressure to obtain Intermediate 44A (0.02 g, 18.00%). $^1$H NMR (400 MHz, DMSO-$d_6$) δ ppm 2.75 (s, 3H), 4.68 (s, 2H), 8.22 (s, 1H), 9.37 (s, 1H), (1 Exchangeable proton not observed). LCMS (Method-O): retention time 0.74 min, [M−H] 215.1.

Intermediate 44

Intermediate 44 was prepared (0.19 g, 77.00%), by using a similar synthetic protocol as that of Intermediate 9 and starting from Intermediate 44A (0.25 g, 1.16 mmol) and dess-martinperiodinane (0.61 g, 1.44 mmol). $^1$H NMR (400 MHz, DMSO-$d_6$) δ ppm 2.80 (s, 3H), 8.80 (s, 1H), 9.42 (s, 1H), 10.23 (s, 1H). LCMS (Method-O): retention time 0.59 min, [M+H] 215.1.

Intermediate 45: 2-(4-formyl-1H-pyrazol-1-yl)-4-methoxypyrimidine-5-carbonitrile

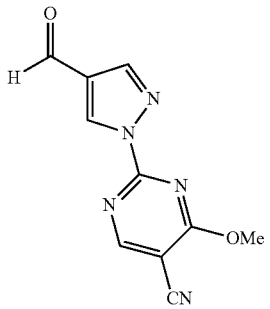

Intermediate 45A:
2-chloro-4-methoxypyrimidine-5-carbonitrile

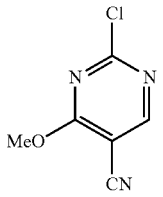

Synthesized according to literature procedures (US2015/291629 A1, 2015).

Intermediate 45

Intermediate 45 was prepared (0.15 g, 55.00%) as an off-white solid, by using a similar synthetic protocol as that of Intermediate 11 and starting from Intermediate 45A (0.20 g, 1.18 mmol) and 1H-pyrazole-4-carbaldehyde (0.17 g, 1.77 mmol). $^1$H NMR (400 MHz, DMSO-$d_6$) δ ppm 4.20 (s, 3H), 8.38 (s, 1H), 9.18 (s, 1H), 9.48 (s, 1H), 10.00 (s, 1H). LCMS (Method-O): retention time 0.75 min, [M+H] 230.1.

Intermediate 46: 2-(4-formyl-1H-imidazol-1-yl)-4-methoxypyrimidine-5-carbonitrile

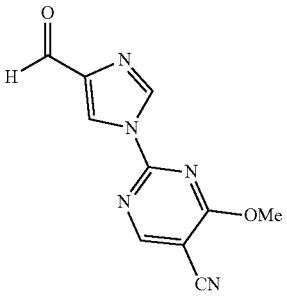

Intermediate 46 was prepared (0.75 g, 55.50%) as an off-white solid, by using a similar synthetic protocol as that of Intermediate 11 and starting from Intermediate 45A (1.00 g, 5.90 mmol)) and 1H-imidazole-4-carbaldehyde (1.13 g, 11.79 mmol). $^1$H NMR (400 MHz, DMSO-$d_6$) δ ppm 4.23 (s, 3H), 8.84 (s, 1H), 8.87 (s, 1H), 9.19 (s, 1H), 9.88 (s, 1H). LCMS (Method-I): retention time 0.80 min, [M+H] 230.2.

Intermediate 47: 6-(4-formyl-1H-imidazol-1-yl)-4-methylnicotinonitrile

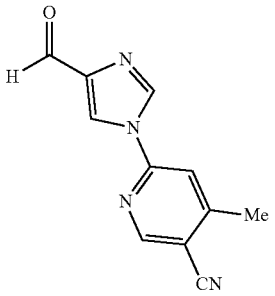

Intermediate 47 was prepared (0.10 g, 9.28%) as an off-white solid, by using a similar synthetic protocol as that of Intermediate 15C and starting from 6-bromo-4-methylnicotinonitrile (1.0 g, 5.08 mmol) and 1H-imidazole-4-carbaldehyde (0.61 g, 6.34 mmol). $^1$HNMR (400 MHz, DMSO-$d_6$) δ ppm 2.59 (s, 3H), 8.17 (s, 1H), 8.79 (s, 1H), 8.84 (s, 1H), 8.95 (s, 1H), 9.86 (s, 1H). LCMS (Method-L): retention time 0.73 min, [M+H] 213.1.

Intermediate 48: 4-(4-formyl-1H-imidazol-1-yl)-2-methoxybenzonitrile

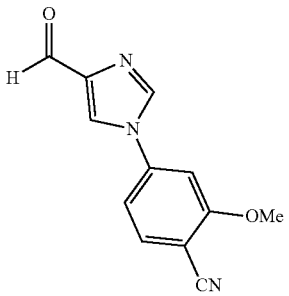

To a stirred solution of 1H-imidazole-4-carbaldehyde (1.00 g, 10.41 mmol) in dioxane (5 mL) was added 4-bromo-2-methoxybenzonitrile (2.20 g, 10.41 mmol), N,N-Dimethylglycine (1.073 g, 10.41 mmol) and $Cs_2CO_3$ (3.39 g, 10.41 mmol) followed by copper(I)iodide (1.98 g, 10.41 mmol). The resulting reaction mixture was heated at 110° C. for 16 h in a sealed tube. The reaction mixture was cooled to ambient temperature, concentrated to dryness under vacuum, diluted with water (40 mL) and extracted with DCM (2×100 mL). The combined organic layers were washed with brine (50 mL), dried over anhydrous sodium sulfate and evaporated under reduced pressure to obtain Intermediate 48 (0.80 g, 33.80%) as brown solid. $^1$H NMR (400 MHz, DMSO-$d_6$) δ ppm 4.04 (s, 3H), 7.56 (dd, J=8.35, 1.95 Hz, 1H), 7.66 (d, J=1.44 Hz, 1H), 7.97 (d, J=8.41 Hz, 1H), 8.67-8.72 (m, 1H), 8.85-8.89 (m, 1H), 9.84-9.87 (m, 1H). LCMS (Method-O): retention time 0.76 min, [M+H] 228.1.

Intermediate 49: 1-(2-methylpyridin-4-yl)-1H-pyrazole-4-carbaldehyde

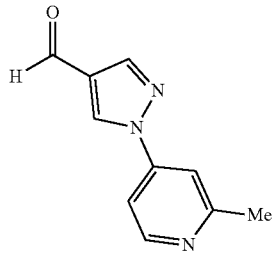

Intermediate 49 was prepared (0.50 g, 49.50%) as an off-white solid, by using a similar synthetic protocol as that of Intermediate 48 and starting from 4-bromo-2-methylpyridine (1.00 g, 5.81 mmol) and 1H-pyrazole-4-carbaldehyde (0.84 g, 8.72 mmol). The compound was taken directly to the subsequent step without further purification or characterization. LCMS (Method-O): retention time 0.69 min, [M+H] 188.2.

Intermediate 50: 2-(4,5-dimethyl-1H-imidazol-1-yl) pyrimidine-5-carbaldehyde

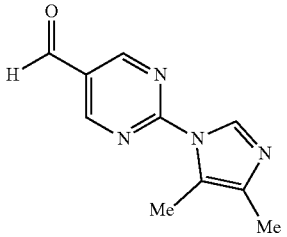

Intermediate 50A: 4,5-dimethyl-1H-imidazole

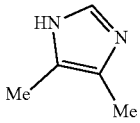

Synthesized according to literature procedures (Angewandte Chemie, 49, (2010), 5322-5326).

Intermediate 50

To a solution of 4,5-dimethyl-1H-imidazole (0.15 g, 1.60 mmol) in acetonitrile (10 mL) was added $K_2CO_3$ (0.44 g, 3.21 mmol), 2-bromopyrimidine-5-carbaldehyde (0.20 g, 1.07 mmol) and the resulting mixture was stirred at ambient temperature for 1.5 h. The reaction mixture was diluted with ethyl acetate (50 mL) and filtered through Celite®. The filtrate was evaporated under reduced pressure. The residue was purified by column chromatography (Redisep—24 g, 40% EtOAc/n-hexane) to obtain Intermediate 50 (0.18 g, 86.00%) as a white solid. $^1$H NMR (400 MHz, DMSO-$d_6$) δ ppm 2.13 (d, J=0.49 Hz, 3H), 2.16 (s, 3H), 8.47 (s, 1H), 9.27 (s, 2H), 10.11 (s, 1H). LCMS: The compound did not ionize well.

Intermediate 51-I: 4-methyl-5((2R,6S)-6-methylpiperazin-2-yl)isobenzofuran-1(3H)-one4-methyl-5-(6-methylpyrazin-2-yl)isobenzofuran-1(3H)-one and Intermediate 51-II: 4-methyl-5-((2S,6R)-6-methylpiperazin-2-yl)isobenzofuran-1(3H)-one (51-I)

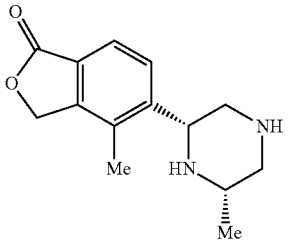

Enantiomer-I

-continued (51-II)

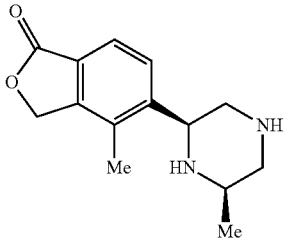

Enantiomer-II

Intermediate 51A: 4-methyl-5-(6-methylpyrazin-2-yl)isobenzofuran-1(3H)-one

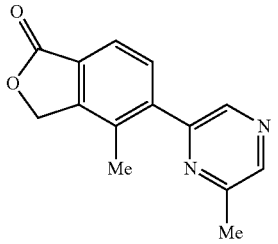

Intermediate 51A was prepared (14.00 g, 80.00%) as an off-white solid, by using a similar synthetic protocol as that of Intermediate 2C and starting from Intermediate 2B (20.00 g, 7.3.00 mmol) and 2-chloro-6-methylpyrazine (9.38 g, 73.0 mmol). $^1$H NMR (400 MHz, DMSO-d6) δ ppm 2.23 (s, 3H), 2.59 (s, 3H) 5.50 (s, 2H), 7.69 (d, J=7.83 Hz, 1H), 7.81 (d, J=7.83 Hz, 1H), 8.62 (s, 1H), 8.69 (s, 1H). LCMS (Method-D): retention time 1.41 min, [M+H] 241.2.

Intermediate 51-I and 51-II

Intermediate 51-I and 51-II was prepared by using a similar synthetic protocol as that of Intermediate 2-I and 2-II and starting from Intermediate 51A (10.00 g, 41.6 mmol). The racemate was separated into two individual enantiomers by SFC [Chiralpak IC (250×4.6 mm) 5 micron; 0.2% $NH_4OH$ in MeOH+ACN (1:1), Flow: 1.2 mL/min. Temperature: 30° C., UV: 235 nm]. First eluted compound (retention time 4.83 min), designated as Intermediate 51-I, was obtained (3.50 g, 41.00%) as brown solid. $^1$H NMR (400 MHz, DMSO-$d_6$) δ ppm 0.96 (d, J=6.02 Hz, 3H) 2.14-2.22 (m, 2H) 2.29 (s, 3H) 2.74-2.84 (m, 3H) 4.02 (dd, J=10.04, 2.51 Hz, 1H) 5.38 (s, 2H) 7.65 (d, J=8.03 Hz, 1H) 7.81 (d, J=8.03 Hz, 1H), (2 Exchangeable proton not observed). LCMS (Method-D): retention time 0.636 min, [M+H] 247.2. Chiral purity (Method-XXVII): retention time 4.86 min, 99.30% ee. SOR: $[\alpha]^{25}_D$=−38.00 (c 0.10, MeOH). To determine stereochemistry of Intermediate 51-I, 5-((2R,6S)-4-(3,5-dibromobenzoyl)-6-methylpiperazin-2-yl)-4-methylisobenzofuran-1(3H)-one was prepared according to literature procedure (WO2011/012896, 2011), and absolute configuration was determined by single-crystal X-ray diffraction method. Second eluted compound (retention time 6.12 min), designated as Intermediate 51-II, was obtained (3.10 g, 36.00%) as brown solid. $^1$H NMR (400 MHz, DMSO-d6) δ ppm 0.97 (d, J=6.02 Hz, 3H), 2.12-2.26 (m, 2H), 2.29 (s, 3H), 2.74-2.84 (m, 3H), 4.02 (dd, J=10.04, 2.51 Hz, 1H), 5.38 (s, 2H), 7.65 (d, J=8.03 Hz, 1H), 7.81 (d, J=8.03 Hz, 1H), (2 Exchangeable proton not observed). LCMS (Method-D): retention time 0.548 min, [M+H] 247.2. Chiral purity (Method-XXVII): retention time 5.96 min, 96.00% ee. SOR: $[\alpha]^{25}_{D}$=+32.00 (c 0.10, MeOH).

Intermediate 52-I: 5-((3R,4R)-4-hydroxypiperidin-3-yl)-4-methylisobenzofuran-1(3H)-one hydrochloride

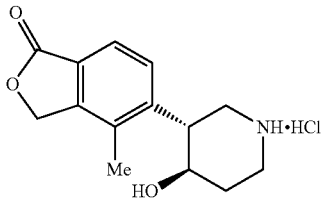

Intermediate 52A-I, II, III and IV: tert-butyl 4-hydroxy-3-(4-methyl-1-oxo-1,3-dihydroisobenzofuran-5-yl)piperidine-1-carboxylate

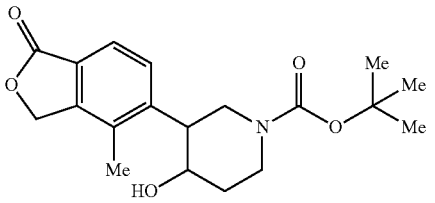

To a solution of Intermediate 4A (4.00 g, 11.58 mmol) in MeOH (100 mL) was added $NaBH_4$ (1.46 g, 23.16 mmol) and the reaction mixture was stirred at ambient temperature for 2 h. The reaction mixture was concentrated to dryness under reduced pressure and diluted with water (100 mL). The solid precipitate was filtered and dried under vacuum to obtain diastereomer-I (2.7 gm). Filtrate was extracted with 10% MeOH in DCM (3×50 mL). The combined organic layers were washed with brine (30 mL), dried over anhydrous sodium sulfate and evaporated under reduced pressure to obtain diastereomer-II (0.8 g). The diastereomer-I was separated into two individual enantiomers by SFC [Lux cellulose-2 (250×4.6 mm) 5 micron; 0.2% $NH_4OH$ in MeOH, Flow: 1.2 mL/min. Temperature: 30° C., UV: 240 nm]. First eluted compound (retention time 3.98 min), designated as Intermediate 52A-I, was obtained (1.20 g, 30.00%) as an off-white solid. $^1$H NMR (400 MHz, DMSO-$d_6$) δ ppm 1.42 (s, 9H), 1.89-1.98 (m, 1H), 2.29 (s, 3H), 2.82 (d, J=9.54 Hz, 3H), 3.17 (d, J=4.02 Hz, 1H), 3.78 (br. s., 1H), 3.95 (br. s., 2H), 4.70 (br. s., 1H), 5.40 (s, 2H), 7.55 (d, J=8.03 Hz, 1H), 7.66 (d, J=8.03 Hz, 1H). Chiral purity (Method-XXVIII): retention time 3.98 min, 100% ee. SOR: $[\alpha]^{25}_{D}$=−38.00 (c 0.1, MeOH). LCMS: The compound did not ionize well. Second eluted compound (retention time 5.85 min), designated as Intermediate 52A-II, was obtained (1.30 g, 32.30%) as an off-white solid. $^1$H NMR (400 MHz, DMSO-$d_6$) δ ppm 1.42 (s, 9H), 1.89-1.98 (m, 1H), 2.29 (s, 3H), 2.82 (d, J=9.54 Hz, 3H), 3.17 (d, J=4.02 Hz, 1H), 3.78 (br. s., 1H), 3.95 (br. s., 2H), 4.70 (br. s., 1H), 5.40 (s, 2H), 7.55 (d, J=8.03 Hz, 1H), 7.66 (d, J=8.03 Hz, 1H). Chiral purity (Method-XXVIII): retention time 5.85 min, 99.3% ee. LCMS: The compound did not ionize well. The diastereomer-II was separated into two individual enantiomers by using similar SFC method as that of diastereomer-I. First eluted compound (retention time 8.61 min), designated as Intermediate 52A-III, was obtained (0.20 g, 5.00%) as an off-white solid. $^1$H NMR (400 MHz, DMSO-d6) δ ppm 1.40 (s, 9H), 1.64-1.82 (m, 2H), 2.26 (s, 3H), 3.06 (d, J=11.04 Hz, 1H), 3.17 (d, J=5.52 Hz, 1H), 3.52 (br. s., 1H), 3.81 (br. s., 2H), 3.97 (br. s., 1H), 4.82 (br. s., 1H), 5.39 (s, 2H), 7.56 (br. s., 1H), 7.59-7.65 (m, 1H). Chiral purity (Method-XXVIII): retention time 8.61 min, 100% ee. LCMS: The compound did not ionize well. Second eluted compound (retention time 9.82 min), designated as Intermediate 52A-IV, was obtained (0.21 g, 5.20%) as an off-white solid. $^1$H NMR (400 MHz, DMSO-d6) δ ppm 1.40 (s, 9H), 1.64-1.82 (m, 2H), 2.26 (s, 3H), 3.06 (d, J=11.04 Hz, 1H), 3.17 (d, J=5.52 Hz, 1H), 3.52 (br. s., 1H), 3.81 (br. s., 2H), 3.97 (br. s., 1H), 4.82 (br. s., 1H), 5.39 (s, 2H), 7.56 (br. s., 1H), 7.59-7.65 (m, 1H). Chiral purity (Method-XXVII): retention time 9.82 min, 97.80% ee. LCMS: The compound did not ionize well.

Intermediate 52-I

To a solution of Intermediate 52A-I (1.20 g, 3.45 mmol) in DCM (50 mL) at 0° C. was added 4N HCl in dioxane (12.95 mL, 51.8 mmol). The resulting mixture was stirred at ambient temperature for 2 h. The reaction mixture was concentrated to dryness, washed with diethylether (2×50 mL) and dried under reduced pressure to obtain Intermediate 52-I (0.90 g, 92.00%) as an off-white solid. $^1$H NMR (400 MHz, DMSO-d6) δ ppm 1.72-1.85 (m, 1H), 2.08 (d, J=13.05 Hz, 1H), 2.30 (s, 3H), 3.08 (d, J=9.04 Hz, 2H), 3.12-3.20 (m, 2H), 3.97 (br. s., 1H), 4.99 (br. s., 1H), 5.40 (d, J=5.52 Hz, 2H), 7.61 (d, J=8.03 Hz, 1H), 7.70 (d, J=8.03 Hz, 1H), 8.96 (br. s., 1H), 9.05 (br. s., 1H), (1 Exchangeable proton not observed). LCMS (Method-D) retention time 0.395 min, [M+H] 248.0. To determine stereochemistry of Intermediate 52-I, 5-((3R,4R)-1-(4-bromobenzoyl)-4-hydroxypiperidin-3-yl)-4-methylisobenzofuran-1(3H)-one was prepared according to literature procedure (WO2011/012896, 2011), and absolute configuration was determined by single-crystal X-ray diffraction method.

Example 1-I: (R)-4-methyl-6-(4-((2-(4-methyl-1-oxo-1,3-dihydroisobenzofuran-5-yl)morpholino)methyl)-1H-pyrazol-1-yl)nicotinonitrile

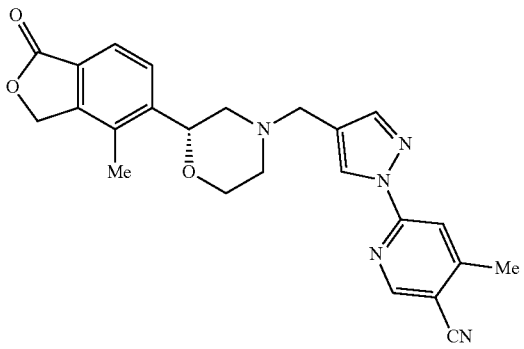

To a solution of Intermediate 6 (0.05 g, 0.23 mmol) in MeOH (1 mL) was added Intermediate 3-I (0.05 g, 0.23 mmol) and the reaction mixture was stirred at ambient temperature for 15 min. $NaCNBH_3$ (0.04 g, 0.71 mmol) was added and stirring was continued for 12 h at ambient temperature. The reaction mixture was diluted with water (15 mL) and extracted with ethyl acetate (2×20 mL). The combined organic layer was washed with brine (20 mL), dried over anhydrous sodium sulfate and evaporated under reduced pressure. The residue was purified by HPLC [XBridge C18 (19×150 mm) 5 micron; Solvent A: 0.1% TFA; Solvent B: Acetonitrile, Gradient: 10-100% B over 25 minutes, Flow: 15 mL/min, retention time 1.60 min, UV 220 nm] to obtain Example 1-I (0.02 g, 17.10%). $^1$H NMR (400 MHz, DMSO-$d_6$) δ ppm 1.86-1.96 (m, 1H), 2.20 (s, 3H), 2.23-2.29 (m, 1H), 2.58 (s, 3H), 2.81 (d, J=11.74 Hz, 1H), 2.92 (d, J=11.49 Hz, 1H), 3.56 (s, 2H), 3.71-3.81 (m, 1H), 3.99 (d, J=9.54 Hz, 1H), 4.81 (d, J=8.07 Hz, 1H), 5.38 (d, J=4.89 Hz, 2H), 7.57-7.63 (m, 1H), 7.64-7.71 (m, 1H), 7.87 (s, 1H), 7.99 (s, 1H), 8.55 (s, 1H), 8.83 (s, 1H). LCMS/HPLC (Method -A): retention time 1.25 min, [M+H] 430.0, purity: 100%. (Method-B): retention time 1.90 min, [M+H] 430.0, purity: 98.3%. Chiral purity (Method-I): retention time 10.04 min, 100% ee, Example 2-I: (R)-4-methyl-6-(4-((3-(4-methyl-1-oxo-1,3-dihydroisobenzofuran-5-yl)piperazin-1-yl)methyl)-1H-pyrazol-1-yl)nicotinonitrile

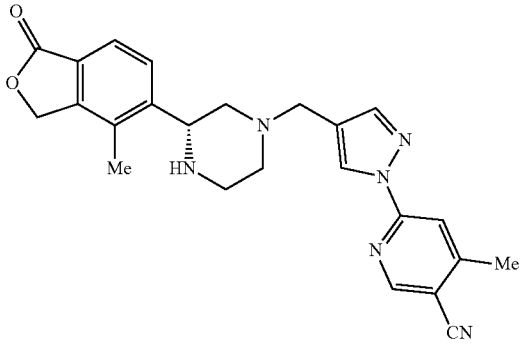

Example 2-I was prepared (0.11 g, 21.36%) as a white solid, by using a similar synthetic protocol as that of Example 1-I and starting from Intermediate 6 (0.25 g, 1.17 mmol) and Intermediate 2-I. $^1$H NMR (400 MHz, DMSO-$d_6$) δ ppm 1.79 (t, J=10.29 Hz, 1H), 2.03-2.18 (m, 1H), 2.25 (s, 3H), 2.66-2.67 (m, 4H), 2.79 (t, J=9.04 Hz, 2H), 2.84-2.92 (m, 1H), 2.94-3.05 (m, 1H), 3.45-3.59 (m, 2H), 4.06 (d, J=9.54 Hz, 1H), 5.36 (d, J=1.51 Hz, 2H), 7.63 (d, J=8.03 Hz, 1H), 7.76 (d, J=8.03 Hz, 1H), 7.85 (s, 1H), 7.98 (s, 1H), 8.52 (s, 1H), 8.82 (s, 1H). HPLC (Method-F): retention time 5.62 min, purity: 98.55%. (Method-G): retention time 5.62 min, purity: 98.55%. LCMS (Method-H): retention time 1.82 min, [M+H] 429.0. Chiral purity (Method-VII): retention time 4.29 min, 100% ee.

Example 3-1: (R)-3-methyl-5-(5-((2-(4-methyl-1-oxo-1,3-dihydroisobenzofuran-5-yl)morpholino)methyl)pyridin-2-yl)benzo [d] oxazol-2(3 H)-one

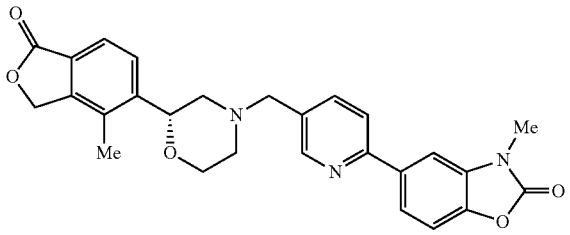

Example 3-I was prepared (0.006 g, 5.13%) as white solid, by using a similar synthetic protocol as that of Intermediate 2B and starting from Intermediate 8 (0.06 g, 0.24 mmol) and Intermediate 5-I. $^1$H NMR (400 MHz, DMSO-$d_6$) δ ppm 1.99 (t, J=10.76 Hz, 1H), 2.23 (s, 3H), 2.26-2.35 (m, 1H), 2.79 (d, J=11.25 Hz, 1H), 2.90 (d, J=10.52 Hz, 1H), 3.42 (s, 3H), 3.64 (s, 2H), 3.74-3.83 (m, 1H), 4.01 (d, J=11.49 Hz, 1H), 4.85 (d, J=8.80 Hz, 1H), 5.38 (d, J=3.67 Hz, 2H), 7.43 (d, J=8.56 Hz, 1H), 7.60-7.66 (m, 1H), 7.66-7.71 (m, 1H), 7.83-7.92 (m, 2H), 7.96 (d, J=1.47 Hz, 1H), 8.01 (d, J=8.56 Hz, 1H), 8.61 (s, 1H). LCMS/HPLC (Method-A): retention time 1.21 min, [M+H] 472.2, purity: 100%. (Method-B): retention time 1.83 min, [M+H] 472.2, purity: 99.40%. Chiral purity (Method-XVIII): retention time 24.29 min, 100% ee.

Example 4: 5-(4-((4,4-difluoro-3-(4-methyl-1-oxo-1,3-dihydroisobenzofuran-5-yl)piperidin-1-yl)methyl)-1H-pyrazol-1-yl)-3-methylbenzo[d]oxazol-2(3H)-one

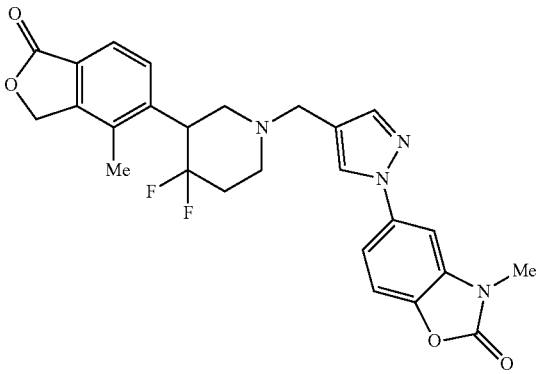

Example 4 was prepared (0.01 g, 13.77%), by using Intermediate 4 (0.05 g, 0.15 mmol) in a manner similar to synthetic protocol described for Intermediate 6. $^1$H NMR (400 MHz, DMSO-$d_6$) δ ppm 2.16 (br. s., 2H), 2.29 (s, 3H), 2.33 (s, 1H), 2.65-2.73 (m, 1H), 2.90 (br. s., 1H), 3.01 (br. s., 1H), 3.39 (s, 3H), 3.63 (s, 2H), 3.68-3.80 (m, 1H), 5.40 (q, J=15.41 Hz, 2H), 7.41 (d, J=8.56 Hz, 1H), 7.56 (dd, J=8.56, 2.20 Hz, 1H), 7.62-7.68 (m, 2H), 7.69-7.71 (m, 1H), 7.74 (d, J=2.20 Hz, 1H), 8.44 (s, 1H). LCMS/HPLC (Method-A): retention time 1.29 min, [M+H] 495.0, purity: 94.70%. (Method-B): retention time 1.87 min, [M+H] 495.1, 95.90%.

Example 5: 6-(4-((4,4-difluoro-3-(4-methyl-1-oxo-1,3-dihydroisobenzofuran-5-yl)piperidin-1-yl)methyl)-1H-pyrazol-1-yl)-4-methylnicotinonitrile

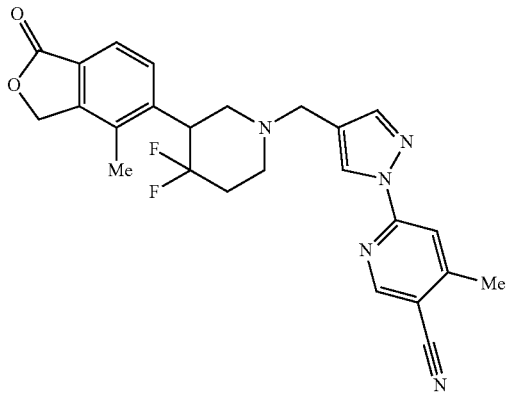

Example 5 was prepared (0.01 g, 12.92%), by using Intermediate 6 (0.04 g, 0.19 mmol) and Intermediate 4C in a manner similar to synthetic protocol described for Example 1-I.

$^1$H NMR (300 MHz, $CDCl_3$) δ ppm 2.34 (s, 3H), 2.44 (br. s., 2H), 2.66 (s, 3H), 3.04 (d, J=10.58 Hz, 1H), 3.22 (t, J=2.46 Hz, 1H), 3.64 (t, J=15.86 Hz, 2H), 4.09-4.18 (m, 1H), 4.20-4.40 (m, 2H), 5.26-5.33 (m, 2H), 7.48 (d, J=8.69 Hz, 1H), 7.80 (d, J=8.31 Hz, 1H), 7.87 (s, 1H), 7.99 (s, 1H), 8.62 (s, 1H), 8.74 (s, 1H). $^{19}$F NMR (400 MHz, DMSO-$d_6$) δ ppm −96.34, −110.26. LCMS/HPLC (Method-A): retention time 1.375 min, [M+H] 464.0, purity: 95.80%. (Method-B): retention time 2.11 min, [M+H] 464.0, 95.20%.

Example 6-I: (R)-6-(5-methoxy-4-((3-(4-methyl-1-oxo-1,3-dihydroisobenzofuran-5-yl)piperazin-1-yl)methyl)-1H-pyrazol-1-yl)-4-methylnicotinonitrile

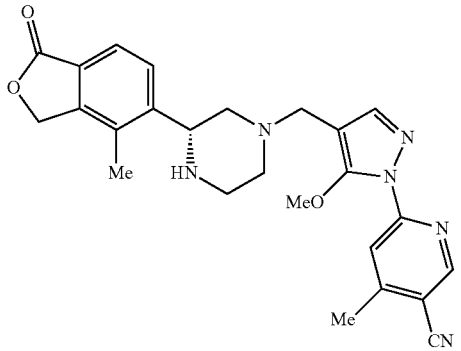

Example 6-I was prepared (0.02 g, 22.08%), as an off-white solid, by using a similar synthetic protocol as that of Example 1-I and starting from Intermediate 9 (0.05 g, 0.20 mmol) and Intermediate 2-I. $^1$H NMR (400 MHz, DMSO-$d_6$) δ ppm 1.87 (t, J=10.76 Hz, 1H), 2.14 (s, 1H), 2.26 (s, 3H), 2.55 (s, 3H), 2.80 (d, J=10.76 Hz, 2H), 2.85-2.93 (m, 1H), 2.99 (d, J=10.03 Hz, 1H), 3.40 (s, 2H), 3.95 (s, 3H), 4.09 (d, J=10.27 Hz, 1H), 5.37 (s, 2H), 7.64 (d, J=8.07 Hz, 1H), 7.73-7.78 (m, 2H), 8.38 (s, 1H), 8.74 (s, 1H), (Exchangeable proton not observed). LCMS/HPLC (Method-A): retention time 1.31 min, [M+H] 459, purity: 100%. (Method-B): retention time 1.78 min, [M+H] 459, purity: 99.40%. Chiral purity (Method-XV): retention time 9.83 min, 82.80% ee.

Example 7-I: (R)-4-methyl-5-(4-((1-(2-methylthiazol-5-yl)-1H-pyrazol-4-yl)methyl)morpholin-2-yl)isobenzofuran-1(3H)-one

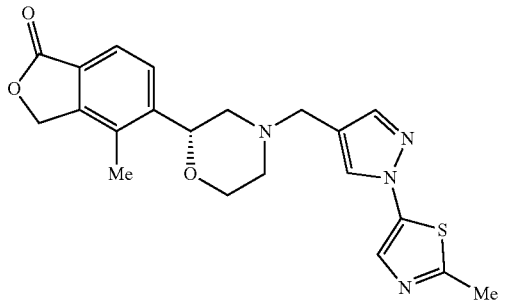

Example 7-I was prepared (0.02 g, 17.25%) as a pale yellow solid, by using a similar synthetic protocol as that of Intermediate 6 and starting from Intermediate 14-I (0.10 g, 0.319 mmol). $^1$H NMR (400 MHz, DMSO-$d_6$) δ ppm 1.87-1.95 (m, 1H), 2.16-2.22 (m, 1H), 2.24 (s, 3H), 2.62 (s, 3H), 2.80 (d, J=11.00 Hz, 1H), 2.91 (d, J=11.74 Hz, 1H), 3.49 (s, 2H), 3.71-3.80 (m, 1H), 3.99 (dd, J=11.49, 2.20 Hz, 1H), 4.81 (dd, J=10.03, 2.20 Hz, 1H), 5.33-5.44 (m, 2H), 7.59-7.70 (m, 3H), 7.86 (s, 1H), 8.33 (s, 1H). LCMS/HPLC (Method-A): retention time 1.06 min, [M+H] 411.1, purity: 100%. (Method-B): retention time 1.52 min, [M+H] 411.1, purity: 99.60%. Chiral purity (Method-XV): retention time 11.36 min, 100% ee.

Example 8-1: (R)-4-cyclopropyl-6-(4-((2-(4-methyl-1-oxo-1,3-dihydroisobenzofuran-5-yl)morpholino)methyl)-1H-pyrazol-1-yl)nicotinonitrile

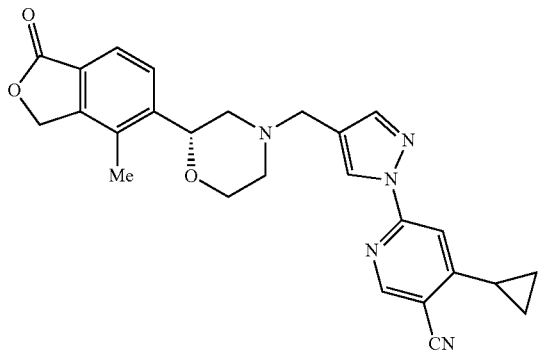

Example 8-I was prepared (0.003 g, 4.27%) as an off-white solid, by using a similar synthetic protocol as that of Intermediate 6 and starting from Intermediate 14-I (0.05 g, 0.16 mmol) and intermediate 10 (0.05 g, 0.23 mmol).

$^1$H NMR (400 MHz, DMSO-$d_6$) δ ppm 1.02-1.11 (m, 2H), 1.26-1.40 (m, 2H), 2.19-2.30 (m, 4H), 3.61 (s, 2H), 3.90 (d, J=11.49 Hz, 2H), 4.18 (d, J=11.25 Hz, 4H), 5.05 (br. s., 1H), 5.33-5.52 (m, 2H), 7.45 (s, 1H), 7.63 (d, J=7.83 Hz, 1H), 7.74 (d, J=8.07 Hz, 1H), 7.98 (s, 1H), 8.72-8.90 (m, 2H). LCMS/HPLC (Method-A): retention time 1.40 min, [M+H] 456.1, purity: 100%. (Method-B): retention time 2.09 min, [M+H] 456.1, purity: 94.50%. Chiral purity (Method-V): retention time 10.54 min, 100% ee.

Example 9-I: (R)-4-methyl-6-(4-((5-(4-methyl-1-oxo-1,3-dihydroi sobenzofuran-5-yl)-2-oxooxazolidin-3-yl)methyl)-1H-pyrazol-1-yl)nicotinonitrile

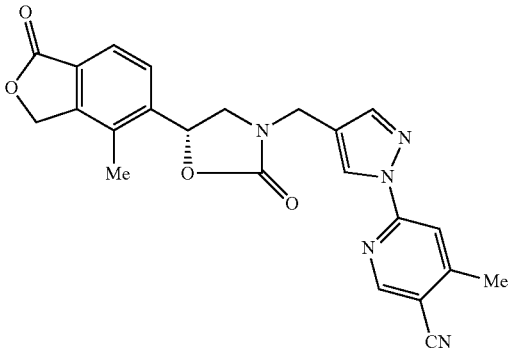

To a solution of Intermediate 12-I (0.06 g, 0.149 mmol) in DCM (5 mL) was added dipyridyl-2-carbonate (0.03 mg, 0.15 mmol), TEA (0.04 mL, 0.29 mmol) and the resulting reaction mixture was stirred at ambient temperature for 16 h. The reaction mixture was concentrated under reduced pressure. The residue was purified by preparative HPLC [XBridge C18 (19×150 mm) 5-μm; Solvent A: 10 mM Ammonium Acetate, Solvent B: methanol, Gradient: 15-57% B over 20 min, then a 5-minute hold at 100% B; Flow: 15 mL/min, retention time 2.70 min, UV 220 nm] to obtain Example 9-I (0.13 g, 19.34%) as an off-white solid. $^1$H NMR (400 MHz, DMSO-$d_6$) δ ppm 2.23 (s, 3H), 2.64 (s, 3H), 4.10 (t, J=9.04 Hz, 1H), 4.28-4.53 (m, 3H), 5.35-5.48 (m, 2H), 5.97 (dd, J=9.04, 7.03 Hz, 1H), 7.55 (d, J=8.03 Hz, 1H), 7.74 (d, J=7.53 Hz, 1H), 7.89 (s, 1H), 8.00 (d, J=1.00 Hz, 1H), 8.64 (s, 1H), 8.85 (s, 1H). LCMS/HPLC (Method-A): retention time 1.69 min, [M+H] 430.1, purity: 95.30%. (Method-B): retention time 1.70 min, [M+H] 430.1, purity: 94.30%. Chiral purity (Method-X): retention time Example 10-I: (R)-4-methyl-6-(4-((2-(4-methyl-1-oxo-1,3-dihydroisobenzofuran-5-yl)-5-oxomorpholino)methyl)-1H-pyrazol-1-yl)nicotinonitrile

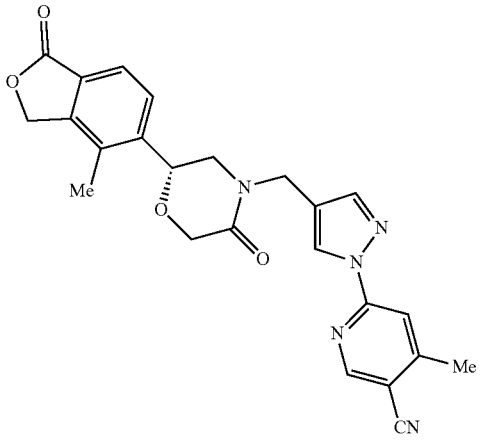

To a stirred solution of Intermediate 13-I (0.05 g, 0.11 mmol) in THF (10 mL) was added tri-n-butylphosphine (0.08 mL, 0.32 mmol) followed by diisopropyl azodicarboxylate (0.04 mL, 0.22 mmol). The resulting reaction mixture was stirred at ambient temperature for 1 h and diluted with water (30 mL). The reaction mixture was extracted with ethyl acetate (3×25 mL). The combined organic layers were washed with brine (25 mL), dried over anhydrous sodium sulfate and evaporated under reduced pressure. The residue was purified by preparative HPLC [XBridge phenyl (19×250 mm) 5 micron; Solvent A: 10 mM $CH_3COONH_4$—PH-4.5, Solvent B: Acetonitrile; Gradient: 40-65% over 24 min; Flow: 17 mL/min, retention time 11.24 min, UV 254 nm] to obtain Example 10-I (0.001 g, 2.50%). $^1$H NMR (400 MHz, DMSO-$d_6$) δ ppm 2.29 (s, 3H), 2.59 (s, 3H), 3.36-3.46 (m, 1H), 3.57 (dd, J=12.23, 3.18 Hz, 1H), 4.28-4.51 (m, 3H), 4.60 (d, J=14.92 Hz, 1H), 5.29 (dd, J=10.52, 3.42 Hz, 1H), 5.34-5.50 (m, 2H), 7.58-7.66 (m, 1H), 7.67-7.76 (m, 1H), 7.91 (s, 1H), 8.01 (s, 1H), 8.65 (s, 1H), 8.85 (s, 1H). LCMS/HPLC (Method-A): retention time 1.67 min, [M+H] 444.1, purity: 100%. (Method-B): retention time 1.65 min, [M+H] 444.1, purity: 100%. Chiral purity (Method-I): retention time 22.89 min, 100% ee.

Example 11-I: (R)-4-methoxy-6-(4-(2-(2-(4-methyl-1-oxo-1,3-dihydroisobenzofuran-5-yl)morpholino)ethyl)-1H-pyrazol-1-yl)nicotinonitrile

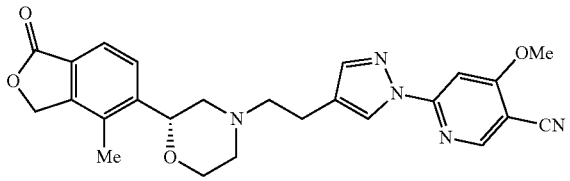

Example 11-I was prepared (0.05 g, 32.65%), by using a similar synthetic protocol as that of Example 1-I and starting from Intermediate 15 (0.07 g, 0.31 mmol) and Intermediate 3-I. $^1$H NMR (400 MHz, DMSO-$d_6$) δ ppm 1.85-2.00 (m, 1H), 2.22-2.33 (m, 3H), 2.60 (br. s., 3H), 2.71 (d, J=5.87 Hz, 2H), 2.89 (d, J=11.98 Hz, 1H), 2.99 (d, J=11.49 Hz, 1H), 3.75 (t, J=11.13 Hz, 1H), 4.00 (d, J=10.03 Hz, 1H), 4.10 (s, 3H), 4.80 (d, J=10.03 Hz, 1H), 5.30-5.51 (m, 2H), 7.58 (s, 1H), 7.60-7.76 (m, 2H), 7.84 (s, 1H), 8.50 (s, 1H), 8.73 (s, 1H). LCMS/HPLC (Method-A): retention time 1.29 min, [M+H] 460.1, purity: 98.12%. (Method-B): retention time 1.95 min, [M+H] 460.1, purity: 97.20%. Chiral purity (Method-I): retention time 10.17 min, 100% ee.

Example 12-I: (R)-6-(5-((2-(4-methyl-1-oxo-1,3-dihydroisobenzofuran-5-yl)morpholino)methyl)-1,3,4-oxadiazol-2-yl)nicotinonitrile

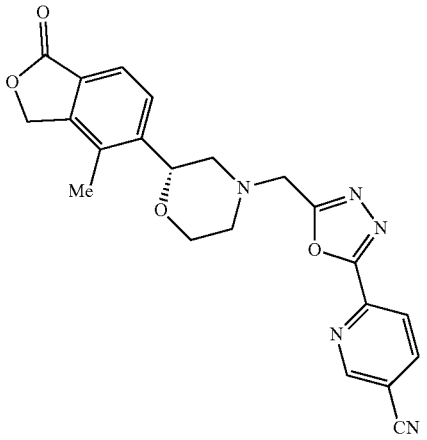

To a stirred solution of Intermediate 16 (0.04 g, 0.18 mmol) and Intermediate 3-I (0.04 g, 0.18 mmol) in ACN (5 mL) was added $K_2CO_3$ (0.07 g, 0.54 mmol) followed by KI (0.003 g, 0.02 mmol). The reaction mixture was stirred at ambient temperature for 14 h, diluted with water (25 mL) and extracted with ethyl acetate (3×15 mL). The combined organic layer was washed with brine (15 mL), dried over anhydrous sodium sulfate and concentrated. The residue was purified by HPLC [XBridge C18 (19×150 mm) 5 micron; Solvent A: 0.1% trifluoroacetic acid; Solvent B: Acetonitrile; Gradient: 5-32% over 20 min, Flow: 15 mL/min, retention time 10.63 min, UV 220 nm] to obtain Example 12-I (0.058 g, 76.31%). $^1$H NMR (400 MHz, DMSO-$d_6$) δ ppm 2.18 (t, J=10.64 Hz, 1H), 2.28 (s, 3H), 2.39-2.48 (m, 1H), 2.89 (d, J=11.00 Hz, 1H), 3.05 (d, J=11.49 Hz, 1H), 3.69-3.84 (m, 1H), 3.96-4.12 (m, 3H), 4.85 (dd, J=9.90, 2.08 Hz, 1H), 5.31-5.47 (m, 2H), 7.57-7.63 (m, 1H), 7.65-7.73 (m, 1H), 8.35 (dd, J=8.31, 0.98 Hz, 1H), 8.57 (dd, J=8.19, 2.08 Hz, 1H), 9.23 (dd, J=2.08, 0.86 Hz, 1H). LCMS/HPLC (Method-A): retention time 1.26 min, [M+H] 418.1, purity: 65 100%. (Method-B): retention time 1.41 min, [M+H] 418.0, purity: 100%. Chiral purity (Method-VII): retention time 17.41 min, 100% ee.

Example 13-I: (R)-4-methyl-6-(5-((3-(4-methyl-1-oxo-1,3-dihydroisobenzofuran-5-yl)piperazin-1-yl)methyl)-1,3,4-oxadiazol-2-yl)nicotinonitrile

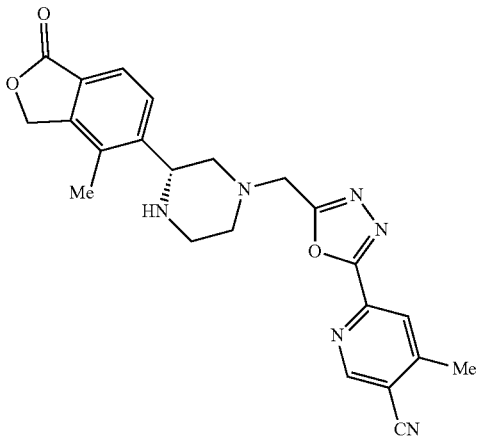

Example 13-I was prepared (0.02 g, 21.80%) by using a similar synthetic protocol as that of Example 12-I and starting from Intermediate 17 (0.04 g, 0.17 mmol) and Intermediate 2-I. $^1$H NMR (400 MHz, DMSO-$d_6$) δ ppm 2.00-2.10 (m, 1H), 2.29 (s, 3H), 2.63 (s, 4H), 2.89 (t, J=10.76 Hz, 4H), 2.97-3.06 (m, 1H), 4.00 (s, 2H), 4.11 (d, J=8.56 Hz, 1H), 5.39 (s, 2H), 7.65 (d, J=8.07 Hz, 1H), 7.77 (d, J=7.83 Hz, 1H), 8.32 (s, 1H), 9.11 (s, 1H). LCMS/HPLC (Method-A): retention time 1.12 min, [M+H] 431.1, purity: 100%. (Method-B): retention time 1.66 min, [M+H] 431.1, purity: 99.56%. Chiral purity (Method-V): retention time 8.77 min, 100% ee.

Example 14-I: (R)-4-methoxy-6-(4-((3-(4-methyl-1-oxo-1,3-dihydroisobenzofuran-5-yl)piperazin-1-yl)methyl)-1H-imidazol-1-yl)nicotinonitrile

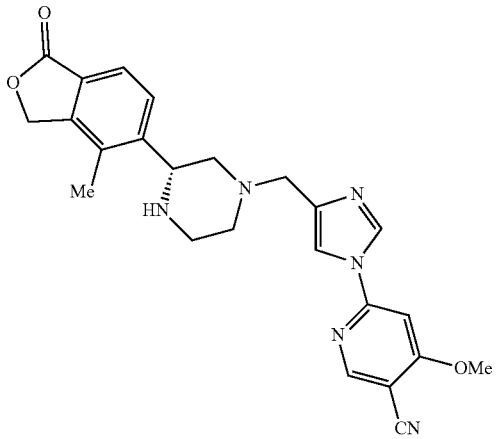

Example 14-I was prepared (0.10 g, 20.13%) by using a similar synthetic protocol as that of Example 1-I and starting from Intermediate 11 (0.25 g, 1.10 mmol) and Intermediate 2-I.

$^1$H NMR (400 MHz, DMSO-$d_6$) δ ppm 1.89 (br. s., 1H), 2.19 (br. s., 1H), 2.27 (s, 3H), 2.81-3.05 (m, 5H), 3.50 (s, 2H), 4.03-4.14 (m, 4H), 5.37 (s, 2H), 7.59 (s, 1H), 7.65 (d, J=8.07 Hz, 1H), 7.78 (d, J=8.07 Hz, 1H), 7.95 (s, 1H), 8.58 (d, J=1.22 Hz, 1H), 8.74 (s, 1H). LCMS/HPLC (Method-A): retention time 0.99 min, [M+H] 445.1, purity: 100%. (Method-B): retention time 1.28 min, [M+H] 445.0, purity: 99.56%. Chiral purity (Method-V): retention time 7.10 min, 84.55% ee.

Example 15-I: (R)-4-methyl-6-(4-((3-(4-methyl-1-oxo-1,3-dihydroisobenzofuran-5-yl)-5-oxopiperazin-1-yl)methyl)-1H-pyrazol-1-yl)nicotinonitrile

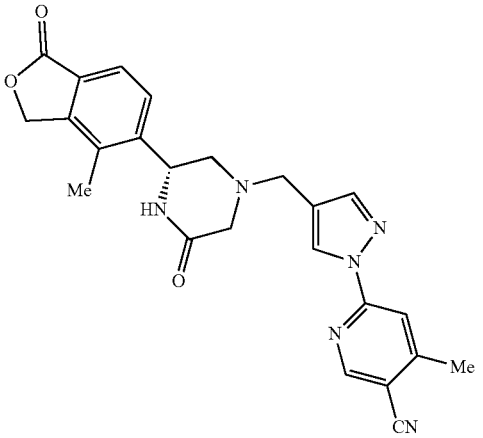

Example 15-I was prepared (0.008 g, 12.95%) as a white solid, by using a similar synthetic protocol as that of Example 1-I and starting from Intermediate 6 (0.03 g, 0.14 mmol) and Intermediate 19-I. $^1$H NMR (400 MHz, DMSO-$d_6$) δ ppm 2.22 (s, 3H), 2.41 (dd, J=11.62, 6.24 Hz, 1H), 2.56 (s, 3H), 2.90 (dd, J=11.98, 4.16 Hz, 1H), 3.05-3.22 (m, 2H), 3.47-3.65 (m, 2H), 4.94 (br. s., 1H), 5.21-5.34 (m, 1H), 5.36-5.46 (m, 1H), 7.56 (d, J=8.07 Hz, 1H), 7.68-7.80 (m, 2H), 7.96 (s, 1H), 8.18 (s, 1H), 8.28 (s, 1H), 8.76 (s, 1H). LCMS/HPLC (Method-A): retention time 1.23 min, [M+H] 443.1, purity: 96.48%. (Method-B): retention time 1.51 min, [M+H] 443.1, purity: 100%. Chiral purity (Method-V): retention time 12.48 min, 92% ee.

Example 16-I: (R)-4-methyl-5-(4-((6-(4-methyl-1H-imidazol-1-yl)pyridin-3-yl)methyl)morpholin-2-yl) isobenzofuran-1(3H)-one

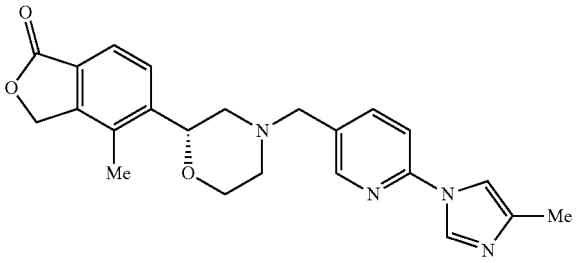

Example 16-I was prepared (0.01 g, 9.26%), by using a similar synthetic protocol as that of Intermediate 23-I and starting from Intermediate 20 (0.05 g, 0.26 mmol) and Intermediate 3-I. $^1$H NMR (400 MHz, DMSO-$d_6$) δ ppm 2.17 (s, 3H), 2.22 (s, 3H), 2.23-2.36 (m, 2H), 2.77 (d, J=11.25 Hz, 1H), 2.87 (d, J=11.98 Hz, 1H), 3.61 (s, 2H), 3.69-3.85 (m, 1H), 3.99 (d, J=9.54 Hz, 1H), 4.82 (d, J=7.58 Hz, 1H), 5.26-5.45 (m, 2H), 7.54-7.75 (m, 4H), 7.92 (dd, J=8.31, 2.20 Hz, 1H), 8.39 (s, 2H). LCMS/HPLC (Method-A): retention time 0.83 min, [M+H] 405.1, purity: 99.20%. (Method-B): retention time 1.56 min, [M+H] 405.0, purity: 95.99%. Chiral purity (Method-X): retention time 12.55 min, 96.10% ee Example 17-I: (R)-4-methoxy-5'-((5-(4-methyl-1-oxo-1,3-dihydroisobenzofuran-5-yl)-2-oxooxazolidin-3-yl)methyl)[2,2'-bipyridine]-5-carbonitrile

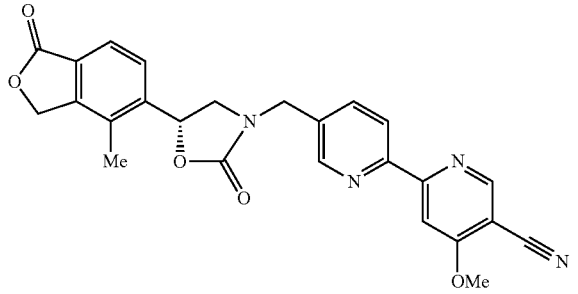

A solution of Intermediate 23-I (0.15 g, 0.35 mmol) in THF (20 mL) at 70° C. was added 1,1'-carbonyldiimidazole (0.06 g, 0.38 mmol) and the resulting reaction mixture was stirred for 1 h. The reaction mixture was cooled to ambient temperature and was evaporated under reduced pressure. The residue was diluted with water (15 mL) and extracted with DCM (3×15 mL). The combined organic layers were washed with brine (10 mL), dried over anhydrous sodium sulfate and evaporated under reduced pressure. The residue was purified by HPLC [Intertsil ODS (250×10 mm) 5 micron; Solvent A: 10 mM $NH_4OAc$ in $H_2O$, Solvent B: Acetonitrile, Gradient: 20-65% over 14 min, Flow: 17 mL/min retention time 15.06 min, UV 254 nm] to obtain Example 17-I (0.02 g, 8.68%). $^1$H NMR (400 MHz, DMSO-$d_6$) δ ppm 2.22 (s, 3H), 4.03-4.07 (m, 2H), 4.11 (s, 3H), 4.51 (d, J=16.00 Hz, 1H), 4.62 (d, J=16.00 Hz, 1H), 5.22-5.48 (m, 2H), 6.02 (t, J=8.19 Hz, 1H), 7.59 (d, J=8.56 Hz, 1H), 7.76 (d, J=8.07 Hz, 1H), 7.95 (d, J=8.07 Hz, 1H), 8.14 (s, 1H), 8.43 (d, J=8.07 Hz, 1H), 8.70 (s, 1H), 8.92 (s, 1H). LCMS/HPLC: (Method-A) retention time: 1.59 min, [M+1]: 457.1, purity: 100%. (Method-B) retention time: 1.65 min, [M+1]: 457.0, purity: 100%. Chiral purity (Method-XVII): retention time 6.39 min, 100% ee Example 18-I: 6-(4-(1-hydroxy-2-((R)-2-(4-methyl-1-oxo-1,3-dihydroisobenzofuran-5-yl)morpholino) ethyl)-1H-pyrazol-1-yl)-4-methylnicotinonitrile (Diastereomer-I & II)

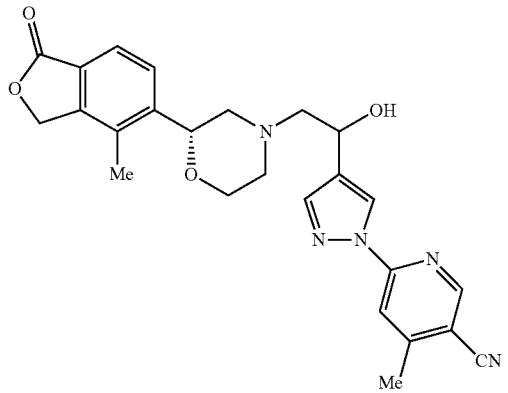

To a solution of Intermediate 24 (0.12 g, 0.53 mmol) in EtOH (10 mL) was added Intermediate 3-I (0.12 g, 0.53 mmol) and the resulting reaction mixture was stirred at 85° C. for 48 h. Ethanol was evaporated under reduced pressure and residue was purified by HPLC [XBridge phenyl (250×19 ID) 5 micron; Solvent A: 10 mM $NH_4HCO_3$—PH-9.5, Solvent B: Acetonitrile; Gradient: 0-62% over 15 min; Flow: 16 mL/min, UV 254 nm]. First eluted compound (retention time 15.33 min), designated as Example 18-I Dia-I (Diastereomer-1) was obtained (0.009 g, 19.00%). $^1$H NMR (400 MHz, DMSO-$d_6$) δ ppm 2.01-2.08 (m, 1H), 2.25 (s, 3H), 2.31-2.34 (m, 1H), 2.36 (d, J=3.01 Hz, 1H), 2.58 (s, 3H), 2.65-2.68 (m, 1H) 2.85 (d, J=10.80 Hz, 1H), 3.07 (d, J=10.80 Hz, 1H), 3.72-3.80 (m, 1H), 3.95-4.03 (m, 1H), 4.79 (d, J=9.54 Hz, 1H), 4.85 (d, J=6.53 Hz, 1H), 5.22 (d, J=5.02 Hz, 1H), 5.39 (d, J,=4.52 Hz, 2H), 7.62 (d, J=8.00 Hz, 1H), 7.67 (d, J=8.00 Hz, 1H), 7.90 (s, 1H), 7.99 (s, 1H), 8.54 (s, 1H), 8.84 (s, 1H). LCMS (Method-H): retention time 1.93 min, [M+H] 460.1, purity: 98.60%. HPLC (Method-F): retention time 5.12 min, purity: 99.14%. (Method-G): retention time 6.03 min, purity: 99.42%. Chiral purity (Method-X): retention time 10.19 min, 97.70% ee.

Second eluted compound (retention time 17.02 min), designated as Example 18-I Dia-II (Diastereomer-II) was obtained (0.008 g 16.00%). $^1$H NMR (400 MHz, DMSO-$d_6$) δ ppm 2.01-2.08 (m, 1H), 2.25 (s, 3H), 2.31-2.34 (m, 1H), 2.36 (d, J=3.01 Hz, 1H), 2.58 (s, 3H), 2.65-2.68 (m, 1H) 2.96 (t, J=,11.80 Hz, 2H), 3.72-3.80 (m, 1H), 3.95-4.03 (m, 1H), 4.79 (d, J=9.54 Hz, 1H), 4.85 (d, J=6.53 Hz, 1H), 5.22 (d, J=5.02 Hz, 1H), 5.39 (d, J,=4.52 Hz, 2H), 7.62 (d, J=8.00 Hz, 1H), 7.67 (d, J=8.00 Hz, 1H), 7.90 (s, 1H), 7.99 (s, 1H), 8.54 (s, 1H), 8.84 (s, 1H). LCMS (Method-H): retention time 1.92 min, [M+H] 460.1, purity: 95.43%. HPLC (Method-F): retention time 5.11 min, purity: 90.01%. (Method-G): retention time 6.00 min, purity: 88.76%. Chiral purity (Method-X): retention time 12.55 min, 96.10% ee.

Example 19-I: (R)-3-methyl-5-(5-((2-(4-methyl-1-oxo-1,3-dihydroisobenzofuran-5-yl)morpholino)methyl)thiazol-2-yl)benzo [d]oxazol-2(3H)-one

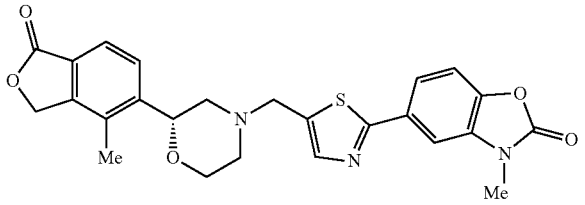

Example 19-I was prepared (0.01 g, 16.97%), by using a similar synthetic protocol as that of Example 3-I and starting from Intermediate 25-I (0.10 g, 0.12 mmol) and Intermediate 8. $^1$H NMR (400 MHz, DMSO-$d_6$) δ ppm 1.94-2.07 (m, 1H), 2.24 (s, 3H), 2.28-2.37 (m, 1H), 2.83-2.91 (m, 1H), 2.96 (d, J=11.74 Hz, 1H), 3.42 (s, 3H), 3.72-3.83 (m, 1H), 3.87 (s, 2H) 4.03 (d, J=9.29 Hz, 1H), 4.83 (s, 1H), 5.38 (d, J=2.45 Hz, 2H), 7.44 (d, J=8.31 Hz, 1H), 7.67 (s, 1H) 7.69 (s, 1H) 7.70 (dd, J=8.00 Hz, 1.60 Hz, 1H), 7.75 (s, 1H) 7.79 (d, J=1.71 Hz, 1H). LCMS/HPLC (Method-A): retention time 1.23 min, [M+H] 478.1, purity: 99.56%. (Method-B): retention time 1.89 min, [M+H] 478.0, purity: 99.59%. Chiral purity (Method-X): retention time 9.67 min, 100% ee.

Example 20-I: (R)-3-methyl-5-(5-(2-(4-methyl-1-oxo-1,3-dihydroisobenzofuran-5-yl)morpholine-4-carbonyl)thiazol-2-yl)benzo[d]oxazol-2(3H)-one

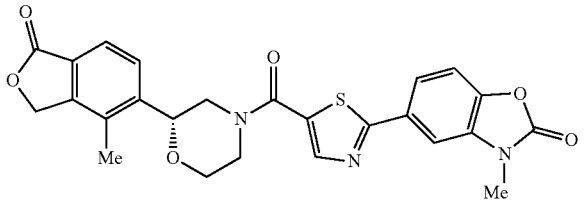

Example 20-I was prepared (0.01 g, 5.29%), by using a similar synthetic protocol as that of Example 3-I and starting from Intermediate 26-I (0.15 g, 0.35 mmol) and Intermediate 8.

$^1$H NMR (400 MHz, DMSO-$d_6$) δ ppm 2.08 (s, 3H), 2.20-2.37 (m, 3H), 3.43 (s, 3H), 3.83 (dd, J=11.49, 8.80 Hz, 1H), 4.12 (d, J=9.78 Hz, 1H), 4.15-4.31 (br. s., 1H), 4.94 (d, J=10.03 Hz, 1H), 5.42 (br. s., 2H), 7.49 (d, J=8.07 Hz, 1H), 7.66-7.83 (m, 3H), 7.87 (d, J=1.71 Hz, 1H), 8.26 (s, 1H). LCMS/HPLC (Method-A): retention time 1.71 min, [M+H] 492.1, purity: 96.82%. (Method-B): retention time 1.73 min, [M+H] 492.0, purity: 97.44%. Chiral purity (Method-XV): retention time 3.40 min, 100% ee.

Example 21-I: (R)-1-(5-((3-(4-methyl-1-oxo-1,3-dihydroisobenzofuran-5-yl)piperazin-1-yl)methyl)thiazol-2-yl)-1H-imidazole-4-carbonitrile

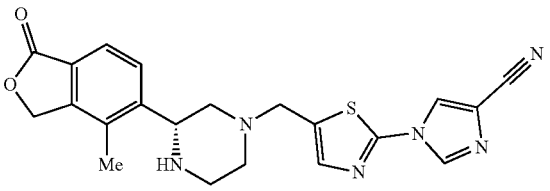

Example 21-I was prepared (0.006 g, 9.11%) as a white solid, by using a similar synthetic protocol as that of Example 1-I and starting from Intermediate 27 (0.03 g, 0.17 mmol) and Intermediate 2-I. $^1$H NMR (400 MHz, DMSO-$d_6$) δ ppm 1.84-2.00 (m, 1H), 2.26 (s, 3H), 2.78-2.94 (m, 4H), 3.02 (d, J=12.23 Hz, 1H), 3.69-3.85 (m, 2H), 4.07 (d, J=8.56 Hz, 1H), 5.27-5.41 (m, 2H), 7.60 (s, 1H), 7.66 (d, J=7.83 Hz, 1H), 7.77 (d, J=7.58 Hz, 1H), 8.64 (s, 1H), 8.85 (s, 1H), (Exchangeable proton not observed). LCMS/HPLC (Method-A): retention time 1.07 min, [M+H] 421.1, purity: 100%. (Method-B): retention time 1.32 min, [M+H] 421.0, purity: 100%. Chiral purity (Method-XVIII): retention time 11.69 min, 100% ee.

Example 22-I: (R)-4-methyl-6-(4-((3-(4-methyl-1-oxo-1,3-dihydroisobenzofuran-5-yl)piperazin-1-yl)methyl)-2H-1,2,3-triazol-2-yl)nicotinonitrile

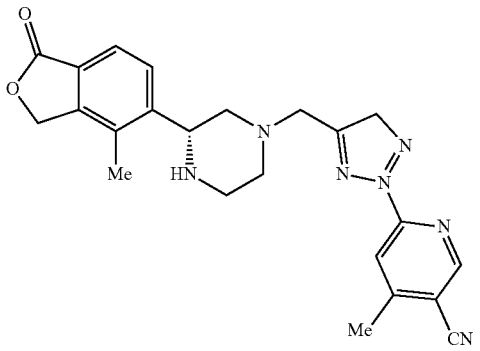

Example 22-I was prepared (0.01 g, 10.83%), by using a similar synthetic protocol as that of Example 1-I and starting from Intermediate 28 (0.04 g, 0.19 mmol) and Intermediate 2-I (0.05 g, 0.206 mmol). $^1$H NMR (400 MHz, DMSO-$d_6$) δ ppm 1.87-1.95 (m, 1H), 2.17-2.23 (m, 1H), 2.26 (s, 3H), 2.61 (s, 3H), 2.80-3.03 (m, 4H), 3.77 (s, 2H), 4.10 (d, J=8.07 Hz, 1H), 5.37 (d, J=2.45 Hz, 2H), 7.65 (d, J=8.07 Hz, 1H), 7.77 (d, J=8.07 Hz, 1H), 8.11 (s, 1H), 8.21 (s, 1H), 8.92 (s, 1H), (Exchangeable proton present). LCMS/HPLC (Method-A): retention time 1.15 min, [M+H] 430, purity: 96.70%. (Method-B): retention time 1.36 min, [M+H] 430, purity: 100%. Chiral purity (Method-XVIII): retention time 26.46 min, 100% ee.

Example 23-I: (R)-4-methyl-6-(4-((3-(4-methyl-1-oxo-1,3-dihydroisobenzofuran-5-yl)piperazin-1-yl)methyl)-1H-1,2,3-triazol-1-yl)nicotinonitrile

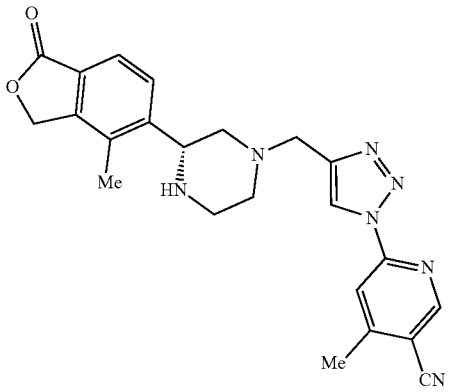

Example 23-I was prepared (0.008 g, 8.83%), by using a similar synthetic protocol as that of Example 1-I and starting from Intermediate 30 (0.04 g, 0.19 mmol) and Intermediate 2-I. $^1$H NMR (400 MHz, DMSO-$d_6$) δ ppm 1.86-1.95 (m, 1H), 2.15-2.29 (m, 4H), 2.64 (s, 3H), 2.81-3.03 (m, 4H), 3.75 (s, 2H), 4.09 (d, J=9.54 Hz, 1H), 5.32-5.43 (m, 2H), 7.64 (d, J=7.83 Hz, 1H), 7.76 (d, J=7.83 Hz, 1H), 8.28 (s, 1H), 8.77 (s, 1H), 8.98 (s, 1H), (Exchangeable proton not observed). LCMS/HPLC (Method-A): retention time 1.43 min, [M+H] 430.0, purity: 98.88%, (Method-B): retention time 1.23 min, [M+H] 430.1, purity: 98.70%. Chiral purity (Method-IX): retention time 12.83 min. 98.50% ee.

Example 24-I: Methyl (R)-4-((1-(5-cyano-4-methylpyridin-2-yl)-1H-pyrazol-4-yl)methyl)-2-(4-methyl-1-oxo-1,3-dihydroisobenzofuran-5-yl)piperazine-1-carboxylate

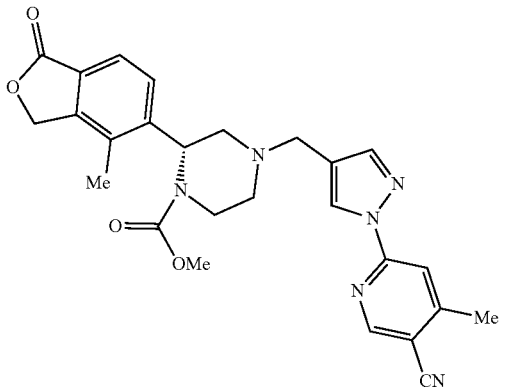

To a stirred solution of Example 2-I (0.03 g, 0.06 mmol) in DCM (3.00 mL) at 0° C. was added TEA (0.03 mL, 0.18 mmol) followed by methyl chloroformate (4.52 μL, 0.06 mmol). The resulting reaction mixture was stirred at ambient temperature for 18 h, diluted with water (15 mL) and extracted with DCM (3×15 mL). The combined organic extracts were washed with brine (15 mL), dried over sodium sulfate and evaporated under reduced pressure. The residue was purified by HPLC [XBridge C18 (19×150 mm) 5 micron; Solvent A: 10-mM ammonium acetate; Solvent B: Acetonitrile, Gradient: 20-100% B over 15 minutes, Flow: 15 mL/min, retention time 2.80 min, UV 220 nm] to obtain Example 24-I (0.003 g, 9.15%). $^1$H NMR (400 MHz, DMSO-$d_6$) δ ppm 2.19 (br. s., 1H), 2.20-2.26 (m, 3H), 2.46 (d, J=4.89 Hz, 1H), 2.56 (s, 3H), 2.89-3.05 (m, 2H), 3.43-3.54 (m, 2H), 3.57 (s, 4H), 3.87 (d, J=11.98 Hz, 1H), 5.25-5.33 (m, 1H), 5.34-5.43 (m, 2H), 7.69 (d, J=8.07 Hz, 1H), 7.76 (s, 1H), 7.95 (s, 1H), 8.02 (d, J=8.07 Hz, 1H), 8.37 (s, 1H), 8.78 (s, 1H). LCMS/HPLC (Method-A): retention time 1.26 min, [M+H] 487.1, purity: 98.94%. (Method-B): retention time 2.02 min, [M+H] 487.1, purity: 100%. Chiral purity (Method-X): retention time 25.56 min, 86.55% ee.

The examples in Table 1 were synthesized using procedures in Example 1 to 24-I.

| Example | Structure | Name | LCMS (M + H) | HPLC/ LCMS Method: RT (min.), Purity | NMR |
|---|---|---|---|---|---|
| 1-II | 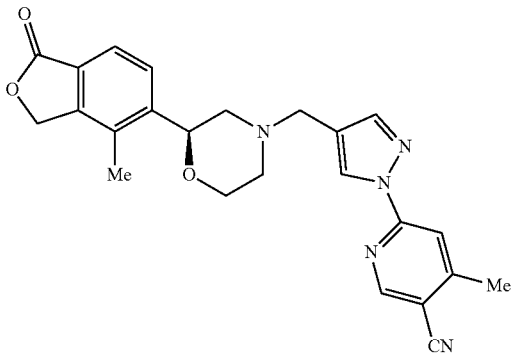 | (S)-4-methyl-6-(4-((2-(4-methyl-1-oxo-1,3-dihydroisobenzofuran-5-yl)morpholino)methyl)-1H-pyrazol-1-yl)nicotinonitrile | 468.1 | A: 1.27, 97.90% B: 1.89, 97.30% XVIII: 18.26, 100% ee | $^1$H NMR (400 MHz, DMSO-$d_6$) δ ppm 1.86-1.96 (m, 1 H), 2.18-2.29 (m, 4 H), 2.58 (s, 3 H), 2.81 (d, J = 11.74 Hz, 1 H), 2.92 (d, J = 11.49 Hz, 1 H), 3.56 (s, 2 H), 3.71-3.81 (m, 1 H), 3.99 (d, J = 9.54 Hz, 1 H), 4.81 (d, J = 8.07 Hz, 1 H), 5.38 (d, J = 4.89 Hz, 2 H), 7.57-7.63 (m, 1 H), 7.64-7.71 (m, 1 H), 7.87 (s, 1 H), 7.99 (s, 1 H), 8.55 (s, 1 H), 8.83 (s, 1 H). |

-continued

| Example | Structure | Name | LCMS (M + H) | HPLC/ LCMS Method: RT (min.), Purity | NMR |
|---|---|---|---|---|---|
| 25-I | 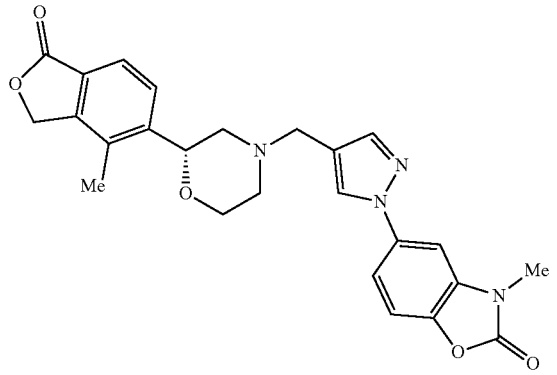 | (R)-3-methyl-5-(4-((2-(4-methyl-1-oxo-1,3-dihydroiso-benzo-furan-5-yl) morpho-lino) methyl)-1H-pyrazol-1-yl) benzo[d] oxazol-2(3H)-one | 461.1 | A: 1.16, 96.80% B: 1.66, 98.20% XIV: 11.59, 100% ee | 400 MHz, DMSO-d6: δ 2.29 (s, 3 H), 3.03-3.41 (m, 3 H), 3.39 (s, 3 H), 3.96 (d, J = 12.40 Hz, 2 H), 4.23-4.32 (m, 3 H), 5.11 (d, J = 10.40 Hz, 1 H), 5.43 (d, J = 4.00 Hz, 2 H), 7.47 (d, J = 8.80 Hz, 1 H), 7.57 (dd, J = 2.40, 8.60 Hz, 1 H), 7.67 (d, J = 8.00 Hz, 1 H), 7.73 (d, J = 2.00 Hz, 1 H), 7.77 (d, J = 7.60 Hz, 1 H), 7.89 (s,1 H), 8.62 (s, 1 H). |
| 26-I | 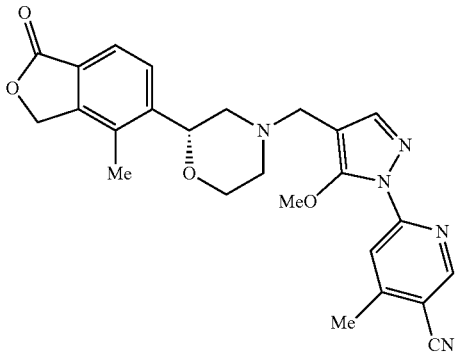 | (R)-6-(5-methoxy-4-((2-(4-methyl-1-oxo-1,3-dihydroiso-benzo-furan-5-yl)morpho-lino) methyl)-1H-pyrazol-1-yl)-4-methyl-nicotino-nitrile | 460.1 | A: 1.40, 100% B: 2.12, 100% XIV: 11.66, 100% ee | $^1$H NMR (400 MHz, DMSO-$d_6$) δ ppm 2.28 (s, 3 H), 2.58 (s, 3 H), 3.01-3.26 (m, 3 H), 3.83-3.95 (m, 1 H), 4.01 (s, 3 H), 4.10-4.31 (m, 3 H), 4.99-5.12 (m, 1 H), 5.42 (d, J = 3.51 Hz, 2 H), 7.65 (s, 1 H), 7.72-7.77 (m, 1 H), 7.82 (s, 1 H), 8.67-8.78 (m, 1 H), 8.81 (s, 1 H), 10.15-10.34 (m, 1 H). |
| 27-I | 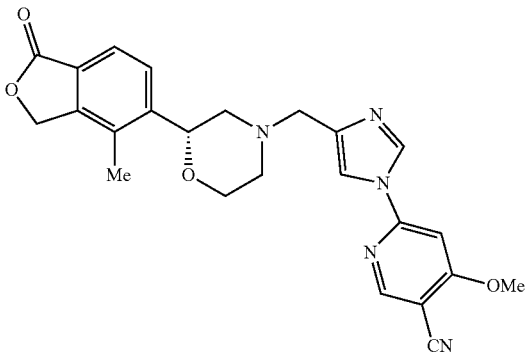 | (R)-4-methoxy-6-(4-((2-(4-methyl-1-oxo-1,3-dihydroiso-benzo-furan-5-yl)morpho-lino) methyl)-1H-imidazol-1-yl) nicotino-nitrile | 446.1 | A: 1.57, 100% B: 1.19, 99.86% V: 8.64, 100% ee | $^1$H NMR (400 MHz, DMSO-$d_6$) δ ppm 1.98-2.0 (m, 1 H), 2.25 (s, 3 H), 2.27-2.36 (m, 1 H), 2.79-2.90 (m, 1 H), 2.95-3.02 (m, 1 H), 3.55 (br. s., 2 H), 3.71-3.81 (m, 1 H), 3.96-4.03 (m, 1 H), 4.10 (s, 3 H), 4.80-4.83 (m, 1 H), 5.39 (d, J = 4.28 Hz, 2 H), 7.58-7.64 (m, 2 H), 7.65-7.69 (m, 1 H), 7.99 (s, 1 H), 8.61 (s, 1 H), 8.75 (s, 1 H). |

-continued

| Example | Structure | Name | LCMS (M + H) | HPLC/ LCMS Method: RT (min.), Purity | NMR |
|---|---|---|---|---|---|
| 28-I | 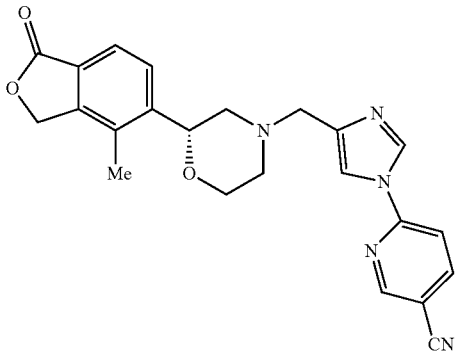 | (R)-6-(4-((2-(4-methyl-1-oxo-1,3-dihydroisobenzofuran-5-yl)morpholino)methyl)-1H-imidazol-1-yl)nicotinonitrile | 416.1 | A: 1.43, 96.32% V: 8.62, 100% ee | $^1$H NMR (400 MHz, DMSO-$d_6$) δ ppm 1.93-2.03 (m, 1 H), 2.25 (s, 3 H), 2.26-2.34 (m, 1 H), 2.82-2.88 (m, 1 H), 2.93-3.01 (m, 1 H), 3.54 (s, 2 H), 3.71-3.80 (m, 1 H), 3.94-4.01 (m, 1 H), 4.79-4.84 (m, 1 H), 5.38 (d, J = 4.46 Hz, 2 H), 7.59-7.63 (m, 2 H), 7.92 (s, 1 H), 8.02 (d, J = 8.68 Hz, 1 H), 8.50 (d, J = 2.26 Hz, 1 H), 8.59 (d, J = 1.10 Hz, 1 H), 8.96 (d, J = 2.08 Hz, 1 H). |
| 29-I | 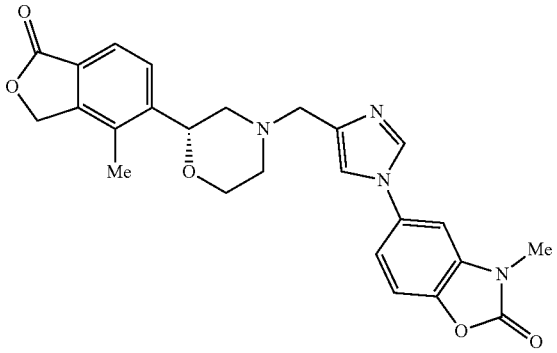 | (R)-3-methyl-5-(4-((2-(4-methyl-1-oxo-1,3-dihydroisobenzofuran-5-yl)morpholino)methyl)-1H-imidazol-1-yl)benzo[d]oxazol-2(3H)-one | 461.1 | A: 1.43, 98.01% B: 1.08, 99.47% V: 10.25, 99.38% ee | $^1$H NMR (400 MHz, DMSO-$d_6$) δ ppm 1.95-2.03 (m, 1 H), 2.25 (s, 3 H), 2.84-2.91 (m, 1 H), 2.97-3.03 (m, 1 H), 3.38 (s, 3 H), 3.39-3.40 (m, 1 H), 3.50-3.53 (m, 2 H), 3.71-3.81 (m, 1 H), 3.96-4.03 (m, 1 H), 4.81 (dd, J = 10.12, 1.80 Hz, 1 H), 5.33-5.35 (m, 2 H), 7.36 (d, J = 2.26 Hz, 1 H), 7.39 (d, J = 7.60-7.69 (m, 4 H), 2.20 Hz, 1 H), 8.17 (d, J = 1.22 Hz, 1 H). |
| 30-I | 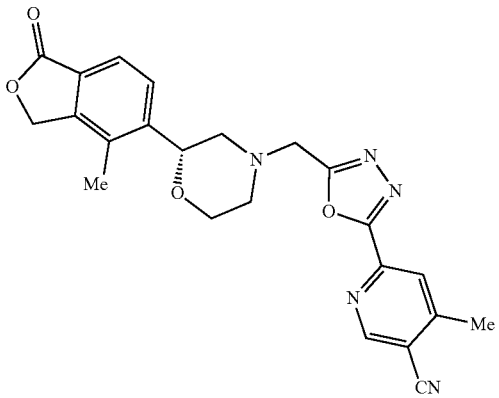 | (R)-4-methyl-6-(5-((2-(4-methyl-1-oxo-1,3-dihydroisobenzofuran-5-yl)morpholino)methyl)-1,3,4-oxadiazol-2-yl)nicotinonitrile | 432.1 | A: 1.39, 98.15% B: 1.54, 97.20% X: 6.62, 100% ee | $^1$H NMR (400 MHz, DMSO-$d_6$) δ ppm 2.22-2.33 (m, 4 H), 2.57 (br. s., 1 H), 2.63 (s, 3 H), 2.96 (d, J = 10.76 Hz, 1 H), 3.11 (d, J = 11.74 Hz, 1 H), 3.75-3.86 (m, 1 H), 4.04 (d, J = 8.80 Hz, 1 H), 4.13 (br. s., 2 H), 4.79-4.93 (m, 1 H), 5.40 (d, J = 2.93 Hz, 2 H), 7.58-7.66 (m, 1 H), 7.66-7.75 (m, 1 H), 8.32 (s, 1 H), 9.12 (s, 1 H). |

-continued

| Example | Structure | Name | LCMS (M + H) | HPLC/ LCMS Method: RT (min.), Purity | NMR |
|---|---|---|---|---|---|
| 31-I | 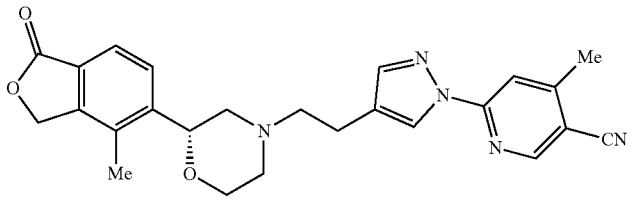 | (R)-4-methyl-6-(4-(2-(2-(4-methyl-1-oxo-1,3-dihydroisobenzofuran-5-yl)morpholino)ethyl)-1H-pyrazol-1-yl)nicotinonitrile | 444.1 | A: 1.84, 99.37% B: 2.04, 99.95% XIX: 9.24, 100% ee | $^1$H NMR (400 MHz, DMSO-$d_6$) δ ppm 1.86-2.00 (m, 1 H), 2.17-2.26 (m, 1 H), 2.28 (s, 3 H), 2.58-2.64 (m, 4 H), 2.68-2.77 (m, 2 H), 2.83-2.92 (m, 2 H), 2.99 (d, J = 11.25 Hz, 1 H), 3.69-3.83 (m, 1 H), 4.00 (d, J = 11.00 Hz, 1 H), 4.80 (d, J = 7.83 Hz, 1 H), 5.29-5.46 (m, 2 H), 7.66 (q, J = 8.07 Hz, 2 H), 7.83 (s, 1 H), 7.96 (s, 1 H), 8.50 (s, 1 H), 8.79-8.87 (m, 1 H). |
| 32-I | 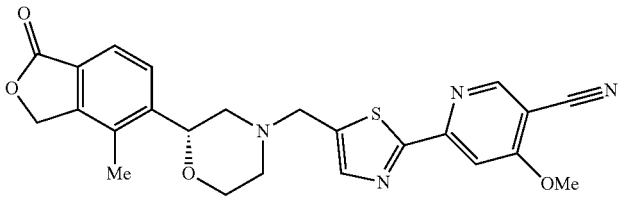 | (R)-4-methoxy-6-(5-((2-(4-methyl-1-oxo-1,3-dihydroisobenzofuran-5-yl)morpholino)methyl)thiazol-2-yl)nicotinonitrile | 463.1 | A: 1.31, 100% B: 1.98, 99.23% XV: 11.34, 100% ee | $^1$H NMR (400 MHz, DMSO-$d_6$) δ ppm 2.02 (t, J = 10.64 Hz, 1 H), 2.22 (s, 3 H), 2.28-2.37 (m, 1 H), 2.82-3.00 (m, 2 H), 3.68-3.88 (m, 1 H), 3.90 (s, 2 H), 4.02 (d, J = 13.21 Hz, 1 H), 4.13 (s, 3 H), 4.84 (d, J = 7.83 Hz, 1 H), 5.30-5.45 (m, 2 H) 7.63 (s, 1 H), 7.66-7.72 (m, 1 H), 7.84 (s, 1 H), 7.90-8.01 (m, 1 H), 8.87 (s, 1 H). |
| 33-I | 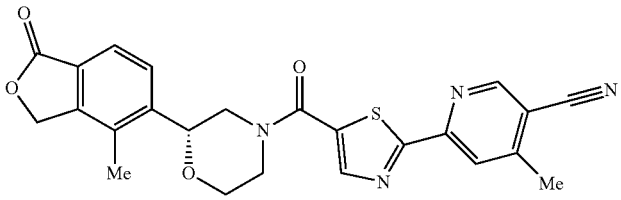 | (R)-4-methyl-6-(5-(2-(4-methyl-1-oxo-1,3-dihydroisobenzofuran-5-yl)morpholine-4-carbonyl)thiazol-2-yl)nicotinonitrile | 461.2 | A: 1.61, 99.48% A: 1.62, 100% V: 16.99, 100% ee | $^1$H NMR (400 MHz, DMSO-$d_6$) δ ppm 2.20 (s, 3 H), 2.27 (br. s., 2 H), 2.32-2.36 (m, 1 H), 2.63 (s, 3 H), 2.66-2.70 (m, 1 H), 3.79-3.88 (m, 1 H), 4.11 (br. s., 1 H), 4.95 (d, J = 9.05 Hz, 1 H), 5.41 (br. s., 2 H), 7.68-7.76 (m, 2 H), 8.27 (s, 1 H), 8.40 (s, 1 H), 9.03 (s, 1 H). |
| 34-I | 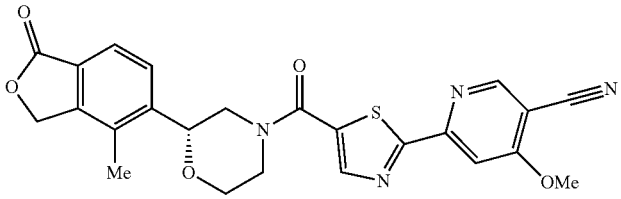 | (R)-4-methoxy-6-(5-(2-(4-methyl-1-oxo-1,3-dihydroisobenzofuran-5-yl)morpholine-4-carbonyl)thiazol-2-yl)nicotinonitrile | 477.1 | A: 1.82, 96.63% B: 1.81, 96.20% V: 17.05, 100% ee | $^1$H NMR (400 MHz, DMSO-$d_6$) δ ppm 2.20 (s, 3 H), 2.27 (br. s., 2 H), 2.31-2.35 (m, 1 H), 2.67 (br. s., 1 H), 3.83 (t, J = 11.62 Hz, 1 H), 4.04-4.11 (m, 1 H), 4.14 (s, 3 H), 4.94 (d, J = 7.58 Hz, 1 H), 5.40 (br. s., 2 H), 7.65-7.78 (m, 2 H), 7.90 (s, 1 H), 8.39 (s, 1 H), 8.92 (s, 1 H). |

-continued

| Example | Structure | Name | LCMS (M + H) | HPLC/ LCMS Method: RT (min.), Purity | NMR |
|---|---|---|---|---|---|
| 35-I | 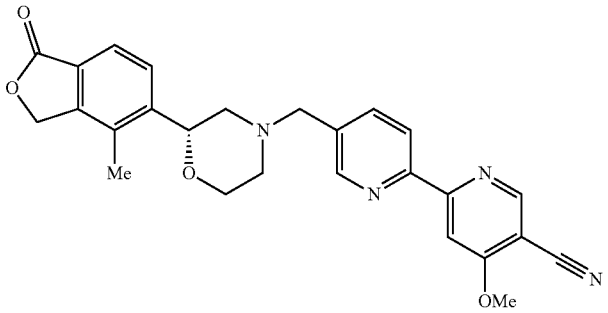 | (R)-4-methoxy-5'-((2-(4-methyl-1-oxo-1,3-dihydroisobenzofuran-5-yl(morpholino)methyl)-[2,2'-bipyridine]-5-carbonitrile | 457.1 | A: 1.27, 94.23% B: 1.95, 95.37% X: 10.00, 100% ee | $^1$H NMR (400 MHz, DMSO-$d_6$) δ ppm 2.24 (s, 3 H), 2.27-2.36 (m, 1 H), 2.76 2.85 (m, 1 H), 2.89-2.95 (m, 1 H), 3.68-3.77 (m, 1 H), 3.78 (br. s., 2 H), 3.95-4.05 (m, 1 H), 4.64 (d, J = 5.02 Hz, 1 H), 4.13 (s, 3 H), 4.98 (br. s., 1 H), 5.34-5.47 (m, 2 H), 7.64 (d, J = 8.07 Hz, 1 H), 7.72 (d, J = 7.34 Hz, 1 H), 8.06 (br. s., 1 H), 8.16 (s, 1 H), 8.48 (d, J = 8.31 Hz, 1 H), 8.77 (br. s., 1 H), 8.94 (s, 1 H). |
| 36-I | 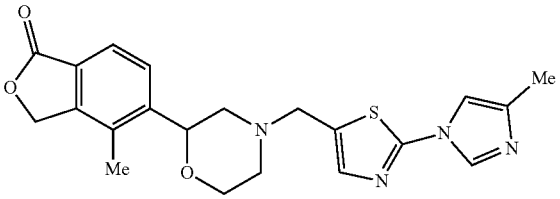 | (R)-4-methyl-5-(4-((2-(4-methyl-1H-imidazol-1-yl)thiazol-5-yl)methyl)morpholin-2-yl)isobenzofuran-1(3H)-one | 411.1 | A: 0.88, 96.07% B: 1.59 94.02% XIV: 6.91, 100% ee | $^1$H NMR (400 MHz, DMSO-$d_6$) δ ppm 2.16 (s, 3 H), 2.24 (s, 3 H), 2.22-2.43 (m, 2 H), 2.85 (d, J = 11.00 Hz, 1 H), 2.95 (d, J = 11.25 Hz, 1 H), 3.73 (d, J = 9.78 Hz, 1 H), 3.80 (s, 2 H), 4.02 (d, J = 9.78 Hz, 1 H), 4.80 (d, J = 7.83 Hz, 1 H) 5.33-5.47 (m, 2 H), 7.49 (s, 2 H), 7.61 (d, J = 8.0 Hz, 1 H), 7.67 (d, J = 8.0 Hz, 1 H), 8.24 (s, 1 H). |
| 37-I | 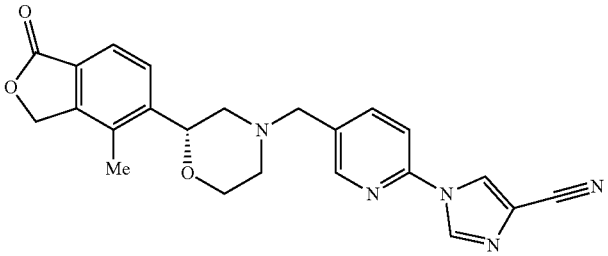 | (R)-1-(5-((2-(4-methyl-1-oxo-1,3-dihydroisobenzofuran-5-yl)morpholino)methyl)pyridin-2-yl)-1H-imidazole-4-carbonitrile | 390.0 | A: 0.92, 95.02% B: 1.18, 95.73% X: 2.76, 100% ee | $^1$H NMR (400 MHz, DMSO-$d_6$) δ ppm 2.23 (s, 3 H), 2.24-2.36 (m, 2 H), 2.77 (d, J = 11.49 Hz, 1 H), 2.89 (d, J = 11.74 Hz, 1 H), 3.66 (s, 2 H), 3.72-3.86 (m, 1 H), 4.00 (d, J = 11.74 Hz, 1 H), 4.75-4.93 (m, 1 H), 5.29-5.46 (m, 2 H), 7.52-7.73 (m, 2 H), 7.88 (d, J = 8.31 Hz, 1 H), 8.05 (dd, J = 8.31, 2.20 Hz, 1 H), 8.50 (d, J = 2.20 Hz, 1 H), 8.74 (d, J = 1.22 Hz, 1 H), 8.91 (d, J = 1.22 Hz, 1 H). |

-continued

| Example | Structure | Name | LCMS (M + H) | HPLC/ LCMS Method: RT (min.), Purity | NMR |
|---|---|---|---|---|---|
| 38-I | 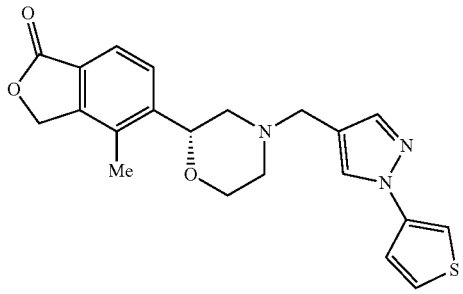 | (R)-4-methyl-5-(4-((1-(thiophen-3-yl)-1H-pyrazol-4-yl)methyl)morpholin-2-yl)isobenzofuran-1(3H)-one | 396.2.0 | A: 0.96 96.60%, B: 1.50, 97.10% XVIII: 9.15, 100% ee | $^1$H NMR (400 MHz, DMSO-$d_6$) δ ppm 1.83-1.96 (m, 1 H), 2.18-2.21 (m, 1 H), 2.24 (s, 3 H), 2.81 (d, J = 11.49 Hz, 1 H), 2.92 (d, J = 11.49 Hz, 1 H), 3.50 (br. s., 2 H), 3.69-3.82 (m, 1 H), 3.99 (d, 11.74 Hz, 1 H), 4.81 (d, J = 8.80 Hz, 1 H), 5.34-5.44 (m, 2 H), 7.50-7.56 (m, 1 H), 7.58-7.70 (m, 5 H), 8.29 (s, 1 H). |
| 39-I | 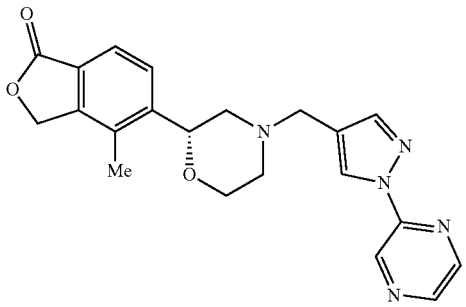 | (R)-4-methyl-5-(4-((1-(pyrazin-2-yl)-1H-pyrazol-4-yl)methyl)morpholin-2-yl)isobenzofuran-1(3H)-one | 392.2 | A: 0.77, 95.20% B: 1.31, 95.20% XVIII: 21.35, 100% ee | $^1$H NMR (400 MHz, DMSO-$d_6$) δ ppm 1.83-1.96 (m, 1 H), 2.18-2.21 (m, 1 H), 2.24 (s, 3 H), 2.81 (d, J = 11.49 Hz, 1 H), 2.92 (d, J = 11.49 Hz, 1 H), 3.50 (br. s., 2 H), 3.69-3.82 (m, 1 H), 3.99 (d, J = 11.74 Hz, 1 H), 4.82 (dd, J = 10.03, 2.20 Hz, 1 H), 5.33-5.45 (m, 2 H), 7.57-7.69 (m, 2 H), 7.87 (s, 1 H), 8.49-8.56 (m, 2 H), 8.60 (d, J = 2.45 Hz, 1 H), 9.20 (d, J = 1.22 Hz, 1 H). |
| 40-I | 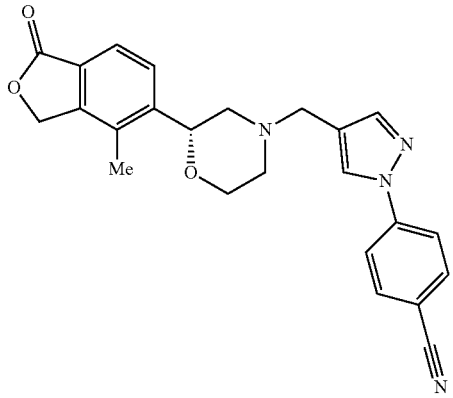 | (R)-4-(4-((2-(4-methyl-1-oxo-1,3-dihydroisobenzofuran-5-yl)morpholino)methyl)-1H-pyrazol-1-yl)benzonitrile | 415.2 | A: 1.00, 96.90% B: 1.55, 96.50% XVIII: 11.29, 100% ee | $^1$H NMR (400 MHz, DMSO-$d_6$) δ ppm 1.92 (t, J = 10.76 Hz, 1 H), 2.18-2.21 (m, 1 H), 2.24 (s, 3 H), 2.82 (d, J = 11.25 Hz, 1 H), 2.93 (d, J = 10.76 Hz, 1 H), 3.53 (s, 2 H), 3.71-3.81 (m, 1 H), 3.99 (d, J = 9.29 Hz, 1 H), 4.81 (d, J = 7.83 Hz, 1 H), 5.32-5.43 (m, 2 H), 7.58-7.70 (m, 2 H), 7.79 (s, 1 H), 7.92-8.00 (m, 2 H), 8.00-8.06 (m, 2 H), 8.60 (s, 1 H). |
| 41-I | 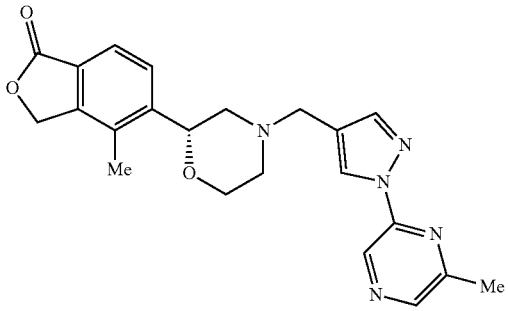 | (R)-4-methyl-5-(4-((1-(6-methylpyrazin-2-yl)-1H-pyrazol-4-yl)methyl)morpholin-2-yl)isobenzofuran-1(3H)-one | 406.2 | A: 0.87, 99.10% B: 1.44, 98.50% XVIII: 20.05, 100% ee | $^1$H NMR (400 MHz, DMSO-$d_6$) δ ppm 1.84-1.97 (m, 1 H), 2.25 (s, 3 H), 2.45 (s, 3 H), 2.76-2.85 (m, 2 H), 2.90-2.98 (m, 1 H), 3.58 (s, 2 H), 3.72-3.84 (m, 1 H), 3.96-4.03 (m, 1 H), 4.78-4.87 (m, 1 H), 5.39 (d, J = 4.89 Hz, 2 H), 7.65 (d, J = 14.92 Hz, 2 H), 7.85 (s, 1 H), 8.47-8.52 (m, 2 H), 8.99 (s, 1 H). |

-continued

| Example | Structure | Name | LCMS (M + H) | HPLC/ LCMS Method: RT (min.), Purity | NMR |
|---|---|---|---|---|---|
| 42-I | 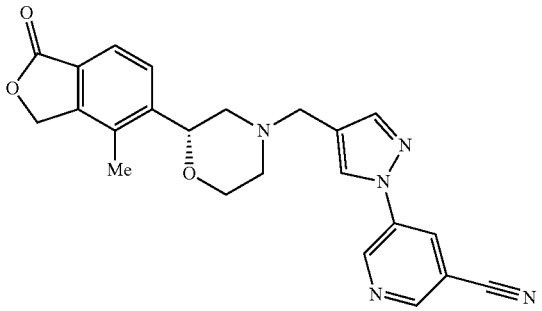 | (R)-5-(4-((2-(4-methyl-1-oxo-1,3-dihydroisobenzofuran-5-yl)morpholino)methyl)-1H-pyrazol-1-yl)nicotinonitrile | 416.2 | A: 0.86, 93.10% B: 1.50, 97.10% | $^1$H NMR (400 MHz, DMSO-$d_6$) δ ppm 1.87-2.01 (m, 1 H), 2.22-2.29 (m, 4 H), 2.82 (br. s., 1 H), 2.94 (d, J = 11.04 Hz, 1 H), 3.55 (s, 2 H), 3.77 (dd, J = 11.55, 9.04 Hz, 1 H), 4.01 (d, J = 9.54 Hz, 1 H), 4.82 (d, J = 8.03 Hz, 1 H), 5.34-5.42 (m, 2 H), 7.59-7.74 (m, 2 H), 7.84 (s, 1 H), 8.62 (s, 1 H), 8.71-8.78 (m, 1 H), 8.93 (d, J = 1.51 Hz, 1 H), 9.38 (d, J = 2.51 Hz, 1 H). |
| 43-I | 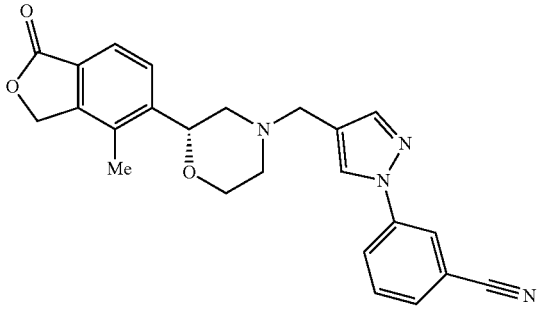 | (R)-3-(4-((2-(4-methyl-1-oxo-1,3-dihydroisobenzofuran-5-yl)morpholino)methyl)-1H-pyrazol-1-yl)benzonitrile | 415.2 | A: 1.02, 97.60%, B: 1.57, 96.70% XVIII: 11.61, 100% ee | $^1$H NMR (400 MHz, DMSO-$d_6$) δ ppm 1.88 (s, 1 H), 2.22-2.28 (m, 3 H), 2.83 (d, J = 11.55 Hz, 1 H), 2.94 (d, J = 10.54 Hz, 1 H), 3.53 (s, 2 H) 3.77 (dd, J = 11.29, 9.29 Hz, 2 H), 4.01 (d, J = 9.54 Hz, 1 H), 4.82 (d, J = 8.03 Hz, 1 H), 5.39 (d, J = 4.52 Hz, 2 H), 7.59-7.78 (m, 5 H), 8.19 (dt, J = 8.03, 1.76 Hz, 1 H), 8.31 (d, J = 1.51 Hz, 1 H), 8.57 (s,1 H). |
| 44-I | 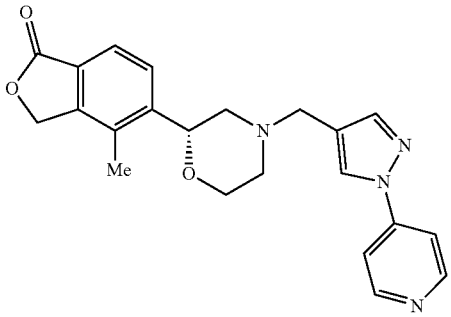 | (R)-4-methyl-5-(4-((1-(pyridin-4-yl)-1H-pyrazol-4-yl)methyl)morpholin-2-yl)isobenzofuran-1(3H)-one | 391.2 | A: 0.54, 99.20% B: 1.18, 98.9% | $^1$H NMR (400 MHz, DMSO-$d_6$) δ ppm 1.88-1.96 (m, 1 H), 2.24 (s, 4 H), 2.82 (d, J = 11.04 Hz, 1 H), 2.93 (d, J = 11.55 Hz, 1 H), 3.53 (s, 2 H), 3.72-3.80 (m, 1 H), 4.00 (dd, J = 11.29, 1.76 Hz, 1 H), 4.82 (dd, J = 10.04, 2.51 Hz, 1 H), 5.38 (d, J = 4.52 Hz, 2 H), 7.65-7.69 (m, 2 H), 7.80 (s, 1 H), 7.85 (s, 2 H), 8.63 (s, 3 H). |

-continued

| Example | Structure | Name | LCMS (M + H) | HPLC/ LCMS Method: RT (min.), Purity | NMR |
|---|---|---|---|---|---|
| 45-I | 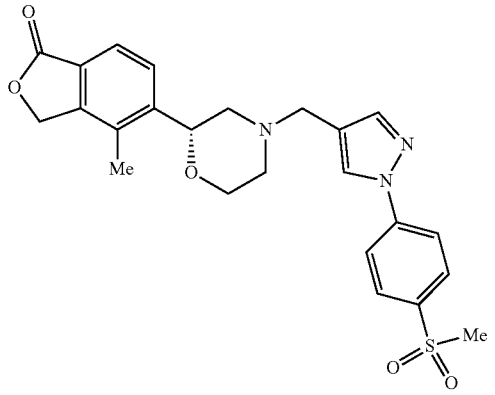 | (R)-4-methyl-5-(4-((1-(4-(methylsulfonyl)phenyl)-1H-pyrazol-4-yl)methyl)morpholin-2-yl)isobenzofuran-1(3H)-one | 468.2 | A: 0.86, 99.30%, B: 1.32, 97.80% | $^1$H NMR (400 MHz, DMSO-$d_6$) δ ppm 1.87-2.01 (m, 1 H), 2.22-2.29 (m, 3 H), 2.34 (dt, J = 3.76, 1.63 Hz, 1 H), 2.82 (br. s., 1 H), 2.94 (d, J = 11.04 Hz, 1 H), 3.21 (s, 3 H), 3.55 (s, 2 H), 3.77 (dd, J = 11.55, 9.04 Hz, 1 H), 4.01 (d, J = 9.54 Hz, 1 H), 4.82 (d, J = 8.03 Hz, 1 H), 5.34-5.42 (m, 2 H), 7.52 (s, 1 H), 7.54-7.67 (m, 6 H), 8.22 (s, 1 H). |
| 46-I | 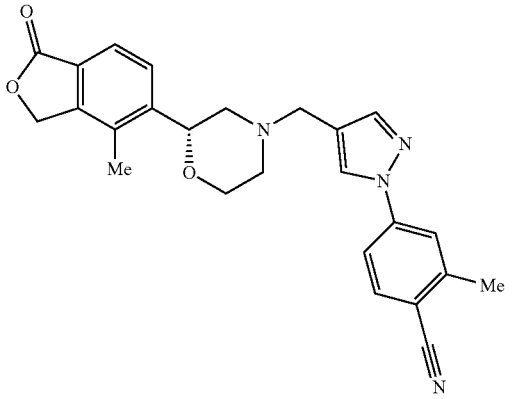 | (R)-2-methyl-4-(4-((2-(4-methyl-1-oxo-1,3-dihydroisobenzofuran-5-yl)morpholino)methyl)-1H-pyrazol-1-yl)benzonitrile | 429.2 | A: 1.09, 98.60% B: 1.68, 98.20% XVIII: 13.04, 100% ee | $^1$H NMR (400 MHz, DMSO-$d_6$) δ ppm 1.87-1.97 (m, 1 H), 2.24 (s, 4 H), 2.55 (s, 3 H), 2.82 (d, J = 11.55 Hz, 1 H), 2.92 (d, J = 11.55 Hz, 1 H), 3.52 (br. s., 2 H), 3.76 (t, J = 11.04 Hz, 1 H), 4.00 (d, J = 10.04 Hz, 1 H), 4.81 (d, J = 9.04 Hz, 1 H), 5.38 (d, J = 4.52 Hz, 2 H), 7.59-7.69 (m, 2 H), 7.92 (s, 1 H), 8.51-8.59 (m, 3 H), 9.19 (s, 1 H). |
| 47-I | 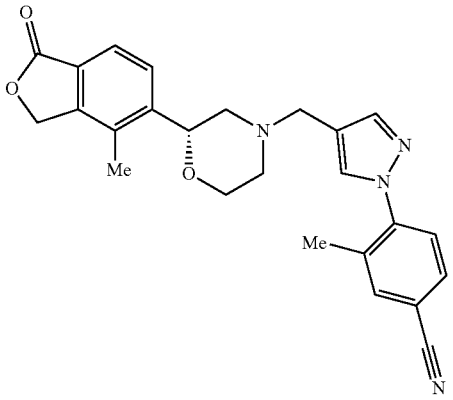 | (R)-3-methyl-4-(4-((2-(4-methyl-1-oxo-1,3-dihydroisobenzofuran-5-yl)morpholino)methyl)-1H-pyrazol-1-yl)benzonitrile | 429.2 | A: 1.01, 97.80% B: 1.56, 99.10% | $^1$H NMR (400 MHz, DMSO-$d_6$) δ ppm 1.91 (t, J = 11.04 Hz, 1 H), 2.24 (s, 4 H), 2.33 (s, 3 H), 2.83 (d, J = 11.04 Hz, 1 H), 2.94 (d, J = 11.04 Hz, 1 H), 3.53 (s, 2 H), 3.76 (td, J = 11.29, 2.51 Hz, 1 H), 4.00 (dd, J = 11.04, 2.01 Hz, 1 H), 4.81 (dd, J = 10.04, 2.01 Hz, 1 H), 5.39 (d, J = 4.02 Hz, 2 H), 7.56-7.64 (m, 2 H), 7.65-7.70 (m, 1 H), 7.73 (s, 1 H), 7.81 (dd, J = 8.03, 1.51 Hz, 1 H), 7.92 (d, J = 1.51 Hz, 1 H), 8.10 (s, 1 H). |

-continued

| Example | Structure | Name | LCMS (M + H) | HPLC/ LCMS Method: RT (min.), Purity | NMR |
|---|---|---|---|---|---|
| 48-I | 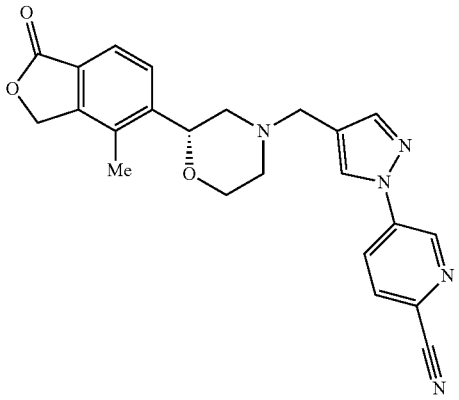 | (R)-5-(4-((2-(4-methyl-1-oxo-1,3-dihydroisobenzofuran-5-yl) morpholino) methyl)-1H-pyrazol-1-yl) picolinonitrile | 416.2 | A: 0.89, 94.50% B: 1.39, 94.60% | $^1$H NMR (400 MHz, DMSO-$d_6$) δ ppm 1.85-1.99 (m, 1 H), 2.24 (s, 4 H), 2.83 (d, J = 11.55 Hz, 1 H), 2.94 (d, J = 11.55 Hz, 1 H), 3.54 (s, 2 H), 3.70-3.83 (m, 1 H), 4.00 (d, J = 11.04 Hz, 1 H), 4.82 (dd, J = 10.04, 2.01 Hz, 1 H), 5.38 (d, J = 5.52 Hz, 2 H), 7.57-7.71 (m, 2 H), 7.87 (s, 1 H), 8.17 (d, J = 9.04 Hz, 1 H), 8.43 (dd, J = 8.53, 2.51 Hz, 1 H), 8.69 (s, 1 H), 9.28 (d, J = 2.01 Hz, 1 H). |
| 49-I | 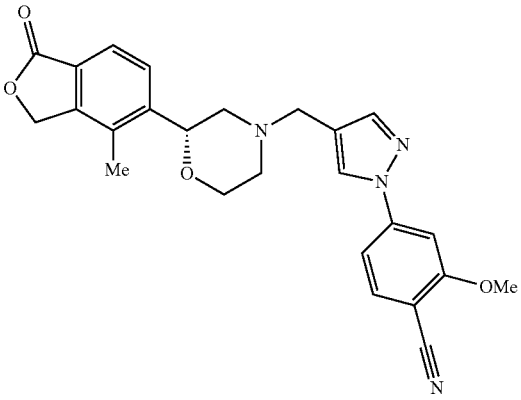 | (R)-2-methoxy-4-(4-((2-(4-methyl-1-oxo-1,3-dihydroisobenzofuran-5-yl) morpholino) methyl)-1H-pyrazol-1-yl) benzonitrile | 445.1 | A: 1.32, 97.40% B: 1.83, 97.60% | $^1$H NMR (400 MHz, DMSO-$d_6$) δ ppm 1.85-1.99 (m, 1 H), 2.24 (s, 4 H), 2.83 (d, J = 11.55 Hz, 1 H), 2.94 (d, J = 11.55 Hz, 1 H), 3.54 (s, 2 H), 3.70-3.83 (m, 1 H), 4.00-4.05 (m, 4 H), 4.82 (br. s., 1 H), 5.39 (d, J = 4.02 Hz, 2 H), 7.53-7.70 (m, 4 H), 7.78-7.84 (m, 2 H), 8.78 (s. 1 H). |
| 50-I | 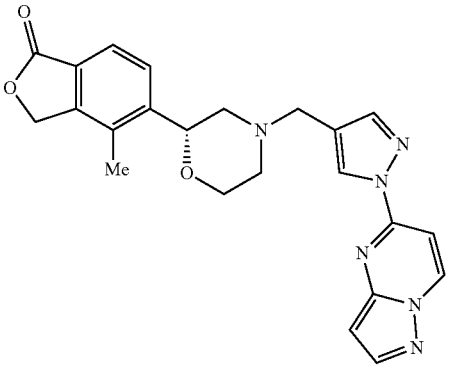 | (R)-4-methyl-5-(4-((1-(pyrazolo [1,5-a] pyrimidin-5-yl)-1H-pyrazol-4-yl) methyl) morpholin-2-yl)isobenzofuran-1 (3H)-one | 431.2 | A: 0.08, 98.80% B: 1.41, 99.30% | $^1$H NMR (400 MHz, DMSO-$d_6$) δ ppm 1.87-1.98 (m, 1 H), 2.24 (s, 4 H), 2.82 (d, J = 11.04 Hz, 1 H), 2.94 (d, J = 11.55 Hz, 1 H), 3.58 (s, 2 H), 3.77 (td, J = 11.42, 2.26 Hz, 1 H), 3.95-4.05 (m, 1 H), 4.83 (dd, J = 9.79, 2.26 Hz, 1 H), 5.34-5.44 (m, 2 H), 6.56-6.64 (m, 1 H), 7.50-7.73 (m, 3 H), 7.88 (s, 1 H), 8.22 (d, J = 2.51 Hz, 1 H), 8.60 (s, 1 H), 9.19 (dd, J = 7.53, 1.00 Hz, 1 H). |

-continued

| Example | Structure | Name | LCMS (M + H) | HPLC/ LCMS Method: RT (min.), Purity | NMR |
|---|---|---|---|---|---|
| 51-I | 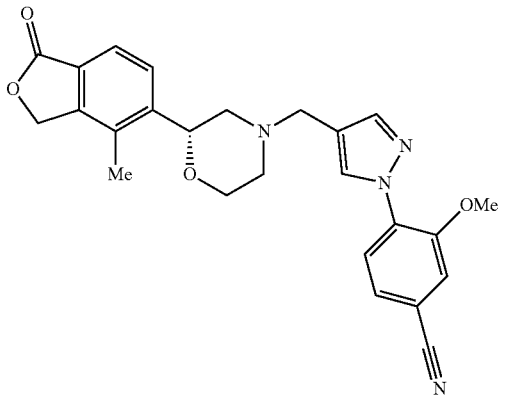 | (R)-3-methoxy-4-(4-((2-(4-methyl-1-oxo-1,3-dihydroisobenzofuran-5-yl)morpholino)methyl)-1H-pyrazol-1-yl)benzonitrile | 445.2 | A: 1.03, 98.40% B: 1.59, 99.40% XVIII: 12.11, 100% ee | $^1$H NMR (400 MHz, DMSO-$d_6$) δ ppm 1.86-1.94 (m, 1 H), 2.22-2.28 (m, 4 H), 2.81 (d, J = 12.05 Hz, 1 H), 2.92 (d, J = 11.55 Hz, 1 H), 3.53 (s, 2 H), 3.72-3.79 (m, 1 H), 3.98 (d, J = 2.01 Hz, 1 H), 4.00 (br. s., 3 H), 4.81 (dd, J = 10.04, 2.01 Hz, 1 H), 5.38 (d, J = 3.51 Hz, 2 H), 7.55 (dd, J = 8.28, 1.76 Hz, 1 H), 7.60-7.63 (m, 1 H), 7.65-7.69 (m, 1 H), 7.73 (s, 1 H), 7.76 (d, J = 1.51 Hz, 1 H), 7.90 (d, J = 8.53 Hz, 1 H), 8.28 (s, 1 H). |
| 52-I | 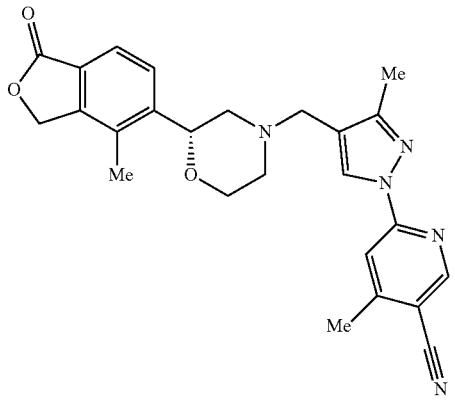 | (R)-4-methyl-6-(3-methyl-4-((2-(4-methyl-1-oxo-1,3-dihydroisobenzofuran-5-yl)morpholino)methyl)-1H-pyrazol-1-yl)nicotinonitrile | 444.1 | A: 1.26, 100% B: 2.13, 98.47% XIV: 10.49, 99.69% | $^1$H NMR (400 MHz, DMSO-$d_6$) δ ppm 1.94 (s, 2 H) 2.23 (s, 3 H) 2.32 (s, 3 H) 2.56 (s, 3 H) 2.77-2.84 (m, 1 H) 2.89 (s, 1 H) 3.49 (s, 2 H) 3.75 (d, J = 1.71 Hz, 1 H) 3.96-4.03 (m, 1 H) 4.80 (d, J = 8.31 Hz, 1 H) 5.38 (d, J = 3.91 Hz, 2 H) 7.60-7.64 (m, 1 H) 7.66-7.70 (m, 1 H) 7.91 (s, 1 H) 8.45 (s, 1 H) 8.79 (s, 1 H). |
| 53-I | 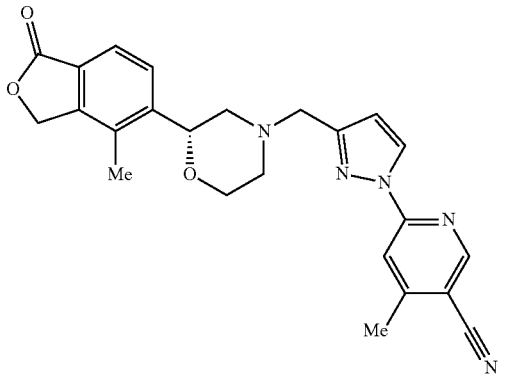 | (R)-4-methyl-6-(3-((2-(4-methyl-1-oxo-1,3-dihydroisobenzofuran-5-yl)morpholino)methyl)-1H-pyrazol-1-yl)nicotinonitrile | 430.2. | A: 1.17, 100% B: 2.04, 95.89% XVIII: 11.72, 100% | $^1$H NMR (400 MHz, DMSO-$d_6$) δ ppm 1.98-2.08 (m, 1 H) 2.23 (s, 3 H) 2.28-2.36 (m, 1 H) 2.59 (s, 3 H) 2.75-2.82 (m, 1 H) 2.88-2.94 (m, 1 H) 3.56-3.68 (m, 1 H) 3.90-3.97 (m, 1 H) 4.00-4.19 (m, 2 H) 4.64-4.73 (m, 1 H) 5.39 (d, J = 6.11 Hz, 2 H) 6.60 (s, 1 H) 7.61 (s, 1H) 7.65-7.71 (m, 1 H) 7.81 (d, J = 1.71 Hz, 1 H) 7.99 (s, 1 H) 8.87 (s, 1 H). |

-continued

| Example | Structure | Name | LCMS (M + H) | HPLC/ LCMS Method: RT (min.), Purity | NMR |
|---|---|---|---|---|---|
| 2-II | 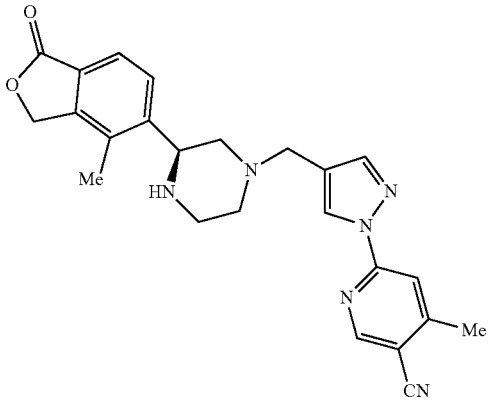 | (S)-4-methyl-6-(4-((3-(4-methyl-1-oxo-1,3-dihydroiso-benzofuran-5-yl) piperazin-1-yl) methyl)-1H-pyrazol-1-yl) nicotino-nitrile | 429.2 | E: 10.23, 99.23% G: 11.07, 99.52% II: 3.56 100% ee. | $^1$H NMR (400 MHz, DMSO-$d_6$) δ ppm 1.79 (t, J = 10.29 Hz, 1 H), 2.03-2.18 (m, 1 H), 2.25 (s, 3 H), 2.66-2.67 (m, 4 H), 2.79 (t, J = 9.04 Hz, 2 H), 2.84-2.92 (m, 1 H), 2.94-3.05 (m, 1 H), 3.45-3.59 (m, 2 H), 4.06 (d, J = 9.54 Hz, 1 H), 5.36 (d, J = 1.51 Hz, 2 H), 7.63 (d, J = 8.03 Hz, 1 H), 7.76 (d, J = 8.03 Hz, 1 H), 7.85 (s, 1 H), 7.98 (s, 1 H), 8.52 (s, 1 H), 8.82 (s, 1 H). |
| 54-I | 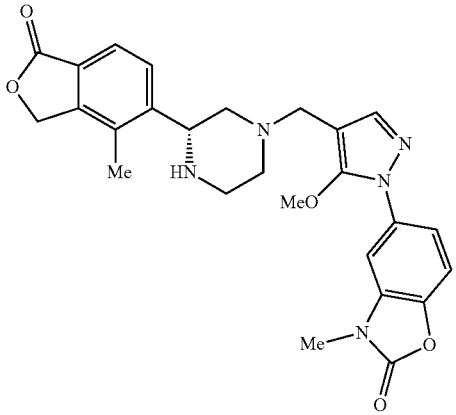 | (R)-5-(5-methoxy-4-((3-(4-methyl-1-oxo-1,3-dihydroiso-benzo-furan-5-yl) piperazin-1-yl) methyl)-1H-pyrazol-1-yl)-3-methyl-benzo [d]oxazol-2(3H)-one | 490.1 | A: 1.19, 98.00% B: 1.55, 98.47% XVIII: 14.42, 100% ee | 1H NMR (400 MHz, $CDCl_3$) δ ppm 2.37 (s, 3 H), 2.72-2.79 (m, 1 H), 2.95-3.04 (m, 2 H), 3.33-3.39 (m, 1 H), 3.46 (s, 3 H), 3.47-3.50 (m, 1 H), 3.51-3.60 (m, 2 H), 3.89-3.96 (m, 1 H), 4.03 (s, 3 H), 4.19-4.25 (m, 1 H), 4.72-4.77 (m, 1 H), 5.27 (s, 2 H), 7.22-7.25 (m, 2 H), 7.32-7.36 (m, 1 H), 7.81 (d, J = 6.50 Hz, 2 H), 8.05 (s, 1 H). |
| 55-I | 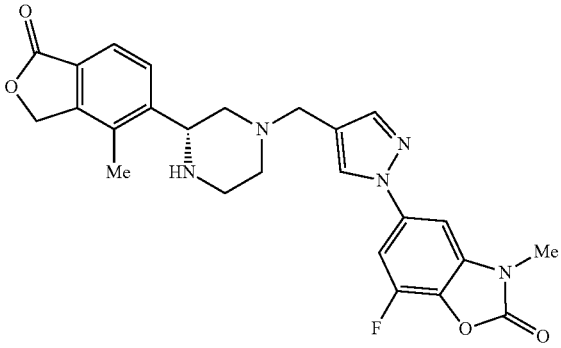 | (R)-7-fluoro-3-methyl-5-(4-((3-(4-methyl-1-oxo-1,3-dihydroiso-benzo-furan-5-yl) piperazin-1-yl) methyl)-1H-pyrazol-1-yl)benzo[d] oxazol-2(3H)-one | 478.0 | A: 1.18, 98.05% B: 1.52, 98.34% XI: 13.14, 100% ee | $^1$H NMR (400 MHz, DMSO-$d_6$) δ ppm 1.75-1.85 (m, 1 H), 2.05-2.15 (m, 1 H), 2.26 (s, 3 H), 2.75-3.01 (m, 4 H), 3.39 (s, 3 H), 3.49 (s, 2 H), 4.10 (d, J = 9.54 Hz, 1 H), 5.37 (s, 2 H), 7.57-7.70 (m, 4 H), 7.78 (d, J = 7.83 Hz, 1 H), 8.46 (s, 1 H), (Exchangeable proton not observed). |

-continued

| Example | Structure | Name | LCMS (M + H) | HPLC/ LCMS Method: RT (min.), Purity | NMR |
|---|---|---|---|---|---|
| 56-I | 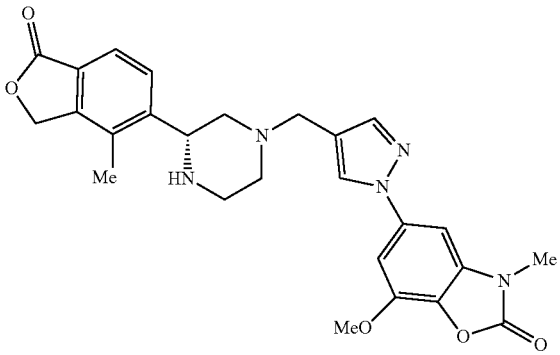 | (R)-7-methoxy-3-methyl-5-(4-((3-(4-methyl-1-oxo-1,3-dihydroisobenzofuran-5-yl) piperazin-1-yl) methyl)-1H-pyrazol-1-yl)benzo[d] oxazol-2(3H)-one | 490.2 | A: 0.90, 92.18% B: 1.20, 95.48% XX: 10.23, 100% ee | $^1$H NMR (400 MHz, DMSO-$d_6$) δ ppm 1.79-1.91 (m, 1 H), 2.12-2.20 (m, 1 H), 2.27 (s, 3 H), 2.86-3.04 (m, 4 H), 3.35 (s, 3 H), 3.51 (br. s., 2 H), 3.96 (s, 3 H), 4.16 (br. s., 1 H), 5.38 (d, J = 2.20 Hz, 2 H), 7.31 (d, J = 1.96 Hz, 1 H), 7.39 (d, J = 1.96 Hz, 1 H), 7.64-7.70 (m, 2 H), 7.78 (d, J = 8.07 Hz, 1 H), 8.47 (s, 1 H), (Exchangeable proton not observed). |
| 57-I | 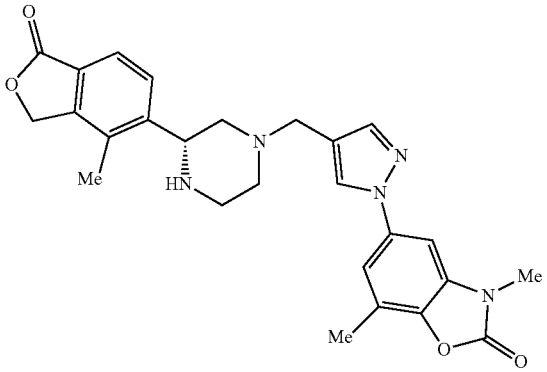 | (R)-3,7-dimethyl-5-(4-((3-(4-methyl-1-oxo-1,3-dihydroiso-benzo-furan-5-yl) piperazin-1-yl) methyl)-1H-pyrazol-1-yl)benzo[d] oxazol-2(3H)-one | 474.1 | A: 1.61, 97.04% B: 1.49, 98.74% XIV: 9.11, 100% ee | 1H NMR (400 MHz, $CD_3OD$) δ ppm 2.42 (s, 3 H), 2.44 (s, 3 H), 2.65-2.78 (m, 2 H), 3.45 (s, 3 H), 3.45-3.58 (m, 4 H), 3.89 (s, 2 H), 4.77 (d, J = 2.51 Hz, 1 H), 5.42 (s, 2 H), 7.38 (d, J = 1.51 Hz, 1 H), 7.41 (d, J = 2.01 Hz, 1 H), 7.72 (d, J = 8.03 Hz, 1 H), 7.76 (s, 1 H), 7.85 (d, J = 8.03 Hz, 1 H), 8.28 (s, 1 H), (Exchangeable proton not observed). |
| 58-I | 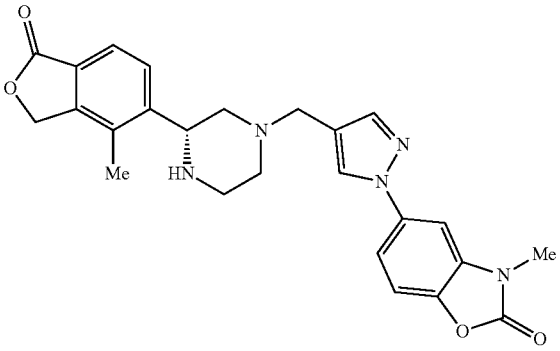 | (R)-3-methyl-5-(4-((3-(4-methyl-1-oxo-1,3-dihydroiso-benzofuran-5-yl) piperazin-1-yl) methyl)-1H-pyrazol-1-yl) benzo[d] oxazol-2(3H)-one | 460.0 | A: 1.08, 95.95% B: 1.38, 95.74% V: 9.53, 92.68% ee | $^1$H NMR (400 MHz, DMSO-$d_6$) δ ppm 1.91 (s, 1 H), 2.17 (s, 1 H), 2.27 (s, 3 H), 2.87 (br. s., 2 H), 2.98 (br. s., 1 H), 3.06 (br. s., 1 H), 3.38 (s, 3 H), 3.52 (br. s., 2 H), 4.19 (br. s., 1 H), 5.38 (d, J = 2.45 Hz, 2 H), 7.41 (d, J = 8.56 Hz, 1 H), 7.57 (dd, J = 8.68, 2.32 Hz, 1 H), 7.63-7.71 (m, 2 H), 7.72-7.80 (m, 2 H), 8.42 (s, 1 H), (Exchangeable proton not observed). |

-continued

| Example | Structure | Name | LCMS (M + H) | HPLC/ LCMS Method: RT (min.), Purity | NMR |
|---|---|---|---|---|---|
| 59-I | 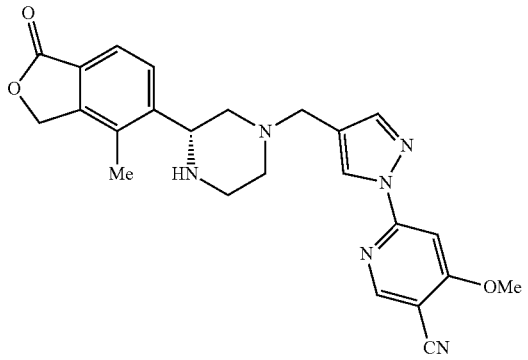 | (R)-4-methoxy-6-(4-((3-(4-methyl-1-oxo-1,3-dihydroisobenzofuran-5-yl)piperazin-1-yl)methyl)-1H-pyrazol-1-yl)nicotinonitrile | 445.1 | A: 1.15, 98.35% B: 1.51, 98.43% V: 8.30, 98.31% ee | $^1$H NMR (400 MHz, DMSO-$d_6$) δ ppm 1.93 (br. s., 1 H), 2.20 (br. s., 1 H), 2.27 (s, 3 H), 2.85 (br. s., 2 H), 2.95-3.12 (m, 2 H), 3.56 (br. s., 2 H), 4.10 (s, 3 H), 4.20 (br. s., 1 H), 5.30-5.47 (m, 3 H), 7.60 (s, 1 H), 7.65-7.72 (m, 1 H), 7.73-7.81 (m, 1 H), 7.87 (s, 1 H), 8.54 (s, 1 H), 8.73 (s, 1 H). |
| 61-I | 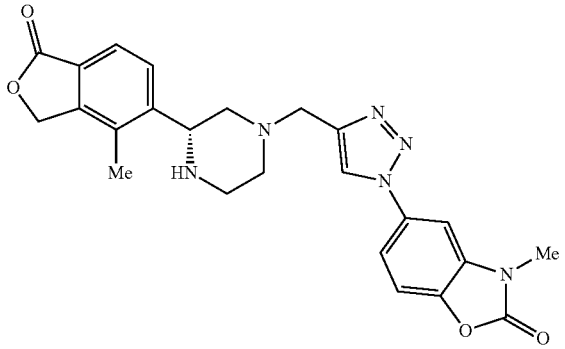 | (R)-3-methyl-5-(4-((3-(4-methyl-1-oxo-1,3-dihydroisobenzofuran-5-yl)piperazin-1-yl)methyl)-1H-1,2,3-triazol-1-yl)benzo[d]oxazol-2(3H)-one | 461.0 | A: 1.07, 96.74% B: 1.24, 98.65% V: 8.68, 100% ee | $^1$H NMR (400 MHz, DMSO-$d_6$) δ ppm 2.02 (br. s., 1 H), 2.28 (s, 3 H), 2.33 (s, 1 H), 2.67 (s, 1 H), 2.90 (d, J = 11.74 Hz, 2 H), 2.98 (br. s., 1 H), 3.08 (d, J = 11.00 Hz, 1 H), 3.40 (s, 3 H), 3.74 (s, 2 H), 4.19 (br. s., 1 H), 5.33-5.44 (m, 2 H), 7.52 (d, J = 8.56 Hz, 1 H), 7.63-7.71 (m, 2 H), 7.78 (d, J = 7.83 Hz, 1 H), 7.88 (d, J = 1.96 Hz, 1 H), (Exchangeable proton not observed). |
| 62-I | 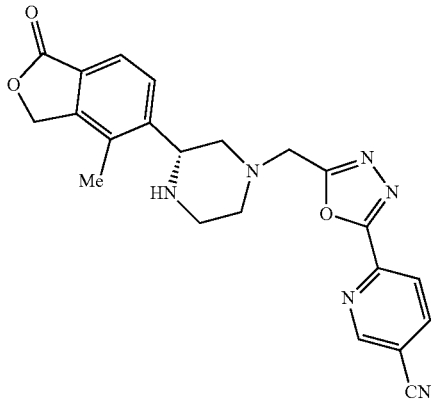 | (R)-6-(5-((3-(4-methyl-1-oxo-1,3-dihydroisobenzofuran-5-yl)piperazin-1-yl)methyl)-1,3,4-oxadiazol-2-yl)nicotinonitrile | 417.0 | A: 0.99, 100% B: 1.14 98.88% XX: 8.88, 100% ee | $^1$H NMR (400 MHz, DMSO-$d_6$) δ ppm 2.04 (t, J = 10.27 Hz, 1 H), 2.29 (s, 3 H), 2.33 (d, J = 1.96 Hz, 1 H), 2.80-2.94 (m, 3 H), 3.00 (d, J = 11.74 Hz, 1 H), 4.00 (s, 2 H), 4.09 (d, J = 10.03 Hz, 1 H), 5.38 (s, 2 H), 7.65 (d, J = 7.83 Hz, 1 H), 7.76 (d, J = 7.83 Hz, 1 H), 8.35 (d, J = 8.31 Hz, 1 H), 8.57 (dd, J = 8.19, 2.08 Hz, 1 H), 9.22 (d, J = 2.20 Hz, 1 H), (Exchangeable proton not observed). |

-continued

| Example | Structure | Name | LCMS (M + H) | HPLC/ LCMS Method: RT (min.), Purity | NMR |
|---|---|---|---|---|---|
| 63-I | 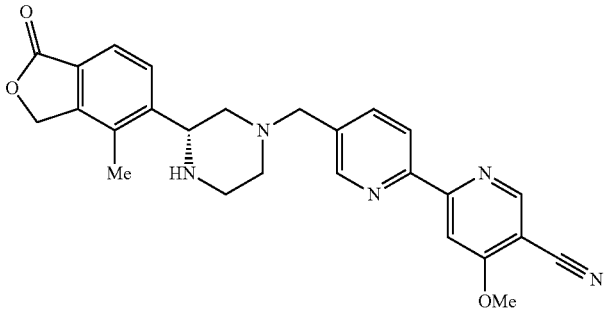 | (R)-4-methoxy-5'-((3-(4-methyl-1-oxo-1,3-dihydroisobenzofuran-5-yl)piperazin-1-yl)methyl)-[2,2'-bipyridine]-5-carbonitrile | 456.1 | A: 1.23, 100% B: 1.63, 100% VIII: 13.51, 100% ee | $^1$H NMR (400 MHz, DMSO-$d_6$) δ ppm 1.91 (br. s., 1 H), 2.16-2.20 (br. s, 1 H), 2.20 (s, 3 H), 2.80 (t, J = 11.13 Hz, 2 H), 2.87-3.10 (m, 2 H), 3.53-3.76 (m, 2 H), 4.12 (s, 3 H), 4.12-4.19 (br. s, 1 H), 5.26-5.43 (m, 2 H), 7.66 (d, J = 7.58 Hz, 1 H), 7.78 (d, J = 7.83 Hz, 1 H), 7.96 (dd, J = 8.31, 1.96 Hz, 1 H), 8.15 (s, 1 H), 8.41 (d, J = 8.07 Hz, 1 H), 8.68 (s, 1 H), 8.91 (s, 1 H), (Exchangeable proton not observed). |
| 64-I | 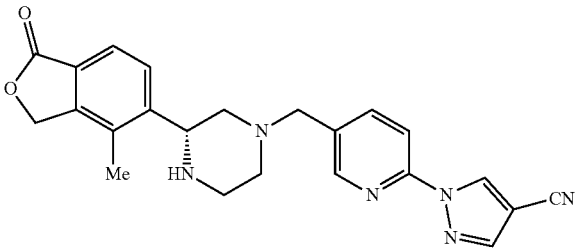 | (R)-1-(5-((3-(4-methyl-1-oxo-1,3-dihydroisobenzofuran-5-yl)piperazin-1-yl)methyl)pyridin-2-yl)-1H-pyrazole-4-carbonitrile | 415.1 | A: 1.19, 100% B: 1.54, 100% IV: 14.93, 99.42% ee | $^1$H NMR (400 MHz, DMSO-$d_6$) δ ppm 1.85 (t, J = 10.39 Hz, 1 H), 2.15 (d, J = 10.76 Hz, 1 H), 2.22 (s, 3 H), 2.64-2.84 (m, 2 H), 2.86-3.04 (m, 2 H), 3.54-3.68 (m, 2 H), 4.08 (d, J = 10.76 Hz, 1 H), 5.36 (d, J = 2.20 Hz, 2 H), 7.64 (d, J = 8.07 Hz, 1 H), 7.77 (d, J = 8.07 Hz, 1 H), 7.90-7.97 (m, 1 H), 7.99-8.07 (m, 1 H), 8.37-8.48 (m, 2 H), 9.39 (s, 1 H), (Exchangeable proton not observed). |
| 65-I | 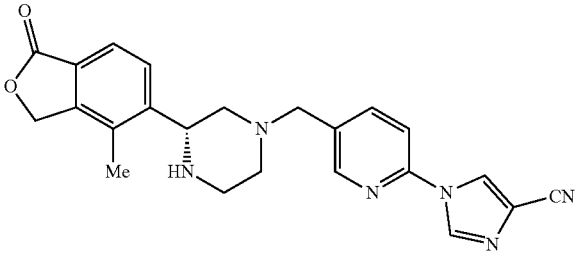 | (R)-1-(5-((3-(4-methyl-1-oxo-1,3-dihydroisobenzofuran-5-yl)piperazin-1-yl)methyl)pyridin-2-yl)-1H-imidazole-4-carbonitrile | 415.2 | A: 0.84, 98.26% B: 1.08, 98.91% IV: 15.06, 98.12% ee | $^1$H NMR (400 MHz, DMSO-$d_6$) δ ppm 1.86 (t, J = 9.90 Hz, 1 H), 2.14 (d, J = 10.76 Hz, 1 H), 2.23 (s, 3 H), 2.76 (t, J = 8.07 Hz, 2 H), 2.90 (d, J = 10.52 Hz, 1 H), 2.99 (d, J = 11.00 Hz, 1 H), 3.55-3.69 (m, 2 H), 4.08 (d, J = 7.83 Hz, 1 H), 5.36 (d, J = 3.42 Hz, 2 H), 7.65 (d, J = 8.07 Hz, 1 H), 7.77 (d, J = 8.07 Hz, 1 H), 7.87 (d, J = 8.31 Hz, 1 H), 8.02 (dd, J = 8.56, 1.96 Hz, 1 H), 8.47 (d, J = 1.96 Hz, 1 H), 8.74 (d, J = 1.22 Hz, 1 H), 8.91 (d, J = 1.22 Hz, 1 H), (Exchangeable proton not observed). |

-continued

| Example | Structure | Name | LCMS (M + H) | HPLC/ LCMS Method: RT (min.), Purity | NMR |
|---|---|---|---|---|---|
| 66-I | 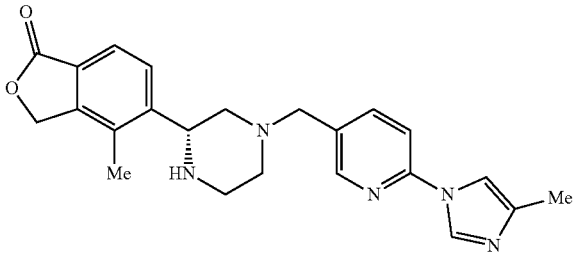 | (R)-4-methyl-5-(4-((6-(4-methyl-1H-imidazol-1-yl) pyridin-3-yl) methyl) piperazin-2-yl)isobenzofuran-1(3H)-one | 404.2 | F: 6.15, 97.63% G: 6.93, 98.08% V: 6.36, 100% ee | $^1$H NMR (400 MHz, DMSO-$d_6$) δ ppm 1.84 (t, J = 9.90 Hz, 1 H), 2.17 (s, 4 H), 2.33 (d, J = 1.71 Hz, 3 H), 2.71-2.81 (m, 2 H), 2.86-2.93 (m, 1 H), 2.99 (d, J = 11.25 Hz, 1 H), 3.51-3.62 (m, 2 H), 4.07 (d, J = 9.54 Hz, 1 H), 5.36 (s, 2 H),7.62-7.66 (m, 2 H), 7.70 (d, J = 8.31 Hz, 1 H), 7.77 (d, J = 8.07 Hz, 1 H), 7.90 (dd, J = 8.19, 2.08 Hz, 1 H), 8.33-8.50 (m, 2 H), (Exchangeable proton not observed). |
| 67-I | 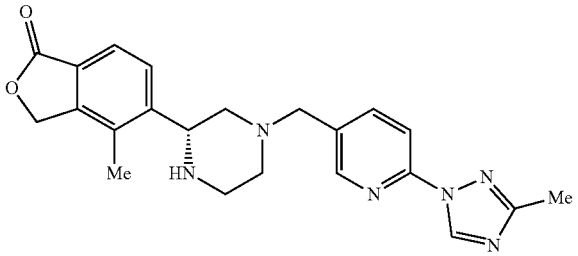 | (R)-4-methyl-5-(4-((6-(3-methyl-1H-1,2,4-triazol-1-yl) pyridin-3-yl) methyl) piperazin-2-yl) isobenzofuran-1(3H)-one | 405.1 | A: 1.01, 100% B: 1.25, 99.51% V: 6.16, 96.66% ee | $^1$H NMR (400 MHz, DMSO-$d_6$) δ 1.75-1.92 (m, 1 H), 2.08-2.18 (m, 1 H), 2.22 (s, 3 H), 2.38 (s, 3 H), 2.64-2.82 (m, 2 H), 2.91 (d, J = 11.74 Hz, 1 H), 2.96-3.05 (m, 1 H), 3.48-3.71 (m, 2 H), 4.08 (d, J = 7.83 Hz, 1 H), 5.36 (s, 2 H), 7.64 (d, J = 8.07 Hz, 1 H), 7.78 (dd, J = 8.19, 3.30 Hz, 2 H), 7.99 (dd, J = 8.31, 1.96 Hz, 1 H), 8.41 (d, J = 2.20 Hz, 1 H), 9.19 (s, 1 H), (Exchangeable proton not observed). |
| 68-I | 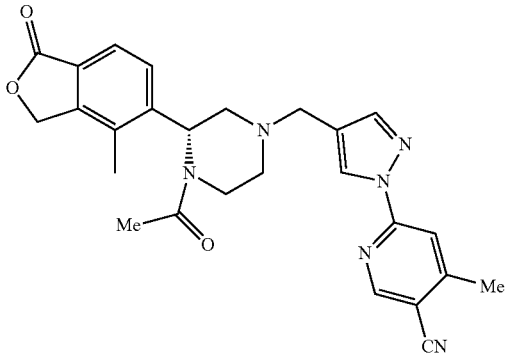 | (R)-6-(4-((4-acetyl-3-(4-methyl-1-oxo-1,3-dihydroisobenzofuran-5-yl) piperazin-1-yl) methyl)-1H-pyrazol-1-yl)-4-methylnicotinonitrile | 471.1 | A: 1.16, 100% B: 1.77, 100% X: 9.45, 100% ee | $^1$H NMR (400 MHz, DMSO-$d_6$) δ ppm 2.05 (d, J = 13.69 Hz, 3 H), 2.13-2.31 (m, 4 H), 2.40 (br. s., 1 H), 2.57 (s, 3 H), 2.91-3.15 (m, 2 H), 3.46-3.66 (m, 3 H), 3.72 (br. s., 1 H), 5.15-5.42 (m, 2 H), 5.72 (br. s., 1 H), 7.68 (d, J = 8.07 Hz, 1 H), 7.81 (br. s., 1 H), 7.96 (s, 1 H), 8.06-8.51 (m, 2 H), 8.78 (s, 1 H). |

-continued

| Example | Structure | Name | LCMS (M + H) | HPLC/ LCMS Method: RT (min.), Purity | NMR |
|---|---|---|---|---|---|
| 69-I | 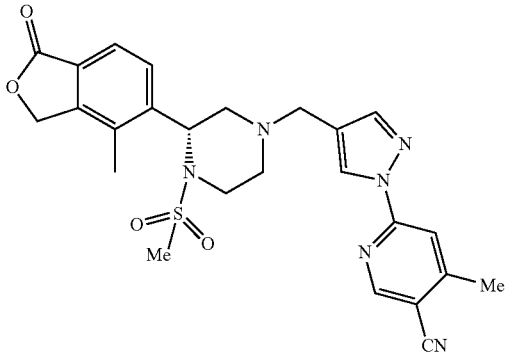 | (R)-4-methyl-6-(4-((3-(4-methyl-1-oxo-1,3-dihydroisobenzofuran-5-yl)-4-(methylsulfonyl)piperazin-1-yl)methyl)-1H-pyrazol-1-yl)nicotinonitrile | 507.0 | A: 1.27, 100% B: 1.85, 100% XIX: 11.31, 87.54% ee | $^1$H NMR (400 MHz, DMSO-$d_6$) δ ppm 2.07 (s, 1 H), 2.28 (s, 3 H), 2.45 (dd, J = 11.37, 5.75 Hz, 1 H), 2.55-2.69 (m, 3 H), 2.73-2.84 (m, 4 H), 2.90 (d, J = 10.76 Hz, 1 H), 3.44-3.51 (m, 1 H), 3.53-3.65 (m, 3 H), 5.15 (t, J = 3.67 Hz, 1 H), 5.25-5.34 (m, 1 H), 5.37-5.47 (m, 1 H), 7.71 (d, J = 8.07 Hz, 1 H), 7.76 (s, 1 H), 7.95 (s, 1 H), 8.15 (d, J = 8.07 Hz, 1 H), 8.40 (s, 1 H), 8.79 (s, 1 H). |
| 70-I | 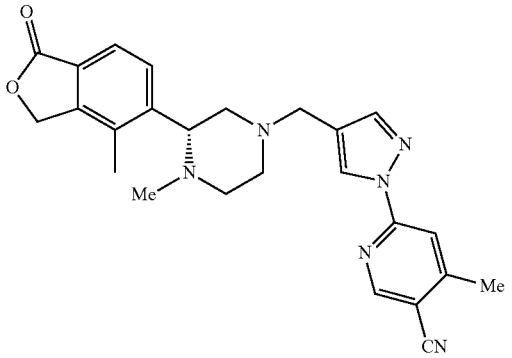 | (R)-4-methyl-6-(4-((4-methyl-3-(4-methyl-1-oxo-1,3-dihydroisobenzofuran-5-yl)piperazin-1-yl)methyl)-1H-pyrazol-1-yl)nicotinonitrile | 443.0 | F: 5.36, 95.73% XX: 6.21, 95.67% X: 4.82, 91.28% ee | $^1$H NMR (400 MHz, DMSO-$d_6$) δ ppm 1.88 (br. s., 1 H), 1.94 (s, 3 H), 2.26 (br. s., 4 H), 2.30-2.35 (m, 1 H), 2.57 (s, 3 H), 2.71 (d, J = 10.54 Hz, 1 H), 2.81-2.97 (m, 2 H), 3.41-3.47 (m, 1 H), 3.50 (s, 2 H), 5.30-5.43 (m, 2 H), 7.65 (s, 2 H), 7.84 (s, 1 H), 7.98 (s, 1 H), 8.52 (s, 1 H), 8.83 (s, 1 H). |
| 71-I | 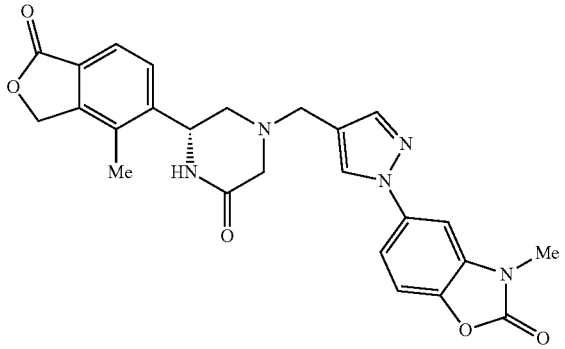 | (R)-3-methyl-5-(4-((3-(4-methyl-1-oxo-1,3-dihydroisobenzofuran-5-yl)-5-oxopiperazin-1-yl)methyl)-1H-pyrazol-1-yl)benzo[d]oxazol-2(3H)-one | 474.0 | A: 1.09, 97.66% B: 1.32, 94.12% IV: 6.81, 100% ee | $^1$H NMR (400 MHz, DMSO-$d_6$) δ 2.22 (s, 3 H), 2.33-2.44 (m, 1 H), 2.94 (dd, J = 11.98, 4.40 Hz, 1 H), 3.14 (s, 2 H), 3.39 (s, 3 H), 3.47-3.63 (m, 2 H), 4.95 (br. s., 1 H), 5.29 (s, 1 H), 5.36-5.45 (m, 1 H), 7.39 (d, J = 8.80 Hz, 1 H), 7.44-7.52 (m, 1 H), 7.54-7.63 (m, 2 H), 7.67-7.77 (m, 2 H), 8.16 (s, 1 H), 8.21 (s, 1 H). |
| 72-I | 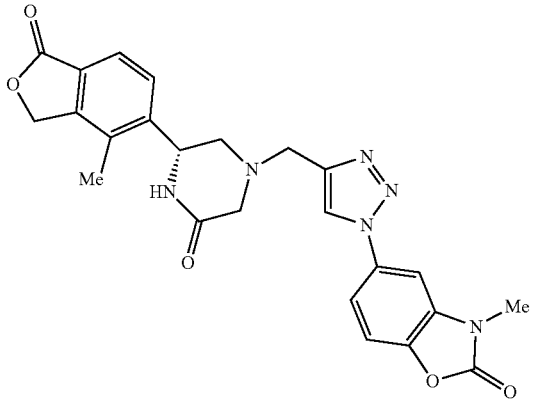 | (R)-3-methyl-5-(4-((3-(4-methyl-1-oxo-1,3-dihydroisobenzofuran-5-yl)-5-oxopiperazin-1-yl)methyl)-1H-1,2,3-triazol-1-yl)benzo[d]oxazol-2(3H)-one | 475.0 | A: 1.21, 97.22% B: 1.12, 100% V: 13.58, 88% ee | $^1$H NMR (400 MHz, DMSO-$d_6$) δ 2.25 (s, 3H), 2.43 (dd, J = 11.74, 6.60 Hz, 1 H), 3.04 (dd, J = 12.10, 4.77 Hz, 1 H), 3.21 (s, 2 H), 3.40 (s, 3 H), 3.78 (s, 2 H), 4.96 (br. s., 1 H), 5.23-5.42 (m, 2 H), 7.46-7.59 (m, 3 H), 7.72 (d, J = 8.07 Hz, 1H), 7.82 (d, J = 1.96 Hz, 1H), 8.17 (s, 1H), 8.45 (s, 1H). |

-continued

| Example | Structure | Name | LCMS (M + H) | HPLC/ LCMS Method: RT (min.), Purity | NMR |
|---|---|---|---|---|---|
| 73-I | 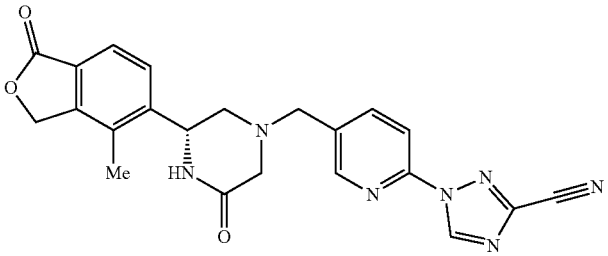 | (R)-1-(5-((3-(4-methyl-1-oxo-1,3-dihydroisobenzofuran-5-yl)-5-oxopiperazin-1-yl)methyl)pyridin-2-yl)-1H-1,2,4-triazole-3-carbonitrile | 430.1 | A: 1.35. 100% B: 1.43, 100% XIV: 8.05, 91.59% ee | $^1$H NMR (400 MHz, DMSO-$d_6$) δ ppm 2.22 (s, 3 H), 3.01 (d, J = 9.78 Hz, 1 H), 3.11-3.25 (m, 3 H), 3.76 (br. s., 2 H), 4.98 (br. s., 1 H), 5.38 (q, J = 15.65 Hz, 2 H), 7.58 (d, J = 7.83 Hz, 1 H), 7.74 (d, J = 8.07 Hz, 1 H), 7.83-7.90 (m, 1 H), 7.91-7.97 (m, 1 H), 8.25 (s, 1 H), 8.42 (s, 1 H), 9.69 (s, 1 H). |
| 74-I | 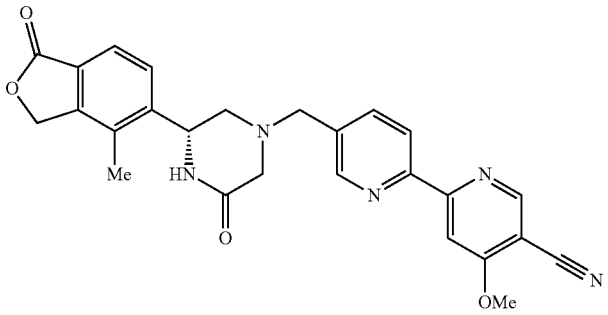 | (R)-4-methoxy-5'-((3-(4-methyl-1-oxo-1,3-dihydroisobenzofuran-5-yl)-5-oxopiperazin-1-yl)methyl)-[2,2'-bipyridine]-5-carbonitrile | 470.1 | A: 1.32, 94.19% B: 1.51, 94.93% XVIII: 14.74, 95.27% ee | $^1$H NMR (400 MHz, DMSO-$d_6$) δ ppm 2.17 (s, 3 H), 2.41-2.45 (m, 1 H), 2.91-2.94 (m, 1 H), 3.16 (q, J = 16.30 Hz, 2 H), 3.57-3.76 (m, 2 H), 4.13 (s, 3 H), 4.96 (br. s., 1 H), 5.20-5.31 (m, 1 H), 5.33-5.43 (m, 1 H), 7.58 (d, J = 8.07 Hz, 1 H), 7.70-7.80 (m, 2 H), 8.11 (s, 1 H), 8.22 (s, 1 H), 8.31 (d, J = 8.07 Hz, 1 H), 8.46 (s, 1 H), 8.91 (s, 1 H). |
| 75-I | 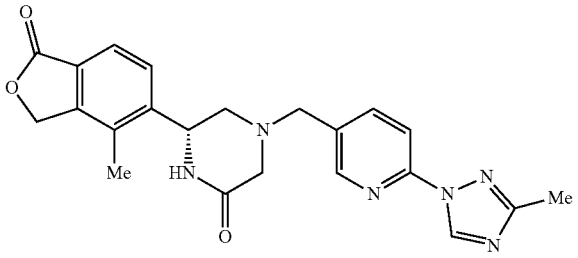 | (R)-6-(4-methyl-1-oxo-1,3-dihydroisobenzofuran-5-yl)-4-((6-(3-methyl-1H-1,2,4-triazol-1-yl)pyridin-3-yl)methyl)piperazin-2-one | 419.1 | A: 1.06, 100% B: 1.18, 100% XIV: 7.21, 94.14% ee | $^1$H NMR (400 MHz, DMSO-$d_6$) δ ppm 2.20 (s, 3 H), 2.38 (s, 3 H), 2.41-2.44 (m, 1 H), 2.93-2.96 (m, 1 H), 3.05-3.19 (m, 2 H), 3.65 (s, 2 H), 4.96 (br. s., 1 H), 5.29-5.46 (m, 2 H), 7.58 (d, J = 8.07 Hz, 1 H), 7.72 (dd, J = 15.77, 8.19 Hz, 2 H), 7.82 (dd, J = 8.44, 2.08 Hz, 1 H), 8.21 (s, 1 H), 8.30 (d, J = 1.96 Hz, 1 H), 9.17 (s, 1 H). |
| 76-I | 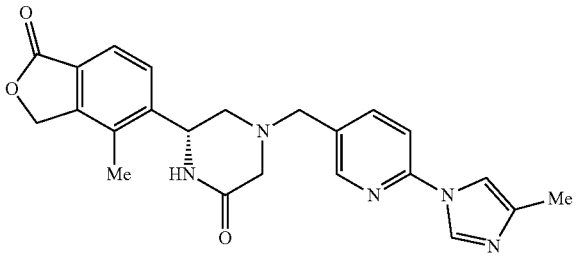 | (R)-6-(4-methyl-1-oxo-1,3-dihydroisobenzofuran-5-yl)-4-((6-(4-methyl-1H-imidazol-1-yl)pyridin-3-yl)methyl)piperazin-2-one | 418.0 | A: 0.90, 100% B: 1.21, 100% IV: 13.83, 94.47% ee | $^1$H NMR (400 MHz, DMSO-$d_6$) δ ppm 2.16 (s, 3 H), 2.20 (s, 3 H), 2.44 (dd, J = 11.86, 6.48 Hz, 1 H), 2.93 (dd, J = 11.74, 4.40 Hz, 1 H), 3.03-3.19 (m, 2 H), 3.62 (s, 2 H) 4.95 (br. s., 1 H), 5.37 (q, J = 15.65 Hz, 2 H), 7.57 (d, J = 8.07 Hz, 1 H), 7.60-7.66 (m, 2 H), 7.67-7.76 (m, 2 H), 8.20 (s, 1 H), 8.25 (s, 1 H), 8.37 (s, 1 H). |

-continued

| Example | Structure | Name | LCMS (M + H) | HPLC/ LCMS Method: RT (min.), Purity | NMR |
|---|---|---|---|---|---|
| 77-I | 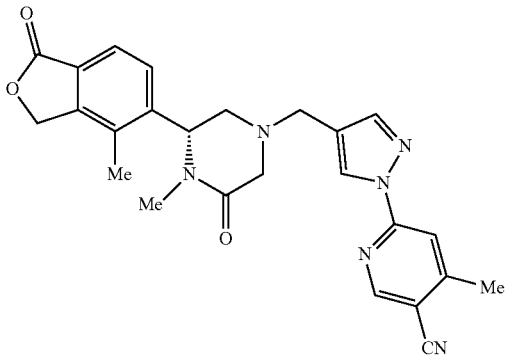 | (R)-4-methyl-6-(4-((4-methyl-3-(4-methyl-1-oxo-1,3-dihydro-isobenzo-furan-5-yl)-5-oxo-piperazin-1-yl) methyl)-1H-pyrazol-1-yl) nicotino-nitrile | 457.2 | A: 1.15, 97.87% B: 1.39, 99.90% XI: 9.28, 100% ee | $^1$H NMR (400 MHz, DMSO-$d_6$) δ ppm 2.23 (s, 3 H), 2.56 (s, 3 H), 2.65 (s, 4 H), 2.67-2.69 (m, 1 H), 2.86-2.90 (m, 1 H), 3.07-3.12 (m, 1 H), 3.31-3.57 (m, 2 H), 4.97 (t, J = 4.0 Hz, 1 H), 5.25-5.29 (m, 1 H), 5.39-5.43 (m, 1 H), 7.35 (d, J = 8.0 Hz, 1 H), 7.60 (s, 1 H), 7.76 (d, J = 8.0 Hz, 1 H), 7.93 (s, 1 H), 8.09 (s, 1 H), 8.72 (s, 1 H). |
| 78-I | 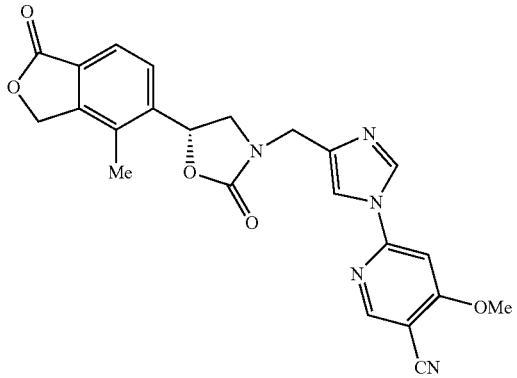 | (R)-4-methoxy-6-(4-((5-(4-methyl-1-oxo-1,3-dihydroiso-benzo-furan-5-yl)-2-oxo-oxazolidin-3-yl) methyl)-1H-imidazol-1-yl) nicotino-nitrile | 446.0 | A: 1.45, 95.92% B: 1.31, 95.39% III: 18.26, 91.42% ee | $^1$H NMR (400 MHz, DMSO-$d_6$) δ ppm 2.24 (s, 3 H), 3.33-3.38 (m, 1 H), 4.11 (s, 3 H), 4.10-4.14 (m, 2 H), 4.31-4.35 (m, 1 H), 5.41 (d, J = 7.03 Hz, 2 H), 5.94-6.01 (m, 1 H), 7.57 (d, J = 8.01 Hz, 1 H), 7.60 (s, 1 H), 7.75 (d, J = 7.95 Hz, 1 H), 8.04 (s, 1 H), 8.64 (s, 1 H), 8.75 (s, 1 H). |
| 79-I | 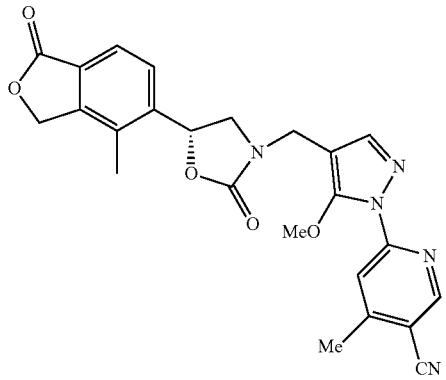 | (R)-6-(5-methoxy-4-((5-(4-methyl-1-oxo-1,3-dihydroiso-benzo-furan-5-yl)-2-oxo-oxazolidin-3-yl) methyl)-1H-pyrazol-1-yl)-4-methyl-nicotino-nitrile | 460.1 | A: 2.19, 100% B: 2.19, 100% XVIII: 9.18, 100% ee | $^1$H NMR (400 MHz, DMSO-$d_6$) δ ppm 2.22 (s, 3 H), 2.55 (s, 3 H), 3.23-3.28 (m, 1 H), 3.95 (s, 3 H), 4.04-4.08 (m, 1 H), 4.28 (d, J = 6.85 Hz, 2 H), 5.40 (d, J = 7.58 Hz, 2 H), 5.92-5.98 (m, 1 H), 7.55 (d, J = 8.0 Hz, 1 H), 7.73-7.78 (m, 2 H), 8.50 (s, 1 H), 8.76 (s, 1 H). |

-continued

| Example | Structure | Name | LCMS (M + H) | HPLC/ LCMS Method: RT (min.), Purity | NMR |
|---|---|---|---|---|---|
| 80-I | 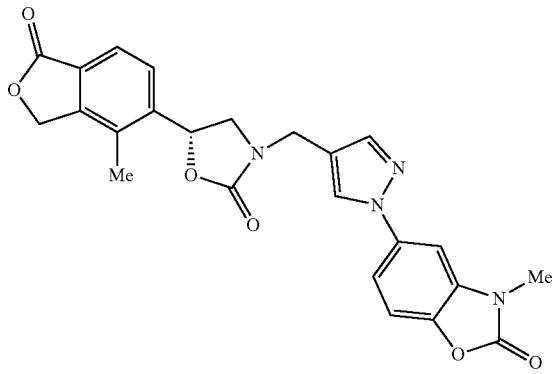 | (R)-3-methyl-5-(4-((5-(4-methyl-1-oxo-1,3-dihydroisobenzofuran-5-yl)-2-oxo-oxazolidin-3-yl)methyl)-1H-pyrazol-1-yl)benzo[d]oxazol-2(3H)-one | 461.1 | A: 1.50, 98.39% B: 1.48, 98.56% V: 13.40, 97.89% ee | $^1$H NMR (400 MHz, DMSO-$d_6$) δ ppm 2.23, (s, 3 H), 3.39 (s, 3 H), 4.05-4.12 (m, 2 H), 4.38 (d, J = 19.56 Hz, 2 H), 5.40 (d, J = 7.58 Hz, 2 H), 5.92-6.01 (m, 1 H), 7.43 (s, 1 H), 7.51-7.59 (m, 2 H), 7.69-7.79 (m, 3 H), 8.48 (s, 1 H). |

Example 81-I: 6-(4-(((3R,5R)-3-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile

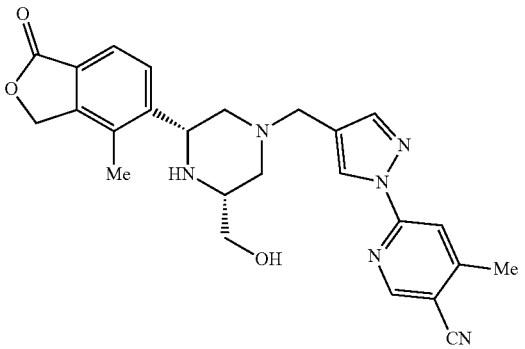

Example 81-I was prepared (0.130 g, 30.10%) as an off-white solid, by using a similar synthetic protocol as that of Example 1-I and starting from Intermediate 38-I (0.35 g, 1.32 mmol) and Intermediate 6 (0.20 g, 0.94 mmol). $^1$H NMR (400 MHz, DMSO-$d_6$) δ ppm 1.73 (dt, J=15.90, 10.15 Hz, 2H), 2.26 (s, 3H), 2.57 (s, 3H), 2.82 (d, J=10.03 Hz, 1H), 2.88-3.02 (m, 2H), 3.37-3.43 (m, 2H), 3.53 (s, 2H), 4.17 (d, J=8.07 Hz, 1H), 4.61 (br. s., 1H), 5.37 (s, 2H), 7.64 (d, J=8.07 Hz, 1H), 7.78 (d, J=8.07 Hz, 1H), 7.84 (s, 1H), 7.98 (s, 1H), 8.51 (s, 1H), 8.82 (s, 1H), (1 Exchangeable proton not observed). HPLC (Method-U): retention time 4.78 min, purity: 99.33%, (Method-T): retention time 4.90 min, purity: 98.18%, LCMS (Method D): retention time 1.66 min, [M+H] 459.2. Chiral purity (Method-XIX): retention time 11.50 min, 100% ee.

Example 82-I: 6-(4-((3,3-dimethyl-5-(4-methyl-1-oxo-1,3-dihydroisobenzofuran-5-yl)piperazin-1-yl)methyl)-2H-1,2,3-triazol-2-yl)-4-methylnicotinonitrile

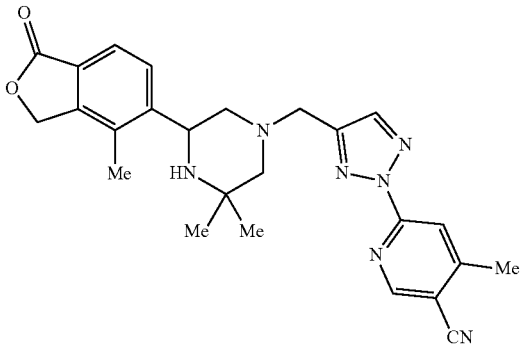

Example 82-I was prepared (0.25 g, 46.60%) as an off-white solid, by using a similar synthetic protocol as that of Example 1-I and starting from Intermediate 40-I (0.30 g, 0.117 mmol) and Intermediate 28 (0.25 g, 0.117 mmol). $^1$H NMR (400 MHz, DMSO-$d_6$) δ 1.07 (s, 3H), 1.32 (s, 3H), 1.83 (t, J=10.1 Hz, 1H), 1.92 (d, J=10.3 Hz, 1H), 2.06 (br. s., 1H), 2.29 (s, 3H), 2.57 (d, J=10.0 Hz, 1H), 2.62 (s, 3H), 2.88 (d, J=8.6 Hz, 1H), 3.79-3.70 (m, 2H), 4.41 (d, J=8.8 Hz, 1H), 5.39 (s, 2H), 7.66 (d, J=8.1 Hz, 1H), 7.80 (d, J=7.8 Hz, 1H), 8.12 (s, 1H), 8.21 (s, 1H), 8.94 (s, 1H). HPLC (Method-U): retention time 4.84 min, purity: 96.03%, (Method-T): retention time 6.27 min, purity: 97.15%, LCMS (Method-D): retention time 2.15 min, [M+H] 458.4. Chiral purity (Method-XV): retention time 4.60 min, 100% ee. SOR: $[\alpha]^{25}D$=−30.00 (c 0.1, DMSO).

Example 83-I: 4-methyl-6-(4-(((3S,5R)-3-methyl-5-(4-methyl-1-oxo-1,3-dihydroisobenzofuran-5-yl)piperazin-1-yl)methyl)-2H-1,2,3-triazol-2-yl)nicotinonitrile

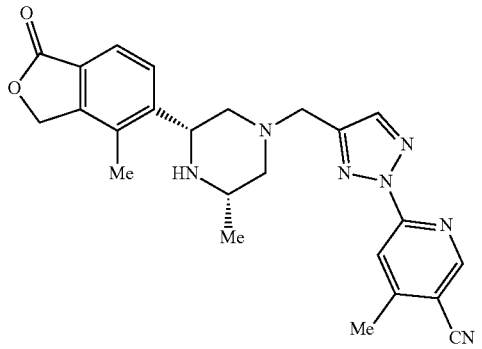

Example 83-I was prepared (0.045 g, 20.41%), by using a similar synthetic protocol as that of Example 1-I and starting from Intermediate 51-I (0.12 g, 0.49 mmol) and Intermediate 28 (0.102 g, 0.49 mmol). $^1$H NMR (400 MHz, DMSO-d6) δ ppm 1.02 (d, J=5.9 Hz, 3H), 1.80 (br. s., 2H), 2.27 (s, 3H), 2.64 (s, 3H), 2.84 (br. s., 2H), 2.96 (br. s., 1H), 3.75 (s, 2H), 4.15 (br. s., 1H), 5.45-5.30 (m, 2H), 7.64 (d, J=8.0 Hz, 1H), 7.79 (d, J=8.0 Hz, 1H), 8.10 (s, 1H), 8.20 (s, 1H), 8.92 (s, 1H), (1 Exchangeable proton not observed). HPLC (Method-U): retention time 6.50 min, purity: 97.70%. (Method-T): retention time 7.53 min, purity: 98.10%. LCMS (Method-7): retention time 1.86 min, [M+H] 444.2, purity: 99.60%. Chiral purity (Method-XIV): retention time 7.27 min, 100% ee.

Example 84-I: 6-(4-(((3R,4R)-4-hydroxy-3-(4-methyl-1-oxo-1,3-dihydroisobenzofuran-5-yl)piperidin-1-yl)methyl)-1H-1,2,3-triazol-1-yl)-4-methylnicotinonitrile

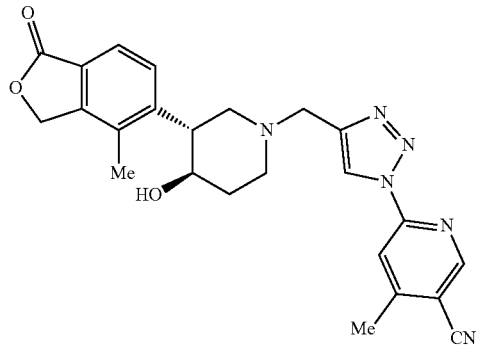

Example 84-I was prepared (0.02 g, 20.68%), by using a similar synthetic protocol as that of Example 1-I and starting from Intermediate 52-I (0.05 g, 0.49 mmol) and Intermediate 30 (0.04 g, 0.49 mmol). $^1$H NMR (400 MHz, DMSO-$d_6$) δ ppm 1.62 (d, J=6.8 Hz, 1H), 1.92 (d, J=10.5 Hz, 1H), 2.18-2.06 (m, 1H), 2.25 (s, 4H), 2.67-2.60 (m, 3H), 2.80 (d, J=10.0 Hz, 1H), 2.94 (br. s., 1H), 3.07 (br. s., 1H), 3.75 (br. s., 3H), 4.56 (d, J=5.1 Hz, 1H), 5.46-5.26 (m, 2H), 7.53 (d, J=7.8 Hz, 1H), 7.63 (d, J=7.8 Hz, 1H), 8.28 (s, 1H), 8.77 (s, 1H), 8.98 (s, 1H). LCMS/HPLC (Method-R): retention time 0.89 min, [M+H] 445.2, purity: 95.00%, (Method-S): retention time 1.20 min, [M+H] 445.2, purity: 100%. Chiral purity (Method-XVIII): retention time 14.30 min, 98.40% ee.

The examples in Table 2 were synthesized using procedures in Example 1-I to 24-I and 81-I to 84-I.

| Example | Structure | Name | LCMS (M + H)$^+$ | HPLC/LCMS Method: RT (min.), Purity | NMR |
|---|---|---|---|---|---|
| 85-I | 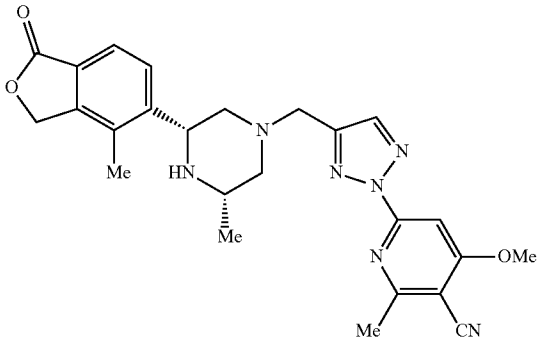 | 2,4-dimethyl-6-(4-(((3S,5R)-3-methyl-5-(4-methyl-1-oxo-1,3-dihydroisobenzofuran-5-yl)piperazin-1-yl)methyl)-2H-1,2,3-triazol-2-yl)nicotinonitrile | 458.3 | S: 1.50, 96.42% R: 1.15, 96.95% V: 7.33, 98.50% ee | $^1$H NMR (400 MHz, DMSO-d6) δ 1.04 (d, J = 5.9 Hz, 3H), 1.84 (br. s., 2 H), 2.24-2.31 (m, 3 H), 2.60 (s, 3 H), 2.69-2.74 (m, 3 H), 2.77-2.88 (m, 2 H), 3.00 (br. s, 1 H), 3.77 (s, 2 H), 4.20 (br. s., 1 H), 5.31-5.46 (m, 2 H), 7.67 (d, J = 7.6 Hz, 1 H), 7.80 (d, J = 8.1 Hz, 1 H), 7.94 (s, 1 H), 8.19 (s, 1 H), (1 Exchangeable proton not observed). |
| 86-I | 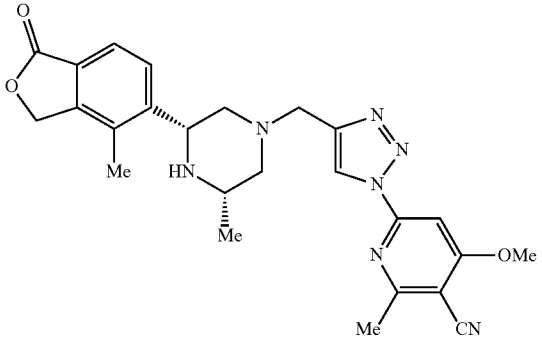 | 4-methoxy-2-methyl-6-(4-(((3S,5R)-3-methyl-5-(4-methyl-1-oxo-1,3-dihydroisobenzofuran-5-yl)piperazin-1-yl)methyl)-1H-1,2,3-triazol-1-yl)nicotinonitrile | 474.3 | S: 1.50, 94.55% R: 1.49, 99.47% XVIII: 13.27, 100% ee | $^1$H NMR (400 MHz, DMSO-d6) δ 1.20-1.34 (m, 3 H), 2.37 (s, 4 H), 2.68 (s, 3 H), 3.18 (s, 2 H), 3.94-3.99 (m, 2 H), 4.15 (s, 3 H), 4.78 (br. s., 1 H), 5.37-5.56 (m, 2 H), 7.75 (s, 1 H), 7.78 (d, J = 8.1 Hz, 1 H), 7.88 (d, J = 7.8 H, 1 H), 8.50 (s, 1 H), 8.86 (s, 1 H), 9.44 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 87-III | 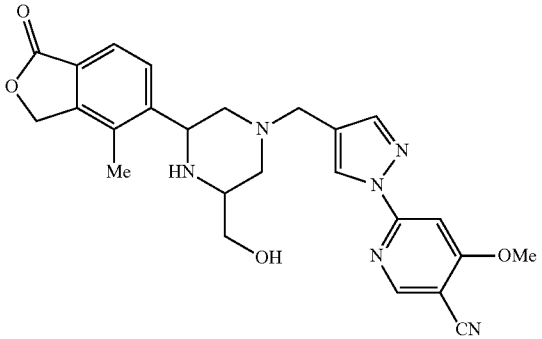 | 6-(4-((3-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile, (Enantiomer-III) | 459.3 | S: 1.39, 100% R: 1.15, 100% XXIV: 5.80, 100% ee | $^1$H NMR (400 MHz, DMSO-d6) δ 1.98-2.14 (m, 1 H), 2.27 (s, 3 H), 2.41 (d, J = 10.3 Hz, 1 H), 2.58 (s, 3 H), 2.65 (d, J = 9.3 Hz, 1 H), 2.73 (d, J = 7.1 Hz, 1 H), 2.92 (d, J = 15.7 Hz, 1 H), 3.46-3.58 (m, 3 H), 3.76 (br. s., 1 H), 4.40 (d, J = 5.6 Hz, 1 H), 4.58 (br. s., 1 H), 5.29-5.45 (m, 2 H), 7.65 (d, J = 8.1 Hz, 1 H), 7.87 (s, 1 H), 7.93-8.05 (m, 2 H), 8.53 (s, 1 H), 8.84 (s, 1 H), (1 Exchangeable proton not observed). |
| 88-III | 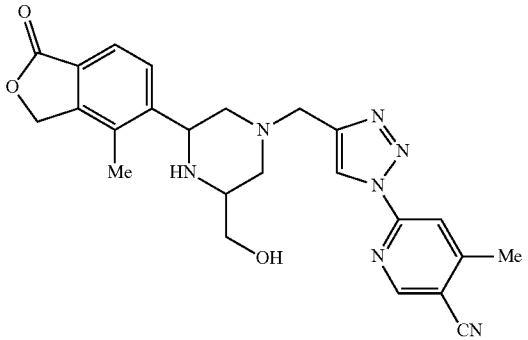 | 6-(4-((3-(hydroxymethyl)-5-(4-methyl-1-oxo-1,3-dihydroisobenzofuran-5-yl)piperazin-1-yl)methyl)-1H-1,2,3-triazol-1-yl)-4-methylnicotinonitrile, (Enantiomer-III) | 460.2 | S: 1.28, 100% R: 1.09, 97.86% XIX: 7.63, 100% ee | $^1$H NMR (400 MHz, DMSO-d6) δ 2.02-2.17 (m, 1 H), 2.27 (s, 3 H), 2.45 (br. s., 1 H), 2.63-2.69 (m, 4 H), 2.79 (d, J = 9.8 Hz, 1 H), 2.91 (d, J = 12.5 Hz, 1 H), 3.53 (br. s., 1 H), 3.74 (s, 3 H), 4.40 (br. s., 1 H), 4.59 (br. s., 1 H), 5.38 (d, J = 2.4 Hz, 2 H), 7.64 (d, J = 8.3 Hz, 1 H), 7.96 (d, J = 7.8 Hz, 1 H), 8.30 (s, 1 H), 8.79 (s, 1 H), 9.01 (s, 1 H), (1 Exchangeable proton not observed). |
| 89-III | 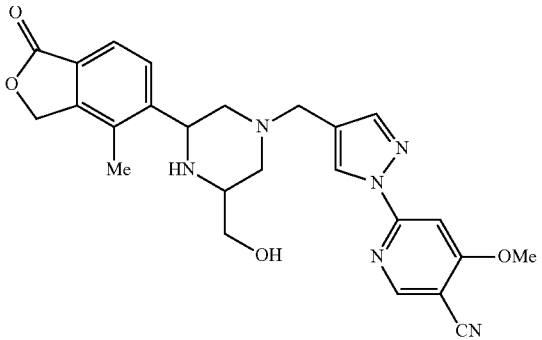 | 6-(4-(((3-(hydroxymethyl)-5-(4-methyl-1-oxo-1,3-dihydroisobenzofuran-5-yl)piperazin-1-yl)methyl)-1H-pyrazol-1-yl)-4-methoxynicotinonitrile, (Enantiomer-III) | 475.3 | S: 1.34, 96.27% R: 1.11, 97.98% VI: 17.65, 100% ee | $^1$H NMR (400 MHz, DMSO-d6) δ 1.99-2.11 (m, 2 H), 2.21-2.31 (m, 3 H), 2.40 (dd, J = 11.1, 3.8 Hz, 1 H), 2.64 (d, J = 8.1 Hz, 1 H), 2.73 (d, J = 7.6 Hz, 1 H), 2.90-2.96 (m, 1 H), 3.51 (s, 3H), 3.75 (d, J = 8.3 Hz, 1 H), 4.11 (s, 3 H), 4.36-4.43 (m, 1 H), 4.57 (br. s., 1 H), 5.32-5.42 (m, 2 H), 7.61 (s, 1 H), 7.65 (d, J = 7.8 Hz, 1 H), 7.88 (s, 1 H), 7.97 (d, J = 8.1 Hz, 1 H), 8.53 (s, 1 H), 8.74 (s, 1 H). |

-continued

| Example | Structure | Name | LCMS (M + H)$^+$ | HPLC/LCMS Method: RT (min.), Purity | NMR |
|---|---|---|---|---|---|
| 90-I | 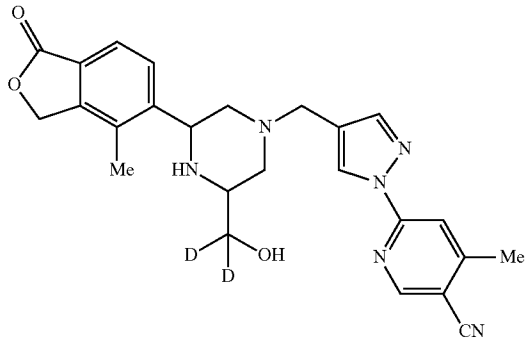 | 6-(4-((3-(hydroxymethyl-d2)-5-(4-methyl-1-oxo-1,3-dihydroisobenzofuran-5-yl)piperazin-1-yl)methyl)-1H-pyrazol-1-yl)-4-methylnicotinonitrile, (Enantiomer-I) | 461.3 | S: 1.33, 100% R: 1.05, 99.36% XVIII: 14.17, 100% ee | $^1$H NMR (400 MHz, DMSO-d6) δ 1.73 (br. s., 2 H), 1.92 (s, 1 H), 2.27 (s, 3 H), 2.58 (s, 3 H), 2.83 (d, J = 10.3 Hz, 1 H), 2.88-3.03 (m, 2 H), 3.54 (br. s., 2 H), 4.18 (d, J = 10.0 Hz, 1 H), 4.60 (br. s., 1 H), 5.30-5.49 (m, 2 H), 7.66 (d, J = 8.1 Hz, 1 H), 7.79 (d, J = 7.8 Hz, 1 H), 7.86 (s, 1 H), 7.99 (s, 1 H), 8.53 (s, 1 H), 8.84 (s, 1 H). |
| 91-I | 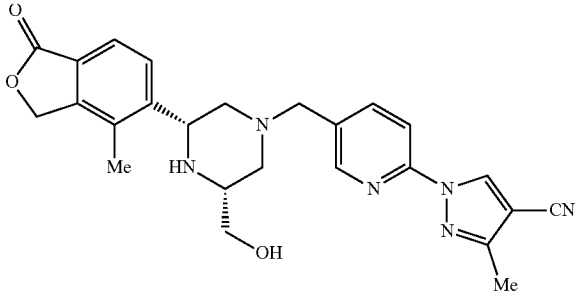 | 1-(5-(((3R,5R)-3-(hydroxymethyl)-5-(4-methyl-1-oxo-1,3-dihydroisobenzofuran-5-yl)piperazin-1-yl)methyl)pyridin-2-yl)-3-methyl-1H-pyrazole-4-carbonitrile | 460.3 | S: 1.13, 100% R: 0.96, 100% XV: 5.55, 100% ee | $^1$H NMR (400 MHz, DMSO-d6) δ 1.80 (d, J = 10.3 Hz, 2 H), 2.26 (s, 3 H), 2.42 (s, 3 H), 2.81 (d, J = 9.0 Hz, 1 H), 2.92 (d, J = 11.5 Hz, 2 H), 3.37 (br. s., 2 H), 3.65 (s, 2 H), 4.21 (br. s., 1 H), 4.65 (br. s., 1 H), 5.30-5.47 (m, 2 H), 7.67 (d, J = 7.8 Hz, 1 H), 7.80 (d, J = 8.3 Hz, 1 H), 8.84 (s, 2 H), 9.36 (s, 1 H), (2 Exchangeable protons not observed). |
| 92-I | 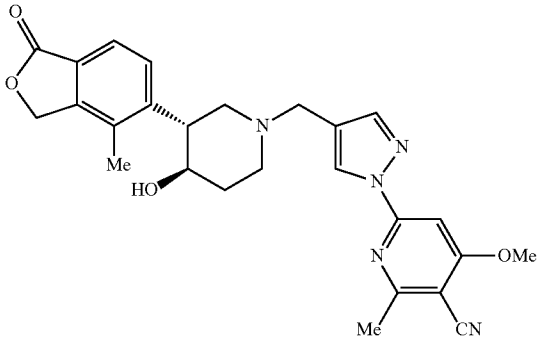 | 6-(4-(((3R,4R)-4-hydroxy-3-(4-methyl-1-oxo-1,3-dihydroisobenzofuran-5-yl)piperidin-1-yl)methyl)-1H-pyrazol-1-yl)-2,4-dimethylnicotinonitrile | 458.2 | S: 1.47, 99.34% R: 1.06, 100% XXI: 3.85, 100% ee | $^1$H NMR (400 MHz, DMSO-$d_6$) δ ppm 1.54-1.70 (m, 1 H), 1.93 (d, J = 9.78 Hz, 1 H), 1.98-2.10 (m, 1 H), 2.18 (t, J = 10.76 Hz, 1 H), 2.24 (s, 3 H), 2.54 (s, 3 H), 2.66 (s, 3 H), 2.73 (d, J = 10.03 Hz, 1 H), 2.92 (d, J = 12.23 Hz, 1 H), 3.01-3.12 (m, 1 H), 3.43-3.57 (m, 2 H), 3.72 (br. s., 1 H), 4.56 (br. s., 1 H), 5.26-5.44 (m, 2 H), 7.52 (d, J = 8.07 Hz, 1 H), 7.59-7.67 (m, 1 H), 7.82 (s, 2 H), 8.49 (s, 1 H). |

-continued

| Example | Structure | Name | LCMS (M + H)$^+$ | HPLC/LCMS Method: RT (min.), Purity | NMR |
|---|---|---|---|---|---|
| 93-I | 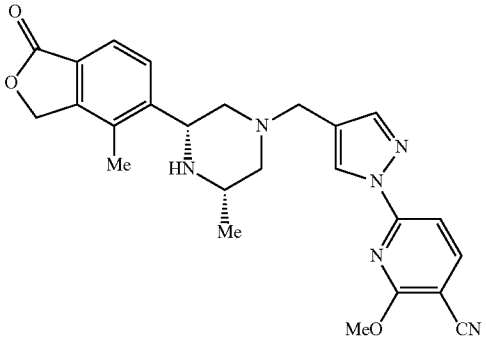 | 2-methoxy-6-(4-(((3S,5R)-3-methyl-5-(4-methyl-1-oxo-1,3-dihydroisobenzofuran-5-yl)piperazin-1-yl)methyl)-1H-pyrazol-1-yl)nicotinonitrile | 459.2 | S: 1.60, 95.30% R: 1.12, 95.10% | $^1$H NMR (400 MHz, DMSO-$d_6$) δ ppm 1.05 (d, J = 5.1 Hz, 3 H), 1.76 (br. s., 2 H), 2.31-2.19 (m, 3 H), 2.83 (d, J = 9.5 Hz, 2 H), 3.00 (br. s., 1 H), 3.52 (s, 2 H), 4.13-3.99 (m, 4 H), 4.17 (d, J = 9.3 Hz, 1 H), 5.49-5.26 (m, 2 H), 7.56 (d, J = 8.3 Hz, 1 H), 7.64-7.66 (d, J = 8 Hz, 1 H), 7.80 (d, J = 7.8 Hz, 1H), 7.86 (s, 1H), 8.35 (d, J = 8.3 Hz, 1H), 8.59 (s, 1H). |
| 94-I | 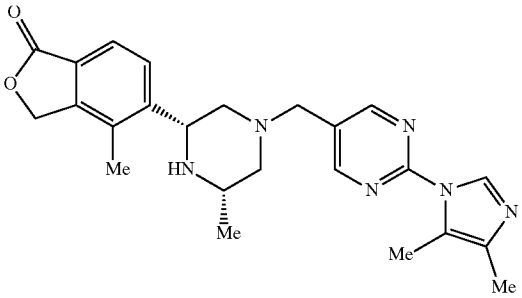 | 5-((2R,6S)-4-((2-(4,5-dimethyl-1H-imidazol-1-yl)pyrimidin-5-yl)methyl)-6-methylpiperazin-2-yl)-4-methylisobenzofuran-1(3H)-one | 433.3 | S: 1.44, 100% R: 0.77, 98.00% XXI: 6.06 96.51% ee | $^1$H NMR (400 MHz, DMSO-d6) δ 1.04 (d, J = 6.1 Hz, 3 H), 1.81 (d, J = 10.3 Hz, 2 H), 2.11 (s, 3 H), 2.31-2.20 (m, 3 H), 2.46 (s, 3 H), 2.80 (br. s., 3 H), 3.61 (s, 2 H), 4.20 (d, J = 5.1 Hz, 1 H), 5.52-5.30 (m, 2 H), 7.67 (d, J = 7.8 Hz, 1 H), 7.81 (d, J = 8.1 Hz, 1 H), 8.31 (s, 1 H), 8.77 (s, 2 H), (1 Exchangeable proton not observed). |
| 95-I | 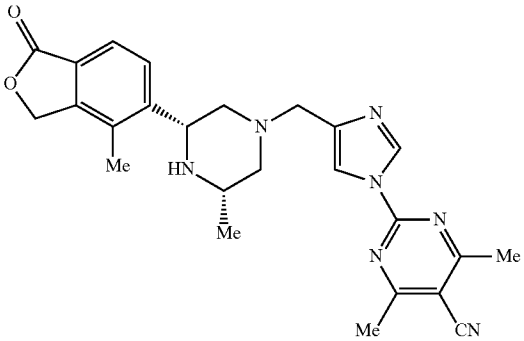 | 4,6-dimethyl-2-(4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile | 458.2 | S: 1.36, 100% R: 0.96, 100% XIX: 9.54 92.65% ee | $^1$H NMR (400 MHz, DMSO-d6) δ 1.23 (d, J = 10.8 Hz, 3 H), 2.34 (s, 3 H), 2.70 (s, 6 H), 3.09 (br. s., 2 H), 3.69 (br. s., 4 H), 4.63 (br. s., 1 H), 5.55-5.33 (m, 2 H), 7.15 (br.s., 1 H), 7.80 (br. s., 2 H), 7.89 (br. s., 1 H), 8.60 (br. s., 1H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 96-I | 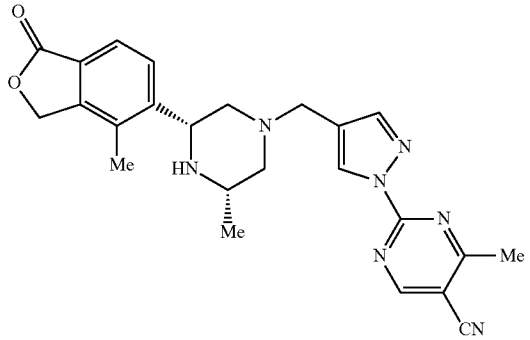 | 4-methyl-2-(4-(((3S,5R)-3-methyl-5-(4-methyl-1-oxo-1,3-dihydroisobenzofuran-5-yl)piperazin-1-yl)methyl)-1H-pyrazol-1-yl)pyrimidine-5-carbonitrile | 444.3 | S: 1.21, 100% B: 0.86, 100% XVIII: 14.76, 97.78% ee | $^1$H NMR (400 MHz, DMSO-d6) δ 1.04 (d, J = 4.6 Hz, 3 H), 1.76 (br. s., 2 H), 2.26 (s, 3 H), 2.69 (s, 3 H), 2.82 (br. s., 2 H), 3.01 (br. s., 1 H), 3.17 (d, J = 4.9 Hz, 1 H), 3.54 (br. s., 1 H), 4.20 (br. s., 1 H), 5.45-5.30 (m, 2 H), 7.66 (d, J = 7.8 Hz, 1 H), 7.78 (d, J = 8.1 Hz, 1 H), 7.88 (s, 1H), 8.56 (s, 1 H), 9.18 (s, 1 H). |
| 97-I | 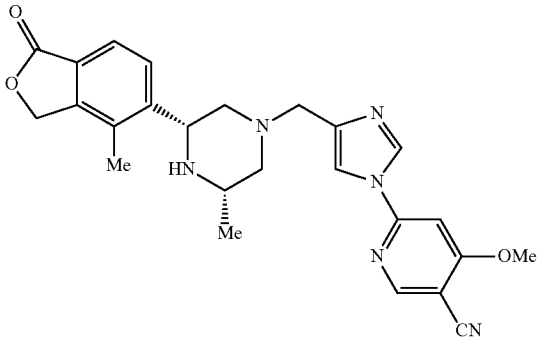 | 4-methoxy-6-(4-(((3S,5R)-3-methyl-5-(4-methyl-1-oxo-1,3-dihydroisobenzofuran-5-yl)piperazin-1-yl)methyl)-1H-imidazol-1-yl)nicotinonitrile | 459.3 | S: 1.25, 99.45% R: 8.78, 100% | $^1$H NMR (400 MHz, DMSO-d6) δ 1.28 (d, J = 6.4 Hz, 3 H), 2.36 (s, 3 H), 2.63-2.55 (m, 1 H), 2.81-2.70 (m, 1 H), 3.30 (d, J = 11.0 Hz, 2 H), 3.66 (br. s., 1 H), 3.92 (br. s., 3 H), 4.13 (s, 3 H), 4.79 (d, J = 12.2 Hz, 1 H), 5.57-5.35 (m, 2 H), 7.66 (s, 1H), 7.80 (d, J = 7.8 Hz, 1 H), 7.87 (d, J = 8.1 Hz, 1 H), 8.14 (s, 1 H), 8.88-8.75 (m, 2 H). |
| 98-I | 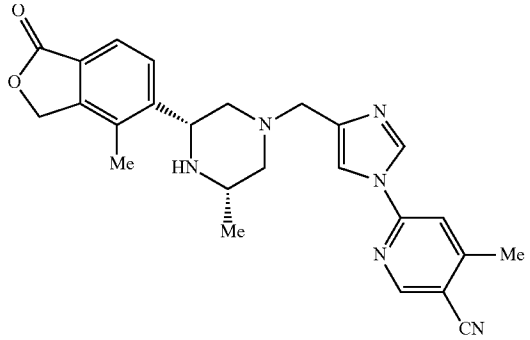 | 4-methyl-6-(4-(((3S,5R)-3-methyl-5-(4-methyl-1-oxo-1,3-dihydroisobenzofuran-5-yl)piperazin-1-yl)methyl)-1H-imidazol-1-yl)nicotinonitrile | 443.3 | R: 0.85, 97.18% S: 1.25, 98.65% XVIII: 13.30, 95.52% ee | $^1$H NMR (400 MHz, DMSO-d6) δ 1.04 (d, J = 6.1 Hz, 3 H), 1.84 (br. s., 2 H), 2.32-2.23 (m, 3 H), 2.56 (s, 3 H), 2.90-2.78 (m, 2 H), 3.00 (br. s., 1 H), 3.52 (s, 2 H), 4.18 (br. s., 1 H), 5.50-5.26 (m, 2 H), 7.66 (d, J = 8.1 Hz, 1 H), 7.80 (d, J = 7.8 Hz, 1 H), 7.86 (s, 1 H), 7.99 (s, 1 H), 8.63-8.45 (m, 1 H), 8.86 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 99-I | 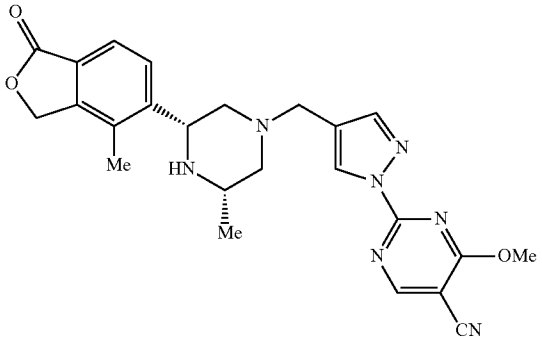 | 4-methoxy-2-(4-(((3S,5R)-3-methyl-5-(4-methyl-1-oxo-1,3-dihydroisobenzofuran-5-yl)piperazin-1-yl)methyl)-1H-pyrazol-1-yl)pyrimidine-5-carbonitrile | 460.3 | R: 0.92, 96.64% S: 1.27, 98.14% XVIII: 14.63, 100% ee | $^1$H NMR (400 MHz, DMSO-d6) δ 1.03 (d, J = 6.1 Hz, 3 H), 1.73 (td, J = 10.5, 3.8 Hz, 2 H), 1.88 (s, 1 H), 2.27 (s, 3 H), 2.80 (d, J = 10.5 Hz, 2 H), 2.97 (br. s., 1 H), 3.52 (s, 2 H), 4.26-4.08 (m, 4 H), 5.48-5.28 (m, 2 H), 7.65 (d, J = 8.3 Hz, 1 H), 7.80 (d, J = 8.1 Hz, 1 H), 7.89 (s, 1 H), 8.59 (s, 1 H), 9.07 (s, 1 H). |
| 100-I | 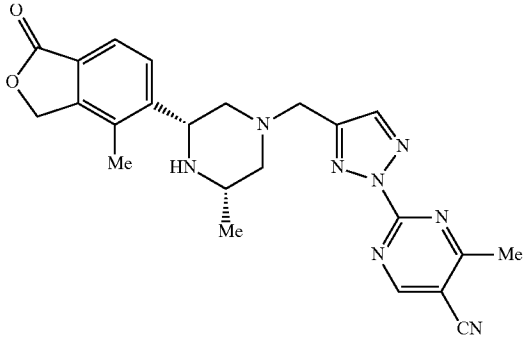 | 4-methyl-2-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyrimidine-5-carbonitrile | 445.2 | S: 1.14, 94.5% R: 8.87, 97.32% XI: 16.27, 100% ee | $^1$H NMR (400 MHz, DMSO-d6) δ 1.03 (d, J = 6.4 Hz, 3 H), 1.87-1.69 (m, 2 H), 2.30-2.21 (m, 3 H), 2.78-2.70 (m, 3 H), 2.82 (d, J = 11.0 Hz, 2 H), 2.98 (br. s., 1 H), 3.78 (s, 2 H), 4.18 (d, J = 8.1 Hz, 1 H), 5.45-5.27 (m, 2 H), 7.66 (d, J = 8.1 Hz, 1 H), 7.80 (d, J = 8.1 Hz, 1 H), 8.26 (s, 1 H), 9.31 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 101-I | 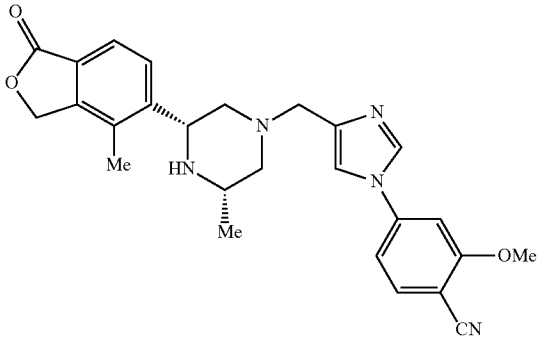 | 2-methoxy-4-(4-(((3S,5R)-3-methyl-5-(4-methyl-1-oxo-1,3-dihydroisobenzofuran-5-yl)piperazin-1-yl)methyl)-1H-imidazol-1-yl)benzonitrile | 458.2 | S: 1.28, 95.64% R: 0.88, 100% XI: 5.88, 100% ee | $^1$H NMR (400 MHz, DMSO-d6) δ 1.10-0.93 (m, 4 H), 1.83-1.68 (m, 2 H), 2.26 (s, 3 H), 2.84 (t, J = 8.1 Hz, 2 H), 3.00-2.91 (m, 1 H), 3.46 (s, 2 H), 4.08-3.95 (m, 3 H), 4.15 (d, J = 8.6 Hz, 1 H), 5.37 (s, 2 H), 7.41 (dd, J = 8.4, 1.8 Hz, 1 H), 7.48 (s, 1 H), 7.65 (d, J = 8.1 Hz, 1 H), 7.92-7.75 (m, 3 H), 8.40 (s, 1 H). |
| 102-I | 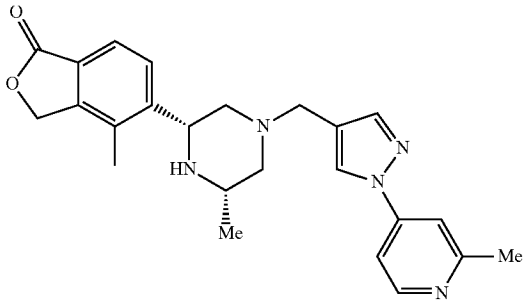 | 4-methyl-5-((2R,6S)-6-methyl-4-((1-(2-methylpyridin-4-yl)-1H-pyrazol-4-yl)methyl)piperazin-2-yl)isobenzofuran-1(3H)-one | 418.2 | S: 1.21, 100% R: 0.63, 100%. XI: 4.31, 100% ee | $^1$H NMR (400 MHz, DMSO-d6) δ 1.34-1.23 (m, 3 H), 2.44-2.34 (m, 3 H), 2.59 (br. s., 1 H), 2.69-2.63 (m, 3 H), 3.17 (d, J = 8.1 Hz, 2 H), 3.67 (br. s., 1 H), 3.80 (br. s., 2 H), 4.77 (d, J = 10.8 Hz, 2 H), 5.46 (q, J = 15.5 Hz, 2 H), 7.90-7.76 (m, 2 H), 8.05-7.91 (m, 2 H), 8.09 (s, 1 H), 8.73 (d, J = 6.1 Hz, 1 H), 8.81 (s, 1 H), (1 Exchangeable proton not observed). |
| 103-I | 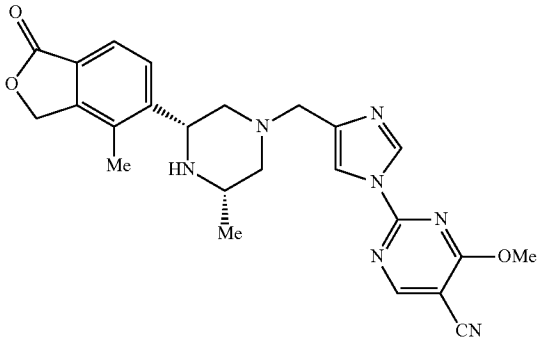 | 4-methoxy-2-(4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile | 460.2 | S: 1.28, 97.98%. R: 0.90, 97.82%. XVIII: 18.68, 100% ee | $^1$H NMR (400 MHz, DMSO-d6) δ 1.03 (d, J = 6.1 Hz, 3 H), 1.88-1.74 (m, 2 H), 1.92 (s, 1 H), 2.31-2.24 (m, 3 H), 2.85 (t, J = 8.2 Hz, 2 H), 2.97 (br. s., 1 H), 3.56-3.48 (m, 2 H), 4.24-4.07 (m, 4 H), 5.47-5.30 (m, 2 H), 7.66 (d, J = 7.8 Hz, 1 H), 7.87-7.74 (m, 2 H), 8.62 (d, J = 1.2 Hz, 1 H), 9.09 (s, 1 H). |

-continued

| Example | Structure | Name | LCMS (M + H)$^+$ | HPLC/LCMS Method: RT (min.), Purity | NMR |
|---|---|---|---|---|---|
| 104-I | 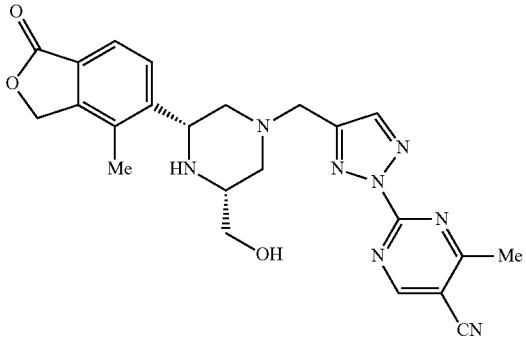 | 2-(4-(((3R,5R)-3-(hydroxymethyl)-5-(4-methyl-1-oxo-1,3-dihydroisobenzofuran-5-yl)piperazin-1-yl)methyl)-2H-1,2,3-triazol-2-yl)-4-methylpyrimidine-5-carbonitrile | 461.2 | S: 0.95, 96.95%. R: 0.82, 100%. | $^1$H NMR (400 MHz, DMSO-d6) δ 1.94-1.72 (m, 2 H), 2.28 (s, 3 H), 2.79-2.70 (m, 4 H), 3.05-2.80 (m, 4 H), 3.45-3.35 (m, 1 H), 3.80 (s, 2 H), 4.20 (d, J = 7.8 Hz, 1 H), 4.64 (t, J = 5.3 Hz, 1 H), 5.48-5.32 (m, 2 H), 7.66 (d, J = 8.1 Hz, 1 H), 7.80 (d, J = 8.1 Hz, 1 H), 8.26 (s, 1 H), 9.30 (s, 1 H). |
| 105-I | 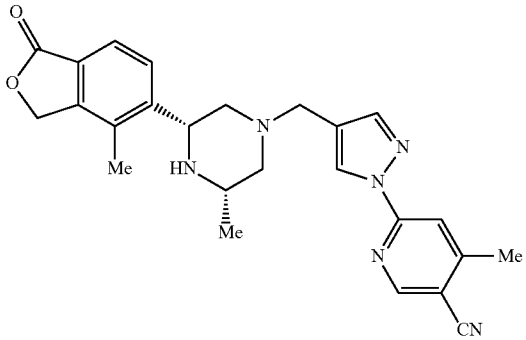 | 4-methyl-6-(4-(((3S,5R)-3-methyl-5-(4-methyl-1-oxo-1,3-dihydroisobenzofuran-5-yl)piperazin-1-yl)methyl)-1H-pyrazol-1-yl)nicotinonitrile | 443.3 | R: 1.01, 100% S: 1.48, 100% XXV: 6.28, 97.70% ee | $^1$H NMR (400 MHz, DMSO-d6) δ ppm 1.02 (d, J = 6.1 Hz, 3 H), 1.72 (br. s., 2 H), 2.25 (s, 3 H), 2.58 (s, 3 H), 2.79 (d, J = 11.2 Hz, 2 H), 2.96 (br. s., 1 H), 3.52 (s, 2 H), 4.16 (br. s., 1 H), 5.44-5.27 (m, 2 H), 7.64 (d, J = 8.1 Hz, 1 H), 7.78 (d, J = 8.1 Hz, 1 H), 7.84 (s, 1 H), 7.98 (s, 1 H), 8.51 (s, 1 H), 8.82 (s, 1 H), (1 Exchangeable proton not observed). |
| 106-I | 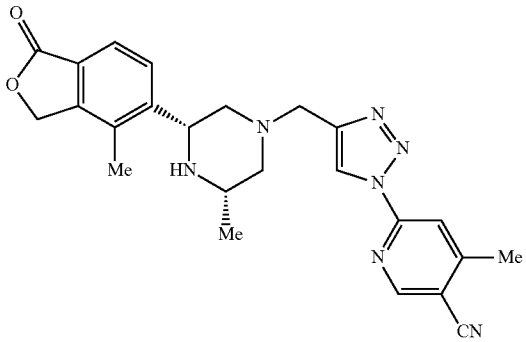 | 4-methyl-6-(4-(((3S,5R)-3-methyl-5-(4-methyl-1-oxo-1,3-dihydroisobenzofuran-5-yl)piperazin-1-yl)methyl)-1H-1,2,3-triazol-1-yl)nicotinonitrile | 444.3 | R: 0.99, 100% S: 1.29, 98.10% XII: 19.17, 98.2% ee | $^1$H NMR (400 MHz, DMSO-d6) δ ppm 1.02 (d, J = 5.9 Hz, 3 H), 1.80 (br. s., 2 H), 2.27 (s, 3 H), 2.64 (s, 3 H), 2.84 (br. s., 2 H), 2.96 (br. s., 1 H), 3.75 (s, 2 H), 4.15 (br. s., 1 H), 5.45-5.30 (m, 2 H), 7.65 (d, J = 8.3 Hz, 1 H), 7.78 (d, J = 8.1 Hz, 1 H), 8.28 (s, 1 H), 8.77 (s, 1 H), 8.98 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 107-I | 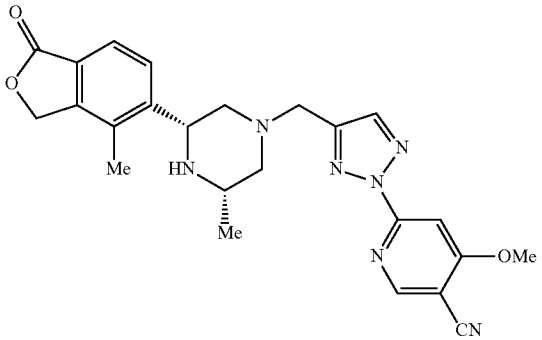 | 4-methoxy-6-(4-(((3S,5R)-3-methyl-5-(4-methyl-1-oxo-1,3-dihydroisobenzofuran-5-yl)piperazin-1-yl)methyl)-2H-1,2,3-triazol-2-yl)nicotinonitrile | 460.3 | R: 1.02, 95.00% S: 1.30, 94.00% XVIII: 16.50, 100% ee | $^1$H NMR (400 MHz, DMSO-d6) δ ppm 1.02 (d, J = 4.6 Hz, 3 H), 1.83 (br. s., 2 H), 2.26 (s, 3 H), 2.81 (d, J = 6.6 Hz, 2 H), 2.97 (br. s., 1 H), 3.77 (br. s., 2 H), 4.23-4.07 (m, 4 H), 5.50-5.28 (m, 2 H), 7.72-7.49 (m, 2 H), 7.79 (d, J = 7.6 Hz, 1 H), 8.22 (s, 1 H), 8.82 (s, 1 H), (1 Exchangeable proton not observed). |
| 108-I | 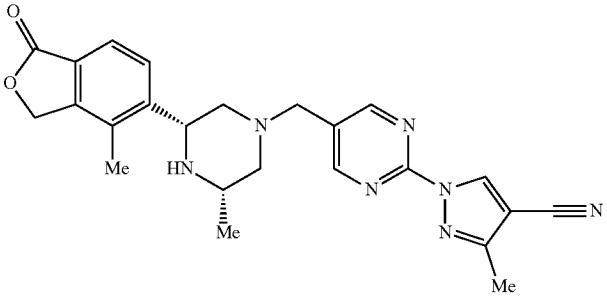 | 3-methyl-1-(5-(((3S,5R)-3-methyl-5-(4-methyl-1-oxo-1,3-dihydroisobenzofuran-5-yl)piperazin-1-yl)methyl)pyrimidin-2-yl)-1H-pyrazole-4-carbonitrile | 444.1 | R: 1.01, 99.20% S: 1.33, 99.00% XII: 8.83, 100% ee | $^1$H NMR (400 MHz, DMSO-d6) δ ppm 1.03 (d, J = 6.1 Hz, 3 H), 1.91-6.7 (m, 2 H), 2.25 (s, 3 H), 2.42 (s, 3 H), 2.79 (t, J = 9.3 Hz, 2 H), 2.99 (br. s., 1 H), 3.63 (s, 2 H), 4.17 (d, J = 8.8 Hz, 1 H), 5.50-5.24 (m, 2 H), 7.66 (d, J = 8.1 Hz, 1 H), 7.81 (d, J = 7.8 Hz, 1 H), 8.83 (s, 2 H), 9.35 (s, 1 H), 1 Exchangeable proton not observed). |
| 109-I | 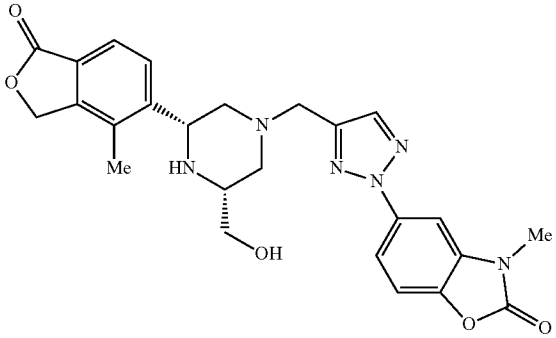 | 5-(4-(((3R,5R)-3-(hydroxymethyl)-5-(4-methyl-1-oxo-1,3-dihydroisobenzofuran-5-yl)piperazin-1-yl)methyl)-2H-1,2,3-triazol-2-yl)-3-methylbenzo[d]oxazol-2(3H)-one | 491.2 | R: 1.26, 100% S: 1.05, 95.00% XXVI: 3.72, 100% ee | $^1$H NMR (400 MHz, DMSO-d6) δ ppm 1.93-1.74 (m, 2 H), 2.28 (s, 3 H), 2.74 (s, 2 H), 3.03-2.80 (m, 2 H), 3.37 (br.s., 2 H), 3.42 (s, 2 H), 3.80-3.68 (m, 2 H), 4.20 (d, J = 8.1 Hz, 1 H), 4.65 (t, J = 5.5 Hz, 1 H), 5.46-5.33 (m, 2 H), 7.49 (d, J = 8.8 Hz, 1 H), 7.67 (d, J = 7.8 Hz, 1 H), 7.75 (dd, J = 8.9, 2.1 Hz, 1 H), 7.81 (d, J = 8.1 Hz, 1 H), 7.84 (d, J = 2.4 Hz, 1 H), 8.05 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 110-I | 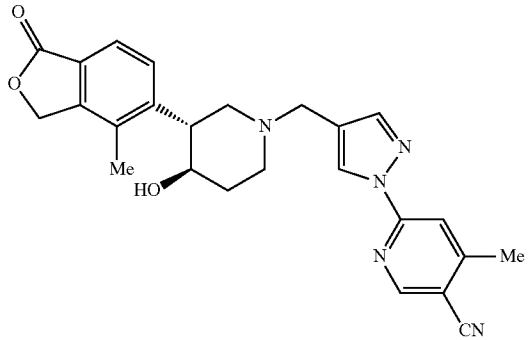 | 6-(4-(((3R,4R)-4-hydroxy-3-(4-methyl-1-oxo-1,3-dihydroisobenzofuran-5-yl)piperidin-1-yl)methyl)-1H-pyrazol-1-yl)-4-methylnicotinonitrile | 444.2 | C: 6.01, 99.30% G: 6.78, 99.30% X: 6.97 99% ee | $^1$H NMR (400 MHz, DMSO-$d_6$) δ ppm 1.62 (d, J = 12.47 Hz, 1 H), 1.93 (d, J = 10.76 Hz, 1 H), 2.04 (t, J = 11.25 Hz, 1 H), 2.14-2.20 (m, 1 H), 2.25 (s, 3 H), 2.58 (s, 3 H), 2.74 (d, J = 11.74 Hz, 1 H), 2.93 (d, J = 10.03 Hz, 1 H), 3.01-3.12 (m, 1 H), 3.49-3.56 (m, 2 H), 3.71 (br. s., 1 H), 4.59 (br. s., 1 H), 5.37 (d, J = 7.34 Hz, 2 H), 7.53 (d, J = 7.83 Hz, 1 H), 7.59-7.65 (m, 1 H), 7.85 (d, J = 1.71 Hz, 1 H), 7.98 (d, J = 0.73 Hz, 1 H), 8.52 (s, 1 H), 8.83 (d, J = 1.96 Hz, 1 H). |
| 111-I | 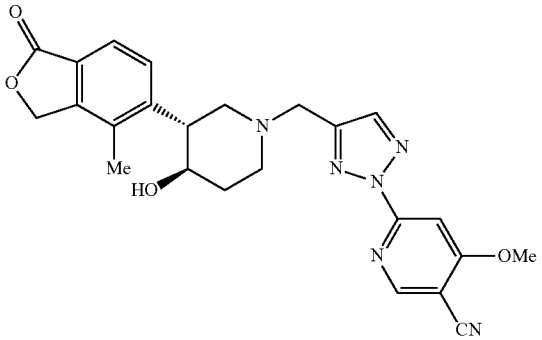 | 6-(4-(((3R,4R)-4-hydroxy-3-(4-methyl-1-oxo-1,3-dihydroisobenzofuran-5-yl)piperidin-1-yl)methyl)-2H-1,2,3-triazol-2-yl)-4-methoxynicotinonitrile | 461.1 | R: 0.90, 95.30% S: 1.20, 94.00% XVIII: 16.31, 100% ee | $^1$H NMR (400 MHz, DMSO-d6) δ ppm 1.70-1.54 (m, 1 H), 1.93 (d, J = 10.3 Hz, 1 H), 2.16 (t, J = 11.2 Hz, 1 H), 2.35-2.21 (m, 4 H), 2.75 (d, J = 11.0 Hz, 1 H), 2.93 (d, J = 11.7 Hz, 1 H), 3.16-3.03 (m, 1 H), 3.88-3.59 (m, 3 H), 4.12 (s, 3 H), 4.61 (d, J = 5.6 Hz, 1 H), 5.50-5.22 (m, 2 H), 7.54 (d, J = 8.1 Hz, 1 H), 7.63 (d, J = 8.1 Hz, 1 H), 7.68 (s, 1 H), 8.22 (s, 1 H), 8.82 (s, 1 H). |

-continued
| Example | Structure | Name | LCMS (M + H)$^+$ | HPLC/LCMS Method: RT (min.), Purity | NMR |
|---|---|---|---|---|---|
| 112-I | 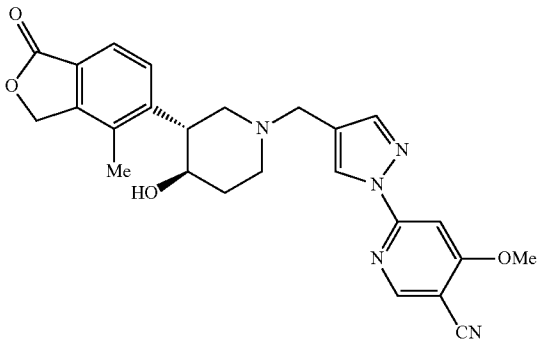 | 6-(4-(((3R,4R)-4-hydroxy-3-(4-methyl-1-oxo-1,3-dihydroisobenzofuran-5-yl)piperidin-1-yl)methyl)-1H-pyrazol-1-yl)-4-methoxynicotinonitrile | 460.2 | R: 0.94, 100%<br>S: 1.30, 100%<br>XVIII: 12.2, 99.1% ee | $^1$H NMR (400 MHz, DMSO-d6) δ ppm 1.63 (br. s., 1 H), 1.91 (s, 1 H), 2.05 (br. s., 1 H), 2.25 (s, 4 H), 2.75 (br. s., 1 H), 2.92 (br. s., 1 H), 3.07 (br. s., 1 H), 3.53 (br. s., 2 H), 3.72 (br. s., 1 H), 4.10 (s, 3 H), 4.57 (br. s., 1 H), 5.45-5.26 (m, 2 H), 7.54 (br. s., 1 H), 7.72-7.57 (m, 2 H), 7.87 (br. s., 1 H), 8.52 (br. s., 1 H), 8.74 (s, 1 H). |

Intermediate 53:

4-methyl-6-(trimethylstannyl)nicotinonitrile

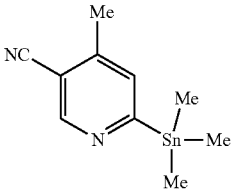

Intermediate 53 was prepared (1.80 g, crude) as a black syrup, by using a similar synthetic protocol as that of Intermediate 23A and starting from 6-bromo-4-methylnicotinonitrile (1.00 g, 5.08 mmol). LCMS (Method-I): retention time 1.40 min, [M+H] 283.1. The compound was taken directly to the subsequent step without further purification or characterization.

Intermediate 54-I: 5-((3R,4R)-1-((2-bromothiazol-5-yl)methyl)-4-hydroxypiperidin-3-yl)-4-methylisobenzofuran-1(3H)-one

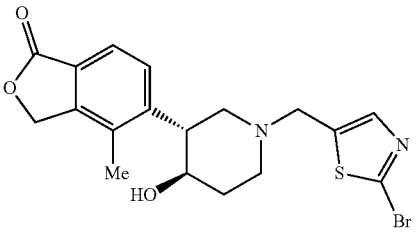

Intermediate 54-I was prepared (0.30 g, 21.77%) as an off-white solid, by using a similar synthetic protocol as that of Intermediate 23-I and starting from Intermediate 52-I (0.36 g, 1.30 mmol) and Intermediate 25B (0.25 g, 1.30 mmol). $^1$H NMR (400 MHz, DMSO-$d_6$) δ ppm 1.56-1.58 (m, 1H), 1.89-1.90 (m, 1H), 2.10 (br. S., 1H), 2.20-2.22 (m, 4H), 2.80 (br. S., 1H), 2.90 (br. S., 1H), 3.10 (br. S., 1H), 3.80-3.85 (m, 3H), 4.62 (br. S., 1H), 5.25-5.27 (m, 2H), 7.50-7.52 (m, 2H), 7.70 (d, J=8.00 Hz, 1H). LCMS (Method-I): retention time 1.01 min, [M+H] 423.2.

Intermediate 55-I: 5-((2R,6S)-4-((2-bromothiazol-5-yl)methyl)-6-methylpiperazin-2-yl)-4-methylisobenzofuran-1(3H)-one

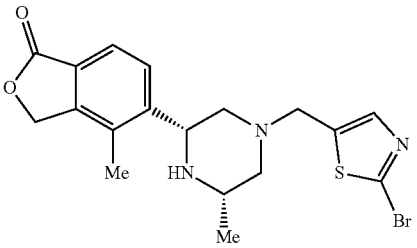

Intermediate 55-I was prepared (0.40 g, 60.60%) as an off-white solid, by using a similar synthetic protocol as that of Intermediate 23-I and stating from Intermediate 51-I (0.38 g, 1.56 mmol) and Intermediate 25B (0.30 g, 1.56 mmol). $^1$H NMR (400 MHz, DMSO-$d_6$) δ ppm 1.10 (s, 3H), 1.80 (br. s, 2H), 2.30 (s, 3H), 2.80 (br. s, 2H), 2.84 (br. s., 1H), 3.85 (s, 2H), 4.16 (br. s., 1H), 5.37 (br. s., 2H), 7.79 (d, J=8.00 Hz, 1H), 7.91-7.92 (m, 2H), (1 Exchangeable proton not observed). LCMS (Method-I): retention time 1.10 min, [M+H] 422.2.

Intermediate 56: 1-(2-methoxypyridin-4-yl)-1H-imidazole-4-carbaldehyde

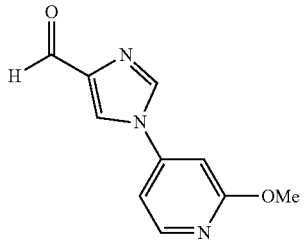

Intermediate 56 was prepared (0.20 g, 19.00%) as an off-white solid, by using a similar synthetic protocol as that of Intermediate 11 and starting from 1H-imidazole-4-carbaldehyde (0.51 g, 5.32 mmol) and 4-bromo-2-methoxypyridine (1.00 g, 5.32 mmol). $^1$H NMR (400 MHz, DMSO-$d_6$) δ ppm 3.92 (s, 3H), 7.36 (d, J=1.60 Hz, 1H), 7.48-7.50 (m, 1H), 8.31 (d, J=6.00 Hz, 1H), 8.32 (d, J=1.20 Hz, 1H), 8.71 (d, J=6.00 Hz, 1H), 9.82 (s, 1H). LCMS (Method-D): retention time 1.08 min, [M+H] 204.2.

Intermediate 57: 1-(2-(difluoromethyl)pyridin-4-yl)-1H-pyrazole-4-carbaldehyde

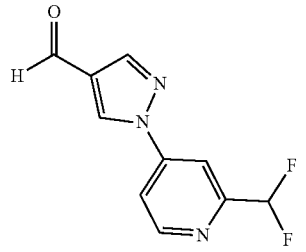

Intermediate 57 was prepared (0.12 g, 55.90%) as an off-white solid, by using a similar synthetic protocol as that of Intermediate 11 and starting from 1H-pyrazole-4-carbaldehyde (0.11 g, 1.15 mmol) and (4-bromo-2-(difluoromethyl)pyridine (0.20 g, 0.96 mmol). LCMS (Method-S): retention time 0.49 min, [M+H] 224.3. The compound was taken directly to the subsequent step without further purification or characterization.

Intermediate 58: 1-(1-(difluoromethyl)-2-oxo-1,2-dihydropyridin-4-yl)-1H-pyrazole-4-carbaldehyde

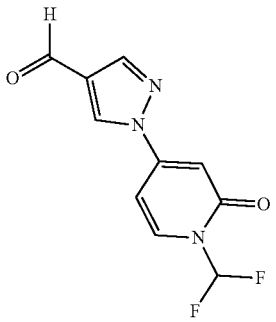

Intermediate 58A: 4-bromo-1-(difluoromethyl)pyridin-2(1H)-one

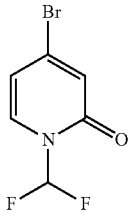

To a solution of 4-bromo-2-chloropyridine (1.25 g, 6.72 mmol) in ACN (100 mL) was added $NaHCO_3$ (8.73 g, 10 mmol) and the resulting reaction mixture was heated at 80° C. for 30 minutes. A solution of 2,2-difluoro-2-(fluorosulfonyl)acetic acid (5.38 mL, 52.00 mmol) in MeCN (15 mL) was added over 10 minutes and the reaction mixture was heated at 80° C. for 2 h. The reaction mixture was cooled to ambient temperature, diluted with water (50 mL), basified with 10% aq. $NaHCO_3$ and extracted with ethyl acetate (2×100 mL). The combined organic layers were washed with brine (50 mL), dried over anhydrous sodium sulfate and evaporated under reduced pressure to obtain Intermediate 58A (3.00 g, 25.80%) as a pale yellow liquid. $^1$H NMR (400 MHz DMSO-$d_6$) δ ppm 6.6 (dd, J=1.20, 3.20 Hz, 1H), 7.56 (d, J=3.20 Hz, 1H), 7.75 (t, J=5.60 Hz, 1H), 7.8 (d, J=3.20 Hz, 1H). LCMS (Method-D): retention time 1.64 min [M+H] 224.2.

Intermediate 58

Intermediate 58 was prepared (0.10 g, 50.00%) as an off-white solid, by using a similar synthetic protocol as that of Intermediate 6 and starting from 1H-pyrazole-4-carbaldehyde (0.09 g, 0.89 mmol) and Intermediate 58A (0.20 g, 0.90 mmol). LCMS (Method-D): retention time 0.73 min. [M+H] 240.2. The compound was taken directly to the subsequent step without further purification or characterization.

Intermediate 59: (2-(5-cyano-4-methylpyridin-2-yl) oxazol-4-yl)methyl methanesulfonate

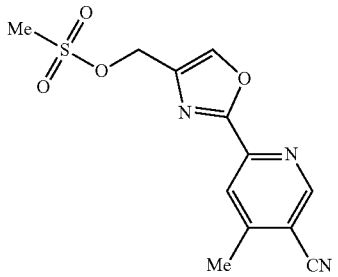

Intermediate 59A: ethyl 2-(5-cyano-4-methylpyridin-2-yl)oxazole-4-carboxylate

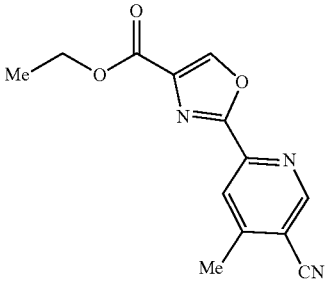

To a solution of 6-bromo-4-methylnicotinonitrile (1.34 g, 7.09 mmol) in toluene (10 mL) was added ethyl oxazole-4-carboxylate (1.00 g, 7.09 mmol), $Cs_2CO_3$ (4.62 g, 14.17 mmol) and tri-o-tolylphosphine (0.21 g, 0.80 mmol). The resulting reaction mixture was degassed with nitrogen for 20 minutes. $Pd(OAc)_2$ (0.16 g, 0.80 mmol) was added and the reaction mixture was degassed again for 10 minutes and then heated at 110° C. for 12 h. The reaction mixture was cooled to ambient temperature, filtered through Celite® and the filtrate was evaporated under reduced pressure. The residue was purified by column chromatography (Redisep—40 g, 30% EtOAc/n-hexane) to obtain Intermediate 59A (0.25 g, 13.71%) as a white solid. $^1$H NMR (400 MHz, DMSO-$d_6$) δ ppm 1.34 (t, J=7.0 Hz, 3H), 2.60 (s, 3H), 4.34 (q, J=7.00 Hz, 2H), 8.31 (s, 1H), 9.07 (s, 1H), 9.10 (s, 1H). LCMS (Method-D): retention time 1.99 min, [M+H] 258.2.

Intermediate 59B: 6-(4-(hydroxymethyl)oxazol-2-yl)-4-methylnicotinonitrile

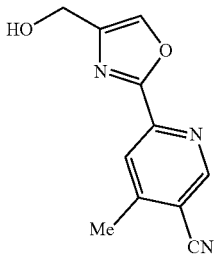

To a solution of Intermediate 59A (0.13 g, 0.51 mmol) in THF (10 mL) was added DIBAL-H (2.10 mL, 2.53 mmol) and the resulting reaction mixture was stirred at ambient temperature for 1 h. The reaction mixture was diluted with a saturated solution of $NH_4Cl$ (2 mL), water (10 mL) and extracted with 10% MeOH in DCM (2×20 mL). The combined organic layers were washed with brine (10 mL), dried over anhydrous sodium sulfate and evaporated under reduced pressure to obtain Intermediate 59B (0.06 g, 55.20%). $^1$H NMR (400 MHz, DMSO-$d_6$) δ ppm 2.65 (s, 3H), 4.49 (br. s., 2H), 5.32 (br. s., 1H), 8.20 (s, 1H), 8.21 (s, 1H), 9.03 (s, 1H). LCMS (Method D): retention time 0.93 min [M+H] 216.2.

Intermediate 59

To a solution of Intermediate 59B (0.04 g, 0.19 mmol) in DCM (10 mL) was added TEA (0.08 mL, 0.56 mmol) and mesyl chloride (0.02 mL, 0.24 mmol) at 0° C. and the resulting reaction mixture was stirred at ambient temperature for 30 minutes. The reaction mixture was diluted with water (5 mL) and extracted with DCM (2×20 mL). The combined organic layers were washed with brine (10 mL), dried over anhydrous sodium sulfate and evaporated under reduced pressure. The residue was purified by column chromatography (Redisep—24 g, 60-70% EtOAc/n-hexane) to obtain Intermediate 59 (0.04 g, 73.40%) as a white solid. $^1$H NMR (400 MHz, DMSO-$d_6$) δ ppm 2.60 (s, 3H), 3.23 (s, 3H), 5.75 (s, 2H), 8.25 (s, 1H), 8.56 (s, 1H), 9.06 (s, 1H). LCMS (Method-D): retention time 1.65 min, [M+H] 294.0.

Intermediate 60:

6-(5-formyloxazol-2-yl)-4-methylnicotinonitrile

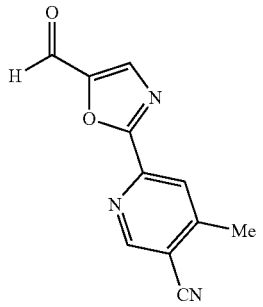

Intermediate 60A: Ethyl 2-(5-cyano-4-methylpyridin-2-yl)oxazole-5-carboxylate

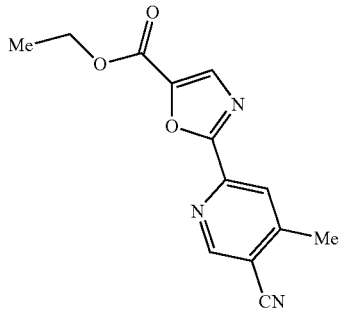

Intermediate 60A was prepared (0.50 g, 34.30%) as an off-white solid, by using a similar synthetic protocol as that of Intermediate 59A and starting from ethyl oxazole-5-carboxylate (0.80 g, 5.67 mmol) and 6-bromo-4-methylnicotinonitrile (1.11 g, 5.67 mmol). $^1$H NMR (400 MHz, DMSO-$d_6$) δ ppm 1.34 (t, J=7.00 Hz, 3H), 2.60 (s, 3H), 4.34 (q, J=7.00 Hz, 2H), 8.26 (s, 1H), 8.30 (s, 1H), 9.10 (s, 1H). LCMS (Method-D): retention time 2.26 min, [M+H] 258.2.

Intermediate 60B: 6-(5-(hydroxymethyl)oxazol-2-yl)-4-methylnicotinonitrile

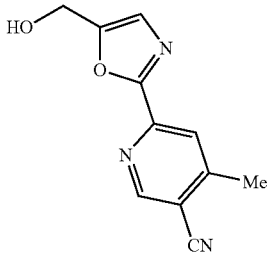

To a solution of Intermediate 60A (0.10 g, 0.34 mmol) in a mixture of THF (10 mL) and MeOH (2 mL) was added $NaBH_4$ (0.05 g, 1.17 mmol) at 0° C. and the resulting reaction mixture was stirred at ambient temperature for 30 minutes. The reaction mixture was diluted with water (20 mL) and extracted with 10% MeOH in DCM (2×30 mL). The combined organic layers were washed with brine (20 mL), dried over anhydrous sodium sulfate and evaporated under reduced pressure. The residue was purified by column chromatography (Redisep—4 g, 60-70% EtOAc/n-Hexane) to obtain Intermediate 60B (0.04 g, 47.80%) as a white solid. $^1$H NMR (400 MHz, DMSO-$d_6$) δ ppm 2.60 (s, 3H), 5.65 (t, J=5.60 Hz, 1H), 5.85-5.99 (m, 1H), 7.36 (s, 1H), 8.18 (s, 1H), 9.03 (s, 1H), (1 Exchangeable proton not observed). LCMS (Method-I): retention time 0.70 min, [M+H] 216.2.

Intermediate 60

Intermediate 60 was prepared (0.06 g, 87.00%) as an off-white solid, by using a similar synthetic protocol as that of Intermediate 9 and starting from Intermediate 60B (0.07 g, 0.32 mmol) and Dess-Martin periodinane (0.18 g, 0.43 mmol). LCMS (Method-1): retention time 0.60 min, [M+H] 214.2. The compound was taken directly to the subsequent step without further purification or characterization.

Intermediate 61: 1-(6-(difluoromethyl)pyridin-3-yl)-1H-imidazole-4-carbaldehyde

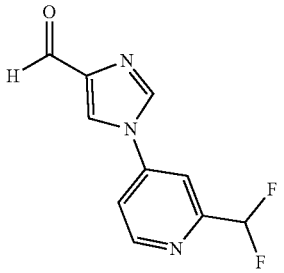

Intermediate 61 was prepared (0.03 g, 13.98%) as an off-white solid, by using a similar synthetic protocol as that of Intermediate 6 and starting from 4-bromo-2-(difluoromethyl)pyridine (0.20 g, 0.96 mmol) and 1H-imidazole-4-carbaldehyde (0.09 g, 0.96 mmol). $^1$H NMR (400 MHz, DMSO-$d_6$) δ ppm 7.00 (t, J=7.20 Hz, 1H), 7.94-7.91 (m, 1H), 8.44-8.41 (m, 1H), 8.64 (s, 1H), 9.85 (s, 1H)), 8.80 (d, J=1.60 Hz, 1H), 9.16 (d, J=3.20 Hz, 1H). LCMS (Method-I): retention time 0.66 min [M+H] 224.0.

Intermediate 62: 4-methyl-6-(4-methyl-1H-imidazol-1-yl)nicotinaldehyde

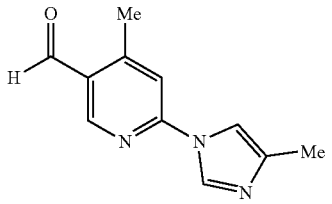

Intermediate 62 was prepared (0.21 g, 54.10%), by using a similar synthetic protocol as that of Intermediate 15C and starting from 4-methyl-1H-imidazole (0.24 g, 2.89 mmol) and 6-chloro-4-methylnicotinaldehyde (0.30 g, 1.93 mmol). $^1$H NMR (400 MHz, DMSO-$d_6$) δ ppm 2.19 (d, J=0.98 Hz, 3H), 2.69 (s, 3H), 7.75 (d, J=1.22 Hz, 1H), 7.80 (s, 1H), 8.53 (d, J=1.22 Hz, 1H), 8.85 (s, 1H), 10.21 (s, 1H). LCMS (Method-D): retention time 1.20 min, [M+H] 202.2.

Intermediate 63: 2-methyl-6-(4-methyl-1H-imidazol-1-yl)nicotinaldehyde

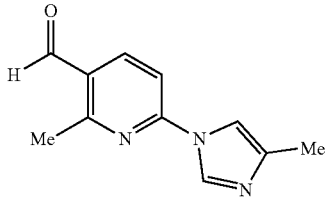

Intermediate 63 was prepared (0.25 g, 64.40%), by using a similar synthetic protocol as that of Intermediate 15C and starting from 4-methyl-1H-imidazole (0.24 g, 2.89 mmol) and 6-chloro-2-methylnicotinaldehyde (0.30 g, 1.93 mmol). $^1$H NMR (400 MHz, DMSO-$d_6$) δ ppm 2.19 (d, J=0.98 Hz, 3H), 2.69 (s, 3H), 7.75 (d, J=1.22 Hz, 1H), 7.80 (s, 1H), 8.53 (d, J=1.22 Hz, 1H), 8.85 (s, 1H), 10.21 (s, 1H). LCMS (Method-D): retention time 1.20 min, [M+H] 202.2.

Intermediate 64:5'-formyl-4,6'-dimethoxy-[2,2'-bipyridine]-5-carbonitrile

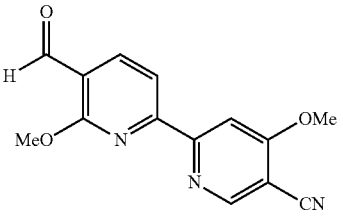

Intermediate 64A:

6-chloro-2-methoxynicotinaldehyde

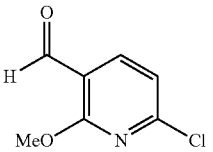

Synthesized according to literature procedures (EP1405859 A1, 2004).

Intermediate 64

Intermediate 64 was prepared (0.15 g, 39.10%) as a pale yellow solid, by using a similar synthetic protocol as that of Intermediate 23B and starting from Intermediate 23A (0.62 g, 2.09 mmol) and Intermediate 64A (0.30 g, 1.75 mmol). $^1$H NMR (400 MHz, DMSO-$d_6$) δ ppm 4.14-4.24 (m, 6H), 8.15-8.22 (m, 2H), 8.28-8.36 (m, 1H), 8.95-9.01 (m, 1H), 10.27-10.35 (m, 1H). LCMS (Method-D): retention time 2.603 min, [M+H] 270.1.

Intermediate 65: 5-fluoro-6-(4-methyl-1H-imidazol-1-yl)nicotinaldehyde

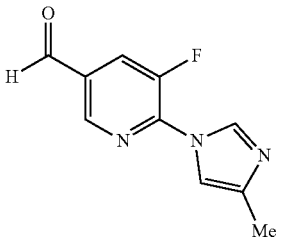

Intermediate 65 was prepared (0.18 g, 59.70%) as a pale yellow solid, by using a similar synthetic protocol as that of Intermediate 11 and starting from 4-methyl-1H-imidazole (0.18 g, 2.20 mmol) and 6-bromo-5-fluoronicotinaldehyde (0.30 g, 1.47 mmol). $^1$H NMR (400 MHz, DMSO-$d_6$) δ ppm 2.18-2.24 (m, 3H), 7.63-7.72 (m, 1H), 8.31-8.44 (m, 2H), 8.87-8.92 (m, 1H), 10.04-10.13 (m, 1H). LCMS (Method-D): retention time 1.16 min, [M+H] 206.0.

Intermediate 66: 6-(4-formyl-5-methyl-1H-pyrazol-1-yl)-4-methylnicotinonitrile

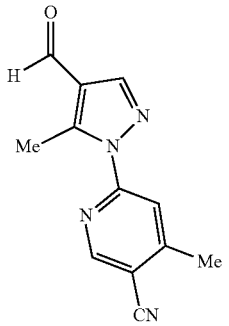

Intermediate 66 was prepared (0.09 g, 14.60%) as an off-white solid, by using a similar synthetic protocol as that of Intermediate 6 and starting from 3-methyl-1H-pyrazole-4-carbaldehyde (0.40 g, 3.63 mmol) and 6-bromo-4-methylnicotinonitrile (0.54 g, 2.72 mmol). $^1$H NMR (400 MHz, DMSO-$d_6$) δ ppm 2.15 (s, 3H), 2.32 (s, 3H), 7.89-7.94 (m, 1H), 7.97-8.07 (m, 1H), 8.38-8.46 (m, 1H), 8.75-8.83 (m, 1H). LCMS (Method-0): retention time 1.14 min, [M+H] 227.0.

Intermediate 67: 6-(4-methyl-1H-imidazol-1-yl)-4-(trifluoromethyl)nicotinaldehyde

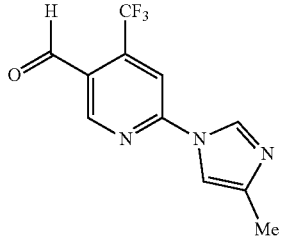

Intermediate 67A:

(6-chloro-4-(trifluoromethyl)pyridin-3-yl)methanol

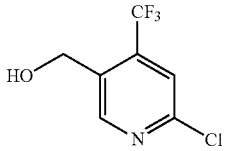

To a stirred solution of 6-chloro-4-(trifluoromethyl)nicotinate (2.00 g, 8.35 mmol) in toluene (25 mL) at −78° C. was added 1M DIBAL-H in toluene (12.52 mL, 12.52 mmol) and the reaction mixture was stirred at −78° C. for 2 h. The resulting reaction mixture was diluted with saturated $NH_4Cl$ (40 mL) and extracted with ethyl acetate (2×75 mL). The combined organic layers were washed with brine (50 mL), dried over anhydrous sodium sulfate and evaporated under reduced pressure to obtain Intermediate 67A (2.20 g, 87.00%). $^1$H NMR (400 MHz, DMSO-$d_6$) δ ppm 4.70 (s, 2H), 5.65-5.77 (m, 1H), 7.88 (s, 1H), 8.76 (s, 1H). LCMS: The compound did not ionize well.

Intermediate 67B:

6-chloro-4-(trifluoromethyl)nicotinaldehyde

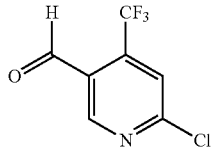

Intermediate 67B was prepared (0.97 g, 75.00%), by using a similar synthetic protocol as that of Intermediate 9 and starting from Intermediate 67A (1.30 g, 6.14 mmol) and Dess-Martin periodinane (2.61 g, 6.14 mmol). $^1$H NMR (400 MHz, DMSO-$d_6$) δ ppm 8.16 (s, 1H), 9.11 (s, 1H), 10.24 (q, J=1.71 Hz, 1H). LCMS: The compound did not ionize well.

Intermediate 67

Intermediate 67 was prepared (0.23 g, 47.20%), by using a similar synthetic protocol as that of Intermediate 15C and starting from Intermediate 67B (0.30 g, 1.43 mmol) and 4-methyl-1H-imidazole (0.17 g, 2.15 mmol). $^1$H NMR (400 MHz, DMSO-$d_6$) δ ppm 3.72-3.76 (m, 3H), 6.88-6.95 (m, 2H), 7.10-7.17 (m, 2H), 7.77-7.81 (m, 1H). LCMS (Method-O): retention time 1.05 min, [M+H] 256.4.

Intermediate 68: 2-(4,5-dimethyl-1H-imidazol-1-yl) pyrimidine-5-carbaldehyde

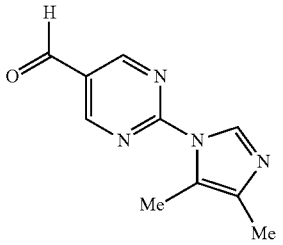

Intermediate 68A: 4,5-dimethyl-1H-imidazole

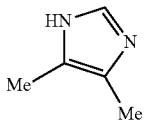

Synthesized according to literature procedures (Angewandte Chemie, 5322-5326, 49, 2010).

Intermediate 68

To a solution of 2-bromopyrimidine-5-carbaldehyde (0.20 g, 1.07 mmol) in ACN (20 mL) was added $K_2CO_3$ (443 mg, 3.21 mmol) followed by Intermediate 68A (0.16 g, 1.60 mmol) and the resulting reaction mixture was stirred at 50° C. for 1.5 h. The reaction mixture cooled to ambient temperature, diluted with ethyl acetate (30 mL) and filtered through Celite®. The filtrate was evaporated under reduced pressure to obtain Intermediate 68 (0.19 g, 86.00%) as a white solid. $^1$H NMR (400 MHz, DMSO-$d_6$) δ ppm 2.13 (d, J=0.49 Hz, 3H), 2.16 (s, 3H), 8.47 (s, 1H), 9.27 (s, 2H), 10.11 (s, 1H). LCMS: The compound did not ionize well.

Intermediate 69: 4-methoxy-6-(4-methyl-1H-imidazol-1-yl)nicotinaldehyde

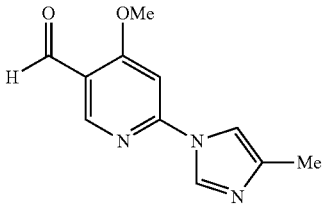

Intermediate 69A: methyl 6-chloro-4-methoxynicotinate

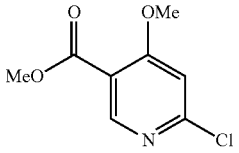

Synthesized according to literature procedures (US2015/166505 A1, 2015).

Intermediate 69B: (6-chloro-4-methoxypyridin-3-yl)methanol

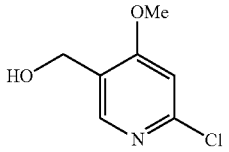

To a stirring solution of Intermediate 69A (2.20 g, 10.91 mmol) in DCM (30 mL) was added 1M DIBAL-H in heptane (16.37 mL, 16.37 mmol) at 0° C. and the resulting reaction mixture was stirred at ambient temperature for 1 h. The resulting reaction mixture was diluted with saturated $NH_4Cl$ (40 mL) and extracted with DCM (3×50 mL). The combined organic layers were washed with brine (30 mL), dried over anhydrous sodium sulfate and evaporated under reduced pressure. The residue was purified by column chromatography (Redisep—24 g, 20% EtOAc/n-hexane) to obtain Intermediate 69B (1.20 g, 63.30%). $^1$H NMR (400 MHz, DMSO-$d_6$) δ ppm 3.88 (s, 3H) 4.46 (dd, J=5.52, 1.00 Hz, 2H), 5.19 (t, J=5.77 Hz, 1H), 7.11 (s, 1H), 8.16 (s, 1H). LCMS (Method-I): retention time 0.69 min, [M+H] 174.4.

Intermediate 69C: 6-chloro-4-methoxynicotinaldehyde

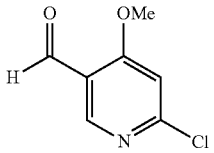

Intermediate 69C was prepared (0.75 g, 63.20%), by using a similar synthetic protocol as that of Intermediate 9 and starting from Intermediate 69B (1.20 g, 6.91 mmol) and Dess-Martin periodinane (2.93 g, 6.91 mmol). $^1$H NMR (400 MHz, DMSO-$d_6$) δ ppm 4.02 (s, 3H), 7.45 (s, 1H), 8.55 (s, 1H), 10.24 (s, 1H). LCMS (Method-D): retention time 1.06 min, [M+H] 172.2.

Intermediate 69

Intermediate 69 was prepared (0.12 g, 37.80%), by using a similar synthetic protocol as that of Intermediate 68 and starting from Intermediate 69C (0.25 g, 1.46 mmol) and 4-methyl-1H-imidazole (0.24 g, 2.91 mmol). $^1$H NMR (400 MHz, DMSO-$d_6$) δ ppm 2.19 (s, 3H), 4.09 (s, 3H), 7.49 (s, 1H), 7.81 (s, 1H), 8.56 (d, J=1.00 Hz, 1H), 8.63 (s, 1H), 10.23 (s, 1H). LCMS (Method-I): retention time 0.89 min, [M+H] 218.3.

Intermediate 70: 2-(5-(difluoromethyl)-4-methyl-1H-imidazol-1-yl)pyrimidine-5-carbaldehyde

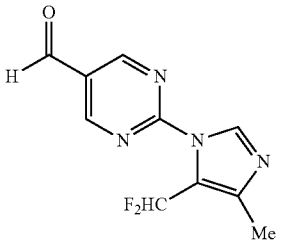

Intermediate 70A: tert-butyl 5-formyl-4-methyl-1H-imidazole-1-carboxylate

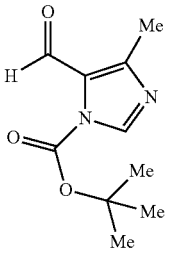

Intermediate 70A was prepared (2.80 g, 73.30%) as a white solid, by using a similar synthetic protocol as that of Intermediate 18B-II and starting from 4-methyl-1H-imidazole-5-carbaldehyde (2.00 g, 18.16 mmol) and $BOC_2O$ (5.06 mL, 21.80 mmol). LCMS (Method-I): retention time 1.07 min, [M−56] 155.9. The compound was taken directly to the subsequent step without further purification or characterization.

Intermediate 70B: tert-butyl 5-(difluoromethyl)-4-methyl-1H-imidazole-1-carboxylate

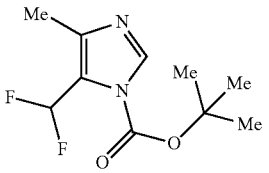

Intermediate 70B was prepared (0.85 g, 51.30%), by using a similar synthetic protocol as that of Intermediate 4B and starting from Intermediate 70A (1.50 g, 7.14 mmol) and DAST (1.89 mL, 14.27 mmol). $^1$H NMR (400 MHz, DMSO-$d_6$) δ ppm 1.58 (s, 9H), 2.44 (t, J=2.26 Hz, 3H), 6.82-7.18 (m, 1H), 8.19 (s, 1H). The compound did not ionize well.

Intermediate 70C: 5-(difluoromethyl)-4-methyl-1H-imidazole

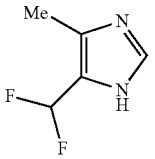

Intermediate 70C was prepared (0.48 g, 99.00%), by using a similar synthetic protocol as that of Intermediate 4C and starting from Intermediate 70B (0.85 g, 3.66 mmol). $^1$H NMR (400 MHz, DMSO-$d_6$) δ ppm 2.38 (t, J=2.08 Hz, 3H), 7.06-7.52 (m, 1H), 9.02 (s, 1H), (1 Exchangeable proton not observed). LCMS (Method-I): retention time 0.58 min, [M+H] 133.4.

Intermediate 70

Intermediate 70 was prepared (0.10 g, 20.90%), by using a similar synthetic protocol as that of Intermediate 68 and starting from Intermediate 70C (0.28 g, 1.68 mmol) and 2-chloropyrimidine-5-carbaldehyde (0.20 g, 1.40 mmol). $^1$H NMR (400 MHz, DMSO-$d_6$) δ ppm 2.69 (t, J=2.32 Hz, 3H), 6.92-7.26 (m, 1H), 8.62 (s, 1H), 9.34 (s, 2H), 10.15 (s, 1H). LCMS (Method-D): retention time 1.50 min, [M+H] 239.0.

Intermediate 71-I and 71-II: 4-methyl-5-(3-methylpiperazin-2-yl)isobenzofuran-1(3H)-one Enantiomer-I (71-I)

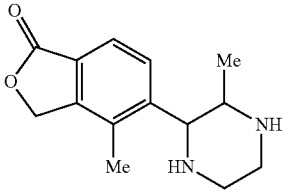

-continued

Enantiomer-II (71-II)

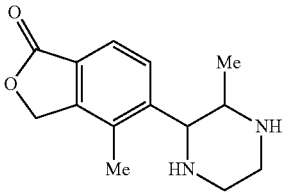

Intermediate 71A: 4-methyl-5-(3-methylpyrazin-2-yl)isobenzofuran-1(3H)-one

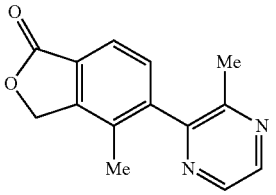

Intermediate 71A was prepared (3.00 g, 65.50%) as an off-white solid, by using a similar synthetic protocol as that of Intermediate 2C and starting from Intermediate 2B (5.00 g, 18.24 mmol) and 2-Chloro-3-methylpyrazine (2.81 g, 21.89 mmol). $^1$H NMR (400 MHz, DMSO-$d_6$) δ ppm 2.03 (s, 3H), 2.32 (s, 3H), 5.49 (s, 2H), 7.51 (d, J=8.03 Hz, 1H), 7.79 (d, J=7.53 Hz, 1H), 8.56-8.64 (m, 2H). LCMS (Method-O): retention time 0.77 min, [M+H] 241.4.

Intermediate 71-I and 71-II

Intermediate 71-I and 71-II was prepared by using a similar synthetic protocol as that of Intermediate 2-I and 2-II and starting from Intermediate 71A (10.00 g, 41.6 mmol). The racemate was separated into two individual enantiomers by SFC [Chiralpak AD-H (250×4.6 mm), 5 micron; 0.2% $NH_4OH$ in MeOH+ACN (1:1), Flow: 1.2 mL/min. Temperature: 27° C., UV: 235 nm]. First eluted compound (retention time 3.37 min), designated as Intermediate 71-I, was obtained (0.65 g, 21.13%) as a brown solid. $^1$H NMR (400 MHz, DMSO-$d_6$) δ ppm 0.7 (d, J=6.02 Hz, 3H), 2.14-2.22 (m, 2H), 2.29 (s, 3H), 2.74-2.84 (m, 3H), 4.02 (dd, J=10.04, 2.51 Hz, 1H), 5.38 (s, 2H), 7.65 (d, J=8.03 Hz, 1H), 7.81 (d, J=8.03 Hz, 1H), (2 Exchangeable protons not observed). LCMS (Method-O): retention time 0.77 min, [M+H] 241.4. Second eluted compound (retention time 4.79 min), designated as Intermediate 71-II, was obtained (1.20 g, 39.00%) as a brown solid. LCMS (Method-O): retention time 0.77 min, [M+H] 241.4. $^1$H NMR (400 MHz, DMSO-$d_6$) δ ppm 0.70 (d, J=6.02 Hz, 3H), 2.14-2.22 (m, 2H), 2.29 (s, 3H), 2.74-2.84 (m, 3H), 4.02 (dd, J=10.04, 2.51 Hz, 1H), 5.38 (s, 2H), 7.65 (d, J=8.03 Hz, 1H), 7.81 (d, J=8.03 Hz, 1H), (2 Exchangeable protons not observed).

Intermediate 72: 5-(4-hydroxy-4-methylpiperidin-3-yl)-4-methylisobenzofuran-1(3H)-one

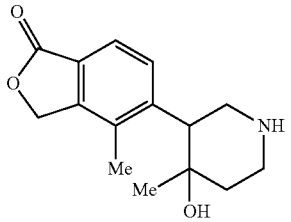

Intermediate 72A: tert-butyl 4-hydroxy-4-methyl-3-(4-methyl-1-oxo-1,3-dihydroisobenzofuran-5-yl) piperidine-1-carboxylate

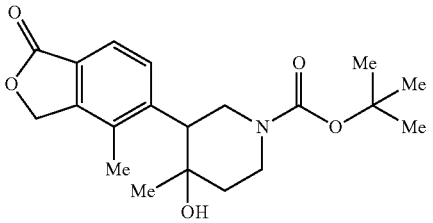

To a stirring solution of Intermediate 4A (1.80 g, 5.21 mmol) in THF (20 mL) was added 3M methylmagnesium chloride in THF (5.21 mL, 15.63 mmol) at 0° C. and the resulting reaction mixture was stirred at ambient temperature for 1 h. Reaction mixture was diluted with saturated $NH_4Cl$ (40 mL) and extracted with EtOAc (3×50 mL). The combined organic layers were washed with brine (30 mL), dried over anhydrous sodium sulfate and evaporated under reduced pressure. The residue was purified by column chromatography (Redisep—40 g, 20-40% EtOAc/n-hexane) to obtain Intermediate 72A (1.00 g, 53.10%). $^1$H NMR (400 MHz, DMSO-$d_6$) δ ppm 0.94 (s, 3H), 1.39 (s, 9H), 1.59 (br. s., 2H), 1.89 (s, 1H), 2.27 (s, 3H), 2.88-2.96 (m, 1H), 3.52-3.65 (m, 1H), 3.79-3.94 (m, 1H), 4.61-4.72 (m, 1H), 5.40 (s, 2H), 7.61 (d, J=8.03 Hz, 1H), 7.82-7.93 (m, 1H), (1 Exchangeable proton not observed). LCMS (Method-D): retention time 2.22 min, [M+H] 362.2.

Intermediate 72

Intermediate 72 was prepared (0.90 g, 87.00%) as an off-white solid, by using a similar synthetic protocol as that of Intermediate 19-I and starting from Intermediate 72A (1.00 g, 2.77 mmol) and TFA (4 mL, 51.9 mmol). $^1$H NMR (400 MHz, DMSO-$d_6$) δ ppm 0.95 (s, 3H), 1.71-1.84 (m, 1H), 1.87-1.96 (m, 1H), 2.28 (s, 3H), 2.96-3.02 (m, 1H), 3.26 (br. s., 2H), 3.37 (br. s., 2H), 5.41 (d, J=5.02 Hz, 2H), 7.66 (d, J=8.03 Hz, 1H), 7.76 (d, J=8.53 Hz, 1H), (2 Exchangeable protons not observed). LCMS (Method-O) retention time 0.52 min, [M+H] 262.2.

Intermediate 73-I: 5-(4-hydroxy-5,5-dimethylpiperidin-3-yl)-4-methylisobenzofuran-1(3H)-one hydrochloride (Diastereomer-I:Enantiomer-I)

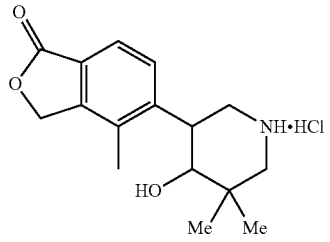

Intermediate 73A: tert-butyl 3,3-dimethyl-5-(4-methyl-1-oxo-1,3-dihydroisobenzofuran-5-yl)-4-xopiperidine-1-carboxylate

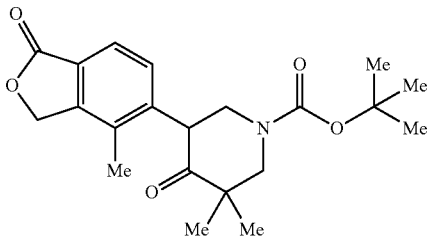

Intermediate 73A was prepared (2.30 g, 28.00%) as an off-white solid, by using a similar synthetic protocol as that of Intermediate 4A and starting from Intermediate 2A (5.00 g, 22.02 mmol) and tert-butyl 3,3-dimethyl-4-oxopiperidine-1-carboxylate (10.01 g, 44.0 mmol). $^1$H NMR (400 MHz, DMSO-$d_6$) δ ppm 1.01-1.07 (m, 3H), 1.21-1.26 (m, 3H), 1.46 (s, 9H), 2.28 (s, 3H), 2.11-2.18 (m, 4H), 4.34-4.44 (m, 1H), 5.35-5.44 (m, 2H), 7.35-7.42 (m, 1H), 7.60-7.70 (m, 1H). LCMS (Method-O): retention time 1.29 min, [M+H] 374.6.

Intermediate 73B-I and 73B-II: tert-butyl 4-hydroxy-3,3-dimethyl-5-(4-methyl-1-oxo-1,3-dihydroisobenzofuran-5-yl)piperidine-1-carboxylate Enantiomer-I (73B-I)

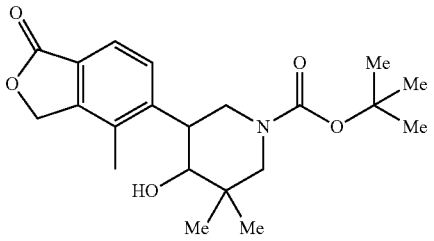

-continued

Enantiomer-II (73B-II)

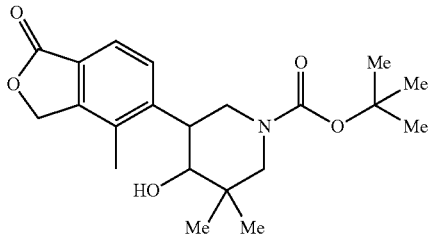

To a stirring solution of Intermediate 73A (3.50 g, 9.37 mmol) in MeOH (20 mL) was added 2M $LiBH_4$ in THF (4.69 mL, 9.37 mmol) and the resulting reaction mixture was stirred at ambient temperature for 2 h. The reaction mixture was concentrated to dryness under reduced pressure, diluted with water (50 mL), and extracted with 10% MeOH in DCM (3×50 mL). The combined organic layers were washed with brine (30 mL), dried over anhydrous sodium sulfate and evaporated under reduced pressure. The residue was purified by preparative HPLC [Sunfire C18 (250×4.6 mm) 5 micron; 10 mM Ammonium acetate in water, Solvent B: Acetonitrile, Gradient: 30-100% B over 16 min, Flow: 25 mL/min UV: 250 nm] to obtain diastereomer-I and II. The diastereomer-I was separated into two individual enantiomers by supercritical fluid chromatography (SFC) [Chiralpak AD-H (250×4.6 mm), 5 micron; 0.2% $NH_4OH$ in MeOH, Flow: 1.2 mL/min. Temperature: 30° C., UV: 240 nm]. First eluted compound (retention time 4.17 min), designated as Intermediate 73B-I, was obtained (0.75 g, 21.31%) as an off-white solid. $^1H$ NMR (400 MHz, DMSO-$d_6$) δ ppm 0.82-0.98 (m, 6H), 1.41 (s, 9H), 2.28 (s, 3H), 2.61-2.85 (m, 2H), 3.01-3.14 (m, 1H), 3.54-3.69 (m, 1H), 3.79-3.99 (m, 1H), 4.53-4.67 (m, 1H), 5.40 (s, 2H), 7.59 (s, 1H), 7.66 (s, 1H), (1 Exchangeable proton not observed). LCMS (Method-D): retention time 2.69 min, [M−55] 320.2. Chiral purity (Method-XXXII): retention time 4.3 min, 100% ee. Second eluted compound (retention time 7.81 min), designated as Intermediate 73B-II, was obtained (0.80 g, 22.73%) as an off-white solid. $^1H$ NMR (400 MHz, DMSO-$d_6$) δ ppm 0.82-0.98 (m, 6H), 1.41 (s, 9H), 2.28 (s, 3H), 2.61-2.85 (m, 2H), 3.01-3.14 (m, 1H), 3.54-3.69 (m, 1H), 3.79-3.99 (m, 1H), 4.53-4.67 (m, 1H), 5.40 (s, 2H), 7.59 (s, 1H), 7.66 (s, 1H), (1 Exchangeable proton not observed). LCMS (Method-D): retention time 2.47 min, [M−55] 320.2. Chiral purity (Method-XXXI): retention time 8.43 min, 99.50% ee.

Intermediate 73-I

Intermediate 73-I was prepared (0.60 g, 96.00%) as an off-white solid, by using a similar synthetic protocol as that of Intermediate 52-I and starting from Intermediate 73B-I (0.75 g, 1.20 mmol) and 4N HCl in dioxane (6 mL, 24.00 mmol). $^1H$ NMR (400 MHz, DMSO-$d_6$) δ ppm 1.00 (s, 3H), 1.12 (s, 3H), 2.31 (s, 4H), 2.92-3.02 (m, 1H), 3.07-3.17 (m, 3H), 3.42-3.49 (m, 1H), 3.70-3.80 (m, 1H), 4.81-4.91 (m, 1H), 5.36-5.45 (m, 2H), 7.61-7.67 (m, 1H), 7.72-7.77 (m, 1H). LCMS (Method-D): retention time 0.53 min, [M+H]

Intermediate 74: 2-(4-formyl-2H-1,2,3-triazol-2-yl)-4,6-dimethylpyrimidine-5-carbonitrile

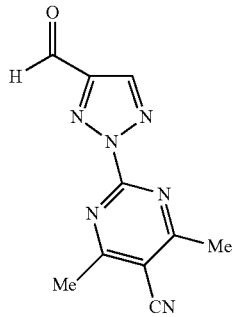

Intermediate 74A: 2-(4-(hydroxymethyl)-2H-1,2,3-triazol-2-yl)-4,6-dimethylpyrimidine-5-carbonitrile

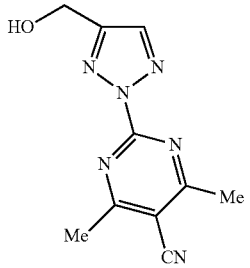

Intermediate 74A was prepared (0.80 g, 9.84%), by using a similar synthetic protocol as that of Intermediate 42 and starting from Intermediate 28A (3.50 g, 35.30 mmol) and Intermediate 42C (7.49 g, 35.30 mmol). $^1H$ NMR (400 MHz, DMSO-$d_6$) δ ppm 2.68-2.76 (m, 6H), 4.69 (s, 2H), 8.21 (s, 1H), (1 Exchangeable proton not observed).

Intermediate 74

Intermediate 74 was prepared (0.81 g, 86.00%), by using a similar synthetic protocol as that of Intermediate 9 and starting from Intermediate 74A (0.95 g, 4.13 mmol). $^1H$ NMR (400 MHz, DMSO-$d_6$) δ ppm 2.79 (s, 6H), 8.79 (s, 1H), 10.24 (s, 1H). LCMS (Method-D): retention time 0.706 min, [M+H] 229.0.

Intermediate 75: 5-(((3S,5R)-3-methyl-5-(4-methyl-1-oxo-1,3-dihydroisobenzofuran-5-yl)piperazin-1-yl)methyl)oxazol-2(3H)-one

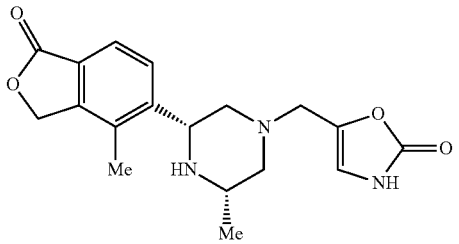

Intermediate 75A: ethyl 2-oxo-3-trityl-2,3-dihydrooxazole-5-carboxylate

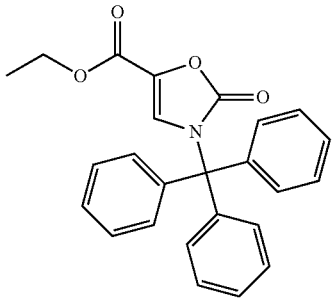

To a stirred solution of ethyl 2-oxo-2,3-dihydrooxazole-5-carboxylate (1.50 g, 9.55 mmol, commercial) in DCM (20 mL) was added TEA (3.99 mL, 28.6 mmol) followed by trityl chloride (2.66 g, 9.55 mmol) and the resulting mixture was stirred at ambient temperature for 14 h. The reaction mixture was diluted with water (30 mL) and extracted with DCM (3×50 mL). The combined organic layers were washed with brine (30 mL), dried over anhydrous sodium sulfate and evaporated under reduced pressure. The residue was purified by column chromatography (Redisep—40 g, 10-20% EtOAc/n-hexane) to obtain Intermediate 75A (3.20 g, 84.00%) as a white solid. $^1$H NMR (300 MHz, DMSO-$d_6$) δ ppm 1.22 (t, J=7.10 Hz, 3H), 4.22 (q, J=7.10 Hz, 2H), 7.22-7.42 (m, 15H), 7.50 (s, 1H). LCMS: The compound did not ionize well.

Intermediate 75B: 5-(hydroxymethyl)-3-trityloxazol-2(3H)-one

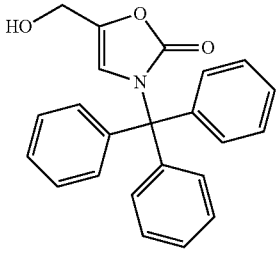

Intermediate 75B was prepared (1.70 g, 59.40%) as a white solid, by using a similar synthetic protocol as that of Intermediate 60B and starting from Intermediate 75A (3.20 g, 8.01 mmol). $^1$H NMR (300 MHz, DMSO-$d_6$) δ ppm 4.15 (d, J=4.79 Hz, 2H), 5.24 (t, J=5.04 Hz, 1H), 6.63 (s, 1H), 7.18-7.44 (m, 15H). LCMS: The compound did not ionize well.

Intermediate 75C: 2-oxo-3-trityl-2,3-dihydrooxazole-5-carbaldehyde

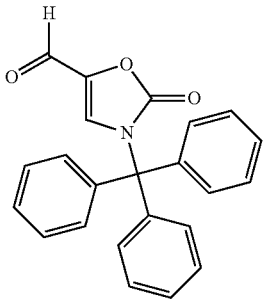

Intermediate 75C was prepared (1.00 g, 59.20%), by using a similar synthetic protocol as that of Intermediate 9 and starting from Intermediate 75B (1.7 g, 4.76 mmol). $^1$H NMR (300 MHz, DMSO-$d_6$) δ ppm 7.18-7.44 (m, 15H), 8.167 (s, 1H), 9.25 (s, 1H). LCMS: The compound did not ionize well.

Intermediate 75D: 5-(((3S,5R)-3-methyl-5-(4-methyl-1-oxo-1,3-dihydroisobenzofuran-5-yl)piperazin-1-yl)methyl)-3-trityloxazol-2(3H)-one

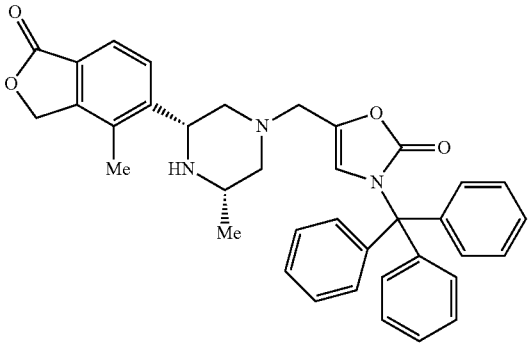

Intermediate 75D was prepared (0.52 g, 63.10%), by using a similar synthetic protocol as that of Intermediate 4 and starting from Intermediate 75C (0.50 g, 1.41 mmol) and Intermediate 51-I (0.45 g, 1.83 mmol). $^1$H NMR (300 MHz, DMSO-$d_6$) δ ppm 0.95-1.04 (m, 3H), 1.64-1.79 (m, 2H), 2.24 (s, 4H), 2.61-2.74 (m, 3H), 2.83-2.95 (m, 2H), 5.41 (s, 2H), 6.63-6.71 (m, 1H), 7.13-7.38 (m, 15H), 7.64-7.71 (m, 1H), 7.74-7.82 (m, 1H), (1 Exchangeable proton not observed). LCMS (Method-D): retention time 3.12, [M+H] 586.6.

Intermediate 75

To a solution of Intermediate 75D (0.52 g, 0.89 mmol) in DCM (10 mL) was added TFA (3 mL, 38.9 mmol) at 0° C. and the resulting reaction mixture was stirred at ambient temperature for 2 h. The reaction mixture was concentrated to dryness, diluted with diethyl ether (100 mL), The solid precipitate was filtered and dried under vacuum to obtain (0.32 g, 64.25%). $^1$H NMR (400 MHz, DMSO-$d_6$) δ ppm 1.29 (d, J=6.53 Hz, 3H), 2.37 (s, 5 H), 3.02-3.14 (m, 2H), 3.53 (d, J=4.52 Hz, 2H), 3.61-3.74 (m, 1H), 4.74-4.83 (m, 1H), 5.47 (d, J=10.54 Hz, 2H), 6.88 (d, J=2.01 Hz, 1H), 7.82 (s, 1H), 7.87 (s, 1H), 10.49-10.56 (m, 1H), (1 Exchangeable proton not observed). LCMS (Method-O): retention time 0.57 min, [M+H] 344.4.

Intermediate 76: 1-(3-methyl-5-(2-oxooxazolidin-3-yl)phenyl)-1H-pyrazole-4-carbaldehyde

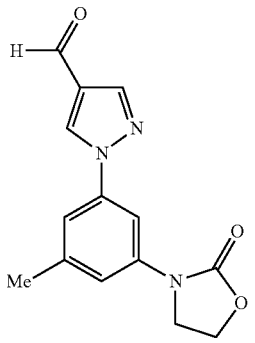

Intermediate 76A: 2-chloroethyl(3-bromo-5-methylphenyl)carbamate

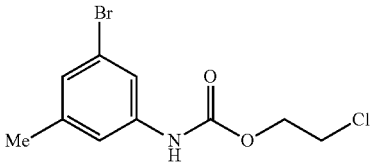

To a stirring solution of 3-bromo-5-methylaniline (5.00 g, 26.9 mmol) in THF (100 mL) was added $K_2CO_3$ (11.14 g, 81 mmol) followed by 2-chloroethyl chloroformate (4.16 mL, 40.3 mmol) and the resulting reaction mixture was refluxed for 4 h. The reaction mixture was cooled to ambient temperature, diluted with 5% $NaHCO_3$ solution (100 mL) and extracted with ethyl acetate (2×100 mL). The combined organic layers were washed with brine (50 mL), dried over anhydrous sodium sulfate and evaporated under reduced pressure to obtain Intermediate 76A (7.00 g, 89.00%) as a white solid. $^1$H NMR (300 MHz, DMSO-$d_6$) δ ppm 2.25 (s, 3H), 3.81-3.95 (m, 2H), 4.32-4.42 (m, 2H), 7.04 (s, 1H), 7.26 (s, 1H), 7.55 (s, 1H), 9.96 (s, 1H). LCMS (Method-D): retention time 2.99 min, [M+H] 291.0.

Intermediate 76B: 3-(3-bromo-5-methylphenyl)oxazolidin-2-one

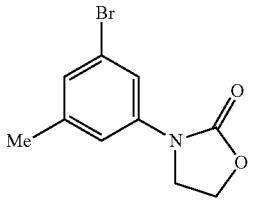

To a solution of Intermediate 76A (7.00 g, 23.93 mmol) in THF (80 mL) was added NaH (2.39 g, 59.80 mmol) and the resulting reaction mixture was stirred at ambient temperature for 4 h. The reaction mixture was diluted with water (30 mL) and extracted with ethyl acetate (3×50 mL). The combined organic layers were washed with brine (30 mL), dried over anhydrous sodium sulfate and evaporated under reduced pressure. The residue was purified by column chromatography (Redisep—40 g, 50% EtOAc/n-hexane) to obtain Intermediate 76B (4.20 g, 68.50%) as a white solid. $^1$H NMR (400 MHz, DMSO-$d_6$) δ ppm 2.32 (s, 3H), 3.98-4.08 (m, 2H), 4.41-4.49 (m, 2H), 7.16 (s, 1H), 7.29-7.36 (m, 1H), 7.69 (t, J=1.76 Hz, 1H). LCMS (Method-D): retention time 2.37 min, [M+H] 257.4.

Intermediate 76

Intermediate 76 was prepared (0.06 g, 7.00%), by using a similar synthetic protocol as that of Intermediate 6 and starting from Intermediate 76B (0.96 g, 3.75 mmol) and 1H-pyrazole-4-carbaldehyde (0.30 g, 3.12 mmol). $^1$H NMR (300 MHz, DMSO-$d_6$) δ ppm 2.25-2.43 (m, 3H), 3.99-4.19 (m, 2H), 4.31-4.53 (m, 2H), 6.47-6.62 (m, 1H), 7.06-7.14 (m, 1H), 7.19-7.24 (m, 1H), 7.41-7.58 (m, 1H), 8.28 (s, 1H), 9.24 (s, 1H). LCMS (Method-O): retention time 1.05 min, [M+H] 272.3.

Intermediate 77: 6-(1H-1,2,4-triazol-1-yl)nicotinaldehyde

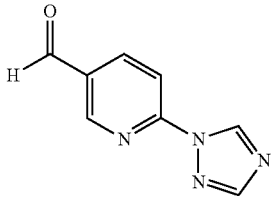

Intermediate 77 was prepared (0.3 g, 49.30%), by using a similar synthetic protocol as that of Intermediate 20 and starting from 6-bromonicotinaldehyde (0.50 g, 2.69 mmol) and 4H-1,2,4-triazole (0.204 g, 2.96 mmol). $^1$H NMR (400 MHz, DMSO-d6) δ ppm 8.07 (d, J=8.31 Hz, 1H), 8.41 (br. s., 1H), 8.51 (d, J=7.83 Hz, 1H), 9.07 (br. s., 1H), 9.52 (br. s., 1H), 10.15 (br. s., 1H). LCMS (Method-O): retention time 0.62 min, [M+H] 175.2.

Intermediate 78: 6-(4-formyl-1H-pyrazol-1-yl)-4-isopropoxynicotinonitrile

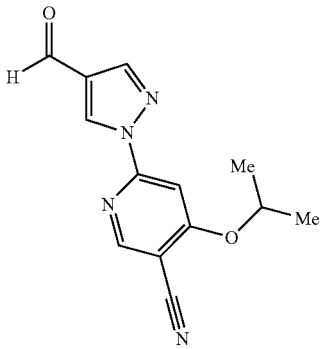

Intermediate 78 was prepared (0.45 g, 54.00%) as a pale yellow solid, by using a similar synthetic protocol as that of Intermediate 20 and starting from 6-chloro-4-isopropoxynicotinonitrile (0.61 g, 3.12 mmol) and 1H-pyrazole-4-carbaldehyde (0.30 g, 3.12 mmol). $^1$H NMR (400 MHz, DMSO-$d_6$) δ ppm 1.36 (d, J=6.05 Hz, 6H), 5.09-5.16 (m, 1H), 7.69 (s, 1H), 8.39 (s, 1H), 8.84 (s, 1H), 9.37 (d, J=0.55 Hz, 1H), 9.99 (s, 1H). LCMS (Method-J): retention time 2.36 min, [M+H] 257.2.

Intermediate 79: 1-(5-formylpyridin-2-yl)-1H-pyrazole-4-carboxamide

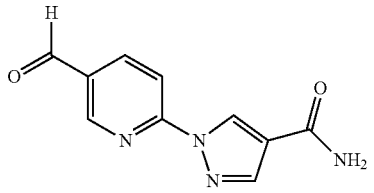

Intermediate 79A: 2-chloro-5-(1,3-dioxolan-2-yl) pyridine (Intermediate-I)

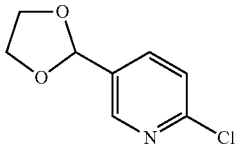

To a stirred solution of 6-chloronicotinaldehyde (5.00 g, 35.30 mmol) in toluene (100 mL) was added ethane-1,2-diol (2.63 g, 42.4 mmol), p-TsOH (0.67 g, 3.53 mmol) and the reaction mixture was refluxed under Dean-Stark conditions for 6 h. The reaction mixture was cooled to ambient temperature and washed with saturated $NaHCO_3$ (50 mL) and brine (50 mL). The separated organic layer was dried over anhydrous sodium sulfate and evaporated under reduced pressure to obtain Intermediate 79A (5.50 g, 77.00%) as a yellow liquid. $^1$H NMR (400 MHz, DMSO-$d_6$) δ ppm 3.95-4.00 (m, 4H), 5.85 (s, 1H), 7.56 (m, J=8.25, 0.43 Hz, 1H), 7.91 (dd, J=8.25, 2.45 Hz, 1H), 8.48 (dd, J=1.83, 0.49 Hz, 1H). LCMS (Method-O): retention time 0.85 min, [M+H] 188.3.

Intermediate 79B: ethyl 1-(5-(1,3-dioxolan-2-yl) pyridin-2-yl)-1H-pyrazole-4-carboxylate

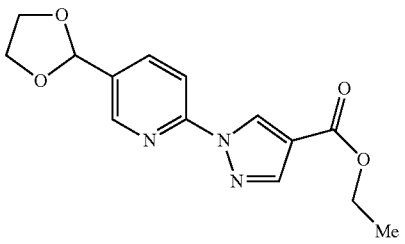

Intermediate 79B was prepared (0.80 g, 27.40%) as an off-white solid, by using a similar synthetic protocol as that of Intermediate 20 and starting from Intermediate 79A (1.50 g, 8.08 mmol) and 1H-pyrazole-4-carboxylate (1.25 g, 8.89 mmol). $^1$H NMR (400 MHz, DMSO-$d_6$) δ ppm 1.31 (t, J=7.09 Hz, 3H), 3.98-4.02 (m, 2H), 4.08-4.13 (m, 2H), 4.28 (q, J=7.09 Hz, 2H), 5.90 (s, 1H), 8.01 (dd, J=8.44, 0.60 Hz, 1H), 8.08-8.11 (m, 1H), 8.23 (d, J=0.69 Hz, 1H), 8.58 (d, J=2.13 Hz, 1H), 9.00 (d, J=0.69 Hz, 1H). LCMS (Method-J): retention time 2.39 min, [M+H] 290.1.

Intermediate 79C: 1-(5-(1,3-dioxolan-2-yl)pyridin-2-yl)-1H-pyrazole-4-carboxamide

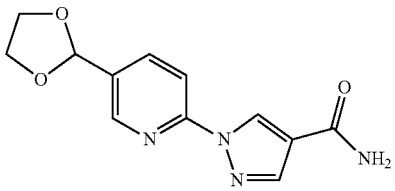

To a stirred solution of Intermediate 79B (0.35 g, 1.21 mmol) in EtOH (10 mL) was added ammonium hydroxide (10 mL, 257 mmol) and the reaction mixture was heated at 60° C. for 40 h. The reaction mixture was cooled to ambient temperature, concentrated to dryness, diluted with water (20 mL) and extracted with 10% MeOH in DCM (3×30 mL).

The combined organic layers were washed with brine (20 mL), dried over anhydrous sodium sulfate and evaporated under reduced pressure to obtain Intermediate 79C (0.20 g, 55.30%) as a yellow solid. $^1$H NMR (400 MHz, DMSO-$d_6$) δ ppm 3.98-4.03 (m, 2H), 4.09-4.13 (m, 2H), 5.90 (s, 1H), 7.24 (br. s, 1H), 7.84 (br. s, 1H), 7.98-8.01 (m, 1H), 8.09 (d, J=2.14 Hz, 1H), 8.15 (d, J=0.55 Hz, 1H), 8.57 (d, J=2.02 Hz, 1H), 9.15 (d, J=0.61 Hz, 1H). LCMS (Method-J): retention time 0.60 min, [M+H] 261.1.

Intermediate 79

To a stirred solution of Intermediate 79C (0.20 g, 0.77 mmol) in a mixture of toluene (3 mL) and water (0.5 mL) was added p-TsOH (0.22 g, 1.15 mmol) and the reaction mixture was heated at 70° C. for 1 h. The reaction mixture was concentrated to dryness, diluted with water (30 mL) and the solid precipitate obtained was isolated by suction filtration and dried under vacuum to obtain Intermediate 79 (0.120 g, 62.80%) as an off-white solid. $^1$H NMR (400 MHz, DMSO-$d_6$) δ ppm 7.30 (br. s., 1H), 7.88 (br. s., 1H), 8.13 (d, J=8.53 Hz, 1H), 8.22 (d, J=0.69 Hz, 1H), 8.46 (dd, J=8.53, 2.20 Hz, 1H), 9.05 (dd, J=2.13, 0.69 Hz, 1H), 9.24 (d, J=0.69 Hz, 1H), 10.12 (s, 1H). LCMS (Method-J): retention time 0.60 min, [M+H] 216.1.

Intermediate 80: 1-(5-formylpyridin-2-yl)-1H-pyrazole-3-carbonitrile

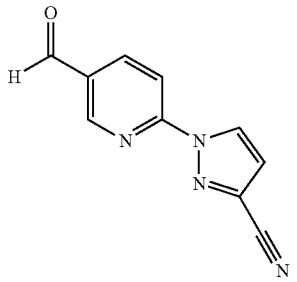

Intermediate 80 was prepared (0.45 g, 84.00%) as a yellow solid, by using a similar synthetic protocol as that of Intermediate 20 and starting from 1H-pyrazole-3-carbonitrile (0.02 g, 2.96 mmol) and 6-bromonicotinaldehyde (0.05 g, 2.69 mmol). $^1$H NMR (400 MHz, DMSO-$d_6$) δ ppm 7.53 (d, J=2.40 Hz, 1H), 8.19 (d, J=8.00 Hz, 1H), 8.49-8.52 (M, 1H), 8.99 (d, J=2.40 Hz, 1H), 9.07 (d, J=1.20 Hz, 1H), 10.15 (s, 1H). LCMS (Method-D): retention time 1.95 min, [M+H] 199.0.

Intermediate 81: 4-ethoxy-6-(4-formyl-1H-pyrazol-1-yl)nicotinonitrile

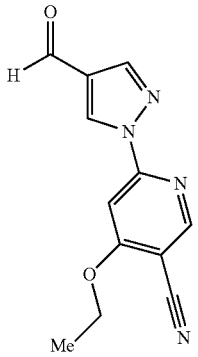

Intermediate 81A: 6-chloro-4-ethoxynicotinonitrile

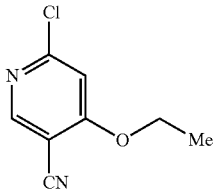

Synthesized according to literature procedures (PCT 2016091042, 2016).

Intermediate 81

Intermediate 81 was prepared (0.30 g, 41.70%), by using a similar synthetic protocol as that of Intermediate 20 and starting from Intermediate 81A (0.30 g, 1.66 mmol) and 1H-pyrazole-4-carboxylate (0.20 g, 1.66 mmol). $^1$H NMR (400 MHz, DMSO-$d_6$) δ ppm 1.40 (d, J=7.20 Hz, 3H), 4.40 (q, J=7.20 Hz, 2H), 8.38 (s, 1H), 8.69 (s, 1H), 8.84 (s, 1H), 9.36 (s, 1H), 9.98 (s, 1H). LCMS (Method-D): retention time 2.12 min, [M+H] 243.2.

Intermediate 82: 1-(3,4-dimethyl-2-oxo-2,3-dihydrobenzo[d]oxazol-5-yl)-1H-pyrazole-4-carbaldehyde

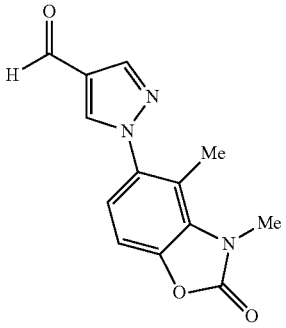

Intermediate 82A: 5-bromo-3,4-dimethylbenzo[d]oxazol-2(3H)-one

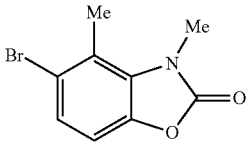

Synthesized according to literature procedures (PCT2017/001991, 2017).

Intermediate 82

To a stirred solution of 1H-pyrazole-4-carbaldehyde (0.25 g, 2.60 mmol) and Intermediate 82A (0.69 g, 2.86 mmol) in DMSO (5 mL) was added $K_2CO_3$ (0.90 g, 6.50 mmol) and was degassed with nitrogen for 5 minutes. To the resulting reaction mixture was added copper (I) iodide (0.25 g, 1.30 mmol) followed by N,N-dimethylglycine (0.13 g, 1.30 mmol) and was heated at 110° C. for 16 h. The reaction 55 mixture was cooled to ambient temperature, diluted with water (40 mL) and extracted with ethyl acetate (2×50 mL). The combined organic layers were dried over anhydrous sodium sulfate and concentrated under reduced pressure. The residue was purified by column chromatography (Redisep—24 g, 20-40% EtOAc/n-hexane) to obtain (0.35 g, 40.80%) as a brown solid, $^1$H NMR (300 MHz, DMSO-$d_6$) δ ppm 2.39 (s, 3H), 3.34 (s, 3H), 7.42 (d, J=1.89 Hz, 1H), 7.51 (d, J=1.89 Hz, 1H), 8.30 (s, 1H), 9.28 (s, 1H), 9.93 (s, 1H). LCMS: (Method-I) retention time: 0.84 min, [M+1]: 258.4.

Intermediate 83: 6-(4-methyl-1H-imidazol-1-yl) pyridazine-3-carbaldehyde

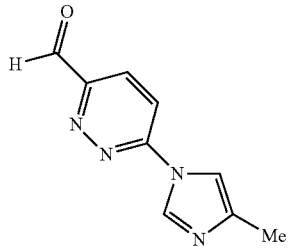

Intermediate 83A: ethyl 6-(4-methyl-1H-imidazol-1-yl)pyridazine-3-carboxylate

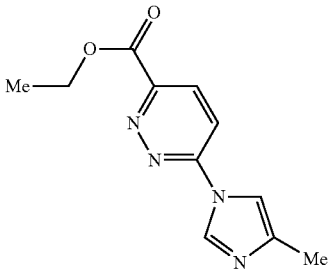

Intermediate 83A was prepared (0.18 g, 72.00%), by using a similar synthetic protocol as that of Intermediate 20 and starting from 4-methyl-1H-imidazole (0.11 g, 1.34 mmol) and ethyl 6-chloropyridazine-3-carboxylate (0.20 g, 1.07 mmol). $^1$H NMR (400 MHz, DMSO-$d_6$) δ ppm 1.38 (t, J=7.12 Hz, 3H), 2.22 (d, J=0.94 Hz, 3H), 4.41-4.47 (m, 2H), 7.86 (t, J=1.19 Hz, 1H), 8.28 (d, J=9.20 Hz, 1H), 8.30 (d, J=8.80 Hz, 1H), 8.64 (d, J=1.32 Hz, 1H). LCMS: The compound did not ionize well.

Intermediate 83B: (6-(4-methyl-1H-imidazol-1-yl) pyridazin-3-yl)methanol

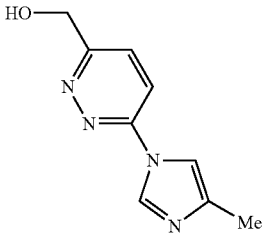

To a solution of Intermediate 83A (0.10 g, 0.43 mmol) in THF (5 mL) was added sodium borohydride (0.17 g, 0.43 mmol) at ambient temperature. MeOH (0.2 mL) was added dropwise and resulting reaction mixture was stirred at ambient temperature for 2 h. The reaction was quenched with saturated ammonium chloride solution, concentrated to dryness, diluted with water (10 mL) and extracted with DOM (2×25 mL). The combined organic layer was washed with brine (10 mL), dried over anhydrous sodium sulfate and evaporated under reduced pressure to obtain Intermediate 83B (0.05 g, 61.00%). $^1$H NMR (300 MHz, DMSO-$d_6$) δ ppm 2.20 (s, 3H), 4.77 (d, J=5.52 Hz, 2H), 5.69 (t, J=5.95 Hz, 1H), 7.76 (s, 1H), 7.89 (d, J=9.07 Hz, 1H), 8.13 (d, J=9.11 Hz, 1H), 8.51 (s, 1H). LCMS: The compound did not ionize well.

Intermediate 83

Intermediate 83 was prepared (0.04 g, 85.00%), by using a similar synthetic protocol as that of Intermediate 9 and starting from Intermediate 83B (0.04 g, 0.21 mmol). LCMS: The compound did not ionize well. The compound was taken directly to the subsequent step without further purification or characterization.

Intermediate 84: 6-(3-formylpyrrolidin-1-yl)-4-methoxynicotinonitrile

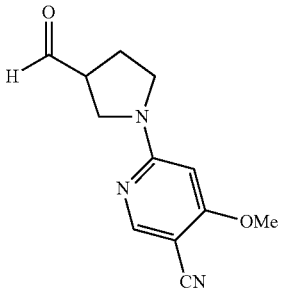

Intermediate 84A: 6-(3-(hydroxymethyl)pyrrolidin-1-yl)-4-methoxynicotinonitrile

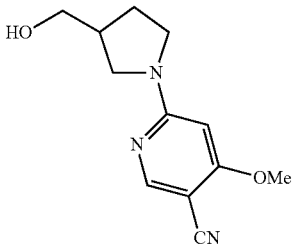

Intermediate 84A was prepared (0.30 g, 68.00%), by using a similar synthetic protocol as that of Intermediate 20 and starting from 6-bromo-4-methoxynicotinonitrile (0.40 g, 1.88 mmol) and pyrrolidin-3-ylmethanol (0.19 g, 1.88 mmol). LCMS (Method-L): retention time 1.26 min, [M+H] 234.2. $^1$H NMR (400 MHz, DMSO-$d_6$) δ ppm 1.90-1.92 (m, 1H), 2.01-2.10 (m, 1H), 2.32-2.35 (m, 1H), 2.39-2.47 (m, 2H), 2.52-2.54 (m, 3H), 3.37-3.49 (m, 1H), 3.92 (s, 3H) 4.73-4.78 (m, 1H), 6.00 (s, 1H), 8.26 (s, 1H).

Intermediate 84

Intermediate 84 was prepared (0.05 g, crude), by using a similar synthetic protocol as that of Intermediate 9 and starting from Intermediate 84A (0.05 g, 0.214 mmol) and Dess-Martin periodinane (0.09 g, 0.214 mmol). LCMS (Method-L): retention time 0.47 min, [M+H] 232.1. The compound was taken directly to the subsequent step without further purification or characterization.

Intermediate 85: 6-(3-formylpyrrolidin-1-yl)-4-methylnicotinonitrile

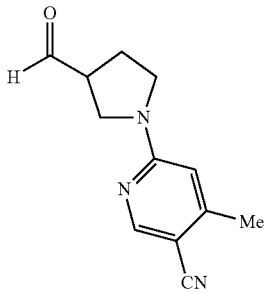

Intermediate 85A: 6-(3-(hydroxymethyl)pyrrolidin-1-yl)-4-methylnicotinonitrile

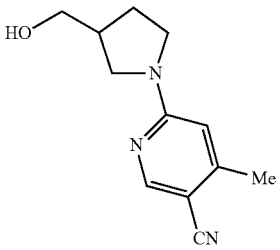

Intermediate 85A was prepared (0.30 g, 25.00%), by using a similar synthetic protocol as that of Intermediate 20 and starting from 6-bromo-4-methylnicotinonitrile (0.40 g, 2.03 mmol) and pyrrolidin-3-ylmethanol (0.20 g, 2.03 mmol). $^1$H NMR (400 MHz, DMSO-$d_6$) δ ppm 1.70-1.80 (m, 1H), 1.97-2.07 (m, 1H), 2.37-2.45 (m, 1H), 2.55-2.58 (m, 1H), 2.66-2.69 (m, 1H), 2.90 (m, 1H), 3.17-3.26 (m, 2H), 3.38 (s, 1H), 3.50-3.60 (m, 2H), 4.74 (t, J=4.98 Hz, 1H), 6.46 (s, 1H), 7.95-7.97 (m, 1H), 8.37 (s, 1H). LCMS (Method-L): retention time 1.30 min, [M+H] 218.2.

Intermediate 85

Intermediate 85 was prepared (0.50 g, 68.10%), by using a similar synthetic protocol as that of Intermediate 9 and starting from Intermediate 85A (0.05 g, 0.230 mmol) and Dess-Martin periodinane (0.10 g, 0.230 mmol). LCMS: The compound did not ionize well. The compound was taken directly to the subsequent step without further purification or characterization.

Intermediate 86: 6-(4-formyl-2-oxopyrrolidin-1-yl)-4-methylnicotinonitrile

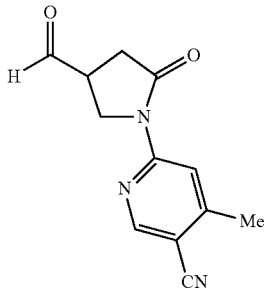

Intermediate 86A: methyl 1-(5-cyano-4-methylpyridin-2-yl)-5-oxopyrrolidine-3-carboxylate

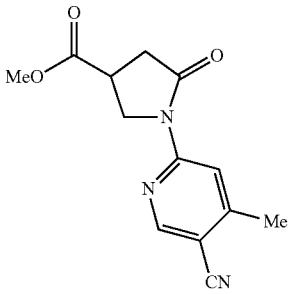

Intermediate 86A was prepared (0.50 g, 76.00%) as a pale yellow solid, by using a similar synthetic protocol as that of Intermediate 15C and starting from 6-bromo-4-methylnicotinonitrile (0.50 g, 2.54 mmol) and methyl 5-oxopyrrolidine-3-carboxylate (0.36 g, 2.54 mmol). $^1$H NMR (400 MHz, DMSO-$d_6$) δ ppm 2.45-2.55 (m, 4H), 2.82-3.00 (m, 2H), 3.43-3.52 (m, 1H), 3.65-3.72 (m, 2H), 4.22 (m, 2H), 8.34 (s, 1H), 8.78 (s, 1H). LCMS (Method-L): retention time 1.03 min, [M+1] 260.1.

Intermediate 86B: 6-(4-(hydroxymethyl)-2-oxopyrrolidin-1-yl)-4-methylnicotinonitrile

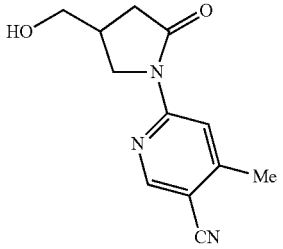

Intermediate 86B was prepared (0.10 g, 22.00%), by using a similar synthetic protocol as that of Intermediate 60B and starting from Intermediate 86A (0.50 g, 1.93 mmol) and $NaBH_4$ (0.18 g, 4.82 mmol). $^1$H NMR (400 MHz, DMSO-$d_6$) δ ppm 2.30-2.35 (m, 3H), 2.70-2.80 (m, 2H), 3.37-3.45 (m, 3H), 3.75-3.85 (m, 1H), 4.00-4.10 (m, 1H), 4.80-4.90 (m, 1H), 8.37 (s, 1H), 8.76 (s, 1H). LCMS (Method-O): retention time 0.75 min, [M+H] 232.1.

Intermediate 86

Intermediate 86 was prepared (0.08 g, 68.10%), by using a similar synthetic protocol as that of Intermediate 9 and starting from Intermediate 86B (0.08 g, 0.346 mmol) and Dess-Martin periodinane (0.15 g, 0.346 mmol). LCMS (Method-L): retention time 0.72 min, [M+H] 230.2. The compound was taken directly to the subsequent step without further purification or characterization.

Intermediate 87: 6-(4-formyl-2-oxopyrrolidin-1-yl)-4-methoxynicotinonitrile

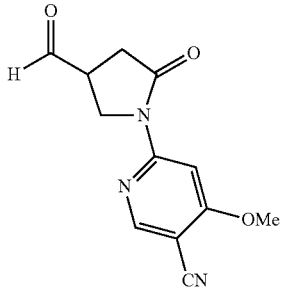

Intermediate 87A: methyl 1-(5-cyano-4-methoxypyridin-2-yl)-5-oxopyrrolidine-3-carboxylate

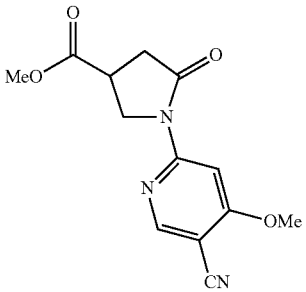

Intermediate 87A was prepared (0.50 g, 59.00%) as a pale yellow solid, by using a similar synthetic protocol as that of Intermediate 15C and starting from 6-bromo-4-methoxynicotinonitrile (0.50 g, 2.35 mmol) and methyl 5-oxopyrrolidine-3-carboxylate (0.34 g, 2.35 mmol). $^1$H NMR (400 MHz, DMSO-$d_6$) δ ppm 2.82-3.00 (m, 2H), 3.43-3.52 (m, 1H), 3.70 (m, 2H), 3.90 (s, 1H), 4.00 (s, 3H), 4.22-4.35 (m, 2H), 8.12 (s, 1H), 8.65 (s, 1H). LCMS (Method-L): retention time 1.01 min, [M+H] 276.9.

Intermediate 87B: 6-(4-(hydroxymethyl)-2-oxyprolidin-1-yl)-4-methoxynicotinonitrile

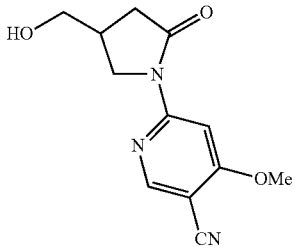

Intermediate 87B was prepared (0.20 g, 44.50%), by using a similar synthetic protocol as that of Intermediate 60B and starting from Intermediate 87A (0.50 g, 1.82 mmol) and $NaBH_4$ (0.17 g, 4.54 mmol). LCMS (Method-L): retention time 0.73 min, [M+H] 248.0. The compound was taken directly to the subsequent step without further purification or characterization.

Intermediate 87

Intermediate 87 was prepared (0.15 g, 68.10%), by using a similar synthetic protocol as that of Intermediate 9 and starting from Intermediate 87B (0.18 g, 0.73 mmol) and Dess-Martin periodinane (0.31 g, 0.73 mmol). LCMS (Method-L): retention time 0.71 min, [M+H] 246.1. The compound was taken directly to the subsequent step without further purification or characterization.

Intermediate 88: 6-(5-formyl-2-oxooxazolidin-3-yl)-4-methylnicotinonitrile

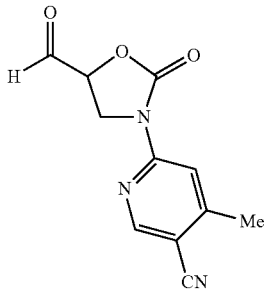

Intermediate 88A: 5-(hydroxymethyl) oxazolidin-2-one

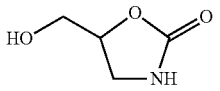

Synthesized according to literature procedures (US2014/206677 A1, 2014).

Intermediate 88B: 6-(5-(hydroxymethyl)-2-oxooxazolidin-3-yl)-4-methylnicotinonitrile

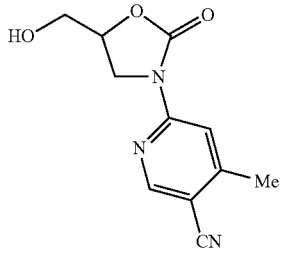

Intermediate 88B was prepared (0.35 g, 35.00%) as a pale yellow solid, by using a similar synthetic protocol as that of Intermediate 15C and starting from Intermediate 88A (0.50 g, 4.27 mmol) and 6-bromo-4-methylnicotinonitrile (0.72 g, 4.27 mmol). $^1$H NMR (400 MHz, DMSO-$d_6$) δ ppm 2.45 (s, 3H), 3.53-3.61 (m, 1H), 3.66-3.73 (m, 1H), 3.99 (dd, J=10.38, 5.93 Hz, 1H), 4.15-4.23 (m, 1H), 4.72-4.79 (m, 1H), 5.22 (t, J=5.21 Hz, 1H), 8.15 (s, 1H), 8.75 (s, 1H). LCMS (Method-L): retention time 0.82 min, [M+1] 234.2.

Intermediate 88

Intermediate 88 was prepared (0.16 g, 64.00%), by using a similar synthetic protocol as that of Intermediate 9 and starting from Intermediate 88B (0.25 g, 1.07 mmol) and Dess-martin periodinane (0.57 g, 1.34 mmol). LCMS: The compound did not ionize well. The compound was taken directly to the subsequent step without further purification or characterization.

Intermediate 89: 1-(5-(methylsulfonyl)pyridin-2-yl)-1H-pyrazole-4-carbaldehyde

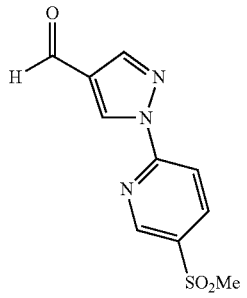

Intermediate 89 was prepared (0.40 g, 75.00%), by using a similar synthetic protocol as that of Intermediate 20 and starting from 2-bromo-5-(methylsulfonyl)pyridine (0.50 g, 2.12 mmol) and 1H-pyrazole-4-carbaldehyde (0.20 g, 2.12 mmol). $^1$H NMR (400 MHz, DMSO-$d_6$) δ ppm 3.43-3.90 (s, 3H), 8.20-8.22 (m, 2H), 8.40 (s, 1H), 8.54-8.57 (m, 1H), 9.00-9.04 (m, 1H), 10.00 (s, 1H). LCMS (Method-L): retention time 0.76 min, [M+H] 252.1.

Intermediate 90: 2-(4-formyl-1H-imidazol-1-yl)-4-methylpyrimidine-5-carbonitrile

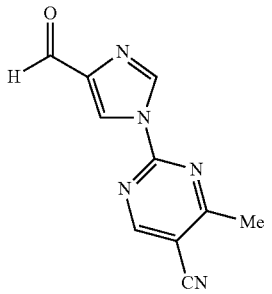

Intermediate 90 was prepared (0.05 g, 9.00%) as a pale yellow solid, by using a similar synthetic protocol as that of Intermediate 15C and starting from Intermediate 43C (0.62 g, 3.12 mmol) and 1H-imidazole-4-carbaldehyde (0.25 g, 2.60 mmol). $^1$H NMR (300 MHz, DMSO-$d_6$) δ ppm 2.70 (s, 3H), 8.80 (s, 2H), 9.30 (s, 1H), 9.80 (s, 1H). LCMS (Method-O): retention time 0.76 min, [M+H] 214.4.

Intermediate 91: 6'-(methylsulfonyl)-[2, 3'-bipyridine]-5-carbaldehyde

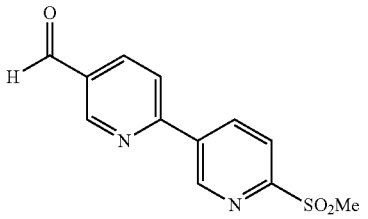

Intermediate 91A: 2-(methylsulfonyl)-5-(4,4,5,5-tetramethyl-1,3,2-dioxaborolan-2-yl)pyridine

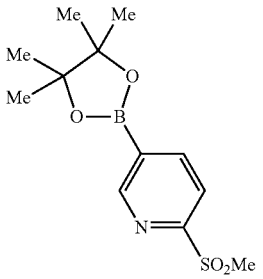

Intermediate 91A was prepared (0.05 g, crude), by using a similar synthetic protocol as that of Intermediate 2B and starting from 5-bromo-2-(methylsulfonyl)pyridine (0.05 g, 0.21 mmol) and bis(pinacolato)diboron (0.07 g, 0.26). LCMS (Method-O): retention time 0.94 min, [M+H] 284.2. The compound was taken directly to the subsequent step without further purification or characterization.

Intermediate 91

Intermediate 91 was prepared (0.30 g, 64%) as an off-white solid, by using a similar synthetic protocol as that of Intermediate 2C and starting from Intermediate 91A (0.50 g, 1.77 mmol) and 6-bromonicotinaldehyde (0.33 g, 1.77 mmol). LCMS (Method-O): retention time 0.94 min, [M+H] 263.2. The compound was taken directly to the subsequent step without further purification or characterization.

Intermediate 92: 2-(4-formyl-2H-1,2,3-triazol-2-yl)-4-methoxypyrimidine-5-carbonitrile

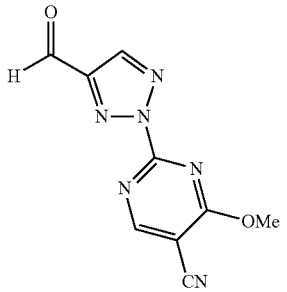

Intermediate 92A: 2-(4-(hydroxymethyl)-2H-1,2,3-triazol-2-yl)-4-methoxypyrimidine-5-carbonitrile

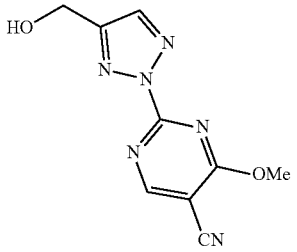

Intermediate 92A was prepared (0.90 g, 65.70%) as an off-white solid, by using a similar synthetic protocol as that of Intermediate 42 and starting from Intermediate 45A (1.00 g, 5.90 mmol) and Intermediate 28A (0.88 g, 8.85 mmol). $^1$H NMR (400 MHz, DMSO-$d_6$) δ ppm 4.18 (s, 3H), 4.69 (d, J=5.84 Hz, 2H), 5.59 (t, J=5.87 Hz, 1H), 8.25 (s, 1H), 9.18 (s, 1H). LCMS (Method-O): retention time 0.60 min, [M+H] 233.2.

Intermediate 92

Intermediate 92 was prepared (0.02 g, crude), by using a similar synthetic protocol as that of Intermediate 9 and starting from Intermediate 92A (0.03 g, 5.90 mmol) and Dess-martinperiodinane (0.06 g, 0.129 mmol). LCMS: The compound did not ionize well. The compound was taken directly to the subsequent step without further purification or characterization.

Intermediate 93: 6-(4-formyl-3-methyl-2-oxo-2,3-dihydro-1H-imidazol-1-yl)-4-methoxynicotinonitrile

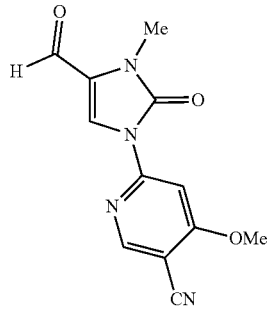

Intermediate 93A: methyl 1-(5-cyano-4-methoxy-pyridin-2-yl)-2-oxo-2,3-dihydro-1H-imidazole-4-carboxylate

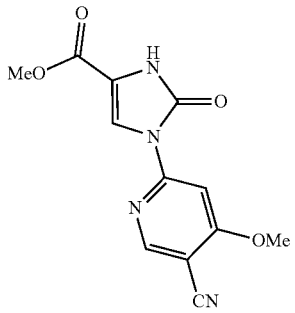

Intermediate 93A was prepared (4.20 g, 70.70%) as a brown solid, by using a similar synthetic protocol as that of Intermediate 15C and starting from 6-chloro-4-methoxynicotinonitrile (4.27 g, 25.3 mmol) and methyl 2-oxo-2,3-dihydro-1H-imidazole-4-carboxylate (3.00 g, 21.11 mmol). $^1$H NMR (400 MHz, DMSO-$d_6$) δ ppm 3.79 (s, 3H), 4.03 (s, 3H), 7.9 (s, 1H), 8.32 (s, 1H), 8.71 (s, 1H), (1 Exchangeable proton was not observed). LCMS (Method-D): retention time 1.81 min, [M+1] 275.

Intermediate 93B: methyl 1-(5-cyano-4-methoxy-pyridin-2-yl)-3-methyl-2-oxo-2,3-dihydro-1H-imidazole-4-carboxylate

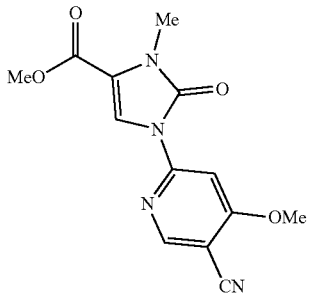

To a stirred solution of Intermediate 93A (2.00 g, 7.29 mmol) in DMF (5 mL) was added $Cs_2CO_3$ (4.75 g, 14.59 mmol) followed by iodomethane (0.91 mL, 14.6 mmol) and the reaction mixture was stirred at ambient temperature for 12 h. DMF was evaporated under reduced pressure and the mixture was diluted with water (50 mL). The solid precipitate was filtered and washed with water (50 mL), diethyl ether (50 mL) and dried under vacuum to obtain Intermediate 93B (1.70 g, 81.00%) as a brown solid. $^1$H NMR (400 MHz, DMSO-$d_6$) δ ppm 3.44 (s, 3H), 3.82 (s, 3H), 4.04 (s, 3H), 8.02 (s, 1H), 8.24 (s, 1H), 8.76 (s, 1H). LCMS (Method-D): retention time 2.34 min, [M+1] 289.2.

Intermediate 93C: 6-(4-(hydroxymethyl)-3-methyl-2-oxo-2,3-dihydro-1H-imidazol-1-yl)-4-methoxynicotinonitrile

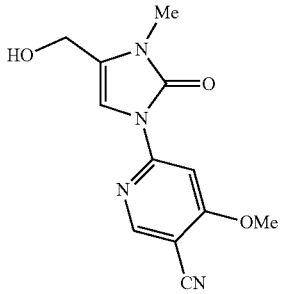

Intermediate 93C was prepared (0.85 g, 92.00%) as a pale yellow solid, by using a similar synthetic protocol as that of Intermediate 60B and starting from Intermediate 93B (1.00 g, 3.47 mmol) and $NaBH_4$ (0.26 g, 6.94 mmol). $^1$H NMR (400 MHz, DMSO-$d_6$) δ ppm 3.24 (s, 3H), 4.01 (s, 3H), 4.36 (br.s, 2H), 5.25 (br.s, 1H), 7.29 (s, 1H), 8.28 (s, 1H), 8.69 (s, 1H). LCMS (Method-D): retention time 1.24 min, [M+1] 261.

Intermediate 93

Intermediate 93 was prepared (0.100 g, 50.00%), by using a similar synthetic protocol as that of Intermediate 9 and starting from Intermediate 93C (0.20 g, 0.76 mmol) and Dess-Martin periodinane (0.39 g, 0.92 mmol). $^1$H NMR (400 MHz, DMSO-$d_6$) δ ppm 3.46 (s, 3H), 4.01 (s, 3H), 8.25 (s, 1H), 8.54 (s, 1H), 8.81 (s, 1H), 9.52 (s, 1H). LCMS (Method-D): retention time 1.91 min, [M+1] 259.

Intermediate 94: 6-(4-formyl-3-isopropyl-2-oxo-2,3-dihydro-1H-imidazol-1-yl)-4-methoxynicotinonitrile

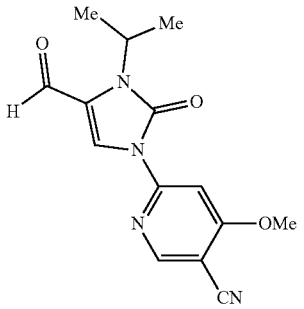

Intermediate 94A: methyl 1-(5-cyano-4-methoxypyridin-2-yl)-3-isopropyl-2-oxo-2,3-dihydro-1H-imidazole-4-carboxylate

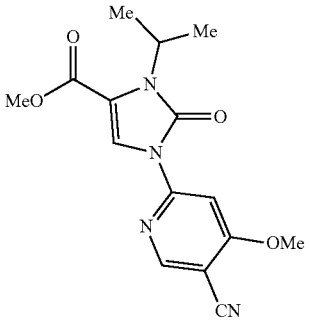

Intermediate 94A was prepared (0.48 g, 41.00%) as a yellow solid, by using a similar synthetic protocol as that of Intermediate 93B and starting from Intermediate 93A (1.00 g, 3.65 mmol) and 2-iodopropane (1.24 g, 7.29 mmol). $^1$H NMR (400 MHz, DMSO-$d_6$) δ ppm 1.45 (d, J=8.00 Hz, 6H), 3.8 (s, 3H), 4.04 (s, 3H), 5.0 (t, J=8.00 Hz, 1H), 8.04 (s, 1H), 8.23 (s, 1H), 8.76 (s, 1H). LCMS (Method-D): retention time 2.70 min, [M+1] 317.2.

Intermediate 94B: 6-(4-(hydroxymethyl)-3-isopropyl-2-oxo-2,3-dihydro-1H-imidazol-1-yl)-4-methoxynicotinonitrile

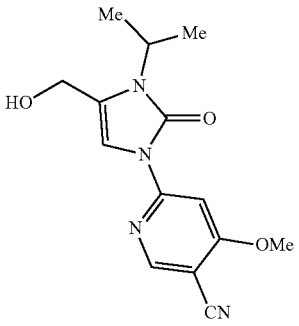

Intermediate 94B was prepared (0.35 g, 96.00%) as a yellow solid, by using a similar synthetic protocol as that of Intermediate 60B and starting from Intermediate 94A (0.40 g, 1.26 mmol) and $NaBH_4$ (0.10 g, 2.53 mmol). $^1$H NMR (400 MHz, DMSO-$d_6$) δ ppm 1.45 (d, J=8.00 Hz, 6H), 4.01 (s, 3H), 4.26-4.35 (m, 3H), 5.25 (br.s, 1H), 7.28 (s, 1H), 8.28 (s, 1H), 8.68 (s, 1H), LCMS (Method-O): retention time 0.9 min, [M+1]289.2.

Intermediate 94

Intermediate 94 was prepared (0.25 g, 49.00%), by using a similar synthetic protocol as that of Intermediate 9 and starting from Intermediate 94B (0.38 g, 1.32 mmol) and Dess-Martin periodinane (0.67 g, 1.58 mmol). $^1$H NMR (400 MHz, DMSO-$d_6$) δ ppm 1.45 (d, J=8.00 Hz, 6H), 4.01 (s, 3H), 5.0 (t, J=8.00 Hz, 1H), 8.25 (s, 1H), 8.61 (s, 1H), 8.87 (s, 1H), 9.45 (s, 1H). LCMS (Method-D): retention time 2.3 min, [M+1] 287.2.

Intermediate 95: 3-methyl-1-(2-methylpyrimidin-4-yl)-2-oxo-2,3-dihydro-1H-imidazole-4-carbaldehyde

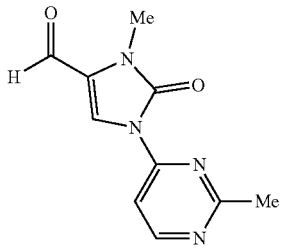

Intermediate 95A: methyl 1-(5-cyano-4-methoxy-pyridin-2-yl)-2-oxo-2,3-dihydro-1H-imidazole-4-carboxylate

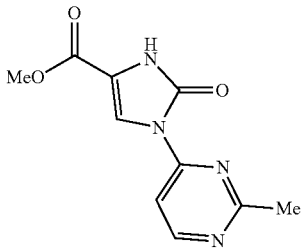

To a solution of methyl 2-oxo-2,3-dihydro-1H-imidazole-4-carboxylate (1.50 g, 10.55 mmol) in DMF (30 mL) was added 4-chloro-2-methylpyrimidine (1.63 g, 12.67 mmol) followed by $Cs_2CO_3$ (6.88 g, 21.11 mmol) and the resulting reaction mixture was heated at 100° C. for 4 h. The reaction mixture was cooled to ambient temperature, concentrated to dryness under reduced pressure and diluted with water (50 mL). The solid precipitate obtained was filtered and dried under vacuum to afford Intermediate 95A (1.20 g, 36.40%). $^1$H NMR (400 MHz, DMSO-$d_6$) δ ppm 2.67 (s, 3H), 3.82 (s, 3H), 7.85 (s, 1H), 8.3 (d, 6.0 Hz, 1H), 8.6 (d, 6.0 Hz, 1H), (1 Exchangeable proton was not observed). LCMS (Method-D): retention time 1.06 min, [M+1] 235.2.

Intermediate 95B: methyl 3-methyl-1-(2-methylpyrimidin-4-yl)-2-oxo-2,3-dihydro-1H-imidazole-4-carboxylate

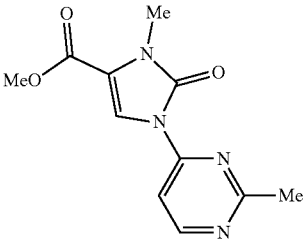

Intermediate 95B was prepared (0.50 g, 47.00%), by using a similar synthetic protocol as that of Intermediate 93B and starting from Intermediate 95A (1.00 g, 4.27 mmol) and 2-iodomethane (0.5 mL, 8.54 mmol). $^1$H NMR (400 MHz, DMSO-$d_6$) δ ppm 2.63 (s, 3H), 3.42 (s, 3H), 3.82 (s, 3H), 8.04 (s, 1H), 8.15 (d, J=6.00 Hz, 1H), 8.75 (d, J=6.00 Hz, 1H). LCMS (Method-D): retention time 1.54 min, [M+1] 249.2.

Intermediate 95C: 4-(hydroxymethyl)-3-methyl-1-(2-methylpyrimidin-4-yl)-1,3-dihydro-2H-imidazol-2-one

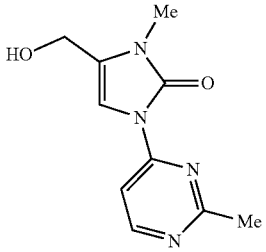

Intermediate 95C was prepared (0.20 g, 45.00%) as a pale yellow solid, by using a similar synthetic protocol as that of Intermediate 60B and starting from Intermediate 95B (0.50 g, 2.014 mmol) and $NaBH_4$ (0.15 g, 4.03 mmol). $^1$H NMR (400 MHz, DMSO-$d_6$) δ ppm 2.58 (s, 3H), 3.22 (s, 3H), 4.36 (d, 5.2 Hz, 2H), 5.24 (s, 1H), 7.3 (s, 1H), 8.15 (d, J=6.00 Hz, 1H), 8.65 (d, J=6.00 Hz, 1H). LCMS (Method-D): retention time 0.55 min, [M+1] 221.5.

Intermediate 95

Intermediate 95 was prepared (0.13 g, 64.00%), by using a similar synthetic protocol as that of Intermediate 9 and starting from Intermediate 95C (0.20 g, 0.91 mmol) and Dess-Martin periodinane (0.46 g, 1.09 mmol). $^1$H NMR (400 MHz, DMSO-$d_6$) δ ppm 2.66 (s, 3H), 3.45 (s, 3H), 8.2 (d, 6.0 Hz, 1H), 8.54 (s, 1H), 8.81 (d, 6.0 Hz, 1H), 9.54 (s, 1H). LCMS (Method-D): retention time 1.08 min, [M+1] 219.2.

Intermediate 96-I: 5-((2R,6S)-4-(6-bromopyridin-3-yl)methyl)-6-methylpiperazin-2-yl)-4-methylisobenzofuran-1(3H)-one

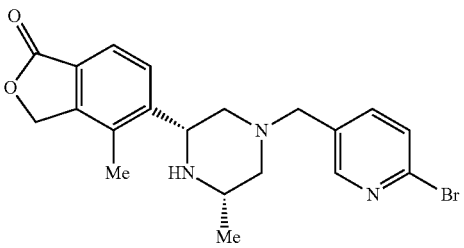

To a stirred solution of 6-bromonicotinaldehyde (0.300 g, 1.61 mmol) in THF (20 mL) was added Intermediate 51-I (0.44 g, 1.77 mmol) and the reaction mixture was continued to stir at ambient temperature for 10 minutes. Sodium triacetoxyborohydride (0.68 g, 3.23 mmol) was added and stirring was continued for 48 h. The reaction mixture was diluted with aq $NaHCO_3$ (30 mL) and extracted with ethyl acetate (2×40 mL). The combined organic layers were washed with brine (30 mL), dried over anhydrous sodium sulfate and evaporated under reduced pressure. The residue was purified by column chromatography (Redisep—40 g, 65-70% EtOAc/n-Hexane) to afford Intermediate 96-I (0.32 g, 47.00%). $^1$H NMR (400 MHz, DMSO-$d_6$) δ ppm 1.01 (d, J=6.02 Hz, 3H), 1.70-1.79 (m, 2H), 2.24 (s, 3H), 2.72 (t, J=8.78 Hz, 2H), 2.96 (td, J=6.53, 3.01 Hz, 1H), 3.52 (s, 2H), 4.15 (dd, J=10.04, 2.51 Hz, 1H), 5.38 (s, 2H), 7.59-7.67 (m, 2H), 7.68-7.72 (m, 1H), 7.80 (d, J=8.03 Hz, 1H), 8.31 (d, J=2.01 Hz, 1H), (1 exchangeable proton not observed). LCMS (Method-D): retention time 1.95 min, [M+H] 417.

Intermediate 97: 5-((2R,6S)-4-((1H-1,2,4-triazol-3-yl)methyl)-6-methylpiperazin-2-yl)-4-methylisobenzofuran-1(3H)-one

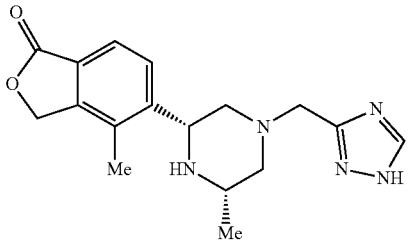

Intermediate 97A: Methyl 1-trityl-1H-1,2,4-triazole-3-carboxylate

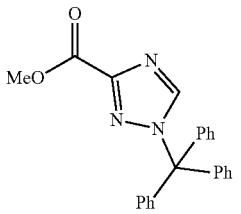

Intermediate 97A was prepared (8.00 g, 45.10%), by using a similar synthetic protocol as that of Intermediate 75Aand starting from 1H-1,2,4-triazole-3-carboxylate (5.00 g, 39.30 mmol) and trityl chloride (13.16 g, 47.20 mmol). $^1$H NMR (400 MHz, DMSO-$d_6$) δ ppm 3.83 (s, 3H), 7.05-7.09 (m, 5H), 7.40-7.42 (m, 10H), 8.38 (s, 1H), LCMS: The compound did not ionize well.

Intermediate 97B: (1-trityl-1H-1,2,4-triazol-3-yl)methanol

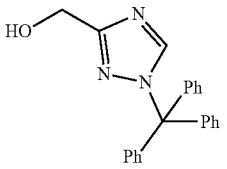

Intermediate 97B was prepared (1.00 g, 50.00%) as an off-white solid, by using a similar synthetic protocol as that of Intermediate 60B and starting from Intermediate 97A (2.00 g, 5.41 mmol) and $NaBH_4$ (0.60 g, 16.24 mmol). $^1$H NMR (400 MHz, DMSO-$d_6$) δ ppm 4.45 (d, J=6.02 Hz, 2H), 5.30 (t, J=6.02 Hz, 1H), 7.05-7.09 (m, 5H), 7.37-7.42 (m, 10H), 8.04 (s, 1H). LCMS: The compound did not ionize well.

Intermediate 97C: 1-trityl-1H-1,2,4-triazole-3-carbaldehyde

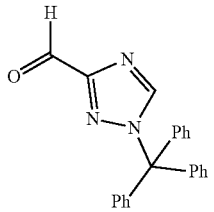

Intermediate 97C was prepared (0.75 g, 90.00%), by using a similar synthetic protocol as that of Intermediate 9 and starting from Intermediate 97B (0.80 g, 2.34 mmol) and Dess-Martin periodinane (2.00 g, 4.70 mmol). $^1$H NMR (400 MHz, DMSO-$d_6$) δ ppm 7.05-7.09 (m, 5H), 7.40-7.42 (m, 10H), 8.38 (s, 1H), 9.45 (s, 1H). LCMS: The compound did not ionize well.

Intermediate 97D: 4-methyl-5-((2R,6S)-6-methyl-4-((1-trityl-1H-1,2,4-triazol-3-yl)methyl)piperazin-2-yl)isobenzofuran-1(3H)-one

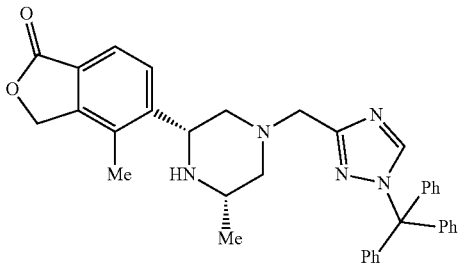

Intermediate 97D was prepared (0.90 g, 71.00%) as a pale yellow solid, by using a similar synthetic protocol as that of Intermediate 96-I and starting from Intermediate 97C (0.75 g, 2.21 mmol) and Intermediate 51-I (0.60 g, 2.43 mmol). $^1$H NMR (300 MHz, DMSO-$d_6$) δ ppm 0.98 (d, J=6.28 Hz, 3H), 1.69-1.86 (m, 2H), 2.23 (s, 3H), 2.68-2.78 (m, 2H), 2.90 (br. s., 1H), 3.60 (s, 2H), 4.10 (d, J=7.10 Hz, 1H), 5.39 (s, 2H), 7.01-7.07 (m, 6H), 7.31-7.38 (m, 9H), 7.64-7.69 (m, 1H), 7.75-7.79 (m, 1H), 8.04 (s, 1H), (1 exchangeable proton not observed). LCMS (Method-D): retention time 4.045 min, [M+H] 570.4.

Intermediate 97

Intermediate 97 was prepared (0.18 g, 28.20%), by using a similar synthetic protocol as that of Intermediate 4C and starting from Intermediate 97D (1.00 g, 1.75 mmol) and 4M HCl in dioxane (0.88 ml, 3.51 mmol). $^1$H NMR (300 MHz, DMSO-$d_6$) δ ppm 1.00 (d, J=6.28 Hz, 3H), 1.72-1.85 (m, 2H), 2.25 (s, 3H), 2.76 (d, J=10.24 Hz, 2H), 2.94 (br. s., 1H), 3.62 (s, 2H), 4.14 (d, J=9.25 Hz, 1H), 5.38 (s, 2H), 7.65 (d, J=8.09 Hz, 1H), 7.78 (d, J=8.26 Hz, 1H), 8.12 (br. s., 1H), 13.9 (br. s., 1H). (1 exchangeable proton not observed). LCMS (Method-D): retention time 0.63 min, [M+H] 328.2.

Intermediate 98: 6-(4-formyl-1H-imidazol-1-yl)-4-methoxynicotinonitrile

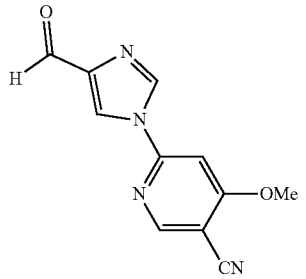

Intermediate 98 was prepared (0.30 g, 25.00%), by using a similar synthetic protocol as that of Intermediate 20 and starting from 1H-imidazole-4-carbaldehyde (0.50 g, 5.20 mmol) and 6-chloro-4-methoxynicotinonitrile (1.05 g, 6.24 mmol). $^1$H NMR (400 MHz, DMSO-$d_6$) δ ppm 4.13 (s, 3H), 7.81 (s, 1H), 8.83 (s, 2H), 8.95 (d, J=1.19 Hz, 1H), 9.87 (s, 1H). LCMS (Method-L): retention time 0.75 min, [M+H] 229.1.

Intermediate 99: 6-(4-formyl-5-methyl-2H-1,2,3-triazol-2-yl)-4-methylnicotinonitrile

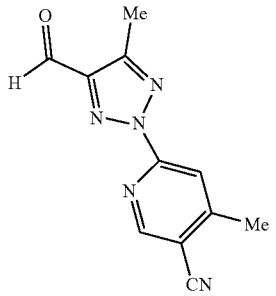

Intermediate 99A: Ethyl 5-methyl-2H-1,2,3-triazole-4-carboxylate

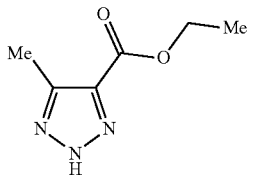

Intermediate 99A was prepared (5.20 g, 35.70%) as a brown solid, by using a similar synthetic protocol as that of Intermediate 28A and starting from ethyl but-2-ynoate (10.00 g, 89.00 mmol) and azidotrimethylsilane (17.76 mL, 134.00 mmol). $^1$H NMR (400 MHz, DMSO-$d_6$) δ ppm 1.31 (t, J=7.09 Hz, 3H), 2.51 (br. s., 3H), 4.30 (q, J=6.93 Hz, 2H), 15.36 (br. s., 1H). LCMS (Method-D): retention time 0.68 min, [M+H] 156.2.

Intermediate 99B: ethyl 1-(5-cyano-4-methylpyridin-2-yl)-5-methyl-1H-1,2,3-triazole-4-carboxylate and Intermediate 99C: ethyl 2-(5-cyano-4-methylpyridin-2-yl)-5-methyl-2H-1,2,3-triazole-4-carboxylate

99B

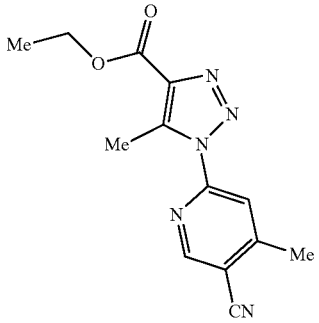

99C

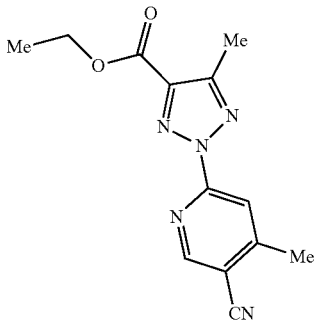

Intermediate 99B and 99C was prepared by using a similar synthetic protocol as that of Intermediate 20 and starting from Intermediate 99A (5.00 g, 32.20 mmol) and 6-bromo-4-methylnicotinonitrile (7.62 g, 38.70 mmol). The regioisomers were separated into individual isomers by HPLC [YMC trait (250×20 mm) 5 micron; Solvent A: 10 mM $NaHCO_3$; Solvent B: Acetonitrile:MeOH (1:1), Gradient: 50-100% B over 15 minutes, Flow: 20 mL/min, UV: 254]. First eluted compound (retention time 10.42 min), designated as Intermediate 99B, was obtained (0.50 g, 5.50%) as an off-white solid. $^1$H NMR (400 MHz, DMSO-$d_6$) δ ppm 1.33-1.38 (m, 3H), 2.67 (s, 3H), 2.83 (s, 3H), 4.39 (q, J=7.03 Hz, 2H), 8.20 (s, 1H), 9.07 (s, 1H). LCMS (Method-D): retention time 2.37 min, [M+H] 272.0. Second eluted compound (retention time 11.65 min), designated as Intermediate 99C, was obtained (3.10 g, 28.40%) as an off-white solid. $^1$H NMR (400 MHz, DMSO-$d_6$) δ ppm 1.33-1.38 (m, 3H), 2.56 (s, 3H), 2.64 (s, 3H), 4.39 (q, J=7.03 Hz, 2H), 8.18 (s, 1H), 8.97 (s, 1H). LCMS (Method-D): retention time 2.45 min, [M+H] 272.0.

Intermediate 99D: 6-(4-(hydroxymethyl)-5-methyl-2H-1,2,3-triazol-2-yl)-4-methylnicotinonitrile

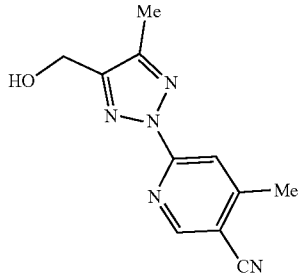

Intermediate 99D was prepared (0.25 g, 48.80%) as a brown solid, by using a similar synthetic protocol as that of Intermediate 60B and starting from Intermediate 99C (0.60 g, 2.21 mmol) and $NaBH_4$ (0.17 g, 4.43 mmol). $^1H$ NMR (400 MHz, DMSO-$d_6$) δ ppm 2.39 (s, 3H), 2.60 (s, 3H), 4.62 (d, J=5.52 Hz, 2H), 5.39 (t, J=5.77 Hz, 1H), 8.04 (s, 1H), 8.89 (s, 1H). LCMS (Method-D): retention time 1.16 min, [M+H] 230.0.

Intermediate 99

Intermediate 99 was prepared (0.25 g, 48.80%), by using a similar synthetic protocol as that of Intermediate 9 and starting from Intermediate 99D (0.20 g, 0.87 mmol) and Dess-Martin periodinane (0.74 g, 1.75 mmol). $^1H$ NMR (400 MHz, DMSO-$d_6$) δ ppm 2.58 (s, 3H), 2.66 (s, 3H), 8.24 (s, 1H), 9.01 (s, 1H), 10.23 (s, 1H). LCMS (Method-D): retention time 1.95 min, [M−H] 226.1.

Intermediate 100: 6-(4-formyl-5-methyl-1H-1,2,3-triazol-1-yl)-4-methylnicotinonitrile

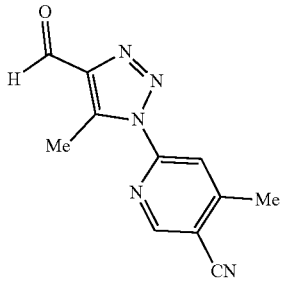

Intermediate 100A: 6-(4-(hydroxymethyl)-5-methyl-1H-1,2,3-triazol-1-yl)-4-methylnicotinonitrile

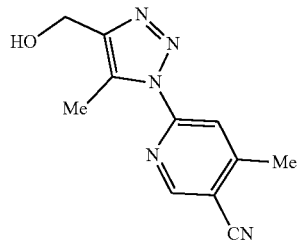

Intermediate 100A was prepared (0.28 g, 71.00%) as an off-white solid, by using a similar synthetic protocol as that of Intermediate 60B and starting from Intermediate 99B (0.40 g, 1.47 mmol) and $NaBH_4$ (0.11 g, 2.95 mmol). $^1H$ NMR (400 MHz, DMSO-$d_6$) δ ppm 2.59 (s, 3H), 2.64 (s, 3H), 4.55 (d, J=5.52 Hz, 2H), 5.19 (t, J=5.77 Hz, 1H), 8.16 (s, 1H), 9.0 (s, 1H). LCMS (Method-D): retention time 1.22 min, [M+H] 230.2.

Intermediate 100

Intermediate 100 was prepared (0.20 g, 56.00%), by using a similar synthetic protocol as that of Intermediate 9 and starting from Intermediate 100A (0.25 g, 1.09 mmol) and Dess-Martin periodinane (0.70 g, 1.64 mmol). $^1H$ NMR (400 MHz, DMSO-$d_6$) δ ppm 2.66 (s, 3H), 2.72 (s, 3H), 8.24 (s, 1H), 9.01 (s, 1H), 10.28 (s, 1H). LCMS (Method-D): retention time 1.97 min, [M+H] 228.2.

Intermediate 101: 1-(2-(5-cyano-4-methylpyridin-2-yl)-2H-1,2,3-triazol-4-yl)ethyl methanesulfonate

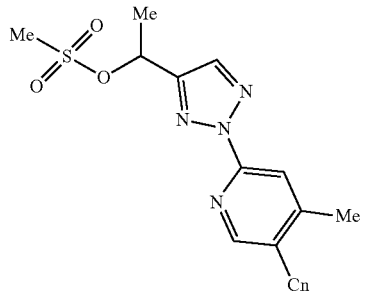

Intermediate 101A: 6-(4-(1-hydroxyethyl)-2H-1,2,3-triazol-2-yl)-4-methylnicotinonitrile

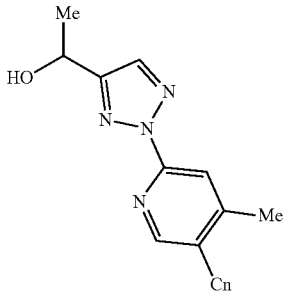

Intermediate 101A was prepared (0.74 g, 80.00%) as an yellow solid, by using a similar synthetic protocol as that of Intermediate 72A and starting from Intermediate 28 (0.80 g, 3.75 mmol). $^1H$ NMR (400 MHz, DMSO-$d_6$) δ ppm 1.48 (d, J=6.53 Hz, 3H), 2.62 (s, 3H), 4.93-5.00 (m, 1H), 5.58 (d, J=5.02 Hz, 1H), 8.10-8.11 (m, 1H), 8.17 (s, 1H), 8.93 (s, 1H). LCMS (Method-D): retention time 1.05 min, [M+H] 230.0.

Intermediate 101

Intermediate 101A was prepared (0.20 g, 56.70%) as a pale yellow solid, by using similar sunthetic protocol as that of Intermediate 59 and starting from Intermediate 101A (0.25 g, 1.09 mmol) and mesyl chloride (0.102 mL, 1.31 mmol). $^1$H NMR (400 MHz, DMSO-$d_6$) δ ppm 1.78 (d, J=6.80 Hz, 3H), 2.64 (s, 3H), 3.28 (s, 3H), 6.03 (q, J=6.80 Hz, 1H), 8.16 (s, 1H), 8.40 (s, 1H), 8.97 (s, 1H). LCMS (Method-D): retention time 1.56 min, [M+H] 308.2.

Intermediate 102:
2-methyl-6-(trimethylstannyl)pyridazin-3(2H)-one

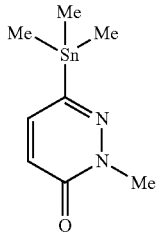

Intermediate 102A:
6-chloro-2-methylpyridazin-3(2H)-one

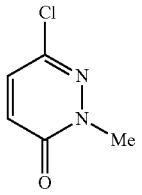

To a stirring solution of 6-chloropyridazin-3(2H)-one (0.35 g, 2.68 mmol) in DMF (10 mL) was added $K_2CO_3$ (0.93 g, 6.70 mmol) followed by methyliodide (0.20 mL, 3.22 mmol) and stirred at ambient temperature for 1 h. The resulting reaction mixture was diluted with water (30 mL) and extracted with ethyl acetate (2×50 mL). The combined organic layers were washed with brine (30 mL), dried over anhydrous sodium sulfate and evaporated under reduced pressure to obtain Intermediate 102A (0.25 g, 56.10%) as an off-white solid. $^1$H NMR (400 MHz, $CDCl_3$) δ ppm 3.75 (s, 3H), 6.92 (d, J=9.76 Hz, 1H), 7.19 (d, J=9.76 Hz, 1H). LCMS (Method-D): retention time 0.66 min, [M+1] 145.2.

Intermediate 102

Intermediate 102 was prepared (0.15 g, crude), by using a similar synthetic protocol as that of Intermediate 23A and starting from Intermediate 102A (0.10 g, 0.69 mmol) and 1,1,1,2,2,2-hexamethyldistannane (0.16 mL, 0.76 mmol). LCMS (Method-O): retention time 1.30 min, [M+1] 275.2. The compound was taken directly to the subsequent step without further purification or characterization.

Intermediate 103: 5-(5-(hydroxymethyl)piperazin-2-yl)-4-methylisobenzofuran-1(3H)-one (Diastereomer-I)

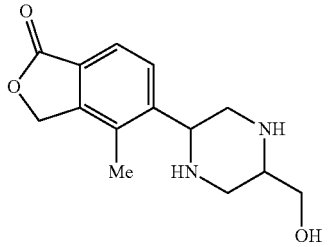

Intermediate 103A: 2-(((tert-butyldimethylsilyl)oxy)methyl)-5-chloropyrazine

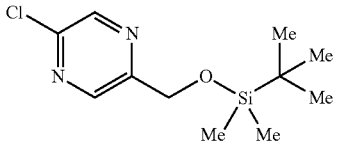

To a stirred solution of (5-chloropyrazin-2-yl)methanol (0.50 g, 3.46 mmol) in DCM (10 mL) was added imidazole (0.94 g, 13.84 mmol) followed by TBDMS-Cl (1.04 g, 6.92 mmol) and stirring continued at ambient temperature for 12 h. The resulting reaction mixture was diluted with water (40 mL) and extracted with DCM (2×40 mL). The combined organic layers were dried over anhydrous sodium sulfate and evaporated under reduced pressure. The residue was purified by column chromatography (Redisep—24 g, 5-10% EtOAc/n-hexane) to obtain Intermediate 103A (0.85 g, 89.00%). $^1$H NMR (400 MHz, DMSO-$d_6$) δ ppm 0.11 (s, 6H), 0.91 (s, 9H), 4.84 (s, 2H), 8.50 (s, 1H), 8.75 (d, J=1.00 Hz, 1H). LCMS (Method-D): retention time 3.69 min, [M+H] 259.

Intermediate 103B: 5-(5-(((tert-butyldimethylsilyl)oxy)methyl)pyrazin-2-yl)-4-methylisobenzofuran-1(3H)-one

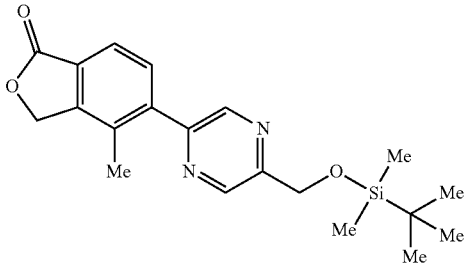

Intermediate 103B (1.80 g, 44.0%) was prepared as a brown solid, by using a similar synthetic protocol as that of Intermediate 103A (2.83 g, 10.94 mmol) and Intermediate 2B (3.00 g, 10.94 mmol). $^1$H NMR (400 MHz, DMSO-$d_6$) δ ppm 0.15 (s, 6H), 0.94 (s, 9H), 2.33 (s, 3H), 4.93 (s, 2H), 5.50 (s, 2H), 7.71 (d, J=8.00

Hz, 1H), 7.8 (d, J=8.00 Hz, 1H), 8.81 (s, 1H), 8.84 (d, J=1.51 Hz, 1H). LCMS (Method-D): retention time 3.78 min, [M+H] 371.2.

Intermediate 103C and 103D: 5-(5-(((tert-butyidimethylsilyl)oxy)methyl)piperazin-2-yl)-4-methylisobenzofuran-1(3H)-one (103C)

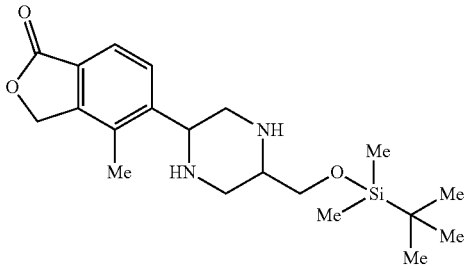

Diastereomer-I (103D)

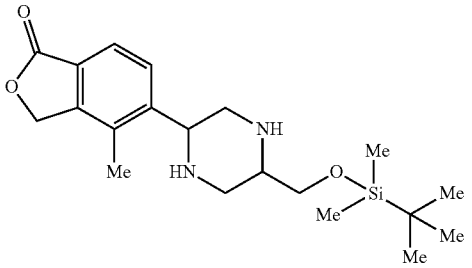

Diastereomer-II

Intermediate 103C and 103D was prepared by using a similar synthetic protocol as that of Intermediate 2-I and 2-II and starting from Intermediate 103B (2.30 g, 6.21 mmol). The two diastereomers were separated by column chromatography (Redisep—40 g, 5-10% EtOAc/n-hexane). First eluted compound designated as Intermediate 103C, was obtained (0.35 g, 30.40%) as a yellow solid. $^1$H NMR (400 MHz, DMSO-$d_6$) δ ppm 0.06 (s, 6H), 0.89 (s, 9H), 2.29 (s, 3H), 2.43 (br. s., 2H), 2.73-2.75 (m, 1H), 2.90-2.92 (m, 1H), 3.02-3.07 (m, 1H), 3.43-3.54 (m, 2H), 3.88-3.93 (m, 1H), 5.38 (s, 2H), 7.65 (d, J=8.03 Hz, 1H), 7.76 (d, J=8.03 Hz, 1H), (2 Exchangeable protons not observed). LCMS (Method-D) retention time 2.34 min, [M+H] 377.3. Second eluted compound designated as Intermediate 103D, was obtained (0.08 g, 7.00%) as a colorless syrup. $^1$H NMR (400 MHz, DMSO-$d_6$) δ ppm 0.08 (s, 6H), 0.89 (s, 9H), 2.26 (s, 1H), 2.29 (s, 3H), 2.55-2.68 (m, 1H), 2.85-2.98 (m, 2H), 3.78 (dd, J=9.54, 7.03 Hz, 1H), 3.90-3.99 (m, 3H), 5.37 (s, 2H), 7.65 (d, J=8.03 Hz, 1H), 7.84 (d, J=8.03 Hz, 1H), (2 Exchangeable protons not observed). LCMS (Method-D) retention time 2.61 min, [M+H] 377.3.

Intermediate 103

To a stirred solution of Intermediate 103C (0.15 g, 0.40 mmol) in DCM (5 mL) was added, 1.4 M HCl in dioxane (0.011 mL, 0.362 mmol) and the reaction mixture was stirred at ambient temperature for 16 h. The reaction mixture was concentrated to dryness under reduced pressure and the residue was washed with diethylether (2×10 mL). The solid obtained was redissolved into ACN (3 mL) and $K_2CO_3$ (0.30 g) was added and the resulting mixture was stirred at ambient temperature for 3 h. The solid precipitate was filtered and dried under vacuum to obtain Intermediate 103 (0.08 g, 79.00%) as a yellow solid. $^1$H NMR (400 MHz, DMSO-$d_6$) δ ppm 2.18-2.23 (m, 2H), 2.30 (s, 3H), 2.86-2.92 (m, 1H), 2.99-3.04 (m, 1H), 3.27-3.31 (m, 3H), 3.89-3.93 (m, 1H), 4.55 (s, 1H), 5.39 (s, 2H), 7.65 (d, J=8.07 Hz, 1H), 7.79 (d, J=8.56 Hz, 1H). (2 Exchangeable protons not observed). LCMS (Method-D): retention time 0.55 min, [M+H] 263.2.

Intermediate 104: 6-(4-(chloromethyl)-1H-pyrazol-1-yl)-4-methylnicotinonitrile

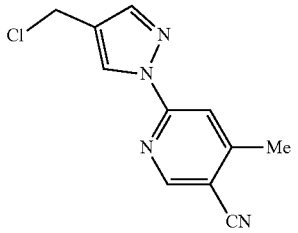

Intermediate 104A: 6-(4-(hydroxymethyl)-1H-pyrazol-1-yl)-4-methylnicotinonitrile

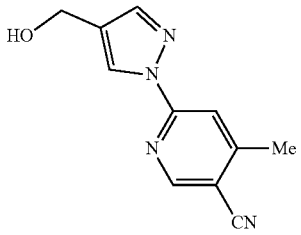

Intermediate 104A was prepared (0.30 g, 41%) as a pale yellow solid, by using a similar synthetic protocol as that of Intermediate 60B and starting from Intermediate 6 (0.50 g, 2.36 mmol) and $NaBH_4$ (0.09 g, 2.36 mmol). $^1$H NMR (400 MHz, DMSO-$d_6$) δ ppm 2.6 (s, 3H), 4.45 (d, J=5.6 Hz, 2H), 5.1 (t, J=5.60 Hz, 1H), 7.86 (s, 1H), 7.99 (s, 1H), 8.5 (s, 1H), 8.85 (s, 1H). LCMS (Method-D): retention time 1.33 min, [M+H] 215.2.

Intermediate 104

Intermediate 104 was prepared (0.02 g, 69.00%), by using a similar synthetic protocol as that of Intermediate 59 and starting from Intermediate 104A (0.20 g, 0.93 mmol) and mesyl chloride (0.087 mL, 1.120 mmol). $^1$H NMR (400 MHz, DMSO-$d_6$) δ ppm 2.6 (s, 3H), 4.8 (s, 2H), 7.86 (s, 1H), 7.99 (s, 1H), 8.5 (s, 1H), 8.85 (s, 1H). LCMS (Method-L): retention time 1.24 min, [M+2] 234.9.

Intermediate 105-I and 105-II: 5-(6-(2-hydroxypropan-2-yl)piperazin-2-yl)-4-methylisobenzofuran-1(3H)-one (105-I)

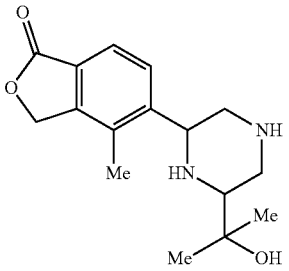

Enantiomer-I:

(105-II)

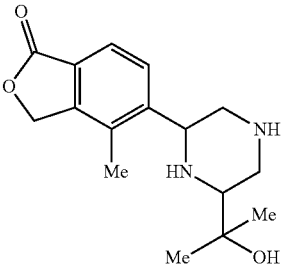

Enantiomer-II:

Intermediate 105A: 2-(6-chloropyrazin-2-yl)propan-2-ol

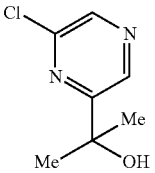

To a stirring solution of methyl 6-chloropyrazine-2-carboxylate (2.50 g, 14.49 mmol) in THF (50 mL) was added methylmagnesium bromide 3M in diethyl ether (12.07 mL, 36.2 mmol) at 0° C. The resulting mixture was stirred at ambient temperature for 30 minutes. The reaction mixture was diluted with saturated $NH_4Cl$ (100 mL) and extracted with ethyl acetate (3×100 mL). The combined organic layers were washed with brine (50 mL), dried over anhydrous sodium sulfate and concentrated under reduced pressure. The residue was purified by column chromatography (Redisep—24 g, 0.40% EtOAc/n-hexane) to obtain Intermediate 105A (0.70 g, 28.00%). $^1$H NMR (400 MHz, DMSO-$d_6$) δ ppm 1.44 (s, 6H), 5.58 (br, s 1H), 8.66 (s, 1H), 8.86 (s, 1H). LCMS: The compound did not ionize well.

Intermediate 105B: 5-(6-(2-hydroxypropan-2-yl)pyrazin-2-yl)-4-methylisobenzofuran-1(3H)-one

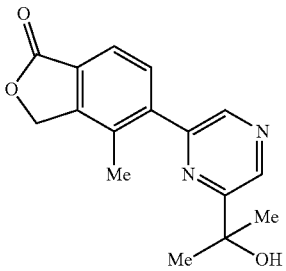

Intermediate 105B was prepared (0.65 g, 78.00%) as an off-white solid, by using a similar synthetic protocol as that 20 of Intermediate 2C and starting from Intermediate 105A (0.50 g, 2.92 mmol) and Intermediate 2B (0.80 g, 2.92 mmol). $^1$H NMR (400 MHz, DMSO-$d_6$) δ ppm 1.51 (s, 6H), 2.27-2.37 (m, 3H), 5.50 (s, 2H), 5.54 (s, 1H), 7.71-7.77 (m, 1H), 7.79-7.85 (m, 1H), 8.77 (s, 1H), 8.95 (s, 1H). LCMS (Method-I): retention time 0.82 min, [M+H] 285.1.

Intermediate 105-I and 105-II

Intermediate 105-I and 105-II was prepared by using a similar synthetic protocol as that of Intermediate 2-I and 2II and starting from Intermediate 105B (0.65 g, 2.28 mmol). The crude residue was purified by preparative HPLC [Luxcellulose $C_5$ (250×30 mm) 5 micron; Solvent: 0.1% DEA+ACN:IPA (90:10), Gradient: 100% over 17 min, Flow: 30 mL/min, UV: 254] to obtain pure recemates. The racemic mixture was separated into two individual enantiomers by supercritical fluid chromatography (SFC) [Chiralpak ADH (250×21 mm) 5 micron; 0.2% $NH_4OH$ in MeOH, Flow: 60.0 g/min. Temperature: 30° C., UV: 235 nm]. First eluted compound (retention time 5.16 min), designated as Intermediate 105-I, was obtained (0.04 g, 5.27%) as an off-white solid. $^1$H NMR (400 MHz, DMSO-$d_6$) δ ppm 1.13 (d, J=3.01 Hz, 6H), 2.23-2.34 (m, 6H), 2.55-2.72 (m, 2H), 2.84 (t, J=9.79 Hz, 2H), 4.03 (d, J=9.54 Hz, 1H), 4.34 (s, 1H), 5.39 (s, 2H), 7.68 (d, J=8.03 Hz, 1H), 7.85 (d, J=8.03 Hz, 1H). LCMS (Method-D): retention time 0.62 min, [M+H] 291.2. Chiral purity (Method-XI): retention time 3.89 min, 100% ee. Second eluted compound (retention time 6.50 min), designated as Intermediate 105-II, was obtained (0.04 g, 5.27%) as an off-white solid. $^1$H NMR (400 MHz, DMSO-$d_6$) δ ppm 1.13 (d, J=3.01 Hz, 6H), 2.20-2.36 (m, 6H), 2.57-2.70 (m, 2H), 2.84 (t, J=8.53 Hz, 2H), 4.03 (d, J=7.03 Hz, 1H), 4.34 (s, 1H), 5.39 (s, 2H), 7.68 (d, J=7.53 Hz, 1H), 7.85 (d, J=8.03 Hz, 1H). LCMS (Method-D): retention time 0.613 min, [M+H] 291.2. Chiral purity (Method-XII): retention time 4.94 min, 100% ee.

Intermediate 106: 5-(4-hydroxypyrrolidin-3-yl)-4-methylisobenzofuran-1(3H)-one hydrochloride (Diastereomer-I)

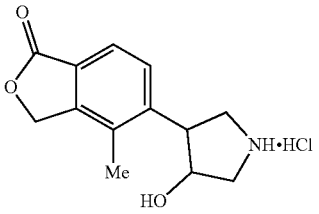

Intermediate 106A: tert-butyl 3-(4-methyl-1-oxo-1,3-dihydroisobenzofuran-5-yl)-4-oxopyrrolidine-1-carboxylate

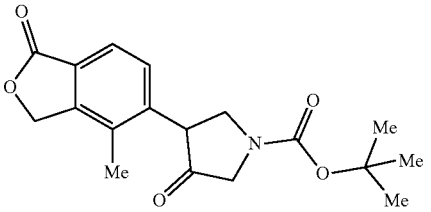

Intermediate 106A was prepared (0.80 g, 10.96%) as an off-white solid, by using a similar synthetic protocol as that of Intermediate 4A and starting from Intermediate 2A (5.00 g, 22.02 mmol) and tert-butyl 3-oxopyrrolidine-1-carboxylate (6.93 g, 37.4 mmol). $^1$H NMR (400 MHz, DMSO-$d_6$) δ ppm 1.27-1.59 (m, 9H), 2.15-2.30 (m, 3H), 3.62 (dd, J=10.79, 8.78 Hz, 1H), 3.80-3.91 (m, 1H), 3.94-4.09 (m, 1H), 4.22-4.33 (m, 1H), 4.37-4.48 (m, 1H), 5.32-5.41 (m, 2H), 7.38 (d, J=8.03 Hz, 1H), 7.58 (d, J=8.03 Hz, 1H). LCMS (Method-I): retention time 1.11 min, [M−H] 330.3.

Intermediate 106B and 106C: tert-butyl 3-hydroxy-4-(4-methyl-1-oxo-1,3-dihydroisobenzofuran-5-yl) pyrrolidine-1-carboxylate (106B)

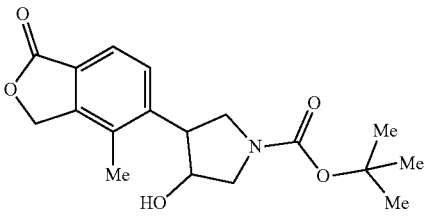

Diastereomer-I

-continued (106C)

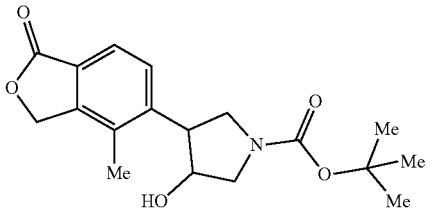

Diastereomer-II

Intermediate 106B and 106C was prepared by using a similar synthetic protocol as that of Intermediate 60B and starting from Intermediate 106A (0.80 g, 2.41 mmol) and $NaBH_4$ (0.18 g, 4.83 mmol). The two diastereomers were separated by supercritical fluid chromatography (SFC) [Chiralpak AD-H (250×21 mm) 5 micron; 0.2% $NH_4OH$ in MeOH, Flow: 70.0 g/min. Temperature: 30° C., UV: 240 nm]. First eluted compound (retention time 4.08 min), designated as Intermediate 106B, was obtained (0.29 g, 36.00%) as an off-white solid. $^1$H NMR: Showed diastereomeric mixture. LCMS (Method-D): retention time 1.96 min and 2.02 min, [(M−100)+H] 334.1. Chiral purity (Method-XII): retention time 2.44 min, 100% ee. Second eluted compound (retention time 7.31 min), designated as Intermediate 106C, was obtained (0.30 g, 37.30%) as an off-white solid. $^1$H NMR: Showed diastereomeric mixture. LCMS (Method-D): retention time 1.95 min and 2.02 min, [(M−100)+H] 334.1. Chiral purity (Method-XII): retention time 4.55 min, 100% ee.

Intermediate 106

Intermediate 106 was prepared (0.20 g, 99.00%) as an off-white solid, by using a similar synthetic protocol as that of Intermediate 52-I and starting from Intermediate 106B (0.25 g, 0.75 mmol). LCMS (Method-I): retention time 0.46 min, [M+H] 234.1. The compound was taken directly to the subsequent step without further purification or characterization.

Intermediate 107: 5-(4-fluoropyrrolidin-3-yl)-4-methylisobenzofuran-1(3H)-one hydrochloride

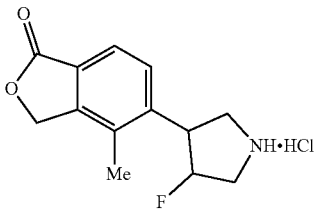

Intermediate 107A: tert-butyl 3-fluoro-4-(4-methyl-1-oxo-1,3-dihydroisobenzofuran-5-yl)pyrrolidine-1-carboxylate

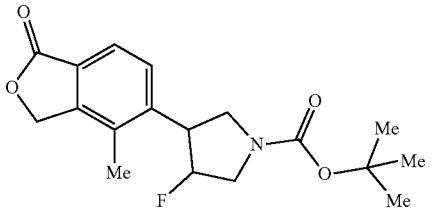

Intermediate 107 was prepared (0.22 g, crude), by using a similar synthetic protocol as that of Intermediate 4B and starting from Intermediate 106A (0.35 g, 1.05 mmol) and DAST (0.69 mL, 5.25 mmol). LCMS: The compound did not ionize well. The compound was taken directly to the subsequent step without further purification or characterization.

Intermediate 107

Intermediate 107 was prepared (0.18 g, 99.00%) as an off-white solid, by using a similar synthetic protocol as that of Intermediate 52-I and starting from Intermediate 108A (0.25 g, 0.75 mmol).

LCMS (Method-I): retention time 0.47 min and 0.57 min, [M+H] 216.5. The compound was taken directly to the subsequent step without further purification or characterization.

Intermediate 108: 6-(4-formyl-1H-pyrazol-1-yl)-4-(trifluoromethyl)nicotinonitrile

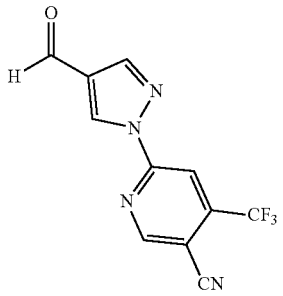

Intermediate 108A: 6-chloro-4-(trifluoromethyl)nicotinonitrile

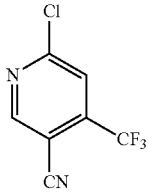

Synthesized according to literature procedures (W02006/68618 A1, 2006).

Intermediate 108

Intermediate 108 was prepared (0.40 g, 48.10%) as an off-white solid, by using a similar synthetic protocol as that of Intermediate 6 and starting from Intermediate 107A (0.77 g, 3.75 mmol) and 1H-pyrazole-4-carbaldehyde (0.30 g, 3.12 mmol). $^1$H NMR (400 MHz, DMSO-$d_6$) δ ppm 8.35 (s, 1H), 8.47 (s, 1H), 9.37 (s, 1H), 9.49 (s, 1H), 10.02 (s, 1H). LCMS: The compound did not ionize well.

Intermediate 109-I: (5R,8aR)-5-(4-methyl-1-oxo-1,3-dihydroisobenzofuran-5-yl)hexahydro-3H-oxazolo[3,4-a]pyrazin-3-one

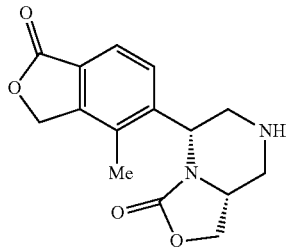

Intermediate 109A-I: tert-butyl (5R,8aR)-5-(4-methyl-1-oxo-1,3-dihydroisobenzofuran-5-yl)-3-oxotetrahydro-3H-oxazolo[3,4-a]pyrazine-7(1H)-carboxylate

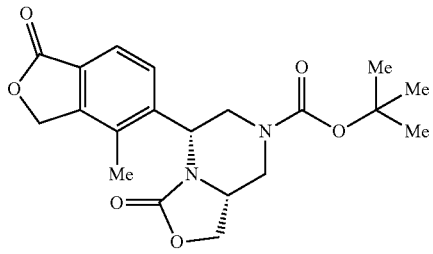

To a stirring solution of Intermediate 38D-I (0.75 g, 2.07 mmol) in THF (20 mL) was added $K_2CO_3$ (0.86 g, 6.21 mmol) followed by triphosgene (0.61 g, 2.07 mmol) and the resulting reaction mixture was heated at 70° C. for 16 h. The reaction mixture was cooled to ambient temperature, diluted with water (30 mL) and extracted with ethyl acetate (3×30 mL). The combined organic layers were washed with brine 20 mL), dried over anhydrous sodium sulfate and evaporated under reduced pressure. The residue was purified by column chromatography (Redisep—12 g, 50% EtOAc/n-hexane) to obtain Intermediate 109A-I (0.700 g, 87.00%) as a pale yellow solid. $^1$H NMR (400 MHz, DMSO-$d_6$) δ ppm 1.15-1.23 (m, 9H), 2.32 (s, 3H), 2.96 (br. s., 1H), 3.49 (dd, J=12.00, 4.00 Hz, 1H), 4.01-4.11 (m, 3H), 4.44-4.50 (m, 1H), 4.78-4.80 (m, 1H), 5.15 (d, J=5.00 Hz, 1H), 5.35-5.41 (m, 2H), 7.58 (d, J=6.50 Hz, 1H), 7.68 (d, J=6.50 Hz, 1H). LCMS (Method-I): retention time 1.34 min, [M+H] 389.2.

Intermediate 109-I

Intermediate 109-I was prepared (0.40 g, 77.00%) as an off-white solid, by using a similar synthetic protocol as that of Intermediate 4C and starting from Intermediate 109A-I (0.70 g, 1.80 mmol). $^1$H NMR (400 MHz, DMSO-$d_6$) δ ppm 2.29-2.38 (m, 3H), 3.00-3.23 (m, 2H), 3.34-3.44 (m, 1H), 3.60 (br. s., 2H), 3.90-4.07 (m, 1H), 4.25-4.37 (m, 1H), 4.43-4.54 (m, 1H), 5.10 (dd, J=11.55, 3.51 Hz, 1H), 5.35-5.52 (m, 2H), 7.61-7.67 (m, 1H), 7.67-7.76 (m, 1H). LCMS (Method-I): retention time 0.5 min, [M+H] 289.2.

Intermediate 110: 6-(5-formylisoxazole-3-yl)-4-methylnicotinonitrile

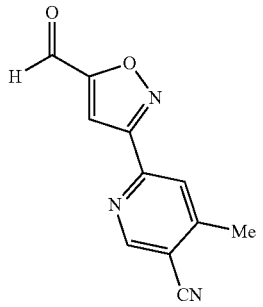

Intermediate 110A: 6-formyl-4-methylnicotinonitrile

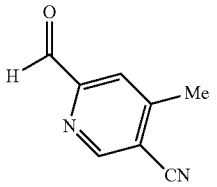

To a stirred solution of 6-bromo-4-methylnicotinonitrile (2.00 g, 10.15 mmol) in DMF (15 mL) was added solid $Na_2CO_3$ (1.08 g, 10.15 mmol) at ambient temperature, under nitrogen atmosphere. The resulting reaction mixture was degassed with nitrogen gas for minutes and added tert-butyl isocyanide (1.01 g, 12.18 mmol), 1,4-bis(diphenylphosphino)butane (0.13 g, 0.30 mmol), palladium(II) acetate (0.07 g, 0.30 mmol) and triethylsilane (1.18 g, 10.15 mmol). The reaction mixture was heated to 65° C. for 5 h and cooled to ambient temperature. The reaction mixture was filtered through Celite® and the filtrate was diluted with water (100 mL) and extracted with ethylacetate (2×100 mL). The combined organic layers were washed with brine (30 mL), dried over anhydrous sodium sulfate and evaporated under reduced pressure. To obtain Intermediate 110A (0.30 g, 20.00%). $^1$H NMR (400 MHz, DMSO-$d_6$) δ ppm 2.61 (s, 3H), 8.01 (s, 1H), 9.15 (s, 1H), 10.01 (s, 1H). LCMS (Method-D): retention time 2.45 min, [M+H] 147.0. The compound was taken directly to the subsequent step without further purification or characterization.

Intermediate 110B: (E)-6-((hydroxyimino)methyl)-4-methylnicotinonitrile

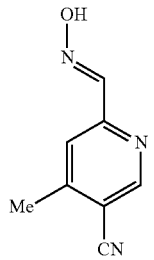

To a stirred solution of Intermediate 110A (0.50 g, 3.00 mmol) in EtOH (10 mL) was added hydroxylamine hydrochloride (0.26 g, 3.70 mmol) and sodium acetate (0.30 g, 3.70 mmol) at ambient temperature, under a nitrogen atmosphere. The resulting suspension was heated to 75° C. for 25 minutes. The reaction mixture was cooled to ambient temperature, diluted with water (60 mL) and extracted with ethyl acetate (2×100 mL). The combined organic layers were washed with brine (30 mL), dried over anhydrous sodium sulfate and evaporated under reduced pressure. The residue was slurried with DCM (5 mL) and the solid was collected by suction filtration and dried under vacuum to obtain Intermediate 110B (0.30 g, 60.00%) as a white solid. $^1$H NMR (400 MHz, DMSO-$d_6$) δ ppm 2.52 (s, 3H), 7.86 (s, 1H), 8.12 (s, 1H), 8.92 (s, 1H), 12.13 (s, 1H). LCMS (Method H): retention time 0.77 min, [M+H] 162.2.

Intermediate 110C: 6-(5-(hydroxymethyl)isoxazol-3-yl)-4-methylnicotinonitrile

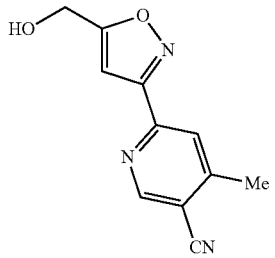

To a solution of Intermediate 110B (0.20 g, 1.24 mmol) in DMF (10 mL) was added N-chlorosuccinimide (0.17 mg, 1.24 mmol) and the resulting reaction mixture was heated at 50° C. for 1 h. The reaction mixture was cooled to ambient 55 temperature and prop-2-yn-1-ol (0.07 g, 1.24 mmol) followed by TEA (0.17 mL, 1.24 mmol) were added and stirred for 3 h. The reaction mixture was diluted with water (30 mL) and extracted with ethyl acetate (3×30 mL). The combined organic layers were washed with brine (20 mL), dried over anhydrous sodium sulfate and evaporated under reduced pressure. The residue was purified by column chromatography (Redisep—12 g, 30% EtOAc/n-hexane) to obtain Intermediate 110C (0.08 g, 30.00%) as an off-white solid. $^1$H NMR (400 MHz, DMSO-$d_6$) δ ppm 2.55-2.63 (m, 3H), 4.67 (dd, J=6.02, 1.00 Hz, 2H), 5.76 (t, J=6.02 Hz, 1H), 6.95 (s, 1H), 8.16 (s, 1H), 9.06 (s, 1H). LCMS (Method-I): retention time 0.9 min, [M+H] 216.0.

Intermediate 110

Intermediate 110 was prepared (0.75 g, 95.00%) as an off-white solid, by using a similar synthetic protocol as that of Intermediate 9 and starting from Intermediate 110C (0.08 g, 0.37 mmol) and Dess-Martin periodinane (0.24 g, 0.56 mmol). $^1$H NMR (400 MHz, DMSO-$d_6$) δ ppm 2.50-2.51 (m, 3H), 7.92 (s, 1H), 8.27 (s, 1H), 9.12 (s, 1H), 9.99 (s, 1H). LCMS: The compound did not ionize well.

Intermediate 111: 6-(4-formyl-1H-imidazol-1-yl)-2,4-dimethylnicotinonitrile

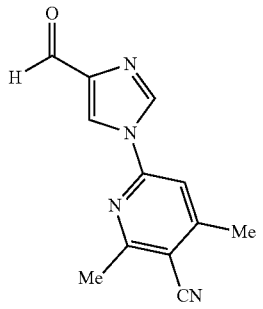

Intermediate 111 was prepared (0.08 g, 29.50%) as an off-white solid, by using a similar synthetic protocol as that of Intermediate 20 and starting from 6-chloro-2,4-dimethylnicotinonitrile (0.20 g, 1.18 mmol) and 1H-imidazole-4-carbaldehyde (0.12 g, 1.12 mmol). $^1$H NMR (400 MHz, DMSO-$d_6$) δ ppm 2.55-2.61 (m, 3H), 2.73 (s, 3H), 7.98 (s, 1H), 8.76 (d, J=0.98 Hz, 1H), 8.81 (d, J=1.22 Hz, 1H), 9.88 (s, 1H). LCMS (Method-I): retention time 0.92 min, [M+1] 227.5.

Intermediate 112: 6-(4-formyl-1H-1,2,3-triazol-1-yl)-2,4-dimethylnicotinonitrile

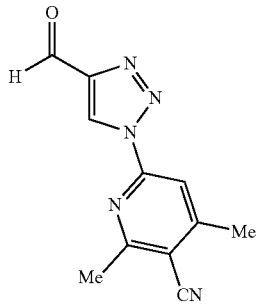

Intermediate 112A: 6-(4-(hydroxymethyl)-1H-1,2,3-triazol-1-yl)-2,4-dimethylnicotinonitrile and Intermediate 112B: 6-(4-(hydroxymethyl)-2H-1,2,3-triazol-2-yl)-2,4-dimethylnicotinonitrile

112A

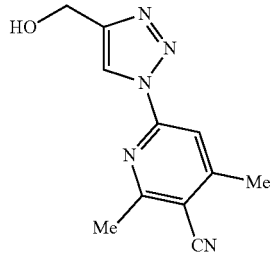

112B

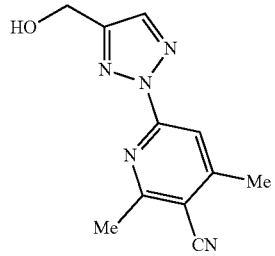

Intermediate 112A and Intermediate 112B was as prepared, by using a similar synthetic protocol as that of Intermediate 20 and starting from Intermediate 28A (1.00 g, 10.09 mmol) and 6-chloro-2,4-dimethylnicotinonitrile (1.85 g, 11.10 mmol). First eluted compound, designated as Intermediate 112A was obtained (0.30 g, 12.97%), as an off-white solid. $^1$H NMR (400 MHz, DMSO-$d_6$) δ ppm 2.63 (s, 3H), 2.74 (s, 3H), 4.64 (d, J=6.00 Hz, 2H), 5.37 (t, J=6.00 Hz, 1H), 8.12 (s, 1H), 8.69 (s, 1H). LCMS (Method-I): retention time 0.77 min, [M+1] 230.4. Second eluted compound, designated as Intermediate 112B was obtained (0.32 g, 13.83%), as an off-white solid. $^1$H NMR (400 MHz, DMSO-$d_6$) δ ppm 2.59 (s, 3H), 2.71 (s, 3H), 4.67 (d, J=6.00 Hz, 2H), 5.53 (t, J=6.00 Hz, 1H), 7.95 (s, 1H), 8.16 (s, 1H). LCMS (Method-I): retention time 0.74 min, [M+1] 230.4.

Intermediate 112

Intermediate 112 was prepared (0.30 g, 66.20%) as an off-white solid, by using a similar synthetic protocol as that of Intermediate 9 and starting from Intermediate 112A (0.32 g, 1.40 mmol). $^1$H NMR (400 MHz, DMSO-$d_6$) δ ppm 2.65 (s, 3H), 2.76 (s, 3H), 8.21 (s, 1H), 9.56 (s, 1H), 10.13 (s, 1H). LCMS (Method-I): retention time 0.98 min, [M−1] 228.4.

Intermediate 113: 6-(4-formyl-2H-1,2,3-triazol-2-yl)-2,4-dimethylnicotinonitrile

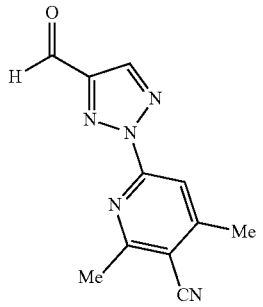

Intermediate 113 was prepared (0.40 g, 86.00%) as an off-white solid, by using a similar synthetic protocol as that of Intermediate 9 and starting from Intermediate 112B (0.32 g, 1.40 mmol). $^1$H NMR (400 MHz, DMSO-$d_6$) δ ppm 2.64 (s, 3H), 2.76 (s, 3H), 8.11 (s, 1H), 8.77 (s, 1H), 10.21 (s, 1H). LCMS (Method-I): retention time 0.93 min, [M+H] 228.4.

Intermediate 114: 6-(4-formyl-1H-1,2,3-triazol-1-yl)-2-methoxy-4-methylnicotinonitrile

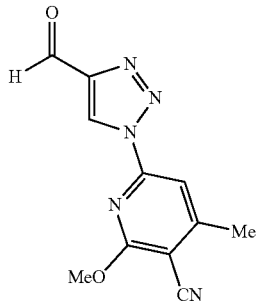

Intermediate 114A:
6-chloro-2-methoxy-4-methylnicotinonitrile and
Intermediate 114B:
2-chloro-6-methoxy-4-methylnicotinonitrile Intermediate-114A

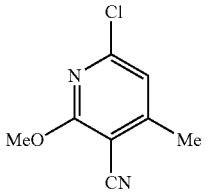

Intermediate-114B

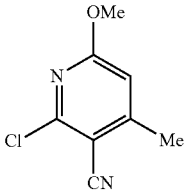

To a stirred solution of 2,6-dichloro-4-methylnicotinonitrile (15.00 g, 80.00 mmol) in MeOH (100 mL) was added sodium methoxide (14.89 mL, 80.00 mmol) and the reaction mixture was stirred at ambient temperature for 16 h. The reaction mixture was diluted with water (300 mL) and extracted with DCM (3×250 mL). The combined organic layers were washed with brine (200 mL), dried over anhydrous sodium sulfate and evaporated under reduced pressure. The residue was purified by SFC [Column: Lux cellulose-2 (50×250 mm) 5 micron; 10% of 0.2% DEA in IPA; total flow: 150 g/min; UV: 220 nm] to obtain Intermediate 114A (5.50 g, 32.30%) as an off-white solid, (retention time: 6.3 min). $^1$H NMR (400 MHz, DMSO-$d_6$) δ ppm 2.46 (s, 3H), 3.99 (s, 3H), 7.27 (s, 1H). LCMS: (Method-I) retention time: 1.22 min, [M+1] 183.3. Intermediate 114B (6.50 g, 40.40%) as an off-white solid, (retention time: 5.8 min). $^1$H NMR (400 MHz, DMSO-$d_6$) δ ppm 2.43 (s, 3H), 3.91 (s, 3H), 6.94 (s, 1H). LCMS (Method-I): retention time 1.29 min, [M+1]183.4.

Intermediate 114C: 6-(4-(hydroxymethyl)-2H-1,2,3-triazol-2-yl)-2-methoxy-4-methylnicotinonitrile and
Intermediate 114D: 6-(4-(hydroxymethyl)-1H-1,2,3-triazol-1-yl)-2-methoxy-4-methylnicotinonitrile

114C

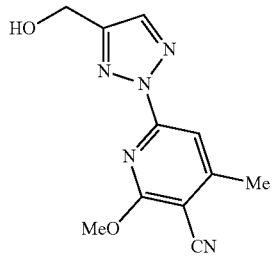

114D

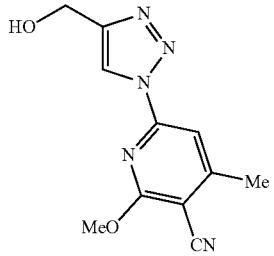

Intermediate 114C and Intermediate 114D was as prepared, by using a similar synthetic protocol as that of Intermediate 20 and starting from Intermediate 114A (2.21 g, 12.11 mmol) and Intermediate 28A (1.00 g, 10.09 mmol). First eluted compound, designated as Intermediate 114C, was obtained (0.15 g, 5.45%) as an off-white solid. $^1$H NMR (400 MHz, DMSO-$d_6$) δ ppm 2.56 (s, 3H), 4.07 (s, 3H), 4.67 (d, J=5.52 Hz, 2H), 5.51 (t, J=5.77 Hz, 1H), 7.68 (s, 1H), 8.16 (s, 1H). LCMS (Method-I): retention time 0.82 min, [M+1] 246.4. Second eluted compound, designated as Intermediate 114D, was obtained (0.25 g, 9.60%), as an off white solid. $^1$H NMR (400 MHz, DMSO-$d_6$) δ ppm 2.55-2.62 (m, 3H), 4.05-4.15 (m, 3H), 4.61-4.72 (m, 2H), 5.38 (t, J=5.77 Hz, 1H), 7.83 (s, 1H), 8.76 (s, 1H). LCMS (Method-I): retention time 0.81 min, [M+1] 246.4.

Intermediate 114

Intermediate 114 was prepared (0.08 g, 36.90%) as an off-white solid, by using a similar synthetic protocol as that of Intermediate 9 and starting from Intermediate 114D (0.23 g, 0.89 mmol). $^1$H NMR (400 MHz, DMSO-$d_6$) δ ppm 2.67 (s, 3H), 4.18 (s, 3H), 7.86 (s, 1H), 8.79 (s, 1H), 10.21 (s, 1H). LCMS (Method-I): retention time 1.03 min, [M+1] 244.4.

Intermediate 115: 6-(4-formyl-2H-1,2,3-triazol-2-yl)-2-methoxy-4-methylnicotinonitrile

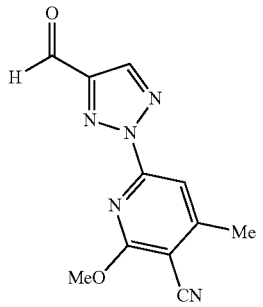

Intermediate 115 was prepared (0.38 g, 82.00%) as an off-white solid, by using a similar synthetic protocol as that of Intermediate 9 and starting from Intermediate 114C (0.40 g, 1.63 mmol). $^1$H NMR (400 MHz, DMSO-$d_6$) δ ppm 2.62 (s, 3H), 4.11 (s, 3H), 7.85 (s, 1H), 8.78 (s, 1H), 10.21 (s, 1H). LCMS (Method-I): retention time 1.06 min, [M+H] 244.0.

Intermediate 116-I and 116-II: 4-methyl-5-(piperidin-3-yl)isobenzofuran-1(3H)-one

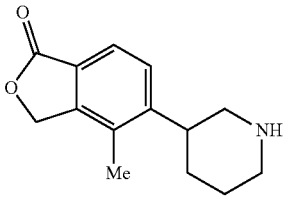

Intermediate 116A: 4-methyl-5-(pyridin-3-yl) isobenzofuran-1(3H)-one

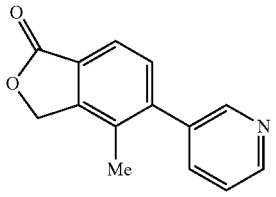

Intermediate 116A was prepared (0.42 g, 85.00%), by using a similar synthetic protocol as that of Intermediate 2C and starting from Intermediate 2A (0.50 g, 2.20 mmol) and pyridin-3-ylboronic acid (0.27 g, 2.20 mmol). $^1$H NMR (400 MHz, $CD_3OD$) δ ppm 2.29 (s, 3H), 5.45 (s, 2H), 7.52 (d, J=7.53 Hz, 1H), 7.56-7.70 (m, 1H), 7.83 (d, J=7.53 Hz, 1H), 7.93 (dt, J=7.91, 1.82 Hz, 1H), 8.46-8.76 (m, 2H). LCMS (Method-D): retention time 1.71 min, [M+H] 226.2.

Intermediate 116-I and 116-II

To a solution of Intermediate 116A (0.42 g, 1.87 mmol) in EtOH (50 mL) was added HCl (0.57 mL, 18.65 mmol) and degassed with nitrogen for 5 minutes. Platinum(IV)oxide (0.09 g, 0.37 mmol) was added and reaction mixture was stirred under $H_2$ gas atmosphere at ambient temperature for 12 h. The reaction mixture was filtered through Celite® and washed with EtOH (40 mL). The filtrate was evaporated under reduced pressure and the racemate was separated into two individual enantiomers by supercritical fluid chromatography (SFC) [Chiralpak IC (250×4.6 mm) 5.0 micron; 0.2% DEA in MeOH, Flow: 1.6 mL/min, Temperature: 25° C., UV: 220 nm]. First eluted compound (retention time 8.18 min), designated as Intermediate 116-I, was obtained (0.12 g, 27.80%) as a brown solid. $^1$H NMR (400 MHz, $CD_3OD$) δ ppm 1.61-2.02 (m, 4H), 2.26-2.47 (m, 3H), 2.69-2.85 (m, 2H), 3.02-3.26 (m, 3H), 5.37 (s, 2H), 7.29-7.60 (m, 1H), 7.70 (d, J=8.03 Hz, 1H), (1 Exchangeable proton not observed). LCMS (Method-D): retention time 0.47 min, [M+H] 232.2. Second eluted compound (retention time 10.32 min), designated as Intermediate 116-II, was obtained (0.08 g, 18.55%) as a brown solid. $^1$H NMR (400 MHz, $CD_3OD$) δ ppm 1.62-1.79 (m, 2H), 1.81-2.01 (m, 2H), 2.23-2.43 (m, 3H), 2.59-2.84 (m, 2H), 2.95-3.24 (m, 3H), 5.36 (s, 2H), 7.49 (d, J=8.03 Hz, 1H), 7.68 (d, J=8.53 Hz, 1H), (1 Exchangeable protons not observed). LCMS (Method-D): retention time 0.52 min, [M+H] 232.2.

Intermediate 117: 2-(4-formyl-1H-pyrazol-1-yl)isonicotinonitrile

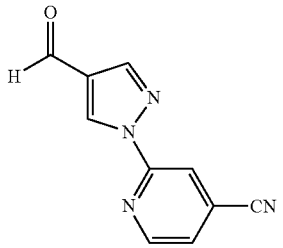

Intermediate 117 was prepared (0.03 g, 22.99%), by using a similar synthetic protocol as that of Intermediate 20 and starting from 1H-pyrazole-4-carbaldehyde (0.05 g, 0.55 mmol) and 2-bromoisonicotinonitrile (0.10 g, 0.55 mmol). $^1$H NMR (400 MHz, $CDCl_3$) δ ppm 7.51 (dd, J=4.88, 1.38 Hz, 1H), 8.09-8.38 (m, 2H), 8.64 (dd, J=5.00, 0.75 Hz, 1H), 9.08 (d, J=0.75 Hz, 1H), 10.02 (s, 1H). LCMS (Method-D): retention time 1.42 min, [M+H] 199.0.

Intermediate 118A and 118B: 5-(5-hydroxypiperidin-3-yl)-4-methylisobenzofuran-1(3H)-one (118A)

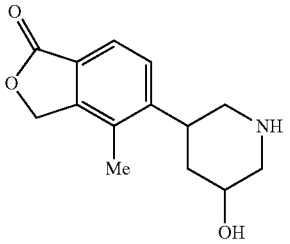

Diastereomer-I

-continued (118B)

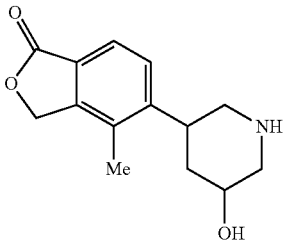

Diastereomer-II

Intermediate 118C: 5-(5-methoxypyridin-3-yl)-4-methylisobenzofuran-1(3H)-one

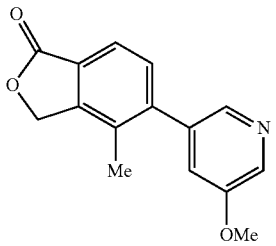

Intermediate 118C was prepared (1.30 g, 24.15%) as a pale yellow solid. by using a similar synthetic protocol as that of Intermediate 2C and starting from Intermediate 2A (3.12 g, 13.73 mmol) and (5-methoxypyridin-3-yl)boronic acid (3.00 g, 19.62 mmol). $^1$H NMR (400 MHz, DMSO-d6) δ ppm 2.23 (s, 3H), 3.89 (s, 3H), 5.47 (s, 2H), 7.38-7.47 (m, 1H), 7.53 (d, J=7.53 Hz, 1H), 7.77 (d, J=8.03 Hz, 1H), 8.20 (d, J=1.51 Hz, 1H), 8.37 (d, J=3.01 Hz, 1H). LCMS (Method-D): retention time 1.58 min, [M+H] 256.2.

Intermediate 118D: 5-(5-hydroxypyridin-3-yl)-4-methylisobenzofuran-1(3H)-one

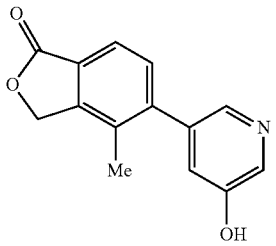

A solution of Intermediate 118C (1.70 g, 6.66 mmol) in 33% HBr in AcOH (28.2 mL, 166 mmol) was heated at 120° C. for 20 h. The reaction mixture was cooled to ambient temperature, concentrated to dryness under reduced pressure to obtain Intermediate 118D (1.20 g, 31.40%) as a brown solid. LCMS (Method-I): retention time 0.71 min, [M+H] 242.4. The compound was taken directly to the subsequent step without further purification or characterization.

Intermediate 118A and 118B

A solution of Intermediate 118A (1.20 g, 4.97 mmol) in AcOH (100 mL) was degassed with nitrogen for 5 minutes. Platinum(IV)oxide (0.01 mL, 0.50 mmol) was added and the reaction mixture was stirred under $H_2$ gas pressure (50 psi) at ambient temperature for 28 h. The reaction mixture was filtered through Celite® and washed with MeOH (40 mL). The filtrate was evaporated under reduced pressure. Two diastereomers were separated by HPLC [Xterra RP 18 (250×4.6 mm) 5 micron; Solvent A: 10 mM Ammonium bicarbonate, Solvent B: ACN+MeOH (1:1), Gradient: 0-100% B over 18 min, Flow: 1 mL/min, UV: 254 nm]. First eluted compound (retention time 10.33 min), designated as Intermediate 118A: Dia-I, was obtained (0.20 g, 16.26%) as a pale yellow solid. $^1$H NMR (400 MHz, DMSO-$d_6$) δ ppm 1.87-2.02 (m, 2H), 2.18-2.36 (m, 3H), 2.81 (d, J=12.05 Hz, 1H), 2.94-3.08 (m, 2H), 3.17 (s, 2H), 3.45-3.58 (m, 1H), 4.69 (br. s., 1H), 5.37 (s, 2H), 6.66 (br. s., 1H), 7.45 (d, J=8.03 Hz, 1H), 7.63 (d, J=8.03 Hz, 1H). LCMS (Method-D): retention time 0.49 min, [M+H] 248.1. Second eluted compound (retention time 12.13 min), designated as Intermediate 118B: Dia-II, was obtained (0.07 g, 5.69%) as a brown solid. $^1$H NMR (400 MHz, DMSO-$d_6$) δ ppm 1.75 (s, 2H), 1.92 (s, 2H), 2.28-2.38 (m, 4H), 2.81 (d, J=12.05 Hz, 1H), 3.17 (s, 1H), 3.61-4.21 (m, 2H), 5.37 (br. s., 2H), 6.65 (br. s., 1H), 7.06-7.32 (m, 1H), 7.38-7.95 (m, 1H). LCMS (Method-D): retention time 0.50 min, [M+H] 248.2.

Intermediate 119A and 119B: 5-(5-methoxypiperidin-3-yl)-4-methylisobenzofuran-1(3H)-one (119A)

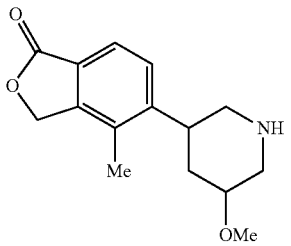

Diastereomer-I (119B)

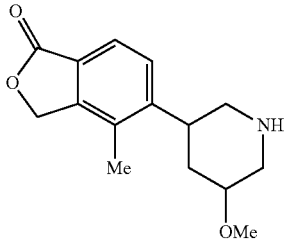

Diastereomer-II

Intermediate 119A and 119B was prepared by using a similar synthetic protocol as that of Intermediate 118A and 118B and starting from Intermediate 118C (1.27 g, 4.97 mmol). Two diastereomers were separated by HPLC [Xterra RP 18 (250×4.6 mm) 5 micron; Solvent A: 10 mM Ammonium bicarbonate, Solvent B: ACN+MeOH (1:1), Gradient: 0-100% B over 18 min, Flow: 1 mL/min, UV: 254 nm]. First eluted compound (retention time 14.48 min), designated as Intermediate 119A: Dia-I, was obtained (0.20 g, 15.39%) as a pale yellow solid. $^1$H NMR (400 MHz, DMSO-$d_6$) δ ppm 1.35-1.85 (m, 5H), 2.16-2.38 (m, 4H), 3.17 (s, 3H), 4.09 (d, J=9.54 Hz, 2H), 4.46 (br. s., 1H), 5.39 (d, J=2.93 Hz, 2H), 7.49 (d, J=7.83 Hz, 1H), 7.65 (d, J=8.31 Hz, 1H). LCMS (Method-D): retention time 0.78 min, [M+H] 262.2. Second eluted compound (retention time 17.38 min), designated as Intermediate 119B: Dia-II, was obtained (0.20 g, 15.39%) as a brown solid. $^1$H NMR (400 MHz, DMSO-$d_6$) δ ppm 1.35-1.85 (m, 5H), 2.16-2.38 (m, 4H), 3.17 (s, 3H), 4.09 (d, J=9.54 Hz, 2H), 4.46 (br. s., 1H), 5.39 (d, J=2.93 Hz, 2H), 7.49 (d, J=7.83 Hz, 1H), 7.65 (d, J=8.31 Hz, 1H). LCMS (Method-D): retention time 0.77 min, [M+H] 262.2.

Intermediate 120: 2-(3,5-dimethyl-4H-1,2,4-triazol-4-yl)pyrimidine-5-carbaldehyde

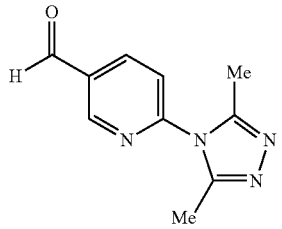

Intermediate 120 was prepared (0.10 g crude), by using a similar synthetic protocol as that of Intermediate 20 and starting from 2-bromopyrimidine-5-carbaldehyde (0.10 g, 0.54 mmol) and 3,5-dimethyl-4H-1,2,4-triazole (0.05 g, 0.54 mmol). LCMS (Method-I): retention time 0.49 min, [M+H] 204.4. The compound was taken directly to the subsequent step without further purification or characterization.

Intermediate 121: 2-(4-formyl-1H-pyrazol-1-yl)-3-methylisonicotinonitrile

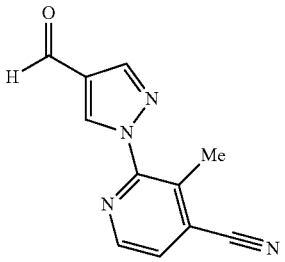

Intermediate 121A: 4-cyano-3-methylpyridine 1-oxide

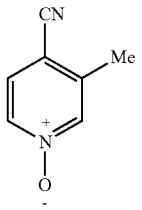

To a solution of 3-methylisonicotinonitrile (5.00 g, 42.30 mmol) in DCM (100 mL) was added 3-chloroperoxybenzoic acid (14.61 g, 85.00 mmol) at 0° C. and the resulting reaction mixture was stirred at ambient temperature for 16 h. The reaction mixture was diluted with water (50 mL), basified with 10% $NaHCO_3$ solution and extracted with ethyl acetate (2×75 mL). The combined organic layers were washed with brine (50 mL), dried over anhydrous sodium sulfate and evaporated under reduced pressure to obtain Intermediate 121A (3.50 g, 61.30%) as a pale yellow solid. $^1$H NMR (400 MHz, DMSO-$d_6$) δ ppm 2.38 (s, 3H), 7.84-7.85 (d, J=6.80 Hz, 1H), 8.21-8.23 (dd, J=1.20 Hz, 6.80 Hz, 1H), 8.41 (s, 1H). LCMS (Method-D): retention time 0.44 min, [M+H] 135.2.

Intermediate 121B: 2-(4-formyl-1H-pyrazol-1-yl)-3-methylisonicotinonitrile

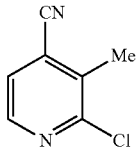

A stirring solution of Intermediate 121A (3.5 g, 26.1 mmol) in $POCl_3$ (48.6 mL, 52 mmol) was heated at 100° C. for 3 h. The reaction mixture was cooled to ambient temperature and poured into cold water (50 mL), basified with 10% $NaHCO_3$ solution and extracted with ethyl acetate (3×100 mL). The combined organic layers were washed with brine (50 mL), dried over anhydrous sodium sulfate and evaporated under reduced pressure. The residue was purified by column chromatography (Redisep—80 g, 0-20% EtOAc/n-Hexane) to obtain Intermediate 121B (0.62 g, 15.57%) as a pale yellow solid. $^1$H NMR (400 MHz, $CDC1_3$) δ ppm 2.41-2.83 (m, 3H), 7.44 (d, J=5.00 Hz, 1H), 8.39 (dd, J=5.00, 0.75 Hz, 1H). LCMS (Method-D): retention time 1.66 min, [M+H] 153.2.

Intermediate 121

Intermediate 121 was prepared (0.03 g 30.25%), by using a similar synthetic protocol as that of Intermediate 20 and starting from 1H-pyrazole-4-carbaldehyde (0.03 g, 0.33 mmol) and Intermediate 121B (0.05 g, 0.33 mmol). $^1$H NMR (400 MHz, DMSO-$d_6$) δ ppm 2.56-2.69 (m, 3H), 7.82-8.07 (m, 1H), 8.12-8.40 (m, 1H), 8.48-8.82 (m, 1H), 8.90-9.29 (m, 1H), 9.99 (s, 1H). LCMS (Method-D): retention time 1.43 min, [M+H] 213.2.

Intermediate 122-I: 5-(5-fluoropiperidin-3-yl)-4-methylisobenzofuran-1(3H)-one

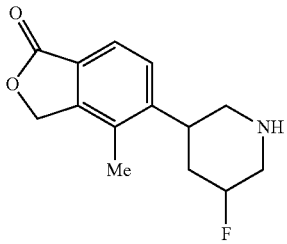

Intermediate 122A: ethyl (4-methoxybenzyl)glycinate

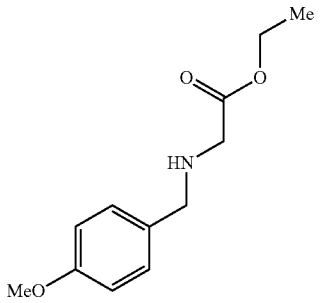

To a stirred solution of (4-methoxyphenyl)methanamine (19.05 mL, 146 mmol) in DCM (250 mL) was added TEA (20.32 mL, 146 mmol) followed by ethyl bromoacetate (16.13 mL, 146 mmol) at 0° C. and the resulting reaction mixture was stirred at ambient temperature for 16 h. The reaction mixture was diluted with water (250 mL) and extracted with DCM (3×250 mL). The combined organic layers were washed with brine (100 mL), dried over anhydrous sodium sulfate and evaporated under reduced pressure. The residue was purified by column chromatography (Redisep—220 g, 35-40% EtOAc/n-hexane)) to obtain Intermediate 122A (21.00 g, 63.90%) as a pale yellow liquid. $^1$H NMR (400 MHz, $CDCl_3$) δ ppm 1.22-1.30 (m, 3H), 3.39 (s, 2H), 3.74 (s, 2H), 3.80 (s, 3H), 4.19 (q, J=7.03 Hz, 2H), 6.68-6.96 (m, 2H), 7.13-7.30 (m, 3H). LCMS (Method-D): retention time 1.80 min, [M+H] 224.0.

Intermediate 122B: ethyl N-(4-methoxybenzyl)-N-(2-oxopropyl)glycinate

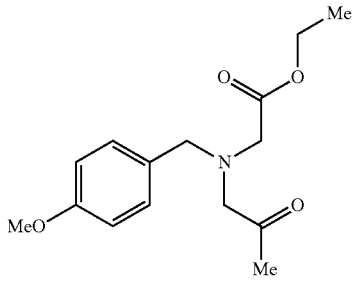

To a stirred solution of Intermediate 122A (21.00 g, 71.90 mmol) in EtOH (250 mL) was added $NaHCO_3$ (11.29 g, 134 mmol) followed by 1-chloropropan-2-one (11.04 mL, 134 mmol) at 0° C. and the reaction mixture was stirred at ambient temperature for 16 h. The reaction mixture was filtered through Celite® and washed with EtOH (50 mL) and the filtrate was evaporated under reduced pressure. The residue was purified by column chromatography (Redisep—220 g, 20% EtOAc/n-hexane) to obtain Intermediate 122B (21.00 g, 80.00%) as a pale yellow liquid. $^1$H NMR (400 MHz, $CDCl_3$) δ ppm 1.26 (t, J=7.25 Hz, 3H), 2.12 (s, 3H), 3.44 (s, 2H), 3.49 (s, 2H), 3.77 (s, 2H), 3.80 (s, 3H), 4.16 (q, J=7.09 Hz, 2H), 6.70-6.98 (m, 2H), 7.26 (s, 2H). LCMS (Method-D): retention time 2.19 min, [M+H] 280.2.

Intermediate 122C: 1-(4-methoxybenzyl)-5-oxo-1,2,5,6-tetrahydropyridin-3-yl trifluoromethanesulfonate

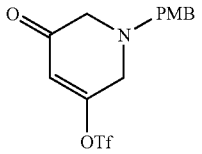

To a stirring solution of Intermediate 122B (16.30 g, 58.40 mmol) in THF (50 mL) was added 1M potassium tert-butoxide in THF (58.4 mL, 58.4 mmol) followed by 2-[n,n-bis(trifluoromethanesulfonyl)amino]-5-chloropyridine (22.91 g, 58.4 mmol) at 0° C. and the resulting reaction mixture was stirred at ambient temperature for 16 h. The reaction mixture was diluted with $NH_4Cl$ solution (50 mL) and extracted with diethyl ether (2×75 mL). The combined organic layers were washed with brine (100 mL), dried over anhydrous sodium sulfate and evaporated under reduced pressure. The residue was purified by column chromatography (Redisep—80 g, 12-15% EtOAc/n-hexane) to obtain Intermediate 122C (4.40 g, 20.64%) as a pale yellow liquid. $^1$H NMR (400 MHz, $CDCl_3$) δ ppm 3.25 (s, 2H), 3.47 (s, 2H), 3.67 (s, 2H), 3.71-4.02 (m, 3H), 6.15 (t, J=1.25 Hz, 1H), 6.74-6.96 (m, 2H), 7.12-7.24 (m, 2H). LCMS (Method-D): retention time 2.81 min, [M+H] 366.2.

Intermediate 122D: 1-(4-methoxybenzyl)-5-(4-methyl-1-oxo-1,3-dihydroisobenzofuran-5-yl)-1,6-dihydropyridin-3(2H)-one

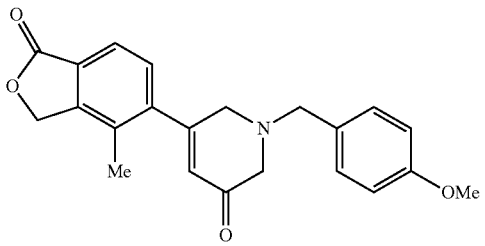

To a solution of Intermediate 122C (4.20 g, 11.50 mmol) in dioxane (100 mL) was added Intermediate 2B (3.15 g, 11.50 mmol) followed by potassium phosphate tribasic (4.88 g, 22.99 mmol) and the resulting mixture was degassed with argon for 15 minutes. $PdCl_2(dppf)_2CH_2Cl_2$ (0.47 g, 0.58 mmol) was added and the resulting reaction mixture was stirred at 40° C. for 12 h. The reaction mixture was cooled to ambient temperature, filtered through Celite® and washed with ethyl acetate (50 mL). The filtrate was evaporated under reduced pressure and the residue was purified by column chromatography (Redisep—40 g, 70% EtOAc/n-hexane) to obtain Intermediate 122D (3.20 g, 72.80%). $^1$H NMR (400 MHz, $CDCl_3$) δ ppm 2.22 (s, 3H), 3.31 (s, 2H), 3.37 (s, 2H), 3.68 (s, 2H), 3.78-3.83 (m, 3H), 5.08-5.34 (m, 2H), 6.07 (t, J=1.76 Hz, 1H), 6.84-6.89 (m, 2H), 7.22-7.24 (m, 1H), 7.25-7.29 (m, 2H), 7.76 (d, J=8.03 Hz, 1H). LCMS (Method-D): retention time 2.39 min, [M+H] 364.2.

Intermediate 122E and 122F: 5-(5-hydroxy-1-(4-methoxybenzyl)piperidin-3-yl)-4-methylisobenzofuran-1(3H)-one (122E)

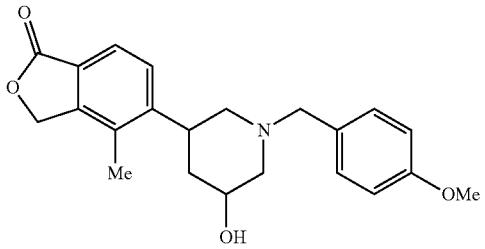

Diastereomer-I (122F)

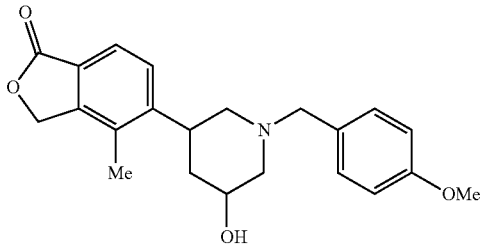

Diastereomer-II

To a solution of Intermediate 122D (2.00 g, 5.50 mmol) in MeOH (50 mL) was added nickel(II) chloride hexahydrate (2.62 g, 11.01 mmol) followed by $NaBH_4$ (0.416 g, 11.01 mmol) and the resulting reaction mixture was stirred at 50° C. for 2 h. The reaction mixture was cooled to ambient temperature, concentrated to dryness under reduced pressure, diluted with 10% $NH_4Cl$ solution (50 mL) and extracted with 10% MeOH in $CHCl_3$ (2×50 mL). The 25 combined organic layers were washed with brine (50 mL), dried over anhydrous sodium sulfate and evaporated under reduced pressure. The diastereomeric mixture was separated by column chromatography (Redisep—40 g, 10% MeOH/$CHCl_3$). First eluted compound, designated as Intermediate 122E: Dia-I, was obtained (0.70 g, 34.60%) as a pale yellow solid. $^1$H NMR (400 MHz, DMSO-$d_6$) δ ppm 1.59-1.80 (m, 4H), 2.06-2.27 (m, 4H), 3.39-3.60 (m, 4H), 3.63-3.78 (s, 3H), 3.82 (br. s., 1H), 4.60 (d, J=5.02 Hz, 1H), 5.13-5.43 (m, 2H), 6.88 (d, J=9.04 Hz, 2H), 7.13-7.36 (m, 2H), 7.62 (s, 2H). LCMS (Method-J): retention time 1.14 min, [M+H] 368.1. Second eluted compound, designated as Intermediate 122F: Dia-II, was obtained (0.90 g, 44.50%) as an off-white solid. $^1$H NMR (400 MHz, DMSO-$d_6$) δ ppm 1.39 (q, J=12.05 Hz, 1H), 1.70-1.97 (m, 3H), 2.21 (s, 3H), 2.63-2.82 (m, 1H), 2.98 (d, J=5.52 Hz, 1H), 3.04-3.21 (m, 1H), 3.38-3.56 (m, 3H), 3.60-3.81 (m, 3H), 4.82 (d, J=5.02 Hz, 1H), 5.36 (s, 2H), 6.73-6.95 (m, 2H), 7.21 (d, J=9.04 Hz, 2H), 7.45 (d, J=8.03 Hz, 1H), 7.63 (d, J=8.03 Hz, 1H). LCMS (Method-D): retention time 0.93 min, [M+H] 368.1.

Intermediate 122G-I and 122G-II: 5-(5-fluoro-1-(4-methoxybenzyl)piperidin-3-yl)-4-methylisobenzofuran-1(3H)-one (122G-I)

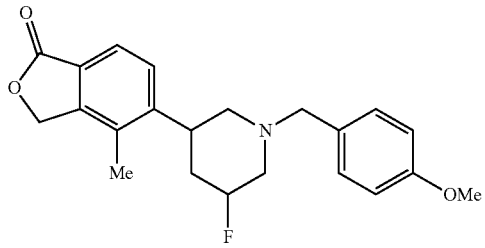

Enantiomer-I (122G-II)

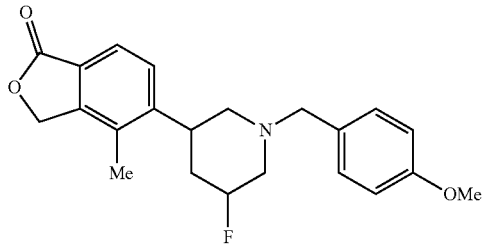

Enantiomer-I

Intermediate 122G-I and 122G-II was prepared by using a similar synthetic protocol as that of Intermediate 4B and starting from Intermediate 122E (0.03 g, 0.33 mmol) and DAST (0.43 mL, 3.27 mmol). The racemate was separated into two individual enantiomers by SFC [Chiralpak AD-H (250×4.6 mm) 5.0 micron; 0.2% $NH_4OH$ in ACN+MaOH (1:1), Flow: 70.0 g/min, Temperature: 30° C., UV 230 nm]. First eluted compound (retention time 5.0 min), designated as Intermediate 122G-I, was obtained (0.120 g, 20.00%) as a pale yellow solid. $^1$H NMR (300 MHz, $CDCl_3$) δ ppm 1.57 (s, 1H), 1.72 (t, J=12.22 Hz, 1H), 2.00 (t, J=11.06 Hz, 1H), 2.12 (td, J=9.91, 5.28 Hz, 1H), 2.24 (s, 2H), 2.26-2.32 (m, 1H), 2.36 (s, 1H), 2.82 (d, J=11.23 Hz, 1H), 3.12-3.36 (m, 1H), 3.50-3.63 (m, 2H), 3.80 (s, 3H), 4.65-4.89 (m, 1H), 5.23 (s, 2H), 6.81-6.89 (m, 2H), 7.15-7.24 (m, 2H), 7.41 (d, J=7.93 Hz, 1H), 7.73 (d, J=7.93 Hz, 1H). $^{19}$F NMR (300 MHz, $CDCl_3$) δ ppm —180.45. LCMS (Method-D): retention time 3.09 min, [M+H] 370.2. Second eluted compound (retention time 7.0 min), designated as Intermediate 122G-II, was obtained (0.110 g, 18.23%) as a pale yellow solid. $^1$H NMR (400 MHz, $CDCl_3$) δ ppm 1.55 (br. s., 1H), 1.61-1.81 (m, 1H), 2.00 (t, J=11.29 Hz, 1H), 2.06-2.17 (m, 1H), 2.24 (s, 2H), 2.27 (br. s., 1H), 2.35 (s, 1H), 2.82 (d, J=11.04 Hz, 1H), 3.18 (br. s., 1H), 3.32 (br. s., 1H, 3.46-3.65 (m, 2H), 3.80 (s, 2H), 4.58-4.92 (m, 1H), 5.15-5.28 (m, 2H), 6.73-6.94 (m, 2H), 7.11-7.24 (m, 2H), 7.41 (d, J=8.03 Hz, 1H), 7.73 (d, J=8.03 Hz, 1H). LCMS (Method-D): retention time 2.91 min, [M+H] 370.5. $^{19}$F NMR (400 MHz, $CDCl_3$) δ ppm −180.46.

Intermediate 122-I

A solution of Intermediate 122G-I (0.12 g, 0.33 mmol) in AcOH (10 mL) was purged with nitrogen for 5 minutes. To the resulting reaction mixture, 20% $Pd(OH)_2$/C (0.01 g, 0.06 mmol) was added and stirred at ambient temperature for 12 h under $H_2$ atmosphere. The reaction mixture was filtered through Celite®, washed with EtOH (10 mL) and the filtrate was concentrated under reduced pressure, diluted with aq. $NaHCO_3$ (20 mL) and extracted with ethyl acetate (2×30 mL). The combined organic layers were washed with brine (10 mL), dried over anhydrous sodium sulfate and evaporated under reduced pressure to obtain Intermediate 122-I (0.08 g, 95.00%) as a brown solid. $^1$H NMR (400 MHz, DMSO-$d_6$) δ ppm 2.22 (br. s., 1H), 2.29 (s, 3H), 2.31 (s, 1H), 2.34 (br. s., 1H), 2.37 (s, 1H), 2.43 (s, 1H), 2.82 (d, J=12.55 Hz, 1H), 3.10 (t, J=10.79 Hz, 1H), 3.24 (d, J=12.55 Hz, 2H), 4.48-4.77 (m, 1H), 5.39 (s, 2H), 7.54 (d, J=8.53 Hz, 1H), 7.66 (d, J=8.03 Hz, 1H). $^{19}$F NMR (300 MHz, DMSO-$d_6$) δ ppm −175.06. LCMS (Method-D): retention time 1.32 min, [M+H] 250.2.

Intermediate 123-I, II, III and IV: 5-(6-(1-hydroxyethyl)piperazin-2-yl)-4-methylisobenzofuran-1(3H)-one

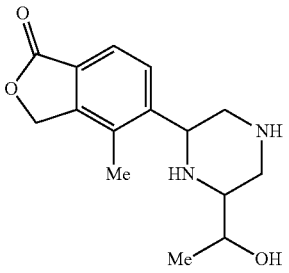

Intermediate 123A: 5-(6-(hydroxymethyl)pyrazin-2-yl)-4-methylisobenzofuran-1(3H)-one

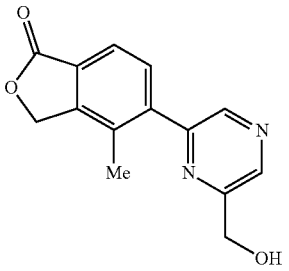

Intermediate 123A was prepared (6.00 g, 87.00%), by using a similar synthetic protocol as that of Intermediate 2C and starting from Intermediate 2B (7.02 g, 25.60 mmol) and (6-chloropyrazin-2-yl)methanol (3.70 g, 25.60 mmol). $^1$H NMR (400 MHz, DMSO-$d_6$) δ ppm 0.98-1.23 (m, 2H), 2.24-2.36 (m, 3H), 5.49 (s, 2H), 7.42-7.60 (m, 1H), 7.70 (d, J=7.53 Hz, 1H), 7.81 (d, J=8.03 Hz, 1H), 8.77 (d, J=6.53 Hz, 2H). LCMS (Method-D): retention time 0.92 min, [M+H] 257.0.

Intermediate 123B: 6-(4-methyl-1-oxo-1,3-dihydroisobenzofuran-5-yl)pyrazine-2-carbaldehyde

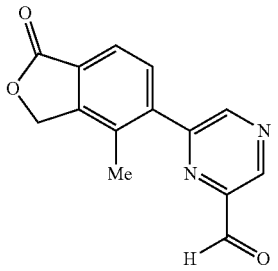

Intermediate 123B was prepared (4.40 g, 55.40%), by using a similar synthetic protocol as that of Intermediate 9 and starting from Intermediate 123A (8.00 g, 31.20 mmol) and Dess-Martin periodinane (26.50 g, 62.40 mmol). $^1$H (400 MHz, $CDCl_3$) δ ppm 2.42 (s, 3H), 5.37 (s, 2H), 7.69 (d, J=7.75 Hz, 1H), 7.94 (d, J=7.75 Hz, 1H), 8.99 (s, 1H), 9.21 (s, 1H), 10.12-10.29 (m, 1H). LCMS (Method-D): retention time 1.18 min, [M+H] 255.0.

Intermediate 123C: 5-(6-(1-hydroxyethyl)pyrazin-2-yl)-4-methylisobenzofuran-1(3H)-one

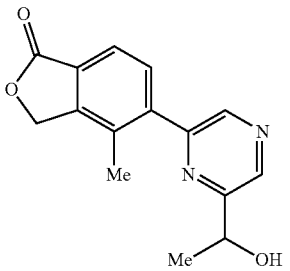

Intermediate 123C was prepared (0.95 g, 89.00%) as a pale yellow solid, by using a similar synthetic protocol as that of Intermediate 72A and starting from Intermediate 123B (1.00 g, 3.93 mmol). $^1$H NMR (400 MHz, DMSO-$d_6$) δ ppm 1.47 (d, J=6.53 Hz, 3H), 2.22-2.39 (m, 3H), 4.90 (dd, J=6.53, 4.52 Hz, 1H), 5.51 (s, 2H), 5.69 (d, J=4.80 Hz, 1H), 7.73 (d, J=8.03 Hz, 1H), 7.83 (d, J=8.03 Hz, 1H), 8.82 (s, 2H). LCMS (Method-I): retention time 0.78 min, [M+H] 271.2.

Intermediate 123-I, II, III and IV

Intermediate 123-I was prepared by using a similar synthetic protocol as that of Intermediate 2-I and 2-II and starting from Intermediate 123C (0.90 g, 3.33 mmol). The racemate was separated into four individual enantiomers by SFC [Chiralpak IC (250×4.6 mm) 5.0 micron; 0.2% $NH_4OH$ in ACN+MeOH (1:1), Flow: 4.0 mL/min, Temperature: 30° C., UV: 235 nm]. First eluted compound (retention time 12.40 min), designated as Intermediate 123-I, was obtained (0.08 g, 8.69%) as a pale yellow solid. $^1$H NMR (400 MHz, DMSO-$d_6$) δ ppm 1.01-1.11 (m, 3H), 1.56-1.76 (m, 2H), 2.15-2.27 (m, 3H), 2.29-2.36 (m, 3H), 2.82 (d, J=11.74 Hz, 2H), 3.17 (s, 1H), 4.00 (dd, J=9.78, 2.45 Hz, 1H), 4.66 (br. s., 1H), 5.28-5.44 (m, 2H), 7.67 (d, J=8.07 Hz, 1H), 7.75-

7.89 (m, 1H). LCMS (Method-D): retention time 0.51 min, [M+H] 277.2. Second eluted compound (retention time 12.80 min), designated as Intermediate 123-II, was obtained (0.03 g, 3.26%) as a pale yellow solid. $^1$H NMR (400 MHz, DMSO-$d_6$) δ 0.98-1.17 (m, 3H), 1.33 (dt, J=13.76, 7.18 Hz, 1H), 2.05 (s, 1H), 2.12-2.25 (m, 2H), 2.25-2.37 (m, 4H), 2.75-2.92 (m, 2H), 3.82-4.13 (m, 2H), 4.51-4.72 (m, 1H), 5.39 (s, 2H), 7.56-7.72 (m, 1H), 7.82 (dd, J=7.95, 4.03 Hz, 1H). LCMS (Method-D): retention time 0.51 min, [M+H] 277.2. Third eluted compound (retention time 15.0 min), designated as Intermediate 123-III, was obtained (0.18 g, 19.56%) as a pale yellow solid. $^1$H NMR (400 MHz, DMSO-$d_6$) δ ppm 0.96-1.15 (m, 3H), 2.10-2.37 (m, 4H), 2.59-2.72 (m, 1H), 2.84 (d, J=13.05 Hz, 1H), 2.96 (d, J=11.04 Hz, 1H), 3.18 (s, 3H), 3.45-3.61 (m, 1H), 4.04 (dd, J=9.79, 2.76 Hz, 1H), 4.46 (br. s., 1H), 5.19-5.49 (m, 2H), 7.67 (d, J=8.03 Hz, 1H), 7.74-7.89 (m, 1H). LCMS (Method-D): retention time 0.59 min, [M+H] 277.2. Fourth eluted compound (retention time 17.47 min), designated as Intermediate 123-IV, was obtained (0.15 g, 16.30%) as a pale yellow solid. $^1$H NMR (400 MHz, DMSO-$d_6$) δ ppm 1.09 (d, J=6.02 Hz, 3H), 2.21 (d, J=11.55 Hz, 1H), 2.26-2.34 (m, 3H), 2.57-2.70 (m, 1H), 2.83 (d, J=12.05 Hz, 1H), 2.95 (d, J=10.04 Hz, 1H), 3.17 (s, 3H), 3.51 (d, J=4.52 Hz, 1H), 3.91-4.18 (m, 1H), 4.46 (d, J=4.02 Hz, 1H), 5.27-5.48 (m, 2H), 7.66 (d, J=8.03 Hz, 1H), 7.81 (d, J=8.03 Hz, 1H). LCMS (Method-D): retention time 0.59 min, [M+H] 277.2.

Intermediate 124: 5-(6-(difluoromethyl)piperazin-2-yl)-4-methylisobenzofuran-1(3H)-one

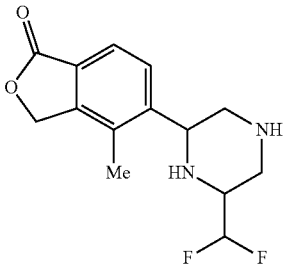

Intermediate 124A: 5-(6-(difluoromethyl)pyrazin-2-yl)-4-methylisobenzofuran-1(3H)-one

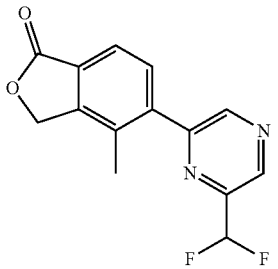

Intermediate 124A was prepared (0.07 g, 64.40%) as a pale yellow solid, by using a similar synthetic protocol as that of Intermediate 4B and starting from Intermediate 123B (0.10 g, 0.39 mmol) and DAST (0.10 mL, 0.78 mmol). $^1$H (400 MHz, $CDCl_3$) δ ppm 2.39 (s, 3H), 5.35 (s, 2H), 6.46-6.98 (m, 1H), 7.65 (d, J=7.53 Hz, 1H), 7.91 (d, J=8.03 Hz, 1H), 8.79-9.07 (m, 2H). LCMS (Method-D): retention time 2.16 min, [M+H] 277.2.

Intermediate 124

Intermediate 124 was prepared (0.30 g, crude) as a pale yellow solid, by using a similar synthetic protocol as that of Intermediate 2-I and 2-II and starting from Intermediate 124A (0.28 g, 1.01 mmol). $^1$H NMR (400 MHz, DMSO-$d_6$) δ ppm 0.94-1.05 (m, 1H), 1.84-1.95 (m, 3H), 2.15-2.40 (m, 2H), 2.74-3.00 (m, 2H), 3.06-3.22 (m, 2H), 4.00-4.22 (m, 1H), 5.27-5.43 (m, 2H), 5.67-6.02 (m, 1H), 7.57-7.73 (m, 1H), 7.80 (dd, J=8.03, 4.02 Hz, 1H). LCMS (Method-I): retention time 0.87 min, [M+H] 283.2.

Intermediate 125: 1-(5-methylpyrazin-2-yl)-1H-pyrazole-4-carbaldehyde

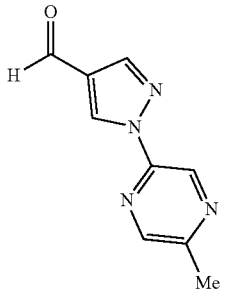

To a solution of 2-chloro-5-methylpyrazine (2.00 g, 15.56 mmol) in DMF (50 mL) was added 1H-pyrazole-4-carbaldehyde (2.24 g, 23.34 mmol) followed by $Cs_2CO_3$ (10.14 g, 31.10 mmol) and the resulting reaction mixture was heated at 100° C. for 6 h. The reaction mixture was cooled to ambient temperature, concentrated to dryness under reduced pressure, diluted with water (50 mL) and extracted with ethyl acetate (2×75 mL). The combined organic layers was washed with brine (30 mL), dried over anhydrous sodium sulfate and evaporated under reduced pressure. The residue was purified by column chromatography (Redisep—80 g, 0-100% EtOAc/n-hexane) to obtain Intermediate 125 (1.10 g, 37.10%) as a pale yellow solid. $^1$H NMR (300 MHz, DMSO-$d_6$) δ ppm 2.58 (s, 3H), 8.36 (s, 1H), 8.54 (s, 1H), 9.14 (s, 1H), 9.31 (s, 1H), 9.98 (s, 1H). LCMS (Method-D): retention time 1.25 min, [M+H] 189.2.

Intermediate 126: 1-(6-methoxypyrimidin-4-yl)-1H-pyrazole-4-carbaldehyde

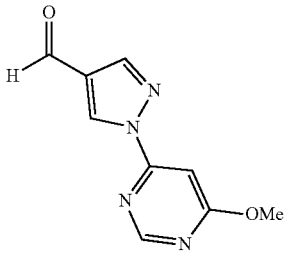

Intermediate 126 was prepared (1.50 g, 53.10%) as an off-white solid, by using a similar synthetic protocol as that of Intermediate 20 and starting from 4-chloro-6-methoxypyrimidine (2.00 g, 13.84 mmol) and 1H-pyrazole-4-carbaldehyde (1.99 g, 20.75 mmol). $^1$H NMR (400 MHz, DMSO-$d_6$) δ ppm 4.03 (s, 3H), 7.30 (d, J=1.00 Hz, 1H), 8.38 (s, 1H), 8.84 (s, 1H), 9.37 (s, 1H), 9.99 (s, 1H). LCMS (Method-D): retention time 1.60 min, [M+H] 205.2.

Intermediate 127: 1-(2-methoxypyrimidin-5-yl)-1H-pyrazole-4-carbaldehyde

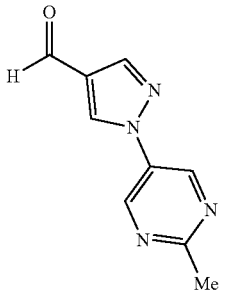

Intermediate 127 was prepared (0.20 g, 18.51%) as an off-white solid, by using a similar synthetic protocol as that of Intermediate 6 and starting from 1H-pyrazole-4-carbaldehyde (0.76 g, 7.94 mmol) and 5-bromo-2-methoxypyrimidine (1.00 g, 5.29 mmol). $^1$H NMR (300 MHz, DMSO-$d_6$) δ ppm 3.99 (s, 3H), 8.36 (s, 1H), 9.14 (s, 2H), 9.22 (s, 1H), 9.94 (s, 1H). LCMS (Method-D): retention time 1.0 min, [M+H] 205.2.

Intermediate 128: 1-(2-methylpyrimidin-5-yl)-1H-pyrazole-4-carbaldehyde

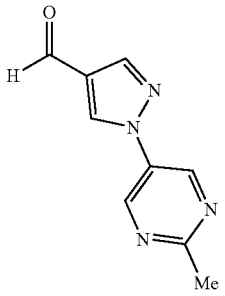

Intermediate 128 was prepared (0.02 g, 18.39%) as an off-white solid, by using a similar synthetic protocol as that of Intermediate 6 and starting from 1H-pyrazole-4-carbaldehyde (0.08 g, 0.87 mmol) and 5-bromo-2-methylpyrimidine (0.10 g, 0.58 mmol). $^1$H NMR (300 MHz, DMSO-$d_6$) δ ppm 2.62-2.89 (m, 3H), 8.39 (s, 1H), 9.25 (s, 2H), 9.34 (s, 1H), 9.95 (s, 1H). LCMS (Method-D): retention time 0.71 min, [M+H] 189.2.

Intermediate 129: 6-(3-formylisoxazol-5-yl)-4-methylnicotinonitrile

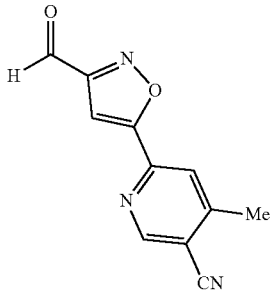

Intermediate 129A: ethyl 5-(tributylstannyl)isoxazole-3-carboxylate

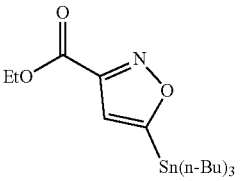

To a solution of ethyl 2-chloro-2-(hydroxyimino)acetate (0.72 g, 4.76 mmol) in diethyl ether (15 mL) was added tributylstannylacetylene (0.92 mL, 3.17 mmol) followed by TEA (0.88 mL, 6.35 mmol) and the resulting reaction mixture was stirred at ambient temperature for 16 h. The reaction mixture was filtered through Celite® and washed with diethyl ether (50 mL). The filtrate was evaporated under reduced pressure to obtain Intermediate 129A (0.60 g, 43.90%) as a pale yellow liquid. $^1$H NMR (300 MHz, $CDCl_3$) δ ppm 0.76-0.95 (m, 12H), 1.02-1.11 (m, 2H), 1.13-1.24 (m, 3H), 1.24-1.35 (m, 5H), 1.37-1.47 (m, 4H), 1.48-1.72 (m, 4H), 4.27-4.58 (m, 2H), 6.80 (s, 1H). LCMS (Method-D): retention time 2.76 min, [M+H] 432.2.

Intermediate 129B: ethyl 5-(5-cyano-4-methylpyridin-2-yl)isoxazole-3-carboxylate

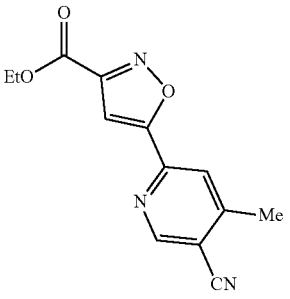

A stirring solution of Intermediate 129A (0.06 g, 1.27 mmol) and 6-bromo-4-methylnicotinonitrile (0.25 g, 1.27 mmol) in dioxane (10 mL) was degassed with nitrogen for 20 minutes. To the stirring solution was added bis(ditertbutyl(4-dimethylaminophenyl)phosphine)dichloropalladium(II) (0.09 g, 0.13 mmol) and was degassed again for 10 minutes. The resulting reaction mixture was heated at 110° C. for 16 h then cooled to ambient temperature and filtered through Celite®. The filtrate obtained, was concentrated under reduced pressure. The residue was purified by column chromatography (Redisep—24 g, 12-14% EtOAc/n-Hexane) to obtain Intermediate 129B (0.07 g, 21.45%) as a pale yellow solid. $^1$H NMR (400 MHz, $CDCl_3$) δ ppm 1.39-1.52 (m, 3H), 2.55-2.81 (m, 3H), 4.35-4.67 (m, 2H), 7.42 (s, 1H), 7.95 (s, 1H), 8.72-8.96 (m, 1H). LCMS (Method-H): retention time 2.71 min, [M+1] 258.2.

Intermediate 129C: 6-(3-(hydroxymethyl)isoxazol-5-yl)-4-methylnicotinonitrile

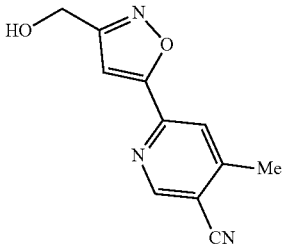

Intermediate 129C was prepared (0.01 g, 71.70%), by using a similar synthetic protocol as that of Intermediate 60B and starting from Intermediate 129B (0.02 g, 0.58 mmol) and $NaBH_4$ (0.09 mg, 2.33 mmol). $^1$H NMR (400 MHz, DMSO-$d_6$) δ ppm 2.55-2.64 (m, 3H), 4.60 (br. s., 2H), 5.61 (d, J=4.02 Hz, 1H), 7.40-7.66 (m, 1H), 8.14 (s, 1H), 8.96-9.10 (m, 1H). LCMS (Method-D): retention time 2.79 min, [M+H] 216.2.

Intermediate 129

Intermediate 129 was prepared (0.08 g, 55.00%), by using a similar synthetic protocol as that of Intermediate 9 and starting from Intermediate 129C (0.01 g, 0.46 mmol) and Dess-Martin periodinane (26.5 g, 62.40 mmol). $^1$H NMR (400 MHz, $CDCl_3$) δ ppm 2.01-2.20 (m, 3H), 7.39 (s, 1H), 7.96 (s, 1H), 8.89 (s, 1H), 10.25 (s, 1H). LCMS (Method-D): retention time 0.75 min, [M+H] 214.0.

Intermediate 130-I: 5-((2R,6S)-4-((1H-imidazol-4-yl)methyl)-6-methylpiperazin-2-yl)-4-methyl-isobenzo-furan-1(3H)-one

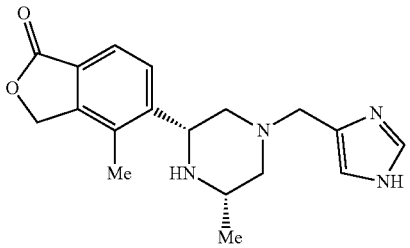

Intermediate 130A: tert-butyl 4-formyl-1H-imidazole-1-carboxylate

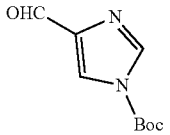

To a stirring solution of 1H-imidazole-4-carbaldehyde (2.00 g, 20.81 mmol) in THF (20 mL) was added DMAP (0.64 g, 5.20 mmol) and TEA (5.80 ml, 41.60 mmol) followed by Boc-anhydride (5.80 mL, 24.98 mmol) and the resulting reaction mixture was stirred as ambient temperature for 18 h. The reaction mixture was concentrated to dryness under reduced pressure and diluted with water (50 mL). The solid precipitate was filtered and dried under vacuum to obtain Intermediate 130A (2.50 g, 49.00%) as a pale yellow solid. $^1$H NMR (400 MHz, DMSO-$d_6$) δ ppm 1.59 (s, 9H), 8.37-8.39 (d, J=5.40 Hz, 2H), 9.80 (s., 1H). LCMS (Method-O): retention time 1.00 min, [M−56] 141.2.

Intermediate 130B-I: tert-butyl 4-(((3S,5R)-3-methyl-5-(4-methyl-1-oxo-1,3-dihydroisobenzo-furan-5-yl)piperazin-1-yl)methyl)-1H-imidazole-1-carboxylate

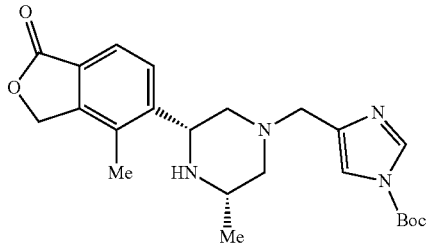

Intermediate 130B-I was prepared (0.8 g, 22.39%), by using a similar synthetic protocol as that of Intermediate 4 and starting from Intermediate 51-I (1.30 g, 5.28 mmol) and Intermediate 130A (1.24 g, 6.33 mmol). $^1$H NMR (400 MHz, $CD_3OD$) δ ppm 0.60-0.62 (d, J=6.00 Hz, 3H), 1.59 (s, 9H), 1.37-1.43 (m, 2H), 2.29-2.31 (m, 2H), 2.66 (s, 3H), 2.94 (s, 2H), 3.69-3.71 (m, 1H), 4.71 (s, 2H), 6.8 (s, 1H), 7.05-7.07 (m, 1H), 7.12-7.14 (m, 1H), 7.25 (s, 1H), 7.51 (s, 1H), (1 Exchangeable proton not observed). LCMS (Method-O): retention time 1.17 min, [M+1] 427.3.

Intermediate 130-I

Intermediate 130-I was prepared (0.65 g, 99.90%), by using a similar synthetic protocol as that of Intermediate 38-I and starting from Intermediate 130B-I (0.70 g, 1.64 mmol). $^1$H NMR (400 MHz, DMSO-$d_6$) δ ppm 1.40 (d, J=6.60 Hz, 3H), 2.39 (s, 3H), 2.82 (m, 2H), 2.98 (m, 1H), 3.48 (s, 2H), 3.97 (s, 2H), 4.9 (br. s., 1H), 5.40-5.53 (m, 2H), 7.75 (s, 1H), 7.81 (d, J=7.80 Hz, 1H), 8.23 (d, J=8.10 Hz, 1H), 9.1 (s, 1H), 10.20 (b.s, 2H). LCMS (Method-O): retention time 0.51 min, [M+H] 327.4.

Intermediate 13I-I: (R)-6-(4-(((2-amino-2-(4-methyl-1-oxo-1,3-dihydroisobenzofuran-5-yl)ethyl)amino)methyl)-1H-pyrazol-1-yl)-4-methylnicotinonitrile

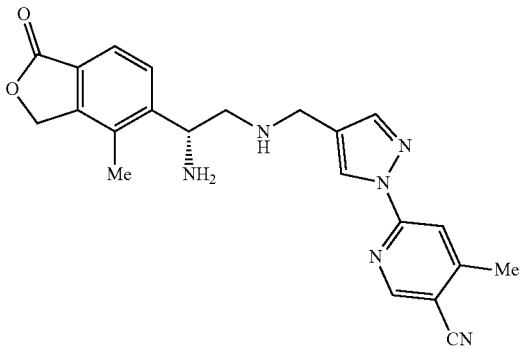

Intermediate 131A-I: (R)-2-(2-amino-1-(4-methyl-1-oxo-1,3-dihydroisobenzofuran-5-yl)ethyl)isoindoline-1,3-dione

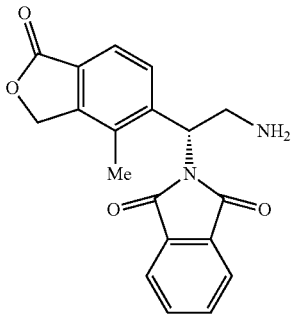

Intermediate 131A-I was prepared (0.15 g, 97.00%), by using a similar synthetic protocol as that of Intermediate 19-I and starting from Intermediate 18C-I (0.20 g, 0.458 mmol) and TFA (2 mL, 26.0 mmol). $^1$H NMR (400 MHz, DMSO-$d_6$) δ ppm 2.33-2.37 (m, 3H), 3.16 (dd, J=13.05, 5.02 Hz, 1H), 3.66 (dd, J=13.05, 9.54 Hz, 1H), 5.35-5.41 (m, 2H), 5.50 (dd, J=9.79, 5.27 Hz, 1H), 7.70 (s, 1H), 7.76-7.81 (m, 1H), 7.82-7.89 (m, 4H). (2 Exchangeable protons not observed). LCMS (Method-I): retention time 0.81 min, [M+H] 337.3.

Intermediate 131B-I: (R)-6-(4-(((2-(1,3-dioxoisoindolin-2-yl)-2-(4-methyl-1-oxo-1,3-dihydroisobenzofuran-5-yl)ethyl)amino)methyl)-1H-pyrazol-1-yl)-4-methylnicotinonitrile

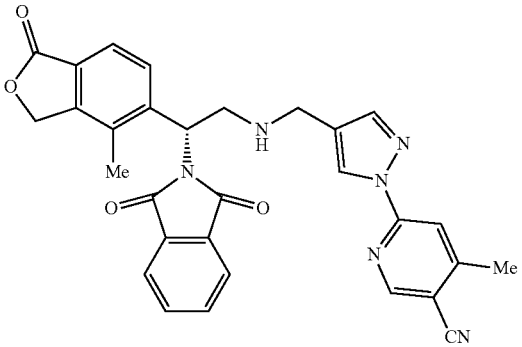

Intermediate 131B-I was prepared (1.1 g, 45.60%) as an off-white solid, by using a similar synthetic protocol as that of Intermediate 4 and starting from Intermediate 131A-I (1.7 g, 3.03 mmol) and 6-(4-formyl-1H-pyrazol-1-yl)-4-methylnicotinonitrile (0.98 g, 3.03 mmol). $^1$H NMR (400 MHz, DMSO-$d_6$) δ ppm 2.27-2.36 (m, 3H), 2.57 (s, 3H), 3.13 (dd, J=12.30, 5.27 Hz, 1H), 3.63-3.75 (m, 3H), 5.37 (d, J=3.01 Hz, 2H), 5.67 (dd, J=10.04, 5.02 Hz, 1H), 7.68 (d, J=8.03 Hz, 1H), 7.75 (s, 1H), 7.81 (d, J=8.03 Hz, 1H), 7.84 (s, 4H), 7.94 (s, 1H), 8.43 (s, 1H), 8.80 (s, 1H). (1 Exchangeable proton not observed). LCMS (Method-I): retention time 1.46 min, [M+H] 533.5.

Intermediate 131-I

Intermediate 131-I was prepared (0.03 g, 51.00%), by using a similar synthetic protocol as that of Intermediate 18-I and starting from Intermediate 131B-I (0.13 g, 0.12 mmol) and hydrazine hydrate (0.06 mL, 1.22 mmol). $^1$H NMR (400 MHz, DMSO-$d_6$) δ 2.15-2.29 (m, 5H), 2.32-2.38 (m, 1H), 2.57 (s, 3H), 2.60-2.70 (m, 1H), 3.17 (s, 1H), 3.59-3.76 (m, 2H), 4.31 (dd, J=8.56, 4.16 Hz, 1H), 5.35 (s, 2H), 7.63 (d, J=8.07 Hz, 1H), 7.76 (d, J=8.07 Hz, 1H), 7.84 (s, 1H), 7.97 (s, 1H), 8.50 (s, 1H), 8.83 (s, 1H). LCMS/HPLC (Method-R): retention time 0.98 min, [M+H] 403.1, purity: 98.53%. (Method-S): retention time 1.28 min, [M+H] 403.1, purity: 98.81%. Chiral purity (Method-XVIII): retention time 5.86 min, 100% ee.

Intermediate 132-I: (R)-5-(4-((5-bromopyrimidin-2-yl)methyl)piperazin-2-yl)-4-methylisobenzofuran-1(3H)-one

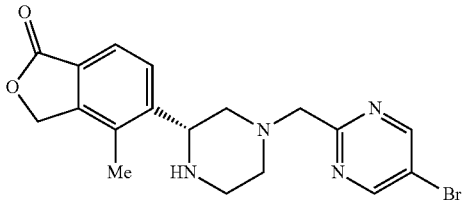

Intermediate 132A:
5-bromo-2-(bromomethyl)pyrimidine

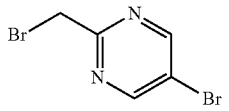

To a stirred solution of 5-bromo-2-methylpyrimidine (5.00 g, 28.90 mmol) in $CCl_4$ (40 mL) was added AIBN (0.48 g, 2.89 mmol) and N-bromosuccinimide (5.14 g, 28.9 mmol) and the reaction mixture was heated at 80° C. for 48 h. The reaction mixture was cooled to ambient temperature. The solid precipitate was filtered off and the filtrate was concentrated under reduced pressure. The residue was purified by column chromatography (Redisep—80 g, 0-15% EtOAc/n-hexane) to obtain Intermediate 132A (1.05 g, 12.98%) as a pale yellow solid. $^1$H NMR (400 MHz, DMSO-$d_6$) δ ppm 4.68 (s, 2H), 9.03 (s, 2H). LCMS (Method-I): retention time 1.03 min, [M+1] 252.9.

Intermediate 132-I

To a stirring solution of Intermediate 123A (0.38 g, 1.63 mmol) and Intermediate 2-I (0.41 g, 1.63 mmol) in THF (20 mL) was added DIPEA (0.69 mL, 3.97 mmol) and the reaction mixture was stirred at room temperature for 16 h. The reaction mixture was diluted with water (40 mL) and extracted with ethyl acetate (3×40 mL). The combined organic layers were washed with brine (30 mL), dried over anhydrous sodium sulfate and evaporated under reduced pressure. The residue was purified by column chromatography (Redisep—24 g, 2-4% MeOH/$CHCl_3$) to obtain Intermediate 132-I (0.32 g, 28.40%) as a brown solid. $^1$H NMR (400 MHz, DMSO-$d_6$) δ ppm 1.89-2.06 (m, 1H), 2.20-2.36 (m, 4H), 2.74-3.01 (m, 4H), 3.74 (s, 2H), 4.01-4.13 (m, 1H), 5.38 (s, 2H), 7.64 (d, J=8.07 Hz, 1H), 7.78 (d, J=8.07 Hz, 1H), 8.96 (s, 2H), (1 Exchangeable proton not observed). LCMS (Method-D): retention time 1.17 min, [M+H] 405.0.

Intermediate 133: 6-(4-formyl-2H-1,2,3-triazol-2-yl)-4-methoxy-2-methylnicotinonitrile

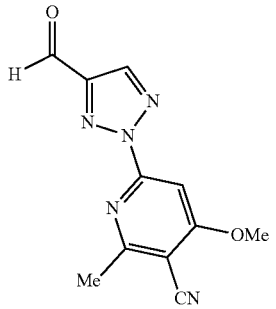

Intermediate 133A: bis(2,4,6-trichlorophenyl) malonate

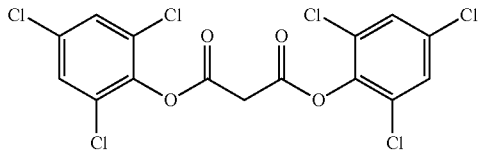

A mixture of malonic acid (20.00 g, 192.00 mmol), 2,4,6-trichlorophenol (76.00 g, 384.00 mmol) and $POCl_3$ (50 mL) was refluxed for 12 h. The reaction mixture was cooled to 70° C. and poured into ice water. The solid precipitate was collected by filtration, washed with water and dried under vacuum to obtain Intermediate 133A (70.30 g, 67.20%) as a pale yellow solid. $^1$H NMR (400 MHz, $CDCl_3$) δ ppm 3.91-4.17 (m, 2H), 7.33-7.59 (m, 4H). LCMS: The compound did not ionize well.

Intermediate 133B: 4-hydroxy-2-methyl-6-oxo-1,6-dihydropyridine-3-carbonitrile

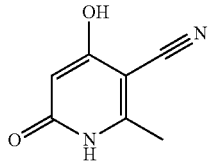

A mixture of 3-aminoacrylonitrile (10.25 g, 151.00 mmol) and Intermediate 133A (70.30 g, 152.00 mmol) in diglyme (75 mL) was heated at 120° C. for 2.5 h. The mixture was cooled to ambient temperature and poured into $Et_2O$ (40 mL) and filtered. The precipitate was washed with $Et_2O$ (15 mL) to obtain Intermediate 133B (13.50 g, 59.70%) as a dark brown solid. $^1$H NMR (400 MHz, DMSO-$d_6$) δ ppm 2.25-2.41 (m, 3H), 5.49 (s, 1H), 11.85 (br. s., 2H). LCMS (Method-I): retention time 0.32 min, [M+1] 151.3.

Intermediate 133C:
4,6-dichloro-2-methylnicotinonitrile

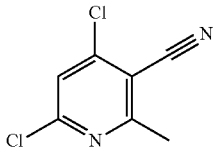

A stirring solution of Intermediate 133B (10.70 g, 71.30 mmol) in $POCl_3$ (6.64 ml, 71.3 mmol) was heated at 100° C. is for 16 h. The reaction mixture was concentrated under reduced pressure, diluted water (200 mL), basified with solid $Na_2CO_3$ and extracted with ethyl acetate (3×200 mL). The combined organic layers were washed with brine (100 mL), dried over anhydrous sodium sulfate and evaporated under reduced pressure. The residue was purified by column chromatography (Redisep—120 g, 0-5% EtOAc/n-Hexane) to obtain Intermediate 133C (8.50 g, 57.40%) as an off-white solid. $^1$H NMR (400 MHz, DMSO-$d_6$) δ ppm 2.69 (s, 3H), 8.02 (s, 1H). LCMS: (Method-I): retention time 1.16 min, [M+1] 188.3.

Intermediate 133D: 6-chloro-4-methoxy-2-methylnicotinonitrile and

Intermediate 133E: 4-chloro-6-methoxy-2-methylnicotinonitrile

133D

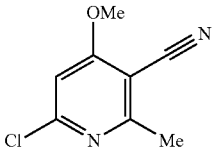

133E

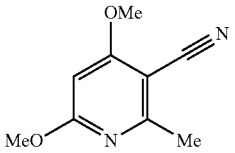

Intermediate 133D and Intermediate 133E was as prepared, by using a similar synthetic protocol as that of Intermediate 114A and starting from Intermediate 133C (8.50 g, 45.40 mmol). First eluted compound, designated as Intermediate 133D, was obtained (5.50 g, 66.30%) as an off-white solid. $^1$H NMR (400 MHz, DMSO-$d_6$) δ ppm 2.57 (s, 3H), 4.02 (s, 3H), 7.35 (s, 1H). LCMS (Method-I): retention time 0.99 min, [M+1]183.3. Second eluted compound, designated as Intermediate 133E, was obtained (1.50 g, 18.07%) as an off-white solid. $^1$H NMR (400 MHz, DMSO-$d_6$) δ ppm 2.62 (s, 3H) 3.94 (s, 3H) 7.17 (s, 1H). LCMS (Method-I): retention time 1.24 min, [M+1] 183.3.

Intermediate 133F: 6-(4-(hydroxymethyl)-2H-1,2,3-triazol-2-yl)-4-methoxy-2-methylnicotinonitrile and Intermediate and 133G: 6-(4-(hydroxymethyl)-1H-1,2,3-triazol-1-yl)-4-methoxy-2-methylnicotinonitrile

133F

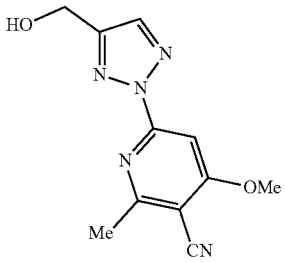

133G

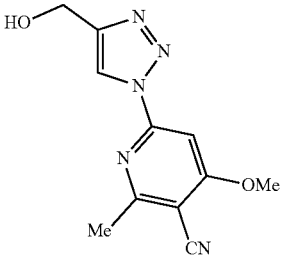

Intermediate 133F and Intermediate 133G was as prepared, by using a similar synthetic protocol as that of Intermediate 20 and starting from Intermediate 133D (1.84 g, 10.09 mmol) and Intermediate 28A (1.00 g, 10.09 mmol). First eluted compound, designated as Intermediate 133F, was obtained (0.37 g, 10.00%) as an off-white solid. $^1$H NMR (400 MHz, DMSO-$d_6$) δ ppm 2.65 (s, 3H), 4.11 (s, 3H), 4.68 (d, J=5.02 Hz, 2H), 5.55 (t, J=5.77 Hz, 1H), 7.56 (s, 1H), 8.17 (s, 1H). LCMS (Method-I): retention time 0.75 min, [M+1] 246.1. Second eluted compound, designated as Intermediate 133G, was obtained (0.27 g, 9.33%) as an off-white solid. $^1$H NMR (400 MHz, DMSO-$d_6$) δ ppm 2.67 (s, 3H), 4.14 (s, 3H), 4.64 (d, J=4.02 Hz, 2H), 5.27-5.42 (m, 1H), 7.74 (s, 1H), 8.68 (s, 1H). LCMS (Method-I): retention time 0.80 min, [M+1] 246.1.

Intermediate 133

Intermediate 133 was prepared (0.35 g, 94.00%) as an off-white solid, by using a similar synthetic protocol as that of Intermediate 9 and starting from Intermediate 133F (0.38 g, 1.53 mmol). $^1$H NMR (400 MHz, DMSO-$d_6$) δ ppm 2.70 (s, 3H), 4.15 (s, 3H), 7.73 (s, 1H), 8.79 (s, 1H), 10.22 (s, 1H). LCMS (Method-I): retention time 0.92 min, [M+H] 244.1.

Intermediate 134: 6-(4-formyl-1H-1,2,3-triazol-1-yl)-4-methoxy-2-methylnicotinonitrile

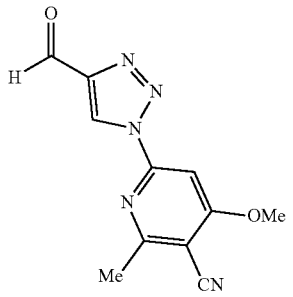

Intermediate 134 was prepared (0.26 g, 95.00%) as an off-white solid, by using a similar synthetic protocol as that of Intermediate 9 and starting from Intermediate 133G (0.28 g, 1.12 mmol). $^1$H NMR (400 MHz, DMSO-$d_6$) δ ppm 2.70 (s, 3H), 4.17 (s, 3H), 7.84 (s, 1H), 9.56 (s, 1H), 10.14 (s, 1H). LCMS (Method-I): retention time 1.00 min, [M−H] 242.1.

Intermediate 135: 1-(4-methoxy-1,3,5-triazin-2-yl)-1H-pyrazole-4-carbaldehyde

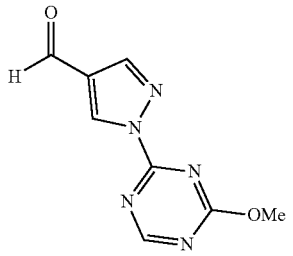

Intermediate 135 was prepared (0.70 g, 32.80%) as an off-white solid, by using a similar synthetic protocol as that of Intermediate 20 and starting from 1H-pyrazole-4-carbaldehyde (1.00 g, 10.41 mmol) and 2-chloro-4-methoxy-1,3,5-triazine (1.52 g, 10.41 mmol). $^1$H NMR (400 MHz, DMSO-$d_6$) δ ppm 4.11 (s, 3H), 8.39 (s, 1H), 8.60 (s, 1H), 9.47 (s, 1H), 10.01 (s, 1H). LCMS (Method-I): retention time 0.62 min, [M+H] 206.2.

Intermediate 136-I: 5-((2R,6R)-6-(hydroxymethyl)-1-methylpiperazin-2-yl)-4-methylisobenzofuran-1(3H)-one

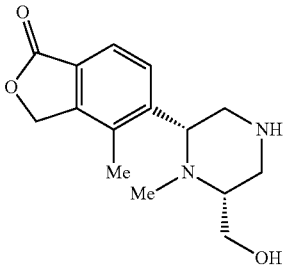

Intermediate 136A-I: tert-butyl (3R,5R)-3-(hydroxymethyl)-4-methyl-5-(4-methyl-1-oxo-1,3-dihydroisobenzofuran-5-yl)piperazine-1-carboxylate

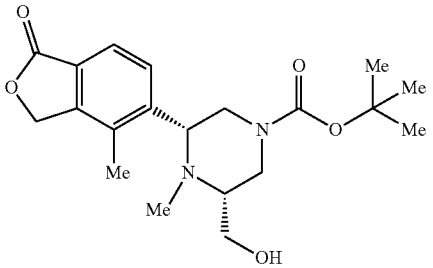

To a stirred solution of Intermediate 38D-I (0.15 g, 0.41 mmol) and paraformaldehyde (0.05 g, 1.63 mmol) in MeOH (15 mL) was added sodium cyanoborohydride (0.51 g, 8.16 mmol) and the resultant mixture was stirred at ambient temperature for 16 h. The reaction mixture was diluted with water (30 mL) and extracted with DCM (3×30 mL). The combined organic layers were washed with brine (20 mL), dried over anhydrous sodium sulfate and evaporated under reduced pressure. The residue was purified by column chromatography (Redisep—24 g, 0-2% MeOH/$CHCl_3$) to obtain Intermediate 136A-I (0.15 g, 96.00%) as an off-white solid. $^1$H NMR (400 MHz, DMSO-$d_6$) δ ppm 1.42 (d, J=2.20 Hz, 9H), 1.98 (d, J=2.20 Hz, 3H), 2.20 (br. s., 1H), 2.33 (br. s., 3H), 2.61-2.80 (m, 3H), 3.17 (dd, J=5.26, 3.06 Hz, 1H), 3.46 (d, J=10.52 Hz, 2H), 3.73 (br. s., 2H), 4.11 (d, J=5.38 Hz, 1H), 4.71 (br. s., 1H), 5.43 (br. s., 1H), 7.72 (br. s., 1H). LCMS (Method-I): retention time 1.06 min, [M+H] 377.3.

Intermediate 136-I

Intermediate 136-I was prepared (0.10 g, 91.00%) as an off-white solid, by using a similar synthetic protocol as that of Intermediate 38-I and starting from Intermediate 136A-I (1.00 g, 10.41 mmol) and 4M HCl in dioxane (5 mL, 20.00 mmol). $^1$H NMR (400 MHz, DMSO-$d_6$) δ ppm 1.98 (s, 3H), 2.33 (s, 3H), 2.55 (br. s., 1H), 2.77 (t, J=11.86 Hz, 1H), 2.90 (t, J=11.98 Hz, 1H), 3.07-3.21 (m, 2H), 3.36-3.53 (m, 2H), 3.63-3.75 (m, 1H), 3.91 (d, J=10.27 Hz, 1H), 4.85 (t, J=5.14 Hz, 1H), 5.31-5.48 (m, 2H), 7.73 (s, 2H). LCMS (Method-I): retention time 0.46 min, [M+H] 277.2.

Intermediate 137: 1-(5-formylpyrimidin-2-yl)-1H-imidazole-4-carbonitrile

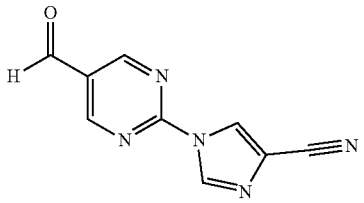

Intermediate 137 was prepared (0.40 g, 37.50%) as an off-white solid, by using a similar synthetic protocol as that of Intermediate 20 and starting from 2-chloropyrimidine-5-carbaldehyde (1.00 g, 5.38 mmol) and 1H-imidazole-4-carbonitrile. $^1$H NMR (400 MHz, DMSO-$d_6$) δ ppm, 8.90 (s, 2H), 9.26 (s, 1H), 10.11 (s, 1H), 10.14 (s, 1H). LCMS (Method-H): retention time 0.91 min, [M+1] 200.05.

Intermediate 138: 2-(4-methyl-1H-imidazol-1-yl)pyrimidine-5-carbaldehyde

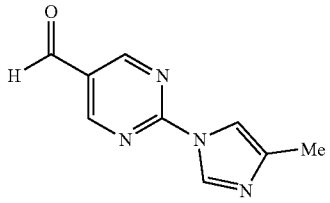

To a stirring solution of 2-chloropyrimidine-5-carbaldehyde (3.00 g, 21.05 mmol) in DMSO (20 mL) was added $K_2CO_3$ (7.27 g, 52.60 mmol) followed by 4-methyl-1H-imidazole (2.59 g, 31.6 mmol) and the resulting mixture was stirred at ambient temperature for 30 minutes. The reaction mixture was poured into ice cold water (50 mL) and extracted with ethyl acetate (3×100 mL). The combined organic layers were washed with brine (50 mL), dried over anhydrous sodium sulfate and concentrated under reduced pressure. The residue was purified by column chromatography (Redisep—24 g, 80% EtOAc/n-hexane) to obtain Intermediate 138 (1.40 g, 34.30%) as a white solid. $^1$H NMR (400 MHz, DMSO-$d_6$) δ ppm 2.20 (s, 3H), 7.72 (t, J=1.2 Hz 1H), 8.56 (d, J=1.2 Hz, 1H), 9.26 (s, 2H) 10.09 (s, 1H). LCMS (Method-D): retention time 1.07 min, [M+H] 189.1.

Intermediate 139: 1-(5-formylpyrimidin-2-yl)-3-methyl-1H-pyrazole-4-carbonitrile

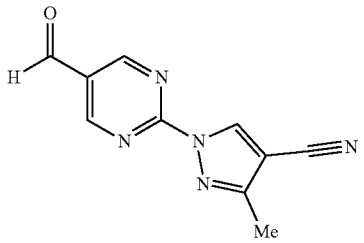

Intermediate 139 was prepared (0.30 g, 40.10%), by using a similar synthetic protocol as that of Intermediate 20 and starting from 2-chloropyrimidine-5-carbaldehyde (0.50 g, 3.51 mmol) and 4-methyl-1H-pyrazole-3-carbonitrile (0.41 g, 3.86 mmol). $^1$H NMR (400 MHz, DMSO-$d_6$) δ ppm 2.30 (d, J=1.00 Hz, 3H), 8.65 (s, 1H), 8.90 (s, 1H), 9.36 (s, 1H), 10.15 (s, 1H). LCMS (Method-D), retention time 1.54 min, Intermediate 140: 6-(4-methyl-1H-1,2,3-triazol-1-yl)nicotinaldehyde

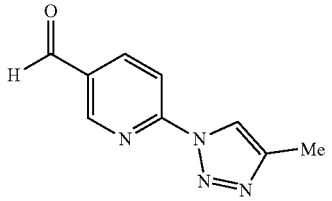

Intermediate 140 was prepared (0.25 g, 46.70%), by using a similar synthetic protocol as that of Intermediate 20 and starting from 6-bromonicotinaldehyde (0.50 g, 2.69 mmol) and 4-methyl-1H-1,2,3-triazole (0.38 g, 4.03 mmol). $^1$H NMR (400 MHz, DMSO-$d_6$) δ ppm 2.31-2.40 (m, 3H), 8.30 (d, J=8.53 Hz, 1H), 8.44-8.54 (m, 1H), 8.70 (s, 1H), 9.10 (d, J=1.51 Hz, 1H), 10.15 (s, 1H). LCMS: (Method-D) retention time: 1.119 min, [M+1]: 189.2.

Intermediate 141: 1-(5-formylpyrimidin-2-yl)-1H-1, 2, 4-triazole-3-carbonitrile

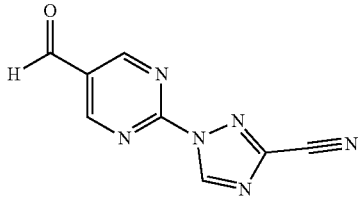

Intermediate 141 was prepared (0.25 g, 46.70%) as a brown solid, by using a similar synthetic protocol as that of Intermediate 20 and starting from 2-chloropyrimidine-5-carbaldehyde (0.50 g, 2.69 mmol) and 1H-1,2,4-triazole-3-carbonitrile (0.38 g, 4.03 mmol). $^1$H NMR (400 MHz, DMSO-$d_6$) δ ppm 8.14-81.6 (d, J=8.80 Hz, 1H), 9.13 (s, 2H), 10.18 (s, 1H). LCMS (Method-H): retention time 1.27 min, [M+H] 201.2.

Intermediate 142: 1-(5-formylpyrimidin-2-yl)-3-methoxy-1H-pyrazole-4-carbonitrile

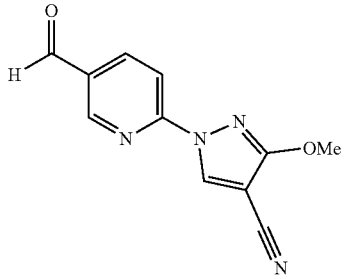

Intermediate 142 was prepared (1.15 g, 93.00%) as an off-white solid, by using a similar synthetic protocol as that of Intermediate 20 and starting from 6-bromonicotinaldehyde (1.00 g, 5.42 mmol) and 3-methoxy-1H-pyrazole-4-carbonitrile (0.80 g, 6.50 mmol). $^1$H NMR (400 MHz, DMSO-$d_6$) δ ppm 4.07 (s, 3H), 7.95-8.00 (m, 1H), 8.45-8.48 (m, 2H), 9.37 (s, 1H), 10.11 (s, 1H). LCMS (Method-D): retention time 2.21 min, [M+H] 229.0.

Intermediate 143: 3-ethyl-1-(5-formylpyridin-2-yl)-1H-pyrazole-4-carbonitrile

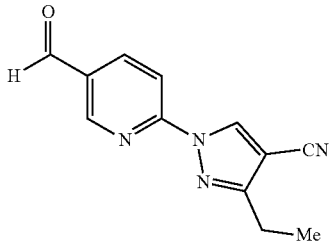

Intermediate 143A: ((E)-2-(ethoxymethylene)-3-oxopentanenitrile

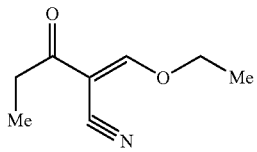

Synthesized according to literature procedures (Australian Journal of Chemistry, 44, 1263-1273, 1991).

Intermediate 143B:
3-ethyl-1H-pyrazole-4-carbonitrile

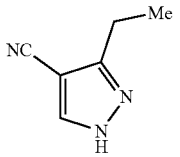

To a solution of Intermediate 143A (5.00 g, 32.60 mmol) in EtOH (50 mL) was added hydrazine hydrate (5.12 mL, 163 mmol) and the reaction mixture was stirred at ambient temperature for 1 h. The reaction mixture was diluted with water (40 mL) and extracted with 10% MeOH in DCM (2×50 mL). The combined organic layers were washed with brine (20 mL) and dried over anhydrous sodium sulfate and evaporated under reduced pressure. The crude product was purified by combiflash (Redisep—40 g, 50% EtOAc/n-Hexane) to obtain Intermediate 143B (3.10 g, 78.00%) as yellow solid. $^1$H NMR (400 MHz, DMSO-$d_6$) δ ppm 1.23 (t, J=7.6 Hz, 3H), 2.73 (q, J=7.6 Hz, 2H), 8.16 (s, 1H), 13.4 (br. s, 1H). LCMS (method-L), retention time 0.75 min, [M+H] 122.1.

Intermediate 143

Intermediate 143 was prepared (0.22 g, 68.70%), by using a similar synthetic protocol as that of Intermediate 20 and starting from Intermediate 143B (0.19 g, 1.61 mmol) and 6-bromonicotinaldehyde (0.25 g, 1.34 mmol). $^1$H NMR (400 MHz, DMSO-$d_6$) δ ppm 1.31 (t, J=7.6 Hz, 3H), 2.82 (q, J=7.6 Hz, 2H), 8.10 (d, J=8.8 Hz, 1H), 8.47 (dd, J=1.6 Hz, J=8.4 Hz, 1H), 9.03 (s, 1H), 9.43 (s, 1H), 10.12 (s, 1H). LCMS (method-L), retention time 1.18 min, [M+H] 227.1.

Intermediate 144: 1-(5-formylpyrimidin-2-yl)-3-methoxy-1H-pyrazole-4-carbonitrile

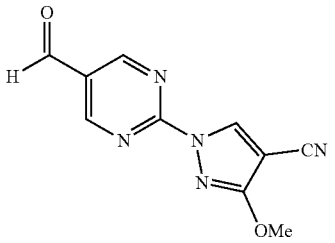

To a stirring solution of 2-chloropyrimidine-5-carbaldehyde (0.25 g, 1.75 mmol) in THF (10 mL) was added 3-methoxy-1H-pyrazole-4-carbonitrile (0.32 g, 2.63 mmol) followed by $K_2CO_3$ (0.36 g, 2.63 mmol) and the resulting reaction mixture was heated at 70° C. for 1 h. The reaction mixture was cooled to ambient temperature, concentrated to dryness under reduced pressure, diluted with water (50 mL) and extracted with ethyl acetate (3×50 mL). The combined organic layers were washed with brine (30 mL), dried over anhydrous sodium sulfate and evaporated under reduced pressure. The residue was purified by column chromatography (Redisep—24 g, 0-50% EtOAc/n-hexane) to obtain Intermediate 144 (0.24 g, 60.00%). $^1$H NMR (400 MHz, DMSO-$d_6$) δ ppm 4.06 (s, 3H), 9.29 (s, 1H), 9.31 (s, 1H), 9.45 (s, 1H), 10.13 (s, 1H). LCMS: The compound did not ionize well.

Intermediate 145: 3-ethyl-1-(5-formylpyrimidin-2-yl)-1H-pyrazole-4-carbonitrile

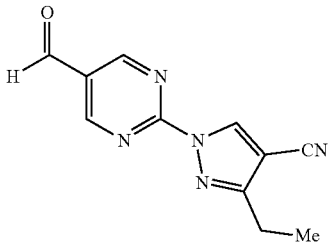

Intermediate 145 was prepared (0.23 g, 57.70%) by using similar synthetic protocol as that of Intermediate 20 and starting from Intermediate 143B (0.32 g, 2.63 mmol) and 2-chloropyrimidine-5-carbaldehyde (0.25 g, 1.75 mmol). $^1$H NMR (400 MHz, DMSO-$d_6$) δ ppm 1.31 (t, J=7.6 Hz, 3H), 2.82 (q, J=3.6 Hz, 2H), 9.34 (s, 2H), 9.49 (s, 1H), 10.14 (s, 1H). LCMS (Method-D): retention time 1.55 min, [M+18+H] 246.1.

Intermediate 146: 3-cyclopropyl-1-(5-formylpyrimidin-2-yl)-1H-pyrazole-4-carbonitrile

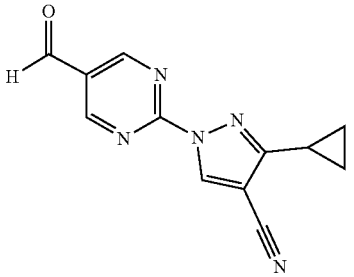

Intermediate 146A:
3-cyclopropyl-1H-pyrazole-4-carbonitrile

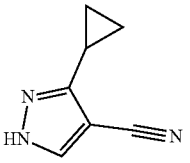

Synthesized according to literature procedures (PCT Int. Appl., 2015052264).

Intermediate 146 was prepared (0.22 g, 51.90%) as an off-white solid, by using similar synthetic protocol as that of Intermediate 144 and starting from 2-chloropyrimidine-5-carbaldehyde (0.25 g, 1.75 mmol) and Intermediate 146A (0.35 g, 2.63 mmol). $^1$H NMR (400 MHz, DMSO-$d_6$) δ ppm 0.99-1.06 (m, 2H), 1.12 (dt, J=8.53, 3.01 Hz, 2H), 2.00-2.20

(m, 1H), 9.23-9.36 (m, 2H), 9.46 (s, 1H), 10.14 (s, 1H). LCMS (Method-D): retention time 1.70 min, [M+H] 240.2.

Intermediate 147: 3-(difluoromethoxy)-1-(5-formylpyridin-2-yl)-1H-pyrazole-4-carbonitrile

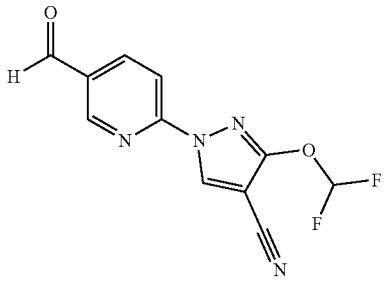

Intermediate 147A: 1-(5-formylpyridin-2-yl)-3-oxo-2,3-dihydro-1H-pyrazole-4-carbonitrile

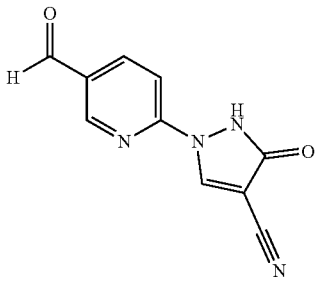

To a solution of Intermediate 142 (0.60 g, 2.63 mmol) in DCM (25 mL) was added $BBr_3$ (0.75 mL, 7.89 mmol) at 0° C. and the resulting reaction mixture was stirred at 50° C. for 16 h. The reaction mixture was cooled to ambient temperature, concentrated to dryness under reduced pressure and diluted with water (50 mL). The solid precipitate was filtered and dried under vacuum to obtain Intermediate 147A (0.80 g, crude). LCMS (Method-L): retention time 1.57 min, [M+H] 294.1. The compound was taken directly to the subsequent step without further purification or characterization.

Intermediate 147

To a stirring solution of Intermediate 147A (0.80 g, 2.71 mmol) in DMF (10 mL) was added sodium chlorodifluoroacetate (0.62 g, 4.07 mmol) followed by $Cs_2CO_3$ (2.65 g, 8.13 mmol) and the resulting reaction mixture was heated at 100° C. for 3 h. The reaction mixture was cooled to ambient temperature and diluted with water (30 mL). The solid precipitate was filtered and dried under vacuum to obtain Intermediate 12 (0.25 g, 16.41%) as an off-white solid. $^1$H NMR (400 MHz, DMSO-$d_6$) δ ppm 7.33-7.86 (m, 1H), 7.93-8.13 (m, 1H), 8.33-8.63 (m, 1H), 9.03 (dd, J=17.32, 1.76 Hz, 1H), 9.29-9.59 (m, 1H), 10.12 (d, J=9.54 Hz, 1H). LCMS (Method-L): retention time 2.20 min, [M+H] 265.2.

Intermediate 148: 3-(difluoromethyl)-1H-pyrazole-4-carbonitrile

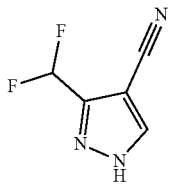

Intermediate 148A: (E)-3-(dimethylamino)acrylonitrile

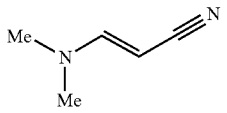

To a solution of 2-cyanoacetic acid (5.00 g, 58.8 mmol) in 1,4-dioxane (30 mL) was added DMF-DMA (8.66 mL, 64.7 mmol) and the resulting reaction mixture was stirred at ambient temperature for 4 h. The reaction mixture was cooled to ambient temperature, concentrated to dryness under reduced pressure to obtain Intermediate 148A (5.90 g crude). $^1$H NMR (400 MHz, $CDCl_3$) δ ppm 2.73 (s, 6H) 6.89 (s, 1H) 6.93 (s, 1H).

Intermediate 148B: (Z)-2-((dimethylamino)methylene)-4,4-difluoro-3-oxobutanenitrile

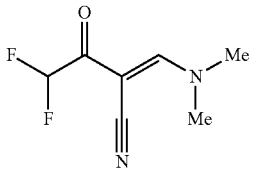

To a solution of Intermediate 148A (2.00 g, 20.81 mmol) in toluene (20 mL) was added TEA (5.80 mL, 41.6 mmol) followed by 2,2-difluoroacetic acid (1.99 g, 20.81 mmol) at 0° C. Then 20% phosgene in toluene (10 mL, 22.89 mmol) was added and resulting reaction mixture was stirred at ambient temperature for 1.5 h. The reaction mixture was concentrated to dryness under reduced pressure, diluted with saturated $NaHCO_3$ (120 mL) and extracted with ethyl acetate (3×50 mL). The combined organic layers were washed with brine (30 mL), dried over anhydrous sodium sulfate and evaporated under reduced pressure to obtain Intermediate 148B (1.70 g, 46.90%) as a brown solid. $^1$H NMR (400 MHz, DMSO-$d_6$) δ ppm 3.35 (s, 6H), 6.31-6.75 (m, 1H), 8.02 (s, 1H). LCMS (Method-O): retention time 0.62 min, [M−H] 175.3.

Intermediate 148

Intermediate 148 was prepared (0.65 g, 32.60%) as a brown solid, by using a similar synthetic protocol as that of Intermediate 143B and starting from Intermediate 148B (1.70 g, 9.76 mmol) and hydrazine hydrate (1.53 mL, 48.80 mmol). $^1$H NMR (400 MHz, DMSO-$d_6$) δ ppm 6.72-7.44 (m, 1H), 8.63 (s, 1H), 9.11-9.87 (m, 1H). LCMS (Method-L): retention time 1.28 min, [M−H] 141.9.

Intermediate 149-I: (R)-5-(4-((2-chloropyrimidin-5-yl)methyl)piperazin-2-yl)-4-methylisobenzofuran-1(3H)-one

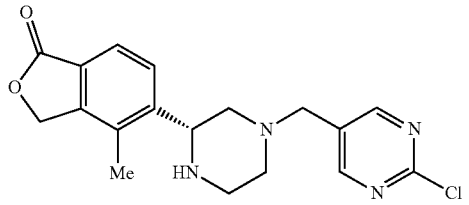

Intermediate 149-I was prepared (0.38 g, 80.00%), by using a similar synthetic protocol as that of Intermediate 143B and starting from Intermediate 2-I (0.27 g, 1.17 mmol) and 2-chloropyrimidine-5-carbaldehyde (0.20 g, 1.40 mmol). $^1$H NMR (400 MHz, DMSO-$d_6$) δ ppm 2.25-2.39 (m, 4H), 2.95 (d, J=11.98 Hz, 3H), 3.52-3.67 (m, 1H), 4.17-4.39 (m, 1H), 4.46-4.75 (m, 2H), 4.85 (d, J=10.03 Hz, 1H), 5.31-5.50 (m, 2H), 7.67-7.81 (m, 1H), 7.92 (d, J=6.60 Hz, 1H), 8.59-8.77 (m, 1H), 8.85 (br. s., 2H), 9.66-9.89 (m, 1H), (1 Exchangeable proton not observed). LCMS (Method-D): retention time 0.91 min, [M+H] 359.0.

Intermediate 150: 6-(4-formyl-1H-pyrazol-1-yl)-4-morpholinonicotinonitrile

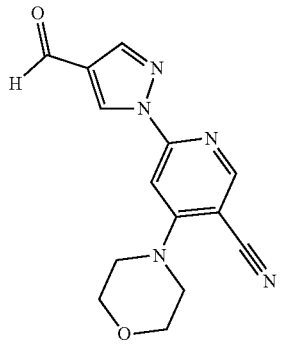

Intermediate 150A: 4-chloro-6-(4-formyl-1H-pyrazol-1-yl)nicotinonitrile and Intermediate 150B: 6-chloro-4-(4-formyl-1H-pyrazol-1-yl)nicotinonitrile

150A

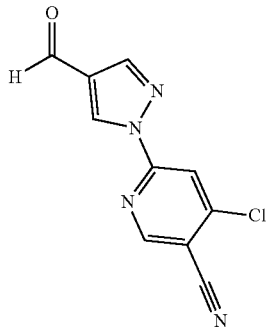

150B

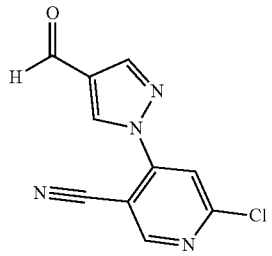

Intermediate 150A and 150B was prepared, by using a similar synthetic protocol as that of Intermediate 15C and starting from 4,6-dichloronicotinonitrile (2.50 g, 14.45 mmol) and 1H-pyrazole-4-carbaldehyde (1.26 g, 13.14 mmol). First eluted compound, designated as Intermediate 150A, was obtained (0.60 g, 19.63%) as a pale yellow solid. $^1$H NMR (400 MHz, DMSO-$d_6$) δ ppm 8.27 (s, 1H), 8.41 (s, 1H), 9.12 (s, 1H), 9.39 (s, 1H), 9.99 (s, 1H). Second 293 eluted compound, designated as Intermediate 150B, was obtained (0.40 g, 13.09%) as a pale yellow solid. $^1$H NMR (400 MHz, DMSO-$d_6$) δ ppm (400 MHz, DMSO-$d_6$) δ ppm 8.33 (s, 1H), 8.50 (s, 1H), 9.05 (s, 1H), 9.43 (s, 1H), 9.99 (s, 1H).

Intermediate 150

To a solution of Intermediate 150A (0.15 g, 0.65 mmol) in THF (10 mL) was added $K_2CO_3$ (0.22 mg, 1.61 mmol) followed by morpholine (0.14 g, 1.61 mmol) and the resulting reaction mixture was stirred for 16 h. The reaction mixture was concentrated to dryness under reduced pressure, diluted with water (50 mL) and extracted with ethyl acetate (3×50 mL). The combined organic layers were washed with brine (30 mL), dried over anhydrous sodium sulfate and evaporated under reduced pressure to obtain Intermediate 150 (0.05 g, 37.00%) as an off-white solid. $^1$H NMR (400 MHz, DMSO-d6) δ ppm 2.19-2.35 (m, 2H), 2.41 (br. s., 2H), 3.49 (s, 2H), 3.77 (d, J=4.52 Hz, 2H), 7.40 (s, 1H), 7.74 (s, 1H), 7.97 (br. s., 1H), 8.47 (s, 1H), 8.61 (s, 1H). LCMS (Method-D): retention time 1.89 min, [M+H] 284.0.

Intermediate 151: 6-(4-formyl-1H-pyrazol-1-yl)-4-(pyrrolidin-1-yl)nicotinonitrile

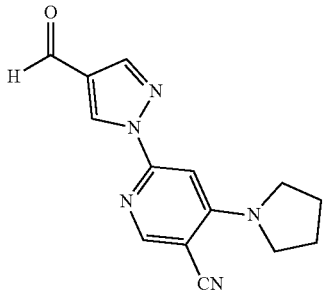

Intermediate 151 was prepared (0.08 g, 46.40%) as an off-white solid, by using a similar synthetic protocol as that of Intermediate 150 and starting from Intermediate 150A (0.15 g, 0.65 mmol) and pyrrolidine (0.12 g, 1.61 mmol). $^1$H NMR (400 MHz, DMSO-$d_6$) δ ppm 1.99 (dt, J=6.27, 3.39 Hz, 4H), 3.69 (br. s., 4H), 7.11 (s, 1H), 8.30 (s, 1H), 8.49 (s, 1H), 9.26 (s, 1H), 9.95 (s, 1H). LCMS (Method-I): retention time 1.09 min, [M+1] 268.4.

Intermediate 152: 1-(5-formylpyridin-2-yl)-1H-1,2,3-triazole-4-carbonitrile

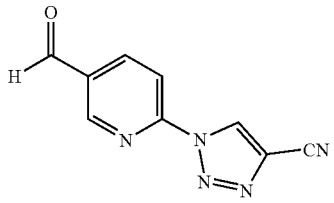

Intermediate 152A: methyl 6-azidonicotinate

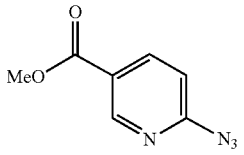

To a stirring solution of methyl 6-fluoronicotinate (9.00 g, 58.00 mmol) in DMF (30 mL) was added sodium azide (3.77 g, 58.0 mmol) and the resulting reaction mixture was heated at 70° C. for 2 h. Th$_{e\ react}$ion mixture was diluted with water (300 mL) and the solid precipitated, was filtered and dried under vacuum to obtain Intermediate 152A (6.80 g, 65.80%). $^1$H NMR (400 MHz, DMSO-$d_6$) δ ppm 3.96 (s, 3H), 8.20 (dd, J=9.35, 1.53 Hz, 1H), 8.30 (m, J=0.98 Hz, 1H), 9.89 (t, J=1.25 Hz, 1H). LCMS (Method-L): retention time 0.73 min, [M+H] 179.1.

Intermediate 152B: methyl 6-(4-(hydroxymethyl)-1H-1,2,3-triazol-1-yl)nicotinate

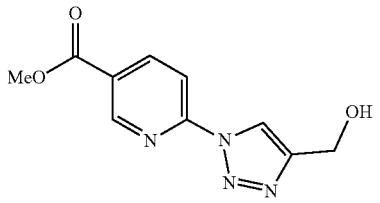

To a stirring solution of Intermediate 152A (3.50 g, 19.65 mmol) and prop-2-yn-1-ol (3.30 g, 58.90 mmol) in a mixture of DMF (50 mL) and MeOH (12 mL) was added copper(I) iodide (0.37 g, 1.96 mmol) and stirring was continued at 90° C. for 4 h. The reaction mixture was cooled to ambient temperature, filtered through Celite® and the filtrate was concentrated under reduced pressure to obtain Intermediate 152B (4.50 g, 98.00%) as a brown solid. $^1$H NMR (400 MHz, DMSO-$d_6$) δ ppm 3.93 (s, 3H), 4.64 (d, J=5.32 Hz, 2H), 5.38 (t, J=5.69 Hz, 1H), 8.27 (d, J=8.56 Hz, 1H), 8.57 (dd, J=8.56, 2.20 Hz, 1H), 8.74 (s, 1H), 9.08 (s, 1H). LCMS (Method-O): retention time 0.71 min, [M+H] 235.1.

Intermediate 152C: methyl 6-(4-formyl-1H-1,2,3-triazol-1-yl)nicotinate

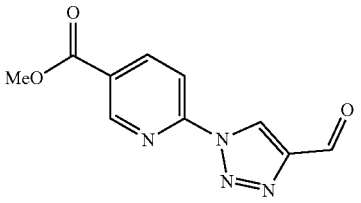

To a solution of Intermediate 152B (4.50 g, 11.91 mmol) in acetone (100 mL) was added manganese dioxide (10.36 g, 119 mmol) and the resulting reaction mixture was stirred at 60° C. for 16 h. The reaction mixture was cooled to ambient temperature, concentrated to dryness under reduced pressure, diluted with DCM (250 mL) and filtered through Celite®. The filtrate was evaporated under reduced pressure to obtain Intermediate 152C (1.90 g, 68.70%) as a brown solid. $^1$H NMR (400 MHz, DMSO-$d_6$) δ ppm 3.98 (s, 3H), 8.36 (dd, J=8.53, 0.76 Hz, 1H), 9.08-9.10 (m, 1H), 9.13 (dd, J=2.20, 0.73 Hz, 1H), 9.61 (s, 1H), 10.15 (s, 1H). LCMS: The compound did not ionize well.

Intermediate 152D: methyl 6-(4-cyano-1H-1,2,3-triazol-1-yl)nicotinate

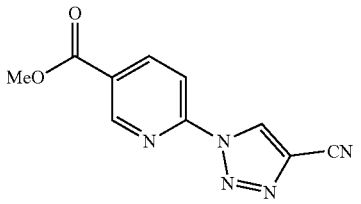

To a stirring solution of Intermediate 152C (1.90 g, 5.73 mmol) in a mixture of pyridine (10 mL) and acetic anhydride (10 mL) was added hydroxylamine hydrochloride (0.59 g, 8.59 mmol) and the resulting reaction mixture was heated at 110° C. for 2 h. The reaction mixture was cooled to ambient temperature, concentrated to dryness under reduced pressure, diluted with $NaHCO_3$ solution (50 mL) and extracted with ethyl acetate (3×50 mL). The combined organic layer was washed with brine (30 mL), dried over anhydrous sodium sulfate and evaporated under reduced pressure to obtain Intermediate 152D (1.00 g, 76.00%) as a brown solid. $^1$H NMR (400 MHz, DMSO-$d_6$) δ ppm 3.94 (s, 3H), 8.34 (d, J=8.50 Hz, 1H), 8.65 (dd, J=8.56, 2.20 Hz, 1H), 9.12 (d, J=1.77 Hz, 1H), 9.90 (s, 1H). LCMS (Method-L): retention time 1.10 min, [M+H] 230.1.

Intermediate 152E: 1-(5-(hydroxymethyl)pyridin-2-yl)-1H-1,2,3-triazole-4-carbonitrile

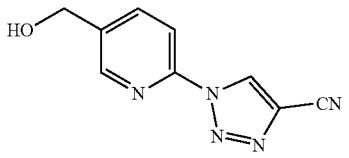

Intermediate 152E was prepared (0.45 g, 46.50%) as an off-white solid, by using a similar synthetic protocol as that of Intermediate 60B and starting from Intermediate 152D (1.00 g, 2.79 mmol) and $NaBH_4$ (0.53 g, 13.96 mmol). $^1$H NMR (400 MHz, DMSO-$d_6$) δ ppm 4.61-4.67 (m, 2H), 5.53 (t, J=5.59 Hz, 1H), 8.06-8.17 (m, 2H), 8.58 (m, 1H), 9.79 (s, 1H). LCMS (Method-L): retention time 0.81 min, [M+H] 202.1.

Intermediate 152

Intermediate 152 was prepared (0.18 g, 74.60%) as an off-white solid, by using a similar synthetic protocol as that of Intermediate 9 and starting from Intermediate 152E (0.42 g, 1.21 mmol) and Dess-Martin periodinane (0.51 g, 1.21 mmol). $^1$H NMR (400 MHz, DMSO-$d_6$) δ ppm 8.39 (d, J=8.41 Hz, 1H), 8.60 (dd, J=8.44, 2.16 Hz, 1H), 9.16 (dd, J=2.13, 0.69 Hz, 1H), 9.92 (s, 1H), 10.19 (s, 1H). LCMS: The compound did not ionize well.

Intermediate 153-I and 153-II: 4-methyl-5-(5-methylpiperazin-2-yl)isobenzofuran-1(3H)-one

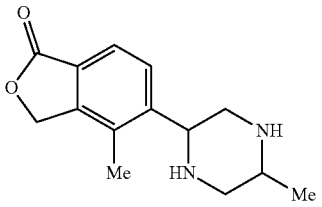

Enantiomer-I (153-I)

-continued

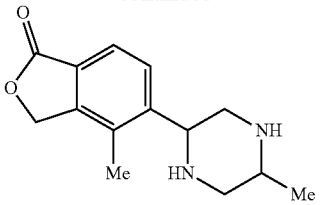

Enantiomer-II (153-II)

Intermediate 153A: 5-(5-methylpyrazin-2-yl)isobenzofuran-1(3H)-one

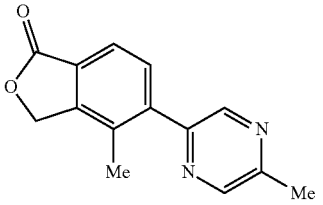

Intermediate 153A was prepared (3.20 g, 49.00%) as an off-white solid, by using a similar synthetic protocol as that of Intermediate 2C and starting from Intermediate 2B (7.46 g, 27.2 mmol) and 2-chloro-5-methylpyrazine (3.50 g, 27.20 mmol). $^1$H NMR (400 MHz, DMSO-$d_6$) δ ppm 2.32 (s, 3H), 2.60 (s, 3H), 5.50 (s, 2H), 7.70 (d, J=7.53 Hz, 1H), 7.81 (d, J=7.53 Hz, 1H), 8.71 (d, J=1.00 Hz, 1H), 8.77 (d, J=1.51 Hz, 1H). LCMS (Method-D): retention time 1.22 min, [M+H] 241.1.

Intermediate 153-I and 153-II

Intermediate 153-I and 153-II was prepared by using a similar synthetic protocol as that of Intermediate 2-I and 2-II and starting from Intermediate 153A (3.20 g, 13.32 mmol). The racemate was separated into two individual enantiomers by SFC [Chiralpak AD-H (250×4.6 mm) 5 micron; 0.2% $NH_4OH$ in MeOH+ACN (1:1), Flow: 1.2 mL/min. Temperature: 30° C., UV: 235 nm]. First eluted compound (retention time 3.1 min), designated as Intermediate 153-I, was obtained (0.60 g, 25.00%) as an off-white solid. $^1$H NMR (400 MHz, DMSO-$d_6$) δ ppm 0.96 (d, J=6.36 Hz, 3H), 2.30 (s, 3H), 2.31-2.46 (m, 2H), 2.66-2.74 (m, 1H), 2.86 (dd, J=11.74, 2.69 Hz, 1H), 2.95 (dd, J=10.88, 2.81 Hz, 1H), 3.91 (dd, J=9.90, 2.81 Hz, 1H), 5.38 (s, 2H), 7.65 (d, J=8.07 Hz, 1H), 7.77 (d, J=8.07 Hz, 1H), (2 Exchangeable protons not observed). LCMS (Method-D): retention time 0.56 min, [M+H] 247.2. Chiral purity (Method-XXXII): retention time 3.11 min, 97.10% ee. Second eluted compound (retention time 4.5 min), designated as Intermediate 153-II, was obtained (0.55 g, 23.00%) as an off-white solid. $^1$H NMR (400 MHz, DMSO-d6) δ ppm 0.96 (d, J=6.36 Hz, 3H), 2.30 (s, 3H), 2.31-2.46 (m, 2H), 2.66-2.74 (m, 1H), 2.86 (dd, J=11.74, 2.69 Hz, 1H), 2.95 (dd, J=10.88, 2.81 Hz, 1H), 3.91 (dd, J=9.90, 2.81 Hz, 1H), 5.38 (s, 2H), 7.65 (d, J=8.07 Hz, 1H), 7.77 (d, J=8.07 Hz, 1H), (2 Exchangeable protons not observed). LCMS (Method-D): retention time 0.38 min, [M+H] 247.2. Chiral purity (Method-XXXII): retention time 4.82 min, 90.00% ee.

Intermediate 154-I: 5-((2R,6S)-1-hydroxy-6-methylpiperazin-2-yl)-4-methylisobenzofuran-1(3H)-one

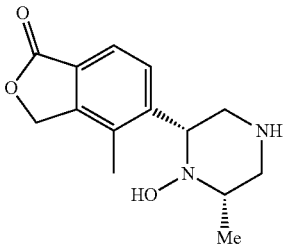

Intermediate 154A-I: tert-butyl (3S,5R)-3-methyl-5-(4-methyl-1-oxo-1,3-dihydroisobenzofuran-5-yl)piperazine-1-carboxylate

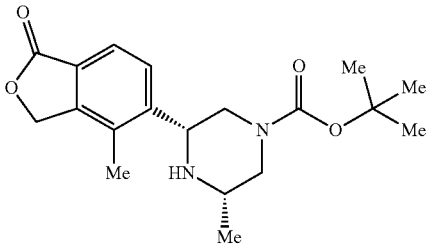

To a stirring solution of Intermediate 51-I (0.20 g, 0.81 mmol) in DCM (20 mL) was added TEA (0.17 mL, 1.22 mmol) followed by Boc-anhydride (0.23 mL, 0.97 mmol) and stirring was continued at ambient temperature for 2 h. The reaction mixture was diluted with 10% NaOH solution (40 mL) and extracted with 10% MeOH in DCM (2×250 mL). The combined organic layer was washed with brine (30 mL), dried over anhydrous sodium sulfate and evaporated under reduced pressure. The residue was purified by column chromatography (Redisep—24 g, 35% EtOAc/n-hexanes) to obtain Intermediate 154A-I (0.20 g, 71.10%). $^1$H NMR (400 MHz, DMSO-$d_6$) δ ppm 1.05 (s, 3H), 1.48 (s, 9H), 2.33 (s, 4H), 2.75-2.83 (m, 2H), 3.82-3.92 (br. s., 1H), 3.94-4.01 (m, 2H), 5.42 (s, 2H), 7.68-7.73 (m, 1H), 7.80-7.86 (m, 1H). LCMS (Method-D): retention time 2.42 min, [M+H] 347.2.

Intermediate 154B-I: tert-butyl (3S,5R)-4-hydroxy-3-methyl-5-(4-methyl-1-oxo-1,3-dihydroisobenzofuran-5-yl)piperazine-1-carboxylate

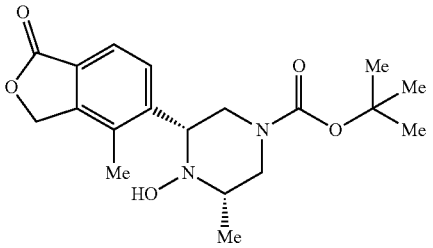

To a stirred solution of Intermediate 154A-I (0.20 g, 0.57 mmol) in DCM (15 mL) and was added m-CPBA (0.10 g, 0.57 mmol) and the resulting reaction mixture was stirred at ambient temperature for 12 h. The reaction mixture was concentrated to dryness under reduced pressure and the residue was purified by preparative HPLC [YMC Triart (150×4.6 mm) 5 micron; 0.1% $NH_4OH$ in Water+ACN (1:1), Flow: 1.2 mL/min. Temperature: 30° C., UV: 235 nm] to obtain Intermediate 154B-I (0.06 mg, 26.30%). $^1$H NMR (400 MHz, DMSO-d6) δ ppm 1.14 (d, J=6.02 Hz, 3H), 1.43 (s, 9H), 2.26-2.36 (m, 3H), 2.68 (d, J=2.01 Hz, 2H), 2.72 (br. s., 1H), 3.80 (d, J=10.54 Hz, 2H), 3.93 (br. s., 1H), 5.42 (s, 2H), 7.68 (d, J=8.03 Hz, 1H), 7.79 (d, J=7.53 Hz, 1H), 8.01 (s, 1H). LCMS (Method-D): retention time 2.44 min, [M+H] 363.4.

Intermediate 154-I

To a stirring solution of Intermediate 154B-I (0.03 g, 0.08 mmol) in DCM (5 mL) was added 4M HCl in dioxane (0.04 mL, 0.16 mmol) and the resulting reaction mixture was stirred at ambient temperature for 2 h. The reaction mixture was concentrated under reduced pressure. The residue was dissolved in diethyl ether (100 mL) and the solid precipitate was filtered and dried under vacuum to obtain Intermediate 154-I (0.02 g, 89.00%). LCMS (Method-P) retention time 0.45 min, [M+H] 263.4. The compound was taken directly to the subsequent step without further purification or characterization Intermediate 155: 4-formyl-4'-methyl-2-oxo-2H-[1,2'-bipyridine]-5'-carbonitrile

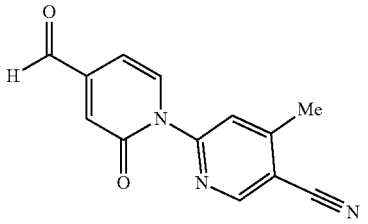

Intermediate 155 was prepared (0.25 g, 25.10%), by using a similar synthetic protocol as that of Intermediate 6 and starting from 2-hydroxyisonicotinaldehyde (0.50 g, 4.06 mmol) and 6-bromo-4-methylnicotinonitrile (0.80 g, 4.06 mmol). $^1$H NMR (400 MHz, DMSO-d6) δ ppm 2.57 (s, 3H) 6.63-6.66 (m, 1H), 7.21 (d, J=1.60 Hz, 1H), 8.05 (t, J=5.2 Hz, 2H), 9.03 (s, 1H), 9.95 (s, 1H), LCMS (Method-D): retention time 2.44 min, [M−H] 238.0.

Intermediate 156: 6-(4-formyl-3-methyl-2-oxo-2,3-dihydro-1H-imidazol-1-yl)-4-methy nicotinonitrile

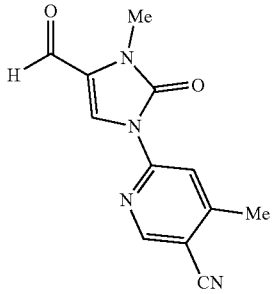

Intermediate 156A: methyl 1-(5-cyano-4-methylpyridin-2-yl)-2-oxo-2,3-dihydro-1H-imidazole-4-carboxylate

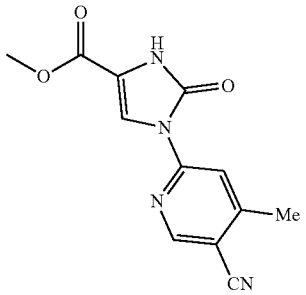

Intermediate 156A was prepared (4.30 g, 79.00%) as a white solid, by using a similar synthetic protocol as that of Intermediate 15C and starting from 6-bromo-4-methylnicotinonitrile (4.16 g, 21.11 mmol) and methyl 2-oxo-2,3-dihydro-1H-imidazole-4-carboxylate (3.00 g, 21.11 mmol). $^1$H NMR (400 MHz, DMSO-$d_6$) δ ppm 2.54 (s, 3H), 3.79 (s, 3H), 7.89 (s, 1H), 8.39 (s, 1H), 8.82 (s, 1H), 11.52 (s, 1H). LCMS (Method-O): retention time 0.88 min, [M+1] 259.1.

Intermediate 156B: methyl 1-(5-cyano-4-methylpyridin-2-yl)-3-methyl-2-oxo-2,3-dihydro-1H-imidazole-4-carboxylate

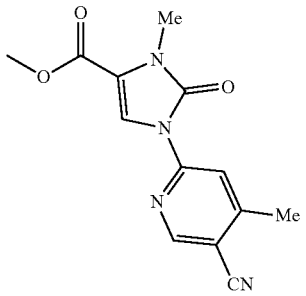

Intermediate 156B was prepared (1.15 g, 99.00%) as a burgundy solid, by using a similar synthetic protocol as that of Intermediate 93B and starting from Intermediate 156A (1.10 g, 4.26 mmol) and iodomethane (2.65 mL, 42.6 mmol). $^1$H NMR (400 MHz, DMSO-$d_6$) δ ppm 2.58 (s, 3H), 3.43 (s, 3H), 3.81 (s, 3H), 8.01 (s, 1H), 8.42 (s, 1H), 8.86 (s, 1H). LCMS (Method-O): retention time 1.07 min, [M+1] 273.5.

Intermediate 156C: 6-(4-(hydroxymethyl)-3-methyl-2-oxo-2,3-dihydro-1H-imidazol-1-yl)-4-methylnicotinonitrile

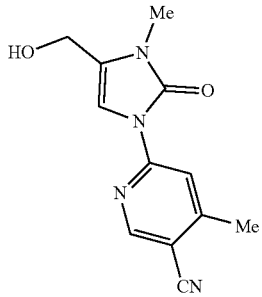

Intermediate 156C was prepared (0.80 g, 69.00%) as a burgundy solid, by using a similar synthetic protocol as that of Intermediate 60B and starting from Intermediate 156B (1.30 g, 4.77 mmol) and $NaBH_4$ (0.90 g, 23.87 mmol). $^1$H NMR (400 MHz, DMSO-$d_6$) δ ppm 2.25 (s, 3H), 3.24 (s, 3H), 4.36 (br.s, 2H), 5.25 (br.s, 1H), 7.28 (s, 1H), 8.45 (s, 1H), 8.79 (s, 1H). LCMS (Method-O): retention time 0.69 min, [M+1] 245.4.

Intermediate 156

Intermediate 156 was prepared (0.070 g, crude) as a white solid, by using a similar synthetic protocol as that of Intermediate 9 and starting from Intermediate 156C (1.50 g, 6.20 mmol). LCMS (Method-O): retention time 0.92 min, [M+1] 243.5. The compound was taken directly to the subsequent step without further purification or characterization.

Intermediate 157: 6-(3-(difluoromethyl)-4-formyl-1H-pyrazol-1-yl)-4-methylnicotinonitrile

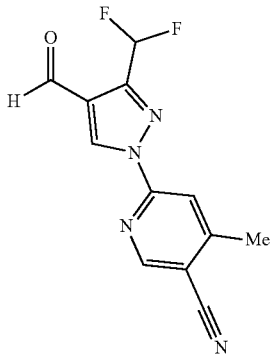

Intermediate 157A: (3-(difluoromethyl)-1H-pyrazol-4-yl)methanol

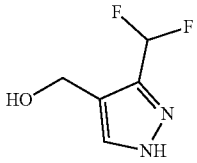

Intermediate 157A was prepared (1.40 g, 71.90%), by using a similar synthetic protocol as that of Intermediate 67A and starting from ethyl 3-(difluoromethyl)-1H-pyrazole-4-carboxylate (2.50 g, 13.15 mmol) and DIBAL-H (39.40 mL, 39.40 mmol). $^1$H NMR (400 MHz, DMSO-d6) δ ppm 4.48 (d, J=5.02 Hz, 2H), 4.96 (t, J=5.27 Hz, 1H), 6.77-7.15 (m, 1H), 7.72 (s, 1H), 13.06 (br. s., 1H). LCMS (Method-D): retention time 0.394 min, [M+H] 149.2.

Intermediate 157B:
3-(difluoromethyl)-1H-pyrazole-4-carbaldehyde

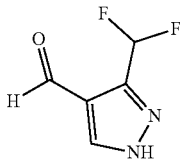

Intermediate 157B was prepared (1.00 g, 50.70%), by using a similar synthetic protocol as that of Intermediate 152C and starting from Intermediate 157A (1.00 g, 6.75 mmol) and manganese dioxide (1.17 g, 13.50 mmol). $^1$H NMR (400 MHz, DMSO-$d_6$) δ ppm 7.01-7.38 (m, 1H), 8.62 (s, 1H), 9.94 (s, 1H), 13.94 (br. s., 1H). LCMS (Method-H): retention time 0.54 min, [M−H] 145.0. $^{19}$F NMR (400 MHz, DMSO-$d_6$) δ ppm −112.87.

Intermediate 157

Intermediate 157 was prepared (0.50 g, 43.50%), by using a similar synthetic protocol as that of Intermediate 6 and starting from Intermediate 157B (0.25 g, 1.71 mmol) and 6-bromo-4-methylnicotinonitrile (0.34 g, 1.711 mmol). $^1$H NMR (400 MHz, DMSO-$d_6$) δ ppm 2.66 (s, 3H), 7.30-7.41 (m, 1H), 8.12 (s, 1H), 8.99 (s, 1H), 9.50 (s, 1H), 10.04 (s, 1H). LCMS (Method-D): retention time 1.48 min, [M−H] 261.0.

Intermediate 158: 6-(3-cyclopropyl-4-formyl-1H-pyrazol-1-yl)-4-methylnicotinonitrile

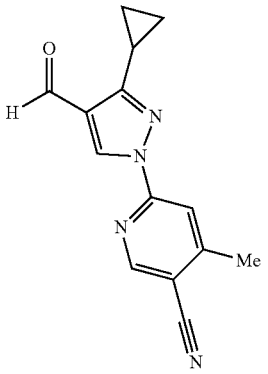

Intermediate 158A:
(3-cyclopropyl-1H-pyrazol-4-yl)methanol

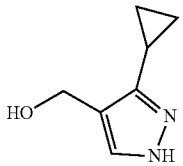

Intermediate 158A was prepared (2.60 g, 67.10%), by using a similar synthetic protocol as that of Intermediate 157A and starting from ethyl 3-cyclopropyl-1H-pyrazole-4-carboxylate (5.00 g, 27.7 mmol). $^1$H NMR (400 MHz, DMSO-d6) δ ppm 0.78-0.90 (m, 4H), 1.78-1.94 (m, 1H), 4.37 (d, J=5.14 Hz, 2H), 4.65 (t, J=5.26 Hz, 1H), 7.24-7.43 (m, 1H), 12.16 (br. s., 1H). LCMS (Method-H): retention time 0.54 min, [M+H] 208.2.

Intermediate 158B:
3-cyclopropyl-1H-pyrazole-4-carbaldehyde

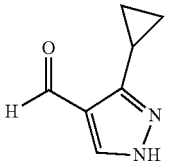

Intermediate 158B was prepared (1.20 g, 39.30%), by using a similar synthetic protocol as that of Intermediate 157B and starting from Intermediate 158A (2.00 g, 14.48 mmol). $^1$H NMR (400 MHz, DMSO-$d_6$) δ ppm 0.78-0.90 (m, 4H), 2.08-2.14 (m, 1H), 7.98-8.19 (m, 1H), 9.90 (s, 1H), (1 Exchangeable proton not observed). LCMS (Method-D): retention time 0.57 min, [M+H] 137.1.

Intermediate 158

Intermediate 158 was prepared (0.03 g, 52.90%), by using a similar synthetic protocol as that of Intermediate 6 and starting from Intermediate 158B (0.03 g, 1.83 mmol) and 6-bromo-4-methylnicotinonitrile (0.04 g, 1.836 mmol). $^1$H NMR (400 MHz, DMSO-$d_6$) δ ppm 0.93-1.12 (m, 4H), 2.50-2.52 (m, 1H), 2.60 (s, 3H), 7.94 (s, 1H), 8.91 (s, 1H), 9.27 (s, 1H), 10.05 (s, 1H). LCMS (Method-H): retention time 2.72 min, [M+H] 253.1.

Intermediate 159: 1-(5-formylpyrimidin-2-yl)-4-methyl-1H-pyrazole-3-carbonitrile

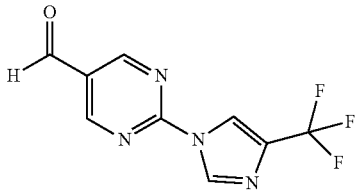

Intermediate 159 was prepared (0.10 g, 58.90%), by using a similar synthetic protocol as that of Intermediate 20 and starting from 2-chloropyrimidine-5-carbaldehyde (0.10 g, 0.70 mmol) and 4-(trifluoromethyl)-1H-imidazole (0.10 g, 0.77 mmol). $^1$H NMR (400 MHz, DMSO-$d_6$) δ ppm 8.62 (t, J=1.60 Hz, 1H), 8.87 (d, J=1.00 Hz, 1H), 9.36 (s, 2H), 10.16 (s, 1H). LCMS (Method-J): retention time 1.80 min, [M+H] 243.0.

Intermediate 160: 2-(4-formyl-2-methyl-1H-imidazol-1-yl)-4-methoxypyrimidine-5-carbonitrile

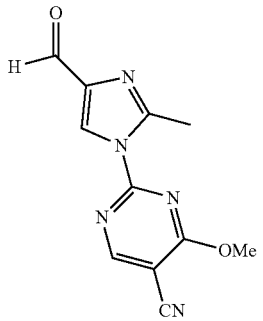

To a stirring solution of 2-methyl-1H-imidazole-4-carbaldehyde (0.24 g, 2.21 mmol) in ACN (25 mL) was added 2-chloro-4-methoxypyrimidine-5-carbonitrile (0.25 g, 1.47 mmol) followed by $K_2CO_3$ (0.20 g, 1.47 mmol) and stirring was continued at ambient temperature for 1 h. The reaction mixture was diluted with water (30 mL). The solid precipitate was filtered, washed with EtOH (2 mL) and dried under vacuum to obtain Intermediate 160 (0.15 g, crude). LCMS (Method-O): retention time 0.81 min, [M+H] 244.1. The compound was taken directly to the subsequent step without further purification or characterization.

Intermediate 161: 6-(4-formyl-1H-imidazol-1-yl)-4-methoxynicotinonitrile

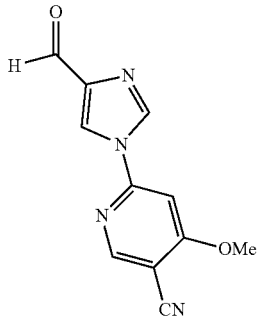

Intermediate 161 was prepared (0.30 g, 25.00%), by using a similar synthetic protocol as that of Intermediate 20 and starting from 1H-imidazole-4-carbaldehyde (0.50 g, 5.20 mmol) and 6-chloro-4-methoxynicotinonitrile (1.05 g, 6.24 mmol). $^1$H NMR (400 MHz, DMSO-$d_6$) δ ppm 4.13 (s, 3H), 7.81 (s, 1H), 8.83 (s, 2H), 8.95 (d, J=1.19 Hz, 1H), 9.87 (s, 1H). LCMS (Method-L): retention time 0.75 min, [M+H] 229.1.

Intermediate 162: 3-(4-(trimethylstannyl)pyridin-2-yl)oxazolidin-2-one

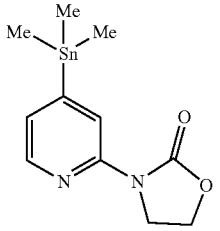

Intermediate 162A: 3-(4-bromopyridin-2-yl)oxazolidin-2-one

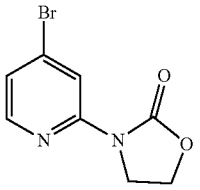

To a stirred solution of 4-bromopyridine-2-amine (5.00 g, 28.90 mmol) in THF (50 mL) was added 2-chloroethyl chloroformate (4.47 mL, 43.30 mmol) and $K_2CO_3$ (11.98 g, 87.00 mmol) and the resulting mixture was heated to 70° C. for 10 h. The reaction mixture was cooled to ambient temperature, concentrated to dryness under reduced pressure, diluted with water (50 mL) and extracted with ethyl acetate (2×100 mL). The combined organic layer was washed with brine (30 mL), dried over anhydrous sodium sulfate and evaporated under reduced pressure. The residue was purified by column chromatography (Redisep—40 g, 10-20% EtOAc/n-hexane) to obtain Intermediate 162A (1.40 g, 20.00%) as a pale yellow solid. $^1$H NMR (400 MHz, DMSO-$d_6$) δ ppm 4.13-4.20 (m, 2H), 4.44-4.50 (m, 2H), 7.41 (dd, J=5.27, 1.76 Hz, 1H), 8.29 (d, J=5.52 Hz, 1H), 8.30 (d, J=1.51 Hz, 1H). LCMS (Method-D), retention time 1.86 min, [M+H] 243.

Intermediate 162

Intermediate 162 was prepared (0.15 g, crude), by using a similar synthetic protocol as that of Intermediate 23A and starting from Intermediate 162A (0.15 g, 0.62 mmol). LCMS (Method-O): retention time 1.30 min, [M+1] 328.2. The compound was taken directly to the subsequent step without further purification or characterization Intermediate 163-I and 163-II: 5-(piperazin-2-yl) isobenzofuran-1(3H)-one (163-I)

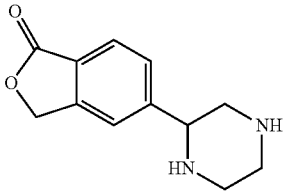

Enantiomer-I (163-II)

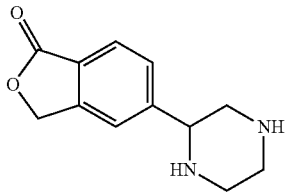

Enantiomer-II

Intermediate 163A: 5-(4,4,5,5-tetramethyl-1,3,2-dioxaborolan-2-yl)isobenzofuran-1(3H)-one

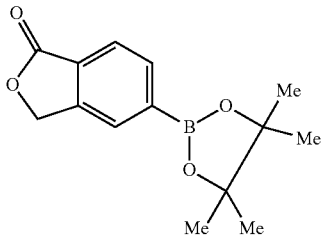

Synthesized according to literature procedures (PCT Int. Appl., 2012037132).

Intermediate 163B: 5-(pyrazin-2-yl)isobenzofuran-1(3H)-one

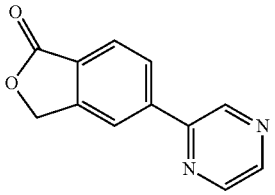

Intermediate 163B was prepared (3.20 g, 49.00%), by using a similar protocol as that of Intermediate 2C and starting from Intermediate 163A (20.44 g, 79.00 mmol) and 2-chloropyrazine (9.00 g, 79.00 mmol). $^1$H NMR (400 MHz, DMSO-$d_6$) δ ppm 5.51 (s, 2H), 8.00 (d, J=8.03 Hz, 1H), 8.35 (dd, J=8.03, 1.51 Hz, 1H), 8.44 (d, J=1.00 Hz, 1H), 8.72 (d, J=2.51 Hz, 1H), 8.81 (dd, J=2.51, 1.51 Hz, 1H), 9.38 (d, J=1.51 Hz, 1H). LCMS (Method-D): retention time 1.11 min, [M+H] 213.0.

Intermediate 163-I and 163-II

Intermediate 163-I and 163-II was prepared by using a similar synthetic protocol as that of Intermediate 2-I and 2-II and starting from Intermediate 163B (5.50 g, 25.90 mmol). The racemate was separated into two individual enantiomers by SFC [Lux Amylose-2 (250×4.6 mm) 5 micron; 0.4% DEA in EtOH, Flow: 3.0 g/min. Temperature: 30° C., UV: 230 nm]. First eluted compound (retention time 1.8 min), designated as Intermediate 163-I, was obtained (0.50 g, 16.70%) as an off-white solid. $^1$H NMR (400 MHz, DMSO-$d_6$) δ ppm 2.43 (d, J=11.55 Hz, 1H), 2.61-2.69 (m, 1H), 2.72-2.86 (m, 2H), 2.92 (d, J=11.55 Hz, 2H), 3.81 (d, J=8.03 Hz, 1H), 5.38 (s, 2H), 7.58 (d, J=8.03 Hz, 1H), 7.68 (s, 1H), 7.78 (d, J=8.03 Hz, 1H), (2 Exchangeable protons not observed). LCMS (Method-D): retention time 0.39 min, [M+H] 219.1. Chiral purity (Method-XV): retention time 3.11 min, 95.80% ee. Second eluted compound (retention time 2.40 min), designated as Intermediate 163-II, was obtained (0.70 g, 23.30%) as an off-white solid. $^1$H NMR (400 MHz, DMSO-$d_6$) δ ppm 2.43 (d, J=11.55 Hz, 1H), 2.61-2.69 (m, 1H), 2.72-2.86 (m, 2H), 2.92 (d, J=11.55 Hz, 2H), 3.81 (d, J=8.03 Hz, 1H), 5.38 (s, 2H), 7.58 (d, J=8.03 Hz, 1H), 7.68 (s, 1H), 7.78 (d, J=8.03 Hz, 1H), (2 Exchangeable protons not observed). LCMS (Method-D) retention time 0.53 min, [M+H] 219.1. Chiral purity (Method-XV): retention time 4.82 min, 90.00% ee.

Intermediate 164-I and 164-II: 4-methyl-5-((2R)-6-methylmorpholin-2-yl)isobenzofuran-1(3H)-one (164-I)

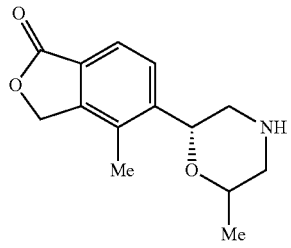

Diastereomer-I (164-II)

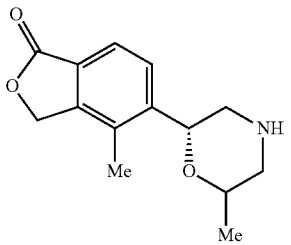

Diastereomer-II

Intermediate 164A-I: 5-((1R)-1-hydroxy-2-((2-hydroxypropyl)amino)ethyl)-4-methylisobenzofuran-1(3H)-one

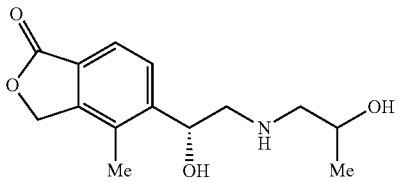

To a stirring solution of Intermediate 1-I (10.00 g, 52.60 mmol) in EtOH (150 mL) was added 1-aminopropan-2-ol (11.85 g, 158.0 mmol) and stirring was continued at 50° C. for 16 h. The reaction mixture was concentrated under reduced pressure and diluted with diethyl ether (50 mL). The solid precipitate was filtered and dried under vacuum to obtain Intermediate 164A-I (8.00 g, 57.40%). $^1$H NMR (400 MHz, DMSO-$d_6$) δ ppm 0.96-1.05 (m, 3H), 1.98 (br. s., 1H), 2.26 (s, 3H), 2.31-2.43 (m, 1H), 2.55-2.69 (m, 1H), 3.47 (br. s., 1H), 4.46 (br. s., 1H), 4.97 (br. s., 1H), 5.38 (d, J=2.01 Hz, 2H), 5.42 (br. s., 1H), 7.65-7.70 (m, 2H), (2 Exchangeable proton not observed). LCMS (Method-O): retention time 0.43 min, [M+H] 266.5.

Intermediate 164-I and 164-II

A stirred solution of Intermediate 164A-I (5.00 g, 18.85 mmol) in 63% HBr (50 mL, 921 mmol) in water was heated at 90° C. for 16 h. The reaction mixture was cooled to ambient temperature, diluted with 10% NaOH solution (100 mL) and extracted with 10% MeOH in DCM (2×250 mL). The combined organic layers were washed with brine (30 mL), dried over anhydrous sodium sulfate and evaporated under reduced pressure. The diastereomer was separated into individual isomer by SFC [Chiralpak AD-H (250×4.6 mm) 5 micron; 0.2% $NH_4OH$ in MeOH, Flow: 4.0 g/min. Temperature: 30° C., UV: 235 nm]. First eluted compound (retention time 6.20 min), designated as Intermediate 164-I, was obtained (0.80 g, 32.00%). $^1$H NMR (400 MHz, DMSO-$d_6$) δ ppm 1.15 (d, J=6.02 Hz, 3H), 2.28 (s, 3H), 2.97-3.09 (m, 2H), 3.32 (br. s., 2H), 3.83 (ddd, J=10.42, 6.15, 2.51 Hz, 1H), 4.89 (dd, J=10.29, 2.26 Hz, 1H), 5.40 (d, J=3.51 Hz, 2H), 7.61 (d, J=8.0 Hz, 1H), 7.68 (d, J=8.0 Hz, 1H), (1 Exchangeable protons not observed). LCMS (Method-D) retention time 0.83 min, [M+H] 248.2. Chiral purity (XXXII): retention time 6.00 min, 99.00% ee. Second eluted compound (retention time 7.80 min), designated as Intermediate 164-II, was obtained (1.00 g, 40.00%) as off-white solid. $^1$H NMR (400 MHz, DMSO-$d_6$) δ ppm 1.15 (d, J=6.02 Hz, 3H), 2.28 (s, 3H), 2.97-3.09 (m, 2H), 3.32 (br. s., 2H), 3.83 (ddd, J=10.42, 6.15, 2.51 Hz, 1H), 4.89 (dd, J=10.29, 2.26 Hz, 1H), 5.40 (d, J=3.51 Hz, 2H), 7.61 (d, J=8.00 Hz, 1H), 7.68 (d, J=8.00 Hz, 1H), (1 Exchangeable protons not observed). LCMS (Method-D) retention time 0.80 min, [M+H] 248.2. Chiral purity (Method-XXXI): retention time 7.62 min, 95.00% ee.

Intermediate 165: 5-(4-((5-bromopyridin-2-yl)methyl)piperazin-2-yl)-4-methylisobenzofuran-1(3H)-one

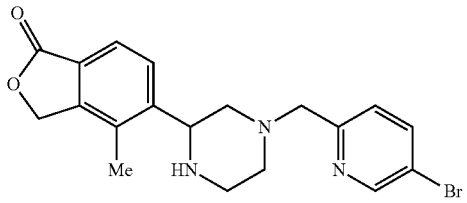

Intermediate 165 was prepared (0.18 g, 15.54%), by using a similar synthetic protocol as that of Intermediate 4 and starting from Intermediate 2-I (0.19 g, 0.81 mmol) and 5-bromopicolinaldehyde (0.15 g, 0.81 mmol). LCMS (Method-D): retention time 1.416 min, [M+2H] 404.0. The compound was taken directly to the subsequent step without further purification or characterization.

Intermediate 166: 2-(1H-1,2,4-triazol-1-yl)pyrimidine-5-carbaldehyde

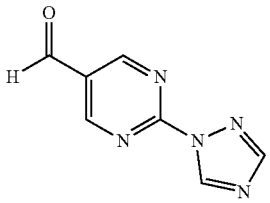

Intermediate 166 was prepared (0.30 g, 33.20%), by using a similar synthetic protocol as that of Intermediate 144 and starting from 2-chloropyrimidine-5-carbaldehyde (0.50 g, 3.51 mmol) and 4H-1,2,4-triazole (0.266 g, 3.86 mmol). $^1$H NMR (400 MHz, DMSO-$d_6$) δ ppm 8.42 (s, 1H), 9.38 (s, 2H), 9.58 (s, 1H), 10.16 (s, 1H). LCMS (Method-D): retention time 0.43 min, [M+H] 174.2.

Intermediate 167: 1-(5-formylpyridin-2-yl)-4-methyl-1H-pyrazole-3-carbonitrile

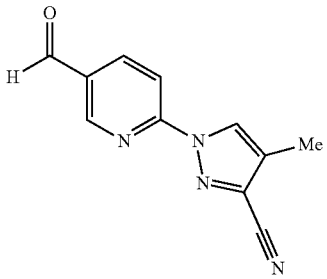

Intermediate 167 was prepared (1.15 g, 52.10%), by using a similar synthetic protocol as that of Intermediate 20 and starting from 6-bromonicotinaldehyde (0.30 g, 1.61 mmol) and 4-methyl-1H-pyrazole-3-carbonitrile (0.19 g, 1.77 mmol). $^1$H NMR (400 MHz, DMSO-$d_6$) δ ppm 2.25 (d, J=1.00 Hz, 3H), 8.15 (d, J=8.53 Hz, 1H), 8.45-8.50 (m, 1H), 8.83 (s, 1H), 9.03-9.07 (m, 1H), 10.14 (s, 1H). LCMS (Method-D): retention time 2.164 min, [M+H] 213.2.

Intermediate 168: 1-(5-formylpyrimidin-2-yl)-4-methyl-1H-pyrazole-3-carbonitrile

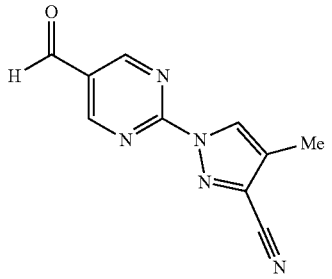

Intermediate 168 was prepared (0.30 g, 40.10%), by using a similar synthetic protocol as that of Intermediate 144 and starting from 2-chloropyrimidine-5-carbaldehyde (0.50 g, 3.51 mmol) and 4-methyl-1H-pyrazole-3-carbonitrile (0.41 g, 3.86 mmol). $^1$H NMR (400 MHz, DMSO-$d_6$) δ ppm 2.23 (d, J=1.00 Hz, 3H), 8.85 (d, J=1.00 Hz, 1H), 8.90 (s, 1H), 9.36 (s, 1H), 10.15 (s, 1H). LCMS (Method-D): retention time 1.54 min, [M+H] 214.0.

Intermediate 169: 1-(5-formylpyrimidin-2-yl)-4-methyl-1H-pyrazole-3-carbonitrile

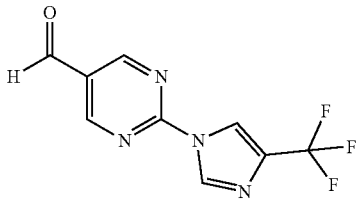

Intermediate 169 was prepared (0.10 g, 58.90%), by using a similar synthetic protocol as that of Intermediate 144 and starting from 2-chloropyrimidine-5-carbaldehyde (0.10 g, 0.70 mmol) and 4-(trifluoromethyl)-1H-imidazole (0.11 g, 0.77 mmol). $^1$H NMR (400 MHz, DMSO-d6) δ ppm 8.62 (t, J=1.60 Hz, 1H), 8.87 (d, J=1.00 Hz, 1H), 9.36 (s, 2H), 10.16 (s, 1H). LCMS (Method-J): retention time 1.80 min, [M+H] 243.0.

Intermediate 170: 1-(5-formylpyridin-2-yl)-4-methyl-1H-pyrazole-3-carbonitrile

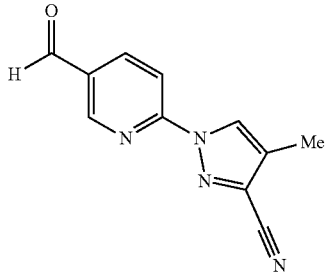

Intermediate 170 was prepared (0.20 g, 58.40%), by using a similar synthetic protocol as that of Intermediate 20 and starting from 6-bromonicotinaldehyde (0.3 g, 1.61 mmol) and 4-methyl-1H-pyrazole-3-carbonitrile (0.19 g, 1.77 mmol). $^1$H NMR (400 MHz, DMSO-$d_6$) δ ppm 2.25 (d, J=1.00 Hz, 3H), 8.15 (d, J=8.53 Hz, 1H), 8.45-8.50 (m, 1H), 8.83 (s, 1H), 9.03-9.07 (m, 1H), 10.14 (s, 1H). LCMS (Method-D): retention time 2.16 min, [M+H] 213.2.

Intermediate 171: 1-(5-formylpyrimidin-2-yl)-4-methyl-1H-pyrazole-3-carbonitrile

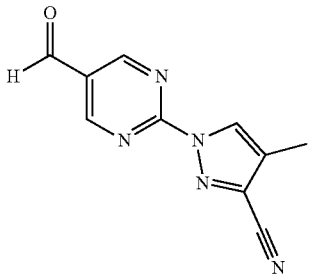

Intermediate 171 was prepared (0.30, 40.10%), by using a similar synthetic protocol as that of Intermediate 144 and starting from 2-chloropyrimidine-5-carbaldehyde (0.50 g, 3.51 mmol) in 4-methyl-1H-pyrazole-3-carbonitrile (0.413 g, 3.86 mmol). $^1$H NMR (400 MHz, DMSO-d6) δ ppm 2.23 (d, J=1.00 Hz, 3H), 8.85 (d, J=1.00 Hz, 1H), 8.90 (s, 1H), 9.36 (s, 1H), 10.15 (s, 1H). LCMS (Method-D): retention time 1.54 min, [M+H] 214.0.

Intermediate 172: 1-(5-formylpyrimidin-2-yl)-4-methyl-1H-pyrazole-3-carbonitrile

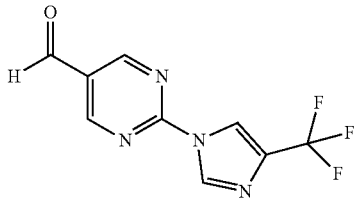

Intermediate 172 was prepared (0.10 g, 58.90%), by using a similar synthetic protocol as that of Intermediate 144 and starting from 2-chloropyrimidine-5-carbaldehyde (0.10 g, 0.70 mmol) and 4-(trifluoromethyl)-1H-imidazole (0.10 g, 0.77 mmol). $^1$H NMR (400 MHz, DMSO-$d_6$) δ ppm 8.62 (t, J=1.6 Hz, 1H), 8.87 (d, J=1.00 Hz, 1H), 9.36 (s, 2H), 10.16 (s, 1H). LCMS (Method-J), retention time 1.80 min, [M+H] 243.0.

Intermediate 173: 6-(1H-1,2,4-triazol-1-yl)nicotinaldehyde

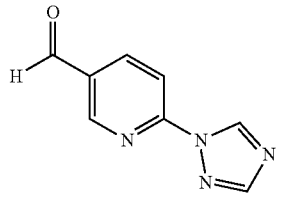

Intermediate 173 was prepared (0.30 g, 49.30%), by using a similar synthetic protocol as that of Intermediate 138 and starting from 6-bromonicotinaldehyde (0.50 g, 2.69 mmol) and 4H-1,2,4-triazole (0.204 g, 2.96 mmol). $^1$H NMR (400 MHz, DMSO-$d_6$) δ ppm 8.07 (d, J=8.31 Hz, 1H), 8.41 (br. s., 1H), 8.51 (d, J=7.83 Hz, 1H), 9.07 (br. s., 1H), 9.52 (br. s., 1H), 10.15 (br. s., 1H), LCMS (Method-O): retention time 0.62 min, [M+H] 175.2.

Intermediate 174-I: (R)-5-(4-((6-bromopyridin-3-yl) methyl)piperazin-2-yl)-4-methylisobenzofuran-1 (3H)-one

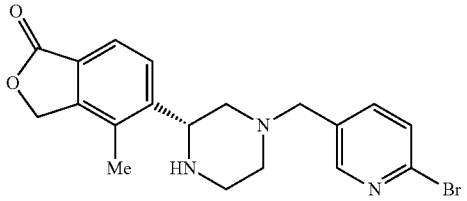

Intermediate 174-I was prepared (0.22 g, 24.50%), by using a similar synthetic protocol as that of Intermediate 4 and starting from Intermediate 2-I (0.18 g, 0.77 mmol) and 5-bromopicolinaldehyde (0.12 g, 0.64 mmol). LCMS (Method-D): retention time 1.02 min, [M+2H] 404.4. The compound was taken directly to the subsequent step without further purification or characterization.

Intermediate 175: N-(3-(4-methyl-1-oxo-1,3-dihydroisobenzofuran-5-yl)piperidin-4-yl)acetamide

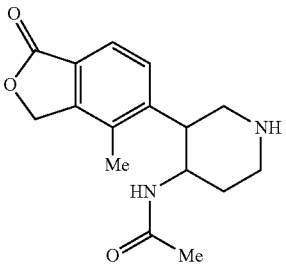

Intermediate 175A: tert-butyl 4-amino-3-(4-methyl-1-oxo-1,3-dihydroisobenzofuran-5-yl)piperidine-1-carboxylate

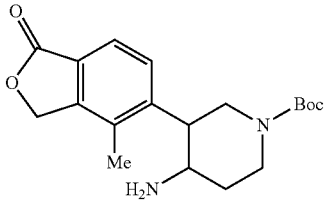

To a stirred solution of Intermediate 4A (0.20 g, 0.58 mmol) in MeOH (20 mL) was added ammonium acetate (0.13 g, 1.74 mmol) and stirring was continued at ambient temperature for 12 h. To the resulting solution, $NaCNBH_4$ (0.07 g, 1.16 mmol) was added and stirring was continued at ambient temperature for 8 h. The reaction mixture was concentrated to dryness under reduced pressure, diluted with saturated solution of $NaHCO_3$ (50 mL) and extracted with ethyl acetate (2×40 mL). The combined organic layer was washed with brine (30 mL), dried over anhydrous sodium sulfate and evaporated under reduced pressure. The residue was taken into diethyl ether (30 mL), and solid precipitate was filtered and dried under vacuum to obtain Intermediate 175A (0.201 g, 99.10%). LCMS (Method-I): retention time 0.91 min, [M−H] 291.5. The compound was taken directly to the subsequent step without further purification or characterization.

Intermediate 175B: tert-butyl 4-acetamido-3-(4-methyl-1-oxo-1,3-dihydroisobenzofuran-5-yl)piperidine-1-carboxylate

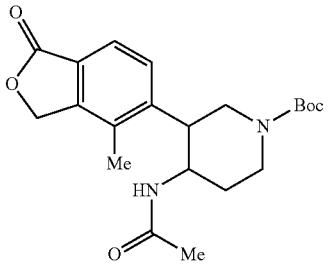

To a stirred solution of Intermediate 175A (0.18 g, 0.52 mmol) in DCM (10 mL) was added TEA (0.22 mL, 1.56 mmol) followed by acetyl chloride (0.06 mL, 0.78 mmol) at 0° C. and the resulting reaction mixture was stirred at ambient temperature for 2 h. The reaction mixture was diluted with water (50 mL) and extracted with DCM (3×50 mL). The combined organic layers were washed with brine (30 mL), dried over anhydrous sodium sulfate and evaporated under reduced pressure. The residue was taken into diethyl ether (20 mL), and solid precipitate was filtered and dried under vacuum to obtain Intermediate 175B (0.20 g, 99.00%) as a yellow solid. LCMS (Method-I): retention time 1.19 min, [M+1] 387.4. The compound was taken directly to the subsequent step without further purification or characterization.

Intermediate 175

Intermediate 175 was prepared (0.160 g, crude) as a yellow solid, by using a similar synthetic protocol as that of Intermediate 19-I and starting from Intermediate 175B (0.15 g, 0.38 mmol)

and TFA (0.300 mL, 3.86 mmol). LCMS (Method-I): retention time 0.38 min, [M+1] 289.6. The compound was taken directly to the subsequent step without further purification or characterization.

Intermediate 176: 1-(6-methyl-4-(2-oxooxazolidin-3-yl)pyridin-2-yl)-1H-pyrazole-4-carbaldehyde

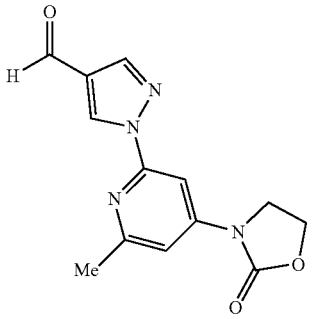

Intermediate 176A: 1-(4-amino-6-methylpyridin-2-yl)-1H-pyrazole-4-carbaldehyde

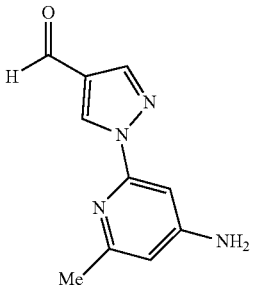

Intermediate 176 was prepared (2.10 g, 64.70%), by using a similar synthetic protocol as that of Intermediate 6 and starting from 1H-pyrazole-4-carbaldehyde (1.54 g, 16.04 mmol) and 2-bromo-6-methylpyridin-4-amine (3.00 g, 16.04 mmol). $^1$H NMR (400 MHz, DMSO-$d_6$) δ ppm 2.31 (s, 3H), 6.21-6.26 (m, 2H), 6.97 (d, J=2.01 Hz, 1H), 7.62 (s, 1H), 8.19 (s, 1H), 9.15 (s, 1H), 9.94 (s, 1H). LCMS (Method-I): retention time 0.74 min, [M+1] 203.4.

Intermediate 176B: 2-chloroethyl (2-(4-formyl-1H-pyrazol-1-yl)-6-methylpyridin-4-yl)carbamate

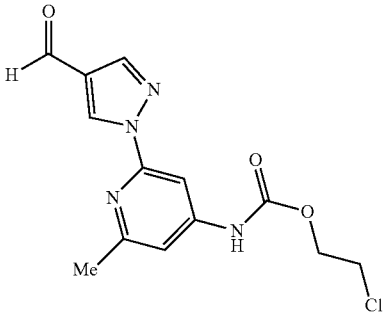

Intermediate 176B was prepared (1.10 g, 72.10%), by using a similar synthetic protocol as that of Intermediate 76A and starting from Intermediate 176A (1.00 g, 4.95 mmol) and 2-chloroethyl carbonochloridate (0.70 mL, 6.43 mmol). $^1$H NMR (400 MHz, DMSO-$d_6$) δ ppm 2.52 (s, 3H), 3.90-3.93 (m, 2H), 4.41-4.43 (m, 2H), 7.33 (s, 1H), 8.03 (s, 1H), 8.26 (s, 1H), 9.24 (s, 1H), 9.96 (s, 1H), 10.59 (s, 1H). LCMS (Method-I): retention time 1.14 min, [M+1] 309.2.

Intermediate 176

Intermediate 176 was prepared (0.60 g, 68.00%), by using a similar synthetic protocol as that of Intermediate 76B and starting from Intermediate 176B (1.00 g, 3.24 mmol) and NaH (0.26 g, 6.48 mmol). $^1$H NMR (400 MHz, DMSO-$d_6$) δ ppm 2.54 (s, 3H), 4.14 (dd, J=9.04, 7.03 Hz, 2H), 4.52 (dd, J=9.04, 7.03 Hz, 2H), 7.35 (d, J=2.01 Hz, 1H), 8.20 (d, J=1.51 Hz, 1H), 8.29 (s, 1H), 9.28 (s, 1H), 9.97 (s, 1H). LCMS (Method-I): retention time 0.90 min, [M+1] 273.1.

Intermediate 177: 1-(6-(2-oxooxazolidin-3-yl)pyridin-2-yl)-1H-pyrazole-4-carbaldehyde

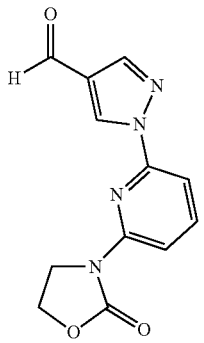

Intermediate 177A: 1-(6-aminopyridin-2-yl)-1H-pyrazole-4-carbaldehyde

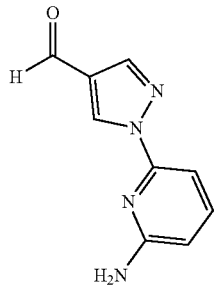

Intermediate 177A was prepared (2.00 g, 51.10%), by using a similar synthetic protocol as that of Intermediate 6 and starting from 1H-pyrazole-4-carbaldehyde (2.00 g, 20.81 mmol) and 6-bromopyridin-2-amine (3.60 g, 20.81 mmol). LCMS (Method-I) retention time 0.72 min, [M+H] 189.4. The compound was taken directly to the subsequent step without further purification or characterization.

Intermediate 177B: 2-chloroethyl (6-(4-formyl-1H-pyrazol-1-yl)pyridin-2-yl)carbamate

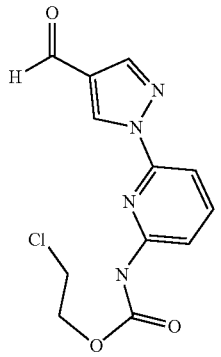

Intermediate 177B was prepared (0.09 g, 60.00%) as a yellow solid, by using a similar synthetic protocol as that of Intermediate 76A and starting from Intermediate 177A (0.05 g, 0.27 mmol) and 2-chloroethyl carbonochloridate (0.04 mL, 0.35 mmol). LCMS (Method-I): retention time 1.06 min, [M+1] 295.4. The compound was taken directly to the subsequent step without further purification or characterization Intermediate 177

Intermediate 177B was prepared (0.01 g, 99.90%) as a yellow solid, by using a similar synthetic protocol as that of Intermediate 76B and starting from Intermediate 177B (0.08 g, 0.27 mmol) and NaH (0.02 g, 0.41 mmol). $^1$H NMR (400 MHz, DMSO-$d_6$) δ ppm 4.20-4.41 (m, 2H), 4.43-4.68 (m, 2H), 7.69 (dd, J=6.53, 2.01 Hz, 1H), 7.87-8.16 (m, 2H), 8.33 (s, 1H), 9.32 (s, 1H), 9.98 (s, 1H). LCMS (Method-I): retention time 0.92 min, [M+1] 259.2.

Intermediate 178: N-(6-(4-formyl-1H-pyrazol-1-yl)pyridin-2-yl)-N-methylmethanesulfonamide

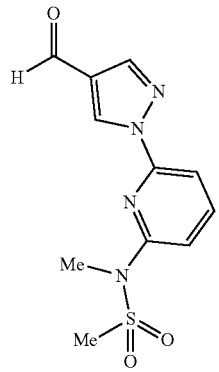

Intermediate 178A: N-(6-(4-formyl-1H-pyrazol-1-yl)pyridin-2-yl)methanesulfonamide

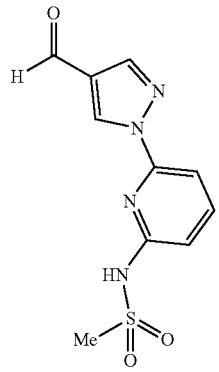

Intermediate 178A was prepared (0.52 g 92.00%) as a yellow solid, by using a similar synthetic protocol as that of Intermediate 59 and starting from Intermediate 177A (0.40 g, 2.13 mmol) and mesyl-Cl (0.23 mL, 2.76 mmol). $^1$H NMR (400 MHz, DMSO-$d_6$) δ ppm 3.76 (s, 3H), 7.82 (d, J=7.53 Hz, 1H), 8.14 (d, J=9.04 Hz, 1H), 8.25-8.32 (m, 1H), 8.37 (s, 1H), 9.40 (s, 1H), 10.00 (s, 1H), (1 Exchangeable proton not observed). LCMS (Method-I): retention time 0.94 min, [M−1] 265.2.

Intermediate 178

Intermediate 178 was prepared (0.150 g, 71.20%) as a pale yellow solid, by using a similar synthetic protocol as that of Intermediate 93B and starting from Intermediate 178A (0.20 g, 0.75 mmol) and iodomethane (1.07 g, 7.51 mmol). $^1$H NMR (400 MHz, DMSO-$d_6$) δ ppm 3.10 (s, 3H), 3.29 (s, 3H), 7.48 (d, J=8.03 Hz, 1H), 7.77 (d, J=8.03 Hz, 1H), 8.08 (t, J=8.03 Hz, 1H), 8.34 (s, 1H), 9.28 (s, 1H), 10.00 (s, 1H). LCMS (Method-I): retention time 0.93 min, [M+1] 281.1.

Intermediate 179: 1-(4-(1,1-dioxidoisothiazolidin-2-yl)-6-methylpyridin-2-yl)-1H-pyrazole-4-carbaldehyde

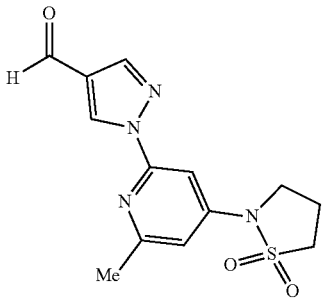

Intermediate 179A: 3-chloro-N-((3-chloropropyl)sulfonyl)-N-(2-(4-formyl-1 H-pyrazol-1-yl)-6-methylpyridin-4-yl)propane-1-sulfonamide

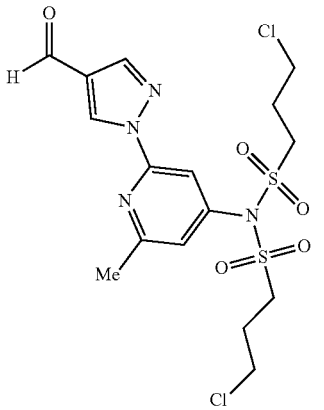

Intermediate 179A was prepared (0.85 g, 53.00%) as a pale yellow solid, by using a similar synthetic protocol as that of Intermediate 59 and starting from Intermediate 176A (0.40 g, 1.97 mmol) and 3-chloropropane-1-sulfonyl chloride (0.70 g, 3.96 mmol). $^1$H NMR (400 MHz, DMSO-$d_6$) δ ppm 1.17 (t, J=7.28 Hz, 4H), 2.64 (s, 3H), 3.71-3.82 (m, 4H), 3.86-3.96 (m, 4H), 7.62 (d, J=1.51 Hz, 1H), 7.88 (s, 1H), 8.36 (s, 1H), 9.35 (s, 1H), 10.00 (s, 1H). LCMS (Method-I): retention time 1.69 min, [M+2H] 485.2.

Intermediate 179B: 3-chloro-N-(2-(4-formyl-1H-pyrazol-1-yl)-6-methylpyridin-4-yl)propane-1-sulfonamide

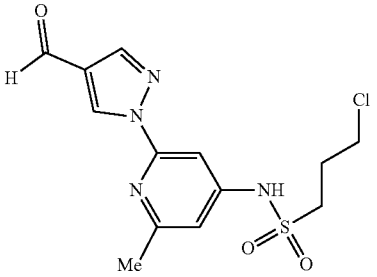

To a solution of Intermediate 179A (0.85 g, 1.76 mmol) in THF (15 mL) was added NaH (0.141 g, 3.52 mmol) and the resulting reaction mixture was stirred for 4 h. The reaction mixture was diluted with saturated $NH_4Cl$ solution (50 mL) and extracted with ethyl acetate (2×50 mL). The combined organic layers were washed with brine (30 mL), dried over anhydrous sodium sulfate and evaporated under reduced pressure. The residue was triturated by diethyl ether (30 mL) and dried under vacuum to obtain Intermediate 179B (0.50 g, 83.00%) as a yellow solid. LCMS (Method-I): retention time 1.11 min, [M+H] 343.2. The compound was taken directly to the subsequent step without further purification or characterization.

Intermediate 179

Intermediate 179 was prepared (0.35 g, 79.54%) as a pale yellow solid, by using a similar synthetic protocol as that of Intermediate 76B and starting from Intermediate 179B (0.50 g, 1.46 mmol) and NaH (0.12 g, 2.92 mmol). $^1$H NMR (400 MHz, DMSO-$d_6$) δ ppm 2.40-2.49 (m, 3H), 3.60-3.69 (m, 3H), 3.83-3.92 (m, 3H), 7.00 (d, J=1.51 Hz, 1H), 7.62 (d, J=2.01 Hz, 1H), 8.28 (s, 1H), 9.27 (s, 1H), 9.97 (s, 1H). LCMS (Method-I): retention time 1.13 min, [M+H] 307.2.

Intermediate 180: (1-(2-methoxypyridin-4-yl)-5-oxopyrrolidin-3-yl)methyl methanesulfonate

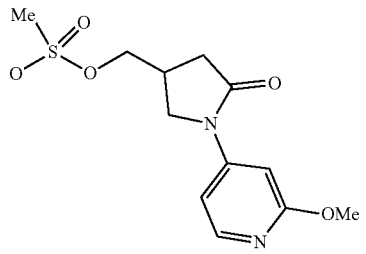

Intermediate 180A: methyl 1-(2-methoxypyridin-4-yl)-5-oxopyrrolidine-3-carboxylate

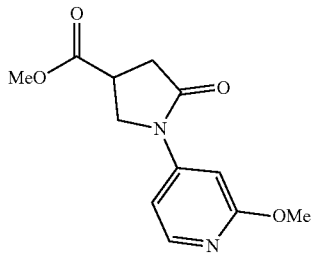

Intermediate 180A was prepared (1.50 g, 86.00%) as a pale yellow solid, by using a similar synthetic protocol as that of Intermediate 15C and starting from 4-bromo-2-methoxypyridine (1.31 g, 6.99 mmol) and methyl 5-oxopyrrolidine-3-carboxylate (1.00 g, 6.99 mmol). $^1$H NMR (400 MHz, DMSO-$d_6$) δ ppm 2.71-2.90 (m, 2H), 3.69 (s, 3H), 3.84 (s, 3H), 3.97 (dd, J=10.04, 5.52 Hz, 2H), 4.03-4.13 (m, 1H), 7.05 (d, J=2.01 Hz, 1H), 7.36 (dd, J=6.02, 2.01 Hz, 1H), 8.09 (d, J=5.52 Hz, 1H). LCMS (Method-I) retention time 0.90 min, [M+H] 251.4.

Intermediate 180B: 4-(hydroxymethyl)-1-(2-methoxypyridin-4-yl)pyrrolidin-2-one

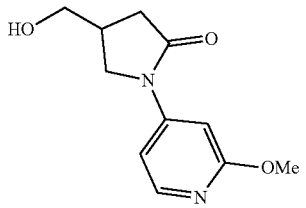

Intermediate 180B was prepared (0.85 g, 96.00%) as a pale yellow solid, by using a similar synthetic protocol as that of Intermediate 60B and starting from Intermediate 180A (1.00 g, 4.00 mmol) and $NaBH_4$ (0.45 g, 11.99 mmol). $^1$H NMR (400 MHz, $CD_3OD$) δ ppm 2.48 (dd, J=16.56, 6.02 Hz, 1H), 2.61-2.80 (m, 2H), 3.55-3.69 (m, 2H), 3.73 (dd, J=10.04, 5.52 Hz, 1H), 3.91 (s, 3H), 4.00 (dd, J=9.54, 8.03 Hz, 1H), 7.14 (d, J=1.51 Hz, 1H), 7.25-7.47 (m, 1H), 8.06 (d, J=6.02 Hz, 1H), (1 Exchangeable proton not observed). LCMS (Method-I): retention time 0.58 min, [M+H] 223.3.

Intermediate 180

Intermediate 180B was prepared (0.45 g, 83.00%) as an off-white solid, by using a similar synthetic protocol as that of Intermediate 59 and starting from Intermediate 180B (0.40 g, 1.80 mmol) and mesyl chloride (0.17 mL, 2.16 mmol). $^1$H NMR (400 MHz, DMSO-$d_6$) δ ppm 2.44 (dd, J=17.32, 6.78 Hz, 1H), 2.69-2.80 (m, 1H), 2.83-2.95 (m, 1H), 3.02-3.14 (m, 1H), 3.16-3.26 (m, 3H), 3.64 (dd, J=10.04, 6.02 Hz, 1H), 3.84 (s, 3H), 3.98 (dd, J=10.04, 8.03 Hz, 1H), 4.12-4.44 (m, 1H), 7.05 (d, J=1.51 Hz, 1H), 7.24-7.54 (m, 1H), 8.10 (d, J=5.52 Hz, 1H). LCMS (Method-I): retention time 0.84 min, [M+H] 301.3.

Intermediate I81: (R)-5-(6,6-dimethylmorpholin-2-yl)-4-methylisobenzofuran-1(3H)-one

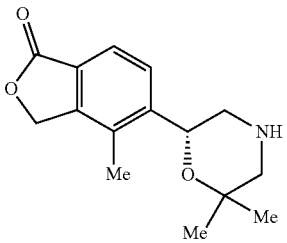

Intermediate I81A-I: (R)-5-(1-hydroxy-2-((2-hydroxy-2-methylpropyl)amino)ethyl)-4-methylisobenzofuran-1(3H)-one

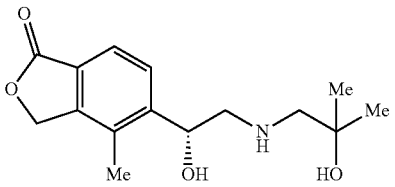

Intermediate 181A-I was prepared (1.00, 34.70%) as a pale yellow solid, by using a similar synthetic protocol as that of Intermediate 164A-I and starting from Intermediate 1-I (1.00 g, 5.26 mmol) and 1-amino-2-methylpropan-2-ol (1.00 g, 11.22 mmol). $^1$H NMR (300 MHz, DMSO-$d_6$) δ ppm 0.98-1.19 (m, 6H), 2.21-2.32 (s, 3H), 2.60-2.67 (m, 2H), 2.70-2.75 (m, 2H), 4.14-4.31 (m, 1H), 4.97-5.12 (m, 1H), 5.34-5.40 (m, 2H), 5.42-5.48 (m, 1H), 7.53-7.80 (m, 2H), (1 Exchangeable proton not observed). LCMS (Method-O): retention time 0.57 min, [M+H] 280.0.

Intermediate I81B-I: (R)-5-(2-(benzyl(2-hydroxy-2-methylpropyl)amino)-1-hydroxyethyl)-4-methyl-isobenzofuran-1(3H)-one

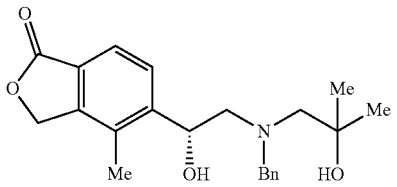

Intermediate 181B-I was prepared (1.30 g, 38.30%) as a pale yellow solid, by using a similar synthetic protocol as that of Intermediate 4 and starting from Intermediate 181A-I (2.00 g, 7.16 mmol) and benzaldehyde (0.91 g, 8.59 mmol). LCMS (Method-L): retention time 0.78 min, [M+1] 370.

Intermediate I81C-I: (R)-5-(4-benzyl-6,6-dimethyl-morpholin-2-yl)-4-methylisobenzofuran-1(3H)-one

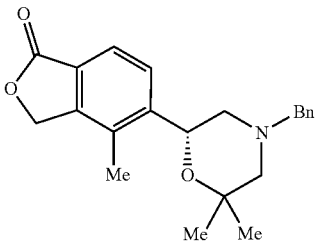

Intermediate 181C-I was prepared (0.45 g, 26.90%) as a brown solid, by using a similar synthetic protocol as that of 50 Intermediate 164-I and starting from Intermediate 181B-I (1.30 g, 3.52 mmol). $^1$H NMR (400 MHz, DMSO-$d_6$) δ ppm 1.20 (s, 3H), 1.43 (s, 3H), 1.75-1.86 (m, 1H), 1.88-2.01 (m, 1H), 2.23 (s, 3H), 2.56-2.70 (m, 1H), 2.75-2.97 (m, 1H), 3.43-3.66 (m, 2H), 4.97-5.15 (m, 1H), 5.38 (s, 2H), 7.33-7.35 (m, 5H), 7.61-7.65 (m, 2H). LCMS (Method-O): retention time 1.67 min, [M+1] 352.4.

Intermediate 181-I

A solution of Intermediate 181B-I (0.40 g, 1.14 mmol) in a mixture of MeOH (40 mL) and THF (10 mL) was purged with nitrogen for 2 minutes. 10% Pd/C (0.100 g, 0.09 mmol)

was added and reaction mixture was stirred at ambient temperature for 16 h under $H_2$ atmosphere. The reaction mixture was filtered through Celite® and filtrate was concentrated under vacuum. The residue was triturated with diethyl ether (50 mL) and dried under vacuum to obtain Intermediate 181-I (0.350 g, 99.00%) as a pale brown solid $^1$H NMR (400 MHz, DMSO-$d_6$) δ ppm 1.17 (s, 3H), 1.36 (s, 3H), 2.35 (s, 3H), 2.50-2.57 (m, 2H), 2.68-2.71 (m, 1H), 2.95 (dd, J=12.80, 2.26 Hz, 1H), 4.97 (dd, J=10.54, 2.51 Hz, 1H), 5.38 (s, 2H), 7.50-7.80 (m, 2H), (1 Exchangeable proton not observed). LCMS (Method-O): retention time 0.81 min, [M+1] 262.4.

Intermediate 182: 1-(5-cyano-4-methoxypyridin-2-yl)-4-formyl-N-methyl-1H-pyrazole-3-carboxamide

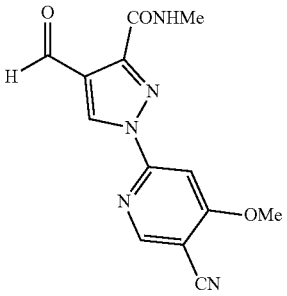

Intermediate 182A: Ethyl 1-(5-cyano-4-methoxypyridin-2-yl)-4-formyl-1H-pyrazole-3-carboxylate

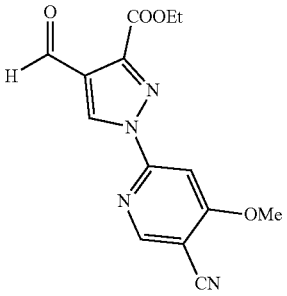

Intermediate 182A was prepared (0.50 g, 21.05%) as a brown solid, by using a similar synthetic protocol as that of Intermediate 6 and starting from 6-chloro-4-methoxynicotinonitrile (1.00 g, 5.93 mmol) and ethyl 4-formyl-1H-pyrazole-3-carboxylate (1.49 g, 8.90 mmol). $^1$H NMR (400 MHz, DMSO-$d_6$) δ ppm 1.35 (d, J=7.60 Hz, 3H), 4.18 (s, 3H), 4.43 (q, J=7.20 Hz, 2H), 7.79 (s, 1H), 8.88 (s, 1H), 9.19 (s, 1H), 10.26 (s, 1H). LCMS (Method-L): retention time 1.11 min, [M+1] 301.4.

Intermediate 182B: 1-(5-cyano-4-methoxypyridin-2-yl)-4-formyl-1H-pyrazole-3-carboxylic acid

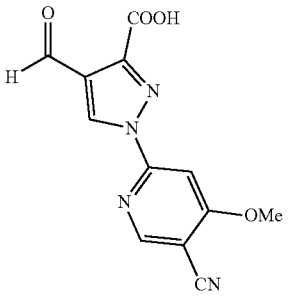

To a solution of Intermediate 182A (0.30 g, 0.99 mmol) in a mixture of water (5 mL) and THF (15 mL) was added LiOH (0.48 g, 1.99 mmol) and the resulting mixture was stirred at ambient temperature for 4 h. The reaction mixture was concentrated under vacuum and diluted with water (30 mL), acidified with 1N HCl solution and extracted with ethyl acetate (2×50 mL). The combined organic layers were washed with brine (50 mL), dried over anhydrous sodium sulfate and evaporated under reduced pressure to obtain Intermediate 182B (0.30 g, 56.30%) as an off-white solid. $^1$H NMR (400 MHz, DMSO-$d_6$) δ ppm 4.11 (s, 3H), 7.65 (s, 1H), 8.73 (s, 1H), 9.09 (s, 1H), (1H exchangeable proton not observed). LCMS (Method-L): retention time 1.03 min, [M+1] 273.1.

Intermediate 182

To a stirring solution of Intermediate 182B (0.10 g, 0.37 mmol) in DMF (10 mL) was added HATU (280 mg, 0.74 mmol), methanamine HCl (0.12 g, 1.84 mmol) followed by TEA (0.26 ml, 1.84 mmol) and the resulting reaction mixture was stirred at ambient temperature for 16 h. The reaction mixture was diluted with water (30 mL) and extracted with ethyl acetate (2×25 mL). The combined organic layers were washed with brine (50 mL), dried over anhydrous sodium sulfate and evaporated under reduced pressure obtain Intermediate 182 (0.20 g, 51.50%) as a brown solid. LCMS (Method-O): retention time 0.87 min, [M+1] 286.4. The compound was taken directly to the subsequent step without further purification or characterization.

Intermediate 183: 1-(5-cyano-4-methoxypyridin-2-yl)-4-formyl-1H-pyrazole-3-carboxamide

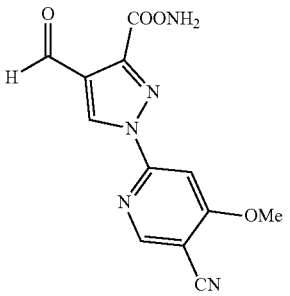

Intermediate 183 was prepared (0.30 g, 15.05%) as a brown solid, by using a similar synthetic protocol as that of Intermediate 182 and starting from Intermediate 182B (0.20 g, 0.74 mmol) and ammonium chloride (0.39 g, 7.35 mmol). LCMS (Method-O): retention time 0.78 min, [M+1] 272. The compound was taken directly to the subsequent step without further purification or characterization.

Intermediate 184: 6-(4-formyl-1H-1,2,3-triazol-1-yl)-4-(methoxy-d3)nicotinonitrile

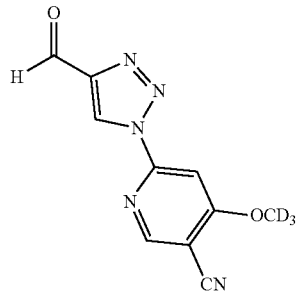

Intermediate 184A: 6-chloro-4-(methoxy-$d_3$) nicotinonitrile

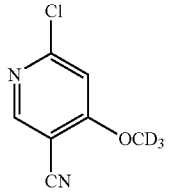

To a stirring solution of $CD_3OD$ (0.20 mL, 5.78 mmol) and NaH (0.116 g, 2.89 mmol) in THF (10 mL) was added 4,6-dichloronicotinonitrile (1.00 g, 5.78 mmol) in DMA (20 mL) at 0° C. The resulting reaction mixture was stirred at ambient temperature for 2 h. The reaction mixture was diluted with water (30 mL) and extracted with ethyl acetate (2×75 mL). The combined organic layers were washed with brine (50 mL), dried over anhydrous sodium sulfate and evaporated under reduced pressure. The residue was purified by column chromatography (Redisep—24 g, 0-100% EtOAc/n-hexane)) to obtain Intermediate 184A (0.25 g, 25.20%) as an off-white solid. $^1$H NMR (300 MHz, $CDCl_3$) δ ppm 7.26 (s, 1H), 8.48 (s, 1H). LCMS (Method-L): retention time 1.09 min, [M+1]173.1.

Intermediate 184B: 6-(4-(hydroxymethyl)-2H-1,2,3-triazol-2-yl)-4-(methoxy-d3)nicotinonitrile and Intermediate 184C: 6-(4-(hydroxymethyl)-1H-1,2,3-triazol-1-yl)-4-(methoxy-d3)nicotinonitrile

184B

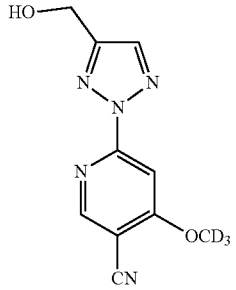

184C

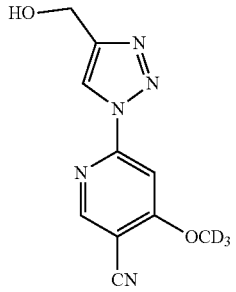

Intermediate 184B and 184C was prepared, by using a similar synthetic protocol as that of Intermediate 20 and starting from Intermediate 184A (0.22 g, 1.28 mmol) and Intermediate 28A (0.25 g, 2.56 mmol). First eluted compound designated as Intermediate 184B, was obtained (0.12 g, 40.00%) as off-white solid. $^1$H NMR (400 MHz, DMSO-$d_6$) δ ppm 4.68 (s, 2H), 5.50 (s, 1H), 7.71 (s, 1H), 8.20 (s, 1H), 8.85 (s, 1H). LCMS (Method-O): retention time 0.70 min, [M+1] 235.5. Second eluted compound designated as Intermediate 184C, was obtained (0.06 g, 19.98%) as a pale yellow solid. $^1$H NMR (400 MHz, DMSO-$d_6$) δ ppm 4.63 (s, 2H), 5.40 (s, 1H), 7.89 (s, 1H), 8.72 (s, 1H), 8.90 (s, 1H). LCMS (Method-O): retention time 0.70 min, [M+1] 235.5.

Intermediate 184

Intermediate 184 was prepared (0.05 g, 99.90%) as a brown solid, by using a similar synthetic protocol as that of Intermediate 9 and starting from Intermediate 184B (0.05 g, 0.21 mm) and Dess-martin periodinane (0.18 g, 0.43 mmol). $^1$H NMR (400 MHz, DMSO-$d_6$) δ ppm 8.01 (s, 1H), 8.98 (s, 1H), 9.61 (s, 1H), 10.15 (s, 1H). LCMS: The compound did not ionize well.

Intermediate 185:
6-(5-methyl-1,2,4-oxadiazol-3-yl)nicotinaldehyde

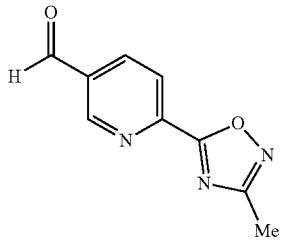

Intermediate 185A: methyl
6-((((1-aminoethyl)amino)oxy)carbonyl)nicotinate

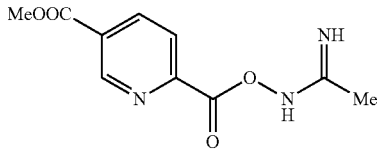

To a solution of 5-(methoxycarbonyl)picolinic acid (0.60 g, 3.31 mmol) in DCM (30 mL) was added oxalyl chloride (0.580 mL, 6.62 mmol) and the resulting reaction mixture was stirred at ambient temperature 1 h. The reaction was evaporated under reduced pressure. The residue was redissolved in THF (20 mL) and added TEA (2.31 ml, 16.56 mmol) followed by (E)-N'-hydroxyacetimidamide (0.37 g, 4.97 mmol). The resulting reaction mixture was stirred at ambient temperature 2 h. The reaction mixture was diluted with water (30 mL) and extracted with ethyl acetate (2×50 mL). The combined organic layers were washed with brine (50 mL), dried over anhydrous sodium sulfate and evaporated under reduced pressure. The residue was purified by column chromatography (Redisep—40 g, 0-100% EtOAc/n-Hexane)) to obtain Intermediate 185A (0.18 g, 22.72%) as an off-white solid. $^1$H NMR (400 MHz, DMSO-$d_6$) δ ppm 1.83 (s, 3H), 3.93 (s, 3H), 6.47 (br.s, 2H), 8.29 (dd, J=0.80, 8.40 Hz, 1H), 8.42 (dd, J=2.00, 8.00 Hz, 1H), 9.17 (s, 1H). LCMS (Method-L): retention time 0.61 min, [M+1] 238.1.

Intermediate 185B: methyl
6-(3-methyl-1,2,4-oxadiazol-5-yl)nicotinate

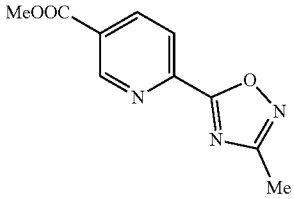

To a stirring solution of Intermediate 185 (0.15 g, 0.63 mmol) in THF (15 mL) was added 1M solution of TBAF in THF (1.26 mL, 1.26 mmol) and resulting reaction mixture was stirred at ambient temperature for 18 h. The reaction mixture was diluted with water (30 mL) and extracted with ethyl acetate (2×25 mL). The combined organic layers were washed with brine (50 mL), dried over anhydrous sodium sulfate and evaporated under reduced pressure. The residue was purified by column chromatography (Redisep—12 g, 0-40% EtOAc/n-hexane) to obtain Intermediate 185B (0.14 g, 100%) as a pale yellow solid. $^1$H NMR (400 MHz, DMSO-$d_6$) δ ppm 2.59 (s, 3H), 4.01 (s, 3H), 8.26 (dd, J=0.80, 8.40 Hz, 1H), 8.49 (dd, J=2.00, 8.00 Hz, 1H), 9.38 (s, 1H). LCMS (Method-L): retention time 0.93 min, [M+1] 220.1.

Intermediate 185C: (6-(3-methyl-1,2,4-oxadiazol-5-yl)pyridin-3-yl)methanol

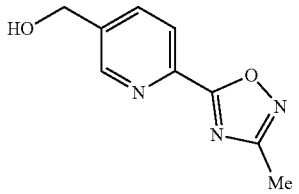

Intermediate 185C was prepared (0.10 g, 96.00%) as an off-white solid, by using a similar synthetic protocol as that of Intermediate 60B and starting from Intermediate 185B (0.12 g, 0.55 mmol) and $NaBH_4$ (0.04 g, 1.00 mmol). $^1$H NMR (400 MHz, DMSO-$d_6$) δ ppm 2.44 (s, 3H), 4.65 (d, J=5.60, 2H), 5.54 (d, J=5.60 Hz, 1H), 7.98 (d, J=6.80 Hz, 1H), 8.19 (d, J=8.00 Hz, 1H), 8.74 (s, 1H). LCMS (Method-I) retention time 0.74 min, [M−H] 192.2.

Intermediate 185

Intermediate 185 was prepared (0.10 g, 39.00%) as a brown solid, by using a similar synthetic protocol as that of Intermediate 9 and starting from Intermediate 185C (0.07 g, 0.37 mm) and Dess-Martin periodinane (0.31 g, 0.73 mmol). LCMS (Method-L): retention time 0.78 min, [M+1] 190.0. The compound was taken directly to the subsequent step without further purification or characterization.

Intermediate 186A and 186B: tert-butyl (5-(4-methyl-1-oxo-1,3-dihydroisobenzofuran-5-yl)piperidin-3-yl)carbamate

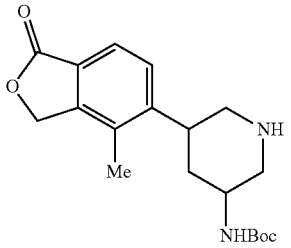

Diastereomer-I (186A)

-continued

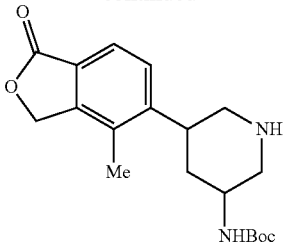

Diastereomer-I (186B)

Intermediate 186C: tert-butyl (5-bromopyridin-3-yl)carbamate

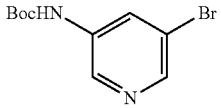

To a stirring solution of 5-bromonicotinic acid HCl salt (4.00 g, 19.80 mmol) in toluene (25 mL) was added TEA (13.80 mL, 99 mmol) followed by diphenylphosphoryl azide (6.54 g, 23.76 mmol) and the resulting mixture was heated at 60° C. for 2 h. The reaction mixture was heated at 100° C. after addition of t-butanol (25 mL), for 18 h. The resulting reaction mixture was evaporated under vacuum, diluted with 10% $NaHCO_3$ solution and extracted with ethyl acetate (2×100 mL). The combined organic layer was washed with brine (50 mL), dried over anhydrous sodium sulfate and evaporated under reduced pressure. The residue was purified by column chromatography (Redisep—40 g, 40-80% EtOAc/n-hexane)) to obtain Intermediate 186C (4.00 g, 74.00%) as a brown solid. $^1$H NMR (300 MHz, DMSO-$d_6$) δ ppm 1.49 (s, 9H), 8.17 (s, 1H), 8.29 (d, J=1.60 Hz, 1H), 8.56 (d, J=1.60 Hz, 1H), 9.82 (s, 1H). LCMS (Method-L): retention time 1.32 min, [M+2] 274.7.

Intermediate 186D: tert-butyl (5-(4-methyl-1-oxo-1,3-dihydroisobenzofuran-5-yl)pyridin-3-yl)carbamate

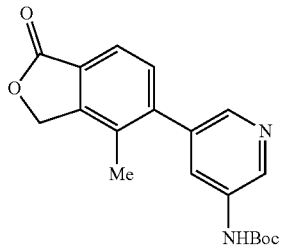

To a stirring solution of Intermediate 186C (4.00 g, 14.65 mmol) in a mixture of dioxane (100 mL) and water (10 mL) was added Intermediate 2B (4.82 g, 17.57 mmol) and $Cs_2CO_3$ (9.54 g, 29.3 mmol). The resulting reaction mixture was purged with nitrogen for 10 minutes and $Pd(Ph_3P)_4$ (0.86 g, 0.73 mmol) was added. The resulting reaction mixture was heated at 100° C. for 18 h and was cooled to ambient temperature. The reaction mixture was filtered through Celite® and the filtrate was concentrated under vacuum. The resulting residue was purified by column chromatography (Redisep—40 g, 0-40% EtOAc/n-Hexane)) to obtain Intermediate 186D (5.00 g, 94.00%) as a light brown solid. $^1$H NMR (300 MHz, DMSO-$d_6$) δ ppm 1.49 (s, 9H), 2.22 (s, 3H), 5.47 (s, 2H), 7.47 (d, J=7.60 Hz, 1H), 7.76 (d, J=7.60 Hz, 1H), 7.93 (d, J=2.00 Hz, 1H), 8.17 (s, 1H), 8.65 (s, 1H), (1H Exchangeable proton not observed). LCMS (Method-O): retention time 1.12 min, [M+1] 341.5.

Intermediate 186A and 186B

Intermediate 186 was prepared as a brown solid, by using a similar synthetic protocol as that of Intermediate 118A and starting from Intermediate 186D (5.00 g, 14.69 mmol). Two diastereomers were separated by SFC [Chiralpak ADH (250×4.6 mm) 5 micron; 0.2% $NH_4OH$ in MeOH, Flow: 1.2 mL/min, Temperature: 27° C., UV: 210 nm]. First eluted compound (retention time 4.08 min), designated as Intermediate 186A: Dia-I, was obtained (0.15 g, 2.96%) as pale yellow solid. $^1$H NMR (400 MHz, DMSO-$d_6$) δ ppm 1.38 (s, 9H), 1.45-1.50 (m, 1H), 1.81-1.96 (m, 1H), 2.33 (s, 3H), 2.40-2.45 (m, 2H), 2.78-2.89 (m, 1H), 2.94-3.11 (m, 2H), 3.36-3.50 (m, 1H), 5.37 (s, 2H), 6.73-6.75 (m, 1H), 7.38 (d, J=8.30 Hz, 1H), 7.64 (d, J=8.30 Hz, 1H). (1 Exchangeable proton not observed). LCMS (Method-O): retention time 0.84 min, [M+1] 347.6. Second eluted compound (retention time 7.99 min), designated as Intermediate 186B: Dia-II, was obtained (0.12 g, 2.37%) as pale yellow solid. $^1$H NMR (400 MHz, DMSO-$d_6$) δ ppm 1.38 (s, 9H), 1.45-1.50 (m, 1H), 1.81-1.96 (m, 1H), 2.33 (s, 3H), 2.40-2.45 (m, 2H), 2.78-2.89 (m, 1H), 2.94-3.11 (m, 2H), 3.36-3.50 (m, 1H), 5.37 (s, 2H), 6.73-6.75 (m, 1H), 7.38 (d, J=8.30 Hz, 1H), 7.64 (d, J=8.30 Hz, 1H), (1 Exchangeable proton not observed). LCMS (Method-O): retention time 0.86 min, [M+1] 347.6.

Intermediate 187: (5-(5-cyano-4-methylpyridin-2-yl)-1,2,4-oxadiazol-3-yl)methyl methanesulfonate

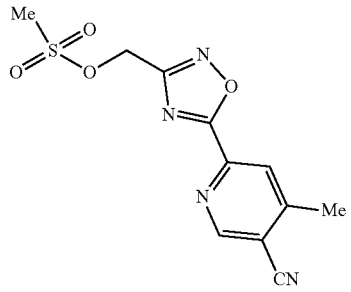

Intermediate 187A: 5-cyano-4-methylpicolinic acid

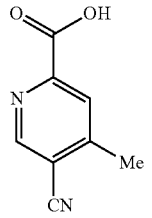

Intermediate 187A was prepared (0.70 g, 76.00%) as an off-white solid, by using a similar synthetic protocol as that of Intermediate 182B and starting from methyl 5-cyano-4-methylpicolinate (1.00 g, 5.68 mmol) and LiOH (0.27 g, 11.35 mmol). $^1$H NMR (300 MHz, DMSO-$d_6$) δ ppm 2.56 (s, 3H), 8.07 (s, 1H), 8.98 (s, 1H), (1H Exchangeable proton not observed). LCMS: (Method-I) retention time: 0.41 min, [M+1]: 163.3.

Intermediate 187B: ethyl 5-(5-cyano-4-methylpyridin-2-yl)-1,2,4-oxadiazole-3-carboxylate

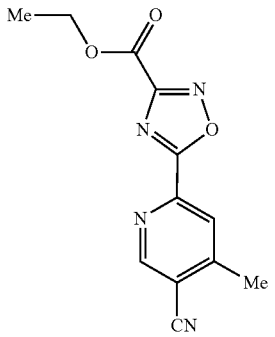

To a stirred solution of Intermediate 187A (0.70 g, 4.32 mmol) in EtOAc (25 mL) was added TEA (2.41 mL, 17.27 mmol), ethyl (Z)-2-amino-2-(hydroxyimino)acetate (0.07 g, 5.18 mmol) followed by 1-propanephosphonic anhydride (5.49 g, 8.63 mmol) at 0° C. and the resulting reaction mixture was heated at 70° C. for 18 h. The reaction mixture was diluted with water (50 mL) and extracted with EtOAc (3×50 mL). The combined organic layers were washed with brine (50 mL), dried over anhydrous sodium sulfate and evaporated under reduced pressure. The residue was purified by column chromatography (Redisep—24 g, 35% EtOAc/n-Hexane) to obtain Intermediate 187B (0.50 g, 44.90%). $^1$H NMR (400 MHz, $CDCl_3$) δ ppm 1.51 (t, J=7.03 Hz, 3H), 2.66-2.77 (s, 3H), 4.59 (q, J=7.36 Hz, 2H), 8.39 (s, 1H), 9.00 (s, 1H). LCMS (Method-I) retention time 1.39 min, [M+H] 259.3.

Intermediate 187C: 6-(3-(hydroxymethyl)-1,2,4-oxadiazol-5-yl)-4-methylnicotinonitrile

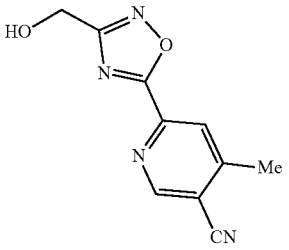

Intermediate 187C was prepared (0.25 g, 42.70%) as an off-white solid, by using a similar synthetic protocol as that of Intermediate 60B and starting from Intermediate 187B (0.70 g, 2.71 mmol) and $NaBH_4$ (0.20 g, 5.42 mmol). $^1$H NMR (300 MHz, DMSO-$d_6$) δ ppm 2.62 (s, 3H), 4.67 (d, J=4.60 Hz, 2H), 5.83 (s, 1H), 8.51 (s, 1H), 9.09 (s, 1H). LCMS (Method-I) retention time 0.74 min, [M−H] 217.0.

Intermediate 187

Intermediate 187 was prepared (0.15 g, 6.61%) as an off-white solid, by using a similar synthetic protocol as that of Intermediate 59 and starting from Intermediate 187C (0.25 g, 1.16 mmol) and mesyl chloride (0.09 mL, 1.16 mmol). $^1$H NMR (300 MHz, DMSO-$d_6$) δ ppm 2.37 (s, 3H), 2.73 (s, 3H), 5.01 (s, 2H), 7.95 (s, 1H), 8.76 (d, J=4.80 Hz, 1H). LCMS (Method-I): retention time 1.08 min, [M+1] 295.2.

Intermediate 188: 1'-methyl-6'-oxo-1',6'-dihydro-[2,3'-bipyridine]-5-carbaldehyde

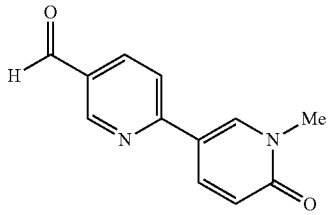

Intermediate 188A: 1-methyl-544,4,5,5-tetramethyl-1,3,2-dioxaborolan-2-yl)pyridin-2(1H)-one

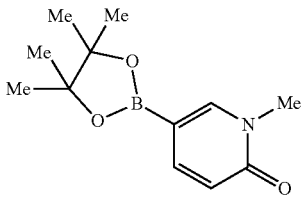

Intermediate 188A was prepared (0.75 g, 60.00%) as a brown solid, by using a similar synthetic protocol as that of Intermediate 2B and starting from 5-bromo-1-methylpyridin-2(1H)-one (0.10 g, 0.53 mmol). LCMS (Method-H): retention time 1.08 min, [M+1] 252.2. The compound was 20 taken directly to the subsequent step without further purification or characterization Intermediate 188

Intermediate 188 was prepared (0.25 g, 24.27%) as a brown solid, by using a similar synthetic protocol as that of Intermediate 2C and starting from Intermediate 188A (0.61 g, 3.27 mmol) and 6-bromonicotinaldehyde. LCMS (Method-O): retention time 0.55 min, [M+1] 215. The compound was taken directly to the subsequent step without further purification or characterization.

Intermediate 189-I, II, III and IV: tert-butyl 3-(hydroxymethyl)-5-(4-methyl-1-oxo-1,3-dihydroisobenzofuran-5-yl)piperidine-1-carboxylate

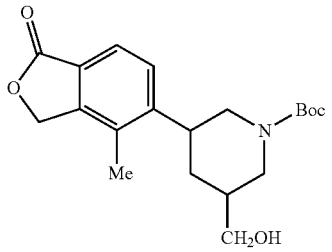

Intermediate 189A: methyl 5-(4-methyl-1-oxo-1,3-dihydroisobenzofuran-5-yl)nicotinate

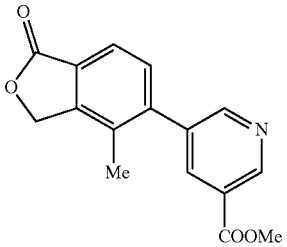

Intermediate 189A was prepared (1.30 g, 63.00%) as a brown solid, by using a similar syunthetic protocol as that of Intermediate 2C and starting from Intermediate 2B (2.00 g, 7.30 mmol) and methyl 5-bromonicotinate (1.50 g, 6.90 mmol). $^1$H NMR (300 MHz, DMSO-$d_6$) δ ppm 2.25 (s, 3H), 3.99 (s, 3H), 5.33 (s, 2H), 7.43 (d, J=7.60 Hz, 1 H), 7.86 (d, J=7.60 Hz, 1H), 8.29 (s, 1H), 8.77 (s, 1H), 9.29 (s, 1H). LCMS (Method-O): retention time 0.68 min, [M+1] 284.1.

Intermediate 189B: methyl 5-(4-methyl-1-oxo-1,3-dihydroisobenzofuran-5-yl)piperidine-3-carboxylate

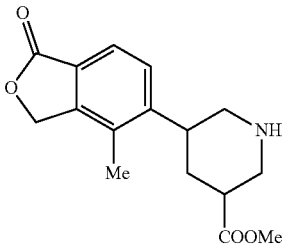

Intermediate 189B was prepared (1.30 g, 98.00%) as a brown solid, by using a similar synthetic protocol as that of Intermediate 118A and starting Intermediate 189A (1.30 g, 4.59 mmol). $^1$H NMR (400 MHz, DMSO-$d_6$) δ ppm 1.97-2.06 (m, 1H), 2.08-2.16 (m, 1H), 2.30 (s, 3H), 2.68-2.73 (m, 1H), 2.75-2.81 (m, 1H), 2.83-2.92 (m, 1H), 2.97-3.08 (m, 1H), 3.11-3.23 (m, 1H), 3.28-3.35 (m, 1H), 3.60 (s, 3H), 5.36 (s, 2H), 7.52 (d, J=8.00 Hz, 1H) 7.62 (d, J=8.00 Hz, 1H), (1 Exchangeable proton not observed). LCMS (Method-O): retention time 0.65 min, [M+1] 290.1.

Intermediate 189C: 1-(tert-butyl) 3-methyl 5-(4-methyl-1-oxo-1,3-dihydroisobenzofuran-5-yl)piperidine-1,3-dicarboxylate

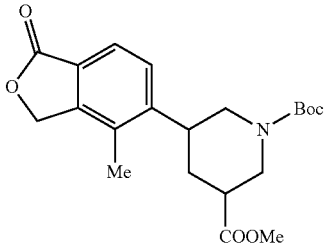

Intermediate 189C was prepared (1.00 g, 70.00%), by using a similar synthetic protocol as that of Intermediate 154A-I and starting from Intermediate 189B (1.30 g, 4.50 mmol). $^1$H NMR (400 MHz, DMSO-$d_6$) δ ppm 1.42 (s, 9H), 1.97-2.06 (m, 1H), 2.08-2.16 (m, 1H), 2.30 (s, 3H), 2.68-2.73 (m, 1H), 2.75-2.81 (m, 1H), 2.83-2.92 (m, 1H), 2.97-3.08 (m, 1H), 3.11-3.23 (m, 1H), 3.28-3.35 (m, 1H), 3.60 (s, 3H), 5.36 (s, 2H), 7.52 (d, J=8.00 Hz, 1H) 7.62 (d, J=8.00 Hz, 1H), LCMS (Method-I): retention time 1.28 min, [M+H] 390.3.

Intermediate 189-I, II, III and IV

To a stirring solution of Intermediate 189C (2.00 g, 5.14 mmol) in THF (20 mL) was added 2M solution of $LiBH_4$ in THF (12.84 mL, 25.70 mmol) and the resulting reaction mixture was heated at 70° C. for 18 h. The reaction mixture was cooled to ambient temperature, diluted with 10% solution of $NH_4Cl$ (100 mL) and extracted with ethyl acetate (2×100 mL). The combined organic layers were washed with brine (50 mL), dried over anhydrous sodium sulfate and evaporated under reduced pressure. The racemate was separated into individual enantiomers by SFC [Chiralpak ADH (250×4.6 mm) 5 micron; 0.2% $NH_4OH$ in MeOH, Flow: 1.2 mL/min, Temperature: 27° C., UV: 210 nm]. First eluted compound (retention time 6.12 min), designated as Intermediate 189-I, was obtained (0.12 g, 6.50%) as a pale yellow solid. $^1$HNMR (400 MHz, DMSO-$d_6$) δ ppm 1.42 (s, 9H), 1.70-1.79 (m, 1H), 1.77 (br. s., 1H), 1.80 (br. s., 1H), 2.29 (s, 3H) 2.64-2.78 (m, 1H), 2.98 (br. s., 1H), 3.39-3.47 (m, 3H), 4.00 (br. s., 1H), 4.20 (br. s., 1H), 4.70 (br. s., 1H), 5.29-5.51 (m, 2H), 7.48 (d, J=8.30 Hz, 1H), 7.65 (d, J=8.30 Hz, 1H). LCMS (Method-O): retention time 1.04 min, [M+1] 362.4. Second eluted compound (retention time 6.37 min), designated as Intermediate 189-II, was obtained (0.04 g, 2.16%) as a pale yellow solid. $^1$H NMR (400 MHz, DMSO-$d_6$) δ ppm 1.42 (s, 9H), 1.70-1.79 (m, 1H), 1.80-1.86 (m., 2H), 2.32 (s, 3H) 2.64-2.78 (m, 1H), 2.96-2.99 (m., 1H), 3.39-3.47 (m, 3H), 3.82-3.90 (m., 1H), 3.94-4.16 (m., 1H), 4.63 (br. s., 1H), 5.40-5.44 (m, 2H), 7.48 (d, J=8.30 Hz, 1H), 7.65 (d, J=8.30 Hz, 1H). LCMS (Method-O): retention time 1.07 min, [M+1] 362.4. Third eluted compound (retention time 7.77 min), designated as Intermediate 189-III, was obtained (0.08 g, 4.33%) as a pale yellow solid. $^1$H NMR (400 MHz, DMSO-$d_6$) δ ppm 1.42 (s, 9H), 1.77-1.92 (m., 3H), 2.29 (s, 3H) 2.64-2.78 (m, 1H), 3.05-3.20 (m, 2H), 3.42-3.52 (m, 2H), 3.80-4.00 (m, 2H), 4.55 (br. s., 1H), 5.4 (s, 2H), 7.50 (d, J=8.30 Hz, 1H), 7.65 (d, J=8.30 Hz, 1H). LCMS (Method-O): retention time 1.04 min, [M+1] 362.4. Fourth eluted compound (retention time 8.38 min), designated as Intermediate 189-IV, was obtained (0.03 g, 1.62%) as a pale yellow solid. $^1$H NMR (400 MHz, DMSO-$d_6$) δ ppm 1.42 (s, 9H), 1.77-1.92 (m, 3H), 2.29 (s, 3H) 2.64-2.78 (m, 1H), 3.05-3.20 (m, 2H), 3.42-3.52 (m, 2H), 3.80-4.00 (m., 2H), 4.55 (br. s., 1H), 5.4 (s, 2H), 7.50 (d, J=8.30 Hz, 1H), 7.65 (d, J=8.30 Hz, 1H). LCMS (Method-O): retention time 1.07 min, [M+1] 362.4.

Intermediate 190: 3-(4-methyl-1-oxo-1,3-dihydroisobenzofuran-5-yl)piperidin-4-yl methylcarbamate

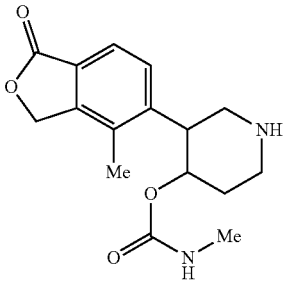

Intermediate 190A: tert-butyl 3-(4-methyl-1-oxo-1,3-dihydroisobenzofuran-5-yl)-4-((methylcarbamoyl)oxy)piperidine-1-carboxylate

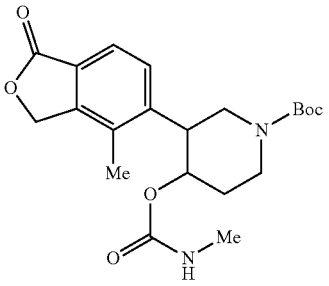

To a stirring solution of Intermediate 52A (0.30 g, 0.86 mmol) in THF (25 ml) was added NaH (41.6 mg, 1.73 mmol) followed by CDI (0.21 g, 1.30 mmol) at 0° C. and the reaction mixture was stirred at ambient temperature for 10 minutes. To the resulting reaction mixture was added methylamine hydrochloride (0.23 g, 3.46 mmol) and stirring at ambient temperature was continued for 18 h. The reaction mixture was diluted with water (30 mL) and extracted with ethyl acetate (2×50 mL). The combined organic layers were washed with brine (50 mL), dried over anhydrous sodium sulfate and evaporated under reduced pressure. The residue was purified by column chromatography (Redisep—40 g, 0-80% EtOAc/n-Hexane)) to obtain Intermediate 190A (0.15 g, 43.00%) as a brown solid. $^1$H NMR (400 MHz, DMSO-$d_6$) δ ppm 1.42 (s, 9H), 2.04-2.13 (m, 1H), 2.30 (s, 3H), 2.42 (s, 3H), 2.77-3.17 (m, 3H), 3.69-3.95 (m, 1H), 3.98-4.19 (m, 2H), 5.07-5.30 (m, 1H), 5.40 (d, J=5.02 Hz, 2H), 6.57-6.90 (m, 1H), 7.54 (d, J=8.53 Hz, 1H), 7.68 (d, J=8.53 Hz, 1H). LCMS (Method-O): retention time 1.16 min, [M−56] 349.5.

Intermediate 190

Intermediate 190 was prepared (0.80 g, 0.55 mmol), by using a similar synthetic protocol as that of Intermediate 38-I and starting from Intermediate 190A (0.15 g, 0.37 mmol). $^1$H NMR (400 MHz, DMSO-$d_6$) δ ppm 2.04-2.13 (m, 1H), 2.30 (s, 3H), 2.42 (s, 3H), 2.77-3.17 (m, 3H), 3.69-3.95 (m, 1H), 3.98-4.19 (m, 2H), 5.07-5.30 (m, 1H), 5.40 (d, J=5.02 Hz, 2H), 6.57-6.90 (m, 1H), 7.54 (d, J=8.53 Hz, 1H), 7.68 (d, J=8.53 Hz, 1H), (1 Exchangeable proton not observed). LCMS (Method-O): retention time 0.44 min, [M+1] 305.5.

Intermediate 191: 4-(5-formyl-2H-tetrazol-2-yl)-2-methylbenzonitrile

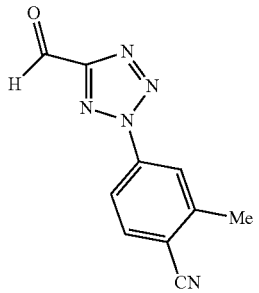

Intermediate 191A: ethyl 2-(4-cyano-3-methylphenyl)-2H-tetrazole-5-carboxylate

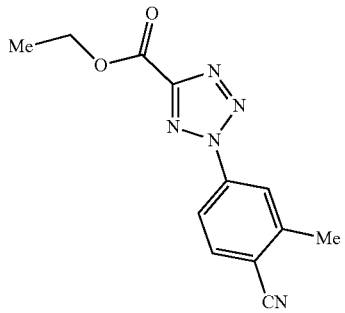

To a stirred solution of 4-amino-2-methylbenzonitrile (1.00 g, 7.57 mmol) in a mixture of EtOH (10 mL) and water (10 mL) at 0° C., was added conc HCl (4.60 mL, 151 mmol) and sodium nitrite (1.04 g, 15.13 mmol). The resulting reaction mixture was stirred for 20 minutes at 0° C. In another 50 mL round bottomed flask was added EtOH (20 mL), benzenesulfonohydrazide (1.30 g, 7.57 mmol) followed by ethyl 2-oxoacetate (1.545 g, 15.13 mmol) and the mixture was stirred at ambient temperature for 1 h. The reaction mixture was evaporated under reduced pressure to obtain (ethyl (E)-2-(2-(phenylsulfonyl)hydrazono)acetate, which was dissolved in pyridine (12.24 mL, 15 mmol) and added into the reaction mixture containing first set of the reaction (diazotization). The resulting reaction mixture was stirred at ambient temperature for 18 h. The reaction mixture was concentrated to dryness under reduced pressure, diluted with water (50 mL) and extracted with ethyl acetate (3×50 mL). The combined organic layers were washed with brine (50 mL), dried over anhydrous sodium sulfate and evaporated under reduced pressure. The residue was purified by column chromatography (Redisep—24 g, 35-55% EtOAc/ n-hexane) to obtain Intermediate 191A (0.15 g, 7.71%). $^1$H NMR (300 MHz, $CD_3OD$) δ ppm 1.48 (t, J=7.20 Hz, 3H), 2.71 (s, 3H), 4.55 (q, J=6.90 Hz, 2H), 8.0 (d, J=8.40 Hz, 1H), 8.22 (m, 1H) 8.33 (s, 1H). LCMS (Method-I) retention time 1.60 min, [M+H] 258.1.

Intermediate 191B: 4-(5-(hydroxymethyl)-2H-tetrazol-2-yl)-2-methylbenzonitrile

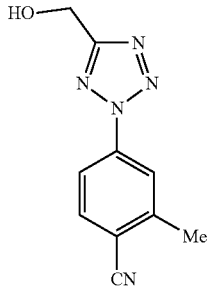

Intermediate 191B was prepared (0.12 g, 83.00%), by using a similar synthetic protocol as that of Intermediate 60B and starting Intermediate 191A (0.15 g, 0.58 mmol). $^1$H NMR (300 MHz, DMSO-$d_6$) δ ppm 2.50 (s, 3H), 4.81 (d, J=6.00 Hz, 2H), 5.81 (t, J=6.00 Hz, 1H), 8.09 (s, 2H) 8.25 (s, 1H). LCMS (Method-I) retention time 0.97 min, [M+H] 216.4.

Intermediate 191

Intermediate 191 was prepared (0.08 g, 67.30%), by using a similar synthetic protocol as that of Intermediate 9 and starting Intermediate 191B (0.12 g, 0.56 mmol) and Dess-Martin periodinane (0.35 g, 0.84 mmol). $^1$H NMR (400 MHz, DMSO-$d_6$) δ ppm 2.66 (s, 3H), 8.11-8.16 (m, 1H), 8.18 (d, J=2.51 Hz, 1H), 8.35 (s, 1H), 10.27 (s, 1H). LCMS (Method-I): retention time 0.87 min, [M−H] 212.0.

Intermediate 192: 1-(4-(2-oxooxazolidin-3-yl)pyridin-2-yl)-1H-pyrazole-4-carbaldehyde

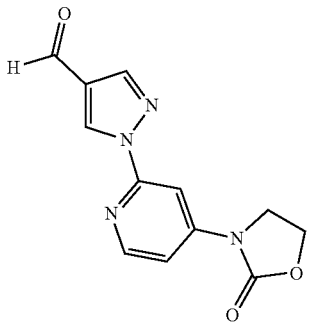

Intermediate 192A: 1-(4-aminopyridin-2-yl)-1H-pyrazole-4-carbaldehyde

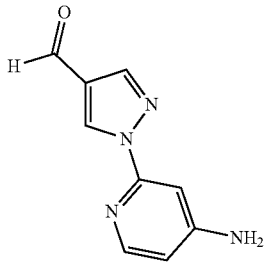

Intermediate 192A was prepared (0.40 g, 26.00%) as a pale yellow solid, by using a similar synthetic protocol as that of Intermediate 6 and starting from 1H-pyrazole-4-carbaldehyde (0.80 g, 8.33 mmol) and 2-bromopyridin-4-amine (1.44 g, 8.33 mmol). $^1$H NMR (400 MHz, DMSO-$d_6$) δ ppm 6.49-6.53 (m, 3H), 7.12 (d, J=2.01 Hz, 1H), 7.93 (d, J=5.52 Hz, 1H), 8.21 (d, J=1.00 Hz, 1H), 9.16 (s, 1H), 9.93 (s, 1H). LCMS (Method-D): retention time 0.73 min, [M+H] 189.1.

Intermediate 192B: 2-chloroethyl (2-(4-formyl-1H-pyrazol-1-yl)pyridin-4-yl)carbamate

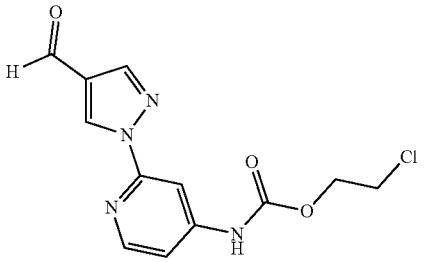

Intermediate 192B was prepared (0.20 g, 43.00%) as a pale yellow solid, by using a similar synthetic protocol as that of Intermediate 76A and starting from Intermediate 192A (0.30 g, 1.60 mmol) and 2-chloroethyl chloroformate (0.27 g, 1.91 mmol). $^1$H NMR (400 MHz, DMSO-$d_6$) δ ppm 3.89-3.93 (m, 2H), 4.41-4.45 (m, 2H), 7.47 (dd, J=5.52, 2.01 Hz, 1H), 8.22 (d, J=2.01 Hz, 1H), 8.28 (s, 1H), 8.36 (d, J=6.02 Hz, 1H), 9.27 (s, 1H), 9.96 (s, 1H), 10.66 (s, 1H). LCMS (Method-D): retention time 1.92 min, [M+H] 295.

Intermediate 192

Intermediate 192 was prepared (0.10 g, 56.00%) as a pale yellow solid, by using a similar synthetic protocol as that of Intermediate 76B and starting from Intermediate 192B (0.15 g, 0.51 mmol) and NaH (0.02 g, 1.018 mmol). $^1$H NMR (400 MHz, DMSO-$d_6$) δ ppm 4.16 (dd, J=8.93, 6.97 Hz, 2H), 4.50-4.55 (m, 2H), 7.52 (dd, J=5.75, 2.08 Hz, 1H), 8.31 (s, 2H), 8.47 (d, J=5.87 Hz, 1H), 9.31 (s, 1H), 9.97 (s, 1H). LCMS (Method-D): retention time 1.20 min, [M+H] 259.1.

Example 113-I: 4,4-methyl-6-(5-(((3S,5R)-3-methyl-5-(4-methyl-1-oxo-1,3-dihydroisobenzofuran-5-yl)piperazin-1-yl)methyl)thiazol-2-yl)nicotinonitrile

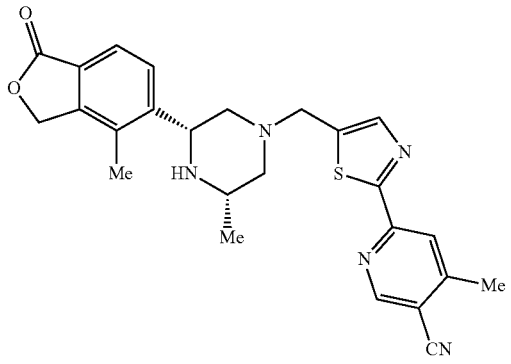

Example 113-I was prepared (0.02 g, 32.30%) as a white solid, by using a similar synthetic protocol as that of Intermediate 23B and starting from Intermediate 55-I (0.20 g, 0.47 mmol) and Intermediate 53 (0.26 g, 0.98 mmol). $^1$H NMR (400 MHz, DMSO-$d_6$) δ ppm 1.20 (s, 3H), 2.25 (s, 3H), 2.50 (s, 3H), 2.60 (br. s, 2H), 2.84 (br. s., 2H), 2.98 (br. s., 1H), 3.71-3.96 (m, 2H), 4.16 (br. s., 1H), 5.37 (br. s., 2H), 7.65 (m, J=8.00 Hz, 1H), 7.79 (d, J=8.00 Hz, 1H), 7.91 (s, 1H), 8.19 (s, 1H), 8.98 (s, 1H), (1 Exchangeable proton not observed). LCMS/HPLC (Method-S): retention time 1.69 min, [M+H] 460.2, purity: 100%. (Method-R): retention time 1.25 min, [M+H] 460.2, purity: 96.09%.

Example 114-I: 6-(4-((4(4-hydroxy-4-methyl-3-(4-methyl-1-oxo-1,3-dihydroisobenzofuran-5-yl)piperidin-1-yl)methyl)-1H-pyrazol-1-yl)-4-methylnicotinonitrile

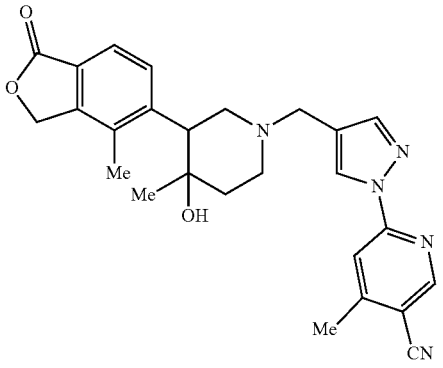

Example 114-I was prepared by using a similar synthetic protocol as that of Example 1-I and starting from Intermediate 72 (0.02 g, 0.919 mmol) and Intermediate 6 (0.02 g, 0.707 mmol). The racemate was separated into individual enantiomers by SFC [Luxcellulose-2 (250×21.5 mm) 5 micron; 0.1% DEA in IPA+ACN (10:90), Flow: 1.0 g/min. Temperature: 30° C., UV: 235 nm]. First eluted compound (retention time 7.34 min), designated as Example 114-I, was obtained (0.01 g, 3.86%) as an off-white solid. $^1$H NMR (400 MHz, DMSO-$d_6$) δ ppm 0.93 (s, 3H), 1.62 (d, J=13.2 Hz, 1H), 1.79 (td, J=12.80, 4.3 Hz, 1H), 2.24 (s, 3H), 2.46-2.39 (m, 1H), 2.59-2.54 (m, 4H), 2.64-2.60 (m, 1H), 2.71 (d, J=10.80 Hz, 1H), 3.12 (dd, J=11.20, 3.4 Hz, 1H), 3.58-3.50 (m, 2H), 4.34 (br. s., 1H), 5.45-5.23 (m, 2H), 7.58 (d, J=7.80 Hz, 1H), 7.88-7.75 (m, 2H), 7.97 (s, 1H), 8.52 (s, 1H), 8.83 (s, 1H). HPLC/LCMS (Method-R): retention time 1.14 min, [M+H] 458.2, purity: 100%. (Method-S): retention time 1.46 min, [M+H] 458.2, purity: 100%. Chiral purity (Method-XXVIII): retention time 7.34 min, 100% ee.

Example 115-I: 4-methyl-6-(4-((2-methyl-3-(4-methyl-1-oxo-1,3-dihydroisobenzofuran-5-yl)piperazin-1-yl)methyl)-1H-pyrazol-1-yl)nicotinonitrile

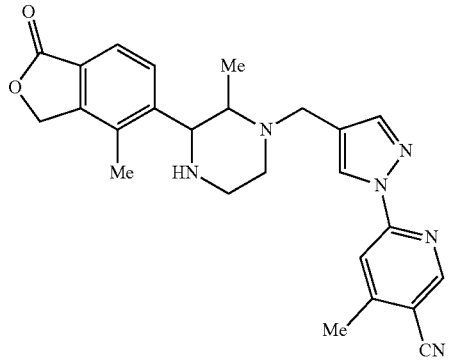

Example 115-I was prepared (0.01 g, 5.86%), by using a similar synthetic protocol as that of Example 1-I and starting from Intermediate 71-I (0.15 g, 0.61 mmol) and Intermediate 6 (0.10 g, 0.47 mmol). $^1$H NMR (400 MHz, DMSO-$d_6$) δ ppm 0.67 (d, J=6.10 Hz, 3H), 2.18 (s, 3H), 2.58 (s, 3H), 2.66 (d, J=10.80 Hz, 1H), 3.08-2.86 (m, 3H), 3.17 (d, J=5.10 Hz, 1H), 3.61 (br. s., 2H), 4.31 (br. s., 1H), 5.35 (s, 2H), 7.66 (s, 2H), 7.90 (s, 1H), 7.99 (s, 1H), 8.56 (s, 1H), 8.84 (s, 1H), (1 Exchangeable proton not observed). LCMS/HPLC (Method-R): retention 1.04 min, [M+H] 443.2, purity: 98.77%. (Method-S): retention time 1.46 min, [M+H] 443.2, purity: 98.63%. Chiral purity (Method-V): retention time 7.99 min, 97.93% ee.

Example 116-I: 6-(4-((4-hydroxy-3,3-dimethyl-5-(4-methyl-1-oxo-1,3-dihydroisobenzofuran-5-yl)piperidin-1-yl)methyl)-1H-pyrazol-1-yl)-4-methylnicotinonitrile

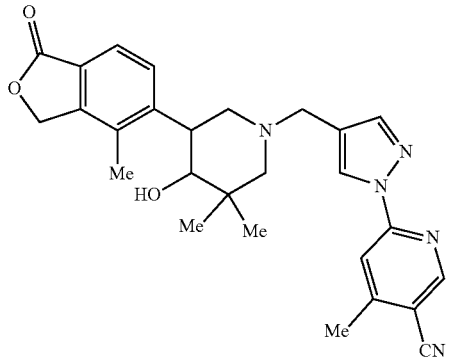

Example 116-I was prepared (0.01 g, 15.60%), by using a similar synthetic protocol as that of Example 1-I and starting from Intermediate 73-I (0.02 g, 0.92 mmol) and Intermediate 6 (0.03 g, 0.14 mmol). $^1$H NMR (400 MHz, DMSO-$d_6$) δ ppm 0.90 (s, 3H), 1.08 (s, 3H), 1.24 (s, 1H), 2.03 (t, J=11.10 Hz, 1H), 2.26 (s, 3H), 2.64-2.56 (m, 4H), 2.78 (d, J=10.30 Hz, 1H), 3.29 (d, J=4.20 Hz, 1H), 3.54-3.38 (m, 3H), 4.42 (d, J=6.10 Hz, 1H), 5.44-5.29 (m, 2H), 7.53 (d, J=8.30 Hz, 1H), 7.63 (d, J=7.80 Hz, 1H), 7.84 (s, 1H), 7.99 (s, 1H), 8.51 (s, 1H), 8.84 (s, 1H). HPLC/LCMS (Method-R): retention time 1.12 min, [M+H] 472.3, purity: 96.20%. (Method-S): retention time 1.82 min, [M+H] 472.3, purity: 94.72%. Chiral purity (Method-V): retention time 4.17 min, 100% ee.

Example 117-I: 4-methyl-6-(5-(((3S,5R)-3-methyl-5-(4-methyl-1-oxo-1,3-dihydroisobenzofuran-5-yl) piperazin-1-yl)methyl)-2-oxooxazol-3(2H)-yl)nicotinonitrile

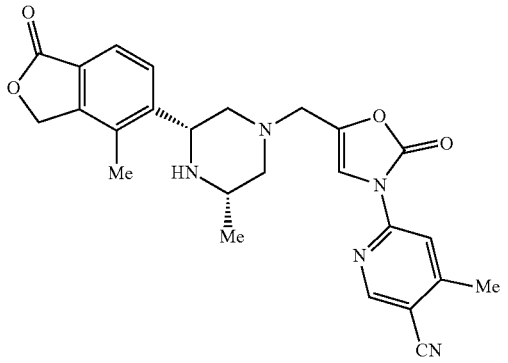

Example 117-I was prepared (0.02 g, 21.10%), by using a similar synthetic protocol as that of Intermediate 15C and starting from Intermediate 75 (0.07 g, 0.204 mmol) and 6-bromo-4-methylnicotinonitrile (0.05 g, 0.245 mmol). $^1$H NMR (400 MHz, DMSO-$d_6$) δ ppm 1.04 (d, J=6.10 Hz, 3H), 1.24 (s, 1H), 1.95-1.74 (m, 2H), 2.30 (s, 3H), 2.61-2.53 (m, 3H), 2.83 (d, J=10.3 Hz, 2H), 2.96 (br. s., 1H), 3.48 (s, 2H), 4.16 (d, J=9.00 Hz, 1H), 5.46-5.30 (m, 2H), 7.66 (d, J=7.80 Hz, 1H), 7.74 (s, 1H), 7.81 (d, J=7.80 Hz, 1H), 8.24-8.15 (m, 1H), 8.84 (s, 1H). LCMS/HPLC (Method-R): retention time 0.93 min, [M+H] 460.2, purity: 97.01%. (Method-S): retention time 1.42 min, [M+H] 460.2, purity: 95.11%.

Example 118-I: (R)-4-methyl-6-(4-((4-(4-methyl-1oxo-1,3-dihydroisobenzofuran-5-yl)-2-oxoimidazolidin-1-yl)methyl)-1H-pyrazol-1-yl)nicotinonitrile

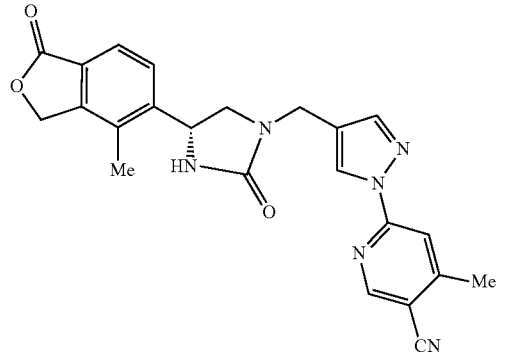

To a stirring solution of Intermediate 131-I (0.05 g, 0.12 mmol) in THF (10 mL) was added TEA (0.03 mL, 0.25 mmol) followed by CDI (0.03 g, 0.18 mmol) and the resulting reaction mixture was heated at 70° C. for 1 h. The reaction mixture was cooled at ambient temperature, diluted with water (20 mL) and extracted with ethyl acetate (2×40 mL). The combined organic layers were washed with brine (20 mL), dried over anhydrous sodium sulfate and evaporated under reduced pressure. The residue was purified by HPLC [XBridge C18 (19×150 mm) 5 micron; Solvent A: 0.1% TFA; Solvent B: Acetonitril; Gradient: 10-40% B over 25 minutes, Flow: 15 mL/min, retention time 13.72 min, UV: 240 nm] to obtain Example 118-I (0.012 g, 20.41%). $^1$H NMR (400 MHz, DMSO-$d_6$) δ ppm 2.23 (s, 3H), 2.57 (s, 3H), 2.93 (dd, J=8.93, 6.48 Hz, 1H), 3.87 (t, J=8.93 Hz, 1H), 4.13-4.34 (m, 2H), 5.06 (t, J=7.09 Hz, 1H), 5.31-5.45 (m, 2H), 7.22 (s, 1H), 7.56 (d, J=8.07 Hz, 1H), 7.71 (d, J=8.07 Hz, 1H), 7.80 (s, 1H), 7.97 (s, 1H), 8.53 (s, 1H), 8.83 (s, 1H). LCMS/HPLC (Method-S): retention time 1.60 min, [M+H] 429.1, purity: 96.70%. (Method-R): retention time 1.61 min, [M+H] 429.1, purity: 97.92%. Chiral purity (Method-XVIII): retention time 13.72 min, 95.00% ee.

Example 119-I: (R)-4-methyl-6444(444-methyl-1-oxo-1,3-dihydroisobenzofuran-5-yl)-1,1-dioxido-1,2,5-thiadiazolidin-2-yl)methyl)-1H-pyrazol-1-yl)nicotinonitrile

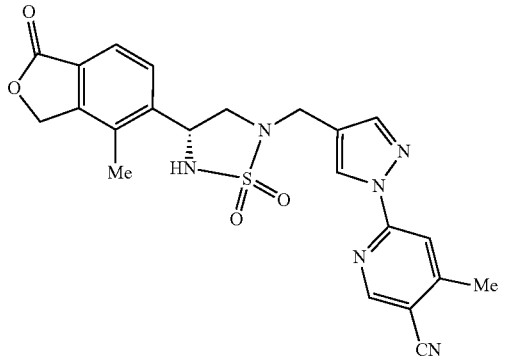

To a stirring solution of Intermediate 131-I (0.06 g, 0.15 mmol) in pyridine (0.50 mL) was added sulfamide (0.30 g, 0.30 mmol) and the resulting reaction mixture was heated at 125° C. for 16 h. The reaction mixture was cooled to ambient temperature, diluted with water (20 mL) and extracted with ethyl acetate (2×50 mL). The combined organic layers were washed with brine (20 mL), dried over anhydrous sodium sulfate and evaporated under reduced pressure. The residue was purified by HPLC [Sunfire OBD-C18 (30×250 mm) 5 micron; SolventA: 10 mM Ammonium acetate; Solvent B: Acetonitrile; Gradient: 20-50% B over 12 minutes, Flow: 25 mL/min, retention time 17.55 min, UV: 240 nm] to obtain Example 119-I (0.02 g, 24.55%) as a white solid. $^1$H NMR (400 MHz, DMSO-$d_6$) δ ppm 2.25 (s, 3H), 2.58 (s, 3H), 2.94 (dd, J=9.90, 7.70 Hz, 1H), 3.92-4.08 (m, 2H), 4.20 (d, J=14.43 Hz, 1H), 5.11 (q, J=7.42 Hz, 1H), 5.30-5.43 (m, 2H), 7.65-7.78 (m, 2H), 7.91 (s, 1H), 7.98 (s, 1H), 8.14 (d, J=7.09 Hz, 1H), 8.65 (s, 1H), 8.84 (s, 1H), LCMS/HPLC (Method-S): retention time 1.42 min, [M+H] 465.1, purity: 100%. (Method-R): retention time 1.41 min, [M+H] 465.1, purity: 100%. [M+H] 465.1, Chiral purity (Method-XVIII): retention time 17.55 min., 97.25% ee.

Example 120-I: 2-methyl-6-(5-(((3S,5R)-3-methyl-5-(4-methyl-1-oxo-1,3-dihydroisobenzofuran-5-yl) piperazin-1-yl)methyl)pyridin-2-yl)pyridazin-3(2H)-one

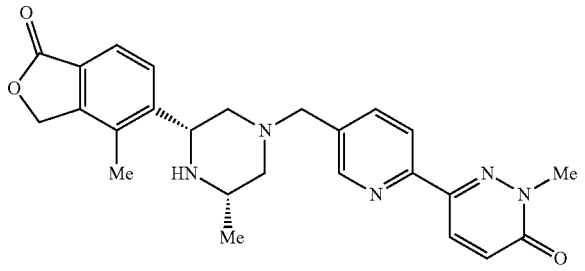

Example 120-I was prepared (0.02 g, 11.00%), by using a similar synthetic protocol as that of Intermediate 23B and starting from of Intermediate 96-I (0.15 g, 0.36 mmol) and Intermediate 102 (0.01 g, 0.36 mmol). $^1$H NMR (400 MHz, DMSO-$d_6$) δ ppm 1.02 (d, J=5.90 Hz, 3H), 1.68-1.82 (m, 2H), 2.23 (s, 3H), 2.76 (t, J=10.00 Hz, 2H), 2.99 (br. s., 1H), 3.52-3.65 (m, 2H), 3.77 (s, 3H), 4.17 (d, J=9.00 Hz, 1H), 5.27-5.46 (m, 2H), 7.07 (d, J=9.80 Hz, 1H), 7.65 (d, J=8.10 Hz, 1H), 7.80 (d, J=8.10 Hz, 1H), 7.89 (dd, J=8.20 Hz, 1.6 Hz, 1H), 8.07 (d, J=8.30 Hz, 1H), 8.29 (d, J=9.80 Hz, 1H), 8.57 (br. s., 1H), (1 Exchangeable proton not observed). LCMS/HPLC (Method-S): retention time 1.17 min, [M+H] 446.2, purity: 100%. (Method-R): retention time 0.60 min, [M+H] 446.2, purity: 99.60%. Chiral purity (Method-XI): retention time 12.50 min, 100% ee.

Example 121-I: 4-methyl-6-(4-(1-(R)-344-methyl-1-oxo-1,3-dihydroisobenzofuran-5-yl)piperazin-1-yl) ethyl)-2H-1,2,3-triazol-2-yl)nicotinonitrile (Dia-I: Ena-I) and Example 121-I: 4-methyl-6-(4-(1-((R)-3-(4-methyl-1-oxo-1,3-dihydroisobenzofuran-5-yl) piperazin-1-yl)ethyl)-2H-1,2,3-triazol-2-yl)nicotinonitrile (Dia-II:Ena-I)

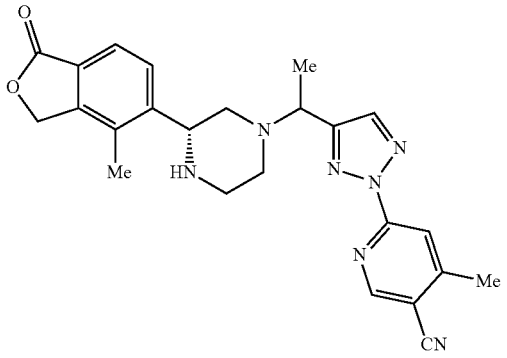

To a stirring solution of Intermediate 101 (0.100 g, 0.325 mmol) in ACN (6 mL) was added Intermediate 2-I (0.08 g, 0.36 mmol) followed by $K_2CO_3$ (0.09 g, 0.65 mmol) and the resulting reaction mixture was stirred at ambient temperature for 4 h. The reaction mixture was diluted by ACN (20 mL) and filtered through celite. The filtrate was evaporated under reduced pressure and the residue was purified by HPLC [Sunfire OBD (250×30 mm) 5 micron; Solvent A: 10-mM Ammonium acetate; Solvent B: Acetonitrile, Gradient: 30-100% B over 15.5 minutes, retention time 12.07, UV: 254 nm] to obtain racemate, which was separated into two individual enantiomers by supercritical fluid chromatography (SFC) [Chiralpak OJ-H (250×21 mm) 5 micron; 0.2% $NH_4OH$ in MeOH+ACN (1:1), Flow: 70.0 mL/min. Temperature: 30° C., UV: 290 nm]. First eluted compound (retention time 5.9 min), designated as Example 121-I, was obtained (0.02 g, 12.20%) as a white solid. $^1$H NMR (400 MHz, DMSO-$d_6$) δ ppm 1.43 (d, J=7.00 Hz, 3H), 1.87 (t, J=10.30 Hz, 1H), 2.12-2.20 (m, 1H), 2.26 (s, 3H), 2.61 (s, 3H), 2.75 (d, J=11.00 Hz, 1H), 2.83-2.92 (m, 2H), 2.99 (br. s., 1H), 4.07 (d, J=7.00 Hz, 2H), 5.37 (s, 2H), 7.61 (d, J=8.00 Hz, 1H), 7.72 (d, J=8.00 Hz, 1H), 8.09 (s, 1H), 8.21 (s, 1H), 8.92 (s, 1H), (1 Exchangeable proton not observed). HPLC (Method-P): retention time 7.92 min, purity: 97.9%. (Method-Q): retention time 6.98 min, purity: 98.0%. LCMS (Method-D): retention time 1.73 min, [M+H] 444.2. Chiral purity (Method-XX): retention time 4.79 min, 99.5% ee. Second eluted compound (retention time 7.70 min), designated as Example 121-II, was obtained (0.02 g, 12.90%) as a white solid. $^1$H NMR (400 MHz, DMSO-$d_6$) δ ppm 1.43 (d, J=7.00 Hz, 3H), 1.87 (t J=10.30 Hz, 1H), 2.12-2.20 (m, 1H), 2.26 (s, 3H), 2.61 (s, 3H), 2.75 (d, J=11.00 Hz, 1H), 2.83-2.92 (m, 2H), 2.99 (br. s., 1H), 4.07 (d, J=7.00 Hz, 2H), 5.37 (s, 2H), 7.61 (d, J=8.00 Hz, 1H), 7.72 (d, J=8.00 Hz, 1H), 8.09 (s, 1H), 8.21 (s, 1H), 8.92 (s, 1H), (1 Exchangeable proton not observed). HPLC (Method-P): retention time 7.83 min, purity: 98.20%. (Method-Q): retention time 7.02 min, purity: 98.8%. LCMS (Method-D): retention time 1.84 min, [M+H] 444.2. Chiral purity (Method-XX): retention time 6.34 min, 98.60% ee.

Example 122-I: 4-methyl-6-(3-(((3S,5R)-3-methyl-5-(4-methyl-1-oxo-1,3-dihydroisobenzofuran-5-yl) piperazin-1-yl)methyl)-1H-1,2,4-triazol-1-yl)nicotinonitrile

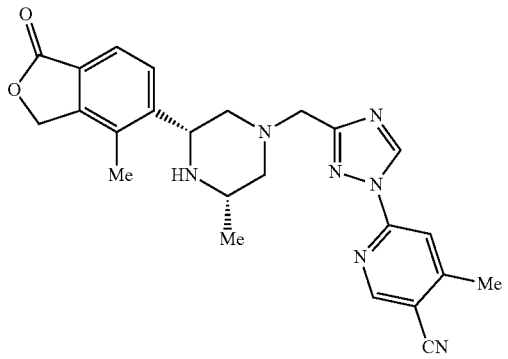

Example 122-I was prepared (0.02 g, 28.40%), by using a similar synthetic protocol as that of Intermediate 20 and starting from Intermediate 97 (0.03 g, 0.09 mmol) and 6-bromo-4-methylnicotinonitrile (0.02 g, 0.110 mmol). $^1$H NMR (400 MHz, DMSO-$d_6$) δ ppm 1.21-1.35 (m, 3H), 2.37 (s, 3H), 2.59-2.70 (m, 4H), 3.14-3.26 (m, 3H), 3.93 (s., 3H), 4.78 (br. s., 1H), 5.38-5.56 (m, 2H), 7.80 (d, J=7.80 Hz, 1H), 7.87 (d, J=7.80 Hz, 1H), 7.93-8.00 (m, 1H), 8.92-8.99 (m, 1H), 9.59 (s, 1H), (1 Exchangeable proton not observed). LCMS/HPLC (Method-S): retention time 1.86 min, [M+H] 444.2, purity: 96.60%. (Method-R): retention time 1.19 min, [M+H] 444.2, purity: 93.30%. Chiral purity (Method-VIII): retention time 4.64 min, 100% ee.

Example 123-I: 6-(4-((2-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile (Dia-I:Ena-I) and Example 123-II: 6-(4-((2-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile (Dia-I:Ena-II)

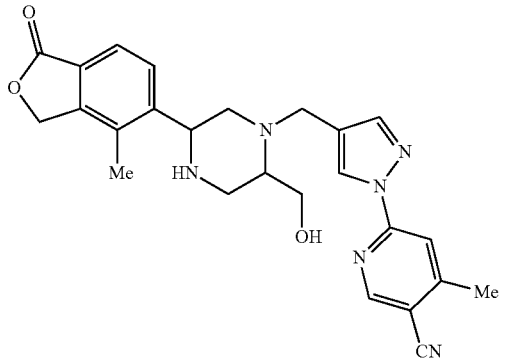

To solution of 103 (Diastereomer-I) (0.06 g, 0.23 mmol) in ACN (5 mL) was added Intermediate 104 (0.08 g, 0.34 mmol) followed by $K_2CO_3$ (0.13 g, 0.91 mmol) and the resulting reaction mixture was heated at 60° C. for 12 h. The reaction mixture was diluted ACN (20 mL) and filtered through celite. The filtrate was evaporated under reduced pressure and the residue was purified by HPLC [Intersil ODS (250×20 mm) 5 micron; Solvent A: 10 mM Ammonium acetate; Solvent B: Acetonitrile, Gradient: 20-100% B over 16 minutes, retention time: 11.8, UV: 220] to obtain racemic mixture, which was separated into two individual enantiomer by supercritical fluid chromatography (SFC) [Lux amylose-2 (250×21 mm) 5 micron; 0.2% $NH_4OH$ in MeOH+Acetonitrile (1:1), Flow: 70.0 mL/min. Temperature: 30° C., UV: 240 nm]. First eluted compound (retention time 6.38), designated as Example 123-I, was obtained (0.005 g, 4.60%) as an off-white solid. $^1$H NMR (400 MHz, DMSO-$d_6$) δ ppm 1.84-1.90 (m, 1H), 2.23 (s, 3H), 2.58 (s, 4H), 2.60-2.62 (m, 1H), 2.75 (dd, J=10.79, 2.26 Hz, 1H), 3.13 (dd, J=11.55, 3.01 Hz, 1H), 3.44-3.49 (m, 1H), 3.68-3.73 (m, 1H), 3.78-3.83 (m, 1H), 3.87 (d, J=15.06 Hz, 1H), 4.01 (d, J=8.03 Hz, 1H), 4.70 (t, J=5.27 Hz, 1H), 5.36 (s, 2H), 7.59-7.63 (m, 1H), 7.70 (d, J=8.03 Hz, 1H), 7.83 (s, 1H), 7.98 (s, 1H), 8.53 (s, 1H), 8.82 (s, 1H), (1 Exchangeable proton not observed). HPLC (Method-P): retention time 9.77 min, purity: 98.80%. (Method-Q): retention time 7.95 min, purity: 97.0%. LCMS (Method-D): retention time 1.55 min, [M+H] 459.2. Chiral purity (Method-XIII) retention time 7.20 min, 100% ee. Second eluted compound (retention time 9.20 min), designated as Example 123-II, was obtained (0.005 g, 4.60%) as an off-white solid. $^1$H NMR (400 MHz, DMSO-$d_6$) δ ppm 1.84-1.90 (m, 1H), 2.23 (s, 3H), 2.58 (s, 4H), 2.60-2.62 (m, 1H), 2.75 (dd, J=10.79, 2.26 Hz, 1H), 3.13 (dd, J=11.55, 3.01 Hz, 1H), 3.44-3.49 (m, 1H), 3.68-3.73 (m, 1H), 3.78-3.83 (m, 1H), 3.87 (d, J=15.06 Hz, 1H), 4.01 (d, J=8.03 Hz, 1H), 4.70 (t, J=5.27 Hz, 1H), 5.36 (s, 2H), 7.59-7.63 (m, 1H), 7.70 (d, J=8.03 Hz, 1H), 7.83 (s, 1H), 7.98 (s, 1H), 8.53 (s, 1H), 8.82 (s, 1H), (1 Exchangeable proton not observed). HPLC (Method-P): retention time 9.96 min, purity: 99.30%. (Method-Q): retention time 8.13 min, purity: 98.70%. LCMS (Method-D): retention time 1.55 min, [M+H] 459.2. Chiral purity (Method-XIII) retention time 10.25 min, 100% ee.

The examples in Table 3 were synthesized using procedures of Example 1-I to 24-I, 81-I to 84-I and 113-I to 123-I.

| Example | Structure | Name | LCMS (M + H)$^+$ | HPLC/LCMS Method: RT (min.), Purity | NMR |
|---|---|---|---|---|---|
| 125-I | 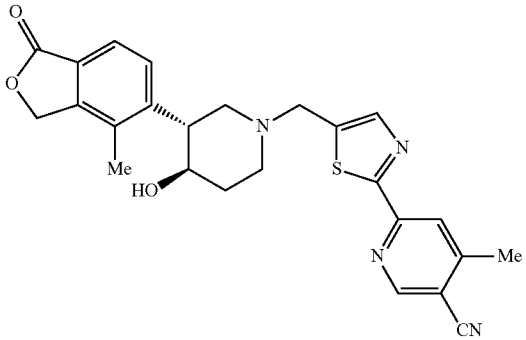 | 6-(5-(((3R,4R)-4-hydroxy-3-(4-methyl-1-oxo-1,3-dihydroisobenzofuran-5-yl)piperidin-1-yl)methyl)thiazol-2-yl)-4-methylnicotinonitrile | 461.2 | S: 1.52, 93.70% R: 1.03, 94.16% | $^1$H NMR (400 MHz, DMSO-d6) δ ppm 1.60 (br. s., 1 H), 1.92 (br. s., 1 H), 2.15 (t, J = 11.0 Hz, 1 H), 2.24 (s, 3 H), 2.32 (d, J = 14.20 Hz, 1 H), 2.65 (s, 3 H), 2.76 (d, J = 9.40 Hz, 1 H), 2.97 (d, J = 11.80 Hz, 1 H), 3.08 (t, J = 8.80 Hz, 1 H), 3.76 (br. s., 1 H), 3.80-3.96 (m, 2 H), 4.62 (d, J = 5.60 Hz, 1 H), 5.26-5.47 (m, 2 H), 7.54 (d, J = 8.00 Hz, 1 H), 7.64 (d, J = 8.00 Hz, 1 H), 7.91 (s, 1 H), 8.18 (s, 1 H), 8.97 (s, 1 H). |
| 126-I | 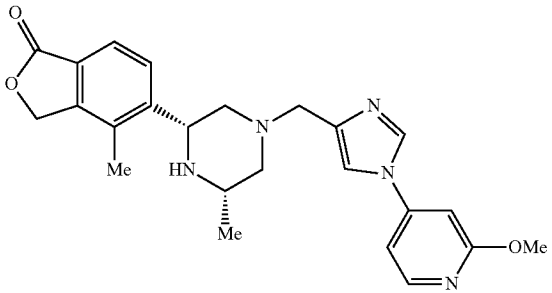 | 5-((2R,6S)-4-((1-(2-methoxypyridin-4-yl)-1H-imidazol-4-yl)methyl)-6-methylpiperazin-2-yl)-4-methylisobenzofuran-1(3H)-one | 434.2 | S: 1.20, 98.20% R: 0.78, 99.82% V: 5.73, 100% ee | $^1$H NMR (400 MHz, DMSO-$d_6$) δ ppm 1.03 (d, J = 6.1 Hz, 3 H), 1.78 (br. s., 2 H), 2.27 (s, 3 H), 2.84 (br. s., 2 H), 2.97 (br. s., 1 H), 3.47 (br. s., 2 H), 3.90 (s, 3 H), 4.18 (br. s, 1 H), 5.38 (s, 2 H), 7.19 (d, J = 1.70 Hz, 1 H), 7.38 (dd, J = 2.00, 6.00 Hz, 1 H), 7.66 (d, J = 7.60 Hz, 1 H), 7.73-7.88 (m, 2 H), 8.23 (d, J = 5.60 Hz, 1 H), 8.45 (s, 1 H), (1 Exchangeable proton not observed). |
| 127-I | 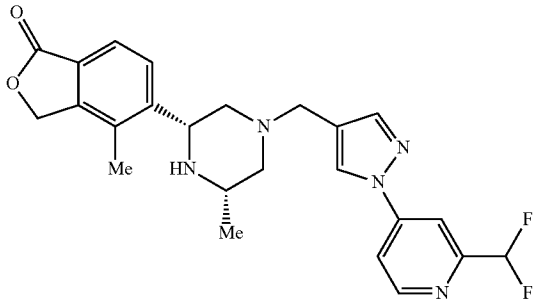 | 5-((2R,6S)-4-((1-(2-(difluoromethyl)pyridin-4-yl)-1H-pyrazol-4-yl)methyl)-6-methylpiperazin-2-yl)-4-methylisobenzofuran-1(3H)-one | 454.2 | S: 1.29, 96.29% R: 0.72, 97.83% | $^1$H NMR (400 MHz, DMSO-$d_6$) δ ppm 1.03 (d, J = 6.00 Hz, 3 H), 1.64-1.81 (m, 2 H), 2.15-2.32 (m, 3 H), 2.81 (d, J = 11.20 Hz, 2 H), 2.98 (br. s., 1 H), 3.49 (s, 2 H), 4.17 (d, J = 9.30 Hz, 1 H), 5.28-5.47 (m, 2 H), 7.00 (s, 1 H), 7.65 (d, J = 8.00 Hz, 1 H), 7.72-7.88 (m, 2 H), 8.01 (d, J = 5.00 Hz, 1 H), 8.13 (d, J = 1.80 Hz, 1 H), 8.61-8.82 (m, 2 H), (1 Exchangeable proton not observed). $^{19}$F NMR (400 MHz, DMSO-$d_6$) δ ppm −115.9. |

-continued

| Example | Structure | Name | LCMS $(M + H)^+$ | HPLC/LCMS Method: RT (min.), Purity | NMR |
|---|---|---|---|---|---|
| 128-I | 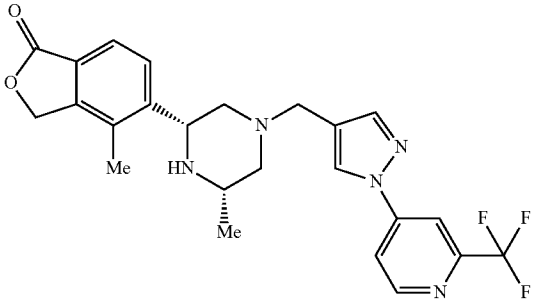 | 4-methyl-5-((2R,6S)-6-methyl-4-((1-(2-(trifluoromethyl)pyridin-4-yl)-1H-pyrazol-4-yl)methyl)piperazin-2-yl)isobenzofuran-1(3H)-one | 472.2 | S: 1.16, 96.16% R: 0.92, 96.93% IX: 4.77, 100% ee | $^1$H NMR (400 MHz, DMSO-$d_6$) δ ppm 1.04 (d, J = 5.60 Hz, 3 H), 1.75 (br. s., 2 H), 2.15-2.31 (m, 3 H), 2.82 (d, J = 8.30 Hz, 2 H), 2.99 (br. s., 1 H), 3.50 (br. s., 2 H), 4.19 (br. s., 1 H), 5.25-5.49 (m, 2 H), 7.66 (d, J = 8.60 Hz, 1 H), 7.80 (d, J = 8.10 Hz, 1 H), 7.86 (s, 1 H), 8.14 (dd, J = 2.20, 5.60 Hz, 1 H), 8.31 (d, J = 2.00 Hz, 1 H), 8.72-8.88 (m, 2 H), (1 Exchangeable proton not observed). $^{19}$F NMR (400 MHz, DMSO-$d_6$) δ ppm −66.70. |
| 129-I | 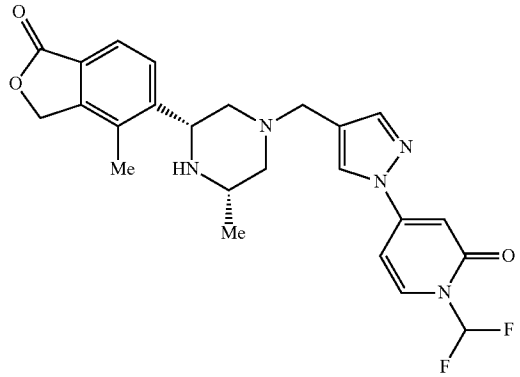 | 1-(difluoromethyl)-4-(4-(((3S,5R)-3-methyl-5-(4-methyl-1-oxo-1,3-dihydroisobenzofuran-5-yl)piperazin-1-yl)methyl)-1H-pyrazol-1-yl)pyridin-2(1H)-one | 470.2 | S: 1.19, 94.05% R: 0.68, 100% XIV: 2.70, 100% ee | $^1$H NMR (400 MHz, DMSO-$d_6$) δ ppm 1.04 (br. s., 3 H), 1.72 (br. s., 2 H), 2.32 (s, 3 H), 2.80 (br. s., 2 H), 2.85-3.13 (m, 1 H), 3.48 (br. s., 2 H), 4.17 (b.r s., 1 H), 5.31-5.49 (m, 2 H), 6.87 (d, J = 2.00 Hz, 1 H), 7.09 (dd, J = 2.00, 8.00 Hz, 1 H), 7.66 (d, J = 7.50 Hz, 1 H), 7.73-7.89 (m, 3 H), 7.89-8.05 (m, 1 H), 8.54-8.66 (m, 1 H), (1 Exchangeable proton not observed). $^{19}$F NMR (400 MHz, DMSO-$d_6$) δ ppm −102.9. |

-continued

| Example | Structure | Name | LCMS (M + H)$^+$ | HPLC/LCMS Method: RT (min.), Purity | NMR |
|---|---|---|---|---|---|
| 130-I | 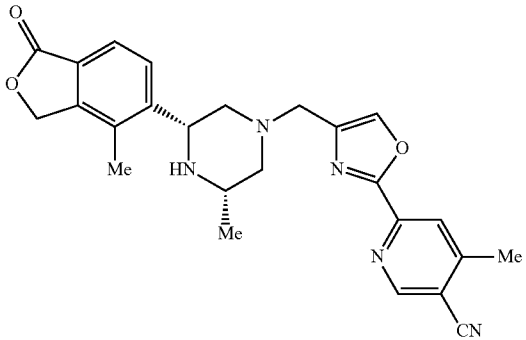 | 1-(5-(((3R,5R)-3-(hydroxymethyl)-5-(4-methyl-1-oxo-1,3-dihydroisobenzofuran-5-yl)piperazin-1-yl)methyl)pyridin-2-yl)-3-methyl-1H-pyrazole-4-carbonitrile | 444.2 | S: 1.31, 100% R: 0.99, 100% | $^1$H NMR (400 MHz, DMSO-$d_6$) δ ppm 1.02 (d, J = 6.40 Hz, 3 H), 1.72-1.88 (m, 2 H), 2.32 (s, 3 H), 2.55 (s, 3 H), 2.85 (d, J = 10.80 Hz, 2 H), 2.98 (d, J = 10.50 Hz, 1 H), 3.55 (s, 2 H), 4.16 (d, J = 8.30 Hz, 1 H), 5.38 (d, J = 2.20 Hz, 2 H), 7.66 (d, J = 7.80 Hz, 1 H), 7.81 (d, J = 8.10 Hz, 1 H), 8.19 (s, 1 H), 8.26 (s, 1 H), 9.02 (s, 1 H), (1 Exchangeable proton not observed). |
| 131-I | 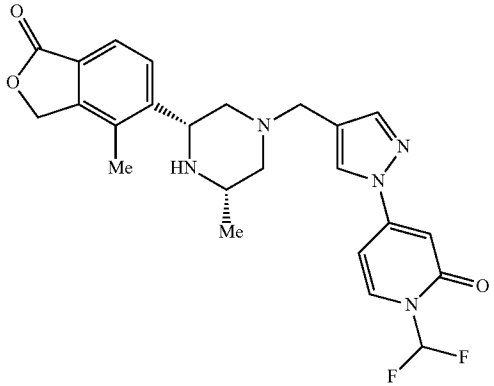 | 1-(difluoromethyl)-4-(4-(((3S,5R)-3-methyl-5-(4-methyl-1-oxo-1,3-dihydroisobenzofuran-5-yl)piperazin-1-yl)methyl)-1H-imidazol-1-yl)pyridin-2(1H)-one | 470.2 | S: 1.08, 100% R: 0.77, 100% V: 2.77, 100% ee | $^1$H NMR (400 MHz, DMSO-$d_6$) δ ppm 1.02 (d, J = 6.10 Hz, 3 H), 1.66-1.85 (m, 2 H), 2.19-2.33 (m, 3 H), 2.83 (d, J = 11.00 Hz, 2 H), 2.96 (br. s., 1 H), 3.45 (s, 2 H), 4.16 (d, J = 8.6 Hz, 1 H), 5.29-5.45 (m, 2 H), 6.81-6.93 (m, 1 H), 6.97 (dd, J = 2.20, 7.80 Hz, 1 H), 7.64 (d, J = 1.20 Hz, 1 H), 7.55-7.72 (m, 1 H), 7.75-7.91 (m, 2 H), 7.99 (d, J = 7.80 Hz, 1 H), 8.47 (s, 1 H), (1 Exchangeable proton not observed). $^{19}$F NMR (400 MHz, DMSO-$d_6$) δ ppm −114.90. |

-continued

| Example | Structure | Name | LCMS (M + H)$^+$ | HPLC/LCMS Method: RT (min.), Purity | NMR |
|---|---|---|---|---|---|
| 132-I | 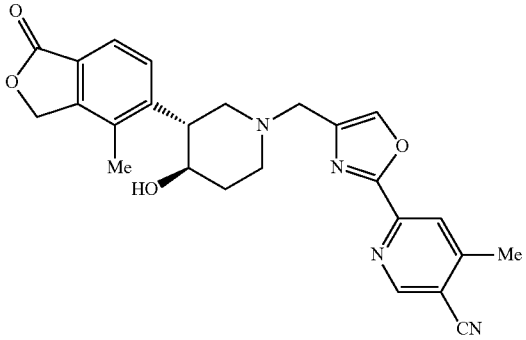 | 6-(4-(((3R,4R)-4-hydroxy-3-(4-methyl-1-oxo-1,3-dihydroisobenzofuran-5-yl)piperidin-1-y)methyl)oxazol-2-yl)-4-methylnicotinonitrile | 445.2 | S: 1.25, 97.81% R: 0.95 95.67% V: 4.37, 100% ee | $^1$H NMR (400 MHz, DMOS-$d_6$) δ ppm 1.58-1.70 (m, 1 H), 1.88-1.97 (m, 1 H), 2.16 (t, J = 11.1 Hz, 1 H), 2.21-2.32 (m, 4 H), 2.55 (m, 3 H), 2.80 (d, J = 11.70 Hz, 1 H), 3.08 (td, J = 3.40, 10.20 Hz, 2 H), 3.56 (s, 2 H), 3.72 (td, J = 5.20, 9.8 Hz, 1 H), 4.58 (d, J = 5.60 Hz, 1 H), 5.25-5.46 (m, 2 H), 7.55 (d, J = 7.80 Hz, 1 H), 7.64 (d, J = 8.10 Hz, 1 H), 8.19 (s, 1 H), 8.26 (s, 1 H), 9.02 (s, 1 H) |
| 133-I | 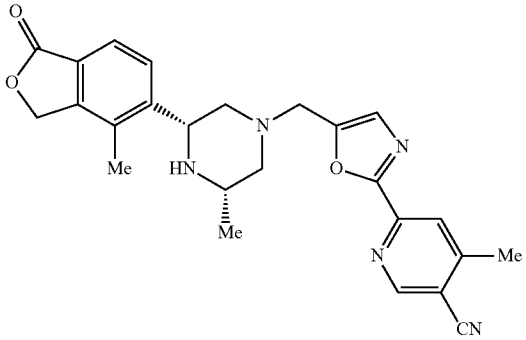 | 4-methyl-6-(4-(((3S,5R)-3-methyl-5-(4-methyl-1-oxo-1,3-dihydroisobenzofuran-5-yl)piperazin-1-yl)methyl)oxazol-2-yl)nicotinonitrile | 444.2 | S: 1.51, 100% R: 1.19, 98.32% XI: 6.58 96.51% ee | $^1$H NMR (400 MHz, DMSO-$d_6$) δ ppm 1.04 (br. s., 3 H), 1.84 (br. s., 2 H), 2.28 (s, 3 H), 2.60 (s, 3 H), 2.84 (br. s., 2 H), 2.97 (br. s., 1 H), 3.76 (br. s., 2 H), 4.17 (br. s., 1 H), 5.39 (s, 2 H), 7.38 (s, 1 H), 7.67 (br. s., 1 H), 7.79 (d, J = 7.80 Hz, 1 H), 8.18 (s, 1 H), 9.02 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 134-I | 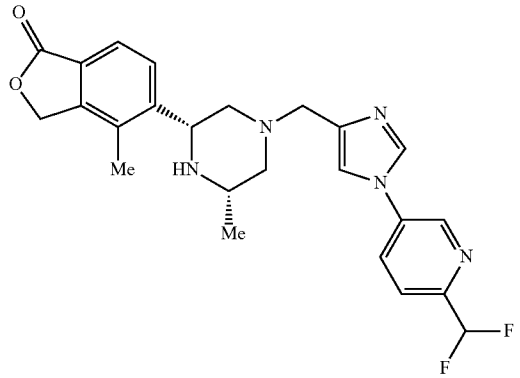 | 5-((2R,6S)-4-((1-(6-(difluoromethyl)pyridin-3-yl)-1H-imidazol-4-yl)methyl)-6-methylpiperazin-2-yl)-4-methylisobenzofuran-1(3H)-one | 454.2 | S: 1.15, 100% R: 0.78, 100% VII: 7.80 100% ee | $^1$H NMR (400 MHz, DMSO-$d_6$) δ ppm 1.03 (d, J = 6.10 Hz, 3 H), 1.82 (br.s., 2 H), 2.32 (s, 3 H), 2.87 (br. s., 2 H), 2.98 (br. s., 1 H), 3.49 (s, 2 H), 4.18 (d, J = 9.00 Hz, 1 H), 5.38 (s, 2 H), 7.02 (s, 1 H), 7.66 (d, J = 7.80 Hz, 1H), 7.72-7.92 (m, 3 H), 8.31 (dd, J = , 2.70, 8.60 Hz, 1 H), 8.38 (d, J = 1.50 Hz, 1 H), 9.07 (d, J = 2.70 Hz, 1 H), (1 Exchangeable proton not observed). |
| 135-I | 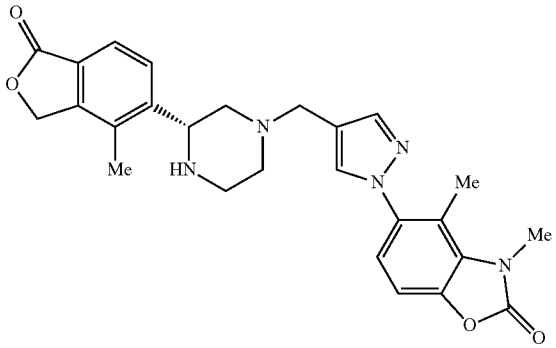 | (R)-3,4-dimethyl-5-(4-((3-(4-methyl-1-oxo-1,3-dihydroisobenzofuran-5-yl)piperazin-1-yl)methyl)-1H-pyrazol-1-yl)benzo[d]oxazol-2(3H)-one | 474.1 | S: 1.31, 98.71% R: 1.02, 99.80% XIV: 9.78, 98.00% ee | $^1$H NMR (400 MHz, DMSO-$d_6$) δ ppm 1.71-1.80 (m, 1 H), 1.91 (br. s., 1 H), 2.10 (t, J = 9.66 Hz, 1 H), 2.24 (d, J = 4.16 Hz, 6 H), 2.77-3.06 (m, 4 H), 3.41-3.52 (m, 2 H), 3.58 (s, 3H), 4.06 (d, J = 8.31 Hz, 1 H), 5.38 (s, 2 H), 7.08 (d, J = 8.31 Hz, 1 H), 7.28 (d, J = 8.56 Hz, 1 H), 7.58-7.70 (m, 2 H), 7.76-7.83 (m, 2 H). |

-continued

| Example | Structure | Name | LCMS $(M + H)^+$ | HPLC/LCMS Method: RT (min.), Purity | NMR |
|---|---|---|---|---|---|
| 136-I | 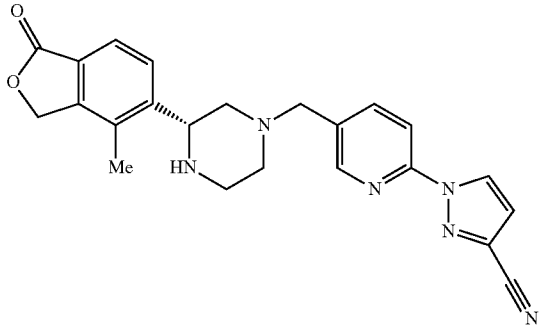 | (R)-1-(5-((3-(4-methyl-1-oxo-1,3-dihydroisobenzofuran-5-yl)piperazin-1-yl)methyl)pyridin-2-yl)-1H-pyrazole-3-carbonitrile | 415.1 | S: 1.70, 98.44% R: 1.36, 99.60% XVIII: 11.56, 98.10% ee | $^1$H NMR (400 MHz, DMSO-$d_6$) δ ppm 1.88 (t, J = 10.76 Hz, 1 H), 2.12-2.29 (m, 4 H), 2.71-2.85 (m, 2 H), 2.86-3.05 (m, 2 H), 3.57-3.71 (m, 2 H), 4.10 (d, J = 7.58 Hz, 1 H), 5.33-5.41 (m, 2 H), 7.27 (d, J = 2.69 Hz, 1 H), 7.65 (d, J = 7.83 Hz, 1 H), 7.78 (d, J = 7.83 Hz, 1 H), 7.95-8.07 (m, 2 H), 8.46 (s, 1 H), 8.85 (d, J = 2.69 Hz, 1 H), (1 Exchangeable proton not observed). |
| 137-I | 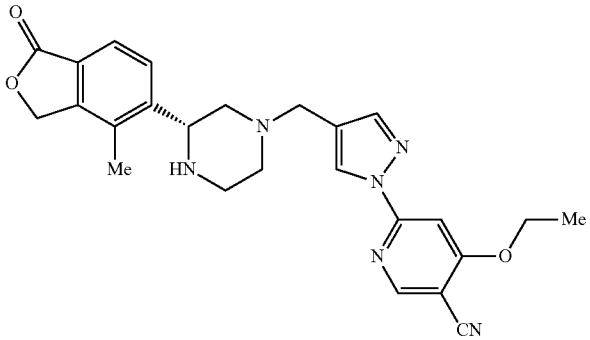 | (R)-4-ethoxy-6-(4-((3-(4-methyl-1-oxo-1,3-dihydroisobenzofuran-5-yl)piperazin-1-yl)methyl)-1H-pyrazol-1-yl)nicotinonitrile | 459.1 | S: 1.74, 97.53% R: 1.39, 97.64% XVIII: 16.38, 99.23% ee | $^1$H NMR (400 MHz, DMSO-$d_6$) δ ppm 1.42 (t, J = 6.97 Hz, 3 H), 1.83 (m, 1 H, 2.14 (m, 1 H), 2.26 (s, 3 H), 2.81 (d, J = 10.03 Hz, 2 H), 2.87-3.07 (m, 2 H), 3.53 (s, 2 H), 4.10 (br. s., 1 H), 4.41 (q, J = 7.09 Hz, 2 H), 5.37 (s, 2 H), 7.57 (s, 1 H), 7.65 (d, J = 8.56 Hz, 1 H), 7.76 (d, J = 7.83 Hz, 1 H), 7.85 (s, 1 H), 8.52 (s, 1 H), 8.72 (s, 1 H), (1 Exchangeable proton not observed). |
| 138-I | 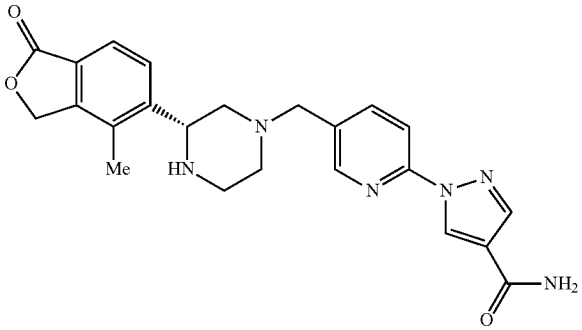 | (R)-1-(5-((3-(4-methyl-1-oxo-1,3-dihydroisobenzofuran-5-yl)piperazin-1-yl)methyl)pyridin-2-yl)-1H-pyrazole-4-carboxamide | 433.1 | S: 1.18, 100% R: 1.00, 100% XVIII: 13.07, 98.77% ee | $^1$H NMR (400 MHz, DMSO-$d_6$) δ ppm 1.87 (t, J = 10.52 Hz, 1 H), 2.13-2.19 (m, 1 H), 2.23 (s, 3 H), 2.78 (dd, J = 17.12, 11.25 Hz, 2 H), 2.87-3.04 (m, 2 H), 3.61 (q, J = 13.37 Hz, 2 H), 4.03-4.14 (m, 1 H), 5.35 (s, 2 H), 7.21 (br. s., 1 H), 7.65 (d, J = 7.83 Hz, 1 H), 7.75-7.85 (m, 2 H), 7.89-8.01 (m, 2 H), 8.12 (s, 1 H), 8.42 (s, 1 H), 9.11 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 139-I | 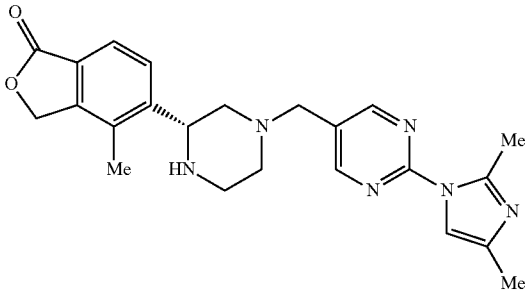 | (R)-5-(4-((2-(2,4-dimethyl-1H-imidazol-1-yl)pyrimidin-5-yl)methyl)piperazin-2-yl)-4-methylisobenzofuran-1(3H)-one | 419.2 | S: .108, 97.08% R: 0.63, 96.86% XVIII: 14.89, 96.79% ee | $^1$H NMR (400 MHz, DMSO-$d_6$) δ ppm 1.85-1.92 (m, 1 H), 2.09 (s, 3 H), 2.12-2.20 (m, 1 H), 2.24 (s, 3 H), 2.60-2.71 (m, 3 H), 2.78 (t, J = 9.41 Hz, 2 H), 2.85-3.03 (m, 2 H), 3.55-3.66 (m, 2 H), 4.08 (d, J = 8.31 Hz, 1 H), 5.36 (d, J = 3.18 Hz, 2 H), 7.54 (d, J = 0.98 Hz, 1 H), 7.65 (d, J = 7.83 Hz, 1 H), 7.78 (d, J = 7.83 Hz, 1 H), 8.70-8.80 (m, 2 H), (1 Exchangeable proton not observed). |
| 140-I | 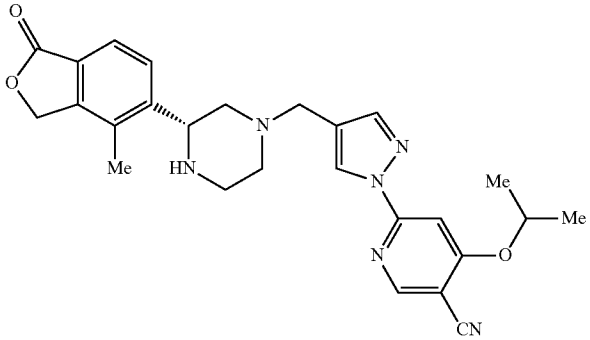 | (R)-4-isopropoxy-6-(4-((3-(4-methyl-1-oxo-1,3-dihydroisobenzofuran-5-yl)piperazin-1-yl)methyl)-1H-pyrazol-1-yl)nicotinonitrile | 473.3 | S: 1.44, 98.04% R: 1.35, 96.80% XIV: 7.60 99.25% ee | $^1$H NMR (400 MHz, DMSO-$d_6$) δ ppm 1.39 (d, J = 6.1 Hz, 7 H), 1.80 (t, J = 10.1 Hz, 1 H), 2.26 (s, 3 H), 2.80 (d, J = 11.03 Hz, 2 H), 2.89 (d, J = 11.03 Hz, 1 H), 2.96-3.03 (m, 1 H), 3.47-3.57 (m, 2 H), 4.07 (d, J = 10.07 Hz, 1 H), 5.06 (dt, J = 12.0, 6.0 Hz, 1 H), 5.37 (s, 2 H), 7.57 (s, 1 H), 7.64 (d, J = 8.20 Hz, 1 H), 7.76 (d, J = 8.00 Hz, 1 H), 7.85 (s, 1 H), 8.52 (s, 1 H), 8.72 (s, 1 H), (1 Exchangeable proton not observed). |
| 141-I | 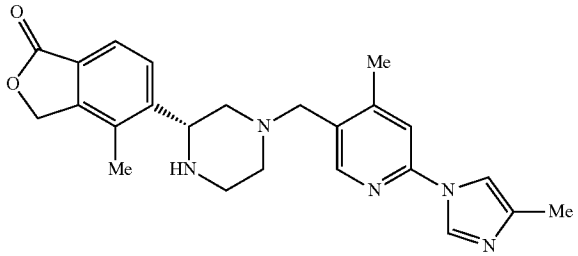 | (R)-4-methyl-5-(4-((4-methyl-6-(4-methyl-1H-imidazol-1-yl)pyridin-3-yl)methyl)piperazin-2-yl)isobenzofuran-1(3H)-one | 418.1 | R: 0.99, 100% S: 1.49, 99.12% V: 6.57 99.43% ee | $^1$H NMR (400 MHz, DMSO-$d_6$) δ ppm 1.91 (s, 1 H), 2.17 (s, 3 H), 2.21 (s, 3 H), 2.46 (s, 3 H), 2.70-2.77 (m, 3 H), 2.85-2.88 (m, 1 H), 2.96-3.02 (m, 1 H), 3.52 (d, J = 7.09 Hz, 2 H), 4.00-4.05 (m, 1 H), 5.36 (s, 2 H), 7.62 (s, 2 H), 7.66 (d, J = 8.07 Hz, 1 H), 7.80 (d, J = 8.07 Hz, 1 H), 8.21 (s, 1 H), 8.36 (d, J = 1.22 Hz, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 142-I | 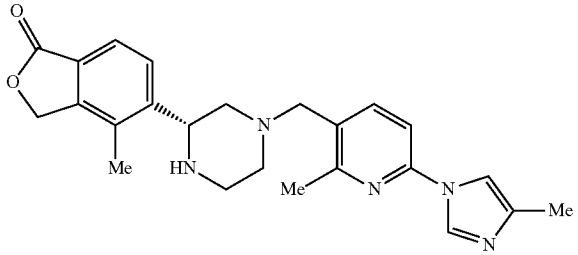 | (R)-4-methyl-5-(4-((2-methyl-6-(4-methyl-1H-imidazol-1-yl)pyridin-3-yl)methyl)piperazin-2-yl)isobenzofuran-1(3H)-one | 418.1 | R: 1.01, 99.50% S: 1.55, 99.05% V: 6.65 100% ee | $^1$H NMR (400 MHz, DMSO-$d_6$) δ ppm 2.17 (s, 3 H), 2.22 (s, 3 H), 2.54 (s, 3 H), 2.67-2.69 (m, 1 H), 2.70-2.77 (m, 3 H), 2.85-2.92 (m, 1 H), 2.96-3.04 (m, 1 H), 3.48-3.55 (m, 2 H), 4.02-4.10 (m, 1 H), 5.36 (s, 2 H), 7.45-7.52 (m, 1 H), 7.58-7.67 (m, 2 H), 7.77-7.84 (m, 2 H), 8.31-8.42 (m, 1 H), (1 Exchangeable proton not observed). |
| 143-I | 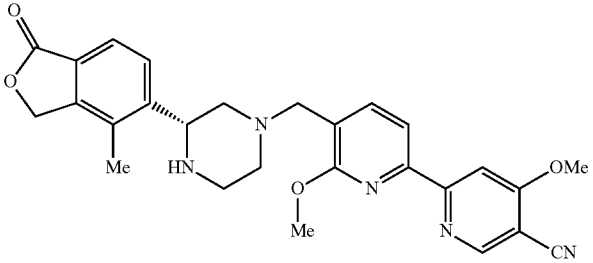 | (R)-4,6'-dimethoxy-5'-((3-(4-methyl-1-oxo-1,3-dihydroisobenzofuran-5-yl)piperazin-1-yl)methyl)-[2,2'-bipyridine]-5-carbonitrile | 486.1 | R: 1.52, 98.06% S: .198, 95.85% V: 8.55, 98.56% ee | $^1$H NMR (400 MHz, DMSO-$d_6$) δ ppm 2.26 (s, 3 H), 2.80 (t, J = 9.90 Hz, 2 H), 2.93-3.03 (m, 2 H), 3.57 (d, J = 3.18 Hz, 2 H), 4.03 (s, 4 H), 4.10-4.16 (m, 5 H), 5.36 (d, J = 2.45 Hz, 2 H), 7.65 (d, J = 7.83 Hz, 1 H), 7.79 (d, J = 8.07 Hz, 1 H), 7.94 (d, J = 7.58 Hz, 1 H), 8.05 (d, J = 7.58 Hz, 1 H), 8.11 (s, 1 H), 8.88 (s, 1 H), (1 Exchangeable proton not observed). |
| 144-I | 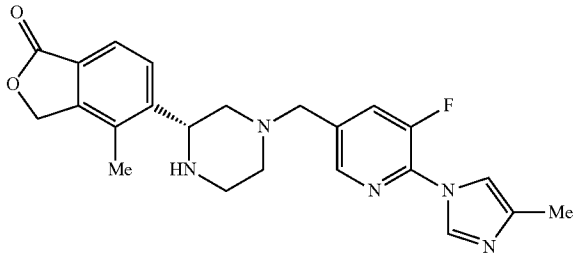 | (R)-5-(4-((5-fluoro-6-(4-mehtyl-1H-imidazol-1-yl)pyridin-3-yl)methyl)piperazin-2-yl)-4-methylisobenzofuran-1(3H)-one | 422.1 | R: 0.95, 100% S: 1.47, 98.31% XVIII: 14.16, 98.50% ee | $^1$H NMR (400 MHz, DMSO-$d_6$) δ ppm 2.18 (s, 3 H), 2.25 (s, 2 H), 2.31-2.34 (m, 1 H), 2.64-2.70 (m, 2 H), 2.73-2.82 (m, 2 H), 2.88-2.96 (m, 1 H), 2.97-3.03 (m, 1 H), 3.62 (d, J = 3.42 Hz, 2 H), 4.08-4.13 (m, 1 H), 5.37 (d, J = 3.42 Hz, 2 H), 7.51 (s, 1 H), 7.66 (s, 1 H), 7.78 (d, J = 8.07 Hz, 1 H), 7.92-7.97 (m, 1 H), 8.19 (s, 1 H), 8.29 (s, 1 H), (1 Exchangeable proton not observed). $^{19}$F NMR (400 MHz, DMSO-$d_6$) δ ppm −130.24. |

-continued

| Example | Structure | Name | LCMS (M + H)$^+$ | HPLC/LCMS Method: RT (min.), Purity | NMR |
|---|---|---|---|---|---|
| 145-I | 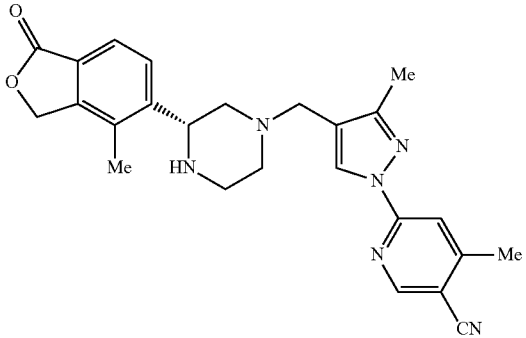 | (R)-4-methyl-6-(3-methyl-4-((3-(4-methyl-1-oxo-1,3-dihydroisobenzofuran-5-yl)piperazin-1-yl)methyl)-1H-pyrazol-1-yl)nicotinonitrile | 443.2 | R: 1.06, 96.45% S: 1.46, 97.52% V: 8.08, 98.28% ee | $^1$H NMR (400 MHz, DMSO-$d_6$) δ ppm 1.83 (t, J = 10.10 Hz, 1 H), 2.17-2.07 (m, 1 H), 2.24 (s, 3 H), 2.32-2.27 (m, 3 H), 2.56 (s, 3 H), 2.79 (t, J = 10.6 Hz, 2 H), 2.92-2.84 (m, 1 H), 3.00 (d, J = 11.70 Hz, 1 H), 3.51-3.39 (m, 2 H), 4.06 (d, J = 7.60 Hz, 1 H), 4.06 (d, J = 7.60 Hz, 1 H), 5.36 (s, 2 H), 7.64 (d, J = 8.10 Hz, 1 H), 7.77 (d, J = 7.80 Hz, 1 H), 7.90 (s, 1 H), 8.41-8.78 (s, 1 H), (1 Exchangeable proton not observed). |
| 146-I | 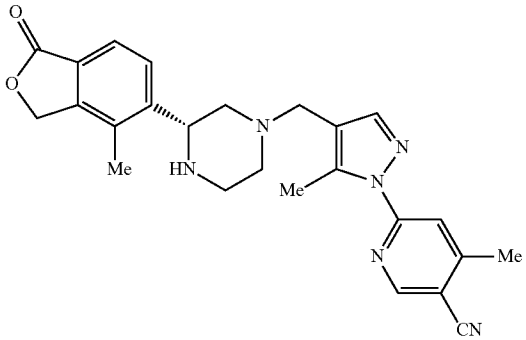 | (R)-4-methyl-6-(5-methyl-4-((3-(4-methyl-1-oxo-1,3-dihydroisobenzofuran-5-yl)piperazin-1-yl)methyl)-1H-pyrazol-1-yl)nicotinonitrile | 443.2 | R: 1.09, 100% S: 1.46, 97.73% V: 8.16, 100% ee | $^1$H NMR (400 MHz, DMSO-$d_6$) δ ppm 1.95-1.82 (m, 1 H), 2.14 (d, J = 13.00 Hz, 1 H), 2.25 (s, 3 H), 2.30 (s, 3 H), 2.56 (s, 3 H), 2.82 (t, J = 10.00 Hz, 2 H), 2.91 (d, J = 14.20 Hz, 1 H), 3.04 (d, J = 11.50 Hz, 1 H), 3.54-3.42 (m, 2 H), 4.12 (d, J = 9.00 Hz, 1 H), 5.46-5.27 (m, 2 H), 7.66 (d, J = 7.60 Hz, 1 H), 7.77 (d, J = 8.10 Hz, 1 H), 7.90 (s, 1 H), 8.43 (s, 1 H), 8.78 (s, 1 H), (1 Exchangeable proton not observed). |
| 147-I | 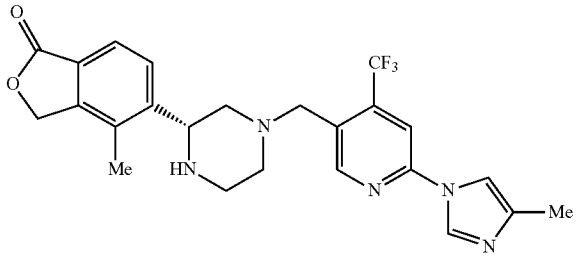 | (R)-4-methyl-5-(4-((6-(4-methyl-1H-imidazol-1-yl)-4-(trifluoromethyl)pyridin-3-yl)methyl)piperazin-2-yl)isobenzofurna-1(3H)-one | 472.1 | R: 0.80, 95.13% S: 1.48, 95.42% V: 5.82, 98.48% ee | $^1$H NMR (400 MHz, DMSO-$d_6$) ∂ ppm 2.18 (s, 3 H), 2.25 (s, 3 H), 2.35 (m, 2 H), 2.84 (d, J = 13.40 Hz, 1 H), 3.08 (s, 2 H), 3.16 (br. s., 2 H), 3.82-3.69 (m, 2 H), 5.47-5.31 (m, 2 H), 7.76-7.70 (m, 1 H), 7.83-7.76 (m, 2 H), 8.05 (s, 1 H), 8.54 (s, 1 H), 8.81 (s, 1 H), (1 Exchangeable proton not observed). $^{19}$F NMR (400 MHz, DMSO-$d_6$) δ ppm −59.25, −60.50, −61.47. |

-continued

| Example | Structure | Name | LCMS (M + H)$^+$ | HPLC/LCMS Method: RT (min.), Purity | NMR |
|---|---|---|---|---|---|
| 148-I | 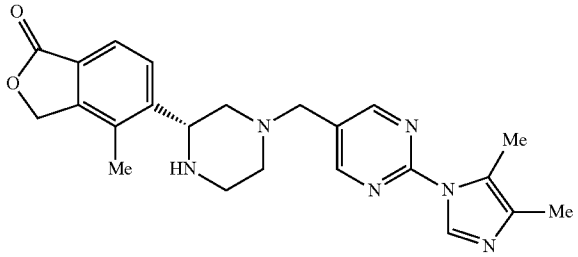 | (R)-5-(4-((2-(4,5-dimethyl-1H-imidazol-1-yl)pyrimidin-5-yl)methyl)piperazin-2-yl)-4-methylisobenzofuran-1(3H)-one | 419.2 | R: 0.68, 94.87% S: 1.17, 95.02% V: 8.32, 100% ee | $^1$H NMR (400 MHz, DMSO-$d_6$) δ ppm 1.93-1.87 (m, 1 H), 2.11 (s, 3 H), 2.20-2.13 (m, 1 H), 2.25 (s, 3 H), 2.45 (s, 3 H), 2.79 (t, J = 9.70 Hz, 2 H), 2.95-2.86 (m, 1 H), 3.03-2.96 (m, 1 H), 3.64-3.53 (m, 2 H), 4.08 (d, J = 9.30 Hz, 1 H), 5.43-5.30 (m, 2 H), 7.65 (d, J = 8.30 Hz, 1 H), 7.78 (d, J = 7.80 Hz, 1 H), 8.30 (s, 1 H), 8.77 (s, 2 H), (1 Exchangeable proton not observed). |
| 149-I | 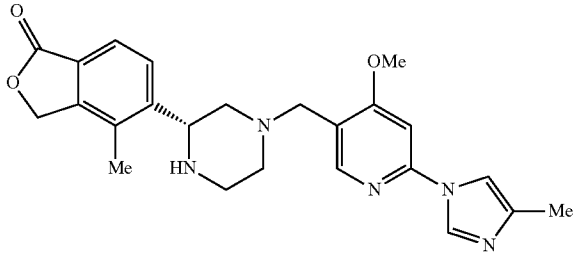 | (R)-5-(4-((4-methoxy-6-(4-methyl-1H-imidazol-1-yl)pyridin-3-yl)methyl)piperazin-2-yl)-4-methylisobenzofuran-1(3H)-one | 434.2 | R: 0.64, 100% S: 1.08, 100% XII: 2.71, 100% ee | $^1$H NMR (400 MHz, DMSO-$d_6$) δ ppm 1.94-1.85 (m, 1 H), 2.17 (s, 4 H), 2.26 (s, 3 H), 2.78 (d, J = 10.30 Hz, 2 H), 2.91 (d, J = 7.80 Hz, 1 H), 3.01-2.95 (m, 1 H), 3.52 (s, 2 H), 3.94 (s, 3 H), 4.07 (br. s., 1 H), 5.37 (s, 2 H), 7.29 (s, 1 H), 7.64 (d, J = 8.10 Hz, 1 H), 7.69 (s, 1 H), 7.78 (d, J = 8.30 Hz, 1 H), 8.21 (s, 1 H), 8.42 (s, 1 H), (1 Exchangeable proton not observed). |
| 150-I | 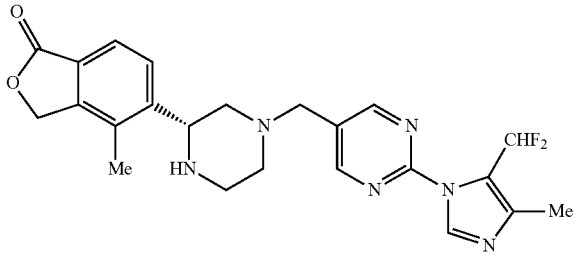 | (R)-5-(4-((2-(5-(difluoromethyl)-4-methyl-1H-imidazol-1-yl)pyrimidin-5-yl)methyl)piperazin-2-yl)-4-methylisobenzofuran-1(3H)-one | 455.3 | S: 1.23, 97.70% R: 0.95, 99.03% XVIII: 6.04, 100% ee | $^1$H NMR (400 MHz, DMSO-$d_6$) δ ppm 2.37-2.33 (m, 3 H), 2.59-2.53 (m, 2 H), 2.63 (t, J = 2.10 Hz, 3 H), 3.08 (d, J = 10.50 Hz, 2 H), 3.43 (br. s., 2 H), 3.79 (s, 2 H), 4.73 (br. s., 1 H), 5.42 (s, 1 H), 5.46 (s, 1 H), 7.14-7.00 (m, 1 H), 7.77 (d, J = 8.10 Hz, 1 H), 7.86 (d, J = 7.80 Hz, 1 H), 8.47 (s, 1 H), 8.89 (s, 2 H), (1 Exchangeable proton not observed). $^{19}$F NMR (400 MHz, DMSO-$d_6$) δ ppm −110.99. |

-continued

| Example | Structure | Name | LCMS (M + H)$^+$ | HPLC/LCMS Method: RT (min.), Purity | NMR |
|---|---|---|---|---|---|
| 151-I | 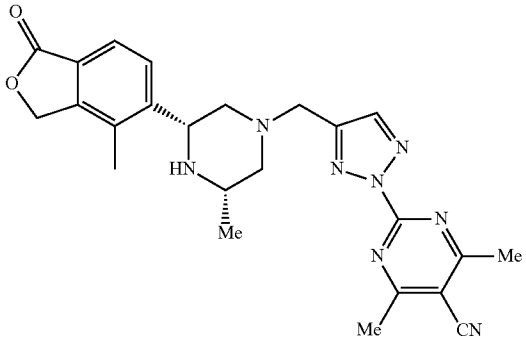 | 4,6-dimethyl-2-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyrimidine-5-carbonitrile | 459.2 | R: 0.95, 97.35% S: 1.19, 100% XXV: 7.12, 100% ee | $^1$H NMR (400 MHz, DMSO-$d_6$) δ ppm 1.04 (d, J = 5.60 Hz, 3 H), 1.82 (br. s., 2 H), 2.28 (s, 3 H), 2.76-2.66 (m, 6 H), 2.81 (br. s., 2 H), 2.99 (br. s., 1 H), 3.78 (s, 2 H), 4.19 (br. s., 1 H), 5.46-5.30 (m, 2 H), 7.67 (d, J = 7.60 Hz, 1 H), 7.80 (d, J = 8.30 Hz, 1 H), 8.24 (s, 1 H), (1 Exchangeable proton not observed). |
| 152-I | 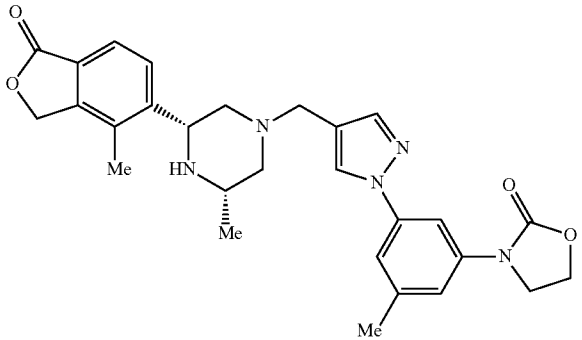 | 3-(3-methyl-5-(4-(((3S,5R)-3-methyl-5-(4-methyl-1-oxo-1,3-dihydroisobenzofuran-5-yl)piperazin-1-yl)methyl)-1H-pyrazol-1-yl)phenyl)oxazolidin-2-one | 502.2 | S: 1.42, 100% R: 0.90, 100% | $^1$H NMR (400 MHz, DMSO-$d_6$) δ ppm 1.03 (d, J = 6.50 Hz, 3 H), 1.79-1.64 (m, 2 H), 2.32-2.18 (m, 3 H), 2.43-2.35 (m, 3 H), 2.81 (d, J = 11.00 Hz, 2 H), 2.97 (br. s., 1 H), 3.48 (s, 2 H), 4.24-4.03 (m, 3 H), 4.56-4.40 (m, 2 H), 5.38 (s, 2 H), 7.30 (s, 1 H), 7.42 (s, 1 H), 7.69-7.58 (m, 2 H), 7.80 (d, J = 8.00 Hz, 1 H), 7.90-7.84 (m, 1 H), 8.37 (s, 1 H), (1 Exchangeable proton not observed). |
| 153-I | 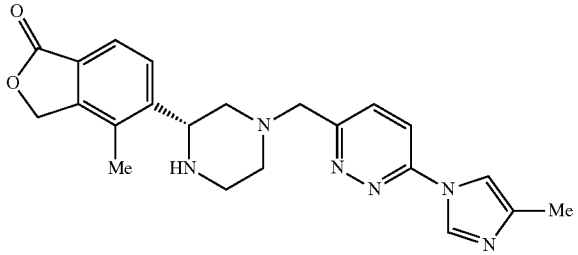 | (R)-4-methyl-5-(4-((6-(4-methyl-1H-imidazol-1-yl)pyridazin-3-yl)methyl)piperazin-2-yl)isobenzofuran-1(3H)-one | 405.4 | S: 1.13, 95.04% R: 0.75, 95.90% | $^1$H NMR (400 MHz, DMSO-$d_6$) δ ppm 1.90-2.01 (m, 1 H), 2.20 (s, 3 H), 2.24 (s, 3 H), 2.27-2.34 (m, 2 H), 2.73-2.80 (m, 2 H), 2.89-3.03 (m, 2 H), 3.85 (d, J = 5.32 Hz, 2 H), 4.05-4.10 (m, 1 H), 5.31-5.41 (m, 2 H), 7.65 (d, J = 8.13 Hz, 1 H), 7.74-7.80 (m, 2 H), 7.93 (d, J = 8.93 Hz, 1 H), 8.12 (d, J = 9.05 Hz, 1 H), 8.51 (s, 1 H). |

-continued

| Example | Structure | Name | LCMS $(M + H)^+$ | HPLC/LCMS Method: RT (min.), Purity | NMR |
|---|---|---|---|---|---|
| 154-I | 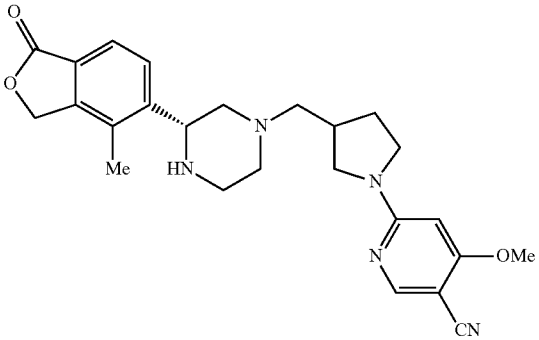 | 4-methoxy-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-I) | 448.2 | G: 9.96, 95.87% F: 8.77, 96.16% XIII: 3.39, 100% ee | $^1$H NMR (400 MHz, DMSO-$d_6$) δ ppm 1.00-1.06 (m, 1 H), 71.73-1.81 (m, 2 H), 2.04-2 .14 (m, 2 H), 2.31 (s, 3 H), 2.34-2.40 (m ,3 H), 2.44-2.48 (m, 2 H), 2.53-2.62 (m, 1 H), 2.78-3.02 (m, 4 H), 3.92 (s, 3 H), 4.03-4.10 (m, 1 H), 5.38 (d, J = 5.77 Hz, 2 H), 6.00 (s, 1 H), 7.65 (d, J = 8.03 Hz, 1 H), 7.80 (d, J = 8.09 Hz, 1 H), 8.26 (s, 1 H), 8.55-8.56 (m, 1 H). |
| 155-I | 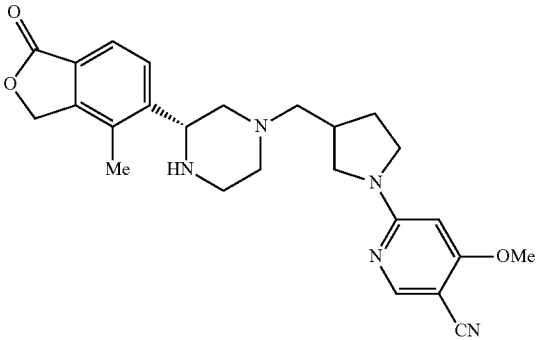 | 4-methoxy-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-II) | 448.2 | F: 8.09 96.88% G: 10.05, 96.44% XIII: 4.72, 97.82% ee | $^1$H NMR (400 MHz, DMSO-$d_6$) δ ppm 1.79-1.86 (m, 2 H), 2.02-2.08 (m, 1 H), 2.30 (s, 3 H), 2.34-2.39 (m, 4 H), 2.76-2.81 (m, 2 H), 2.84-2.93 (m, 5 H), 2.95-3.01 (m, 1 H), 3.39-3.46 (m, 1 H), 3.92 (s, 3 H), 4.07 (d, J = 9.79 Hz, 1 H), 5.38 (d, J = 4.14 Hz, 2 H), 6.00 (s, 1 H), 7.65 (d, J = 8.09 Hz, 1 H), 7.80 (d, J = 7.91 Hz, 1 H), 8.25 (s, 1 H). |

-continued

| Example | Structure | Name | LCMS (M + H)$^+$ | HPLC/LCMS Method: RT (min.), Purity | NMR |
|---|---|---|---|---|---|
| 156-I | 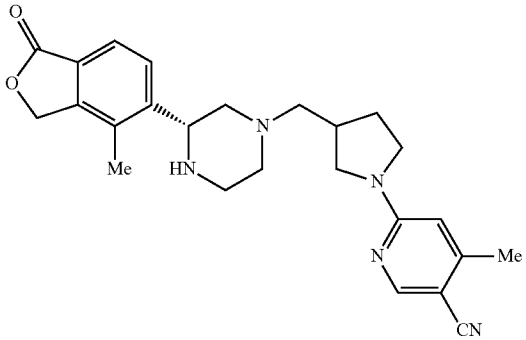 | 4-methyl-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-I) | 432.2 | F: 9.61 96.97% G: 10.62, 97.28% XIII: 3.05, 99.92% ee | $^1$H NMR (400 MHz, DMSO-$d_6$) δ ppm 1.79-1.86 (m, 2 H), 2.00-2.14 (m, 3 H), 2.30 (s, 3 H), 2.33 (m, 4 H), 2.34-2.39 (m, 2 H), 2.53-2.61 (m, 1 H), 2.77-2.93 (m, 4 H), 2.94-3.01 (m, 1 H), 3.35-3.46 (m, 2 H), 4.06 (d, J = 7.91 Hz, 1 H), 5.38 (d, J = 5.96 Hz, 2 H), 6.46 (s, 1 H), 7.65 (d, J = 7.97 Hz, 1 H), 7.79 (d, J = 7.91 Hz, 1 H), 8.36 (s, 1 H). |
| 157-I | 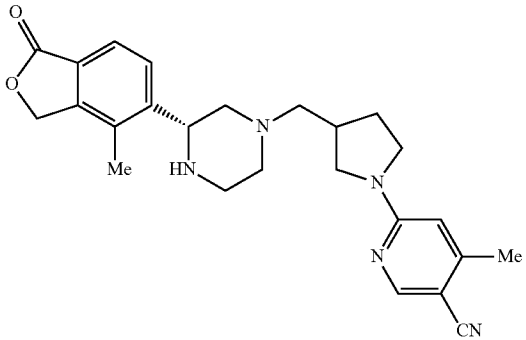 | 4-methyl-5-(3-(((R)-3-(4-methyl-1-oxo-1,3-dihydroisobenzofuran-5-yl)piperazin-1-yl)methyl)pyrrolidin-1-yl)nicotinonitrile (Diastereomer-II) | 432.2 | F: 9.60 97.43% G: 10.59, 97.53% XIII: 3.86, 95.66% ee | $^1$H NMR (400 MHz, DMSO-$d_6$) δ ppm 1.10-1.16 (m, 1 H), 1.79-1.87 (m, 1 H), 2.30 (s, 3 H), 2.33 (m, 5 H), 2.33-2.37 (m, 3 H), 2.53-2.61 (m, 1 H), 2.77-2.93 (m, 4 H), 2.94-3.01 (m, 1 H), 3.08-3.15 (m, 1 H), 3.35-3.46 (m, 2 H), 4.06 (d, J = 7.91 Hz, 1 H), 5.38 (d, J = 3.95 Hz, 2 H), 6.46 (s, 1 H), 7.65 (d, J = 8.16 Hz, 1 H), 7.79 (d, J = 8.03 Hz, 1 H), 8.36 (s, 1 H). |

-continued

| Example | Structure | Name | LCMS (M + H)$^+$ | HPLC/LCMS Method: RT (min.), Purity | NMR |
|---|---|---|---|---|---|
| 158-I | 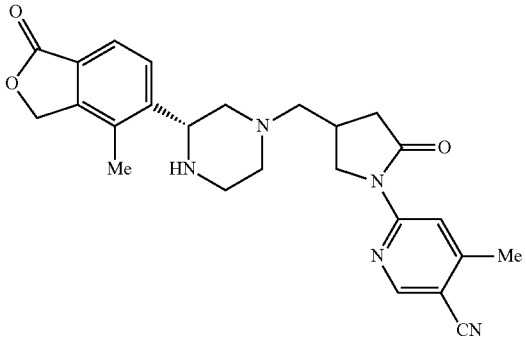 | 4-methyl-6-(4-(((R)-3-(4-methyl-1-oxo-1,3-dihydroisobenzofuran-5-yl)piperazin-1-yl)methyl)-2-oxopyrrolidin-1-yl)nicotinonitrile (Diastereomer-II) | 446.2 | F: 9.97 95.67% G: 12.43, 96.68% XIII: 4.57, 98.7% ee | $^1$H NMR (400 MHz, DMSO-$d_6$) δ ppm 1.12-1.20 (m, 1 H), 1.80-1.90 (m, 1 H), 2.00-2.10 (m, 1 H), 2.29-2.35 (m, 3 H), 2.45-2.58 (m, 2 H), 2.54-2.58 (m, 5 H), 2.65-2.90 (m, 5 H), 3.70-3.80 (m, 1 H), 4.05-4.15 (m, 2 H), 5.39 (d, J = 4.65 Hz, 2 H), 7.66 (d, J = 8.13 Hz, 1 H), 7.80 (d, J = 8.31 Hz, 1 H), 8.37 (s, 1 H), 8.78 (s, 1 H). |
| 159-I | 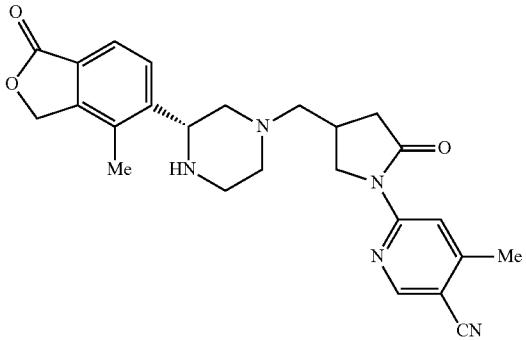 | 4-methoxy-6-(4-(((R)-3-(4-methyl-1-oxo-1,3-dihydroisobenzofuran-5-yl)piperazin-1-yl)methyl)-2-oxopyrrolidin-1-yl)nicotinonitrile (Diastereomer-I) | 462.3 | S: .122 97.06% R: 0.97, 96.87% XIII: 5.20, 97.50% ee | $^1$H NMR (400 MHz, DMSO-$d_6$) δ ppm 1.85-1.93 (m, 1 H), 2.07-2.11 (m, 1 H), 2.30 (s, 3 H), 2.37-2.45 (m, 2 H), 2.69-2.81 (m, 3 H), 2.84-2.96 (m, 2 H), 2.98-3.05 (m, 3 H), 3.47-3.57 (m, 2 H), 3.72-3.78 (m, 3 H), 4.07-4.15 (m, 1 H), 5.38 (d, J = 3.91 Hz, 2 H), 7.66 (d, J = 7.83 Hz, 1 H), 7.78 (d, J = 8.01 Hz, 1 H), 8.16 (s, 1 H), 8.64 (s, 1 H). |

-continued

| Example | Structure | Name | LCMS (M + H)$^+$ | HPLC/LCMS Method: RT (min.), Purity | NMR |
|---|---|---|---|---|---|
| 160-I | 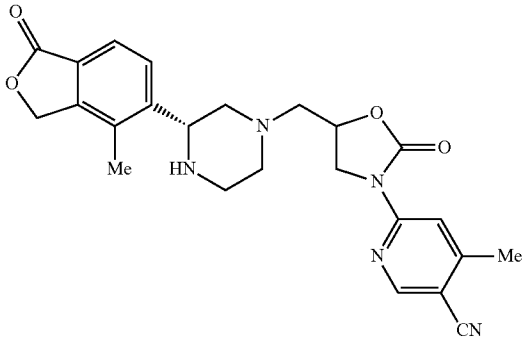 | 4-methyl-6-(5-(((R)-3-(4-methyl-1-oxo-1,3-dihydroisobenzofuran-5-yl)piperazin-1-yl)methyl)-2-oxooxazolidin-3-yl)nicotinonitrile (Diastereomer-II) | 448.2 | Q: 8.61, 94.33% D: .167, 99.28% | $^1$H NMR (400 MHz, DMSO-$d_6$) δ ppm 1.99 (s, 1 H), 2.29 (s, 3 H), 2.46-2.48 (m, 3 H), 2.59-2.62 (m, 2 H), 2.71-2.75 (m, 3 H), 2.81-2.87 (m, 4 H), 3.80-3.89 (m, 1 H), 3.90-3.96 (m, 1 H), 4.23-4.29 (m, 1 H), 5.40 (s, 2 H), 7.66 (d, J = 7.72 Hz, 1 H), 7.80 (d, J = 8.03 Hz, 1 H), 8.16 (s, 1 H), 8.78 (s, 1 H). |
| 161-I | 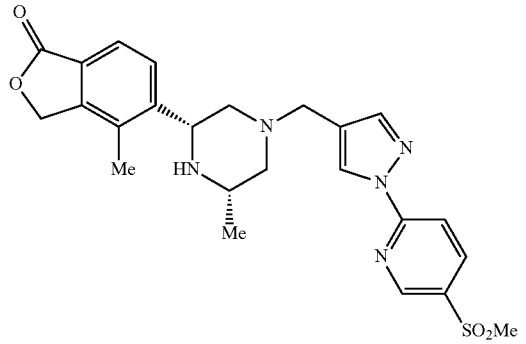 | 4-methyl-5-((2R,6S)-6-methyl-4-((1-(5-(methylsulfonyl)pyridin-2-yl)-1H-pyrazol-4-yl)methyl)piperazin-2-yl)isobenzofuran-1(3H)-one | 482.2 | S: 1.26, 95.63%. R: 0.85, 96.50%. XVIII: 17.07, 100% ee | $^1$H NMR (400 MHz, DMSO-$d_6$) δ ppm 1.04 (d, J = 6.10 Hz, 3 H), 1.74 (br. s., 2 H), 2.27 (s, 3 H), 2.82 (d, J = 8.30 Hz, 2 H), 2.98 (br s., 1 H), 3.35 (s, 3 H), 3.55 (br. s., 2 H), 4.18 (br. s., 1 H), 5.46-5.27 (m, 2 H), 7.66 (d, J = 7.80 Hz, 1 H), 7.80 (d, J = 7.80 Hz, 1 H), 7.87 (s, 1 H), 8.10 (d, J = 8.80 Hz, 1 H), 8.46 (dd, J = 8.80, 2.40 Hz, 1 H), 8.58 (s, 1 H), 8.93 (d, J = 2.20 Hz, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 162-I | 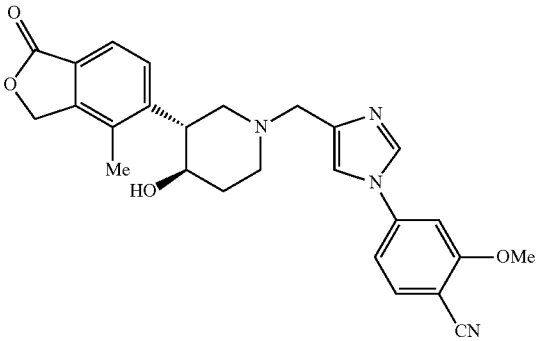 | 4-(4-(((3R,4R)-4-hydroxy-3-(4-methyl-1-oxo-1,3-dihydroisobenzofuran-5-yl)piperidin-1-yl)methyl)-1H-imidazol-1-yl)-2-methoxybenzonitrile | 459.2 | S: 1.19, 100% R: 0.97, 100% XXIX: 3.00, 100% ee | $^1$H NMR (400 MHz, DMSO-$d_6$) δ ppm 1.96 (br. s., 1 H), 2.13-2.43 (m, 4 H), 2.74 (m, 1 H), 2.79-3.07 (m, 2 H), 3.07-3.20 (m, 2 H), 3.82 (br. s., 1 H), 3.94-4.12 (m, 4 H), 4.68 (br. s., 1 H), 5.36 (br. s., 2 H), 7.46-7.56 (m, 4 H), 7.61-7.79 (m, 2 H), 7.94-8.13 (m, 1 H), (1 Exchangeable proton not observed). |
| 163-I | 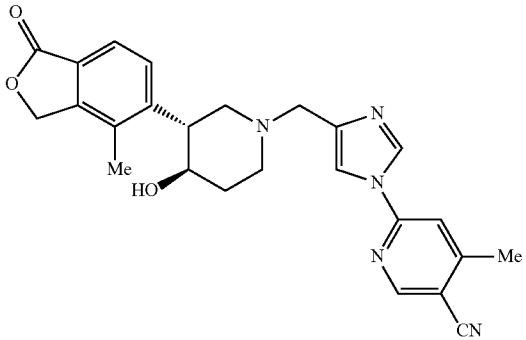 | 6-(4-(((3R,4R)-4-hydroxy-3-(4-methyl-1-oxo-1,3-dihydroisobenzofuran-5-yl)piperidin-1-yl)methyl)-1H-imidazol-1-yl)-4-methylnicotinonitrile | 444.5 | P: 4.27, 98.40% Q: 5.59, 98.86% | $^1$H NMR (400 MHz, DMSO-$d_6$) δ ppm 1.60-1.80 (m, 1 H), 1.92-1.97 (m, 1 H), 2.23-2.30 (m, 1 H), 2.35 (S, 3 H), 2.76-2.91 (m, 3 H), 2.95-3.16 (m, 2 H), 3.44-3.61 (m, 2 H), 3.65-3.80 (m, 2 H), 4.51 (s, 1 H), 5.37 (d, J = 6.40 Hz, 2 H), 7.54 (d, J = 8.03 Hz, 1 H), 7.64 (d, J = 7.91 Hz, 1 H), 7.85 (br. s., 1 H), 8.00 (s, 2 H), 8.55 (br. s., 1 H), 8.86 (s, 1 H). |

-continued

| Example | Structure | Name | LCMS (M + H)$^+$ | HPLC/LCMS Method: RT (min.), Purity | NMR |
|---|---|---|---|---|---|
| 164-I | 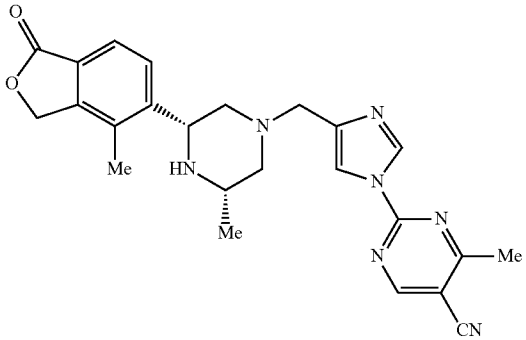 | 4-methyl-2-(4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile | 444.3 | S: 1.32, 100% R: 0.98, 96.43% XXIX: 3.45, 93.48% ee | $^1$H NMR (400 MHz, DMSO-d6) δ ppm 1.02 (d, J = 6.10 Hz, 3 H), 1.88-1.71 (m, 2 H), 2.20-2.32 (m, 3 H), 2.67-2.74 (m, 3 H), 2.76-2.88 (m, 2 H), 2.96 (ddd, J = 9.60, 6.50, 2.70 Hz, 1 H), 3.52 (s, 2 H), 4.16 (dd, J = 10.00, 2.20 Hz, 1 H), 5.47-5.29 (m, 2 H), 7.65 (d, J = 7.80 Hz, 1 H), 7.89-7.75 (m, 2 H), 8.56 (d, J = 1.20 Hz, 1 H), 9.22 (s, 1 H), (1 Exchangeable proton not observed). |
| 165-I | 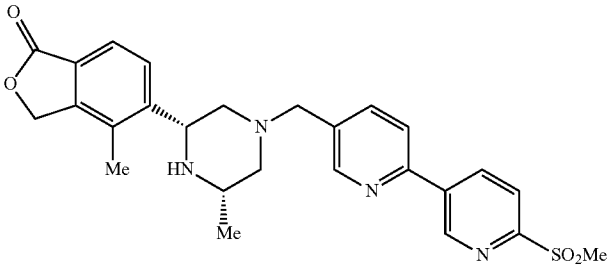 | 4-methyl-5-((2R,6S)-6-methyl-4-((6'-(methylsulfonyl)-[2,3'-bipyridin]-5-yl)methyl)piperazin-2-yl)isobenzofuran-1(3H)-one | 493.2 | S: 1.27, 99.27% R: 0.81, 98.46% XXIX: 9.99, 100% ee | $^1$H NMR (400 MHz, DMSO-d$_6$) δ ppm 1.03 (d, J = 6.40 Hz, 3 H), 1.64-1.88 (m, 2 H), 2.25 (s, 3 H), 2.99 (br. s., 2 H), 2.79 (d, J = 10.30 Hz, 2 H), 3.34 (s, 3 H), 3.64 (s, 2 H), 4.19 (d, J = 9.50 Hz, 1 H), 5.46-5.28 (m, 2 H), 7.66 (d, J = 8.10 Hz, 1 H), 7.81 (d, J = 8.10 Hz, 1 H), 7.93 (dd, J = 8.10, 2.00 Hz, 1 H), 8.09-8.25 (m, 2 H), 8.70 (d, J = 1.70 Hz, 1 H), 8.78 (dd, J = 8.10, 2.20 Hz, 1 H), 9.39-9.49 (m, 1 H). |
| 166-I | 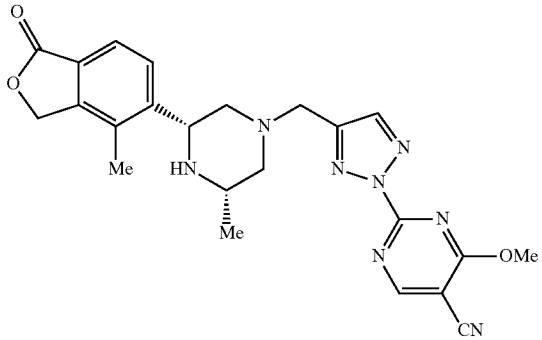 | 4-methoxy-2-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyrimidine-5-carbonitrile | 461.3 | P: 6.75, 95.94% Q: 8.64, 96.38% V: 5.85, 100% ee | $^1$H NMR (400 MHz, DMSO-d$_6$) δ ppm 1.02 (d, J = 6.21 Hz, 3 H), 1.77-1.87 (m, 2 H), 2.26 (s, 3 H), 2.80 (d, J = 10.60 Hz, 2 H), 2.94-3.01 (m, 1 H), 3.77 (s, 2 H), 4.17-4.19 (m, 4 H), 5.37 (d, J = 3.01 Hz, 2 H), 7.65 (d, J = 7.97 Hz, 1 H), 7.79 (d, J = 7.97 Hz, 1 H), 8.25 (s, 1 H), 9.15 (s, 1 H). (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 167-I | 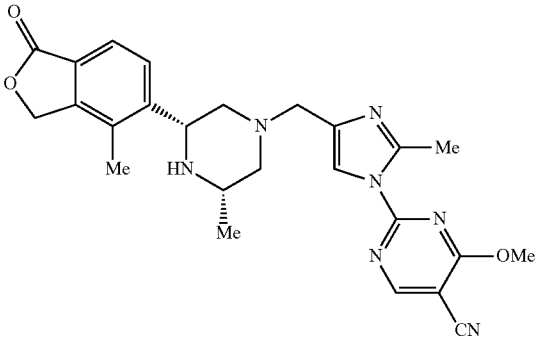 | 4-methoxy-2-(2-methyl-4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile | 474.3 | Q: 9.51, 99.30% P: 5.20, 99.42% | $^1$H NMR (400 MHz, DMSO-$d_6$) δ ppm 1.73-1.84 (m, 3 H), 1.91 (s, 2 H), 2.28 (s, 3 H), 2.54-2.58 (m, 2 H), 2.66-2.69 (m, 1 H), 2.72 (s, 1 H), 2.79-2.88 (m, 3 H), 2.92-2.99 (m, 2 H), 4.15 (m, 4 H), 4.16-5.38 (d, J = 1.51 Hz, 2 H), 7.65 (d, J = 7.84 Hz, 1 H), 7.75 (s, 1 H), 7.80 (d, J = 7.91 Hz, 1 H), 9.09 (s, 1 H). |
| 168-I | 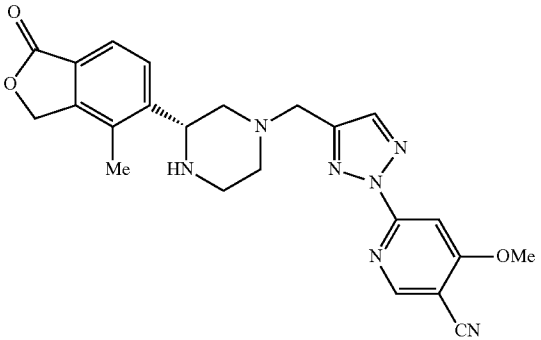 | (R)-4-methoxy-6-(4-((3-(4-methyl-1-oxo-1,3-dihydroisobenzofuran-5-yl)piperazin-1-yl)methyl)-2H-1,2,3-triazol-2-yl)nicotinonitrile | 446.2 | E: 8.07, 99.40% G: 9.30, 99.10% XIV: 9.58, 99.00% ee | $^1$H NMR (400 MHz, DMSO-$d_6$) δ ppm 1.90 (t, J = 10.39 Hz, 1 H), 2.21 (d, J = 2.93 Hz, 1 H), 2.27 (s, 3 H), 2.79-2.94 (m, 3 H), 2.96-3.03 (m, 1 H), 3.77 (s, 2 H), 4.09 (d, J = 8.07 Hz, 1 H), 4.13 (s, 3 H), 5.38 (d, J = 2.45 Hz, 2 H), 7.65 (d, J = 8.07 Hz, 1 H), 7.70 (s, 1 H), 7.78 (d, J = 7.83 Hz, 1 H0, 8.23 (s, 1 H), 8.83 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 169-I | 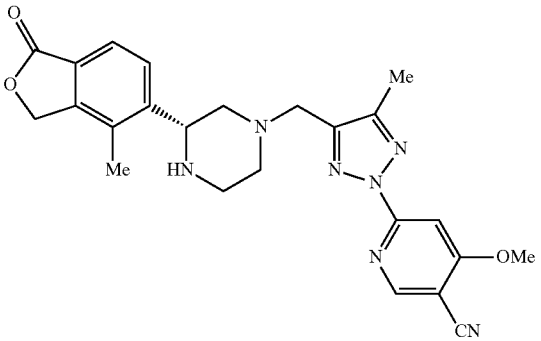 | (R)-4-methyl-6-(4-methyl-5-((3-(4-methyl-1-oxo-1,3-dihydroisobenzofuran-5-yl)piperazin-1-yl)methyl)-2H-1,2,3-triazol-2-yl)nicotinonitrile | 444.3 | S: .129, 97.2% R: 1.05, 98.06% XIV: 6.83, 100% ee | $^1$H NMR (400 MHz, DMSO-$d_6$) δ ppm 1.91 (t, J = 10.4 Hz, 1 H), 2.13-2.23 (m, 1 H), 2.25 (s, 3 H), 2.42 (s, 3 H), 2.59 (s, 3 H), 2.78 (d, J = 11.20 Hz, 2 H), 2.83-2.92 (m, 1 H), 2.96-3.04 (m, 1 H), 3.63-3.77 (m, 2 H), 4.06 (d, J = 7.80 Hz, 1 H), 5.36 (s, 2 H), 7.64 (d, J = 7.80 Hz, 1 H), 7.78 (d, J = 7.80 Hz, 1 H), 8.03 (s, 1 H), 8.88 (s, 1 H), (1 Exchangeable proton not observed). |
| 170-I | 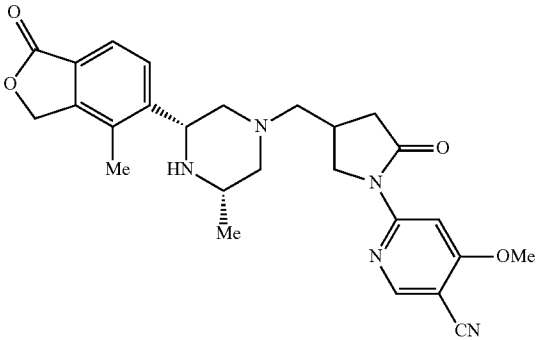 | 4-methoxy-6-(4-(((3S,5R)-3-methyl-5-(4-methyl-1-oxo-1,3-dihydroisobenzofuran-5-yl)pipeazin-1-yl)methyl)-2-oxopyrrolidin-1-yl)nicotinonitrile (Diastereomer-I) | 476.3 | S: .149, 100% R: 1.07, 99.06% XXXI: 4.36, 100% ee | $^1$H NMR (400 MHz, DMSO-$d_6$) δ ppm 1.04 (d, J = 6.10 Hz, 3 H), 1.74 (t, J = 9.80 Hz, 2 H), 2.31 (s, 3 H), 2.33-2.48 (m, 3 H), 2.64-2.89 (m, 4 H), 2.96 (br. s., 1 H), 3.77 (dd, J = 11.0, 5.40 Hz, 1 H), 3.97 (s, 3 H), 4.12 (dd, J = 11.40, 7.70 Hz, 2 H), 5.31-5.50 (m, 2 H), 7.67 (d, J = 8.10 Hz, 1 H), 7.82 (d, J = 8.10 Hz, 1 H), 8.18 (s, 1 H), 8.66 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 171-I | 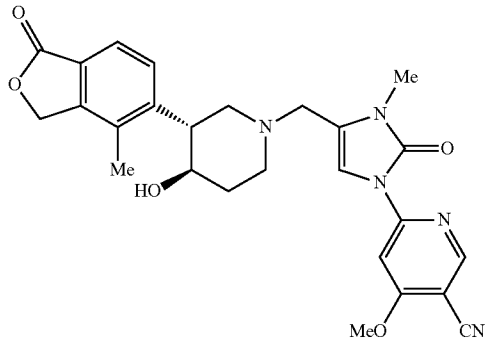 | 6-(4-(((3R,4R)-4-hydroxy-3-(4-methyl-1-oxo-1,3-dihydroisobenzofuran-5-yl)piperidin-1-yl)methyl)-3-methyl-2-oxo-2,3-dihydro-1H-imidazol-1-yl)-4-methoxynicotinonitrile | 490.2 | P: 9.20, 99.40% Q: 5.03, 98.10% XXVII: 5.46, 100% ee | $^1$H NMR (400 MHz, DMSO-$d_6$) δ ppm 1.55-1.66 (m, 1 H), 1.91-1.98 (m, 1 H), 2.07-2.15 (m, 1 H), 2.25 (s, 4 H), 2.74-2.81 (m, 1 H), 2.92-2.99 (m, 1 H), 3.01-3.08 (m, 1 H), 3.30 (s, 3 H), 3.43 (d, J = 9.04 Hz, 2 H), 3.71-3.80 (m, 1 H), 4.01 (s, 3 H), 4.60 (d, J = 5.52 Hz, 1 H), 5.36 (d, J = 8.53 Hz, 2 H), 7.27 (s, 1 H), 7.56 (s, 1 H), 7.63-7.66 (m, 1 H), 8.27 (s, 1 H), 8.66 (s, 1 H). |
| 172-I | 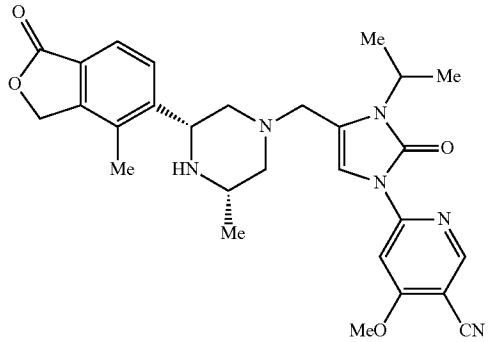 | 6-(3-isopropyl-4-(((3S,5R)-3-methyl-5-(4-methyl-1-oxo-1,3-dihydroisobenzofuran-5-yl)piperazin-1-yl)methyl)-2-oxo-2,3-dihydro-1H-imidazol-1-yl)-4-methoxynicotinonitrile | 517.3 | S: 1.88, 98.00% R: 1.35, 98.45% XXX: 6.78, 96.70% ee | $^1$H NMR (400 MHz, DMSO-$d_6$) δ ppm 1.05 (d, J = 6.40 Hz, 3 H), 1.51 (d, J = 6.80 Hz, 3 H), 1.50 (d, J = 6.60 Hz, 3 H), 1.67-1.79 (m, 2 H), 2.24 (s, 3 H), 2.63 (br. s., 1 H), 2.72-2.80 (m, 1 H), 2.85 (d, J = 10.00 Hz, 1 H), 2.88-2.99 (m, 1 H), 3.45 (d, J = 14.20 Hz, 1 H), 4.02 (s, 3H), 4.10 (d, J = 9.30 Hz, 1 H), 4.36-4.48 (m, 1 H), 5.37 (s, 2 H), 7.26 (s, 1 H), 7.67 (d, J = 8.10 Hz, 1 H), 7.83 (d, J = 7.80 Hz, 1 H), 8.28 (s, 1 H), 8.65 (s, 1 H), (1 Exchangeable proton not observed). |
| 173-I | 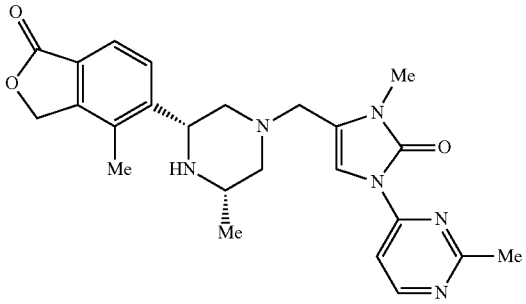 | 3-methyl-4-(((3S,5R)-3-methyl-5-(4-methyl-1-oxo-1,3-dihdyroisobenzofuran-5-yl)piperazin-1-yl)methyl)-1-(2-methylpyrimidin-4-yl)-1,3-dihydro-2H-imidazol-2-one | 449.3 | S: 1.29, 98.42% R: 0.78, 97.30% VI: 12.32, 100% ee | $^1$H NMR (400 MHz, DMSO-$d_6$) δ ppm 1.04 (d, J = 6.10 Hz, 3 H), 1.84-1.64 (m, 2 H), 2.26 (s, 3 H), 2.56 (s, 3 H), 2.83 (t, J = 8.40 Hz, 2 H), 2.87-2.99 (m, 1 H), 3.29 (s, 3 H), 3.40 (s, 2 H), 4.12 (d, J = 7.80 Hz, 1 H), 5.38 (s, 2 H), 7.27 (s, 1 H), 7.67 (d, J = 8.30 Hz, 1 H), 7.82 (d, J = 8.10 Hz, 1 H), 8.18 (d, J = 5.60 Hz, 1 h), 8.66 (d, J = 5.60 Hz, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 174-I | 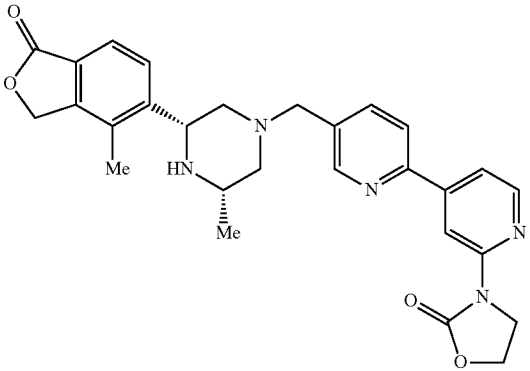 | 3-(5-(((3S,5R)-3-methyl-5-(4-methyl-1-oxo-1,3-dihydroisobenzofuran-5-yl)piperazin-1-yl)methyl)-[2,4'-bipyridin]-2'-yl)oxazolidin-2-one | 500.3 | S: .137, 98.95% R: 0.66, 98.40% XVII: 11.04, 100% ee | $^1$H NMR (400 MHz, DMSO-d$_6$) δ ppm 1.04 (br. s., 3 H), 1.78 (d, J = 13.00 Hz, 2 H), 1.92 (s, 1 H), 2.25 (s, 3 H), 2.80 (br. s., 2 H), 2.99 (br. s., 1 H), 3.61 (br. s., 2 H), 4.07-4.30 (m, 3 H), 4.42-4.54 (m, 2 H), 5.29-5.47 (m, 2 H), 7.47-7.56 (m, 1 H), 7.59-7.75 (m, 1 H), 7.75-7.88 (m, 2 H), 7.94 (d, J = 8.10 Hz, 1 H), 8.28 (s, 1 H), 8.60 (s, 1 H), (1 Exchangeable proton not observed). |
| 175-I | 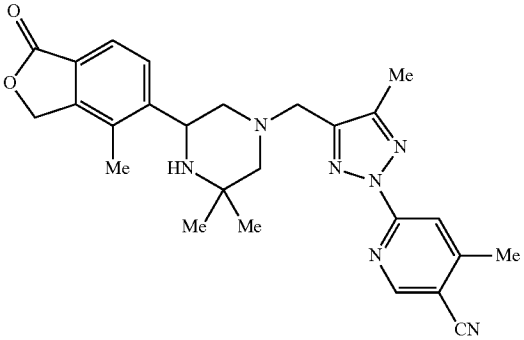 | 6-(4-((3,3-dimethyl-5-(4-methyl-1-oxo-1,3-dihydroisobenzofuran-5-yl)piperazin-1-yl)methyl)-5-methyl-2H-1,2,3-triazol-2-yl)-4-methylnicotinonitrile (Enantiomer-I) | 472.3 | S: .196, 98.70% R: 1.41, 98.60% VIII: 3.60 100% ee | $^1$H NMR (400 MHz, DMSO-d$_6$) δ ppm 1.07 (s, 3 H), 1.20-1.41 (m, 3 H), 1.82 (t, J = 9.00 Hz, 1 H), 1.93 (d, J = 9.80 Hz, 1 H), 2.06 (d, J = 13.20 Hz, 1 H), 2.26 (s, 3 H), 2.45 (s, 3 H), 2.54-2.64 (m, 3 H), 2.79 (d, J = 10.00 Hz, 1 H), 3.68 (s, 2 H), 4.38 (d, J = 9.50 Hz, 1 H), 5.37 (s, 2 H), 7.66 (d, J = 8.60 Hz, 1 H), 7.79 (d, J = 8.10 Hz, 1 H), 8.03 (s, 1 H), 8.88 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 176-I | 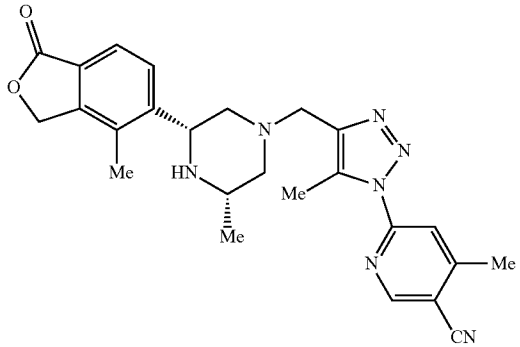 | 4-methyl-6-(5-methyl-4-(((3S,5R)-3-methyl-5-(4-methyl-1-oxo-1,3-dihydroisobenzofuran-5-yl)piperazin-1-yl)methyl)-1H-1,2,3-triazol-1-yl)nicotinonitrile | 458.3 | S: 1.69, 96.05% R: 1.09, 96.40% VIII: 10.08 100% ee | $^1$H NMR (400 MHz, DMSO-$d_6$) δ ppm 1.02 (d, J = 6.10 Hz, 3 H), 1.73-1.90 (m, 2 H), 2.21-2.31 (m, 3 H), 2.59 (s, 3 H), 2.64 (s, 3 H), 2.75-2.87 (m, 2 H), 2.95 (br. s., 1 H), 3.61-3.74 (m, 2 H), 4.15 (d, J = 8.10 Hz, 1 H), 5.31-5.43 (m, 2 H), 7.66 (d, J = 8.10 Hz, 1 H), 7.80 (d, J = 7.80 Hz, 1 H), 8.17 (s, 1 H), 9.01 (s, 1 H), (1 Exchangeable proton not observed). |
| 177-I | 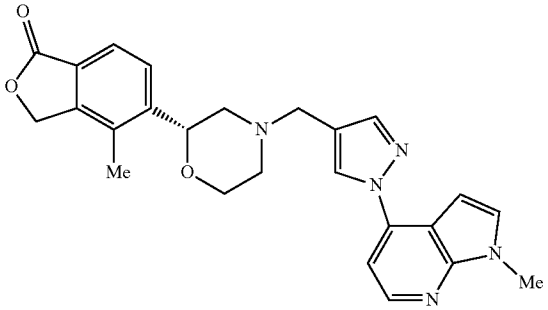 | (R)-4-methyl-5-(4-((1-(1-methyl-1H-pyrrolo[2,3-b]pyridin-4-yl)-1H-pyrazol-4-yl)methyl)morpholin-2-yl)isobenzofuran-1(3H)-one | 444.2 | A: 1.41, 98.80% B: 0.95, 98.40% | $^1$H NMR (400 MHz, DMSO-$d_6$) δ ppm 2.30 (s, 3 H), 3.15-3.20 (m, 2 H), 3.50-3.90 (m, 2 H), 3.90-3.40 (m, 5 H), 4.40 (br. s., 2 H), 5.10 (br. s., 1 H), 5.40-5.50 (m, 2 H), 7.10 (m, 1 H), 7.52 (d, J = 5.20 Hz, 1 H), 7.64-7.68 (m, 2 H), 7.75 (d, J = 8.00 Hz, 1 H), 8.0 (s, 1 H), 8.35 (d, J = 8.00 Hz, 1 H), 8.90 (s, 1 H). |
| 178-I | 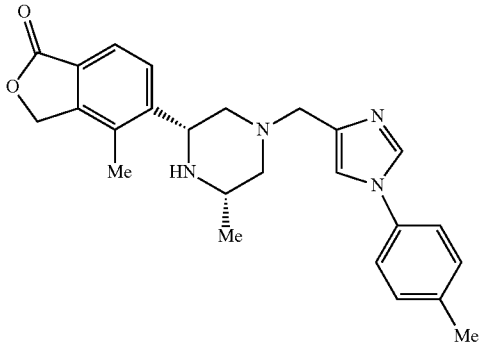 | 4-methyl-5-((2R,6S)-6-methyl-4-((1-(p-tolyl)-1H-imidazol-4-yl)methyl)piperazin-2-yl)isobenzofuran-1(3h)-one | 417.3 | A: 1.35, 97.80% B: 0.79, 99.10% | $^1$H NMR (400 MHz, DMSO-$d_6$) δ ppm 1.03 (d, J = 6.02 Hz, 3 H), 1.72-1.83 (m, 2 H), 2.27 (s, 3 H) 2.34 (s, 3 H), 2.85 (d, J = 11.5 Hz, 2 H), 2.90-3.00 (m, 1 H), 3.45 (s, 2 H), 4.15 (dd, J = 10.04, 2.01 Hz, 1 H), 5.38 (s, 2 H), 7.30 (d, J = 8.53 Hz, 2 H), 7.49-7.56 (m, 3 H), 7.65 (d, J = 7.53 Hz, 1 H), 7.82 (s, 1 H), 8.06-8.07 (m, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 179-I | 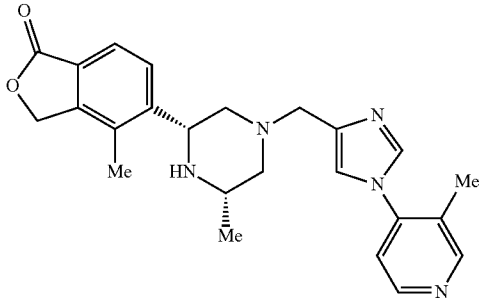 | 4-methyl-5-((2R,6S)-6-methyl-4-((1-(3-methylpyridin-4-yl)-1H-imidazol-4-yl)methyl)piperazin-2-yl)isobenzofuran-1(3H)-one | 418.2 | A: 0.97, 96.90% B: 0.53, 94.90% | $^1$H NMR (400 MHz, DMSO-$d_6$) δ ppm 1.03 (d, J = 6.02 Hz, 3 H), 1.72-1.83 (m, 2 H), 2.24-2.31 (m, 6 H), 2.85 (d, J = 11.55 Hz, 2 H), 2.90-3.00 (m, 1 H), 3.45 (s, 2 H), 4.15 (dd, J = 10.04, 2.01 Hz, 1 H), 5.38 (s, 2 H), 7.30 (d, J = 8.53 Hz, 2 H), 7.65 (d, J = 7.53 Hz, 1 H), 7.82 (d, J = 7.53 Hz, 1 H), 7.92 (s, 1 H), 7.52 (d, J = 5.20 Hz, 1 H), 8.61 (s, 1 H), (1 Exchangeable proton not observed). |
| 180-I | 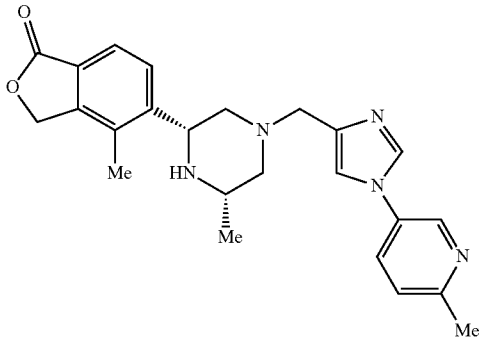 | 4-methyl-5-((2R,6S)-6-methyl-4-((1-(6-methylpyridin-3-yl)-1H-imidazol-4-yl)methyl)piperazin-2-yl)isobenzofuran-1(3H)-one | 418.2 | A: 1.00, 98.60% B: 0.59, 95.40% | $^1$H NMR (400 MHz, DMSO-$d_6$) δ ppm 1.02 (d, J = 6.02 Hz, 3 H), 1.69-1.85 (m, 2 H), 2.23 (s, 3 H), 2.50 (s, 3 H), 2.85 (br. s., 2 H), 2.95 (d, J = 3.51 Hz, 1 H), 3.43-3.50 (m, 2 H), 4.15 (d, J = 9.54 Hz, 1 H), 5.38 (s, 2 H), 7.39 (d, J = 8.53 Hz, 1 H), 7.65 (d, J = 8.03 Hz, 2 H), 7.80 (d, J = 8.03 Hz, 1 H), 7.98 (s, 1 H), 8.12-8.32 (m, 1 H), 8.77 (d, J = 2.51 Hz, 1 H), (1 Exchangeable proton not observed). |
| 181-I | 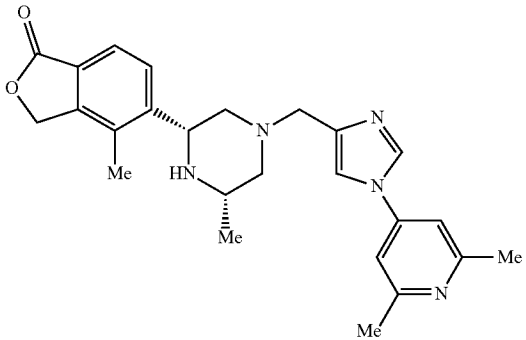 | 5-((2R,6S)-4-((1-(2,6-dimethylpyridin-4-yl)-1H-imidazol-4-yl)methyl)-6-methylpiperazin-2-yl)-4-methylisobenzofuran-1(3H)-one | 432.3 | A: 0.99, 99.50% B: 0.79, 94.90% | $^1$H NMR (400 MHz, DMSO-$d_6$) δ ppm 0.97-1.07 (m, 3 H), 1.74-1.82 (m, 2 H), 2.27 (s, 3 H), 2.46 (s, 6 H), 2.83 (d, J = 10.80 Hz, 2 H), 2.96 (br. s., 1 H), 3.39-3.41 (m, 2 H), 4.15 (d, J = 8.20 Hz, 1 H), 5.38 (br. s., 2 H), 7.44 (s, 1 H), 7.64-7.66 (m, 2 H), 7.80 (d, J = 8.00 Hz, 1 H), 7.95-7.97 (m, 1 H), 8.80 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 182-I | 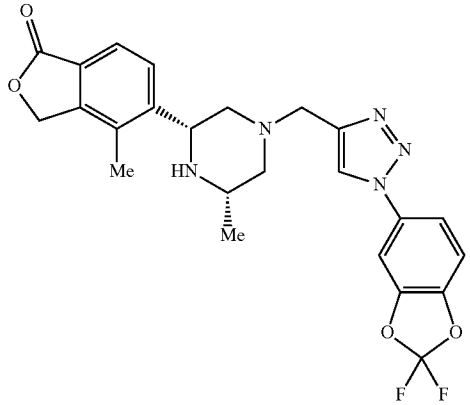 | 5-((2R,6S)-4-((1-(2,2-difluorobenzo[d][1,3]di-oxol-5-yl)-1H-imidazol-4-yl)methyl)-6-methylpiperazin-2-yl)-4-methylisobenzofuran-1(3H)-one | 483.3 | A: 1.48, 97.10% B: 0.92, 97.80% | $^1$H NMR (400 MHz, DMSO-$d_6$) δ ppm 0.96-1.06 (m, 3 H), 1.80 (br. s., 2 H), 2.27 (s, 3 H), 2.80-2.90 (m, 3 H), 3.40 (br. s., 2 H), 4.10 (br. s., 1 H), 5.32-5.45 (m, 2 H), 7.50-7.60 (m, 3 H), 7.70-7.75 (m, 2 H), 7.85-7.90 (m, 2 H), (1 Exchangeable proton not observed). |
| 183-I | 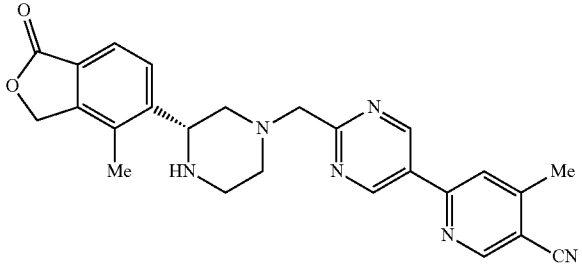 | (R)-4-methyl-6-(2-((3-(4-methyl-1-oxo-1,3-dihydroisobenzofuran-5-yl)piperazin-1-yl)methyl)pyrimidin-5-yl)nicotinonitrile | 441.2 | A: 0.93, 9.97% B: 1.12, 100% XVIII: 23.32, 95.58% ee | $^1$H NMR (400 MHz, DMSO-$d_6$) δ ppm 2.03 (t, J = 10.40 Hz, 1 H), 2.27 (s, 3 H), 2.32 (d, J = 3.4 Hz, 1 H), 2,59 (s, 3 H), 2.81-3.05 (m, 4 H), 3.84 (s, 2 H), 4.10 (d, J = 8.60 Hz, 1 H), 5.37 (s, 2 H), 7.64 (d, J = 7.80 Hz, 1 H), 7.79 (d, J = 7.80 Hz, 1 H), 8.31 (s, 1 H), 9.06 (s, 1 H), 9.44 (s, 2 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 184-I | 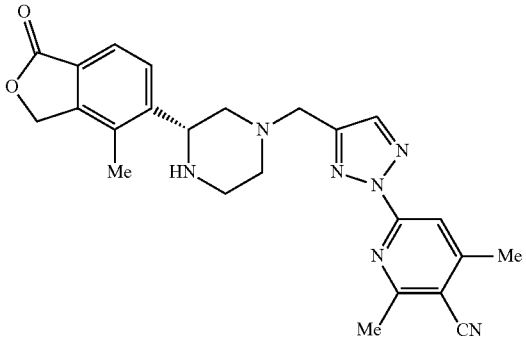 | (R)-2,4-dimethyl-6-(4-((3-(4-methyl-1-oxo-1,3-dihydroisobenzofuran-5-yl)piperazin-1-yl)methyl)-2H-1,2,3-triaozl-2-yl)nicotinonitrile | 444.2 | A: 1.04, 100% B: 1.27, 99.69% XIV: 10.30 98.57% ee | $^1$H NMR (400 MHz, DMSO-$d_6$) δ ppm 1.84-1.97 (m, 1 H), 2.16-2.24 (m, 1 H), 2.26 (s, 3 H), 2.59 (s, 3 H), 2.69-2.73 (m, 3 H), 2.82 (d, J = 10.0 Hz, 2 H), 2.88-2.95 (m, 1 H), 2.97-3.05 (m, 1 H), 3.76 (s, 2 H), 4.10 (d, J = 9.30 Hz, 1 H), 5.31-5.48 (m, 2 H), 7.65 (d, J = 8.10 Hz, 1 H), 7.77 (d, J = 8.10 Hz, 1 H), 7.93 (s, 1 H), 8.18 (s, 1 H), (1 Exchangeable proton not observed). |
| 185-I | 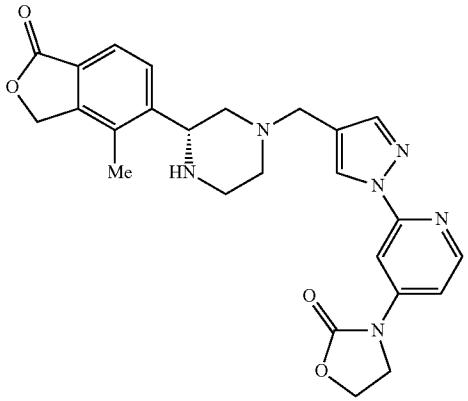 | (R)-3-(2-(4-((3-(4-methyl-1-oxo-1,3-dihydroisobenzofuran-5-yl)piperazin-1-yl)methyl)-1H-pyrazol-1-yl)pyridin-4-yl)oxazolidin-2-one | 475.1 | S: .135, 100% R: 1.11, 100% XIV: 15.72, 98.00% ee | $^1$H NMR (400 MHz, DMSO-$d_6$) δ ppm 1.79 (t, J = 10.15 Hz, 1 H), 2.07-2.15 (m, 1 H), 2.25 (s, 3 H), 2.77-3.01 (m, 3 H), 3.17 (d, J = 5.14 Hz, 1 H), 3.46-3.56 (m, 2 H), 4.04-4.17 (m, 3 H), 4.47-4.54 (m, 2 H), 5.36 (s, 2 H), 7.42 (dd, J = 5.87, 2.20 Hz, 1 H), 7.63 (d, J = 8.07 Hz, 1 H), 7.72-7.79 (m, 2 H), 8.16 (d, J = 2.20 Hz, 1 H), 8.35 (d, J = 5.87 Hz, 1 H), 8.47 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 186-I | 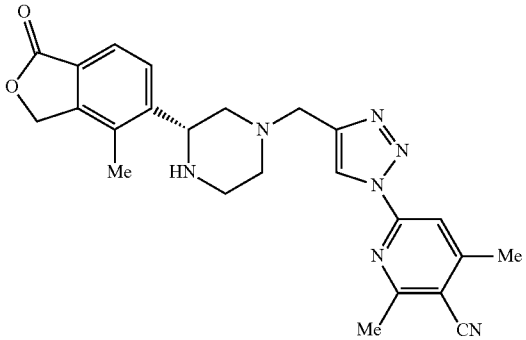 | (R)-2,4-dimethyl-6-(4-((3-(4-methyl-1-oxo-1,3-dihydroisobenzofuran-5-yl)piperazin-1-yl)methyl)-1H-1,2,3-triazol-1-yl)nicotinonitrile | 444.2 | C: 6.15, 98.53% G: 6.95, 99.21% V: 11.71, 99.21% ee | $^1$H NMR (400 MHz, DMSO-$d_6$) δ ppm 1.87 (t, J = 10.39 Hz, 1 H), 2.12-2.22 (m, 1 H), 2.26 (s, 3 H), 2.62 (s, 3 H), 2.69-2.75 (m, 3 H), 2.78-2.92 (m, 3 H), 2.95-3.02 (m, 1 H), 3.74 (s, 2 H), 4.06 (d, J = 7.58 Hz, 1 H), 5.38 (s, 2 H), 7.64 (d, J = 8.07 Hz, 1 H), 7.76 (d, J = 8.07 Hz, 1 H), 8.10 (s, 1 H), 8.74 (s, 1 H), (1 Exchangeable proton not observed). |
| 187-I | 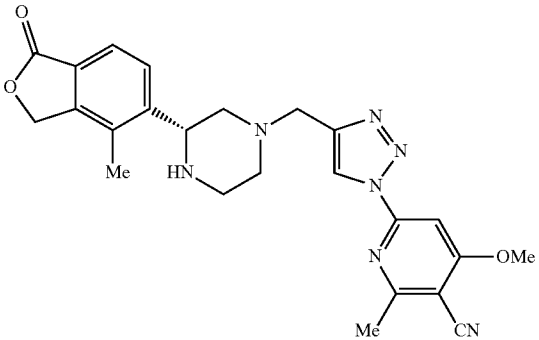 | (R)-4-methoxy-2-methyl-6-(4-((3-(4-methyl-1-oxo-1,3-dihydroisobenzofuran-5-yl)piperaizn-1-yl)methyl)-1H-1,2,3-triazol-1-yl)nicotinonitrile | 460.3 | R: 1.06, 100% S: 1.27, 99.47% V: 10.37, 98.87% ee | $^1$H NMR (400 MHz, DMSO-$d_6$) δ ppm 1.87-1.98 (m, 1 H), 2.14-2.24 (m, 1 H), 2.27 (s, 3 H), 2.64-2.69 (m, 3 H), 2.85 (t, J = 9.50 Hz, 2 H), 2.92 (d, J = 10.00 Hz, 1 H), 2.97-3.05 (m, 1 H), 3.76 (s, 2 H), 4.04-4.19 (m, 4 H), 5.31-5.46 (m, 2 H), 7.65 (d, J = 7.80 Hz, 1 H), 7.73 (s, 1 H), 7.76 (d, J = 7.80 Hz, 1 H), 8.75 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 188-I | 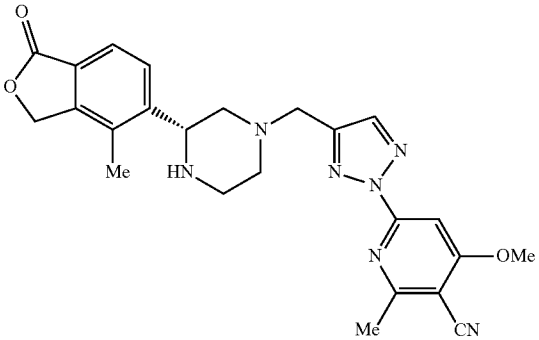 | (R)-4-methoxy-2-methyl-6-(4-((3-(4-methyl-1-oxo-1,3-dihydroisobenzofuran-5-yl)piperazin-1-yl)methyl)-2H-1,2,3-triazol-2-yl)nicotinonitrile | 460.3 | R: 1.02, 100% S: 1.20, 98.54% V: 8.18, 99.14% ee | $^1$H NMR (400 MHz, DMSO-$d_6$) δ ppm 1.91 (t, J = 10.30 Hz, 1 H), 2.13-2.25 (m, 1 H), 2.26 (s, 3 J), 2.64 (s, 3 H), 2.82 (d, J = 11.20 Hz, 2 H), 2.90 (t, J = 11.02 Hz, 1 H), 3.00 (d, J = 12.00 Hz, 1 H), 3.76 (s, 2 H), 4.03-4.17 (m, 4 H), 5.27-5.46 (m, 2 H), 7.55 (s, 1 H), 7.65 (d, J = 8.10 Hz, 1 H), 7.78 (d, J = 8.10 Hz, 1 H), 8.19 (s, 1 H), (1 Exchangeable proton not observed). |
| 189-I | 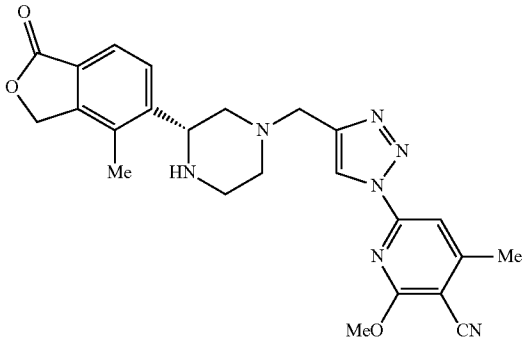 | (R)-2-methoxy-4-methyl-6-(4-((3-(4-methyl-1-oxo-1,3-dihydroisobenzofuran-5-yl)piperazin-1-yl)methyl)-1H-1,2,3-triazol-1-yl)nicotinonitrile | 460.3 | R: 1.13, 100% S: 1.35, 100% VI: 14.78, 98.24% ee | $^1$H NMR (400 MHz, DMSO-$d_6$) δ ppm 1.87-1.98 (m, 1 H), 2.14-2.24 (m, 1 H), 2.28 (s, 3 H), 2.59 (s, 3 H), 2.85 (t, J = 9.50 Hz, 2 H), 2.91 (br. s., 2 H), 3.78 (br. s., 2 H), 4.11 (s, 4 H), 5.39 (d, J = 3.70 Hz, 2 H), 7.71 (br. s., 1 H), 7.80-7.74 (m, 1 H), 7.83 (s, 1 H), 8.85 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 190-I | 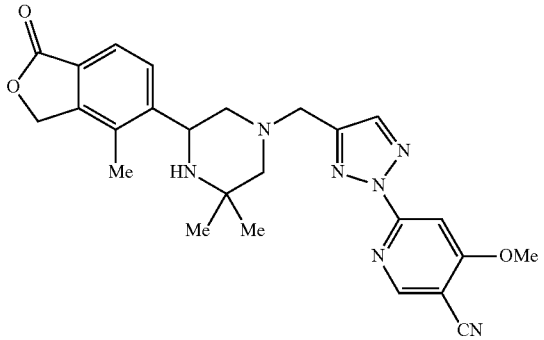 | 6-(4-((3,3-dimethyl-5-(4-methyl-1-oxo-1,3-dihydroisobenzofuran-5-yl)piperazin-1-yl)methyl)-2H-1,2,3-triazol-2-yl)-4-methoxynicotinonitrile (Enantiomer-I) | 474.3 | R: 1.10, 97.63% S: 1.53, 96.84% XVIII: 17.70, 100% ee | $^1$H NMR (400 MHz, DMSO-$d_6$) δ ppm 1.07 (s, 3 H), 1.32 (s, 3 H), 1.85 (t, J = 10.40 Hz, 1 H), 1.93 (d, J = 10.50 Hz, 1 H), 2.04 (br. s., 1 H), 2.29 (s, 3H), 2.57 (d, J = 10.80 Hz, 1 H), 2.88 (d, J = 10.00 Hz, 1 H), 3.65-3.88 (m, 2 H), 4.13 (s, 3 H), 4.42 (d, J = 9.00 Hz, 1 H), 5.32-5.47 (m, 2 H), 7.65 (d, J = 8.10 Hz, 1 H), 7.70 (s, 1 H), 7.80 (d, J = 8.10 Hz, 1 H), 8.21 (s, 1 H), 8.83 (s, 1 H). |
| 191-I | 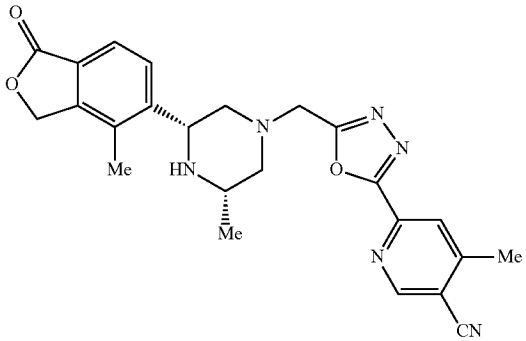 | 4-methyl-6-(5-(((3S,5R)-3-methyl-5-(4-methyl-1-oxo-1,3-dihydroisobenzofuran-5-yl)piperazin-1-yl)methyl)-1,3,4-oxadiazol-2-yl)nicotinonitrile | 445.2 | A: 0.95, 100% B: 1.26, 100% XIV: 8.77, 100% | $^1$H NMR (400 MHz, DMSO-$d_6$) δ 1.03 (d, J = 6.40 Hz, 3 H), 1.87-2.03 (m, 2 H), 2.30 (s, 3 H), 2.63 (s, 3 H), 2.78-2.93 (m, 2 H), 2.99 (br. s., 1 H), 4.00 (s, 2 H), 4.19 (d, J = 7.60 Hz, 1 H), 5.40 (s, 2 H), 7.66 (d, J = 8.10 Hz, 1 H), 7.79 (d, J = 8.10 Hz, 1 H), 8.32 (s, 1 H), 9.11 (s, 1 H), (1 Exchangeable proton not observed). |
| 192-I | 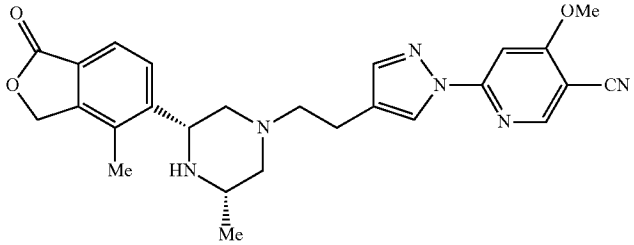 | 4-methoxy-6-(4-(2-((3S,5R)-3-methyl-5-(4-methyl-1-oxo-1,3-dihydroisobenzofuran-5-yl)piperazin-1-yl)ethyl)-1H-pyrazol-1-yl)nicotinonitrile | 433.3 | R: 0.54, 100% S: 1.26, 94.95% XV: 6.26, 100% ee | $^1$H NMR (400 MHz, DMSO-$d_6$) δ ppm 1.05 (d, J = 6.10 Hz, 3 H), 1.24 (s, 1 H), 1.65-1.82 (m, 2 H), 2.27-2.34 (m, 3 H), 2.56 (d, J = 7.10 Hz, 1 H), 2.59-2.65 (m, 3 H), 2.65-2.74 (m, 2 H), 2.88 (d, J = 10.30 Hz, 2 H), 2.96 (br. s., 1 H), 4.16 (d, J = 9.80 Hz, 1 H), 5.32-5.47 (m, 2 H), 7.62-7.72 (m, 2 H), 7.78-7.90 (m, 2 H), 8.52 (s, 1 H), 8.73 (d, J = 5.60 Hz, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 193-I | 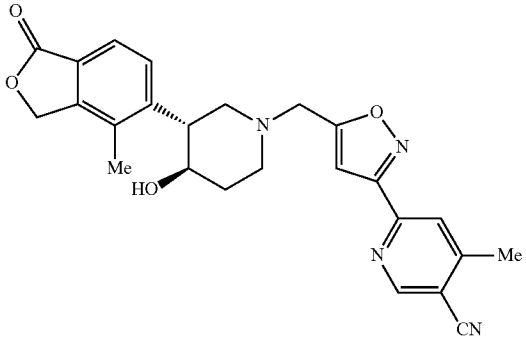 | 6-(5-(((3R,4R)-4-hydroxy-3-(4-methyl-1-oxo-1,3-dihydroisobenzofuran-5-yl)piperidin-1-yl)methyl)isoxazol-3-yl)-4-methylnicotinonitrile | 445.3 | R: 1.17, 100% S: 1.58, 100% XVIII: 5.84, 100% ee | $^1$H NMR (400 MHz, DMSO-$d_6$) δ ppm 1.59-1.70 (m, 1 H), 1.94 (d, J = 9.50 Hz, 1 H), 2.16-2.41 (m, 5 H), 2.59 (s, 3 H), 2.79 (d, J = 11.20 Hz, 1 H), 2.95 (d, J = 10.30 Hz, 1 H), 3.09 (t, J = 10.40 Hz, 1 H), 3.64-3.77 (m, 1 H), 3.86 (br. s., 2 H), 4.61 (d, J = 5.40 Hz, 1 H), 5.30-5.49 (m, 2 H), 6.99 (s, 1 H), 7.54 (d, J = 8.10 Hz, 1 H), 7.64 (d, J = 7.80 Hz, 1 H), 8.15 (s, 1 H), 9.05 (s, 1 H). |
| 194-I | 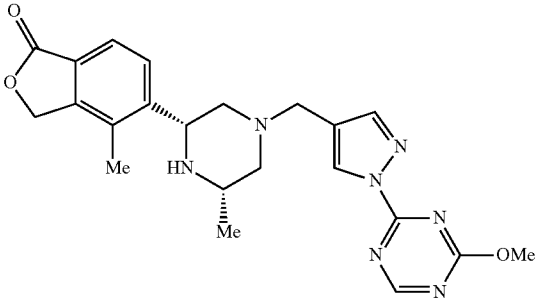 | 5-((2R,6S)-4-((1-(4-methoxy-1,3,5-triazin-2-yl)-1H-pyrazol-4-yl)methyl)-6-methylpiperazin-2-yl)-4-methylisobenzofuran-1(3H)-one | 436.2 | R: 0.76, 100% S: 1.09, 100% VIII: 9.06, 100% ee | $^1$H NMR (400 MHz, DMSO-$d_6$) δ ppm 0.93-1.11 (m, 3 H), 1.73 (td, J = 10.6, 4.3 Hz, 2 H), 2.26 (s, 3 H), 2.80 (d, J = 10.80 Hz, 2 H), 2.94-3.02 (m, 1 H), 3.45-3.58 (m, 2 H), 3.98-4.11 (m, 3 H), 4.13-4.21 (m, 1 H), 5.31-5.47 (m, 2 H), 7.65 (d, J = 8.10 Hz, 1 H), 7.79 (d, J = 8.10 Hz, 1 H), 7.95-7.86 (m, 1 H), 8.57 (s, 1 H), 8.96 (s, 1 H), (1 Exchangeable proton not observed). |
| 195-I | 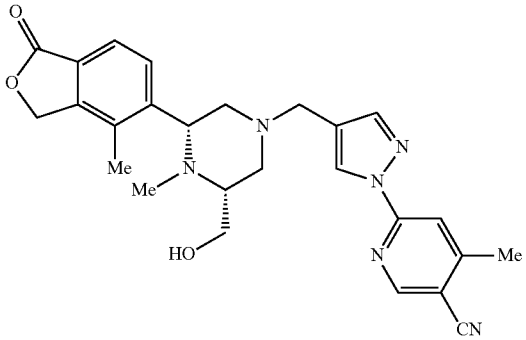 | 6-(4-(((3R,5R)-3-(hydroxymethyl)-4-methyl-5-(4-methyl-1-oxo-1,3-dihydroisobenzofuran-5-yl)piperaizn-1-yl)methyl)-1H-pyrazol-1-yl)-4-methylnicotinonitrile | 473.3 | R: 1.10, 96.00% S: 1.47, 95.73% XV: 4.2Z, 100% ee | $^1$H NMR (400 MHz, DMSO-$d_6$) δ ppm 1.88 (br. s., 1 H), 1.93-2.08 (m, 4 H), 2.27 (br. s., 3 H), 2.36 (d, J = 10.00 Hz, 1 H), 2.58 (s, 3 H), 2.72 (d, J = 11.70 Hz, 1 H), 3.09 (d, J = 11.00 Hz, 1 H), 3.18 (d, J = 4.60 Hz, 1 H), 3.43-3.54 (m, 2 H), 3.58-3.73 (m, 2 H), 4.55 (b.r s., 1 H), 5.30 5.47 (m, 2 H), 7.59-7.73 (m, 2 H), 7.84 (s, 1 H), 7.99 (s, 1 H), 8.52 (s, 1 H), 8.83 (s, 1 H). |

-continued

| Example | Structure | Name | LCMS (M + H)$^+$ | HPLC/LCMS Method: RT (min.), Purity | NMR |
|---|---|---|---|---|---|
| 196-I | 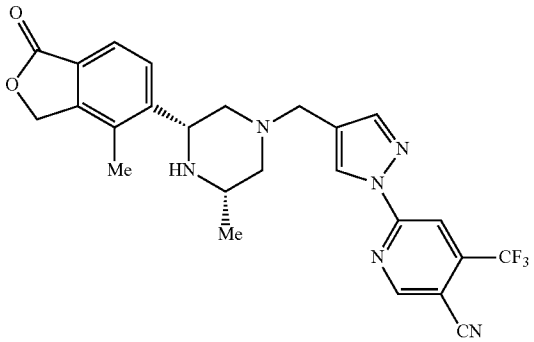 | 6-(4-(((3S,5R)-3-methyl-5-(4-methyl-1-oxo-1,3-dihydroisobenzofuran-5-yl)piperazin-1-yl)methyl)-1H-pyraozl-1-yl)-4-(trifluoromethyl)nicotinonitrile | 497.3 | R: 1.91, 100% S: 2.07, 100% XXVIII: 4.19, 96.40% ee | $^1$H NMR (400 MHz, DMSO-$d_6$) δ ppm 1.02 (d, J = 6.10 Hz, 3 H), 1.64-1.81 (m, 2 H), 2.27 (s, 3 H), 2.81 (d, J = 9.80 Hz, 2 H), 2.97 (br. s., 1 H), 3.55 (s, 2 H), 4.17 (d, J = 9.00 Hz, 1 H), 5.28-5.46 (m, 2 H), 7.65 (d, J = 8.10 Hz, 1 H), 7.79 (d, J = 7.80 Hz, 1 H), 7.96 (s, 1 H), 8.24 (s, 1 H), 8.61 (s, 1 H), 9.23 (s, 1 H), (1 Exchangeable proton not observed). $^{19}$F NMR (400 MHz, DMSO-$d_6$) δ ppm −63.47. |
| 197-I | 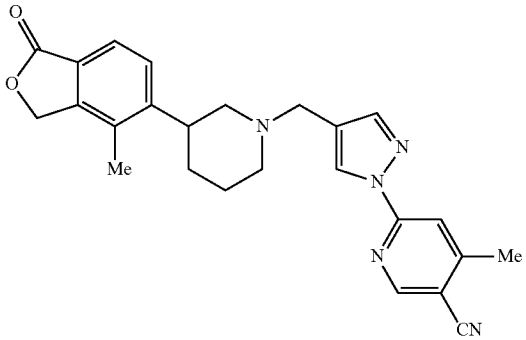 | 4-methyl-6-(4-((3-(4-methyl-1-oxo-1,3-dihydroisobenzofuran-5-yl)piperidin-1-yl)methyl)-1H-pyraozl-1-yl)nicotinonitrile (Enantiomer-I) | 428.1 | S: 1.98, 98.50% R: 1.40, 94.37% V: 11.03, 97.37% ee | $^1$H NMR (400 MHz, DMSO-$d_6$) δ ppm 1.51 (br. s., 1 H), 1.75 (br. s., 3 H), 2.04 (br. s., 2 H), 2.24 (s, 3 H), 2.54-2.62 (m, 3 H), 2.73-3.00 (m, 2 H), 3.04-3.24 (m, 1 H), 3.53 (br. s., 2 H), 5.36 (s, 2 H), 7.49 (d, J = 8.07 Hz, 1 H), 7.63 (d, J = 7.09 Hz, 1 H), 7.87 (br. s., 1 H), 7.99 (s, 1 H), 8.54 (br. s., 1 H), 8.83 (s, 1 H). |
| 198-I | 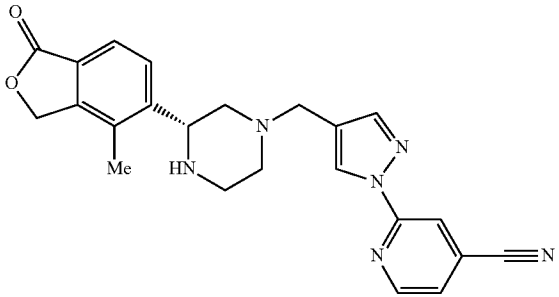 | (R)-2-(4-((3-(4-methyl-1-oxo-1,3-dihydroisobenzofuran-5-yl)piperazin-1-yl)methyl)-1H-pyraozl-1-yl)isonicotinonitrile | 415.1 | S: 1.20, 100% R: 0.87, 100% | $^1$H NMR (400 MHz, DMSO-$d_6$) δ ppm 1.83 (t, J = 10.90 Hz, 1 H), 2.14 (t, J = 9.80 Hz, 1 H), 2.26 (s, 3 H), 2.81 (d, J = 8.10 Hz, 2 H), 2.94-2.86 (m, 1 H), 3.05-2.97 (m, 1 H), 3.59-3.45 (m, 2 H), 4.10 (d, J = 9.30 Hz, 1 H), 5.45-5.30 (m, 2 H), 7.64 (d, J = 8.10 Hz, 1 H), 7.80-7.70 (m, 2 H), 7.83 (s, 1 H), 8.22 (s, 1 H), 8.51 (s, 1 H), 8.68 (d, J = 5.10 Hz, 1 H), (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 199-IV | 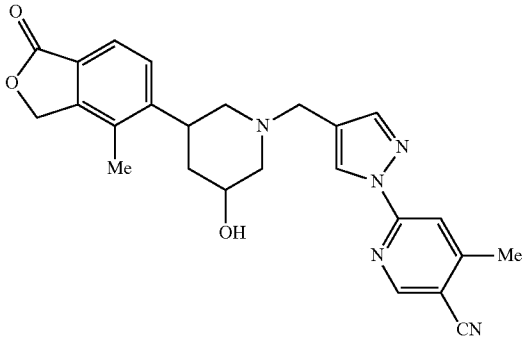 | 6-(4-((3-hydroxy-5-(4-methyl-1-oxo-1,3-dihydroisobenzofuran-5-yl)piperidin-1-yl)methyl)-1H-pyrazol-1-yl)-4-methylnicotinonitrile (Enantiomer-IV) | 459.3 | S: 1.42, 97.51% R: 1.01, 96.70% XVIII: 19.33, 100% ee | $^1$H NMR (400 MHz, DMSO-$d_6$) δ ppm 1.70 (br. s., 2 H), 2.25 (s, 4 H), 2.58 (s, 3 H), 2.77 (br. s., 2 H), 3.57 (br. s., 3 H), 3.86 (br. s., 1 H), 4.63 (br. s., 1 H), 5.36 (s, 2H), 7.67-7.52 (m, 2 H), 7.89 (s, 1 H), 7.99 (s, 1H), 8.57 (s, 1 H), 8.83 (s, 1 H), (1 Exchangeable proton not observed). |
| 200-II | 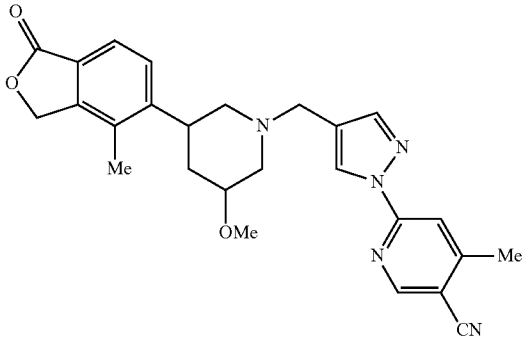 | 6-(4-((3-methoxy-5-(4-methyl-1-oxo-1,3-dihydroisobenzofuran-5-yl)piperidin-1-yl)methyl)-1H-pyrazol-1-yl)-4-methylnicotinonitrile (Enantiomer-II) | 458.2 | S: 1.66, 97.24% R: 1.13, 97.40% XVIIII: 18.01, 100% ee | $^1$H NMR (400 MHz, DMSO-$d_6$) δ ppm 1.41-1.30 (m, 1 H), 1.84 (t, J = 10.60 Hz, 1 H), 1.95 (t, J = 10.80 Hz, 1 H), 2.14 (s, 1 H), 2.24 (s, 3 H), 2.58 (s, 3 H), 2.81 (d, J = 11.70 Hz, 1 H), 3.16 (d, J = 11.20 Hz, 1 H), 3.24 (d, J = 6.10 Hz, 1 H), 3.29 (s, 3 H), 3.48 (s, 1 H), 3.69-3.55 (m, 2 H), 5.36 (s, 2 H), 7.48 (d, J = 7.80 Hz, 1 H), 7.62 (d, J = 8.30 Hz, 1 H), 7.86 (s, 1 H), 7.99 (s, 1 H), 8.54 (s, 1 H), 8.83 (s, 1 H). |
| 201-I | 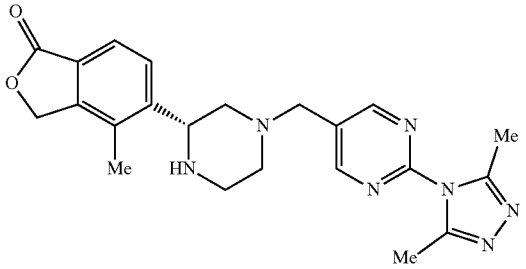 | (R)-5-(4-((2-(3,5-dimethyl-4H-1,2,4-triazol-4-yl)pyrimidn-5-yl)methyl)piperazin-2-yl)-4-methylisobenzofuran-1(3H)-one | 420.2 | S: 0.88, 97.02% R: 0.70, 96.77% | $^1$H NMR (400 MHz, DMSO-$d_6$) δ ppm 1.95-1.83 (m, 1 H), 2.23-2.08 (m, 2 H), 2.32-2.24 (m, 6 H), 2.70 (s, 3 H), 2.80 (t, J = 10.90 Hz, 2 H), 2.92 (t, J = 10.30 Hz, 1 H), 3.07-2.98 (m, 1 H), 3.73-3.54 (m, 2 H), 4.11 (d, J = 8.30 Hz, 1 H), 5.48-5.29 (m, 2 H), 7.66 (d, J = 7.80 Hz, 1 H), 7.79 (d, J = 7.80 Hz, 1 H), 8.86 (s, 2 H). |

-continued

| Example | Structure | Name | LCMS $(M + H)^+$ | HPLC/LCMS Method: RT (min.), Purity | NMR |
|---|---|---|---|---|---|
| 202-I | 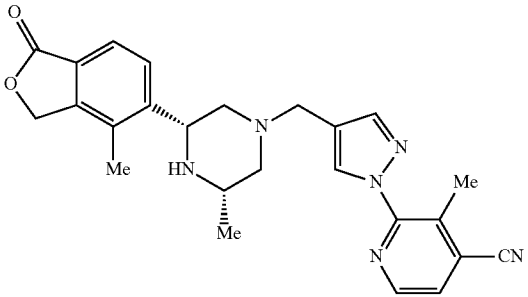 | 3-methyl-2-(4-(((3S,5R)-3-methyl-5-(4-methyl-1-oxo-1,3-dihdyroisobenzofuran-5-yl)piperazin-1-yl)methyl)-1H-pyrazol-1-yl)isonicotinonitrile | 443.3 | S: 1.41, 99.79% R: 0.94, 99.70% XVIII: 8.45, 100% ee | $^1$H NMR (400 MHz, DMSO-$d_6$) δ ppm 1.17 (t, J = 7.20 Hz, 3 H), 2.36 (s, 3 H), 2.68 (s, 3 H), 2.99-2.87 (m, 2 H), 3.15 (br. s., 2 H), 3.64 (br. s., 1 H), 3.76 (br. s., 1 H), 3.84 (s, 1 H), 4.75 (br. s., 1 H), 5.60-5.37 (m, 2 H), 7.87-7.73 (m, 3 H), 7.90 (d, J = 4.90 Hz, 1 H), 8.32 (br. s., 1 H), 8.42 (br. s., 1 H), 8.59 (d, J = 4.60 Hz, 1 H). |
| 203-I | 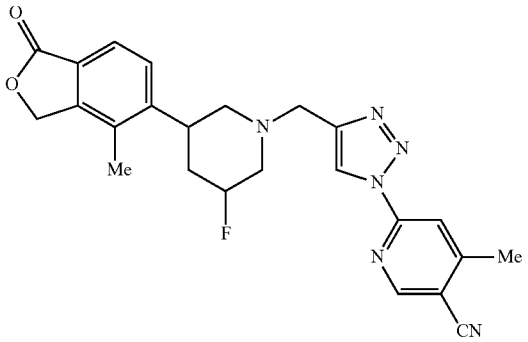 | 6-(4-((3-fluoro-5-(4-methyl-1-oxo-1,3-dihydroisobenzofuran-5-yl)piperidin-1-yl)methyl)-1H-1,2,3-triaozl-1-yl)-4-methylnicotinonitrile (Enantiomer I) | 447.2 | S: 1.66, 100% R: 1.17, 100% XXVIII: 6.53, 100% ee | $^1$H NMR (400 MHz, DMSO-$d_6$) δ ppm 1.79-1.65 (m, 1 H), 2.24-2.03 (m, 3 H), 2.26 (s, 3 H), 2.67-2.60 (m, 3 H), 2.86 (d, J = 10.80 Hz, 1 H), 3.21 (t, J = 10.80 Hz, 1 H), 3.31 (d, J = 3.90 Hz, 1 H), 3.96-3.79 (m, 2 H), 4.95-4.68 (m, 1 H), 5.38 (s, 2 H), 7.54 (d, J = 8.10 Hz, 1 H), 7.65 (d, J = 8.10 Hz, 1 H), 9.00 (s, 1 H), 8.85 (s, 1 H), 8.30 (s, 1 H). $^{19}$F NMR (300 MHz, DMSO-$d_6$) δ ppm −178.31. |
| 204-I | 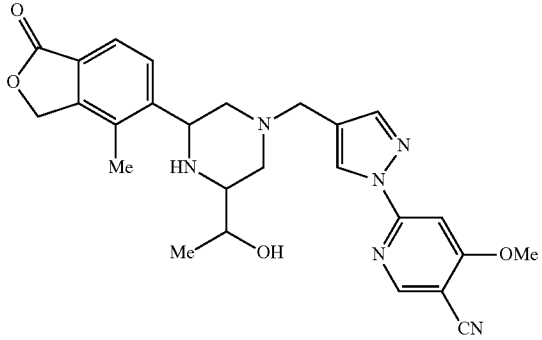 | 6-(4-((3-(1-hydroxyethyl)-5-(4-methyl-1-oxo-1,3-dihydroisobenzofuran-5-yl)piperazin-1-yl)methyl)-1H-pyrazol-1-yl)-4-methoxynicotinonitrile (Enantiomer-I) | 489.3 | S: 1.38, 99.33% R: 1.05, 97.87% XXVIII: 5.73, 95.11% ee | $^1$H NMR (400 MHz, DMSO-$d_6$) δ ppm 1.10 (d, J = 6.0 Hz, 3 H), 1.77 (br. s., 2 H), 2.27 (s, 3 H), 2.74 (s, 3 H), 3.01 (br. s., 1 H), 3.54 (br. s., 3 H), 4.11 (s, 3 H), 4.15 (br. s., 1 H), 4.54 (br. s., 1 H), 5.39 (s, 2 H), 7.61 (s, 1 H), 7.66 (d, J = 6.40 Hz, 1 H), 7.80 (d, J = 8.30 Hz, 1 H), 7.87 (s, 1 H), 8.53 (br. s., 1 H), 8.75 (s, 1 H). |

-continued

| Example | Structure | Name | LCMS (M + H)$^+$ | HPLC/LCMS Method: RT (min.), Purity | NMR |
|---|---|---|---|---|---|
| 205-I | 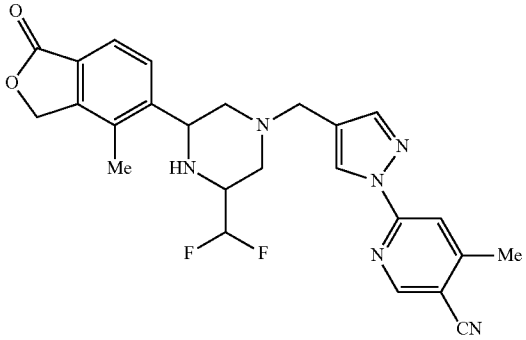 | 6-(4-((3-(difluoromethyl)-5-(4-methyl-1-oxo-1,3-dihydroisobenzofuran-5-yl)piperazin-1-yl)methyl)-1H-pyrazol-1-yl)-4-methylnicotinonitrile (Enantiomer-I) | 479.2 | S: 1.80, 94.40% R: 1.23, 94.62% X: 4.29, 89.07% ee | $^1$H NMR (400 MHz, DMSO-d$_6$) δ ppm 1.77 (br. s., 1 H), 2.01 (br. s., 1 H), 2.14-2.08 (m, 1 H), 2.27 (s, 3 H), 2.58 (s, 3 H), 2.84 (br. s., 2 H), 2.94 (br. s., 1 H), 3.62 (br. s., 2 H), 4.24 (b.r s., 1 H), 5.49-5.30 (m, 2 H), 5.96 (br. s., 1 H), 7.67 (d, J = 7.60 Hz, 1 H), 7.77 (d, J = 8.10 Hz, 1 H), 7.88 (br. s., 1 H), 8.00 (s, 1 H), 8.57 (br. s., 1 H), 8.84 (s, 1 H). $^{19}$F NMR (400 MHz, DMSO-d$_6$) δ ppm −126.20, −126.07. |
| 206-I | 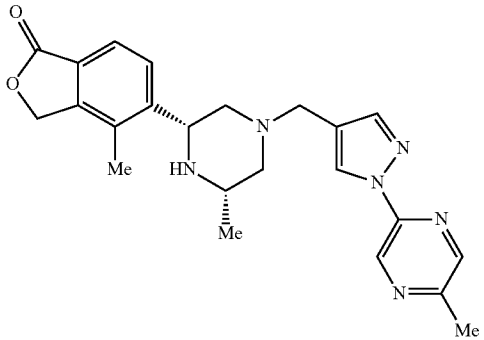 | 4-methyl-5-((2R,6S)-6-methyl-4-((1-(5-methylpyrazin-2-yl)-1H-pyrazol-4-yl)methyl)piperazin-2-yl)isobenzofuran-1(3H)-one | 419.3 | R: 0.63, 94.20% S: 1.40, 95.10% VIII: 5.80, 100% ee | $^1$H NMR (400 MHz, DMSO-d$_6$) δ ppm 1.03 (d, J = 6.10 Hz, 3 H), 1.73 (br. s., 2 H), 2.31-2.18 (m, 3 H), 2.56-2.52 (m, 4 H), 2.81 (d, J = 10.30 Hz, 2 H), 2.98 (br. s., 1 H), 3.53 (s, 2 H), 4.16 (br. s., 1 H), 5.37 (d, J = 2.00 Hz, 2 H), 7.65 (d, J = 7.80 Hz, 1 H), 7.88-7.74 (m, 2 H), 8.40 (s, 1 H), 8.45 (s, 1 H), 9.05 (d, J = 1.50 Hz, 1 H). |
| 207-I | 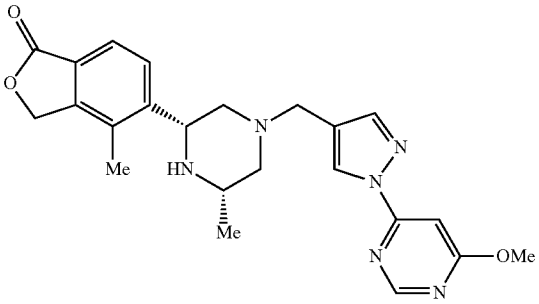 | 5-((2R,6S)-4-((1-(6-methoxypyrimidin-4-yl)-1H-pyrazol-4-yl)methyl)-6-methylpiperazin-2-yl)-4-methylisobenzofuran-1(3H)-one | 435.2 | S: 1.34, 99.14% R: 0.73, 100% XXV: 13.93, 98.14% ee | $^1$H NMR (400 MHz, DMSO-d$_6$) δ ppm 1.02 (d, J = 6.10 Hz, 3 H), 1.80-1.61 (m, 2 H), 2.26 (s, 3 H), 2.79 (d, J = 10.30 Hz, 2 H), 2.96 (br. s., 1 H), 3.18 (d, J = 5.40 Hz, 1 H), 3.51 (s, 2 H), 3.99 (s, 3 H), 4.15 (d, J = 8.60 Hz, 1 H), 5.47-5.29 (m, 2 H), 7.16 (d, J = 1.00 Hz, 1 H), 7.65 (d, J = 8.10 Hz, 1 H), 7.79 (d, J = 8.10 Hz, 1 H), 7.88-7.81 (m, 1 H), 8.49 (s, 1 H), 8.71 (d, J = 1.00 Hz, 1 H). |

-continued

| Example | Structure | Name | LCMS (M + H)$^+$ | HPLC/LCMS Method: RT (min.), Purity | NMR |
|---|---|---|---|---|---|
| 208-I | 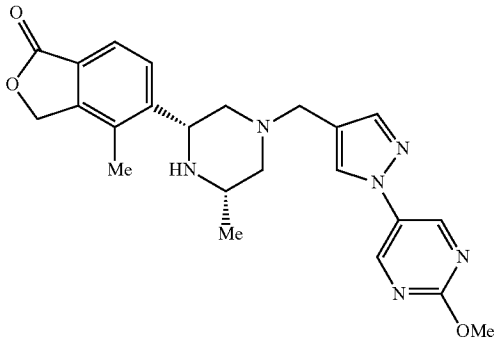 | 5-((2R,6S)-4-((1-(2-methoxypyrimidin-5-yl)-1H-pyrazol-4-yl)methyl)-6-methylpiperazin-2-yl)-4-methylisobenzofuran-1(3H)-one | 435.3 | S: 1.07, 95.74% R: 0.55, 98.67% XIV: 5.56, 100% ee | $^1$H NMR (400 MHz, DMSO-$d_6$) δ ppm 1.03 (d, J = 5.60 Hz, 3 H), 1.73 (d, J = 10.30 Hz, 2 H), 2.27 (s, 3 H), 2.82 (d, J = 10.30 Hz, 2 H), 2.98 (br. s., 1 H), 3.48 (s, 2 H), 3.97 (s, 3 H), 4.18 (br. s., 1 H), 5.47-5.28 (m, 2 H), 7.66 (d, J = 7.80 Hz, 1 H), 7.72 (s, 1 H), 7.80 (d, J = 8.10 Hz, 1 H), 8.42 (s, 1 H), 9.05 (s, 2 H), (1 Exchangeable proton not observed). |
| 209-I | 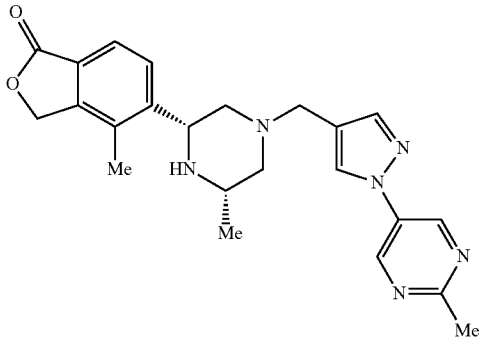 | 4-methyl-5-((2R,6S)-6-methyl-4-((1-(2-methylpyrimidin-5-yl)-1H-pyrazol-4-yl)methyl)piperazin-2-yl)isobenzofuran-1(3H)-one | 419.2 | S: 0.98, 93.79% R: 0.50, 98.28% XXVI: 9.79, 100% ee | $^1$H NMR (400 MHz, DMSO-$d_6$) δ ppm 1.04 (d, J = 6.10 Hz, 3 H), 1.72 (br. s., 2 H), 2.33-2.14 (m, 3 H), 2.70-2.60 (m, 3 H), 2.82 (d, J = 8.60 Hz, 2 H), 2.98 (br. s., 1 H), 3.49 (s, 2 H), 4.16 (br. s., 1 H), 5.45-5.30 (m, 2 H), 7.66 (d, J = 8.10 Hz, 1 H), 7.76 (s, 1 H), 7.80 (d, J = 8.10 Hz, 1 H), 8.53 (s, 1 H), 9.22-9.09 (m, 2 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 210-I | 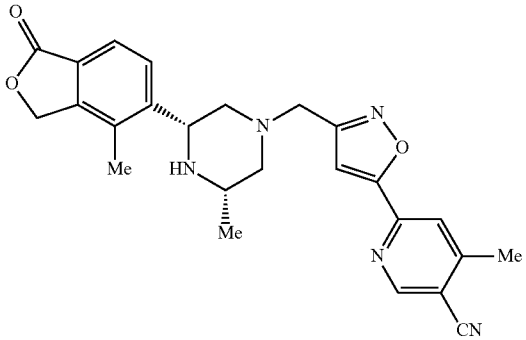 | 4-methyl-6-(3-(((3S,5R)-3-methyl-5-(4-methyl-1-oxo-1,3-dihydroisobenzofuran-5-yl)piperazin-1-yl)methyl)isoxazol-5-yl)nicotinonitrile | 444.2 | R: 1.50, 94.28% S: 1.13, 95.39% | $^1$H NMR (400 MHz, DMSO-$d_6$) δ ppm 1.04 (d, J = 6.10 Hz, 3 H), 1.94-1.80 (m, 3 H), 2.27 (s, 3 H), 2.64-2.54 (m, 4 H), 2.82 (d, J = 10.30 Hz, 2 H), 3.00 (br. s., 1 H), 3.72 (s, 2 H), 4.19 (d, J = 8.10 Hz, 1 H), 5.38 (s, 2 H), 7.23 (s, 1 H), 7.66 (d, J = 8.10 Hz, 1 H), 7.80 (d, J = 7.80 Hz, 1 H), 8.14 (s, 1 H), 9.04 (s, 1 H). |
| 211-I | 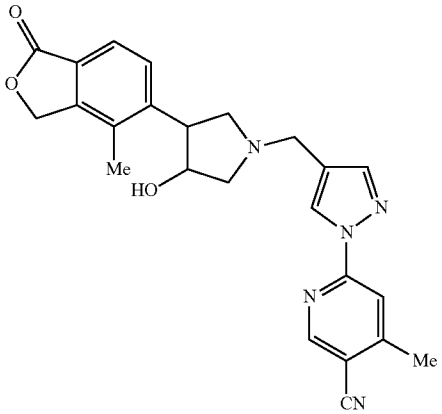 | 6-(4-((3-hydroxy-4-(4-methyl-1-oxo-1,3-dihydroisobenzofuran-5-yl)pyrrolidin-1-yl)methyl)-1H-pyrazol-1-yl)-4-methylnicotinonitrile (Diastereomer-I: Enantiomer-I) | 430.2 | R: 0.99, 100% S: 1.25, 100% XVIII: 16.83, 99.40% ee | $^1$H NMR (400 MHz, DMSO-d6) δ ppm 2.26 (s, 3 H), 2.58 (s, 3 H), 2.84-3.03 (m, 2 H), 3.19 (dd, J = 10.10, 5.70 Hz, 1 H), 3.51-3.63 (m, 1 H), 3.70 (s, 2 H), 4.38-4.48 (m, 1 H), 4.51 (d, J = 4.90 Hz, 1 H), 5.36 (s, 2 H), 7.54 (d, J = 7.80 Hz, 1 H), 7.59 (d, J = 8.10 Hz, 1 H), 7.91 (s, 1 H), 7.99 (s, 1 H), 8.59 (s, 1 H), 8.85 (s, 1 H). (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 212-II | 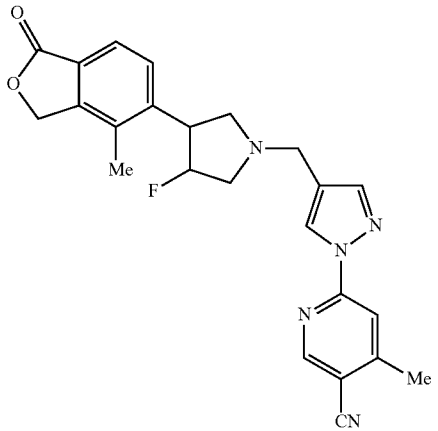 | 6-(4-((3-fluoro-4-(4-methyl-1-oxo-1,3-dihydroisobenzofuran-5-yl)pyrrolidin-1-yl)methyl)-1H-pyrazol-1-yl)-4-methylnicotinonitrile (Diastereomer-I: Enantiomer-II) | 432.2 | R: 1.12, 94.07% S: 1.80, 93.34% VIII: 4.92, 99.73% ee | $^1$H NMR (400 MHz, DMSO-$d_6$) δ ppm 2.30 (s, 3 H), 2.59 (s, 3 H), 2.93-3.02 (m, 1 H), 3.05 (br. s., 1 H), 3.24-3.29 (m, 1 H), 3.39 (d, J = 6.10 Hz, 1 H), 3.69 (s, 2 H), 3.74 (d, J = 5.60 Hz, 1 H), 3.78-3.88 (m, 1 H), 5.40 (s, 2 H), 7.53 (d, J = 8.30 Hz, 1 H), 7.69 (d, J = 7.80 Hz, 1 H), 7.92 (s, 1 H), 8.01 (s, 1 H), 8.60 (s, 1 H), 8.86 (s, 1 H). $^{19}$F NMR (400 MHz, DMSO-$d_6$) δ ppm −164.03. |
| 213-I | 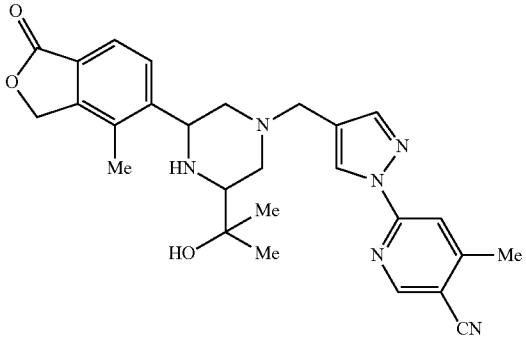 | 6-(4-((3-(2-hydroxypropan-2-yl)-5-(4-methyl-1-oxo-1,3-dihydroisobenzofuran-5-yl)piperazin-1-yl)methyl)-1H-pyrazol-1-yl)-4-methynicotinonitrile (Enantiomer-I) | 487.3 | R: 1.18, 93.00% S: 1.61, 93.00% XXV: 6.47, 100% ee | $^1$H NMR (400 MHz, DMSO-$d_6$) δ ppm 1.14 (d, J = 3.90 Hz, 6 H), 1.71 (t, J = 10.40 Hz, 1 H), 1.82 (t, J = 10.50 Hz, 1 H), 2.26 (s, 3 H), 2.58 (s, 3 H), 2.73-2.85 (m, 2 H), 2.92 (d, J = 10.00 Hz, 1 H), 3.51 (d, J = 13.90 Hz, 1 H), 3.59 (d, J = 13.70 Hz, 1 H), 4.15 (d, J = 7.60 Hz, 1 H), 4.40 (br. s., 1 H), 5.37 (s, 2 H), 7.66 (d, J = 7.80 Hz, 1 H), 7.82 (d, J = 7.80 Hz, 1 H), 7.86 (s, 1 H), 7.99 (s, 1 H), 8.53 (s, 1 H), 8.83 (s, 1 H). (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 214-I | 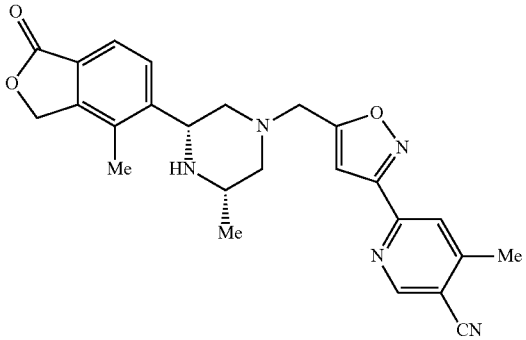 | 4-methyl-6-(5-(((3S,5R)-3-methyl-5-(4-methyl-1-oxo-1,3-dihydroisobenzofuran-5-yl)piperazin-1-yl)methyl)isoxazol-3-yl)nicotinonitrile | 444.2 | R: 1.16, 97.73% S: 1.56, 97.61% XVIII: 5.63, 100% ee | $^1$H NMR (400 MHz, DMSO-$d_6$) δ ppm 1.03 (d, J = 6.10 Hz, 3 H), 1.86 (dt, J = 13.60, 10.5 Hz, 2 H), 2.28 (s, 3 H), 2.55-2.65 (m, 4 H), 2.83 (d, J = 10.80 Hz, 2 H), 2.93-3.04 (m, 1 H), 3.86 (s, 2 H), 4.17 (d, J = 8.10 Hz, 1 H), 5.39 (s, 2 H), 6.98 (s, 1 H), 7.65 (d, J = 7.80 Hz, 1 H), 7.73-7.83 (m, 1 H), 8.15 (s, 1 H), 9.05 (s, 1 H). |
| 215-I | 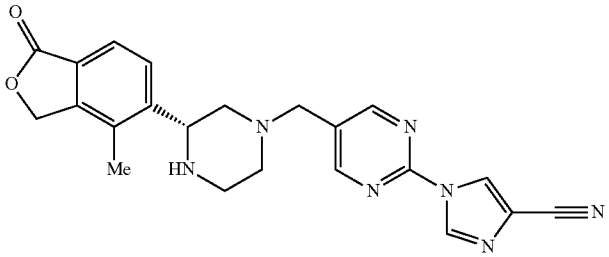 | (R)-4-methyl-5-(4-((2-(4-methyl-1H-imidazol-1-yl)pyrimidin-5-yl)methyl)piperazin-2-yl)isobenzofuran-1(3H)-one | 416.20 | A: 1.07, 99.60% B: 1.32, 98.32% XVIII: 16.98, 98.00% ee | $^1$H NMR (400 MHz, DMSO-$d_6$) δ ppm 1.87-1.96 (m, 1 H), 2.12-2.17 (m, 1 H), 2.24 (s, 3 H), 2.75-2.85 (m, 2 H), 2.94 (d, J = 12.96 Hz, 1 H), 3.02 (d, J = 11.98 Hz, 1 H), 3.54-3.65 (m, 2 H), 4.12 (d, J = 8.80 Hz, 1 H), 5.31-5.43 (m, 2 H), 7.62-7.69 (m, 2 H), 7.77 (d, J = 7.83 Hz, 1 H), 8.44 (d, J = 1.22 Hz, 1 H), 8.75 (s, 2 H), (1 Exchangeable proton not observed). |
| 216-I | 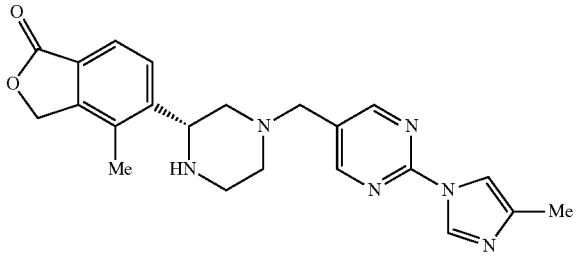 | (R)-1-(5-((3-(4-methyl-1-oxo-1,3-dihydroisobenzofuran-5-yl)piperazin-1-yl)methyl)pyrimidin-2-yl)-1H-imidazole-4-carbonitrile | 405.20 | E: 7.08, 97.55% G: 8.03, 98.45% XIV: 7.18, 98.01% ee | $^1$H NMR (400 MHz, DMSO-$d_6$) δ ppm 1.87-1.96 (m, 1 H), 2.12-2.17 (m, 1 H), 2.18 (s, 3 H), 2.24 (s, 3 H), 2.75-2.85 (m, 2 H), 2.94 (d, J = 12.96 Hz, 1 H), 3.02 (d, J = 11.98 Hz, 1 H), 3.54-3.65 (m, 2 H), 4.12 (d, J = 8.80 Hz, 1 H), 5.31-5.43 (m, 2 H), 7.62-7.69 (m, 2 H), 7.77 (d, J = 7.83 Hz, 1 H), 8.44 (d, J = 1.22 Hz, 1 H), 8.75 (s, 2 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 217-I | 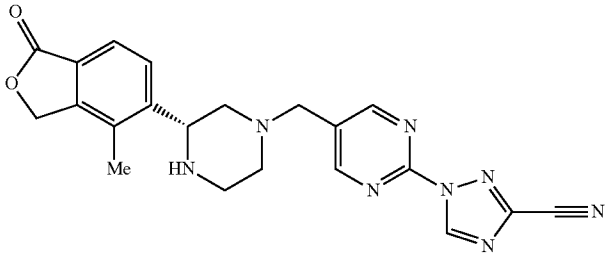 | (R)-1-(5-((3-(4-methyl-1-oxo-1,3-dihydroisobenzofuran-5-yl)piperazin-1-yl)methyl)pyrimidin-2-yl)-1H-1,2,4-triazole-3-carbonitrile | 417.5 | S: 1.14, 98.53% R: 1.34, 99.21% XVIII: 24.93, 100% ee | $^1$H NMR (400 MHz, DMSO-$d_6$) δ ppm 1.92 (t, J = 10.64 Hz, 1 H), 2.15-2.22 (m, 1 H), 2.25 (s, 3 H), 2.80 (t, J = 9.05 Hz, 2 H), 2.87-2.96 (m, 1 H), 2.96-3.05 (m, 1 H), 3.58-3.74 (m, 2 H), 4.11 (d, J = 8.80 Hz, 1 H), 5.28-5.43 (m, 2 H), 7.65 (d, J = 8.07 Hz, 1 H), 7.78 (d, J = 8.07 Hz, 1 H), 8.94 (s, 2 H), 9.78 (s, 1 H), (1 Exchangeable proton not observed). |
| 218-I | 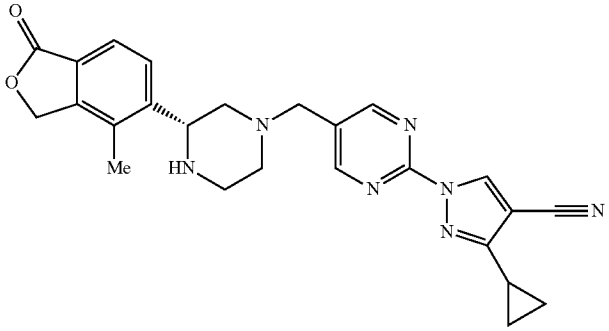 | (R)-3-cyclopropyl-1-(5-((3-(4-methyl-1-oxo-1,3-dihydroisobenzofuran-5-yl)piperazin-1-yl)methyl)pyrimidin-2-yl)-1H-pyrazole-4-carbonitrile | 456.5 | S: .108, 99.41% R: 1.32, 99.66% XVIII: 19.26, 98.54% ee | $^1$H NMR (400 MHz, DMSO-$d_6$) δ ppm 1.03-0.88 (m, 2 H), 1.17-1.04 (m, 2 H), 1.87 (t, J = 10.3 Hz, 1 H), 2.11-2.02 (m, 1 H), 2.20-2.11 (m, 1 H), 2.24 (s, 3 H), 2.77 (t, J = 12.00 Hz, 2 H), 2.94-2.84 (m, 1 H), 3.07-2.96 (m, 1 H), 3.74-3.50 (m, 2 H), 4.07 (d, J = 8.10 Hz, 1 H), 5.48-5.24 (m, 2 H), 7.64 (d, J = 8.10 Hz, 1 H), 7.77 (d, J = 8.10 Hz, 1 H), 8.81 (s, 2 H), 9.32 (s, 1 H). (1 Exchangeable proton not observed). |
| 219-I | 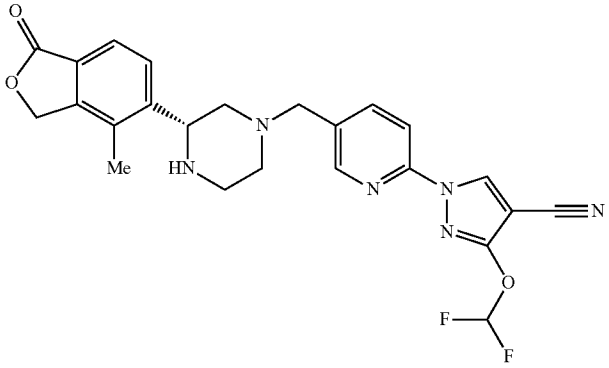 | (R)-3-(difluoromethoxy)-1-(5-((3-(4-methyl-1-oxo-1,3-dihydroisobenzofuran-5-yl)piperazin-1-yl)methyl)pyridin-2-yl)-1H-pyrazole-4-carbonitrile | 481.3 | S: 1.29, 99.02% R: 1.60, 99.41% XVIII: 7.03, 100% ee | $^1$H NMR (400 MHz, DMSO-d6) δ ppm 1.16 (t, J = 7.20 Hz, 3 H), 2.32 (s, 3 H), 2.93 (dd, J = 12.20, 7.1 Hz, 2 H), 3.03 (br. s., 2 H), 3.42 (br. s., 2 H), 3.78 (br. s., 2 H), 4.73 (br. s., 1 H), 5.43 (d, J = 14.20 Hz, 1 H), 7.58 (t, J = 53.50 Hz, 1 H), 7.80-7.67 (m, 1 H), 7.90-7.81 (m, 1 H), 8.06 (dd, J = 8.40, 2.10 Hz, 1 H), 8.50 (d, J = 1.70 Hz, 1 H), 9.40 (s, 1 H). $^{19}$F NMR (300 MHz, DMSO-$d_6$) δ ppm −84.69. |

-continued

| Example | Structure | Name | LCMS (M + H)$^+$ | HPLC/LCMS Method: RT (min.), Purity | NMR |
|---|---|---|---|---|---|
| 220-I | 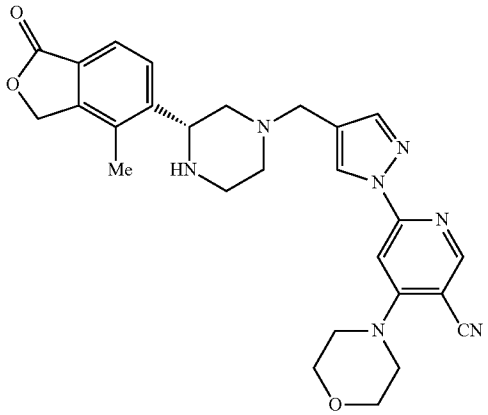 | (R)-6-(4-((3-(4-methyl-1-oxo-1,3-dihydroisobenzofuran-5-yl)piperazin-1-yl)methyl)-1H-pyrazol-1-yl)-4-morpholinonicotinonitrile | 500.2 | S: 0.96, 99.62% R: 1.27, 97.76% XIV: 10.79, 99.64% ee | $^1$H NMR (400 MHz, DMSO-$d_6$) δ 2.33 (s, 3 H), 2.60 (br. s., 1 H), 3.16 (br.s., 2 H), 3.21 (br. s., 1 H), 3.48-3.34 (m, 2 H), 3.60-3.54 (m, 4 H), 3.80-3.74 (m, 4 H), 3.83 (br.s., 2 H), 4.74 (d, J = 10.80 Hz, 1 H), 5.52-5.39 (m, 2 H), 7.38 (s, 1 H), 7.75 (d, J = 8.10 Hz, 1 H), 7.84 (d, J = 7.80 Hz, 1 H), 8.60 (s, 1 H), 7.87 (s, 1 H), 8.63 (s, 1 H), (1 Exchangeable proton not observed). |
| 221-I | 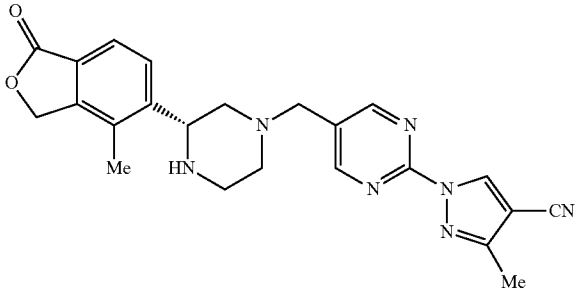 | (R)-3-methyl-1-(5-((3-(4-methyl-1-oxo-1,3-dihydroisobenzofuran-5-yl)piperazin-1-yl)methyl)pyrimidin-2-yl)-1H-pyraozle-4-carbonitrile | 430.20 | G: 11.37, 97.70% F: 10.57, 97.50% XVIII: 18.61, 98.90% ee | $^1$H NMR (400 MHz, DMSO-$d_6$) δ ppm 1.91 (s, 1 H), 2.15-2.23 (m, 1 H), 2.24 (s, 3 H), 2.41 (s, 3 H), 2.72-2.85 (m, 2 H), 2.94 (d, J = 10.52 Hz, 1 H), 3.01 (d, J = 9.54 Hz, 1 H), 3.57-3.71 (m, 2 H), 4.11 (d, J = 9.54 Hz, 1 H), 5.29-5.43 (m, 2 H), 7.66 (d, J = 8.07 Hz, 1 H), 7.78 (d, J = 7.83 Hz, 1 H), 8.83 (s, 2 H), 9.34 (s, 1 H). (1 Exchangeable proton not observed). |
| 222-I | 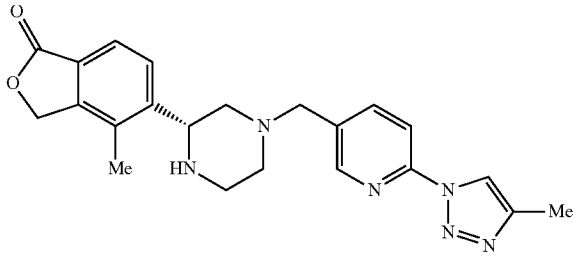 | (R)-4-methyl-5-(4-((6-(4-methyl-1H-1,2,3-triazol-1-yl)pyridin-3-yl)methyl)piperazin-2-yl)isobenzofuran-1(3H)-one | 405.00 | B: 1.42, 100% A: 1.18, 100% XIV: 7.16, 98.10% ee | $^1$H NMR (400 MHz, DMSO-$d_6$) δ ppm 1.93 (br. s., 1 H), 2.15-2.22 (m, 1 H), 2.24 (s, 3 H) 2.37 (s, 3 H), 2.80 (t, J = 12.47 Hz, 2 H), 2.96 (br. s., 1 H), 3.03 (b.r s., 1 H), 3.57-3.71 (m, 2 H), 4.17 (br. s., 1 H), 5.28-5.43 (m, 2 H), 7.67 (d, J = 7.34 Hz, 1 H), 7.78 (d, J = 8.07 Hz, 1 H), 8.01-8.14 (m, 2 H), 8.49 (s, 1 H), 8.56 (s, 1 H). (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 223-I | 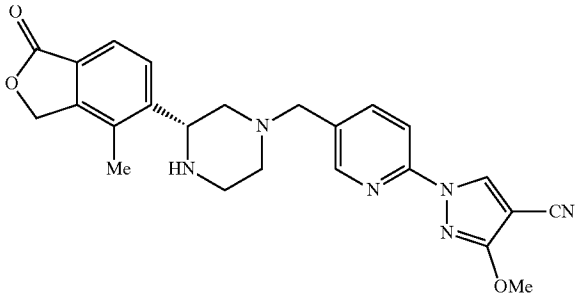 | (R)-3-methoxy-1-(5-((3-(4-methyl-1-oxo-1,3-dihydroisobenzofuran-5-yl)piperazin-1-yl)methyl)pyridin-2-yl)-1H-pyrazole-4-carbonitrile | 445.10 | B: 1.81, 100% A: 1.48, 100% XIV: 7.96, 98.66% ee | $^1$H NMR (400 MHz, DMSO-$d_6$) δ ppm 1.85 (t, J = 10.52 Hz, 1 H), 2.09-2.20 (m, 1 H), 2.22 (s, 3 H) 2.71-2.81 (m, 2 H), 2.92 (d, J = 10.03 Hz, 1 H), 2.96-3.03 (m, 1 H), 3.51-3.66 (m, 2 H), 4.04 (m, 4 H), 4.08 (d, J = 9.29 Hz, 1 H), 5.36 (d, J = 1.22 Hz, 2 H), 7.65 (d, J = 8.07 Hz, 1 H), 7.73-7.83 (m, 1 H), 7.95-8.02 (m, 1 H), 8.39 (d, J = 1.96 Hz, 1 H), 9.21 (s, 1 H). (1 Exchangeable proton not observed). |
| 224-I | 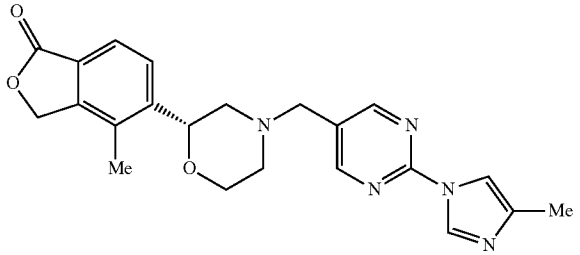 | (R)-4-methyl-5-(4-((2-(4-methyl-1H-imidazol-1-yl)pyrimidin-5-yl)methyl)morpholin-2-yl)isobenzofuran-1(3H)-one | 406.3 | C: 7.89, 98.69% G: 8.99, 98.54% XVIII: 20.31 100% ee | $^1$H NMR (400 MHz, DMSO-$d_6$) δ ppm 1.95-2.04 (m, 1 H), 2.17 (s, 3 H), 2.22 (s, 3 H), 2.23-2.36 (m, 1 H), 2.70 (d, J = 9.60 Hz, 1 H), 2.90 (d, J = 12.00 Hz, 1 H), 3.57 (s, 2 H), 3.65-3.77 (m, 1 H), 3.97 (d, J = 7.20 Hz, 1 H), 4.82 (d, J = 7.58 Hz, 1 H), 5.26-5.45 (m, 2 H), 7.61-7.68 (m, 3 H), 8.47 (dd, J = 8.31, 2.20 Hz, 1 H), 8.78 (s, 2 H). |
| 225-I | 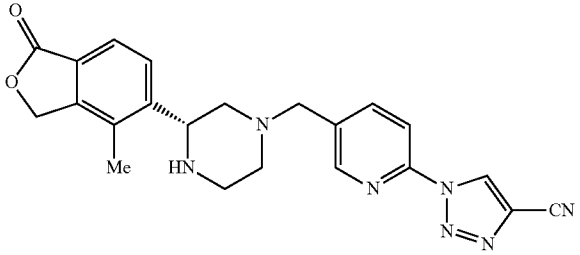 | (R)-1-(5-((3-(4-methyl-1-oxo-1,3-dihydroisobenzofuran-5-yl)piperazin-1-yl)methyl)pyridin-2-yl)-1H-1,2,3-triazole-4-carbonitrile | 416.2 | B: 1.24, 100% A: 0.99, 100% XIV: 7.96, 97.30% ee | $^1$H NMR (400 MHz, DMSO-$d_6$) δ ppm 1.95-1.84 (m, 1 H), 2.21-2.14 (m, 1 H), 2.24 (s, 3 H), 2.78 (t, J = 9.80 Hz, 2 H), 2.92 (d, J = 9.80 Hz, 1 H), 2.99 (s, 1 H), 3.61-3.73 (m, 2 H), 4.10 (d, J = 10.50 Hz, 1 H), 5.43-5.29 (m, 2 H), 7.65 (d, J = 7.80 Hz, 1 H), 7.78 (d, J = 8.10 Hz, 1 H), 8.21-8.08 (m, 2 H), 8.57 (s, 1 H), 9.78 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 226-I | 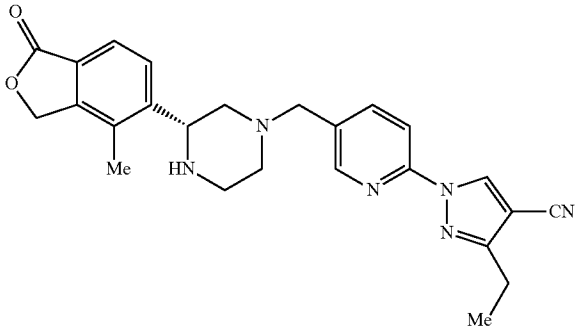 | (R)-3-ethyl-1-(5-((3-(4-methyl-1-oxo-1,3-dihydroisobenzofuran-5-yl)piperazin-1-yl)methyl)pyridin-2-yl)-1H-pyrazole-4-carbonitrile | 443.2 | B: 1.67, 100% A: 1.25, 98.15% XIV: 7.78, 99.0% ee | $^1$H NMR (400 MHz, DMSO-$d_6$) δ ppm 1.30 (t, J = 7.60 Hz, 3 H), 1.85 (t, J = 10.30 Hz, 1 H), 2.10-2.20 (m, 1 H), 2.22 (s, 3 H), 2.70-2.85 (m, 4 H), 2.94-2.85 (m, 1 H), 3.06-2.95 (m, 1 H), 3.60 (q, J = 13.50 Hz, 2 H), 4.08 (d, J = 10.00 Hz, 1 H), 5.24-5.48 (m, 2 H), 7.64 (d, J = 7.80 Hz, 1 H), 7.77 (d, J = 8.10 Hz, 1 H), 7.90 (d, J = 8.30 Hz, 1 H), 7.99 (dd, J = 8.40, 2.1 Hz, 1 H), 8.41 (d, J = 2.00 Hz, 1 H), 9.27 (s, 1 H), (1 Exchangeable proton not observed). |
| 227-I | 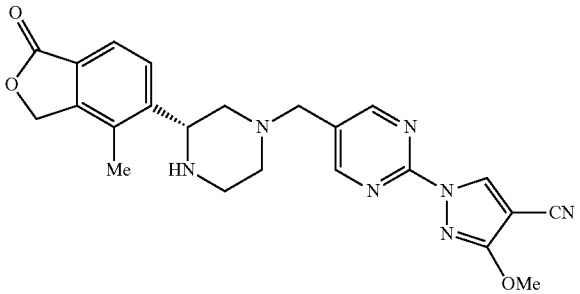 | (R)-3-methoxy-1-(5-((3-(4-methyl-1-oxo-1,3-dihydroisobenzofuran-5-yl)piperazin-1-yl)methyl)pyrimidin-2-yl)-1H-pyrazole-4-carbonitrile | 446.2 | B: 1.17, 95.59% A: 0.97, 94.45% XVIII: 18.87, 97.5% ee | $^1$H NMR (400 MHz, DMSO-$d_6$) δ ppm 1.87 (t, J = 10.50 Hz, 1 H), 2.11-2.20 (m, 2 H), 2.21-2.30 (m, 3 H), 2.77 (t, J = 12.30 Hz, 2 H), 2.84-2.94 (m, 1 H), 2.95-3.06 (m, 1 H), 3.53-3.74 (m, 2 H), 4.03 (s, 3H), 4.07 (d, J = 7.50 Hz, 1 H), 5.27-5.50 (m, 2 H), 7.64 (d, J = 8.00 Hz, 1 H), 7.78 (d, J = 8.00 Hz, 1 H), 8.80 (s, 2 H), 9.30 (s, 1 H) |
| 228-I | 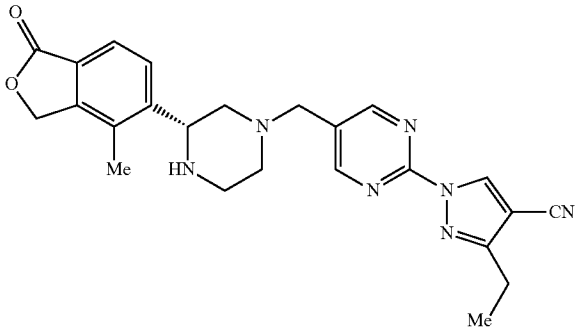 | (R)-3-ethyl-1-(5-((3-(4-methyl-1-oxo-1,3-dihydroisobenzofuran-5-yl)piperazin-1-yl)methyl)pyrimidin-2-yl)-1H-pyrazole-4-carbonitrile | 444.3 | B: 1.24, 99.34% A: 1.04, 100% XVIII: 18.45, 98.08% ee | $^1$H NMR (400 MHz, DMSO-$d_6$) δ ppm 9.34 (s, 1 H), 8.83 (s, 2 H), 7.78 (d, J = 8.10 Hz, 1 H), 7.65 (d, J = 8.10 Hz, 1 H), 5.47-5.26 (m, 2 H), 4.11 (d, J = 9.30 Hz, 1 H), 3.73-3.52 (m, 2 H), 3.06-2.97 (m, 1 H), 2.96-2.87 (m, 1 H), 2.85-2.71 (m, 4 H), 2.24 (s, 3 H), 2.22-2.12 (m, 1 H), 1.90 (t, J = 10.30 Hz, 1 H), 1.29 (t, J = 7.60 Hz, 3 H). (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 229-I | 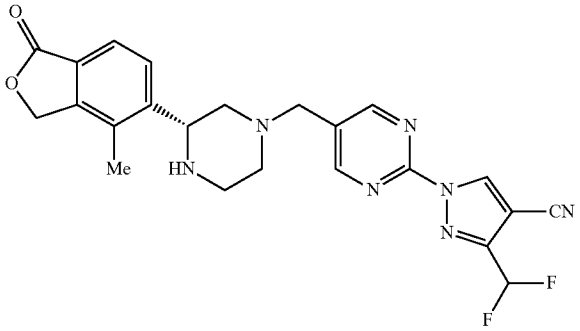 | (R)-3-(difluoromethyl)-1-(5-((3-(4-methyl-1-oxo-1,3-dihydroisobenzofuran-5-yl)piperazin-1-yl)methyl)pyrimidin-2-yl)-1H-pyrazole-4-carbonitrile | 466.3 | B: 1.25, 95.14% A: 1.02, 96.07% XIV: 10.12, 98.00% ee | $^1$H NMR (400 MHz, DMSO-$d_6$) δ ppm 1.90 (t, J = 9.80 Hz, 1 H), 2.09-2.22 (m, 1 H), 2.24 (s, 3 H), 2.79 (t, J = 11.00 Hz, 2 H), 2.92 (d, J = 9.80 Hz, 1 H), 2.96-3.05 (m, 1 H), 3.95-3.76 (m, 2 H), 4.09 (d, J = 8.80 Hz, 1 H), 5.21-5.48 (m, 2 H), 7.23-7.49 (t, J = 52.80 Hz, 1 H), 7.65 (d, J = 7.80 Hz, 1 H), 7.78 (d, J = 8.10 Hz, 1 H), 8.90 (s, 2 H), 9.62 (s, 1 H), (1 Exchangeable proton not observed). $^{19}$F NMR (400 MHz, DMSO-$d_6$) δ ppm −114.59. |
| 230-I | 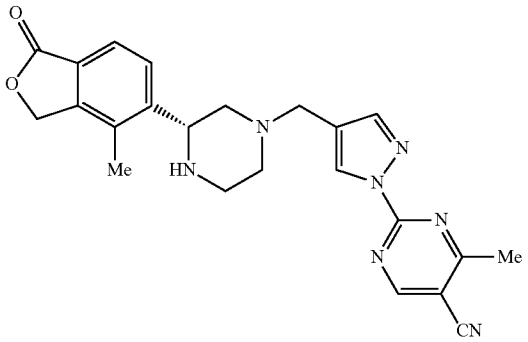 | (R)-4-methyl-2-(4-((3-(4-methyl-1-oxo-1,3-dihydroisobenzofuran-5-yl)piperazin-1-yl)methyl)-1H-pyrazol-1-yl)pyrimidine-5-carbonitrile | 430.2 | B: 1.05, 98.55% A: 0.76, 97.72% XVIIII: 18.27, 99.00% ee | $^1$H NMR (400 MHz, DMSO-$d_6$) δ ppm 1.91 (s, 1 H), 2.27 (s, 4 H), 2.70 (s, 3 H), 2.86 (br. s., 2 H), 2.99 (s, 1 H), 3.08 (br. s., 1 H), 3.56 (br. s., 2 H), 4.23 (b.r s., 1 H), 5.22-5.50 (m, 2 H), 7.68 (d, J = 8.30 Hz, 1 H), 7.76 (d, J = 8.30 Hz, 1 H), 7.89 (s, 1 H), 8.59 (s, 1 H), (9.20 (s, 1 H), (1 Exchangeable proton not observed). |
| 231-I | 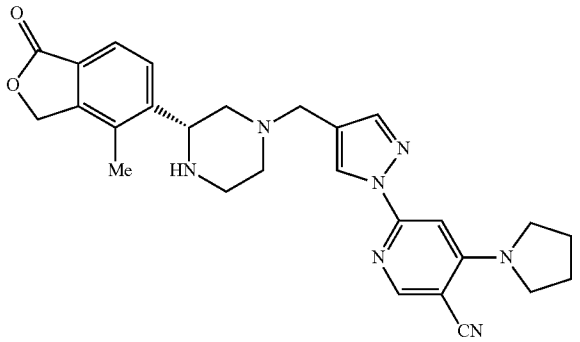 | (R)-2-(4-((3-(4-methyl-1-oxo-1,3-dihydroisobenzofuran-5-yl)piperazin-1-yl)methyl)-1H-pyrazol-1-yl)-5-(pyrrolidin-1-yl)isonicotinonitrile | 484.3 | B: 1.45, 99.72% A: 1.09, 100% XVIIII: 15.10, 100% ee | $^1$H NMR (400 MHz, DMSO-$d_6$) δ ppm 1.97-2.01 (m, 4 H), 2.34 (s, 4 H), 3.05 (d, J = 10.30 Hz, 2 H), 3.17 (s, 2 H), 3.40 (br. s., 1 H), 3.67 (br. s., 5 H), 4.72 (b.s., 1 H), 5.45 (d, J = 12.70 Hz, 2 H), 7.03 (s, 1 H), 7.69-7.76 (m, 1H), 7.79 (s, 1 H), 7.85 (d, J = 7.80 Hz, 1 H), 8.41 (s, 1 H), 8.53 (s, 1 H), 8.88 (s, 1 H), 9.33 (s, 1 H). |

-continued

| Example | Structure | Name | LCMS (M + H)$^+$ | HPLC/LCMS Method: RT (min.), Purity | NMR |
|---|---|---|---|---|---|
| 232-I | 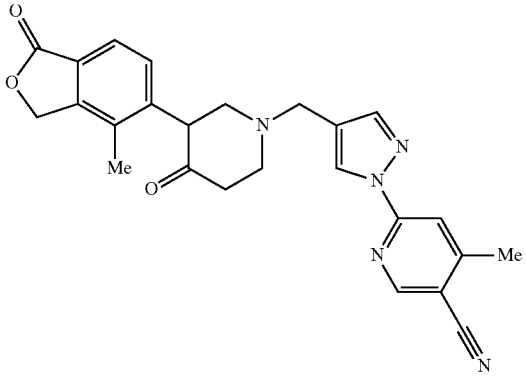 | 4-methyl-6-(4-((3-(4-methyl-1-oxo-1,3-dihydroisobenzofuran-5-yl)-4-oxopiperidin-1-yl)methyl)-1H-pyrazol-1-yl)nicotinonitrile | 442.2 | R: 1.34, 62.00% S: 1.86, 100% | $^1$H NMR (400 MHz, DMSO-$d_6$) δ ppm 2.15 (s, 3 H), 2.35 (d, J = 14.43 Hz, 1 H), 2.58 (s, 3 H), 2.62-2.71 (m, 2 H), 2.73-2.89 (m, 1 H), 3.20 (br. s., 2 H), 3.75 (s, 2 H), 4.27 (dd, J = 11.37, 5.50 Hz, 1 H), 5.30-5.44 (m, 2 H), 7.42 (d, J = 8.07 Hz, 1 H), 7.62 (d, J = 7.58 Hz, 1 H), 7.93 (s, 1 H), 7.99 (s, 1 H), 8.62 (s, 1 H), 8.84 (s, 1 H). |
| 233-I | 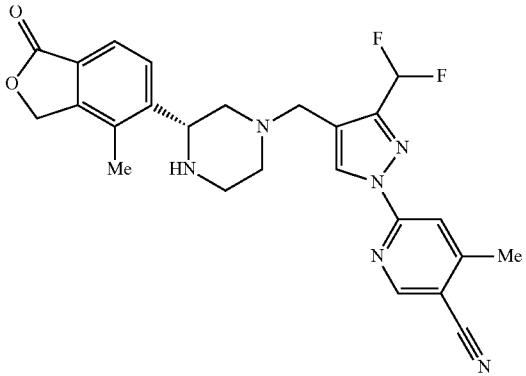 | (R)-6-(3-(difluoromethyl)-4-((3-(4-methyl-1-oxo-1,3-dihydroisobenzofuran-5-yl)piperazin-1-yl)methyl)-1H-pyrazol-1-yl)-4-methylnicotinonitrile | 479.1 | R: 1.59, 99.30% S: 1.94, 98.00% XVIIII: 10.70, 100% ee | $^1$H NMR (400 MHz, DMSO-$d_6$) δ ppm 1.89 (br. s., 1 H), 2.19 (br. s., 1 H), 2.24 (s, 3 H), 2.60 (s, 3 H), 2.76-2.89 (m, 2 H), 2.94 (br. s., 1 H), 3.03 (br. s., 1 H), 3.51-3.67 (m, 2 H), 4.12 (br. s., 1 H), 5.36 (d, J = 3.18 Hz, 2 H), 7.08-7.39 (m, 1 H), 7.66 (d, J = 7.58 Hz, 1 H), 7.77 (d, J = 7.83 Hz, 1 H), 8.02 (s, 1 H), 8.66 (s, 1 H), 8.89 (s, 1 H). (1 Exchangeable proton not observed). $^{19}$F NMR (400 MHz, DMSO-$d_6$) δ ppm −114.2. |

-continued

| Example | Structure | Name | LCMS (M + H)$^+$ | HPLC/LCMS Method: RT (min.), Purity | NMR |
|---|---|---|---|---|---|
| 234-I | 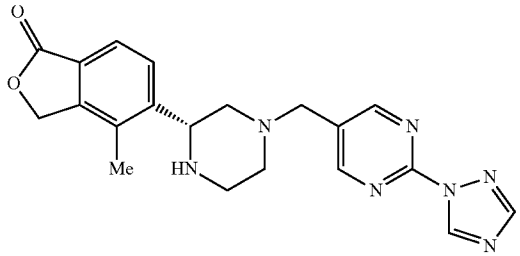 | (R)-5-(4-((2-(1H-1,2,4-triazol-1-yl)pyrimidin-5-yl)methyl)piperazin-2-yl)-4-methylisobenzofuran-1(3H)-one | 392.1 | R: 0.93, 97.00% S: 1.06, 93.50% XIV: 7.53, 100% ee | $^1$H NMR (400 MHz, DMSO-$d_6$) δ ppm 1.86-1.95 (m, 1 H), 2.13-2.22 (m, 1 H), 2.25 (s, 3 H), 2.64-2.84 (m, 2 H), 2.86-3.05 (m, 2 H), 3.65 (d, J = 8.07 Hz, 2 H), 4.09 (d, J = 8.31 Hz, 1 H), 5.36 (d, J = 4.40 Hz, 2 H), 7.65 (d, J = 7.83 Hz, 1 H), 7.78 (d, J = 7.58 Hz, 1 H), 8.32 (s, 1 H), 8.87 (s, 2 H), 9.43 (s, 1 H). (1 Exchangeable proton not observed). |
| 235-I | 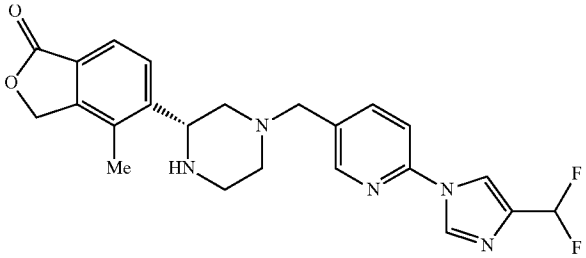 | (R)-5-(4-((6-(4 (difluoromethyl)-1H-imidazol-1-yl)pyridin-3-yl)methyl)piperazin-2-yl)-4-methylisobenzofuran-1(3H)-one | 440.1 | R: .119, 95.40% S: 1.45, 98.40% XIV: 6.79, 88.00% ee | $^1$H NMR (400 MHz, DMSO-$d_6$) δ ppm 1.79-1.90 (m, 1 H), 2.09-2.19 (m, 1 H), 2.23 (s, 3 H), 2.72-2.80 (m, 2 H), 2.86-2.93 (m, 1 H), 2.94-3.03 (m, 1 H), 3.49-3.53 (m, 2 H), 4.07 (d, J = 7.58 Hz, 1 H), 5.36 (s, 2 H), 6.82-7.14 (m, 1 H), 7.64 (d, J = 7.83 Hz, 1 H), 7.78 (d, J = 8.07 Hz, 1 H), 7.86 (d, J = 8.07 Hz, 1 H), 7.97 (dd, J = 8.31, 2.20 Hz, 1 H), 8.29 (s, 1 H), 8.44 (d, J = 1.71 Hz, 1 H), 8.62 (s, 1 H). (1 Exchangeable proton not observed). $^{19}$F NMR (400 MHz, DMSO-$d_6$) δ ppm −112.0. |
| 236-I | 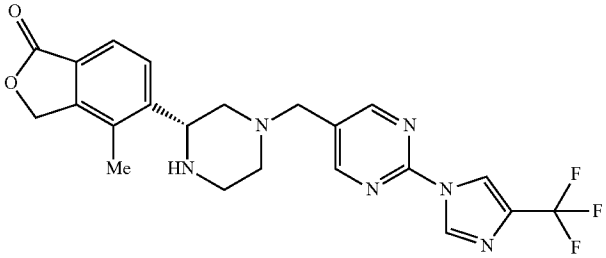 | (R)-4-methyl-5-(4-((2-(4-(triflouromethyl)-1H-imidazol-1-yl)pyrimidin-5-yl)methyl)piperazin-2-yl)isobenzofuran-1(3H)-one | 459.1 | A: 1.34, 96.60% B: 1.65, 97.40% XIV: 6.82, 97.00% ee | $^1$H NMR (400 MHz, DMSO-$d_6$) δ ppm 1.94 (br. s., 1 H), 2.21 (b.r. s., 1 H), 2.25 (s, 3 H), 2.82 (br. s., 2 H), 2.91-3.08 (m, 2 H), 3.66 (d, J = 5.87 Hz, 2 H), 4.13 (br. s., 1 H), 5.37 (d, J = 6.36 Hz, 2 H), 7.67 (d, J = 8.31 Hz, 1 H), 7.78 (d, J = 8.07 Hz, 1 H), 8.52 (s, 1 H), 8.76 (s, 1 H), 8.86 (s, 2 H). (1 Exchangeable proton not observed). $^{19}$F NMR (400 MHz, DMSO-$d_6$) δ ppm −61.7. |

-continued

| Example | Structure | Name | LCMS (M + H)$^+$ | HPLC/LCMS Method: RT (min.), Purity | NMR |
|---|---|---|---|---|---|
| 237-I | 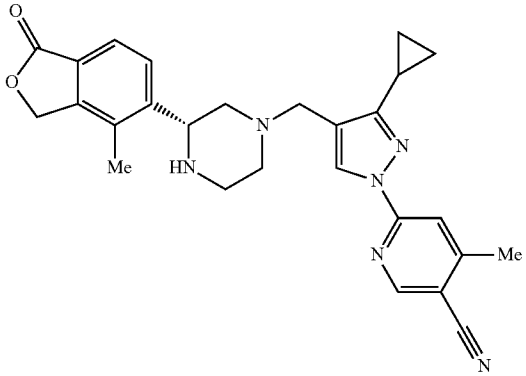 | (R)-6-(3-cyclopropyl-4-((3-(4-methyl-1-oxo-1,3-dihydroisobenzofuran-5-yl)piperazin-1-yl)methyl)-1H-pyrazol-1-yl)-4-methylnicotinonitrile | 469.1 | R: 1.57, 97.90% S: 2.30, 98.00% XVII: 8.49, 100% ee | $^1$H NMR (400 MHz, DMSO-d6) δ ppm 0.89-0.99 (m, 4 H), 1.84 (t, J = 10.03 Hz, 1 H), 2.05-2.19 (m, 2 H), 2.25 (s, 3 H), 2.54 (s, 3 H), 2.76-2.96 (m, 3 H), 3.01 (d, J = 12.23 Hz, 1 H), 3.54 (d, J = 9.78 Hz, 2 H), 4.08 (d, J = 8.07 Hz, 1 H), 5.36 (s, 2 H), 7.64 (d, J = 8.07 Hz, 1 H), 7.74-7.83 (m, 2 H), 8.39 (s, 1 H), 8.76 (s, 1 H). (1 Exchangeable proton not observed). |
| 238-I | 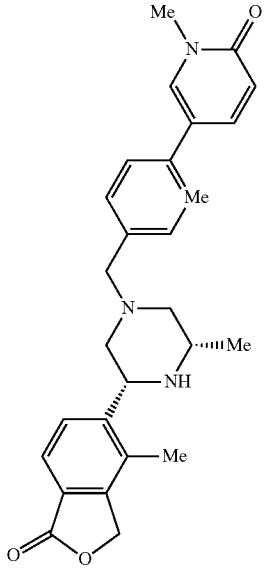 | 1'-methyl-5-(((3S,5R)-3-methyl-5-(4-methyl-1-oxo-1,3-dihydroisobenzofuran-5-yl)piperazin-1-yl)methyl)-[2,3'-bipyridin]-6'(1'H)-one | 445.2 | R: 0.46, 100% S: 1.02, 96.10% | $^1$H NMR (400 MHz, DMSO-$d_6$) δ ppm 1.15-1.24 (m, 3 H), 2.20-2.24 (m, 4 H), 2.52-2.55 (m, 2 H), 2.96 (br. s., 3 H), 3.54 (s, 3 H), 3.68 (br. s., 2 H), 5.54-5.31 (m, 2 H), 6.50 (d, J = 9.30 Hz, 1 H), 7.79 (s, 4 H), 8.16 (dd, J = 9.40, 2.60 Hz, 1 H), (8.53 (d, J = 2.70 Hz, 2 H). (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 239-I | 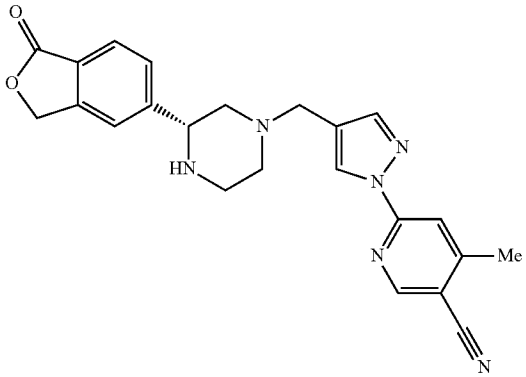 | (R)-4-methyl-6-(4-((3-(1-oxo-1,3-dihydroisobenzofuran-5-yl)piperazin-1-yl)methyl)-1H-pyrazol-1-yl)nicotinonitrile | 415.2 | R: 0.93, 95.50% S: 1.23, 95.40% | $^1$H NMR (400 MHz, DMSO-$d_6$) δ ppm 1.83-1.97 (m, 1 H), 2.06-2.18 (m, 1 H), 2.58 (s, 3 H), 2.75-2.92 (m, 3 H), 3.00 (d, J = 10.5 Hz, 1 H), 3.53 (s, 2 H), 3.96 (d, J = 8.6 Hz, 1 H), 5.37 (s, 2 H), 7.61 (d, J = 8.10 Hz, 1 H), 7.69 (s, 1 H), 7.78 (d, J = 7.80 Hz, 1 H), 7.84 (s, 1 H), 7.98 (s, 1 h), 8.53 (s, 1 H), 8.83 (s, 1 H). (1 Exchangeable proton not observed). |
| 240-I | 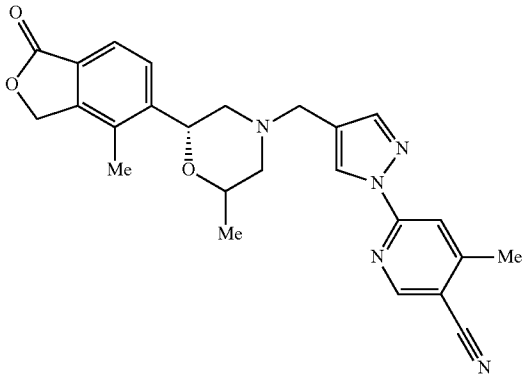 | 4-methyl-6-(4-(((6R)-2-methyl-6-(4-methyl-1-oxo-1,3-dihydroisobenzofuran-5-yl)morpholino)methyl)-1H-pyrazol-1-yl)nicotinonitrile (Diasteromer-I) | 444.2 | R: 1.16, 100% S: 1.78, 94.30% XVIII: 14.40, 98.00% ee | $^1$H NMR (400 MHz, DMSO-$d_6$) δ ppm 1.17 (d, J = 6.10 Hz, 3 H), 1.86 (br. s., 2 H), 2.24 (s, 3 H), 2.58 (s, 3 H), 2.88 (d, J = 11.50 Hz, 2 H), 3.56 (br. s., 2 H), 3.84 (br. s., 1 H), 4.87 (d, J = 10.00 Hz, 1 H), 5.49-5.26 (m, 2 H), 7.61 (d, J = 8.10 Hz, 1 H), 7.68 (d, J = 7.80 Hz, 1 H), 7.87 (s, 1 H), 7.99 (s, 1 H), 8.55 (br. s., 1 H), 8.83 (s, 1 H). |

-continued

| Example | Structure | Name | LCMS (M + H)$^+$ | HPLC/LCMS Method: RT (min.), Purity | NMR |
|---|---|---|---|---|---|
| 241-I | 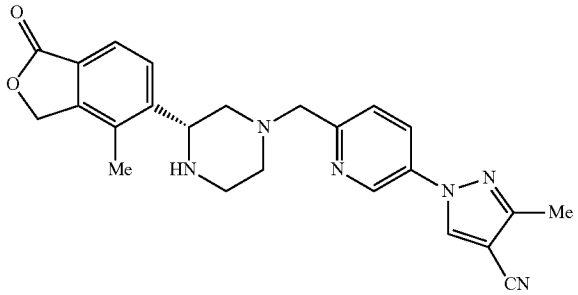 | (R)-3-methyl-1-(6-((3-(4-methyl-1-oxo-1,3-dihydroisobenzofuran-5-yl)piperazin-1-yl)methyl)pyridin-3-yl)-1H-pyrazole-4-carbonitrile | 429.1 | R: 0.94, 98.10% S: 1.18, 94.30% | $^1$H NMR (400 MHz, DMSO-$d_6$) δ ppm 2.34 (s, 3 H), 2.41 (s, 3 H), 2.60 (d, J = 13.00 Hz, 2 H), 3.09 (d, J = 12.50 Hz, 2 H), 3.42 (br. s., 2 H), 3.89 (br. s., 2 H), 4.78 (br. s., 1 H), 5.54-5.34 (m, 2 H), 7.67 (d, J = 8.30 Hz, 1 H), 7.76 (d, J = 8.10 Hz, 1 H), 7.85 (d, J = 8.10 Hz, 1 H), 8.24 (dd, J = 8.60, 2.4 Hz, 1 H), 9.01 (d, J = 2.20 Hz, 2 H), 9.29 (s, 1 H). |
| 242-I | 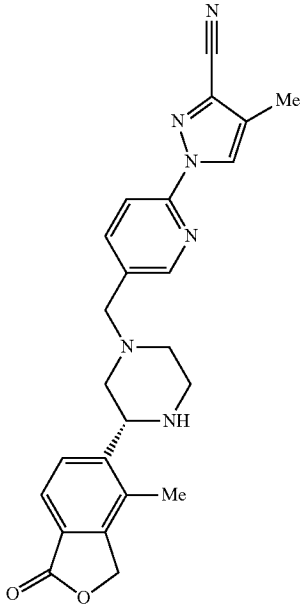 | (R)-4-methyl-1-(5-((3-(4-methyl-1-oxo-1,3-dihydroisobenzofuran-5-yl)piperazin-1-yl)methyl)pyridin-2-yl)-1H-pyrazole-3-carbonitrile | 429.1 | R: 1.54, 97.80% S: 1.89, 95.10% XVIIII: 14.07, 100% ee | $^1$H NMR (400 MHz, DMSO-$d_6$) δ ppm 1.85 (t, J = 9.66 Hz, 1 H), 2.11-2.19 (m, 1 H), 2.23 (d, J = 4.16 Hz, 6 H), 2.71-2.82 (m, 2 H), 2.90 (t, J = 11.37 Hz, 1 H), 2.99 (d, J = 11.00 Hz, 1 H), 3.54-3.68 (m, 2 H), 4.08 (d, J = 7.34 Hz, 1 H), 5.36 (s, 2 H), 7.64 (d, J = 8.07 Hz, 1 H), 7.78 (d, J = 8.07 Hz, 1 H), 7.91-7.96 (m, 1 H), 7.98-8.03 (m, 1 H), 8.43 (s, 1 H), 8.69 (s, 1 H). (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 243-I | 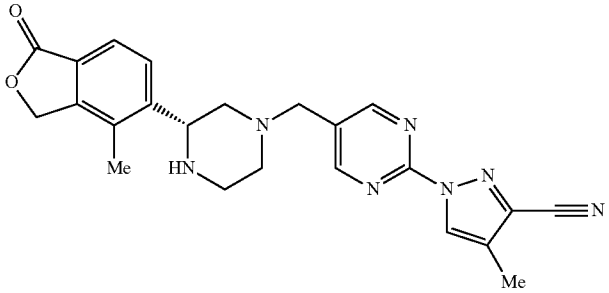 | (R)-4-methyl-1-(5-((3-(4-methyl-1-oxo-1,3-dihydroisobenzofuran-5-yl)piperazin-1-yl)methyl)pyrimidin-2-yl)-1H-pyrazole-3-carbonitrile | 431.0 | R: 1.00, 98.90% S: 1.24, 99.30% XVIII: 9.09, 100% ee | $^1$H NMR (400 Mhz, DMSO-$d_6$) δ ppm 1.97-1.82 (m, 1 H), 2.13-2.21 (m, 1 H), 2.222-2.29 (m, 6 H), 2.80 (t, J = 11.60 Hz, 2 H), 2.88-2.96 (m, 1 H), 2.97-3.05 (m, 1 H), 3.55-3.74 (m, 2 H), 4.10 (d, J = 8.60 Hz, 1 H), 5.26-5.48 (m, 2 H), 7.65 (d, J = 8.10 Hz, 1 H), 7.78 (d, J = 8.10 Hz, 1 H), 8.72 (d, J = 0.70 Hz, 1 H), 8.86 (s, 2 H), (1 Exchangeable proton not observed). |
| 244-II | 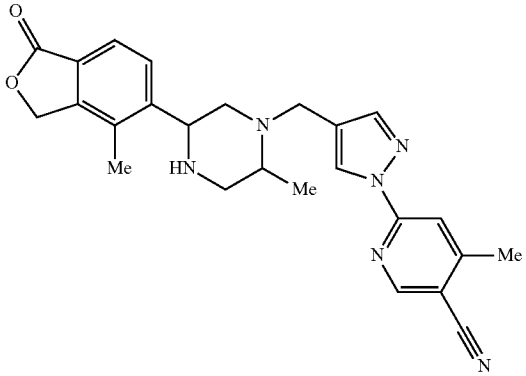 | 4-methyl-6-(4-((2-methyl-5-(4-methyl-1-oxo-1,3-dihydroisobenzofuran-5-yl)piperazin-1-yl)methyl)-1H-pyrazol-1-yl)nicotinonitrile Enantiomer-II) | 443.2 | R: 135, 100% S: 1.73, 100% XVIII: 9.09, 100% ee | $^1$H NMR (400 MHz, DMSO-$d_6$) δ ppm 1.32 (d, J = 6.10 Hz, 3 H), 2.30-2.33 (m, 3 H), 2.58 (s, 3 H), 2.79 (br. s., 1 H), 3.06-3.15 (m, 3 H), 3.89 (d, J = 14.40 Hz, 2 H), 3.99 (d, J = 14.90 Hz, 1 H), 4.70 (d, J = 8.80 Hz, 1 H), 5.50-5.39 (m, 2 H), 7.66 (d, J = 8.10 Hz, 1 H), 7.83 (d, J - 8.10 Hz, 1 H), 7.91 (s, 1 H), 8.00 (s, 1 H), 8.65 (s, 1 H), 8.84 (s, 1 H), (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 245-I | 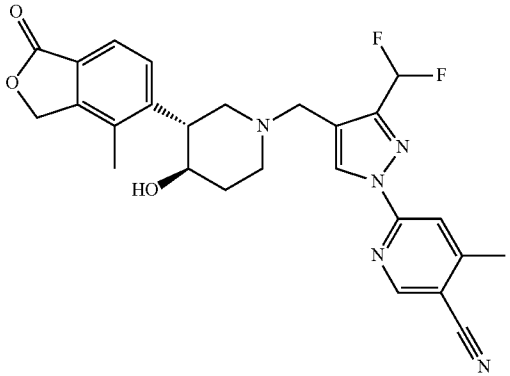 | 6-(3-(difluoromethyl)-4-(((3R,4R)-4-hydroxy-3-(4-methyl-1-oxo-1,3-dihydroisobenzofuran-5-yl)piperidin-1-yl)methyl)-1H-pyrazol-1-yl)-4-methylnicotinonitrile | 494.2 | R: .118, 100% S: 1.71, 98.90% XXVI: 4.36, 100% ee | $^1$H NMR (400 MHz, DMSO-$d_6$) δ ppm 1.64 (d, J = 9.30 Hz, 1 H), 1.92 (br. s., 1 H), 2.00-2.12 (m, 1 H), 2.23 (s, 4 H), 2.55 (s, 3 H), 2.58-2.66 (m, 1 H), 2.72 (d, J = 11.70 Hz, 1 H), 2.95 (d, J = 10.30 Hz, 1 H), 3.01-3.14 (m, 1 H), 3.46-3.67 (m, 2 H), 3.75 (br. s., 1 H), 4.60 (d, J = 5.40 Hz, 1 H), 5.48-5.24 (m, 2 H), 7.54 (d, J = 7.60 Hz, 1 H), 7.63 (d, J = 8.30 Hz, 1 H), 8.02 (s, 1 H), 8.65 (s, 1 H), 8.90 (s, 1 H). $^{19}$F NMR (400 MHz, DMSO-$d_6$) δ ppm −114.00 |
| 246-I | 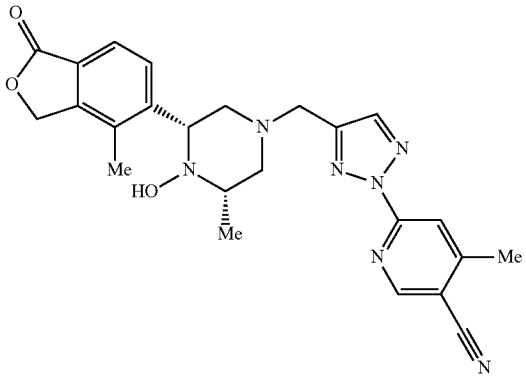 | 6-(4-(((3S,5R)-4-hydroxy-3-methyl-5-(4-methyl-1-oxo-1,3-dihydroisobenzofuran-5-yl)piperazin-1-yl)methyl)-2H-1,2,3-triazol-2-yl)-4-methylnicotinonitrile | 460.3 | R: 0.76, 97.20% S: 1.30, 93.30% XXV: 15.22, 98.00% ee. | $^1$H NMR (400 MHz, DMSO-$d_6$) δ ppm 1.20-1.11 (m, 3 H), 2.26 (s, 3 H), 2.30-2.33 (m, 1 H) 2.55-2.66 (m, 4 H), 2.74 (s, 1 H), 2.80 (br. s., 1 H), 4.25 (br. s., 3 H), 5.31-5.49 (m, 2 H), 7.72 (d, J = 8.10 Hz, 1 H), 7.80 (d, J = 7.80 Hz, 1 H), 7.96-8.22 (m, 2 H), 8.33 (s, 1 H), 8.92-9.05 (m, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 247-I | 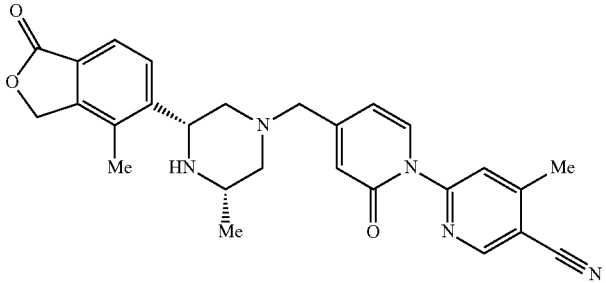 | 4'-methyl-4-(((3S,5R)-3-methyl-5-(4-methyl-1-oxo-1,3-dihydroisobenzofuran-5-yl)piperazin-1-yl)methyl)-2-oxo-2H-[1,2'-bipyridine]-5'-carbonitrile | 470.2 | R: 1.18, 96.30% S: 1.52, 100% XIV: 3.45, 100% ee | $^1$H NMR (400 MHz, DMSO-$d_6$) δ ppm 1.04 (d, J = 6.10 Hz, 3 H), 2.32-2.25 (m, 3 H), 2.58 (s, 3 H), 2.75-2.72 (m, 1 H), 2.79 (d, J = 11.50 Hz, 2 H), 2.90 (s, 1 H), 3.01 (br. s., 1 H), 3.42 (s, 2 H), 4.20 (d, J = 10.30 Hz, 1 H), 5.39 (s, 2 H), 6.51-6.39 (m, 2 H), 7.67 (d, J = 7.80 Hz, 1 H), 7.82 (d, J = 8.10 Hz, 1 H), 7.91 (d, J = 7.30 Hz, 1 H), 8.01 (s, 1 H), 8.99 (s, 1 H), (1 Exchangeable proton not observed). |
| 248-I | 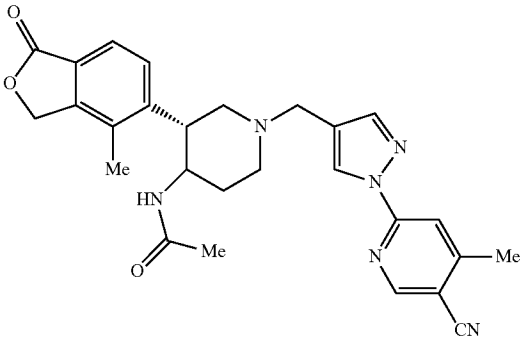 | N-(1-((1-(5-cyano-4-methylpyridin-2-yl)-1H-pyrazol-4-yl)methyl)-3-(4-methyl-1-oxo-1,3-dihydroisobenzofuran-5-yl)piperidin-4-yl)acetamide (Diastereomer-II Enantiomer-I) | 485.3 | S: 1.28, 100% R: 0.94, 100% XXV: 4.99, 100% ee | $^1$H NMR (400 MHz, DMSO-$d_6$) δ ppm 1.56 (s, 3 H), 1.65-1.57 (m, 1 H), 1.98-1.79 (m, 2 H), 2.18 (t, J = 11.70 Hz, 1 H), 2.24 (s, 3 H), 2.56 (s, 3 H), 2.98-2.85 (m, 2 H), 3.22-3.13 (m, 2 H), 4.13-4.04 (m, 1 H), 4.17 (d, J = 4.60 Hz, 1 H), 5.42-5.23 (m, 2 H), 7.39 (d, J= 7.80 Hz, 1 H), 7.57 (d, J = 7.80 Hz, 1 H), 7.69 (d, J = 8.80 Hz, 1 H), 7.83 (s, 1 H), 7.95 (s, 1 H), 8.50 (s, 1 H), 8.80 (s, 1 H). |

-continued

| Example | Structure | Name | LCMS (M + H)$^+$ | HPLC/LCMS Method: RT (min.), Purity | NMR |
|---|---|---|---|---|---|
| 249-I | 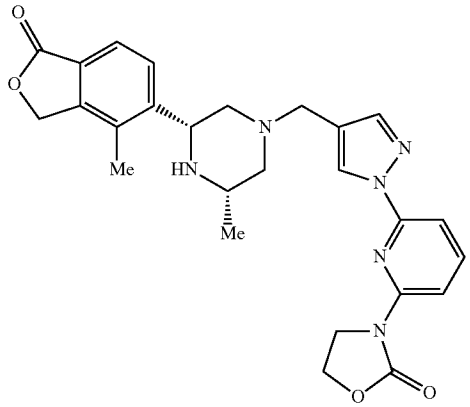 | 3-(6-(4-(((3S,5R)-3-methyl-5-(4-methyl-1-oxo-1,3-dihydroisobenzofuran-5-yl)piperazin-1-yl)methyl)-1H-pyrazol-1-yl)pyridin-2-yl)oxazolidin-2-one | 489.3 | S: 1.41, 93.18% R: 1.01, 94.16% VIII: 5.38, 100% ee | $^1$H NMR (400 MHz, DMSO-$d_6$) δ ppm 1.03 (d, J = 6.10 Hz, 3 H), 1.72-1.75 (m, 2 H), 2.31 (s, 3 H), 2.80 (br. s., 2 H), 2.98 (br. s., 1 H), 3.50-3.48 (m, 2 H), 4.17 (d, J = 9.80 Hz, 1 H), 4.39-4.23 (m, 2 H), 4.61-4.39 (m, 2 H), 5.38 (s, 2 H), 7.59 (dd, J = 7.10, 1.70 Hz, 1 H), 7.66 (d, J = 8.10 Hz, 1 H), 7.74 (s, 1 H), 7.81 (d, J = 8.10 Hz, 1 H), 8.09-7.91 (m, 2 H), 8.47 (s, 1 H), (1 Exchangeable proton not observed). |
| 250-I | 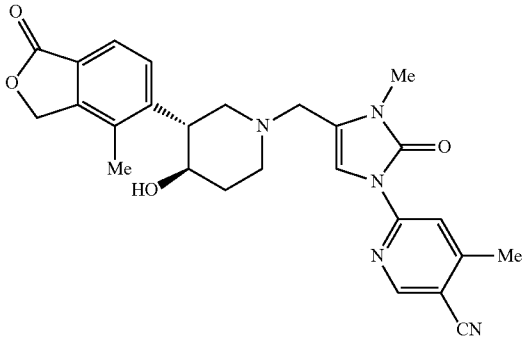 | 6-(4-(((3R,4R)-4-hydroxy-3-(4-methyl-1-oxo-1,3-dihydroisobenzofuran-5-yl)piperidin-1-yl)methyl)-3-methyl-2-oxo-2,3-dihydro-1H-imidazol-1-yl)-4-methylnicotinonitrile | 474.4 | S: 1.44, 100% R: 0.95, 100% VIII: 5.92, 100% ee | $^1$H NMR (400 MHz, DMSO-$d_6$) δ ppm 1.25 (s, 2 H), 1.69-1.54 (m, 1 H), 2.03-1.87 (m, 1 H), 2.11 (t, J = 11.40 Hz, 1 H), 2.31-2.16 (m, 4 H), 2.78 (d, J = 11.00 Hz, 1 H), 2.97 (d, J = 12.50 Hz, 1 H), 3.05 (td, J = 10.40, 3.40 Hz, 1 H), 3.29 (s, 3H), 3.50-3.36 (m, 2 H), 3.81-3.70 (m, 1 H), 4.60 (d, J = 5.40 Hz, 1 H), 5.45-5.24 (m, 2 H), 7.26 (s, 1 H), 7.55 (d, J = 7.80 Hz, 1 H), 7.64 (d, J = 7.80 Hz, 1 H), 8.44 (s, 1 H), 8.76 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 251-I | 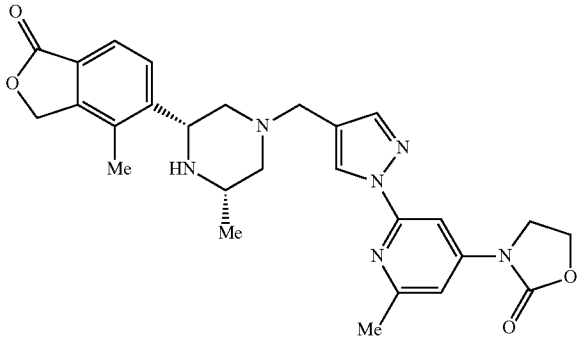 | 3-(2-methyl-6-(4-(((3S,5R)-3-methyl-5-(4-methyl-1-oxo-1,3-dihydroisobenzofuran-5-yl)piperazin-1-yl)methyl)-1H-pyrazol-1-yl)pyridin-4-yl)oxazolidin-2-one | 503.2 | S: .139, 100% R: 0.95, 100% XV: 4.95, 100% ee | $^1$H NMR (400 MHz, DMSO-$d_6$) δ ppm 1.04 (d, J = 4.40 Hz, 3 H), 1.73 (br. s., 2 H), 2.27 (s, 3 H), 2.48 (s, 4 H), 2.81 (d, J = 9.00 Hz, 2 H), 2.98 (br. s., 1 H), 3.52 (br. s., 2 H), 4.26-4.03 (m, 3 H), 4.57-4.44 (m, 2 H), 5.38 (s, 2 H), 7.27 (d, J = 1.70 Hz, 1 H), 7.66 (d, J = 8.10 Hz, 1 H), 7.72 (s, 1 H), 7.80 (d, J = 8.10 Hz, 1 H), 8.06 (s, 1 H), 8.45 (s, 1 H). |
| 252-I | 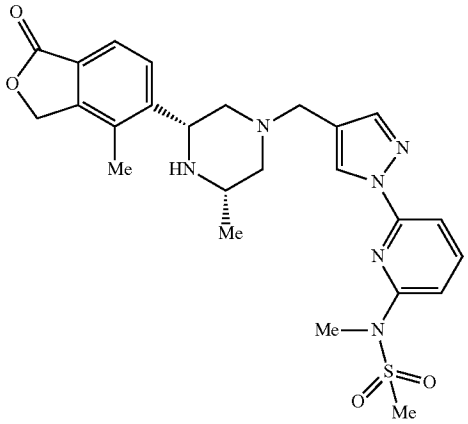 | N-methyl-N-(6-(4-(((3S,5R)-3-methyl-5-(4-methyl-1-oxo-1,3-dihydroisobenzofuran-5-yl)piperazin-1-yl)methyl)-1H-pyrazol-1-yl)pyridin-2-yl)methanesulfonamide | 511.3 | S: 1.42, 97.31% R: 1.00, 97.44% XV: 3.94, 98.52% ee | $^1$H NMR (400 MHz, DMSO-$d_6$) δ ppm 1.03 (d, J = 6.10 Hz, 3 H), 1.73 (br. s., 2 H), 2.26 (s, 3 H), 2.74 (s, 1 H), 2.82 (d, J = 9.80 Hz, 2 H), 2.97 (br. s., 1 H), 3.26-3.22 (m, 3 H), 3.38 (s, 3 H), 3.55-3.46 (m, 2 H), 4.17 (d, J = 8.60 Hz, 1 H), 5.44-5.29 (m, 2 H), 7.33 (d, J = 7.80 Hz, 1 H), 7.70-7.60 (m, 2 H), 7.76 (s, 1 H), 7.81 (d, J - 8.10 Hz, 1 H), 8.04-7.95 (m, 1 H), 8.44 (s, 1 H). |

-continued

| Example | Structure | Name | LCMS (M + H)$^+$ | HPLC/LCMS Method: RT (min.), Purity | NMR |
|---|---|---|---|---|---|
| 253-I | 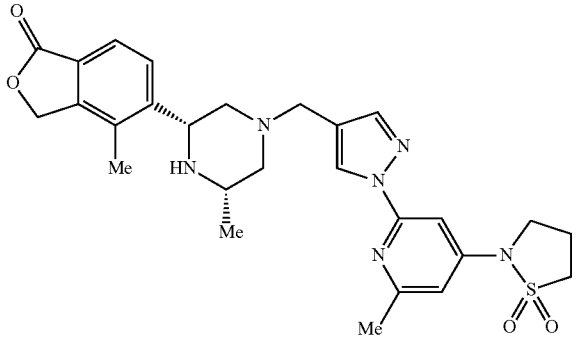 | 5-((2R,6S)-4-((1-(4-(1,1-dioxidoisothiazolidin-2-yl)-6-methylpyridin-2-yl)-1H-pyrazol-4-yl)methyl)-6-methylpiperazin-2-yl)-4-methylisobenzofuran-1(3H)-one | 537.3 | S: 1.41, 96.07% R: 0.99, 97.18% XVII: 8.82, 100% ee | $^1$H NMR (400 MHz, DMSO-$d_6$) δ ppm 1.03 (d, J = 6.40 Hz, 3 H), 1.24-1.20 (s, 2 H), 1.71 (t, J = 10.10 Hz, 2 H), 2.48-2.40 (m, 6 H), 2.80 (d, J = 10.80 Hz, 2 H), 2.97 (br. s., 1 H), 3.56-3.44 (m, 2 H), 3.64 (t, J = 7.20 Hz, 2 H), 3.86 (t, J = 6.60 Hz, 2 H), 4.16 (d, J = 8.80 Hz, 1 H), 5.38 (s, 2 H), 6.87 (d, J = 1.70 Hz, 1 H), 7.52 (d, J - 1.70 Hz, 1 H), 7.64 (d, J = 8.10 Hz, 1 H), 7.70 (s, 1 H), 7.80 (d, J = 8.10 Hz, 1 H), 8.42 (s, 1 H), (1 Exchangeable proton not observed). |
| 254-I | 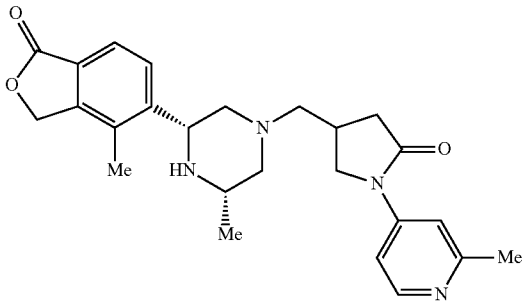 | 1-(2-methoxypyridin-4 -yl)-4-(((3S,5R)-3-methyl-5-(4-methyl-1-oxo-1,3-dihydroisobenzofuran-5-yl)piperazin-1-yl)methyl)pyrrolidin-2-one (Diastereomer-I) | 451.3 | S: .123, 100% R: 0.47, 100% XXV: 7.16, 97.00% ee | $^1$H NMR (400 MHz, DMSO-$d_6$) δ ppm 1.09 (d, J = 4.40 Hz, 3 H), 1.73 (q, J = 10.60 Hz, 2 H), 2.31 (s, 3 H), 2.43-2.32 (m, 3 H), 2.75-2.59 (m, 2 H), 2.81 (t, J = 11.50 Hz, 2 H), 2.96 (br. s., 1 H), 3.55 (dd, J = 9.80, 5.60 Hz, 1 H), 3.87-3.77 (m, 3 H), 3.92 (dd, J = 9.70, 7.70 Hz, 1 H), 4.15 (d, J = 8.60 Hz, 1 H), 5.48-5.30 (m, 2 H), 7.05 (d, J = 1.50 Hz, 1 H), 7.36 (dd, J = 6.00, 1.80 Hz, 1 H), 7.66 (d, J = 7.80 Hz, 1 H), 7.82 (d, J = 7.80 Hz, 1 H), 8.08 (d, J = 5.90 Hz, 1 H), (1 Exchangeable proton not observed). |
| 255-I | 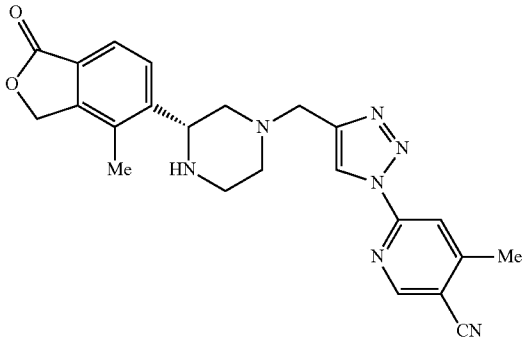 | (R)-4-methoxy-6-(4-((3-(4-methyl-1-oxo-1,3-dihydroisobenzofuran-5-yl)piperazin-1-yl)methyl)-1H-1,2,3-triazol-1-yl)nicotinonitrile | 446.2 | G: 12.33, 99.40% E: 10.51, 98.80% XVIII: 20.06, 100% ee | $^1$H NMR (400 MHz, DMSO-$d_6$) δ ppm 1.84-1.94 (m, 1 H), 2.13-2.22 (m, 1 H), 2.26 (s, 3 H), 2.78-2.92 (m, 3 H), 2.93-3.01 (m, 1 H), 3.74 (s, 2 H), 4.03-4.09 (m, 1 H), 4.16 (s, 3 H), 5.37 (s, 2 H), 7.64 (d, J = 8.03 Hz, 1 H), 7.76 (d, J = 8.03 Hz, 1 H), 7.88 (s, 1 H), 8.77 (s, 1 H), 8.88 (s, 1 H), (1 Exchangeable proton not observed). |

-continued

| Example | Structure | Name | LCMS $(M + H)^+$ | HPLC/LCMS Method: RT (min.), Purity | NMR |
|---|---|---|---|---|---|
| 256-II | 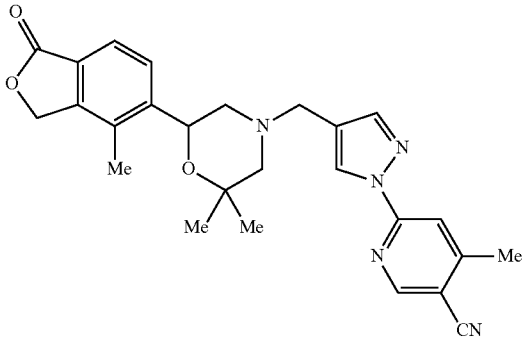 | 6-(4-((2,2-dimethyl-6-(4-methyl-1-oxo-1,3-dihydroisobenzofuran-5 -yl)morpholino)methyl)-1H-pyrazol-1-yl)-4-methylnicotinonitrile (Enantiomer-II) | 458.0 | G: 14.03, 95.39% C: 12.55, 95.71% XIII: 3.82, 95.27% ee | $^1$H NMR (300 MHz, DMSO-$d_6$) δ ppm 12.0 (s, 3 H), 1.41 (s, 3 H), 1.67-1.77 (m, 1 H), 1.87-1.93 (m, 1 H), 2.26 (s, 3 H), 2.60 (s, 3 H), 2.69-2.72 (m, 1 H), 2.93-2.96 (m, 1 H), 3.42-3.67 (m, 2 H), 5.08 (d, J = 8.69 Hz, 1 H), 5.38 (s, 2 H), 7.64 (q, J = 7.93 Hz, 2 H), 7.87 (d, J = 2.40 Hz, 1 H), 7.99 (s, 1 H), 8.55 (d, J = 2.40 Hz, 1 H), 8.84 (s, 1 H). |
| 257-I | 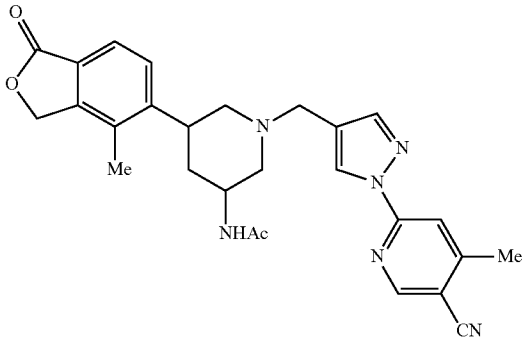 | N-(1-((1-(5-cyano-4-mehtylpyridin-2-yl)-1H-pyrazol-4-yl)methyl)-5-(4-methyl-1-oxo-1,3-dihydroisobenzofuran-5-yl)piperidin-3-yl)acetamide (Enantiomer-I) | 485.1 | R: 1.08, 100% S: 1.43, 100% XXI: 2.38, 100% ee. | $^1$H NMR (400 MHz, DMSO-$d_6$) δ ppm 1.47-1.37 (m, 1 H), 1.79 (s, 3 H), 1.88 (d, J = 12.00 Hz, 1 H), 1.98 (t, J = 10.90 Hz, 1 H), 2.26 (s, 3 H), 2.59 (s, 3 H), 2.86 (d, J = 11.00 Hz, 1 H), 3.02 (br. s., 1 H), 3.21 (s, 1 H), 3.61 (s, 2 H), 3.93 (s, 1 H), 5.38 (s, 2 H), 7.42 (d, J = 8.10 Hz, 1 H), 7.66 (d, J = 8.30 Hz, 1 H), 7.81 (d, J = 7.60 Hz, 1 H), 7.87 (s, 1 H), 8.00 (s, 1 H), 8.55 (s, 1 H), 8.84 (s, 1 H), (1 Exchangeable proton not observed). |

-continued

| Example | Structure | Name | LCMS (M + H)$^+$ | HPLC/LCMS Method: RT (min.), Purity | NMR |
|---|---|---|---|---|---|
| 258-I | 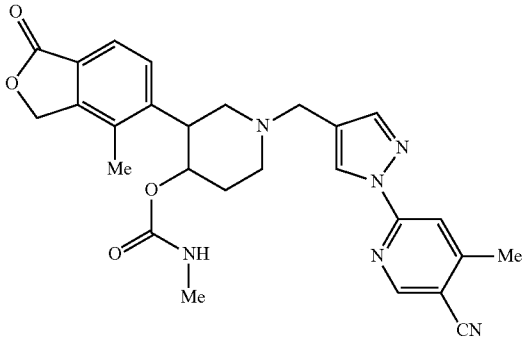 | 1-((1-(5-cyano-4-methylpyridin-2-yl)-1H-pyrazol-4-yl)methyl)-3-(4-methyl-1-oxo-1,3-dihydroisobenzofuran-5-yl)piperidin-4-yl methylcarbamate (Enantiomer-I) | 501.5 | R: 1.10, 95.00% S: 1.55, 96.00% XXII: 6.23, 94.05% ee | $^1$H NMR (400 MHz, DMSO-$d_6$) δ ppm 1.66 (d, J = 11.70 Hz, 1 H), 2.20-1.99 (m, 2 H), 2.33-2.23 (m, 4 H), 2.42 (d, J = 4.60 Hz, 3 H), 2.58 (s, 3 H), 2.84 (d, J = 9.50 Hz, 1 H), 2.97 (d, J = 11.00 Hz, 1 H), 3.50-3.68 (m, 2 H), 5.00-4.75 (m, 1 H), 5.36 (s, 2 H), 6.73 (d, J = 4.40 Hz, 1 H), 7.52 (d, J = 7.80 Hz, 1 H), 7.64 (d, J = 8.10 Hz, 1 H), 7.87 (s, 1 H), 7.99 (s, 1 H), 8.54 (s, 1 H), 8.83 (s, 1 H), (1 Exchangeable proton not observed). |
| 259-I | 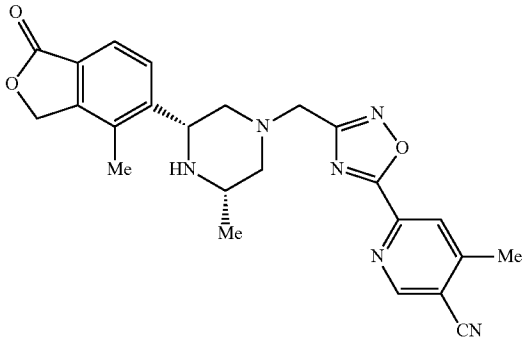 | 4-methyl-6-(3-(((3S,5R)-3-methyl-5-(4-methyl-1-oxo-1,3-dihydroisobenzofuran-5-yl)piperazin-1-yl)methyl)-1,2,4-oxadiazol-5-yl)nicotinonitrile | 445.2 | R: 1.05, 100% S: 1.35, 99.10% | $^1$H NMR (400 MHz, DMSO-$d_6$) δ ppm 1.12-0.93 (m, 3 H), 1.94 (dt, J = 17.20, 10.40 Hz, 2 H), 2.23-2.34 (m, 3 H), 2.68-2.60 (m, 3 H), 2.88 (t, J = 12.00 Hz, 2 H), 3.05-2.93 (m, 1 H), 3.84 (s, 2 H), 4.17 (d, J = 8.10 Hz, 1 H), 5.47-5.32 (m, 2 H), 7.66 (d, J = 7.80 Hz, 1 H), 7.80 (d, J = 8.10 Hz, 1 H), 8.40 (s, 1 H), 8.74 (br. s., 1 H), 9.15 (s, 1 H). |

-continued

| Example | Structure | Name | LCMS $(M + H)^+$ | HPLC/LCMS Method: RT (min.), Purity | NMR |
|---|---|---|---|---|---|
| 260-I | 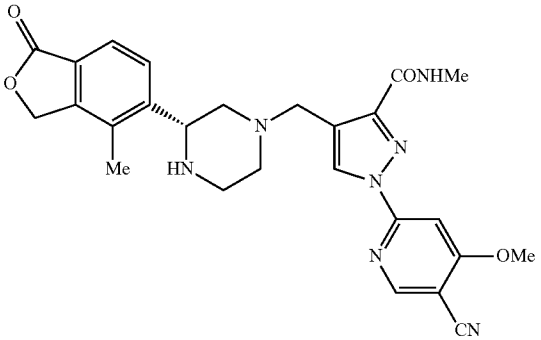 | (R)-1-(5-cyano-4-methoxypyridin-2-yl)-N-methyl-4-((3-(4-methyl-1-oxo-1,3-dihydroisobenzofuran-5-yl)piperazin-1-yl)methyl)-1H-pyraozl-3-carboxamide | 502.2 | R: 0.94, 100% S: 1.22, 98.74% XIV: 9.16, 98.74% ee | $^1$H NMR (400 MHz, DMSO-$d_6$) δ ppm 1.95 (br. s., 1 H), 2.21 (b.r s., 1 H), 2.27 (s, 4 H), 2.96-2.77 (m, 6 H), 3.04 (br. s., 1 H), 3.76 (br. s., 2 H), 4.14 (s, 3 H), 5.42-5.33 (m, 2 H), 7.67 (d, J = 7.30 Hz, 1 H), 7.73 (s, 1 H), 7.77 (d, J = 8.30 Hz, 1 H), 8.60 (s, 1 H), 8.78 (s, 1 H), 9.17 (br. s., 1 H), (1 Exchangeable proton not observed). |
| 261-II | 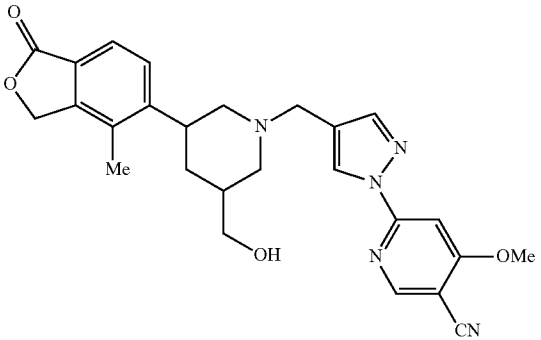 | 6-(4-((3-(hydroxymethyl)-5-(4-methyl-1-oxo-1,3-dihydroisobenzofuran-5-yl)piperidin-1-yl)methyl)-1H-pyrazol-1-yl)-4-methylnicotinonitrile (Diastereomer-II: Enantiomer-II) | 458.2 | R: 1.08, 100% S: 1.44, 100% XXVII: 4.90, 100% ee. | $^1$H NMR (400 MHz, DMSO-$d_6$) δ ppm 1.64-1.45 (m, 1 H), 1.78 (d, J = 12.20 Hz, 1 H), 2.14 (br. s., 1 H), 2.28 (s, 3 H), 2.59-2.54 (m, 1 H), 2.61 (s, 3 H), 3.11 (d, J = 7.60 Hz, 1H), 3.37-3.28 (m, 2 H), 3.56-3.46 (m, 1 H), 3.37-3.43 (m, 2 H), 4.39 (br. s., 2 H), 4.88 (br. s., 1 H), 5.41 (s, 2 H), 7.53 (d, J= 8.10 Hz, 1H), 7.73 (d, J = 8.10 Hz, 1 H), 8.06 (s, 2 H), 9.01-8.86 (m, 2 H). |

-continued

| Example | Structure | Name | LCMS (M + H)$^+$ | HPLC/LCMS Method: RT (min.), Purity | NMR |
|---|---|---|---|---|---|
| 262-I | 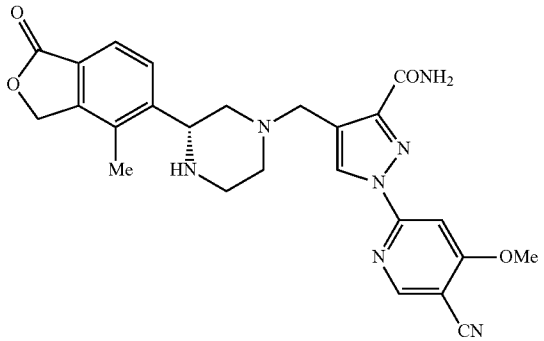 | (R)-1-(5-cyano-4-methoxypyridin-2-yl)-4-((3-(4-methyl-1-oxo-1,3-dihydroisobenzofuran-5-yl)piperazin-1-yl)methyl)-1H-pyrazole-3-carboxamide | 488.2 | R: 0.86, 100% S: 1.13, 100% XIV: 9.31, 100% ee | $^1$H NMR (400 MHz, DMSO-$d_6$) δ ppm 2.34 (s, 4 H), 2.93 (dd, J = 12.20, 6.40 Hz, 1 H), 3.11 (d, J = 11.70 Hz, 2 H), 3.97 (br. s., 2 H), 4.13 (s, 3 H), 4.74 (br. s., 1 H), 5.57-5.28 (m, 2 H, 7.56 (br. s., 1 H), 7.72 (d, J = 8.10 Hz, 1 H), 7.83 (d, J = 7.80 Hz, 1 H), 7.89 (s, 1 H), 8.11 (br. s., 1 H), 8.65 (br. s., 1 H), 8.79 (s, 1 H), 8.87 (br. s., 1 H), 9.37 (br.s., 1 H), (1 Exchangeable proton not observed). |
| 263-I | 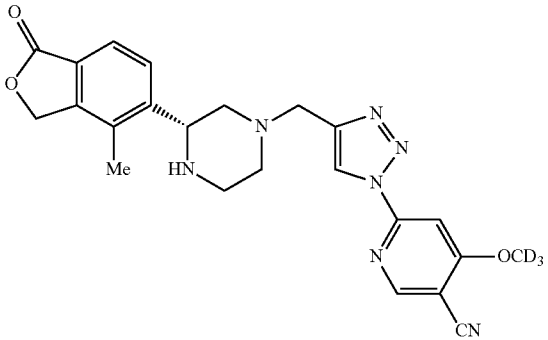 | (R)-4-(methoxy-d3)-6-(4-((3-(4-methyl-1-oxo-1,3-dihydroisobenzofuran-5-yl)piperazin-1-yl)methyl)-1H-1,2,3-triazol-1-yl)nicotinonitrile | 449.2 | R: 0.95, 100%, S: 1.3, 98.70% | $^1$H NMR (400 MHz, DMSO-$d_6$) δ ppm 1.91 (s, 1 H), 2.27 (s, 3 H), 2.45 (br. s., 1 H), 2.86 (br. s., 3 H), 3.00 (br. s., 1 H), 3.76 (s, 2 H), 4.12 (br. s., 1 H), 5.44-5.31 (m, 2 H), 7.66 (d, J = 8.10 Hz, 1 H), 7.76 (d, J = 8.30 Hz, 1 H), 7.88 (s, 1 H), 8.78 (s, 1 H), 8.88 (s, 1 H), (1 Exchangeable proton not observed). |
| 264-I | 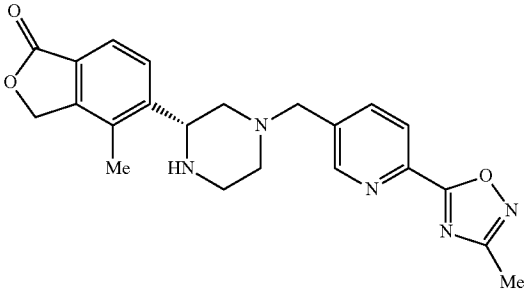 | (R)-4-methyl-5-(4-((6-(3-methyl-1,2,4-oxadiazol-5-yl)pyridin-3-yl)methyl)piperazin-2-yl)isobenzofuran-1(3H)-one | 406.2 | R: 0.85, 98.08% S: 1.07, 100% | $^1$H NMR (400 MHz, DMSO-$d_6$) δ ppm 1.99 (br. S., 1 H), 2.25 (s, 4 H), 2.45 (s, 3 H), 2.81 (t, J = 12.80 Hz, 2 H), 3.11-2.95 (m, 2 H), 3.63-3.78 - (m, 2 H), 4.20 (br.s., 1 H), 5.44-5.30 (m, 2 H), 7.68 (d, J = 7.60 Hz, 1 H), 7.78 (d, J = 8.10 Hz, 1 H), 8.03 (dd, J = 8.10, 2.00 Hz, 1 H), 8.20 (d, J= 8.10 Hz, 1 H), 8.75 (d, J = 1.50 Hz, 1 H), (1 Exchangeable proton not observed). |

-continued
| Example | Structure | Name | LCMS $(M + H)^+$ | HPLC/LCMS Method: RT (min.), Purity | NMR |
|---|---|---|---|---|---|
| 265-I | 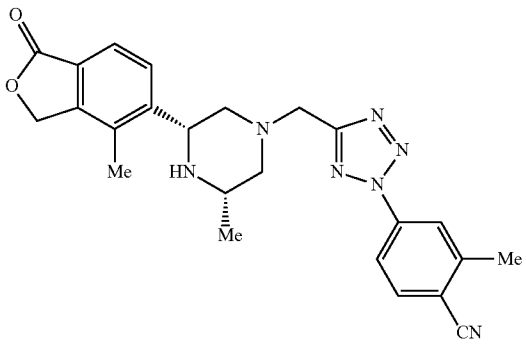 | 2-methyl-4-(5-(((3S,5R)-3-methyl-5-(4-methyl-1-oxo-1,3-dihydroisobenzofuran-5-yl)piperazin-1-yl)methyl)-2H-tetrazol-2-yl)benzonitrile | 444.2 | R: 1.23, 97.88% S: 1.63, 100% VIII: 4.75, 98.84% ee | $^1$H NMR (400 MHz, DMSO-$d_6$) δ ppm 1.03 (d, J = 5.90 Hz, 3 H), 2.00-1.78 (m, 2 H), 2.32-2.21 (m, 3 H), 2.66-2.56 (m, 3 H), 3.05-2.79 (m, 3 H), 4.04-3.86 (m, 2 H), 4.17 (d, J = 2.7 Hz, 1 H), 5.39 (s, 2 H), 7.66 (d, J = 7.80 Hz, 1 H), 7.79 (d, J = 8.10 Hz, 1 H), 8.15-7.99 (m, 2 H), 8.23 (s, 1 H), (1 Exchangeable proton not observed). |

Intermediate 193: 6-(5-formylisoxazol-3-yl)-4-methoxynicotinonitrile

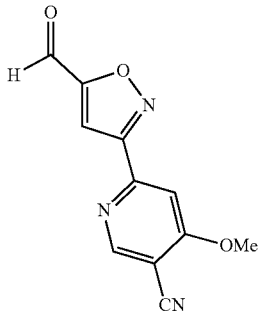

Intermediate 193A: methyl 5-cyano-4-methoxypicolinate

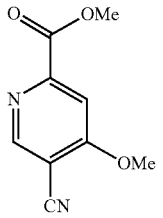

Intermediate 193A was prepared (6.00 g, 52.60%) as an off-white solid, by using a similar synthetic protocol as that of Intermediate 16A and starting from 6-chloro-4-methoxynicotinonitrile (10.00 g, 59.30 mmol). $^1$H NMR (400 MHz, DMSO-$d_6$) δ ppm 3.93 (s, 3H), 4.11 (s, 3H), 7.82 (s, 1H), 8.94 (s, 1H). LCMS (Method-I): retention time 0.79 min, [M+H] 192.9.

Intermediate 193B: 6-(hydroxymethyl)-4-methoxynicotinonitrile

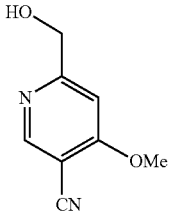

To a stirred solution of methyl 5-cyano-4-methoxypicolinate (3.00 g, 15.61 mmol) in a mixture of THF (50 mL) and EtOH (50 mL) was added calcium chloride (4.33 g, 39.00 mmol) followed by $NaBH_4$ (2.36 g, 62.40 mmol) and the resulting reaction mixture was stirred at ambient temperature for 16 h. The reaction mixture was concentrated to dryness under reduced pressure, diluted with saturated solution of $NaHCO_3$ (100 mL) and extracted with ethyl acetate (3×100 mL). The combined organic layer was washed with brine (50 mL), dried over anhydrous sodium sulfate and evaporated under reduced pressure to obtain Intermediate 193B (1.80 g, 70.20%) as an off-white solid. $^1$H NMR (400 MHz, DMSO-$d_6$) δ ppm 4.02 (s, 3H), 4.60 (d, J=3.00 Hz, 2H), 5.72 (t, J=3.50 Hz, 1H), 7.30 (s, 1H), 8.71 (s, 1H). LCMS (Method-I): retention time 0.56 min, [M+H] 164.9.

Intermediate 193C: 6-formyl-4-methoxynicotinonitrile

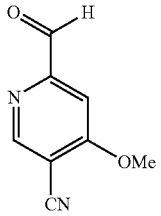

Intermediate 193C was prepared (1.70 g, 96.00%) as an off-white solid, by using a similar synthetic protocol as that of Intermediate 9 and starting from Intermediate 193B (1.80 g, 10.96 mmol) and Dess-Martin periodinane (6.98 g, 16.45 mmol). $^1$H NMR (400 MHz, DMSO-$d_6$) δ ppm 4.12 (s, 3H), 7.70 (s, 1H), 9.06 (s, 1H), 9.99 (s, 1H). LCMS: The compound did not ionize well.

Intermediate 193D: (E)-6-((hydroxyimino)methyl)-4-methoxynicotinonitrile

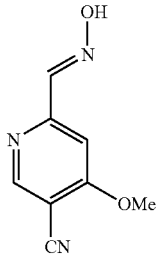

Intermediate 193D was prepared (0.90 g, 78.00%) as an off-white solid, by using a similar synthetic protocol as that of Intermediate 110B and starting from Intermediate 193C (1.05 g, 6.48 mmol) and hydroxylamine hydrochloride (0.54 g, 7.77 mmol). $^1$H NMR (400 MHz, DMSO-$d_6$) δ ppm 4.04 (s, 3H), 7.50 (s, 1H), 8.11 (s, 1H), 8.81 (s, 1H), 12.14 (s, 1H). LCMS (Method-I): retention time 0.73 min, [M+H] 177.9.

Intermediate 193E: 6-(5-(hydroxymethyl)isoxazol-3-yl)-4-methoxynicotinonitrile

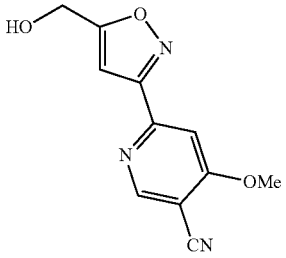

Intermediate 193E was prepared (0.15 g, 25.50%) as an off-white solid, by using a similar synthetic protocol as that of Intermediate 110C and starting from Intermediate 193D (0.77 g, 3.75 mmol) and prop-2-yn-1-ol (0.14 g, 2.54 mmol). $^1$H NMR (400 MHz, DMSO-$d_6$) δ ppm 4.12 (s, 3H), 4.66 (d, J=5.00 Hz, 2H), 5.77 (t, J=5.00 Hz, 1H), 6.97 (s, 1H), 7.79 (s, 1H), 8.95 (s, 1H). LCMS (Method-I): retention time 0.84 min, [M+H] 232.0.

Intermediate 193

Intermediate 193 was prepared (0.17 g, 90.00%) as an off-white solid, by using a similar synthetic protocol as that of Intermediate 9 and starting from Intermediate 193E (0.19 g, 0.82 mmol) and Dess-Martin periodinane (0.52 g, 1.23 mmol). $^1$H NMR (400 MHz, DMSO-$d_6$) δ ppm 4.12 (s, 3H), 7.94 (s, 1H), 8.16 (s, 1H), 9.00 (s, 1H), 9.99 (s, 1H). LCMS: The compound did not ionize well.

Intermediate 194: 2-(1-(difluoromethyl)-2-oxo-1,2-dihydropyridin-4-yl)-2H-1,2,3-triazole-4-carbaldehyde

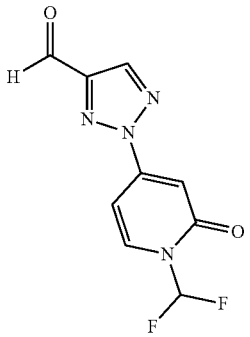

Intermediate 194A: 1-(difluoromethyl)-4-(4-(hydroxymethyl)-2H-1,2,3-triazol-2-yl)pyridin-2(1H)-one

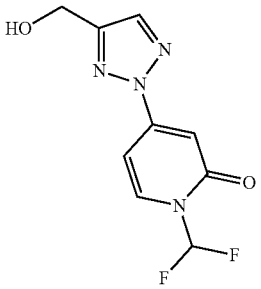

Intermediate 194A was prepared (0.20 g, 61.70%) as an of-white solid, by using a similar synthetic protocol as that of Intermediate 42 and starting from Intermediate 28A (0.13 g, 1.33 mmol) and Intermediate 58A (0.30 g, 1.33 mmol). $^1$H NMR (400 MHz, DMSO-$d_6$) δ ppm 4.62 (d, J=5.52 Hz, 2H), 5.42 (s, 1H), 7.14 (d, J=2.01 Hz, 1H), 7.16-7.21 (m, 1H), 7.85-8.04 (m, 1H), 8.07 (d, J=7.53 Hz, 1H), 8.91 (s, 1H). $^{19}$F NMR (400 MHz, DMSO-$d_6$) δ ppm -101.0. LCMS (Method-D): retention time 0.54 min, [M+H] 243.0.

Intermediate 194

Intermediate 194 was prepared (0.08 g, 40.40%), by using a similar synthetic protocol as that of Intermediate 9 and starting from Intermediate 194A (0.20 g, 0.82 mmol) and Dess-Martin periodinane (0.70 g, 1.65 mmol). $^1$H NMR (400 MHz, DMSO-$d_6$) δ ppm 7.16-7.23 (m, 1H), 7.24-7.27 (m, 1H), 7.70-8.07 (m, 1H), 8.12-8.18 (m, 1H), 9.76 (s, 1H), 10.13 (s, 1H). LCMS (Method-7): retention time 0.98 min, [M+H] 241.0.

Intermediate 195: 1-(2-(difluoromethyl)pyrimidin-4-yl)-1H-imidazole-4-carbaldehyde

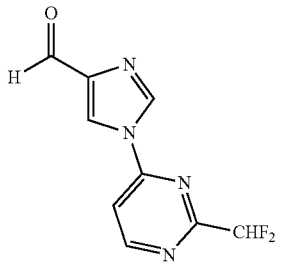

Intermediate 195A: 4-chloropyrimidine-2-carbaldehyde

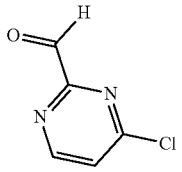

To a stirred solution of 4-chloropyrimidine-2-carbonitrile (0.25 g, 1.79 mmol) in THF (5 mL) was added 1M DIBAL-H in heptane (1.79 mL, 1.79 mmol) at −78° C. and the resulting reaction mixture was stirred at ambient temperature for 3 h. The reaction mixture was diluted with a saturated solution of $NH_4Cl$ (20 mL) and extracted with 10% MeOH in DCM (2×30 mL). The combined organic layers were washed with brine (20 mL), dried over anhydrous sodium sulfate and evaporated under reduced pressure to obtain Intermediate 195A (0.100 g, crude). LCMS (Method-D): retention time 0.42 min [M+H] 143.2. The compound was taken directly to the subsequent step without further purification or characterization.

Intermediate 195B: 4-chloro-2-(difluoromethyl)pyrimidine

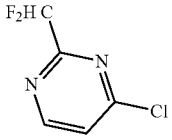

Intermediate 195B was prepared (0.80 g, 36.70%), by using a similar synthetic protocol as that of Intermediate 4B and starting from Intermediate 195A (1.70 g, 11.93 mmol) and DAST (3.15 mL, 23.85 mmol). $^1$H NMR (300 MHz, $CDCl_3$) δ ppm 6.44-6.80 (m, 1H), 7.49 (d, J=5.40 Hz, 1H), 8.76 (d, J=5.40 Hz, 1H). $^9$F NMR (400 MHz, DMSO-$d_6$) δ ppm −118.95. The compound did not ionize well.

Intermediate 195

To a stirring solution of Intermediate 195B (0.01 g, 0.06 mmol) in 1,4-Dioxane (5 mL) was added $K_2CO_3$ (0.02 g, 0.122 mmol) followed by 1H-imidazole-4-carbaldehyde (0.01 g, 0.09 mmol) and the resulting reaction mixture was stirred at 80° C. for 12 h. The reaction mixture was cooled to ambient temperature, filtered through Celite® and washed with ethyl acetate (10 mL). The filtrate was evaporated under reduced pressure to obtain Intermediate 195 (0.005 g, 36.70%). LCMS (Method-D): retention time 0.92 min, [M+H] 225.2. $^1$H NMR (400 MHz, $CDCl_3$) δ ppm 6.54-6.81 (m, 1H), 7.51 (m, 1H), 8.40 (d, J=1.6 Hz, 1H), 8.58 (d, J=1.2 Hz, 1H), 9.02 (d, J=5.6 Hz, 1H), 10.01 (s, 1H). $^{19}$F NMR (400 MHz, DMSO-$d_6$) δ ppm -119.25.

Intermediate 196: 4-(5-formyl-2H-tetrazol-2-yl)-2-methoxybenzonitrile

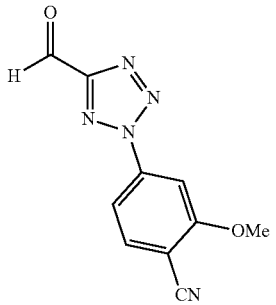

Intermediate 196A: ethyl 2-(4-cyano-3-methoxyphenyl)-2H-tetrazole-5-carboxylate

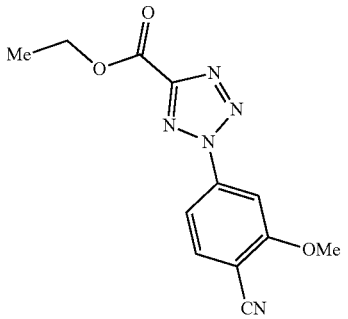

Intermediate 196A was prepared (0.15 g, 7.71%) as a brown solid, by using a similar synthetic protocol as that of Intermediate 191A and starting from 4-amino-2-methoxybenzonitrile (1.00 g, 6.75 mmol). $^1$H NMR (400 MHz, $CDCl_3$) δ ppm 1.48-1.52 (t, J=6.80 Hz, 3H), 4.09 (s, 3H), 4.56-4.62 (m, 2H), 7.79 (d, J=8.40 Hz, 1H), 7.85 (d, J=1.60 Hz, 1H), 7.91-7.94 (m, 1H). LCMS (Method-I) retention time 1.60 min, [M+H] 274.2.

Intermediate 196B: 4-(5-(hydroxymethyl)-2H-tetrazol-2-yl)-2-methoxybenzonitrile

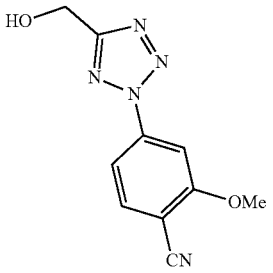

Intermediate 196B was prepared (0.06 g, 54.50%), by using a similar synthetic protocol as that of Intermediate 60B and starting Intermediate 196A (0.13 g, 0.48 mmol) and $NaBH_4$ (0.07 g, 1.90 mmol). $^1$H NMR (300 MHz, DMSO-$d_6$) δ ppm 4.07 (s, 3H), 4.82 (d, J=7.20 Hz, 2H), 5.84 (t, J=8.00 Hz, 1H), 7.80-7.86 (m, 2H), 8.06 (m, 1H). LCMS (Method-I) retention time 1.52 min, [M+H] 232.2.

Intermediate 196

Intermediate 196 was prepared (0.95 g, crude), by using a similar synthetic protocol as that of Intermediate 9 and starting from Intermediate 196B (0.10 g, 0.43 mmol) and Dess-Martin periodinane (0.37 g, 0.86 mmol). LCMS (Method-I): retention time 1.29 min, [M−H]228.2. The compound was taken directly to the subsequent step without further purification or characterization.

Intermediate 197: (1-(5-cyano-4-methoxypyridin-2-yl)-3-methyl-2-oxoimidazolidin-4-yl) methyl methanesulfonate

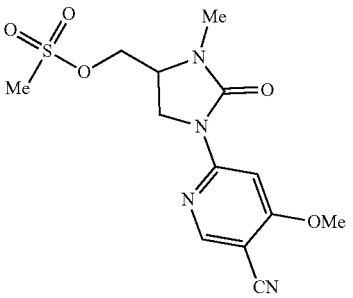

Intermediate 197A: 6-(4-(hydroxymethyl)-3-methyl-2-oxoimidazolidin-1-yl)-4-methoxynicotinonitrile

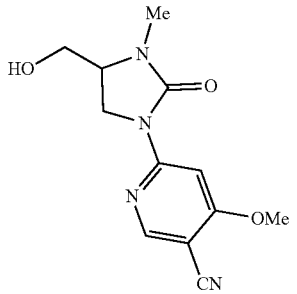

A solution of Intermediate 93C (0.50 g, 1.92 mmol) in ethyl acetate (20 mL) was purged with nitrogen for 2 minutes. 10% Pd/C (0.10 g, 0.96 mmol) was added and reaction mixture was stirred at ambient temperature for 20 h under $H_2$ atmosphere. The reaction mixture was filtered through Celite® and filtrate was concentrated under vacuum to obtain Intermediate 197A (0.25 g, 47.10%) as an off-white solid. $^1$H NMR (400 MHz, DMSO-$d_6$) δ ppm 2.83 (s, 3H), 3.46-3.53 (m, 1H), 3.62-3.73 (m, 2H), 3.79 (dd, J=10.79, 5.27 Hz, 1H), 3.93 (s, 3H), 3.97-4.04 (m, 1H), 4.98 (t, J=5.52 Hz, 1H), 8.06 (s, 1H), 8.54 (s, 1H). LCMS (Method-D): retention time 1.22 min, [M+H] 263.2.

Intermediate 197

Intermediate 197 was prepared (0.24 g, 81.00%) as a pale yellow solid, by using a similar synthetic protocol as that of Intermediate 59 and starting from Intermediate 197A (0.20 g, 0.76 mmol) and mesyl chloride (0.07 mL, 0.91 mmol). $^1$H NMR (400 MHz, DMSO-$d_6$) δ ppm 2.87 (s, 3H), 3.24 (s, 3H), 3.80 (dd, J=10.79, 4.77 Hz, 1H), 3.94 (s, 3H), 4.02-4.09 (m, 1H), 4.10-4.16 (m, 1H), 4.36 (dd, J=11.04, 3.51 Hz, 1H), 4.50 (dd, J=11.04, 3.01 Hz, 1H), 8.04 (s, 1H), 8.56 (s, 1H). LCMS (Method-D): retention time 1.69 min, [M+H] 340.9.

Intermediate 198: 1-methyl-5-(((3S,5R)-3-methyl-5-(4-methyl-1-oxo-1,3-dihydroisobenzofuran-5-yl) piperazin-1-yl)methyl)-1,3-dihydro-2H-imidazol-2-one TFA salt

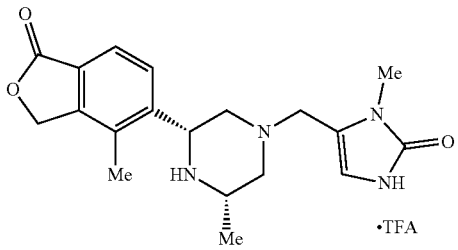

Intermediate 198A: 1-(tert-butyl) 4-methyl 3-methyl-2-oxo-2,3-dihydro-1H-imidazole-1,4-di-carboxylate

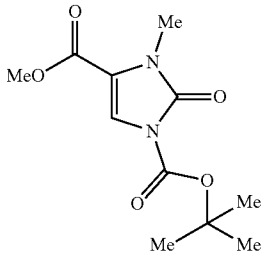

To a stirred solution of methyl 2-oxo-2,3-dihydro-1H-imidazole-4-carboxylate (5.00 g, 35.20 mmol) in MeCN (25 mL) was added $K_2CO_3$ (4.86 g, 35.20 mmol) followed by $BOC_2O$ (8.17 mL, 35.2 mmol) at 0° C. and the resulting reaction mixture was stirred at ambient temperature for 14 h. The reaction mixture was diluted with MeCN (50 mL) and $K_2CO_3$ (14.55 g, 105.00 mmol), iodomethane (6.58 mL, 105.00 mmol) was added and the resulting reaction mixture was stirred at ambient temperature for additional 14 h. The reaction mixture was filtered through Celite® and the filtrate was concentrated under reduced pressure. The residue was purified by column chromatography (Redisep—40 g, 10-20% EtOAc/n-hexane) to obtain Intermediate 198A (3.70 g, 41.10%) as a white solid. $^1$H NMR (400 MHz, DMSO-$d_6$) δ ppm 1.53 (s, 9H), 3.30 (s, 3H), 3.79 (s, 3H), 7.40 (s, 1H). LCMS (Method-O): retention time 1.17 min, [M−55] 201.2.

Intermediate 198B: methyl 3-methyl-2-oxo-2,3-dihydro-1H-imidazole-4-carboxylate TFA salt

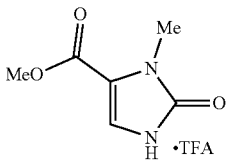

To a stirred solution of Intermediate 198A (3.70 g, 14.44 mmol) in DCM (20 mL) at 0° C. was added TFA (10 mL, 130 mmol) and the resulting mixture was stirred at ambient temperature for 2 h. The reaction mixture was concentrated under reduced pressure. The residue was dissolved in diethyl ether (50 mL) and the solid precipitate was filtered and dried under vacuum to obtain Intermediate 198B (0.22 g, 98.00%). $^1$H NMR (400 MHz, DMSO-$d_6$) δ ppm 3.30 (s, 3H), 3.37 (s, 3H), 5.33 (br. s., 1H), 7.38 (s, 1H), 10.96 (br. s., 1H). LCMS (Method-O): retention time 0.16 min, [M+H] 156.9 Intermediate 198C: methyl 3-methyl-2-oxo-1-trityl-2, 3-dihydro-1H-imidazole-4-carboxylate

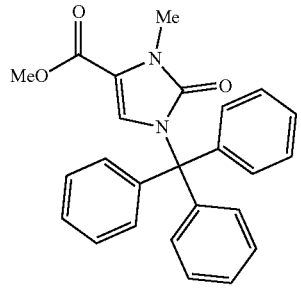

Intermediate 198C was prepared (2.90 g, 56.80%) as a white solid, by using a similar synthetic protocol as that of Intermediate 75A and starting from Intermediate 198B (2.00 g, 12.81 mmol) and trityl chloride (4.29 g, 15.37 mmol). $^1$H NMR (400 MHz, DMSO-$d_6$) δ ppm 3.27 (s, 3H), 3.69 (s, 3H), 7.11-7.40 (m, 16H). LCMS (Method-D): retention time 3.28 min, [M+H] 399.2.

Intermediate 198D: 4-(hydroxymethyl)-3-methyl-1-trityl-1,3-dihydro-2H-imidazol-2-one

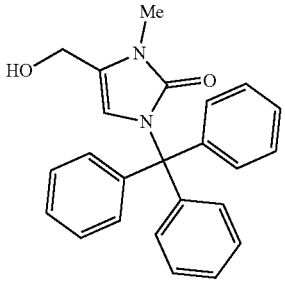

To a stirred solution of Intermediate 198C (5.00 g, 12.55 mmol) in THF (40 mL) was added 2M solution of $LiBH_4$ in THF (18.82 mL, 37.6 mmol) at 0° C. and the resulting reaction mixture was stirred at ambient temperature for 14 h. The reaction mixture was diluted with water (50 mL) and extracted with ethyl acetate (3×50 mL). The combined organic layers were washed with brine (50 mL), dried over anhydrous sodium sulfate and evaporated under reduced pressure. The residue was purified by column chromatography (Redisep—40 g, 50-80% EtOAc/n-hexane) to obtain Intermediate 198D (3.30 g, 71.00%) as a white solid. $^1$H NMR (400 MHz, DMSO-$d_6$) δ ppm 3.06 (s, 3H), 4.21 (d, J=6.80, 2H), 5.03 (t, J=14.00, 1H), 6.07 (s, 1H), 7.09-7.17 (m, 6H), 7.22-7.37 (m, 9H). LCMS (Method-D): retention time 2.42 min, [M+H] 371.2.

Intermediate 198E: (3-methyl-2-oxo-1-trityl-2,3-dihydro-1H-imidazol-4-yl)methyl methanesulfonate

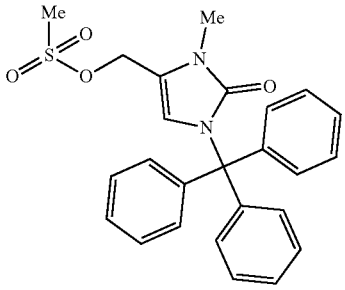

Intermediate 198E was prepared (1.40 g 99.17%), by using a similar synthetic protocol as that of Intermediate 59 and starting from Intermediate 198D (2.00 g, 5.40 mmol) and mesyl-Cl (0.50 mL, 6.48 mmol). $^1$H NMR (400 MHz, DMSO-$d_6$) δ ppm 3.04-3.13 (s, 3H), 3.16-3.28 (s, 3H), 4.38 (s, 2H), 6.67 (s, 1H), 7.20-7.38 (m, 15H). LCMS: The compound did not ionize well.

Intermediate 198F-I: 3-methyl-4-(((3S,5R)-3-methyl-5-(4-methyl-1-oxo-1,3-dihydroisobenzofuran-5-yl)piperazin-1-yl)methyl)-1-trityl-1,3-dihydro-2H-imidazol-2-one

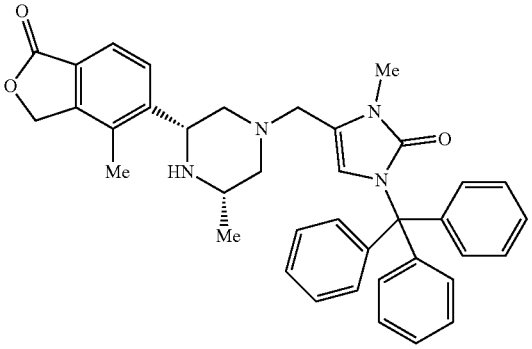

To a stirred solution of Intermediate 51-I (0.50 g, 2.02 mmol) in MeCN (40 mL) was added Intermediate 198E (0.70 g, 1.56 mmol), sodium iodide (0.234 g, 1.561 mmol), $K_2CO_3$ (0.647 g, 4.68 mmol) followed by 4-methyl-1H-imidazole (0.18 g, 2.21 mmol) and the resulting mixture was heated at 65° C. for 4 h. The reaction mixture was cooled to ambient temperature, filtered through Celite® and the filtrate was evaporated under reduced pressure. The residue was purified by column chromatography (Redisep—40 g, 5-10% MeOH/$CHCl_3$) to obtain Intermediate 198F-I (0.30 g, 32.10%). $^1$H NMR (400 MHz, DMSO-$d_6$) δ ppm 0.98-1.11 (m, 3H), 2.16-2.28 (m, 3H), 2.34-2.47 (m, 1H), 2.54-2.62 (m, 2H), 2.63-2.79 (m, 3H), 2.87 (br. s., 1H), 3.09 (s, 3H), 3.17-3.30 (m, 1H), 4.04 (d, J=14.00, 1H), 5.42 (s, 2H), 6.06 (s, 1H), 7.10-7.32 (m, 15H), 7.67 (d, J=10.80, 1H), 7.80 (d, J=10.40, 1H). LCMS (Method-O): retention time 1.87 min, [M+H] 599.3.

Intermediate 198-I

Intermediate 198-I was prepared (0.55 g 93.20%), by using a similar synthetic protocol as that of Intermediate 198B and starting from Intermediate 198F-I (1.00 g, 1.67 mmol) and TFA (5 mL, 64.90 mmol). $^1$H NMR (400 MHz, DMSO-$d_6$) δ ppm 1.28 (d, J=3.00, 3H), 2.17-2.45 (m, 3H), 2.96-3.26 (m, 5H), 3.27-3.44 (m, 5H), 4.70 (br.s., 1H), 5.39-5.53 (m, 2H), 6.32 (s, 1H), 7.29-7.33 (m, 1H), 7.79-7.91 (m, 2H), 8.49-8.84 (m, 1H), (1 Exchangeable proton not observed). LCMS (Method-O): retention time 0.57 min, [M+H] 357.1.

Example 266-I: 3-methyl-4-(((3S,5R)-3-methyl-5-(4-methyl-1-oxo-1,3-dihydroisobenzofuran-5-yl) piperazin-1-yl)methyl)-1-(2-methylpyridin-4-yl)-1,3-dihydro-2H-imidazol-2-one

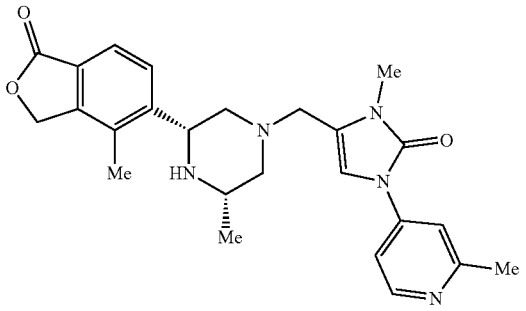

Example 266-I was prepared (0.02 g, 18.73%), by using a similar synthetic protocol as that of Intermediate 15C and starting from Intermediate 198-I (0.08 g, 0.23 mmol) and 4-bromo-2-methylpyridine (0.05 g, 0.27 mmol). $^1$H NMR (400 MHz, DMSO-$d_6$) δ ppm 1.06 (d, J=4.90 Hz, 3H), 1.75 (br. s., 2H), 2.27 (s, 3H), 2.46 (s, 3H), 2.87 (br. s., 2H), 2.98 (br. s., 1H), 3.28 (s, 2H), 3.33 (s, 3H), 4.18 (br. s., 1H), 5.52-5.29 (m, 2H), 7.18 (s, 1H), 7.78-7.54 (m, 3H), 7.82 (d, J=8.10 Hz, 1H), 8.40 (d, J=5.40 Hz, 1H), (1 Exchangeable proton not observed). LCMS/HPLC (Method-R): retention time 0.83 min, [M+H] 448.3, purity: 97.78%. (Method-S): retention time 1.34 min, [M+H] 448.3, purity: 97.09%.

Chiral purity (Method-XVIII): retention time 13.72 min, 95.00% ee.

The examples in Table 4 were synthesized using procedures of Example 1-I to 24-I, 81-I to 84-I, 113-I to 123-I and 266I

| Example | Structure | Name | LCMS (M + H)$^+$ | HPLC/ LCMS Method: RT (min.), Purity | NMR |
|---|---|---|---|---|---|
| 267-I | 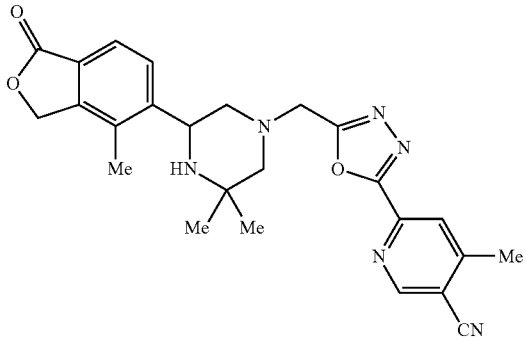 | 6-(5-(3,3-dimethyl-5-(4-methyl-1-oxo-1,3-dihydroiso-benzofuran-5-yl)piperazin-1-yl)methyl)-1,3,4-oxadiazol-2-yl)-4-methylnico-tinonitrile (Enantiomer-I) | 459.3 | R: 1.20, 100% S: 1.62, 100% | $^1$H NMR (400 MHz, DMSO-$d_6$) δ ppm 1.07 (s, 3 H), 1.30 (s, 3 H), 1.89-1.99 (m, 1 H), 2.06 (d, J = 10.00 Hz, 1 H), 2.31 (s, 3 H), 2.63 (s, 4 H), 2.95 (d, J = 10.00 Hz, 1 H), 3.99 (s, 2 H), 4.40 (d, J = 8.10 Hz, 1 H), 5.39 (s, 2 H), 7.66 (d, J = 8.10 Hz, 1 H), 7.78 (d, J = 8.10 Hz, 1 H), 8.32 (s, 1 H), 9.12 (s, 1 H), (1 Exchangeable proton not observed). |
| 268-I | 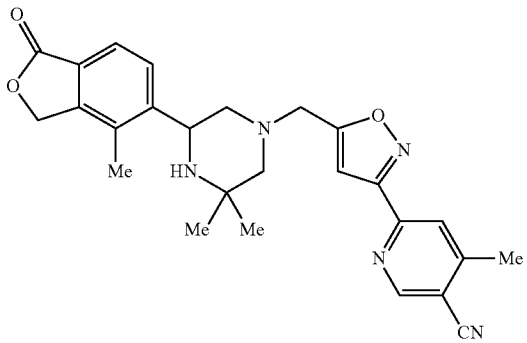 | 6-(5-((3,3-dimethyl-5-(4-methyl-1-oxo-1,3-dihydroiso-benzofuran-5-yl)piperazin-l-yl)methyl) isoxazol-3-yl)-4-methylnico-tinonitrile (Enantiomer-I) | 458.2 | R: 1.46, 100% S: 1.98, 100% XV: 8.87, 100% ee | $^1$H NMR (400 MHz, DMSO-$d_6$) 8 ppm (s, 3 H), 1.32 (s, 3 H), 1.88 (t, J = 10.60 Hz, 1 H), 1.97 (d, J = 10.30 Hz, 1 H), 2.26-2.33 (m, 3 H), 2.54-2.65 (m, 4 H), 2.88 (d, J = 9.50 Hz, 1 H), 3.84 (s, 2 H), 4.40 (d, J = 8.10 Hz, 1 H), 5.37 (s, 2 H), 6.96 (s, 1 H), 7.64 (d, J = 8.10 Hz, 1 H), 7.77 (d, J = 8.10 Hz, 1 H), 8.14 (s, 1 H), 9.04 (s, 1 H), (1 Exchangeable proton not observed). |

-continued

| Example | Structure | Name | LCMS (M + H)$^+$ | HPLC/ LCMS Method: RT (min.), Purity | NMR |
|---|---|---|---|---|---|
| 269-I | 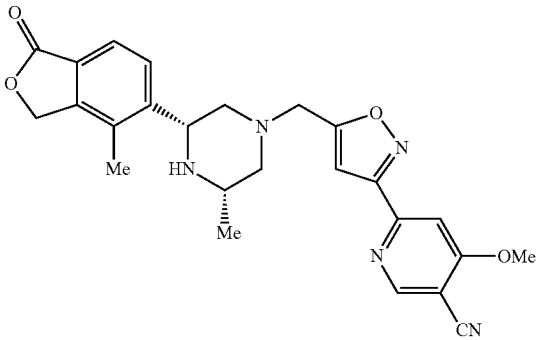 | 4-methoxy-6-(5-(((3S,5R)-3-methyl-5-(4-methyl-l-oxo-1,3-dihydroiso-benzofuran-5-yl)piperazin-1-yl)methyl) isoxazol-3-yl) nicotinonitrile | 460.3 | R: 1.30, 96.82% S: 1.67, 96.12% VIII: 6.79, 100% ee | $^1$H NMR (400 MHz, DMSO-$d_6$) 8 ppm 1.03 (d, J = 6.10 Hz, 3 H), 1.74-1.94 (m, 2 H), 2.29 (s, 3 H), 2.83 (br. s., 2 H), 2.99 (br. s., 1 H), 3.86 (s, 2 H), 4.12 (s, 3 H), 4.18 (d, J = 7.60 Hz, 1 H), 5.39 (s, 2 H), 7.01 (s, 1 H), 7.66 (d, J = 8.10 Hz, 1 H), 7.89-7.72-7.89 (m, 2 H), 8.94 (s, 1 H), (1 Exchangeable proton not observed). |
| 270-I | 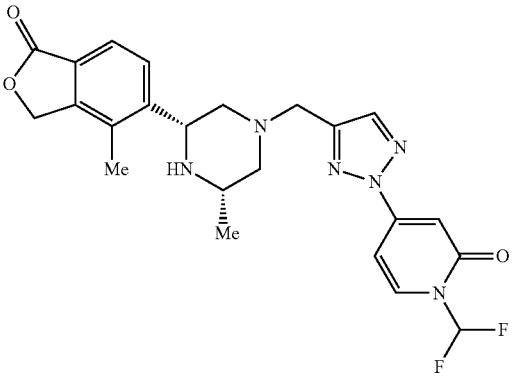 | l-(difluoro-methyl)-4-(4-((3S,5R)-3-methyl-5-(4-methyl-l-oxo-1,3-dihydroiso-benzofuran-5-yl) piperazin-l-yl)methyl)-2H-1,2,3-triazol-2-yl)pyridin-2(lH)-one. | 471.1 | R: 1.10, 100% S: 1.55, 100% XXIX: 3.35, 100% ee | $^1$H NMR (400 MHz, DMSO-$d_6$) 8 ppm 8.24 (s, 1 H), 8.02 (d, J = 7.80 Hz, 1 H), 7.88 (s, 1 H), 7.80 (d, J = 8.10 Hz, 1 H), 7.66 (d, J = 7.80 Hz, 1 H), 7.10 (dd, J = 7.90, 2.30 Hz, 1 H), 6.88 (d, J = 2.20 Hz, 1 H), 5.47-5.27 (m, 2 H), 4.18 (d, J = 8.30 Hz, 1 H), 3.76 (s, 2 H), 2.98 (br. s., 1 H), 2.81 (d, J = 9.80 Hz, 2 H), 2.33 (s, 3 H), 1.83 (d, J = 9.00 Hz, 2 H), 1.03 (d, J = 6.10 Hz, 3 H), (1 Exchangeable proton not observed). $^{19}$F NMR (400 MHz, DMSO-$d_6$) δ ppm- 103.0. |
| 271-I | 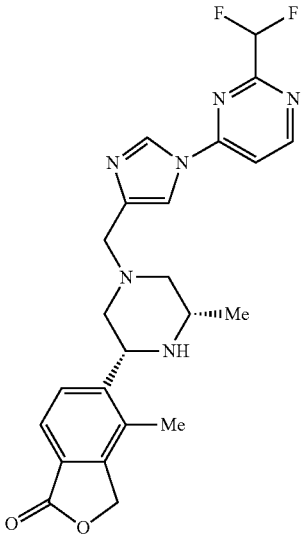 | 5-((2R,6S)-4-((l-(2-(difluoromethyl) pyrimidin-4-yl)-1H-imidazol-4-yl)methyl)-6-methylpiperazin-2-yl)-4-methyliso-benzofuran-1(3H)-one | 455.3 | S: 1.31, 100% R: 0.98, 100% VIII: 3.83, 100% ee | $^1$H NMR (400 MHz, DMSO-$d_6$) 8 ppm 1.02 (d, J = 6.10 Hz, 3H), 1.80 (q, J = 10.00 Hz, 2 H), 2.31-2.18 (m, 3 H), 2.91-2.69 (m, 2 H), 2.96 (br. s., 1 H), 3.51 (s, 2 H), 4.16 (d, J = 9.00 Hz, 1 H), 5.49-5.26 (m, 2 H), 6.97 (s, 1 H), 7.64 (d, J = 7.80 Hz, 1 H), 7.79 (d, J = 7.80 Hz, 1 H), 7.91 (s, 1 H), 8.08 (d, J = 5.60 Hz, 1 H), 8.65 (s, 1 H), 9.05 (d, J = 5.60 Hz, 1 H), (1 Exchangeable proton not observed). $^{19}$F NMR (400 MHz, DMSO-$d_6$) δ ppm- 119.33 |

-continued

| Example | Structure | Name | LCMS (M + H)+ | HPLC/ LCMS Method: RT (min.), Purity | NMR |
|---|---|---|---|---|---|
| 272-I | 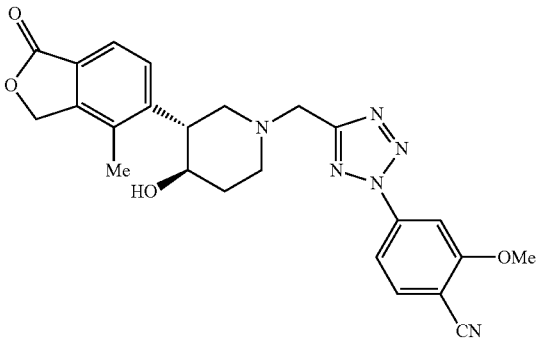 | 4-(5-(((3R,4R)-4-hydroxy-3-(4-methyl-1-oxo-1,3-dihydroiso-benzofuran-5-yl) piperidin-1-yl)methyl)-2H-tetrazol-2-yl)-2-methoxy-benzonitrile | 461.2 | S: 1.60, 100% R: 1.22, 100% | $^1$H NMR (400 MHz, DMSO-$d_6$) 8 ppm 1.68-1.56 (m, 1 H), 1.99-1.85 (m, 2 H), 2.31-2.19 (m, 4 H), 2.41-2.31 (m, 1 H), 2.85 (d, J = 10.80 Hz, 1 H), 2.98 (d, J = 10.80 Hz, 1 H), 3.13-3.04 (m, 1 H), 3.17 (s, 1 H), 3.72 (br. s., 1 H), 3.98 (s, 3 H), 4.59 (d, J = 5.40 Hz, 1 H), 5.47-5.28 (m, 2H), 7.54 (d, J = 7.80 Hz, 1 H), 7.63 (d, J = 8.10 Hz, 1 H), 7.80 (d, J = 8.30 Hz, 1 H), 7.85 (s, 1 H), 8.04 (d, J = 8.60 Hz, 1 H). |
| 273-I | 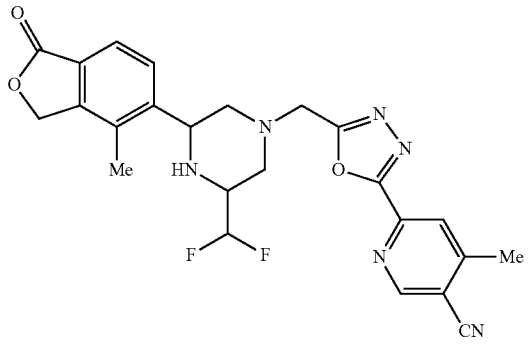 | 6-(5-((3-(difluoro-methyl)-5-(4-methyl-1-oxo-1,3-dihydroiso-benzofuran-5-yl) piperazin-1-yl)methyl)-1,3,4-oxadiazol-2-yl)-4-methylnico-tinonitrile (Enantiomer-I) | 481.2 | S: 1.67, 100% R: 1.27, 100% | $^1$H NMR (400 MHz, DMSO-$d_6$) 8 ppm 2.02 (t, J = 10.50 Hz, 1 H), 2.33-2.15 (m, 4 H), 2.63 (s, 3 H), 2.88 (br. s., 1 H), 2.95 (d, J = 10.80 Hz, 1 H), 3.02 (d, J = 9.00 Hz, 1 H), 3.31 (br. s., 1 H), 4.10 (s, 2 H), 4.24 (d, J = 9.80 Hz, 1 H), 5.45-5.37 (m, 2 H), 5.96 (d, J = 4.40 Hz, 1 H), 7.68 (d, J = 8.10 Hz, 1 H), 7.78 (d, J = 8.10 Hz, 1 H), 8.33 (s, 1 H), 9.12 (s, 1 H) |
| 274-I | 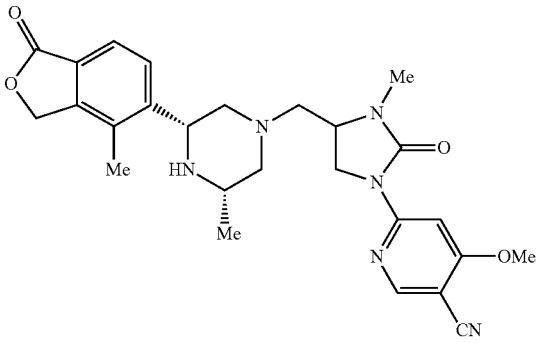 | 4-methoxy-6-(3-methyl-4-(((3S,5R)-3-methyl-5-(4-methyl-1 -oxo-1,3-dihydroiso-benzofuran-5-yl) piperazin-1-yl)methyl)-2-(dazolidin-1-yl)nico-tinonitrile (Diastereomer-I) | 491.2 | P: 8.11, 99.10% Q: 7.37, 99.30% XXXIII: 14.00, 100% ee | $^1$H NMR (400 MHz, DMSO-$d_6$) 8 ppm 1.02 (d, J = 6.53 Hz, 3 H), 1.75-1.84 (m, 2 H), 2.28 (s, 3 H), 2.60-2.66 (m, 2 H), 2.82 (d, J = 10.54 Hz, 2 H), 2.86-2.93 (m, 4 H), 3.78 (dd, J = 10.79, 5.27 Hz, 1 H), 3.85-3.92 (m, 1 H), 3.94 (s, 3 H), 4.02-4.14 (m, 2 H), 5.40 (s, 2 H), 7.67 (d, J = 8.03 Hz, 1 H), 7.82 (d, J = 8.03 Hz, 1 H), 8.06 (s, 1 H), 8.56 (s, 1 H) (1 Exchangeable proton not observed). |
| 275-I | 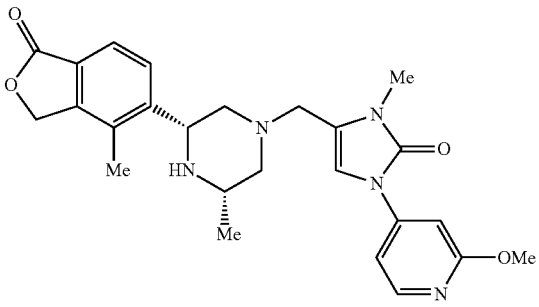 | 1-(2-methoxy-pyridin-4-yl)-3-methyl-4-(((3S,5R)-3-methyl-5-(4-methyl-1-oxo-1,3-dihydroiso-benzofuran-5-yl)piperazin-1-yl)methyl)-l,3-dihydro-2H-imidazol-2-one | 464.3 | R: 1.00, 96.14% S: 1.50, 97.76% | $^1$H NMR (400 MHz, DMSO-$d_6$) 8 ppm 1.06 (br. s., 3 H), 2.27 (s, 3 H), 2.85 (br. s., 3 H), 2.95 (br. s., 3 H), 3.28 (s, 2 H), 3.32 (s, 3 H), 3.86 (s, 3 H), 4.14 (br. s, 1 H), 5.38 (s, 2 H), 7.19 (s, 1 H), 7.34 (d, J = 1.70 Hz, 1 H), 7.50 (dd, J = 5.90, 2.00 Hz, 1 H), 7.68 (d, J = 7.30 Hz, 1 H), 7.82 (d, J = 7.80 Hz, 1 H), 8.14 (d, J = 5.90 Hz, 1 H). |

-continued

| Example | Structure | Name | LCMS (M + H)+ | HPLC/ LCMS Method: RT (min.), Purity | NMR |
|---|---|---|---|---|---|
| 276-I | 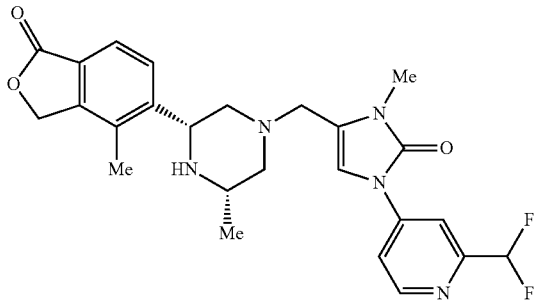 | 1-(2-(difluoromethyl) pyridin-4-yl)-3-methyl-4-((3S,5R)-3-methyl-5-(4-methyl-1-oxo-1,3-dihydroiso-benzofuran-5-yl) piperazin-l-yl)methyl)-1,3-dihydro-2H-imidazol-2-one | 484.3 | R: 1.14, 98.10% S: 1.52, 96.63% XV: 8.55 100% ee | $^1$H NMR (400 MHz, DMSO-$d_6$) δ ppm 1.05 (d, J = 5.10 Hz, 3 H), 1.72 (br. s., 2 H), 2.27 (s, 3 H), 2.86 (br. s., 2 H), 2.96 (br. s., 1 H), 3.33 (s, 3 H), 3.30 (s, 3 H), 4.14 (br. s., 1 H), 5.46-5.27 (m, 2 H), 6.95 (s, 1 H), 7.33 (s, 1 H), 7.68 (d, J = 8.10 Hz, 1 H), 7.82 (d, J = 8.10 Hz, 1 H), 8.00 (d, J = 4.60 Hz, 1 H), 8.29 (s, 1 H), 8.65 (d, J = 5.60 Hz, 1H) |

Intermediate 199-I: 4-methyl-5-(2R,6S)-6-methylpiperazin-2-yl)isobenzofuran-1(3H)-one-3,3-$d_2$ TFA Salt

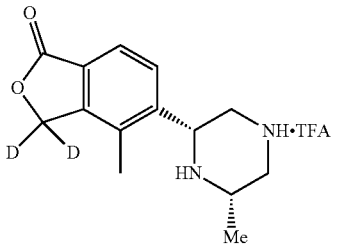

Intermediate 199A-I: tert-butyl (3S,5R)-3-methyl-5-(4-methyl-1-oxo-1,3-dihydroisobenzofuran-5-yl-3-d) piperazine-1-carboxylate

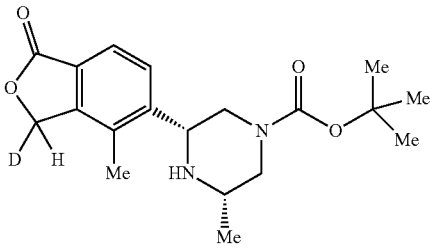

To a stirred solution of Intermediate 51-I (1.50 g, 4.33 mmol) in THF (150 mL) was added 1M LiHMDS in THF (21.65 mL, 21.65 mmol) and the reaction mixture was stirred at ambient temperature for 30 minutes. To the resulting reaction mixture was added $D_2O$ (5.09 mL, 281 mmol) and stirring at ambient temperature was continued for 15 minutes. The reaction mixture was diluted with water (100 mL) and extracted with ethyl acetate (2×100 mL). The combined organic layers were washed with brine (50 mL), dried over anhydrous sodium sulfate and evaporated under reduced pressure. The residue was purified by column chromatography (Redisep—40 g, 60-80% EtOAc/n-hexane) to obtain Intermediate 199A-I (1.00 g, 33.20%) as a white solid. $^1$H NMR (300 MHz, DMSO-$d_6$) δ ppm 1.05 (s, 3H), 1.42 (s, 9H), 2.32 (s, 3H), 2.42 (br s, 1H), 2.70-2.88 (m, 2H), 3.91-4.04 (m, 3H), 5.37-5.44 (m, 1H), 7.69 (d, J=7.90 Hz, 1H), 7.82 (d, J=7.90 Hz, 1H), (1 Exchangeable proton not observed). LCMS (Method-D): retention time 2.46 min, [M+H] 348.2.

Intermediate 199B-I and 199C-I: tert-butyl (3S,5R)-3-methyl-5-(4-methyl-1-oxo-1,3-dihydroisobenzofuran-5-yl-3,3-d2)piperazine-1-carboxylate

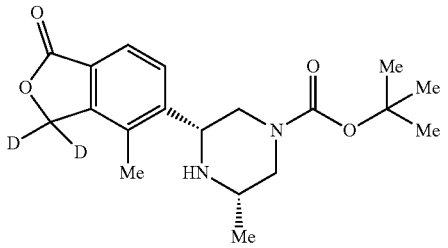

199B-I: mono-D and di-D isotopic ratio 28:72

199C-I: mono-D and di-D isotopic ratio 17:83

Intermediate 199B-I was prepared (0.40 g, 39.80%) as a white solid, by using a similar synthetic protocol as that of Intermediate 199A-I and starting from Intermediate I99A-I (1.00 g, 2.89 mmol) and 1M LiHMDS (14.39 mL, 14.39 mmol). $^1$H NMR (300 MHz, DMSO-$d_6$) δ ppm 1.05 (s, 3H), 1.42 (s, 9H), 2.32 (s, 3H), 2.42 (br s, 1H), 2.70-2.88 (m, 2H), 3.91-4.04 (m, 3H), 7.69 (d, J=7.90 Hz, 1H), 7.82 (d, J=7.90 Hz, 1H), (1 exchangeable proton not observed). LCMS (Method-D): retention time 2.47 min, [M+H] 349.2. The isotopic ratio of mono-D and di-D (28:72) was determined by $^1$H NMR.

Intermediate 199C-I was prepared (0.20 g, 19.88%) as a white solid, by using a similar synthetic protocol as that of Intermediate 199A and starting from Intermediate I99B-I (0.40 g, 1.15 mmol) and 1M LiHMDS (5.76 mL, 5.76 mmol). $^1$H NMR (300 MHz, DMSO-$d_6$) δ ppm 1.05 (s, 3H), 1.42 (s, 9H), 2.32 (s, 3H), 2.42 (br., s., 1H), 2.70-2.88 (m, 2H), 3.91-4.04 (m, 3H), 7.69 (d, J=7.90 Hz, 1H), 7.82 (d, J=7.90 Hz, 1H), (1 exchangeable proton not observed). LCMS (Method-D): retention time 2.47 min, [M+H] 349.2. The isotopic ratio of mono-D and di-D (17:83) was determined by $^1$H NMR.

Intermediate 199-I

Intermediate 199-I was prepared (0.18 g, 87.00%) as a pale yellow solid, by using a similar synthetic protocol as that of Intermediate 198B and starting from Intermediate 199C-I (0.20 g, 0.57 mmol) and TFA (0.88 mL, 11.48 mmol). $^1$H NMR (400 MHz, DMSO-$d_6$) δ ppm $^1$H NMR (400 MHz, DMSO-$d_6$) δ ppm 1.29 (d, J=6.00 Hz, 3H), 2.38 (s, 3H), 3.0-3.20 (m, 2H), 3.55-3.68 (m, 3H), 4.86 (br., s., 1H), 7.88-7.82 (m, 2H), (2 Exchangeable proton not observed). LCMS (Method-J): retention time 0.40 min, [M+H] 249.2.

Intermediate 200-I: 4-methyl-6-(4-(((3S,5R)-3-methyl-5-(4-methyl-1-oxo-1,3-dihydroisobenzofuran-5-yl-3-d)piperazin-1-yl)methyl)-2H-1,2,3-triazol-2-yl)nicotinonitrile

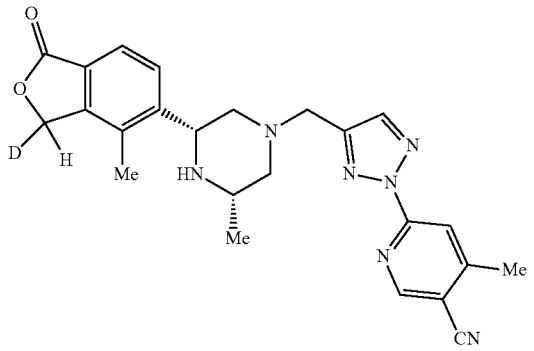

To a stirred solution of Example 83-I (0.10 g, 0.22 mmol) in THF (10 mL) at −50° C. was added 1M LiHMDS in THF (1.13 mL, 1.13 mmol) and the reaction mixture was stirred at same temperature for 10 minutes. To the resulting reaction mixture was added $D_2O$ (2.0 mL, 113 mmol) and stirring at −50° C. was continued for 10 minutes. The reaction mixture was diluted with water (15 mL) and extracted with ethyl acetate (3×20 mL). The combined organic layers were washed with brine (10 mL), dried over anhydrous sodium sulfate and evaporated under reduced pressure. The residue was purified by column chromatography (Redisep—24 g, 3-4% MeOH/DCM) to obtain Intermediate 200-I (0.045 g, 40.00%) as an off-white solid. $^1$H NMR (400 MHz, DMSO-$d_6$) δ ppm 1.02 (d, J=5.60 Hz, 3H), 1.75 (m, 2H), 2.27 (s, 3H), 2.38-2.41 (m, 2H), 2.71 (s, 3H), 2.75-2.86 (m, 2H), 3.76 (s, 2H), 4.05-4.29 (m, 1H), 5.34-5.37 (m, 1H), 7.50 (d, J=8.00 Hz, 1H), 7.80 (d, J=8.00 Hz, 1H), 8.07-8.26 (m, 2H), 8.87-9.03 (m, 1H). LCMS (Method-D): retention time 1.15 min, [M+H] 445.0. The isotopic ratio of mono-D and di-D (27:73) was determined by $^1$H NMR.

Example 277-I: 4-methyl-6-(4-(((3S,5R)-3-methyl-5-(4-methyl-1-oxo-1,3-dihydroisobenzofuran-5-yl-3,3-$d_2$)piperazin-1-yl)methyl)-2H-1,2,3-triazol-2-yl)nicotinonitrile

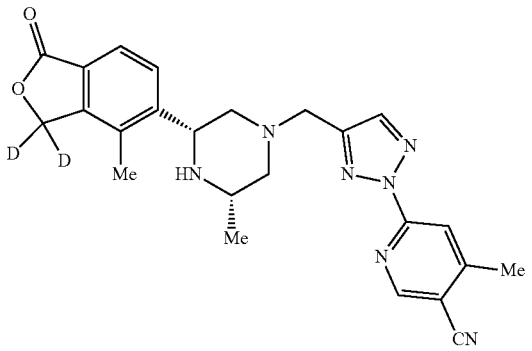

Example 277-I was prepared (0.01 g, 14.80%) as a white solid by using a similar synthetic protocol as that of Intermediate 96-I and starting from Intermediate 199-I (0.05 g, 0.188 mmol) and Intermediate 28 (0.04 g, 0.188 mmol). $^1$H NMR (400 MHz, DMSO-$d_6$) δ ppm 1.02 (d, J=5.60 Hz, 3H), 1.75-1.88 (m, 2H), 2.26 (s, 3H), 2.61 (s, 3H), 2.74-2.86 (m, 2H), 2.92-3.04 (m, 1H), 3.76 (s, 2H), 4.14-4.18 (m, 1H), 7.65 (d, J=7.60 Hz, 1H), 7.79 (d, J=8.10 Hz, 1H), 8.11 (s, 1H), 8.20 (s, 1H), 8.92 (s, 1H), (1 Exchangeable proton not observed). HPLC (Method-P): retention time 7.71 min, purity: 98.20%, (Method-Q): retention time 5.65 min, purity: 98.17%. LCMS (Method D): retention time 1.93 min, [M+H] 446.2. The isotopic ratio of mono-D and di-D (17:83) was determined by $^1$H NMR.

Alternative Procedure for Example 277-I

Example 277-I was prepared (0.001 g, 2.82%) as a white solid by using a similar synthetic protocol as that of Intermediate 199A-I and starting from Intermediate 200-I (0.04 g, 0.101 mmol) and 1M LiHMDS (0.50 mL, 0.50 mmol). $^1$H NMR (400 MHz, DMSO-$d_6$) δ ppm 1.02 (d, J=5.60 Hz, 3H), 1.75-1.88 (m, 2H), 2.26 (s, 3H), 2.61 (s, 3H), 2.74-2.86 (m, 2H), 2.92-3.04 (m, 1H), 3.76 (s, 2H), 4.14-4.18 (m, 1H), 7.65 (d, J=7.60 Hz, 1H), 7.79 (d, J=8.10 Hz, 1H), 8.11 (s, 1H), 8.20 (s, 1H), 8.92 (s, 1H), (1 Exchangeable proton not observed). HPLC (Method-P): retention time 7.49 min, purity: 92.50%, (Method-Q): retention time 6.54 min, purity: 93.04%. LCMS (Method-D): retention time 1.84 min, [M+H] 446.2. Chiral purity (Method-VIII): retention time 4.99 min, 100% ee. The isotopic ratio of mono-D and di-D (5:95) was determined by $^1$H NMR.

The examples in Table 5 were synthesized using procedures of Example 1-I to 24-I, 81-I to 84-I, 113-I to 123-I, 266-I and 277I

| Example | Structure | Name | LCMS (M + H)+ | HPLC/ LCMS Method: RT (min.), Purity | NMR |
|---|---|---|---|---|---|
| 278-I | 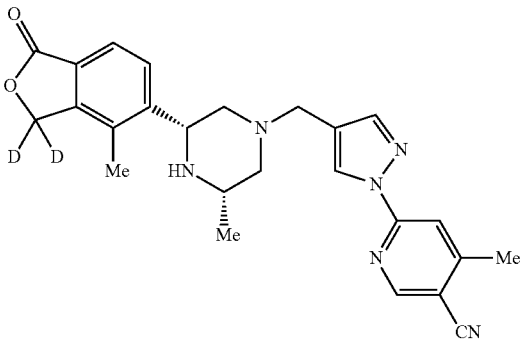 | 4-methyl-6-(4-(((3S,5R)-3-methyl-5-(4-methyl-1-oxo-1,3-dihydroisobenzofuran-5-yl-3,3-d2) piperazin-1-yl)methyl)-1H-pyrazol-l-yl)nicotinonitrile (Isotopic ratio of mono-D and di-D: 17:83) | 445.2 | P: 4.83, 96.00% Q: 6.29, 97.80% | $^1$H NMR (400 MHz, DMSO-$d_6$) δ ppm 1.00 (d, J = 6.00 Hz, 3 H), 1.69 (br., s., 2 H), 2.12 (s, 3 H), 2.56 (s, 3 H), 2,77 (d, J = 9.50 Hz, 2 H), 2.94 (s, 1 H), 3.50 (s, 2 H), 4.13 (d, J = 8.50 Hz, 1 H), 7.62 (d, J = 7.50 Hz, 1 H), 7.70-7.89 (m, 2 H), 7.96 (s, 1 H), 8.50 (s, 1 H), 8.81 (s, 1 H), (1 Exchangeable proton not observed). |
| 279-I | 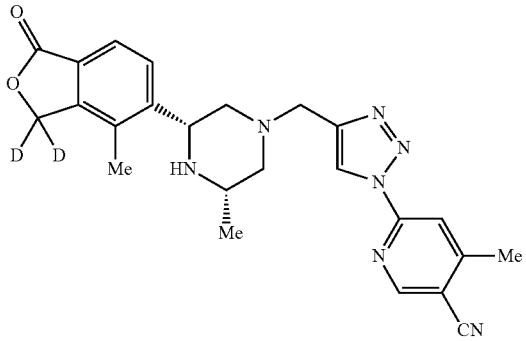 | 4-methyl-6-(4-(((3S,5R)-3-methyl-5-(4-methyl-1-oxo-1,3-dihydroisobenzofuran-5-yl-3,3-d2) piperazin-1-yl)methyl)-1H-1,2,3-triazol-1-yl) nicotinonitrile (Isotopic ratio of mono-D and di-D: 17:83) | 446.2 | P: 8.22, 97.00% Q: 9.50, 96.30% | $^1$H NMR (400 MHz, DMSO-$d_6$) δ ppm 1.01 (d, J = 6.00 Hz, 3 H), 1.66-1.87 (m, 2 H), 2.25 (s, 3 H), 2.56 (s, 3 H), 2.82 (t, J = 8.80 Hz, 2 H), 2.95 (br., s., 1 H), 3.73 (s, 2 H), 4.14 (d, J = 7.50 Hz, 1 H), 7.64 (d, J = 8.00 Hz, 1 H), 7.78 (d, J = 8.00 Hz, 1 H), 8.27 (s, 1 H), 8.76 (s, 1 H), 8.98 (s, 1 H), (1 Exchangeable proton not observed). |
| 280-I | 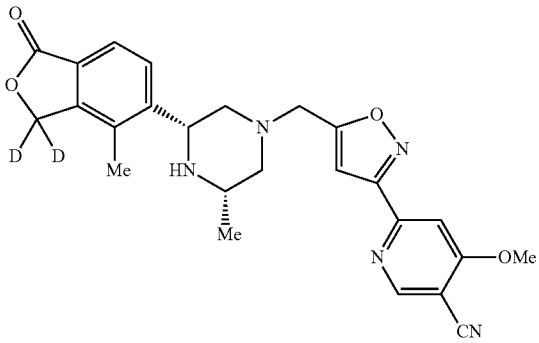 | 4-methyl-6-(5-(((3S,5R)-3-methyl-5-(4-methyl-1-oxo-1,3-dihydroisobenzofuran-5-yl-3,3-d2) piperazin-1-yl)methyl)-1,3,4-oxadiazol-2-yl)nicotinonitrile (Isotopic ratio of mono-D and di-D: 22:78) | 447.2 | T: 5.26, 94.27% S: 12.13, 95.10% | $^1$H NMR (400 MHz, DMSO-$d_6$) δ ppm 1.03 (d, J = 6.50 Hz, 3 H), 1.84-2.08 (m, 2 H), 2.28 (s, 3 H), 2.80-3.94 (m, 3 H), 3.99 (s, 3 H), 4.18 (d, J = 8.00 Hz, 3 H), 7.50 (d, J = 8.00 Hz, 1 H), 7.85 (d, J = 8.00 Hz, 1 H), 8.33 (s, 1 H), 9.12 (s, 1 H), (1 Exchangeable proton not observed). |
| 281-I | 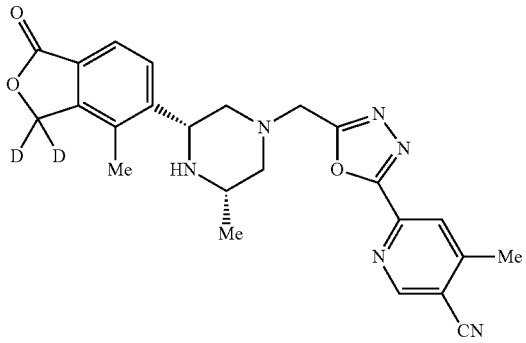 | 4-methoxy-6-(5-((3S,5R)-3-methyl-5-(4-methyl-l-oxo-1,3-dihydroisobenzofuran-5-yl-3,3-d2) piperazin-1-yl)methyl) isoxazol-3-yl)nicotinonitrile (Isotopic ratio of mono-D and di-D: 22:78) | 462.2 | P: 4.53, 90.04% R: 5.64, 90.00% | $^1$H NMR (400 MHz, DMSO-$d_6$) δ ppm 1.03 (d, J = 6.50 Hz, 3 H), 1.75-1.85 (m, 2 H), 2.25 (s, 3 H), 2.81-2.90 (m, 2 H), 2.95-3.0 (m, 1 H), 3.85 (s, 2 H), 4.01-4.23 (m, 4 H), 7.01 (s, 1 H), 7.66 (d, J = 8.00 Hz, 1 H), 7.73-7.85 (m, 2 H), 8.94 (s, 1 H), (1 Exchangeable proton not observed). |

BIOLOGICAL ASSAYS

The pharmacological properties of the compounds of this invention may be confirmed by a number of biological assays. The exemplified biological assays, which follow, have been carried out with compounds of the invention.

When more than one data point has been generated for any particular test for a particular compound, it is represented as an average in the table.

Thallium Flux Assay

Solutions and reagents: Thallium flux assay was performed using FluxOR kit (F10017, Life Technologies). Loading buffer, assay buffer and stimulus buffer were prepared using kit components. HBSS (Hank's balanced salt solution, Cat#14025-092) was purchased separately from Life Technologies.

To prepare 10 ml of loading buffer: 10 μl of FluxOR dye (reconstituted in DMSO) was first added to 100 μl of powerload concentrate and this mix along with 100 μl of Probenicid (100×) was then added to 9.79 ml of HBSS. Assay buffer (10 ml) was prepared by addition of 2 ml of FluxOR chloride free buffer (5×), 100 μl of Probenicid (100×), and 0.2 ml of Ouabain (13.77 mM) to 7.7 ml of deionized water. Stimulus buffer was composed of 15 mM $Tl_2SO_4$, 0.75 mM $K_2SO_4$ in FluxOR chloride free buffer (diluted to 1× using deionized water). The final concentration of $Tl_2SO_4$ and $K_2SO_4$ in the assay plate was 3 mM and 0.15 mM, respectively.

Plating and induction of cells: The CHO T-Rex hROMK (human $K_{ir}1.1$) stable cell line was maintained in Ham's F12 media supplemented with 10% FBS, 1% Penicillin-Streptomycin, 500 μg/ml Zeocin and 10 μg/ml Blasticidin at 37° C. in a 5% $CO_2$ incubator. One day before the experiment, the cells were dissociated by incubation with Versene solution (15040-066, Life Technologies) for 10 minutes at 37° C. followed by addition of growth media. The cell suspension was centrifuged at 1200 rpm for 5 min. After discarding the supernatant, the cells were resuspended in fresh growth media and cell concentration was determined using a hemocytometer. Next, 0.5 μg/ml of Doxycycline was added to the cell suspension to induce hROMK channel expression and 50 μl (10,000 cells/well) of cell suspension was added to each well of a poly-D lysine coated 384 well black, optically clear bottom plate (6007718, Perkin Elmer). The assay plate was kept at 37° C. in a 5% $CO_2$ incubator.

Assay protocol: On the day of experiment, media was removed and loading buffer was added (30 μl/well) to the assay plate. The cells were incubated in the loading buffer for 30 minutes at 37° C. The loading buffer was then replaced by assay buffer (30 μl/well) followed by addition of test compounds or controls. The cells were incubated with compounds for 30 minutes and the plate was then mounted on FlexStation (Molecular Devices) for fluorescence read out with excitation and emission wavelengths at 488 and 525 nm, respectively. Each well was read for 90 sec at 2 sec interval and the stimulus buffer was added after 20 seconds of baseline recording. The final DMSO concentration was either 0.5 or 1% in the assay plate. Positive and negative controls were defined by addition of DMSO or 3 μM of a standard ROMK inhibitor, respectively, to the wells instead of a test compound.

Data analysis: The slope (over a period of 15 seconds) of fluorescence increase after stimulus buffer addition was exported from SoftMax Pro into a custom made software where it was converted to % inhibition. A 10-point concentration response curve was used to estimate the $IC_{50}$ value of test compounds.

the data in Table 6 is reported with two significant figures.

TABLE 6

| Patent Example Number | Human ROMK Th Flux IC50 (nM) |
|---|---|
| 1-I | 14 |
| 2-I | 15 |

TABLE 6-continued

| Patent Example Number | Human ROMK Th Flux IC50 (nM) |
|---|---|
| 3-I | 210 |
| 4 | 640 |
| 5 | 270 |
| 6-I | 40 |
| 7-I | 1000 |
| 8-I | 280 |
| 9-I | 44 |
| 10-I | 620 |
| 11-I | 30 |
| 12-I | 530 |
| 13-I | 110 |
| 14-I | 36 |
| 15-I | 84 |
| 16-I | 33 |
| 17-I | 900 |
| 18-I | 870 |
| 19-I | 180 |
| 20-I | 490 |
| 21-I | 93 |
| 22-I | 26 |
| 23-I | 30 |
| 24-I | 500 |
| 1-II | 800 |
| 25-I | 51 |
| 26-I | 69 |
| 27-I | 32 |
| 28-I | 85 |
| 29-I | 120 |
| 30-I | 260 |
| 31-I | 190 |
| 32-I | 24 |
| 33-I | 690 |
| 34-I | 190 |
| 35-I | 120 |
| 36-I | 680 |
| 37-I | 16 |
| 38-I | 3400 |
| 39-I | 770 |
| 40-I | 27 |
| 41-I | 980 |
| 42-I | 490 |
| 43-I | 110 |
| 44-I | 200 |
| 45-I | 370 |
| 46-I | 26 |
| 47-I | 49 |
| 48-I | 62 |
| 49-I | 23 |
| 50-I | 670 |
| 51-I | 29 |
| 52-I | 2.8 |
| 53-I | 370 |
| 2-II | 1200 |
| 54-I | 110 |
| 55-I | 86 |
| 56-I | 150 |
| 57-I | 59 |
| 58-I | 60 |
| 59-I | 20 |
| 61-I | 57 |
| 62-I | 170 |
| 63-I | 60 |
| 64-I | 8.8 |
| 65-I | 14 |
| 66-I | 33 |
| 67-I | 110 |
| 68-I | 1700 |
| 69-I | 900 |
| 70-I | 59 |
| 71-I | 800 |
| 72-I | 550 |
| 73-I | 150 |
| 74-I | 570 |
| 75-I | 680 |
| 76-I | 300 |
| 77-I | 820 |
| 78-I | 810 |

TABLE 6-continued

| Patent Example Number | Human ROMK Th Flux IC50 (nM) |
|---|---|
| 79-I | 320 |
| 80-I | 490 |
| 81-I | 22 |
| 82-I | 13 |
| 83-I | 23 |
| 84-I | 52 |
| 85-I | 45 |
| 86-I | 64 |
| 87-III | 62 |
| 88-III | 36 |
| 89-III | 30 |
| 90-I | 49 |
| 91-I | 56 |
| 92-I | 35 |
| 93-I | 44 |
| 94-I | 39 |
| 95-I | 26 |
| 96-I | 27 |
| 97-I | 28 |
| 98-I | 45 |
| 99-I | 33 |
| 100-I | 40 |
| 101-I | 26 |
| 102-I | 48 |
| 103-I | 25 |
| 104-I | 36 |
| 105-I | 26 |
| 106-I | 57 |
| 107-I | 26 |
| 108-I | 30 |
| 109-I | 56 |
| 110-I | 25 |
| 111-I | 23 |
| 112-I | 18 |
| 113-I | 25 |
| 114-I | 32 |
| 115-I | 23 |
| 116-I | 39 |
| 117-I | 34 |
| 118-I | 290 |
| 119-I | 140 |
| 120-I | 160 |
| 121-I | 31 |
| 122-I | 50 |
| 123-I | 74 |
| 125-I | 30 |
| 126-I | 34 |
| 127-I | 21 |
| 128-I | 66 |
| 129-I | 26 |
| 130-I | 52 |
| 131-I | 75 |
| 132-I | 170 |
| 133-I | 84 |
| 134-I | 43 |
| 135-I | 170 |
| 136-I | 28 |
| 137-I | 26 |
| 138-I | 670 |
| 139-I | 36 |
| 140-I | 26 |
| 141-I | 69 |
| 142-I | 76 |
| 143-I | 63 |
| 144-I | 24 |
| 145-I | 15 |
| 146-I | 25 |
| 147-I | 87 |
| 148-I | 27 |
| 149-I | 52 |
| 150-I | 100 |
| 151-I | 43 |
| 152-I | 490 |
| 153-I | 84 |
| 154-I | 12 |
| 155-I | 11 |
| 156-I | 14 |

TABLE 6-continued

| Patent Example Number | Human ROMK Th Flux IC50 (nM) |
|---|---|
| 157-I | 12 |
| 158-I | 36 |
| 159-I | 16 |
| 160-I | 130 |
| 161-I | 170 |
| 162-I | 260 |
| 163-I | 29 |
| 164-I | 31 |
| 165-I | 67 |
| 166-I | 30 |
| 167-I | 26 |
| 168-I | 20 |
| 169-I | 23 |
| 170-I | 39 |
| 171-I | 27 |
| 172-I | 160 |
| 173-I | 55 |
| 174-I | 220 |
| 175-I | 31 |
| 176-I | 120 |
| 177-I | 500 |
| 178-I | 220 |
| 179-I | 360 |
| 180-I | 77 |
| 181-I | 150 |
| 182-I | 260 |
| 183-I | 180 |
| 184-I | 30 |
| 185-I | 100 |
| 186-I | 18 |
| 187-I | 43 |
| 188-I | 37 |
| 189-I | 25 |
| 190-I | 17 |
| 191-I | 29 |
| 192-I | 16 |
| 193-I | 44 |
| 194-I | 60 |
| 195-I | 66 |
| 196-I | 35 |
| 197-I | 15 |
| 198-I | 83 |
| 199-IV | 16 |
| 200-II | 64 |
| 201-I | 190 |
| 202-I | 140 |
| 203-I | 43 |
| 204-I | 220 |
| 205-I | 71 |
| 206-I | 82 |
| 207-I | 53 |
| 208-I | 190 |
| 209-I | 100 |
| 210-I | 41 |
| 211-I | 30 |
| 212-II | 97 |
| 213-I | 1200 |
| 214-I | 6.6 |
| 215-I | 11 |
| 216-I | 25 |
| 217-I | 24 |
| 218-I | 33 |
| 219-I | 21 |
| 220-I | 29 |
| 221-I | 22 |
| 222-I | 60 |
| 223-I | 18 |
| 224-I | 27 |
| 225-I | 19 |
| 226-I | 14 |
| 227-I | 28 |
| 228-I | 14 |
| 229-I | 21 |
| 230-I | 32 |
| 231-I | 240 |
| 232-I | 480 |
| 233-I | 22 |

TABLE 6-continued

| Patent Example Number | Human ROMK Th Flux IC50 (nM) |
|---|---|
| 234-I | 78 |
| 235-I | 83 |
| 236-I | 75 |
| 237-I | 69 |
| 238-I | 470 |
| 239-I | 63 |
| 240-I | 42 |
| 241-I | 41 |
| 242-I | 10 |
| 243-I | 13 |
| 244-II | 17 |
| 245-I | 18 |
| 246-I | 870 |
| 247-I | 330 |
| 248-I | 1500 |
| 249-I | 120 |
| 250-I | 27 |
| 251-I | 61 |
| 252-I | 72 |
| 253-I | 400 |
| 254-I | 1600 |
| 255-I | 33 |
| 256-II | 57 |
| 257-I | 1400 |
| 258-I | 250 |
| 259-I | 53 |
| 260-I | 430 |
| 261-II | 27 |
| 262-I | 120 |
| 263-I | 23 |
| 264-I | 580 |
| 265-I | 22 |
| 266-I | 36 |
| 267-I | 16 |
| 268-I | 20 |
| 269-I | 24 |
| 270-I | 580 |
| 271-I | 100 |
| 272-I | 65 |
| 273-I | 720 |
| 274-I | 58 |
| 275-I | 42 |
| 276-I | 35 |
| 277-I | 38 |

ROMK Manual Patch Clamp Assay

Cell culture conditions: Cells were maintained in conditions similar to those for Thallium flux assay. hROMK channel expression was induced by adding 0.6 μg/ml of Doxycycline 16-24 hrs prior to the experiments. On the day of experiment, the cells were dissociated using Versene, resuspended in growth media and plated onto coverslips 15 minutes prior to use.

Electrophysiology: The coverslip plated with cells was placed in the experiment chamber perfused with bath solution composed of (in mM): 135 NaCl, 5 KCl, 2 $CaCl_2$, 1 $MgCl_2$, 10 HEPES, 5 Glucose (pH 7.4). Patch pipettes with resistance between 2-5 Megaohms, when filled with a solution containing (in mM): 135 KCl, 1 EGTA, 1 $MgCl_2$, 10 HEPES, 2 $Na_2ATP$ (pH 7.3), were used to form gigaseals. The cells were voltage clamped at −75 mV in whole-cell configuration using an Axopatch 200b or Multiclamp 700b (Molecular Devices) amplifier controlled by pClamp Software (Molecular Devices). The current was recorded by applying a voltage step to −120 mV every 10 seconds. For each compound, 4-6 concentrations were applied for 3-8 minutes in a successive manner starting with the lowest concentration. At the end of the experiment, the cells were perfused with bath solution containing 2 mM $Ba^{2+}$ to isolate the contribution of hROMK current.

Data analysis: Raw current values (5 traces each for control, different compound concentration and $Ba^{2+}$ treatment groups) were exported from Clampfit into Microsoft Excel where the current remaining after application of $Ba^{2+}$ was subtracted from raw current to obtain hROMK specific current. These hROMK current values (average of 5 traces for each group) were then imported into a custom made template to generate a concentration response curve, which was subsequently fitted with a four parameter equation to calculate the $IC_{50}$ value of the test compound.

The data in Table 7 is reported with two significant figures.

TABLE 7

| Patent Example Number | ROMK EP IC50 (nM) |
|---|---|
| 1-I | 11 |
| 2-I | 5.7 |
| 3-I | 44 |
| 14-I | 51 |
| 16-I | 11 |
| 22-I | 25 |
| 23-I | 4.9 |
| 37-I | 22 |
| 59-I | 4.8 |
| 61-I | 40 |
| 65-I | 9.8 |
| 66-I | 4.7 |
| 67-I | 29 |
| 82-I | 7.9 |
| 83-I | 6.8 |
| 84-I | 57 |
| 87-III | 57 |
| 90-I | 74 |
| 92-I | 23 |
| 94-I | 14 |
| 96-I | 12 |
| 97-I | 43 |
| 98-I | 23 |
| 99-I | 29 |
| 100-I | 25 |
| 101-I | 34 |
| 102-I | 17 |
| 103-I | 29 |
| 105-I | 11 |
| 106-I | 10 |
| 107-I | 18 |
| 108-I | 21 |
| 109-I | 54 |
| 110-I | 16 |
| 111-I | 62 |
| 121-I | 740 |
| 126-I | 17 |
| 127-I | 14 |
| 130-I | 20 |
| 139-I | 30 |
| 148-I | 19 |
| 151-I | 64 |
| 164-I | 30 |
| 165-I | 39 |
| 166-I | 13 |
| 167-I | 18 |
| 168-I | 29 |
| 171-I | 26 |
| 173-I | 21 |
| 175-I | 17 |
| 184-I | 10 |
| 187-I | 25 |
| 188-I | 18 |
| 189-I | 17 |
| 190-I | 13 |
| 191-I | 21 |
| 193-I | 20 |
| 195-I | 79 |
| 207-I | 18 |
| 210-I | 20 |
| 216-I | 14 |

TABLE 7-continued

| Patent Example Number | ROMK EP IC50 (nM) |
|---|---|
| 221-I | 13 |
| 228-I | 20 |
| 230-I | 19 |
| 240-I | 34 |
| 244-II | 22 |
| 255-I | 9.1 |
| 263-I | 23 |
| 267-I | 17 |

hERG Manual Patch Clamp Assay hERG electrophysiology assay: The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 $CaCl_2$, 1 $MgCl_2$, 10 Glucose, 10 HEPES (pH 7.4, NaOH) at room temperature. Borosilicate patch pipettes had tip resistances of 2-4 Mohms when filled with an internal solution containing: 130 KCl, 1 $MgCl_2$, 1 $CaCl_2$, 10 EGTA, 10 HEPES, 5 ATP-$K_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in a custom made template. The percent inhibitions at different concentrations were plotted to obtain a concentration response curve, which was subsequently fitted with a four parameter equation to calculate hERG $IC_{50}$ value.

Some compounds of the present invention were tested in the hERG assay. Preferred compounds have low hERG inhibition or a high $IC_{50}$.

TABLE 8

| Patent Example Number | hERG EP % Inh @ 1 uM |
|---|---|
| 1-I | 26 |
| 2-I | 19 |
| 3-I | 26 |
| 6-I | 38 |
| 9-I | 47 |
| 11-I | 40 |
| 14-I | 1.7 |
| 15-I | 5.8 |
| 16-I | 7.3 |
| 21-I | 8.5 |
| 22-I | 6.0 |
| 23-I | 12 |
| 25-I | 8.7 |
| 26-I | 20 |
| 27-I | 11 |

TABLE 8-continued

| Patent Example Number | hERG EP % Inh @ 1 uM |
|---|---|
| 28-I | 15 |
| 32-I | 6.2 |
| 35-I | 20 |
| 37-I | 6.2 |
| 40-I | 54 |
| 46-I | 43 |
| 47-I | 49 |
| 48-I | 78 |
| 49-I | 27 |
| 51-I | 43 |
| 52-I | 72 |
| 57-I | 26 |
| 59-I | 15 |
| 63-I | 23 |
| 64-I | 45 |
| 65-I | 21 |
| 66-I | 0 |
| 67-I | 7.1 |
| 70-I | 8.4 |
| 81-I | 7.7 |
| 82-I | 7.1 |
| 83-I | 11 |
| 84-I | 6.7 |
| 85-I | 11 |
| 86-I | 8.8 |
| 87-III | 4.9 |
| 88-III | 8.3 |
| 89-III | 14 |
| 90-I | 2.6 |
| 91-I | 0 |
| 92-I | 5.2 |
| 93-I | 23 |
| 94-I | 4.3 |
| 95-I | 13 |
| 96-I | 9.6 |
| 98-I | 9.3 |
| 99-I | 9.6 |
| 100-I | 3.6 |
| 101-I | 3.0 |
| 102-I | 5.6 |
| 103-I | 14 |
| 104-I | 3.4 |
| 105-I | 9.7 |
| 106-I | 0.98 |
| 107-I | 13 |
| 108-I | 8.7 |
| 109-I | 3.6 |
| 110-I | 9.2 |
| 111-I | 5.1 |
| 112-I | 22 |
| 114-I | 4.2 |
| 115-I | 45 |
| 116-I | 6.4 |
| 121-I | 10 |
| 122-I | 6.6 |
| 123-I | 7.2 |
| 125-I | 8.3 |
| 126-I | 7.8 |
| 127-I | 16 |
| 128-I | 19 |
| 129-I | 32 |
| 130-I | 8.4 |
| 134-I | 22 |
| 136-I | 29 |
| 137-I | 23 |
| 139-I | 6.6 |
| 140-I | 49 |
| 141-I | 7.1 |
| 142-I | 8.5 |
| 143-I | 49 |
| 144-I | 7.8 |
| 145-I | 25 |
| 146-I | 16 |
| 148-I | 8.8 |
| 149-I | 7.6 |
| 150-I | 14 |
| 151-I | 5.1 |

TABLE 8-continued

| Patent Example Number | hERG EP % Inh @ 1 uM |
|---|---|
| 153-I | 10 |
| 154-I | 43 |
| 155-I | 26 |
| 156-I | 51 |
| 157-I | 40 |
| 158-I | 20 |
| 159-I | 21 |
| 163-I | 4.5 |
| 164-I | 6.0 |
| 165-I | 5.4 |
| 166-I | 6.0 |
| 167-I | 11 |
| 168-I | 22 |
| 169-I | 12 |
| 170-I | 26 |
| 171-I | 16 |
| 173-I | 4.0 |
| 175-I | 15 |
| 184-I | 6.1 |
| 185-I | 9.6 |
| 187-I | 11 |
| 188-I | 18 |
| 189-I | 8.9 |
| 190-I | 9.1 |
| 191-I | 4.3 |
| 192-I | 46 |
| 193-I | 14 |
| 194-I | 11 |
| 195-I | 5.9 |
| 196-I | 18 |
| 197-I | 75 |
| 198-I | 0 |
| 199-IV | 22 |
| 200-II | 27 |
| 203-I | 16 |
| 205-I | 10 |
| 207-I | 10 |
| 210-I | 5.2 |
| 211-I | 58 |
| 214-I | 22 |
| 215-I | 29 |
| 216-I | 5.6 |
| 217-I | 16 |
| 218-I | 39 |
| 219-I | 75 |
| 220-I | 30 |
| 221-I | 5.4 |
| 222-I | 12 |
| 223-I | 56 |
| 225-I | 39 |
| 226-I | 33 |
| 227-I | 18 |
| 228-I | 16 |
| 229-I | 25 |
| 230-I | 2.2 |
| 233-I | 31 |
| 236-I | 20 |
| 237-I | 37 |
| 239-I | 18 |
| 240-I | 8.3 |
| 241-I | 18 |
| 242-I | 36 |
| 243-I | 9.8 |
| 245-I | 17 |
| 249-I | 9.1 |
| 250-I | 20 |
| 251-I | 7.6 |
| 252-I | 8.8 |
| 255-I | 9.5 |
| 256-II | 13 |
| 259-I | 8.6 |
| 261-II | 44 |
| 263-I | 10 |
| 265-I | 20 |
| 266-I | 3.1 |
| 267-I | 9.9 |
| 268-I | 9.0 |

TABLE 8-continued

| Patent Example Number | hERG EP % Inh @ 1 uM |
|---|---|
| 269-I | 9.5 |
| 272-I | 5.2 |
| 274-I | 43 |
| 275-I | 8.4 |
| 276-I | 5.4 |
| 277-I | 7.0 |

What is claimed is:

1. A compound having the structure of Formula (I)

(I)

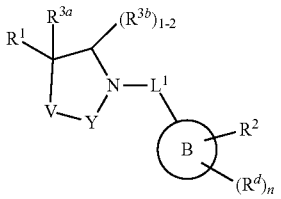

or a salt thereof, wherein:

$R^1$ is:

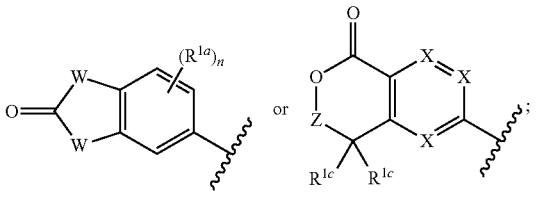

each W is independently $NR^{1b}$ *or O*;

Z is a bond or $CHR^{1d}$;

X is independently N or $CR^{1a}$, wherein X is N at only 0, 1, or 2 positions;

each $R^{1a}$ is independently H, F, Cl, —OH, —CN, $C_{1-3}$ alkyl, $C_{1-3}$fluoroalkyl, $C_{3-6}$ cycloalkyl, $C_{1-3}$ alkoxy, or $C_{1-3}$ fluoroalkoxy;

each $R^{1b}$ is independently H, $C_{1-3}$ alkyl, $C_{2-3}$ fluoroalkyl, *or* $C_{3-6}$ cycloalkyl;

$R^{1c}$ is independently H, deuterium, $C_{1-4}$ alkyl, $C_{1-4}$ fluoroalkyl, or $C_{3-6}$ cycloalkyl;

$R^{1d}$ is H, $C_{1-3}$ alkyl, $C_{1-4}$ fluoroalkyl, or $C_{3-6}$ cycloalkyl;

Y is —$C(R^6)_2$—, —$C(R^6)_2$—$C(R^6)_2$—,—C(O)—, —C(O)—$C(R^6)_2$—, —$C(R^6)_2$—C(O)—, or —$SO_2$—;

V is —O—, —$NR^4$—, —$CR^5R^5$—, —S—, —S(O)—, —$SO_2$—, or —C(O)—; wherein if V is —O—, —S—, —S(O)—, —$SO_2$—, or —C(O)—, then Y is not —$SO_2$—, and wherein if V is —O—, —S—, or $NR^4$, then Y is not $C(R^6)_2$, and wherein if V is —S(O)—, —$SO_2$—, or C(═O)—, then Y is not —C(═O)—, —C(═O)—$C(R^6)_2$—;

$L^1$ is —$C(R)_2$—, —C(O)—, or —$C(R)_2$—$C(R)_2$—; wherein R is independently H, F, OH, $C_{1-3}$ alkyl, $C_{1-3}$ hydroxyalkyl, $C_{1-3}$ alkoxyalkyl, or $C_{1-3}$ fluoroalkyl; wherein R is not —OH or F if it is attached to a carbon atom that is adjacent to a nitrogen atom:

Ring B is phenyl, pyridinyl, pyrimidinyl, [pyrrazolyl] *pyrazolyl*, thiazolyl, imidazolyl, triazolyl, tetrazolyl, oxadiazolyl, thiadiazolyl, isoxazolyl, isothiazolyl, pyrrolyl, pyrazinyl, oxazolyl, pyridazinyl, pyrrolidinyl, or imidazolidinyl;

$R^2$ is a $C_{6-10}$ aryl, or a 5 to 10 membered heterocycle ring containing 1 to 4 heteroatoms selected from N, O, and S, the heterocycle ring optionally containing an oxo substitution, the aryl or heterocycle ring are substituted with 0-3 $R^{2a}$;

$R^{2a}$ is independently OH, =O, CN, halo, $C_{1-4}$ alkyl, $C_{1-4}$ deuteroalkyl, $C_{1-4}$ fluoroalkyl, $C_{1-4}$ alkoxy, $C_{1-4}$ deuteroalkoxy, $C_{1-4}$ fluoroalkoxy, $C_{3-6}$ cycloalkyl, $C_{3-6}$ cycloalkoxy, $C(=O)NR^{4b}R^{4b}$, $C(=O)C_{1-4}$ alkyl, $SO_2R^e$, $NR^{4b}SO_2R^{4b}$, or a 4 to 6 membered heterocycle having 1, 2, 3, or 4 heteroatoms selected from O, S, and N, the heterocycle optionally containing an oxo substitution and is substituted with 0-3 $R^{2b}$;

$R^{2b}$ is independently $C_{1-3}$ alkyl, $C_{1-3}$ [fluoralkyl] *fluoroalkyl*, $C_{1-3}$ hydroxyalkyl, $C_{3-6}$ cycloalkyl, or $C_{3-6}$ fluorocycloalkyl;

$R^{3a}$ is H, halo, OH, CN, $C_{13}$ alkyl, $C_{1-3}$ hydroxyalkyl, $C_{1-3}$ fluoroalkyl, $C_{1-3}$ alkoxy, or $C_{3-6}$ cycloalkyl, wherein if V is —O—, —$NR^4$—, —S—, —S(O)—, —$SO_2$—, or —C(=O)—, then $R^{3a}$ is not halo, and wherein if V is —O—, —$NR^4$—, *or* —S—, then $R^{3a}$ is not OH[,] *or* CN;

$R^{3b}$ is H, =O, $C_{1-3}$ alkyl, $C_{1-3}$ hydroxyalkyl, $C_{1-3}$fluoroalkyl, $C_{1-3}$ alkoxy, or $C_{3-6}$ cycloalkyl;

$R^4$ is H, $C_{1-3}$ alkyl, $C_{2-3}$ fluoroalkyl, $C_{2-3}$ hydroxyalkyl, $CO_2R^{4a}$, $C(O)R^{4a}$, $SO_2R^{4a}$, $C(O)N(R^{4b}R^{4b})$, $SO_2N(R^{4b}R^{4b})$, or OH;

$R^{4a}$ is $C_{1-3}$ alkyl, $C_{1-3}$ fluoroalkyl, $C_{3-6}$ cycloalkyl, $C_{3-6}$ fluorocycloalkyl, $C_{6-10}$ aryl or a 4 to 10 membered heterocycle having 1, 2, 3 or 4 heteroatoms selected from O, S, and N, the aryl or heterocycle being substituted with 0-3 $R^{4c}$;

$R^{4b}$ is independently H, $C_{1-3}$ alkyl, $C_{2-3}$ fluoroalkyl, $C_{3-6}$ cycloalkyl, $C_{3-6}$ fluorocycloalkyl, $C_{6-10}$ aryl or a 4 to 10 membered heterocycle having 1, 2, 3 or 4 heteroatoms selected from O, S, and N;

alternatively, 2 $R^{4b}$s, along with the atom to which they are attached, join to form a 3 to 6 membered saturated ring containing an additional 0-2 heteroatoms selected from O, S, and N;

$R^{4c}$ is independently H, F, Cl, or $C_{1-3}$ alkyl;

$R^5$ is independently H, F, OH, $C_{1-3}$ alkoxy, $C_{1-3}$ fluoroalkoxy, $C_{1-3}$ alkyl, $C_{1-3}$ fluoroalkyl, $C_{1-3}$ hydroxyalkyl, $C_{3-6}$ cycloalkyl, $C_{3-6}$ fluorocycloalkyl, $NR^{5b}R^{5b}$, O—$R^{5c}$, or 2 $R^5$s are =O; wherein if one $R^5$ is F, OH or $NR^{5b}R^{5b}$, then the other $R^5$ is not OH, or $NR^{5b}R^{5b}$;

$R^{5b}$ is independently H, $C_{1-3}$ alkyl, $C_{3-6}$ cycloalkyl, $C(O)R^a$, $SO_2R^a$, or $C(O)NR^bR^b$; alternatively, 2 $R^{5b}$s, along with the atom to which they are attached, join to form a 3 to 6 membered saturated ring containing 0-2 heteroatoms selected from O, S, or N;

$R^{5c}$ is independently H, $C_{1-3}$ alkyl, $C_{3-6}$ cycloalkyl, or $C(O)NR^bR^b$;

$R^6$ is independently H, OH, F, $C_{1-3}$ alkyl, $C_{1-3}$ deuteroalkyl, $C_{1-3}$ fluoroalkyl, $C_{3-6}$ cycloalkyl, $C_{3-6}$ fluorocycloalkyl, $C_{1-3}$ alkoxy, $C_{1-3}$ hydroxyalkyl, $C_{1-3}$ hydroxydeuteroalkyl, $C_{1-3}$ alkoxyalkyl, or $C_{1-3}$ fluoroalkoxyalkyl, or $NR^{6b}R^{6b}$; wherein if one $R^6$ on one carbon atom is F, OH or $NR^{6b}R^{6b}$, then the other $R^6$ on the same carbon atom is not OH or $NR^{6b}R^{6b}$;

$R^{6b}$ is independently H, $C_{1-3}$ alkyl, $C_{3-6}$ cycloalkyl, $C(O)R^a$, $SO_2R^a$, or $C(O)NR^bR^b$; alternatively, 2 $R^6$s along with the same atom to which they are attached can form a 3 to 6 membered saturated ring containing 0-2 heteroatoms selected from O, S, and N;

$R^a$ is independently H, $C_{1-3}$ alkyl, $C_{2-3}$ fluoroalkyl, $C_{3-6}$ cycloalkyl, $C_{3-6}$ fluorocycloalkyl, $C_{6-10}$ aryl or a 4 to 10 membered heterocycle having 1, 2, 3, or 4 heteroatoms selected from O, S, and N;

$R^b$ is independently H, $C_{1-3}$ alkyl, $C_{2-3}$ fluoroalkyl, $C_{3-6}$ cycloalkyl, $C_{3-6}$ fluorocycloalkyl, $C_{6-10}$ aryl or a 4 to 10 membered heterocycle having 1, 2, 3 or 4 heteroatoms selected from O, S, and N;

alternatively, 2 $R^b$'s along with the atom to which they are attached, join to form a 3 to 6 membered saturated ring, containing 0-2 heteroatoms selected from O, S, and N;

each $R^d$ is independently H, F, $C_{1-3}$ alkyl, $C_{1-3}$ fluoroalkyl, $C_{1-3}$ alkoxy, $C_{1-3}$ fluoroalkoxy, $C_{1-3}$ hydroxyalkyl, $C_{3-6}$ cycloalkyl, halo, OH, =O, CN, $OCF_3$, $OCHF_2$, $CHF_2CF_3$, or $C(O)NR^eR^e$;

each $R^e$ is independently H, $C_{1-3}$ alkyl, $C_{2-3}$ fluoroalkyl, $C_{3-6}$ cycloalkyl, $C_{2-3}$ hydroxyalkyl, $C_{2-3}$ alkoxyalkyl, $C_{6-10}$ aryl, or a 5 to 10 membered heteroaryl having 1, 2, 3, or 4 heteroatoms selected from O, S, and N;

alternatively, 2 $R^e$s along with the atom to which they are attached, join to form a 3 to 6 membered saturated ring, containing 0-2 heteroatoms selected from O, S, or N; and n is 0, 1, or 2.

2. A compound of claim 1, or salt thereof, wherein:

$R^1$ is:

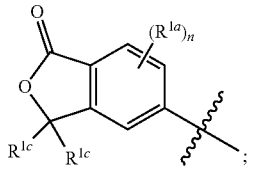

each $R^{1a}$ is independently selected from F, Cl, $C_{1-3}$ alkyl, $C_{1-3}$ fluoroalkyl, and $C_{3-6}$ cycloalkyl;

$R^{1c}$ is independently H, deuterium, $C_{1-2}$ alkyl, or $C_{3-6}$ cycloalkyl; and n is zero, 1, or 2.

3. A compound of claim 2, or salt thereof, wherein:

$R^2$ is phenyl, pyridinyl, indolyl, indazolyl, benzo[d]oxazol-onyl, pyrazolo[4,3-b]pyridinyl, pyridin-2-onyl, pyrazolyl, [1,2,4]triazolo[1,5-a]pyridinyl, imidazo[1,2-b]pyridazinyl, pyrazinyl, pyrazolo[1,5-a]pyrimidinyl, thiazolyl, thiophenyl, 1,2,3-triazolyl, benzo[d][1,2,3]triazolyl, [1,2,4]triazolo[4,3-b]pyridazinyl, benzo[d]imidazolyl, imidazolyl, pyrazolo[3,4-b]pyridinyl, pyrazolo[3,4-c]pyridinyl, pyrazolo[4,3-c]pyridinyl, pyrrolyl, pyrrolo[2,3-b]pyridinyl, pyrrolo[2,3-c]pyridinyl, pyrrolo[3,2-b]pyridinyl, pyrrolo[3,2-c]pyridinyl, pyrazolo[1,5-a]pyrimidinyl, tetrazolyl, 1,2,4-triazolyl, isothiazolyl, isoxazolyl, oxazolyl, pyridazinyl, pyrimidinyl, or benzo[d]oxazol-2-onyl, triazolyl, oxadiazolyl, or pyrrolopyridinyl, each being substituted with 0-3 $R^{2a}$.

4. A compound of claim 3, or salt thereof, wherein:

Ring B is pyridinyl, pyrimidinyl, [pyrrazolyl] *pyrazolyl*, thiazolyl, imidazolyl, triazolyl, tetrazolyl, oxadiazolyl, thiadiazolyl, isoxazolyl, pyrazinyl, oxazolyl, or pyridazinyl.

5. A compound of claim 4, or salt thereof, wherein:

V is —O—, —$CR^5R^5$—, or —C(=O)—;

wherein if V is —O—, or $NR^4$, then Y is not $C(R^6)_2$;

Y is —$C(R^6)_2$—, —$C(R^6)_2$—$C(R^6)_2$—, —C(=O)—, —C(=O)—$C(R^6)_2$—, or —$C(R^6)_2$—C(O)—; and $L^1$ is —$C(R)_2$—, —C(O)—, or —$CH_2$—$C(R)_2$—; wherein R is independently from hydrogen, F, OH, $C_{1-3}$ alkyl, $C_{1-3}$ hydroxyalkyl, $C_{1-3}$ alkoxyalkyl, or $C_{1-3}$fluoroalkyl.

6. A compound of claim 5, or salt thereof, wherein:

$R^2$ is phenyl, pyridinyl, indolyl, indazolyl, benzo[d]oxazol-2(3H)-onyl, pyrazolo[4,3-b]pyridinyl, pyridin-2(1H)-onyl, pyrazolyl, pyrimidinyl, imidazolyl, pyrazolyl, triazolyl, oxadiazolyl, thiadiazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, *or* pyrazolo[1,5-a]pyrimidinyl, [or benzo[d]oxazol-2(3H )-only,] each being substituted with 0-3 $R^{2a}$; and $R^{2a}$ is OH, =O, CN, halo, $C_{1-4}$ alkyl, [$SO_2C_{1-4}$] *$SO_2C_{1-3}$* alkyl, *or* oxazolidin-2-one substituted with 0-1 $R^{2b}$;

$R^{2b}$ is $C_{1-3}$alkyl, $C_{1-3}$ fluoroalkyl, $C_{1-3}$ alkoxy, or $C_{1-3}$ fluoroalkoxy.

7. A compound of claim 6, or salt thereof, wherein:

$R^1$ is

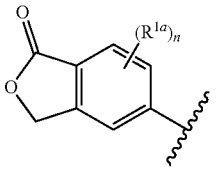

$R^{1a}$ is independently H or —$CH_3$.

8. The compound according to claim 7, or salt thereof, wherein:

Ring B is pyridinyl, triazolyl, thiazolyl, oxadiazolyl, imidazolyl, or [pyrrazolyl] *pyrazolyl*; and $R^2$ is phenyl, pyridinyl, pyrimidinyl, benzo[d]oxazol-2(3H)-onyl, imidazolyl, pyrazolyl, triazolyl, or oxadiazolyl, each being substituted with 0-3 $R^{2a}$.

9. The compound according to claim 8, or salt thereof, wherein:

V is —O—, —$NR^4$—, or —$CR^5R^5$—;

Y is —$C(R^6)_2$—$C(R^6)_2$— or —$C(R^6)_2$—;

$L^1$ is —$C(R)_2$—; wherein R is independently hydrogen, F, OH, $C_{1-3}$ alkyl, $C_{1-3}$ hydroxyalkyl, $C_{1-3}$ alkoxyalkyl, or $C_{1-3}$ fluoroalkyl; and $R^6$ is independently H, $C_{1-3}$-alkyl, $C_{1-3}$-fluoroalkyl, or $C_{3-6}$-cycloalkyl.

10. A compound of claim 1, or salt thereof, wherein the compound is selected from (R)-4-methyl-6-(4-((2-(4-methyl-1-oxo-1,3-dihydroisobenzofuran-5-yl)morpholino)methyl)-1H-pyrazol-1-yl)nicotinonitrile;

(R)-4-methyl-6-(4-((3-(4-methyl-1-oxo-1,3-dihydroisobenzofuran-5-yl)piperazin-1-yl)methyl)-1H-pyrazol-1-yl)nicotinonitrile;

(R)-3-methyl-5-(5-((2-(4-methyl-1-oxo-1,3-dihydroisobenzofuran-5-yl)morpholino)methyl)pyridin-2-yl)benzo[d]oxazol-2(3H)-one;

5-(4-((4,4-difluoro-3-(4-methyl-1-oxo-1,3-dihydroisobenzofuran-5-yl)piperidin-1-yl)methyl)-1H-pyrazol-1-yl)-3-methylbenzo[d] oxazol-2(3H)-one;

6-(4-((4,4-difluoro-3-(4-methyl-1-oxo-1,3-dihydroisobenzofuran-5-yl)piperidin-1-yl)methyl)-1H-pyrazol-1-yl)-4-methylnicotinonitrile;

(R)-6-(5-methoxy-4-((3-(4-methyl-1-oxo-1,3-dihydroisobenzofuran-5-yl)piperazin-1-yl)methyl)-1H-pyrazol-1-yl)-4-methylnicotinonitrile;

(R)-4-methyl-5-(4-((1-(2-methylthiazol-5-yl)-1H-pyrazol-4-yl)methyl)morpholin-2-yl)isobenzofuran-1(3H)-one;

(R)-4-cyclopropyl-6-(4-(2-(4-methyl-1-oxo-1,3-dihydroisobenzofuran-5-yl)morpholino)methyl)-1H-pyrazol-1-yl)nicotinonitrile;

(R)-4-methyl-6-(4-((5-(4-methyl-1-oxo-1,3-dihydroisobenzofuran-5-yl)-2-oxooxazolidin-3-yl)methyl)-1H-pyrazol-1-yl)nicotinonitrile;

(R)-4-methyl-6-(4-((2-(4-methyl-1-oxo-1,3-dihydroisobenzofuran-5-yl)-5-oxomorpholino)methyl)-1H-pyrazol-1-yl)nicotinonitrile;

[(R)-4-methoxy-6 (4 (2 (2 (4 methyl-1-oxo-1,3-dihydroisobenzofuran-5-yl)morpholino)ethyl)-1H-pyrazol-1-yl)nicotinonitrile;]

*(R)-4-methoxy-6-(4-(2-(2-(4-methyl-1-oxo-1,3-dihydroisobenzofuran-5-yl)morpholino)ethyl)-1H-pyrazol-1-yl)nicotinonitrile;*

(R)-6-(5-((2-(4-methyl-1-oxo-1,3-dihydroisobenzofuran-5-yl)morpholino)methyl)-1,3,4-oxadiazol-2-yl)nicotinonitrile;

(R)-4-methyl-6-(5-((3-(4-methyl-1-oxo-1,3-dihydroisobenzofuran-5-yl)piperazin-1-yl)methyl)-1,3,4-oxadiazol-2-yl)nicotinonitrile;

(R)-4-methoxy-6-(4-((3-(4-methyl-1-oxo-1,3-dihydroisobenzofuran-5-yl)piperazin-1-yl)methyl)-1H-imidazol-1-yl)nicotinonitrile;

(R)-4-methyl-6-(4-((3-(4-methyl-1-oxo-1,3-dihydroisobenzofuran-5-yl)-5-oxopiperazin-1-yl)methyl)-1H-pyrazol-1-yl)nicotinonitrile;

(R)-4-methyl-5-(4-((6-(4-methyl-1H-imidazol-1-yl)pyridin-3-yl)methyl)morpholin-2-yl)isobenzofuran-1(3H)-one;

(R)-4-methoxy-5'-((5-(4-methyl-1-oxo-1,3-dihydroisobenzofuran-5-yl)-2-oxooxazolidin-3-yl)methyl)-[2,2'-bipyridine]-5-carbonitrile;

6-(4-(1-hydroxy-2-((R)-2-(4-methyl-1-oxo-1,3-dihydroisobenzofuran-5-yl)morpholino)ethyl)-1H-pyrazol-1-yl)-4-methylnicotinonitrile (Diastereomer-I & II);

(R)-3-methyl-5-(5-((2-(4-methyl-1-oxo-1,3-dihydroisobenzofuran-5-yl)morpholino)methyl)thiazol-2-yl)benzo[d]oxazol-2(3H)-one;

(R)-3-methyl-5-(5-(2-(4-methyl-1-oxo-1,3-dihydroisobenzofuran-5-yl)morpholine-4-carbonyl)thiazol-2-yl)benzo[d]oxazol-2(3H)-one;

(R)-1-(5-((3-(4-methyl-1-oxo-1,3-dihydroisobenzofuran-5-yl)piperazin-1-yl)methyl)thiazol-2-yl)-1H-imidazole-4-carbonitrile;

(R)-4-methyl-6-(4-((3-(4-methyl-1-oxo-1,3-dihydroisobenzofuran-5-yl)piperazin-1-yl)methyl)-2H-1,2,3-triazol-2-yl)nicotinonitrile;

(R)-4-methyl-6-(4-((3-(4-methyl-1-oxo-1,3-dihydroisobenzofuran-5-yl)piperazin-1-yl)methyl)-1H-1,2,3-triazol-1-yl)nicotinonitrile;

Methyl-(R)-4-((1-(5-cyano-4-methylpyridin-2-yl)-1H-pyrazol-4-yl)methyl)-2-(4-methyl-1-oxo-1,3-dihydroisobenzofuran-5-yl)piperazine-1-carboxylate;

(S)-4-methyl-6-(4-((2-(4-methyl-1-oxo-1,3-dihydroisobenzofuran-5-yl)morpholino)methyl)-1H-pyrazol-1-yl)nicotinonitrile;

(R)-3-methyl-5-(4-((2-(4-methyl-1-oxo-1,3-dihydroisobenzofuran-5-yl)morpholino)methyl)-1H-pyrazol-1-yl)benzo[d]oxazol-2(3H)-one;

(R)-6-(5-methoxy-4-((2-(4-methyl-1-oxo-1,3-dihydroisobenzofuran-5-yl)morpholino)methyl)-1H-pyrazol-1-yl)-4-methylnicotinonitrile;

(R)-4-methoxy-6-(4-((2-(4-methyl-1-oxo-1,3-dihydroisobenzofuran-5-yl)morpholino)methyl)-1H-imidazol-1-yl)nicotinonitrile;

(R)-6-(4-((2-(4-methyl-1-oxo-1,3-dihydroisobenzofuran-5-yl)morpholino)methyl)-1H-imidazol-1-yl)nicotinonitrile;

(R)-3-methyl-5-(4-((2-(4-methyl-1-oxo-1,3-dihydroisobenzofuran-5-yl)morpholino)methyl)-1H-imidazol-1-yl)benzo[d]oxazol-2(3H)-one;

(R)-4-methyl-6-(5-((2-(4-methyl-1-oxo-1,3-dihydroisobenzofuran-5-yl)morpholino)methyl)-1,3,4-oxadiazol-2-yl)nicotinonitrile;

[(R)-4-methyl-6 (4 (2 (2 (4 methyl-1-oxo-1,3-isobenzofuran-5-yl)morpholino)ethyl)-1H-pyrazol-1-yl)nicotinonitrile;]

*(R)-4-methyl-6-(4-(2-(2-(4-methyl-1-oxo-1,3-isobenzofuran-5-yl)morpholino)ethyl)-1H-pyrazol-1-yl)nicotinonitrile;*

(R)-4-methoxy-6-(5-((2-(4-methyl-1-oxo-1,3-dihydroisobenzofuran-5-yl)morpholino)methyl)thiazol-2-yl)nicotinonitrile;

(R)-4-methyl-6-(5-(2-(4-methyl-1-oxo-1,3-dihydroisobenzofuran-5-yl)morpholine-4-carbonyl)thiazol-2-yl)nicotinonitrile;

(R)-4-methoxy-6-(5-(2-(4-methyl-1-oxo-1,3-dihydroisobenzofuran-5-yl)morpholine-4-carbonyl)thiazol-2-yl)nicotinonitrile;

(R)-4-methoxy-5'-((2-(4-methyl-1-oxo-1,3-dihydroisobenzofuran-5-yl)morpholino)methyl)-[2,2'-bipyridine]-5-carbonitrile;

(R)-4-methyl-5-(4-((2-(4-methyl-1H-imidazol-1-yl)thiazol-5-yl)methyl)morpholin-2-yl)isobenzofuran-1(3H)-one;

(R)-1-(5-((2-(4-methyl-1-oxo-1,3-dihydroisobenzofuran-5-yl)morpholino)methyl)pyridin-2-yl)-1H-imidazole-4-carbonitrile;

(R)-4-methyl-5-(4-((1-(thiophen-3-yl)-1H-pyrazol-4-yl)methyl)morpholin-2-yl)isobenzofuran-1(3H)-one;

(R)-4-methyl-5-(4-((1-(pyrazin-2-yl)-1H-pyrazol-4-yl)methyl)morpholin-2-yl)isobenzofuran-1(3H)-one;

(R)-4-(4-((2-(4-methyl-1-oxo-1,3-dihydroisobenzofuran-5-yl)morpholino)methyl)-1H-pyrazol-1-yl)benzonitrile;

(R)-4-methyl-5-(4-((1-(6-methylpyrazin-2-yl)-1H-pyrazol-4-yl)methyl)morpholin-2-yl)isobenzofuran-1(3H)-one;

(R)-5-(4-((2-(4-methyl-1-oxo-1,3-dihydroisobenzofuran-5-yl)morpholino)methyl)-1H-pyrazol-1- yl)nicotinonitrile;

(R)-3-(4-((2-(4-methyl-1-oxo-1,3-dihydroisobenzofuran-5-yl)morpholino)methyl)-1H-pyrazol-1-yl)benzonitrile;

(R)-4-methyl-5-(4-((1-(pyridin-4-yl)-1H-pyrazol-4-yl)methyl)morpholin-2-yl)isobenzofuran-1(3H)-one;

(R)-4-methyl-5-(4-((1-(4-(methylsulfonyl)phenyl)-1H-pyrazol-4-yl)methyl)morpholin-2-yl)isobenzofuran-1(3H)-one;

(R)-2-methyl-4-(4-((2-(4-methyl-1-oxo-1,3-dihydroisobenzofuran-5-yl)morpholino)methyl)-1H-pyrazol-1-yl)benzonitrile;

(R)-3-methyl-4-(4-((2-(4-methyl-1-oxo-1,3-dihydroisobenzofuran-5-yl)morpholino)methyl)-1H-pyrazol-1-yl)benzonitrile;

(R)-5-(4-((2-(4-methyl-1-oxo-1,3-dihydroisobenzofuran-5-yl)morpholino)methyl)-1H-pyrazol-1-yl)picolinonitrile;

(R)-2-methoxy-4-(4-((2-(4-methyl-1-oxo-1,3-dihydroisobenzofuran-5-yl)morpholino)methyl)-1H-pyrazol-1-yl)benzonitrile;

(R)-4-methyl-5-(4-((1-(pyrazolo[1,5-a]pyrimidin-5-yl)-1H-pyrazol-4-yl)methyl)morpholin-2-yl)isobenzofuran-1(3H)-one;

(R)-3-methoxy-4-(4-((2-(4-methyl-1-oxo-1,3-dihydroisobenzofuran-5-yl)morpholino)methyl)-1H-pyrazol-1-yl)benzonitrile;

(R)-4-methyl-6-(3-methyl-4-((2-(4-methyl-1-oxo-1,3-dihydroisobenzofuran-5-yl)morpholino)methyl)-1H-pyrazol-1-yl)nicotinonitrile;

(R)-4-methyl-6-(3-((2-(4-methyl-1-oxo-1,3-dihydroisobenzofuran-5-yl)morpholino)methyl)-1H-pyrazol-1-yl)nicotinonitrile;

(S)-4-methyl-6-(4-(3-(4-methyl-1-oxo-1,3-dihydroisobenzofuran-5-yl)piperazin-1-yl)methyl)-1H-pyrazol-1-yl)nicotinonitrile;

(R)-5-(5-methoxy-4-((3-(4-methyl-1-oxo-1,3-dihydroisobenzofuran-5-yl)piperazin-1-yl)methyl)-1H-pyrazol-1-yl)-3-methylbenzo[d]oxazol-2(3H)-one;

(R)-7-fluoro-3-methyl-5-(4-((3-(4-methyl-1-oxo-1,3-dihydroisobenzofuran-5-yl)piperazin-1-yl)methyl)-1H-pyrazol-1-yl)benzo[d]oxazol-2(3H)-one;

(R)-7-methoxy-3-methyl-5-(4-((3-(4-methyl-1-oxo-1,3-dihydroisobenzofuran-5-yl)piperazin-1-yl)methyl)-1H-pyrazol-1-yl)benzo[d]oxazol-2(3H)-one;

(R)-3,7-dimethyl-5-(4-((3-(4-methyl-1-oxo-1,3-dihydroisobenzofuran-5-yl)piperazin-1-yl)methyl)-1H-pyrazol-1-yl)benzo[d]oxazol-2(3H)-one;

(R)-3-methyl-5-(4-((3-(4-methyl-1-oxo-1,3-dihydroisobenzofuran-5-yl)piperazin-1-yl)methyl)-1H-pyrazol-1-yl)benzo[d]oxazol-2(3H)-one;

(R)-4-methoxy-6-(4-((3-(4-methyl-1-oxo-1,3-dihydroisobenzofuran-5-yl)piperazin-1-yl)methyl)-1H-pyrazol-1-yl)nicotinonitrile;

(R)-3-methyl-5-(4-((3-(4-methyl-1-oxo-1,3-dihydroisobenzofuran-5-yl)piperazin-1-yl)methyl)-1H-1,2,3-triazol-1-yl)benzo[d]oxazol-2(3H)-one;

(R)-6-(5-((3-(4-methyl-1-oxo-1,3-dihydroisobenzofuran-5-yl)piperazin-1-yl)methyl)-1,3,4-oxadiazol-2-yl)nicotinonitrile;

(R)-4-methoxy-5'-((3-(4-methyl-1-oxo-1,3-dihydroisobenzofuran-5-yl)piperazin-1-yl)methyl)-[2,2'-bipyridine]-5-carbonitrile;

(R)-1-(5-((3-(4-methyl-1-oxo-1,3-dihydroisobenzofuran-5-yl)piperazin-1-yl)methyl)pyridin-2-yl)-1H-pyrazole-4-carbonitrile;

(R)-1-(5-((3-(4-methyl-1-oxo-1,3-dihydroisobenzofuran-5-yl)piperazin-1-yl)methyl)pyridin-2-yl)-1H-imidazole-4-carbonitrile;

(R)-4-methyl-5-(4-((6-(4-methyl-1H-imidazol-1-yl)pyridin-3-yl)methyl)piperazin-2-yl)isobenzofuran-1(3H)-one;

(R)-4-methyl-5-(4-((6-(3-methyl-1H-1,2,4-triazol-1-yl)pyridin-3-yl)methyl)piperazin-2-yl)isobenzofuran-1(3H)-one;

(R)-6-(4-((4-acetyl-3-(4-methyl-1-oxo-1,3-dihydroisobenzofuran-5-yl)piperazin-1-yl)methyl)-1H-pyrazol-1-yl)-4-methylnicotinonitrile;

(R)-4-methyl-6-(4-((3-(4-methyl-1-oxo-1,3-dihydroisobenzofuran-5-yl)-4-(methylsulfonyl)piperazin-1-yl)methyl)-1H-pyrazol-1-yl)nicotinonitrile;

(R)-4-methyl-6-(4-((4-methyl-3-(4-methyl-1-oxo-1,3-dihydroisobenzofuran-5-yl)piperazin-1-yl)methyl)-1H-pyrazol-1-yl)nicotinonitrile;

(R)-3-methyl-5-(4-((3-(4-methyl-1-oxo-1,3-dihydroisobenzofuran-5-yl)-5-oxopiperazin-1-yl)methyl)-1H-pyrazol-1-yl)benzo[d]oxazol-2(3H)-one;

(R)-3-methyl-5-(4-((3-(4-methyl-1-oxo-1,3-dihydroisobenzofuran-5-yl)-5-oxopiperazin-1-yl)methyl)-1H-1,2,3-triazol-1-yl)benzo[d]oxazol-2(3H)-one;

(R)-1-(5-((3-(4-methyl-1-oxo-1,3-dihydroisobenzofuran-5-yl)-5-oxopiperazin-1-yl)methyl)pyridine-2-yl)-1H-1,2,4-triazole-3-carbonitrile;

(R)-4-methoxy-5'-((3-(4-methyl-1-oxo-1,3-dihydroisobenzofuran-5-yl)-5-oxopiperazin-1-yl)methyl)-2,2'-bipyridine-5-carbonitrile;

(R)-6-(4-methyl-1-oxo-1,3-dihydroisobenzofuran-5-yl)-4-((6-(3-methyl-1H-1,2,4-triazol-1-yl)pyridin-3-yl)methyl)piperazin-2-one;

(R)-6-(4-methyl-1-oxo-1,3-dihydroisobenzofuran-5-yl)-4-((6-(4-methyl-1H-imidazol-1-yl)pyridin-3-yl)methyl)piperazin-2-one;

(R)-4-methyl-6-(4-((4-methyl-3-(4-methyl-1-oxo-1,3-dihydroisobenzofuran-5-yl)-5-oxopiperazin-1-yl)methyl)-1H-pyrazol-1-yl)nicotinonitrile;

(R)-4-methoxy-6-(4-((5-(4-methyl-1-oxo-1,3-dihydroisobenzofuran-5-yl)-2-oxooxazolidin-3-yl)methyl)-1H-imidazol-1-yl)nicotinonitrile;

(R)-6-(5-methoxy-4-((5-(4-methyl-1-oxo-1,3-dihydroisobenzofuran-5-yl)-2-oxooxazolidin-3-yl)methyl)-1H-pyrazol-1-yl)-4-methylnicotinonitrile;

(R)-3-methyl-5-(4-((5-(4-methyl-1-oxo-1,3-dihydroisobenzofuran-5-yl)-2-oxooxazolidin-3-yl)methyl)-1H-pyrazol-1-yl)benzo[d]oxazol-2(3H)-one;

6-(4-(((3R,5R)-3-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile;

6-(4-((3,3-dimethyl-5-(4-methyl-1-oxo-1,3-dihydroisobenzofuran-5-yl)piperazin-1-yl)methyl)-2H-1,2,3-triazol-2-yl)-4-methylnicotinonitrile;

4-methyl-6-(4-(((3S,5R)-3-methyl-5-(4-methyl-1-oxo-1,3-dihydroisobenzofuran-5-yl)piperazin-1-yl)methyl)-2H-1,2,3-triazol-2-yl)nicotinonitrile;

6-(4-(((3R,4R)-4-hydroxy-3-(4-methyl-1-oxo-1,3-dihydroisobenzofuran-5-yl)piperidin-1-yl)methyl)-1H-1,2,3-triazol-1-yl)-4-methylnicotinonitrile;

2,4-dimethyl-6-(4-(((3S,5R)-3-methyl-5-(4-methyl-1-oxo-1,3-dihydroisobenzofuran-5-yl)piperazin-1-yl)methyl)-2H-1,2,3-triazol-2-yl)nicotinonitrile;

4-methoxy-2-methyl-6-(4-(((3S,5R)-3-methyl-5-(4-methyl-1-oxo-1,3-dihydroisobenzofuran-5-yl)piperazin-1-yl)methyl)-1H-1,2,3-triazol-1-yl)nicotinonitrile;

6-(4-((3-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile, (Enantiomer-III);

6-(4-((3-(hydroxymethyl)-5-(4-methyl-1 oxo-1,3-dihydroisobenzofuran-5-yl)piperazin-1-yl)methyl)-1H-1,2,3-triazol-1-yl)-4-methylnicotinonitrile, (Enantiomer-III);

6-(4-((3-(hydroxymethyl)-5-(4-methyl-1-oxo-1,3-dihydroisobenzofuran-5-yl)piperazin-1-yl)methyl)-1H-pyrazol-1-yl)-4-methoxynicotinonitrile, (Enantiomer-III);

6-(4-((3-(hydroxymethyl-d2)-5-(4-methyl-1-oxo-1,3-dihydroisobenzofuran-5-yl)piperazin-1-yl)methyl)-1H-pyrazol-1-yl)-4-methylnicotinonitrile, (Enantiomer-I);

1-(5-(((3R,5R)-3-(hydroxymethyl)-5-(4-methyl-1-oxo-1,3-dihydroisobenzofuran-5-yl)piperazin-1-yl)methyl)pyridin-2-yl)-3-methyl-1H-pyrazole-4-carbonitrile;

6-(4-(((3R,4R)-4-hydroxy-3-(4-methyl-1-oxo-1,3-dihydroisobenzofuran-5-yl)piperidin-1-yl)methyl)-1H-pyrazol-1-yl)-2,4-dimethylnicotinonitrile;

2-methoxy-6-(4-(((3S,5R)-3-methyl-5-(4-methyl-1-oxo-1,3-dihydroisobenzofuran-5-yl)piperazin-1-yl)methyl)-1H-pyrazol-1-yl)nicotinonitrile;

5-((2R,6S)-4-((2-(4,5-dimethyl-1H-imidazol-1-yl)pyrimidin-5-yl)methyl)-6-methylpiperazin-2-yl)-4-methylisobenzofuran-1(3H)-one;

4,6-dimethyl-2-(4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile;

4-methyl-2-(4-(((3S,5R)-3-methyl-5-(4-methyl-1-oxo-1,3-dihydroisobenzofuran-5-yl)piperazin-1-yl)methyl)-1H-pyrazol-1-yl)pyrimidine-5-carbonitrile;

4-methoxy-6-(4-(((3S,5R)-3-methyl-5-(4-methyl-1-oxo-1,3-dihydroisobenzofuran-5-yl)piperazin-1-yl)methyl)-1H-imidazol-1-yl)nicotinonitrile;

4-methyl-6-(4-(((3S,5R)-3-methyl-5-(4-methyl-1-oxo-1,3-dihydroisobenzofuran-5-yl)piperazin-1-yl)methyl)-1H-imidazol-1-yl)nicotinonitrile;

4-methoxy-2-(4-(((3S,5R)-3-methyl-5-(4-methyl-1-oxo-1,3-dihydroisobenzofuran-5-yl)piperazin-1-yl)methyl)-1H-pyrazol-1-yl)pyrimidine-5-carbonitrile;

4-methyl-2-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyrimidine-5-carbonitrile;

2-methoxy-4-(4-(((3S,5R)-3-methyl-5-(4-methyl-1-oxo-1,3-dihydroisobenzofuran-5-yl)piperazin-1-yl)methyl)-1H-imidazol-1-yl)benzonitrile;

4-methyl-5-((2R,6S)-6-methyl-4-((1-(2-methylpyridin-4-yl)-1H-pyrazol-4-yl)methyl)piperazin-2-yl)isobenzofuran-1(3H)-one;

4-methoxy-2-(4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile;

2-(4-(((3R,5R)-3-(hydroxymethyl)-5-(4-methyl-1-oxo-1,3-dihydroisobenzofuran-5-yl)piperazin-1-yl)methyl)-2H-1,2,3-triazol-2-yl)-4-methylpyrimidine-5-carbonitrile;

4-methyl-6-(4-(((3S,5R)-3-methyl-5-(4-methyl-1-oxo-1,3-dihydroisobenzofuran-5-yl)piperazin-1-yl)methyl)-1H-pyrazol-1-yl)nicotinonitrile;

4-methyl-6-(4-(((3S,5R)-3-methyl-5-(4-methyl-1-oxo-1,3-dihydroisobenzofuran-5-yl)piperazin-1-yl)methyl)-1H-1,2,3-triazol-1-yl)nicotinonitrile;

4-methoxy-6-(4-(((3S,5R)-3-methyl-5-(4-methyl-1-oxo-1,3-dihydroisobenzofuran-5-yl)piperazin-1-yl)methyl)-2H-1,2,3-triazol-2-yl)nicotinonitrile;

3-methyl-1-(5-(((3S,5R)-3-methyl-5-(4-methyl-1-oxo-1,3-dihydroisobenzofuran-5-yl)piperazin-1-yl)methyl)pyrimidin-2-yl)-1H-pyrazole-4-carbonitrile;

5-(4-(((3R,5R)-3-(hydroxymethyl)-5-(4-methyl-1-oxo-1,3-dihydroisobenzofuran-5-yl)piperazin-1-yl)methyl)-2H-1,2,3-triazol-2-yl)-3-methylbenzo[d]oxazol-2(3H)-one;

6-(4-(((3R,4R)-4-hydroxy-3-(4-methyl-1-oxo-1,3-dihydroisobenzofuran-5-yl)piperidin-1-yl)methyl)-1H-pyrazol-1-yl)-4-methylnicotinonitrile;

6-(4-(((3R,4R)-4-hydroxy-3-(4-methyl-1-oxo-1,3-dihydroisobenzofuran-5-yl)piperidin-1-yl)methyl)-2H-1,2,3-triazol-2-yl)-4-methoxynicotinonitrile;

6-(4-(((3R,4R)-4-hydroxy-3-(4-methyl-1-oxo-1,3-dihydroisobenzofuran-5-yl)piperidin-1-yl)methyl)-1H-pyrazol-1-yl)-4-methoxynicotinonitrile;

4,4-methyl-6-(5-(((3S,5R)-3-methyl-5-(4-methyl-1-oxo-1,3-dihydroisobenzofuran-5-yl)piperazin-1-yl)methyl)thiazol-2-yl)nicotinonitrile;

6-(4-((4-hydroxy-4-methyl-3-(4-methyl-1-oxo-1,3-dihydroisob enzofuran-5-yl)piperidin-1-yl)methyl)-1H-pyrazol-1-yl)-4-methylnicotinonitrile;

4-methyl-6-(4-((2-methyl-3-(4-methyl-1-oxo-1,3-dihydroisobenzofuran-5-yl)piperazin-1-yl)methyl)-1H-pyrazol-1-yl)nicotinonitrile;

6-(4-((4-hydroxy-3,3-dimethyl-5-(4-methyl-1-oxo-1,3-dihydroisobenzofuran-5-yl)piperidin-1-yl)methyl)-1H-pyrazol-1-yl)-4-methylnicotinonitrile;

4-methyl-6-(5-(((3S,5R)-3-methyl-5-(4-methyl-1-oxo-1,3-dihydroisobenzofuran-5-yl)piperazin-1-yl)methyl)-2-oxooxazol-3(2H)-yl)nicotinonitrile;

(R)-4-methyl-6-(4-((4-(4-methyl-1-oxo-1,3-dihydroisobenzofuran-5-yl)-2-oxoimidazolidin-1-yl)methyl)-1H-pyrazol-1-yl)nicotinonitrile;

(R)-4-methyl-6-(4-((4-(4-methyl-1-oxo-1,3-dihydroisobenzofuran-5-yl)-1,1-dioxido-1,2,5-thiadiazolidin-2-yl)methyl)-1H-pyrazol-1-yl)nicotinonitrile;

2-methyl-6-(5-(((3S,5R)-3-methyl-5-(4-methyl-1-oxo-1,3-dihydroisobenzofuran-5-yl)piperazin-1-yl)methyl)pyridin-2-yl)pyridazin-3(2H)-one;

4-methyl-6-(4-(1-((R)-3-(4-methyl-1-oxo-1,3-dihydroisobenzofuran-5-yl)piperazin-1-yl)ethyl)-2H-1,2,3-triazol-2-yl)nicotinonitrile (Dia-I:Ena-I);

4-methyl-6-(4-(1-((R)-3-(4-methyl-1-oxo-1,3-dihydroisobenzofuran-5-yl)piperazin-1-yl)ethyl)-2H-1,2,3-triazol-2-yl)nicotinonitrile (Dia-II:Ena-I);

4-methyl-6-(3-(((3S,5R)-3-methyl-5-(4-methyl-1-oxo-1,3-dihydroisobenzofuran-5-yl)piperazin-1-yl)methyl)-1H-1,2,4-triazol-1-yl)nicotinonitrile;

6-(4-((2-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile (Dia-I:Ena-I);

6-(4-((2-(hydroxymethyl)-5-(4-methyl-1-oxo-1,3-dihydroisobenzofuran-5-yl)piperazin-1-yl)methyl)-1H-pyrazol-1-yl)-4-methylnicotinonitrile (Dia-I:Ena-II);

6-(5-(((3R,4R)-4-hydroxy-3-(4-methyl-1-oxo-1,3-dihydroisobenzofuran-5-yl)piperidin-1-yl)methyl)thiazol-2-yl)-4-methylnicotinonitrile;

5-((2R,6S)-4-((1-(2-methoxypyridin-4-yl)-1H-imidazol-4-yl)methyl)-6-methylpiperazin-2-yl)-4-methylisobenzofuran-1(3H)-one;

5-((2R,6S)-4-((1-(2-(difluoromethyl)pyridin-4-yl)-1H-pyrazol-4-yl)methyl)-6-methylpiperazin-2-yl)-4-methylisobenzofuran-1(3H)-one;

4-methyl-5-((2R,6S)-6-methyl-4-((1-(2-(trifluoromethyl)pyridin-4-yl)-1H-pyrazol-4-yl)methyl)piperazin-2-yl)isobenzofuran-1(3H)-one;

[1-(difluoromethyl)-4-(4-(((3 S,5R)-3-methyl-5-(4-methyl-1-oxo-1,3-dihydroisobenzofuran-5-yl)piperazin-1-yl)methyl)-1H-pyrazol-1-yl)pyridin-2(1H)-one;]

*1-(difluoromethyl)-4-(4-(((3S,5R)-3-methyl-5-(4-methyl-1-oxo-1,3-dihydroisobenzofuran-5-yl)piperazin-1-yl)methyl)-1H-pyrazol-1-yl)pyridin-2(1H)-one;*

1-(5-(((3R,5R)-3-(hydroxymethyl)-5-(4-methyl-1-oxo-1,3-dihydroisobenzofuran-5-yl)piperazin--yl)methyl)pyridin-2-yl)-3-methyl-1H-pyrazole-4-carbonitrile;

1-(difluoromethyl)-4-(4-(((3S,5R)-3-methyl-5-(4-methyl-1-oxo-1,3-dihydroisobenzofuran-5-yl)piperazin-1-yl)methyl)-1H-imidazol-1-yl)pyridin-2(1H)-one;

6-(4-(((3R,4R)-4-hydroxy-3-(4-methyl-1-oxo-1,3-dihydroisobenzofuran-5-yl)piperidin-1-yl)methyl)oxazol-2-yl)-4-methylnicotinonitrile;

4-methyl-6-(5-(((3S,5R)-3-methyl-5-(4-methyl-1-oxo-1,3-dihydroisobenzofuran-5-yl)piperazin-1-yl)methyl)oxazol-2-yl)nicotinonitrile;

5-((2R,6S)-4-((1-(6-(difluoromethyl)pyridin-3-yl)-1H-imidazol-4-yl)methyl)-6-methylpiperazin-2-yl)-4-methylisobenzofuran-1(3H)-one;

(R)-3,4-dimethyl-5-(4-((3-(4-methyl-1-oxo-1,3-dihydroisobenzofuran-5-yl)piperazin-1-yl)methyl)-1H-pyrazol-1-yl)benzo[d]oxazol-2(3H)-one;

(R)-1-(5-((3-(4-methyl-1-oxo-1,3-dihydroisobenzofuran-5-yl)piperazin-1-yl)methyl)pyridin-2-yl)-1H-pyrazole-3-carbonitrile;

(R)-4-ethoxy-6-(4-((3-(4-methyl-1-oxo-1,3-dihydroisobenzofuran-5-yl)piperazin-1-yl)methyl)-1H-pyrazol-1-yl)nicotinonitrile;

(R)-1-(5-((3-(4-methyl-1-oxo-1,3-dihydroisobenzofuran-5-yl)piperazin-1-yl)methyl)pyridin-2-yl)-1H-pyrazole-4-carboxamide;

(R)-5-(4-((2-(2,4-dimethyl-1H-imidazol-1-yl)pyrimidin-5-yl)methyl)piperazin-2-yl)-4-methylisobenzofuran-1(3H)-one;

(R)-4-isopropoxy-6-(4-((3-(4-methyl-1-oxo-1,3-dihydroisobenzofuran-5-yl)piperazin-1-yl)methyl)-1H-pyrazol-1-yl)nicotinonitrile;

(R)-4-methyl-5-(4-((4-methyl-6-(4-methyl-1H-imidazol-1-yl)pyridin-3-yl)methyl)piperazin-2-yl)isobenzofuran-1(3H)-one;

(R)-4-methyl-5-(4-((2-methyl-6-(4-methyl-1H-imidazol-1-yl)pyridin-3-yl)methyl)piperazin-2-yl)isobenzofuran-1(3H)-one;

(R)-4,6'-dimethoxy-5'-((3-(4-methyl-1-oxo-1,3-dihydroisobenzofuran-5-yl)piperazin-1-yl)methyl)-[2,2'-bipyridine]-5-carbonitrile;

(R)-5-(4-((5-fluoro-6-(4-methyl-1H-imidazol-1-yl)pyridin-3-yl)methyl)piperazin-2-yl)-4-methylisobenzofuran-1(3H)-one;

(R)-4-methyl-6-(3-methyl-4-((3-(4-methyl-1-oxo-1,3-dihydroisobenzofuran-5-yl)piperazin-1-yl)methyl)-1H-pyrazol-1-yl)nicotinonitrile;

(R)-4-methyl-6-(5-methyl-4-((3-(4-methyl-1-oxo-1,3-dihydroisobenzofuran-5-yl)piperazin-1-yl)methyl)-1H-pyrazol-1-yl)nicotinonitrile;

(R)-4-methyl-5-(4-((6-(4-methyl-1H-imidazol-1-yl)-4-(trifluoromethyl)pyridin-3-yl)methyl)piperazin-2-yl)isobenzofuran-1(3H)-one;

(R)-5-(4-((2-(4,5-dimethyl-1H-imidazol-1-yl)pyrimidin-5-yl)methyl)piperazin-2-yl)-4-methylisobenzofuran-1(3H)-one;

(R)-5-(4-((4-methoxy-6-(4-methyl-1H-imidazol-1-yl)pyridin-3-yl)methyl)piperazin-2-yl)-4-methylisobenzofuran-1(3H)-one;

(R)-5-(4-((2-(5-(difluoromethyl)-4-methyl-1H-imidazol-1-yl)pyrimidin-5-yl)methyl)piperazin-2-yl)-4-methylisobenzofuran-1(3H)-one;

4,6-dimethyl-2-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyrimidine-5-carbonitrile;

3-(3-methyl-5-(4-(((3S,5R)-3-methyl-5-(4-methyl-1-oxo-1,3-dihydroisobenzofuran-5-yl)piperazin-1-yl)methyl)-1H-pyrazol-1-yl)phenyl)oxazolidin-2-one;

(R)-4-methyl-5-(4-((6-(4-methyl-1H-imidazol-1-yl)pyridazin-3-yl)methyl)piperazin-2-yl)isobenzofuran-1(3H)-one;

4-methoxy-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-I);

4-methoxy-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-II);

4-methyl-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-I);

4-methyl-6-(3-(((R)-3-(4-methyl-1-oxo-1,3-dihydroisobenzofuran-5-yl)piperazin-1-yl)methyl)pyrrolidin-1-yl)nicotinonitrile (Diastereomer-II);

4-methyl-6-(4-(((R)-3-(4-methyl-1-oxo-1,3-dihydroisobenzofuran-5-yl)piperazin-1-yl)methyl)-2-oxopyrrolidin-1-yl)nicotinonitrile (Diastereomer-II);

4-methoxy-6-(4-(((R)-3-(4-methyl-1-oxo-1,3-dihydroisobenzofuran-5-yl)piperazin-1-yl)methyl)-2-oxopyrrolidin-1-yl)nicotinonitrile (Diastereomer-I);

4-methyl-6-(5-(((R)-3-(4-methyl-1-oxo-1,3-dihydroisobenzofuran-5-yl)piperazin-1-yl)methyl)-2-oxooxazolidin-3-yl)nicotinonitrile (Diastereomer-II);

4-methyl-5-((2R,6S)-6-methyl-4-((1-(5-(methylsulfonyl)pyridin-2-yl)-1H-pyrazol-4-yl)methyl)piperazin-2-yl)isobenzofuran-1(3H)-one;

4-(4-(((3R,4R)-4-hydroxy-3-(4-methyl-1-oxo-1,3-dihydroisobenzofuran-5-yl)piperidin-1-yl)methyl)-1H-imidazol-1-yl)-2-methoxybenzonitrile;

6-(4-(((3R,4R)-4-hydroxy-3-(4-methyl-1-oxo-1,3-dihydroisobenzofuran-5-yl)piperidin-1-yl)methyl)-1H-imidazol-1-yl)-4-methylnicotinonitrile;

4-methyl-2-(4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile; -yl) isobenzofuran-1(3H)-one;

4-methoxy-2-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyrimidine-5-carbonitrile;

4-methoxy-2-(2-methyl-4-(((3S,5R)-3-methyl-5-(4-methyl-1-oxo-1,3-dihydroisobenzofuran-5-yl)piperazin-1-yl)methyl)-1H-imidazol-1-yl)pyrimidine-5-carbonitrile;

(R)-4-methoxy-6-(4-((3-(4-methyl-1-oxo-1,3-dihydroisobenzofuran-5-yl)piperazin-1-yl)methyl)-2H-1,2,3-triazol-2-yl)nicotinonitrile;

(R)-4-methyl-6-(4-methyl-5-((3-(4-methyl-1-oxo-1,3-dihydroisobenzofuran-5-yl)piperazin-1-yl)methyl)-2H-1,2,3-triazol-2-yl)nicotinonitrile;

4-methoxy-6-(4-(((3S,5R)-3-methyl-5-(4-methyl-1-oxo-1,3-dihydroisobenzofuran-5-yl)piperazin-1-yl)methyl)-2-oxopyrrolidin-1-yl)nicotinonitrile (Diastereomer-I);

6-(4-(((3R,4R)-4-hydroxy-3-(4-methyl-1-oxo-1,3-dihydroisobenzofuran-5-yl)piperidin-1-yl)methyl)-3-methyl-2-oxo-2,3-dihydro-1H-imidazol-1-yl)-4-methoxynicotinonitrile;

6-(3-isopropyl-4-((3S,5R)-3-methyl-5-(4-methyl-1-oxo-1,3-dihydroisobenzofuran-5-yl)piperazin-1-yl)methyl)-2-oxo-2,3-dihydro-1H-imidazol-1-yl)-4-methoxynicotinonitrile;

3-methyl-4-(((3S,5R)-3-methyl-5-(4-methyl-1-oxo-1,3-dihydroisobenzofuran-5-yl)piperazin-1-yl)methyl)-1-(2-methylpyrimidin-4-yl)-1,3-dihydro-2H-imidazol-2-one;

3-(5-(((3S,5R)-3-methyl-5-(4-methyl-1-oxo-1,3-dihydroisobenzofuran-5-yl)piperazin-1-yl)methyl)-[2,4'-bipyridin]-2'-yl)oxazolidin-2-one;

6-(4-((3,3-dimethyl-5-(4-methyl-1-oxo-1,3-dihydroisobenzofuran-5-yl)piperazin-1-yl)methyl)-5-methyl-2H-1,2,3-triazol-2-yl)-4-methylnicotinonitrile (Enantiomer-I);

4-methyl-6-(5-methyl-4-(((3S,5R)-3-methyl-5-(4-methyl-1-oxo-1,3-dihydroisobenzofuran-5-yl)piperazin-1-yl)methyl)-1H-1,2,3-triazol-1-yl)nicotinonitrile;

(R)-4-methyl-5-(4-((1-(1-methyl-1H-pyrrolo[2,3-b]pyridin-4-yl)-1H-pyrazol-4-yl)methyl)morpholin-2-yl)isobenzofuran-1(3H)-one;

4-methyl-5-((2R,6S)-6-methyl-4-((1-(p-tolyl)-1H-imidazol-4-yl)methyl)piperazin-2-yl)isobenzofuran-1(3H)-one;

4-methyl-5-((2R,6S)-6-methyl-4-((1-(3-methylpyridin-4-yl)-1H-imidazol-4-yl)methyl)piperazin-2-yl)isobenzofuran-1(3H)-one;

4-methyl-5-((2R,6S)-6-methyl-4-((1-(6-methylpyridin-3-yl)-1H-imidazol-4-yl)methyl)piperazin-2-yl)isobenzofuran-1(3H)-one;

5-((2R,6S)-4-((1-(2,6-dimethylpyridin-4-yl)-1H-imidazol-4-yl)methyl)-6-methylpiperazin-2-yl)-4-methylisobenzofuran-1(3H)-one;

5-((2R,6S)-4-((1-(2,2-difluorobenzo[d][1,3]dioxol-5-yl)-1H-imidazol-4-yl)methyl)-6-methylpiperazin-2-yl)-4-methylisobenzofuran-1(3H)-one;

(R)-4-methyl-6-(2-((3-(4-methyl-1-oxo-1,3-dihydroisobenzofuran-5-yl)piperazin-1-yl)methyl)pyrimidin-5-yl)nicotinonitrile;

(R)-2,4-dimethyl-6-(4-((3-(4-methyl-1-oxo-1,3-dihydroisobenzofuran-5-yl)piperazin-1-yl)methyl)-2H-1,2,3-triazol-2-yl)nicotinonitrile;

(R)-3-(2-(4-((3-(4-methyl-1-oxo-1,3-dihydroisobenzofuran-5-yl)piperazin-1-yl)methyl)-1H-pyrazol-1-yl)pyridin-4-yl)oxazolidin-2-one;

(R)-2,4-dimethyl-6-(4-((3-(4-methyl-1-oxo-1,3-dihydroisobenzofuran-5-yl)piperazin-1-yl)methyl)-1H-1,2,3-triazol-1-yl)nicotinonitrile;

(R)-4-methoxy-2-methyl-6-(4-((3-(4-methyl-1-oxo-1,3-dihydroisobenzofuran-5-yl)piperazin-1-yl)methyl)-1H-1,2,3-triazol-1-yl)nicotinonitrile;

(R)-4-methoxy-2-methyl-6-(4-((3-(4-methyl-1-oxo-1,3-dihydroisobenzofuran-5-yl)piperazin-1-yl)methyl)-2H-1,2,3-triazol-2-yl)nicotinonitrile;

(R)-2-methoxy-4-methyl-6-(4-((3-(4-methyl-1-oxo-1,3-dihydroisobenzofuran-5-yl)piperazin-1-yl)methyl)-1H-1,2,3-triazol-1-yl)nicotinonitrile;

6-(4-((3,3-dimethyl-5-(4-methyl-1-oxo-1,3-dihydroisobenzofuran-5-yl)piperazin-1-yl)methyl)-2H-1,2,3-triazol-2-yl)-4-methoxynicotinonitrile (Enantiomer-I);

4-methyl-6-(5-(((3S,5R)-3-methyl-5-(4-methyl-1-oxo-1,3-dihydroisobenzofuran-5-yl)piperazin-1-yl)methyl)-1,3,4-oxadiazol-2-yl)nicotinonitrile;

4-methoxy-6-(4-(2-((3S,5R)-3-methyl-5-(4-methyl-1-oxo-1,3-dihydroisobenzofuran-5-yl)piperazin-1-yl)ethyl)-1H-pyrazol-1-yl)nicotinonitrile;

6-(5-(((3R,4R)-4-hydroxy-3-(4-methyl-1-oxo-1,3-dihydroisobenzofuran-5-yl)piperidin-1-yl)methyl)isoxazol-3-yl)-4-methylnicotinonitrile;

5-((2R,6S)-4-((1-(4-methoxy-1,3,5-triazin-2-yl)-1H-pyrazol-4-yl)methyl)-6-methylpiperazin-2-yl)-4-methylisobenzofuran-1(3H)-one;

6-(4-(((3R,5R)-3-(hydroxymethyl)-4-methyl-5-(4-methyl-1-oxo-1,3-dihydroisobenzofuran-5-yl)piperazin-1-yl)methyl)-1H-pyrazol-1-yl)-4-methylnicotinonitrile;

6-(4-(((3S,5R)-3-methyl-5-(4-methyl-1-oxo-1,3-dihydroisobenzofuran-5-yl)piperazin-1-yl)methyl)-1H-pyrazol-1-yl)-4-(trifluoromethyl)nicotinonitrile;

4-methyl-6-(4-((3-(4-methyl-1-oxo-1,3-dihydroisobenzofuran-5-yl)piperidin-1-yl)methyl)-1H-pyrazol-1-yl)nicotinonitrile (Enantiomer-I);

(R)-2-(4-((3-(4-methyl-1-oxo-1,3-dihydroisobenzofuran-5-yl)piperazin-1-yl)methyl)-1H-pyrazol-1-yl)isonicotinonitrile;

6-(4-((3-hydroxy-5-(4-methyl-1-oxo-1,3-dihydroisobenzofuran-5-yl)piperidin-1-yl)methyl)-1H-pyrazol-1-yl)-4-methylnicotinonitrile (Enantiomer-IV);

6-(4-((3-methoxy-5-(4-methyl-1-oxo-1,3-dihydroisobenzofuran-5-yl)piperidin-1-yl)methyl)-1H-pyrazol-1-yl)-4-methylnicotinonitrile (Enantiomer-II);

(R)-5-(4-((2-(3,5-dimethyl-4H-1,2,4-triazol-4-yl)pyrimidin-5-yl)methyl)piperazin-2-yl)-4-methylisobenzofuran-1(3H)-one;

3-methyl-2-(4-((3S,5R)-3-methyl-5-(4-methyl-1-oxo-1,3-dihydroisobenzofuran-5-yl)piperazin-1-yl)methyl)-1H-pyrazol-1-yl)isonicotinonitrile;

6-(4-((3-fluoro-5-(4-methyl-1-oxo-1,3-dihydroisobenzofuran-5-yl)piperidin-1-yl)methyl)-1H-1,2,3-triazol-1-yl)-4-methylnicotinonitrile (Enantiomer-I);

6-(4-((3-(1-hydroxyethyl)-5-(4-methyl-1-oxo-1,3-dihydroisobenzofuran-5-yl)piperazin-1-yl)methyl)-1H-pyrazol-1-yl)-4-methoxynicotinonitrile (Enantiomer-I);

6-(4-((3-(difluoromethyl)-5-(4-methyl-1-oxo-1,3-dihydroisobenzofuran-5-yl)piperazin-1-yl)methyl)-1H-pyrazol-1-yl)-4-methylnicotinonitrile (Enantiomer-I);

4-methyl-5-((2R,6S)-6-methyl-4-((1-(5-methylpyrazin-2-yl)-1H-pyrazol-4-yl)methyl)piperazin-2-yl)isobenzofuran-1(3H)-one;

5-((2R,6S)-4-((1-(6-methoxypyrimidin-4-yl)-1H-pyrazol-4-yl)methyl)-6-methylpiperazin-2-yl)-4-methylisobenzofuran-1(3H)-one;

5-((2R,6S)-4-((1-(2-methoxypyrimidin-5-yl)-1H-pyrazol-4-yl)methyl)-6-methylpiperazin-2-yl)-4-methylisobenzofuran-1(3H)-one;

4-methyl-5-((2R,6S)-6-methyl-4-((1-(2-methylpyrimidin-5-yl)-1H-pyrazol-4-yl)methyl)piperazin-2-yl)isobenzofuran-1(3H)-one;

4-methyl-6-(3-(((3 S,5R)-3-methyl-5-(4-methyl-1-oxo-1,3-dihydroisobenzofuran-5-yl)piperazin-1-yl)methyl)isoxazol-5-yl)nicotinonitrile;

6-(4-((3-hydroxy-4-(4-methyl-1-oxo-1,3-dihydroisobenzofuran-5-yl)pyrrolidin-1-yl)methyl)-1H-pyrazol-1-yl)-4-methylnicotinonitrile (Diastereomer-I: Enantiomer-I);

6-(4-((3-fluoro-4-(4-methyl-1-oxo-1,3-dihydroisobenzofuran-5-yl)pyrrolidin-1-yl)methyl)-1H-pyrazol-1-yl)-4-methylnicotinonitrile (Diastereomer-I: Enantiomer-II);

6-(4-((3-(2-hydroxypropan-2-yl)-5-(4-methyl-1-oxo-1,3-dihydroisobenzofuran-5-yl)piperazin-1-yl)methyl)-1H-pyrazol-1-yl)-4-methylnicotinonitrile (Enantiomer-I);

4-methyl-6-(5-(((3S,5R)-3-methyl-5-(4-methyl-1-oxo-1,3-dihydroisobenzofuran-5-yl)piperazin-1-yl)methyl)isoxazol-3-yl)nicotinonitrile;

(R)-4-methyl-5-(4-((2-(4-methyl-1H-imidazol-1-yl)pyrimidin-5-yl)methyl)piperazin-2-yl)isobenzofuran-1(3H)-one;

(R)-1-(5-((3-(4-methyl-1-oxo-1,3-dihydroisobenzofuran-5-yl)piperazin-1-yl)methyl)pyrimidin-2-yl)-1H-imidazole-4-carbonitrile;

(R)-1-(5-((3-(4-methyl-1-oxo-1,3-dihydroisobenzofuran-5-yl)piperazin-1-yl)methyl)pyrimidin-2-yl)-1H-1,2,4-triazole-3-carbonitrile;

(R)-3-cyclopropyl-1-(5-((3-(4-methyl-1-oxo-1,3-dihydroisobenzofuran-5-yl)piperazin-1-yl)methyl)pyrimidin-2-yl)-1H-pyrazole-4-carbonitrile;

(R)-3-(difluoromethoxy)-1-(5-((3-(4-methyl-1-oxo-1,3-dihydroisobenzofuran-5-yl)piperazin-1-yl)methyl)pyridin-2-yl)-1H-pyrazole-4-carbonitrile;

(R)-6-(4-((3-(4-methyl-1-oxo-1,3-dihydroisobenzofuran-5-yl)piperazin-1-yl)methyl)-1H-pyrazol-1-yl)-4-morpholinonicotinonitrile;

(R)-3-methyl-1-(5-((3-(4-methyl-1-oxo-1,3-dihydroisobenzofuran-5-yl)piperazin-1-yl)methyl)pyrimidin-2-yl)-1H-pyrazole-4-carbonitrile;

(R)-4-methyl-5-(4-((6-(4-methyl-1H-1,2,3-triazol-1-yl)pyridin-3-yl)methyl)piperazin-2-yl)isobenzofuran-1(3H)-one;

(R)-3-methoxy-1-(5-((3-(4-methyl-1-oxo-1,3-dihydroisobenzofuran-5-yl)piperazin-1-yl)methyl)pyridin-2-yl)-1H-pyrazole-4-carbonitrile;

(R)-4-methyl-5-(4-((2-(4-methyl-1H-imidazol-1-yl)pyrimidin-5-yl)methyl)morpholin-2-yl)isobenzofuran-1(3H)-one;

(R)-1-(5-((3-(4-methyl-1-oxo-1,3-dihydroisobenzofuran-5-yl)piperazin-1-yl)methyl)pyridin-2-yl)-1H-1,2,3-triazole-4-carbonitrile;

(R)-3-ethyl-1-(5-((3-(4-methyl-1-oxo-1,3-dihydroisobenzofuran-5-yl)piperazin-1-yl)methyl)pyridin-2-yl)-1H-pyrazole-4-carbonitrile;

(R)-3-methoxy-1-(5-((3-(4-methyl-1-oxo-1,3-dihydroisobenzofuran-5-yl)piperazin-1-yl)methyl)pyrimidin-2-yl)-1H-pyrazole-4-carbonitrile;

(R)-3-ethyl-1-(5-((3-(4-methyl-1-oxo-1,3-dihydroisobenzofuran-5-yl)piperazin-1-yl)methyl)pyrimidin-2-yl)-1H-pyrazole-4-carbonitrile;

(R)-3-(difluoromethyl)-1-(5-((3-(4-methyl-1-oxo-1,3-dihydroisobenzofuran-5-yl)piperazin-1-yl)methyl)pyrimidin-2-yl)-1H-pyrazole-4-carbonitrile;

(R)-4-methyl-2-(4-((3-(4-methyl-1-oxo-1,3-dihydroisobenzofuran-5-yl)piperazin-1-yl)methyl)-1H-pyrazol-1-yl)pyrimidine-5-carbonitrile;

(R)-2-(4-((3-(4-methyl-1-oxo-1,3-dihydroisobenzofuran-5-yl)piperazin-1-yl)methyl)-1H-pyrazol-1-yl)-5-(pyrrolidin-1-yl)isonicotinonitrile;

4-methyl-6-(4-((3-(4-methyl-1-oxo-1,3-dihydroisobenzofuran-5-yl)-4-oxopiperidin-1-yl)methyl)-1H-pyrazol-1-yl)nicotinonitrile;

(R)-6-(3-(difluoromethyl)-4-((3-(4-methyl-1-oxo-1,3-dihydroisobenzofuran-5-yl)piperazin-1-yl)methyl)-1H-pyrazol-1-yl)-4-methylnicotinonitrile;

(R)-5-(4-((2-(1H-1,2,4-triazol-1-yl)pyrimidin-5-yl)methyl)piperazin-2-yl)-4-methylisobenzofuran-1(3H)-one;

(R)-5-(4-((6-(4 (difluoromethyl)-1H-imidazol-1-yl)pyridin-3-yl)methyl)piperazin-2-yl)-4-methylisobenzofuran-1(3H)-one;

(R)-4-methyl-5-(4-((2-(4-(trifluoromethyl)-1H-imidazol-1-yl)pyrimidin-5-yl)methyl)piperazin-2-yl)isobenzofuran-1(3H)-one;

(R)-6-(3-cyclopropyl-4-((3-(4-methyl-1-oxo-1,3-dihydroisobenzofuran-5-yl)piperazin-1-yl)methyl)-1H-pyrazol-1-yl)-4-methylnicotinonitrile;

1'-methyl-5-(((3S,5R)-3-methyl-5-(4-methyl-1-oxo-1,3-dihydroisobenzofuran-5-yl)piperazin-1-yl)methyl)-[2,3'-bipyridin]-6'(1'H)-one;

(R)-4-methyl-6-(4-((3-(1-oxo-1,3-dihydroisobenzofuran-5-yl)piperazin-1-yl)methyl)-1H-pyrazol-1-yl)nicotinonitrile;

4-methyl-6-(4-(((6R)-2-methyl-6-(4-methyl-1-oxo-1,3-dihydroisobenzofuran-5-yl)morpholino)methyl)-1H-pyrazol-1-yl)nicotinonitrile (Diastereomer-I);

(R)-3-methyl-1-(6-((3-(4-methyl-1-oxo-1,3-dihydroisobenzofuran-5-yl)piperazin-1-yl)methyl)pyridin-3-yl)-1H-pyrazole-4-carbonitrile;

(R)-4-methyl-1-(5-((3-(4-methyl-1-oxo-1,3-dihydroisobenzofuran-5-yl)piperazin-1-yl)methyl)pyridin-2-yl)-1H-pyrazole-3-carbonitrile;

(R)-4-methyl-1-(5-((3-(4-methyl-1-oxo-1,3-dihydroisobenzofuran-5-yl)piperazin-1-yl)methyl)pyrimidin-2-yl)-1H-pyrazole-3-carbonitrile;

4-methyl-6-(4-((2-methyl-5-(4-methyl-1-oxo-1,3-dihydroisobenzofuran-5-yl)piperazin-1-yl)methyl)-1H-pyrazol-1-yl)nicotinonitrile (Enantiomer-II);

6-(3-(difluoromethyl)-4-(((3R,4R)-4-hydroxy-3-(4-methyl -1-oxo-1,3-dihydroisobenzofuran-5-yl)piperidin-1-yl)methyl)-1H-pyrazol-1-yl)-4-methylnicotinonitrile;

6-(4-(((3S,5R)-4-hydroxy-3-methyl-5-(4-methyl-1-oxo-1,3-dihydroisobenzofuran-5-yl)piperazin-1-yl)methyl)-2H-1,2,3-triazol-2-yl)-4-methylnicotinonitrile;

4'-methyl-4-(((3S,5R)-3-methyl-5-(4-methyl-1-oxo-1,3-dihydroisobenzofuran-5-yl)piperazin-1-yl)methyl)-2-oxo-2H-[1,2'-bipyridine]-5'-carbonitrile;

N-(1-((1-(5-cyano-4-methylpyridin-2-yl)-1H-pyrazol-4-yl)methyl)-3-(4-methyl-1-oxo-1,3-dihydroisobenzofuran-5-yl)piperidin-4-yl)acetamide (Diastereomer-II Enantiomer-I);

3-(6-(4-(((3S,5R)-3-methyl-5-(4-methyl-1-oxo-1,3-dihydroisobenzofuran-5-yl)piperazin-1-yl)methyl)-1H-pyrazol-1-yl)pyridin-2-yl)oxazolidin-2-one;

6-(4-(((3R,4R)-4-hydroxy-3-(4-methyl-1-oxo-1,3-dihydroisobenzofuran-5-yl)piperidin-1-yl)methyl)-3-methyl-2-oxo-2,3-dihydro-1H-imidazol-1-yl)-4-methylnicotinonitrile;

3-(2-methyl-6-(4-(((3S,5R)-3-methyl-5-(4-methyl-1-oxo-1,3-dihydroisobenzofuran-5-yl)piperazin-1-yl)methyl)-1H-pyrazol-1-yl)pyridin-4-yl)oxazolidin-2-one;

N-methyl-N-(6-(4-(((3S,5R)-3-methyl-5-(4-methyl-1-oxo-1,3-dihydroisobenzofuran-5-yl)piperazin-1-yl)methyl)-1H-pyrazol-1-yl)pyridin-2-yl)methanesulfonamide;

5-((2R,6S)-4-((1-(4-(1,1-dioxidoisothiazolidin-2-yl)-6-methylpyridin-2-yl)-1H-pyrazol-4-yl)methyl)-6-methylpiperazin-2-yl)-4-methylisobenzofuran-1(3H)-one;

1-(2-methoxypyridin-4-yl)-4-(((3S,5R)-3-methyl-5-(4-methyl-1-oxo-1,3-dihydroisobenzofuran-5-yl)piperazin-1-yl)methyl)pyrrolidin-2-one (Diastereomer-I);

(R)-4-methoxy-6-(4-((3-(4-methyl-1-oxo-1,3-dihydroisobenzofuran-5-yl)piperazin-1-yl)methyl)-1H-1,2,3-triazol-1-yl)nicotinonitrile;

6-(4-((2,2-dimethyl-6-(4-methyl-1-oxo-1,3-dihydroisobenzofuran-5-yl)morpholino)methyl)-1H-pyrazol-1-yl)-4-methylnicotinonitrile (Enantiomer-II);

N-(1-((1-(5-cyano-4-methylpyridin-2-yl)-1H-pyrazol-4-yl)methyl)-5-(4-methyl-1-oxo-1,3-dihydroisobenzofuran-5-yl)piperidin-3-yl)acetamide (Enantiomer-I);

1-((1-(5-cyano-4-methylpyridin-2-yl)-1H-pyrazol-4-yl)methyl)-3-(4-methyl-1-oxo-1,3-dihydroisobenzofuran-5-yl)piperidin-4-ylmethylcarbamate (Enantiomer-I);

4-methyl-6-(3-(((3S,5R)-3-methyl-5-(4-methyl-1-oxo-1,3-dihydroisobenzofuran-5-yl)piperazin-1-yl)methyl)-1,2,4-oxadiazol-5-yl)nicotinonitrile;

(R)-1-(5-cyano-4-methoxypyridin-2-yl)-N-methyl-4-((3-(4-methyl-1-oxo-1,3-dihydroisobenzofuran-5-yl)piperazin-1-yl)methyl)-1H-pyrazole-3-carboxamide;

6-(4-((3-(hydroxymethyl)-5-(4-methyl-1-oxo-1,3-dihydroisobenzofuran-5-yl)piperidin-1-yl)methyl)-1H-pyrazol-1-yl)-4-methylnicotinonitrile (Diastereomer-II Enantiomer-II);

(R)-1-(5-cyano-4-methoxypyridin-2-yl)-4-((3-(4-methyl-1-oxo-1,3-dihydroisobenzofuran-5-yl)piperazin-1-yl)methyl)-1H-pyrazole-3-carboxamide;

(R)-4-(methoxy-d3)-6-(4-((3-(4-methyl-1-oxo-1,3-dihydroisobenzofuran-5-yl)piperazin-1-yl)methyl)-1H-1,2,3-triazol-1-yl)nicotinonitrile;

(R)-4-methyl-5-(4-((6-(3-methyl-1,2,4-oxadiazol-5-yl)pyridin-3-yl)methyl)piperazin-2-yl)isobenzofuran-1(3H)-one;

2-methyl-4-(5-(((3S,5R)-3-methyl-5-(4-methyl-1-oxo-1,3-dihydroisobenzofuran-5-yl)piperazin-1-yl)methyl)-2H-tetrazol-2-yl)benzonitrile;

3-methyl-4-(((3S,5R)-3-methyl-5-(4-methyl-1-oxo-1,3-dihydroisobenzofuran-5-yl)piperazin-1-yl)methyl)-1-(2-methylpyridin-4-yl)-1,3-dihydro-2H-imidazol-2-one;

6-(5-((3,3-dimethyl-5-(4-methyl-1-oxo-1,3-dihydroisobenzofuran-5-yl)piperazin-1-yl)methyl)-1,3,4-oxadiazol-2-yl)-4-methylnicotinonitrile (Enantiomer-I);

6-(5-((3,3-dimethyl-5-(4-methyl-1-oxo-1,3-dihydroisobenzofuran-5-yl)piperazin-1-yl)methyl)isoxazol-3-yl)-4-methylnicotinonitrile (Enantiomer-I);

4-methoxy-6-(5-(((3S,5R)-3-methyl-5-(4-methyl-1-oxo-1,3-dihydroisobenzofuran-5-yl)piperazin-1-yl)methyl)isoxazol-3-yl)nicotinonitrile;

1-(difluoromethyl)-4-(4-(((3S,5R)-3-methyl-5-(4-methyl-1-oxo-1,3-dihydroisobenzofuran-5-yl)piperazin-1-yl)methyl)-2H-1,2,3-triazol-2-yl)pyridin-2(1H)-one;

5-((2R,6S)-4-((1-(2-(difluoromethyl)pyrimidin-4-yl)-1H-imidazol-4-yl)methyl)-6-methylpiperazin-2-yl)-4-methylisobenzofuran-1(3H)-one;

4-(5-(((3R,4R)-4-hydroxy-3-(4-methyl-1-oxo-1,3-dihydroisobenzofuran-5-yl)piperidin-1-yl)methyl)-2H-tetrazol-2-yl)-2-methoxybenzonitrile;

6-(5-((3-(difluoromethyl)-5-(4-methyl-1-oxo-1,3-dihydroisobenzofuran-5-yl)piperazin-1-yl)methyl)-1,3,4-oxadiazol-2-yl)-4-methylnicotinonitrile (Enantiomer-I);

4-methoxy-6-(3-methyl-4-(((3S,5R)-3-methyl-5-(4-methyl-1-oxo-1,3-dihydroisobenzofuran-5-yl)piperazin-1-yl)methyl)-2-oxoimidazolidin-1-yl)nicotinonitrile (Diastereomer-I);

1-(2-methoxypyridin-4-yl)-3-methyl-4-(((3S,5R)-3-methyl-5-(4-methyl-1-oxo-1,3-dihydroisobenzofuran-5-yl)piperazin-1-yl)methyl)-1,3-dihydro-2H-imidazol-2-one;

1-(2-(difluoromethyl)pyridin-4-yl)-3-methyl-4-(((3S,5R)-3-methyl-5-(4-methyl-1-oxo-1,3-dihydroisobenzofuran-5-yl)piperazin-1-yl)methyl)-1,3-dihydro-2H-imidazol-2-one; and 4-methoxy-6-(5-(((3S,5R)-3-methyl-5-(4-methyl-1-oxo-1,3-dihydroisobenzofuran-5-yl-3,3-d2)piperazin-1-yl)methyl)isoxazol-3-yl)nicotinonitrile.

11. A pharmaceutical composition comprising one or more compounds according to claim 1, or a salt thereof; and a pharmaceutically acceptable carrier or diluent.

12. A pharmaceutical composition, which comprises a pharmaceutically acceptable carrier and a compound as defined in claim 1, or pharmaceutically acceptable salt, alone or in combination with another therapeutic agent.

13. A method for the treatment of a cardiovascular disease, which comprises administering to a patient having said disease a therapeutically affective amount of a compound of claim 1, or pharmaceutically acceptable salt thereof.

14. The method of claim 13, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

15. A method for promoting diuresis or natriuresis, which comprises administering to a patient in need thereof a therapeutically affective amount of a compound of claim 1, or pharmaceutically acceptable salt thereof.

16. A compound of claim 5, or salt thereof, wherein:

$R^2$ is phenyl, pyridinyl, indolyl, indazolyl, benzo[d]oxazol-2(3H)-onyl, pyrazolo[4,3-b]pyridinyl, pyridin-2(1H)-onyl, pyrazolyl, pyrimidinyl, imidazolyl, pyrazolyl, triazolyl, oxadiazolyl, thiadiazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, *or* pyrazolo[1,5-a]pyrimidinyl, [or benzo[d]oxazol-2(3H)-only,] each being substituted with 0-3 $R^{2a}$; and $R^{2a}$ is OH, =O, CN, halo, $C_{1-4}$ alkyl, $C_{1-4}$ fluoroalkyl, $C_{14}$ alkoxy, or $C_{1-4}$ fluoroalkoxy.

17. A compound of claim 16, or salt thereof, wherein:

$R^1$ is

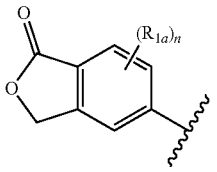

$R^{1a}$ is independently H or —$CH_3$.

18. The compound according to claim 17, or salt thereof, wherein:

Ring B is pyridinyl, triazolyl, thiazolyl, oxadiazolyl, imidazolyl, or [pyrrazolyl] *pyrazolyl*; and $R^2$ is phenyl, pyridinyl, pyrimidinyl, benzo[d]oxazol-2(3H)-onyl, imidazolyl, pyrazolyl, triazolyl, or oxadiazolyl, each being substituted with 0-3 [$R^{ea}$] $R^{2a}$.

19. The compound according to claim 18, or salt thereof, wherein:

V is —O—, —$NR^4$—, or —$CR^5R^5$—;

Y is —$C(R^6)_2$—$C(R^6)_2$— or —$C(R^6)_2$—;

$L^1$ is —$C(R)_2$—; wherein R is independently hydrogen, F, OH, $C_{1-3}$ alkyl, $C_{1-3}$ hydroxyalkyl, $C_{1-3}$ alkoxyalkyl, or $C_{1-3}$ fluoroalkyl; and $R^6$ is independently H, $C_{1-3}$-alkyl, $C_{1-3}$-fluoroalkyl, or $C_{3-6}$-cycloalkyl.

20. A compound, wherein the compound is

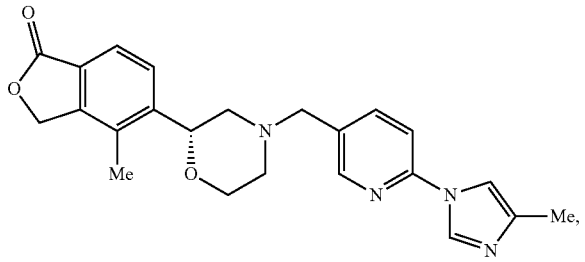

or salt thereof.

21. A compound, wherein the compound is

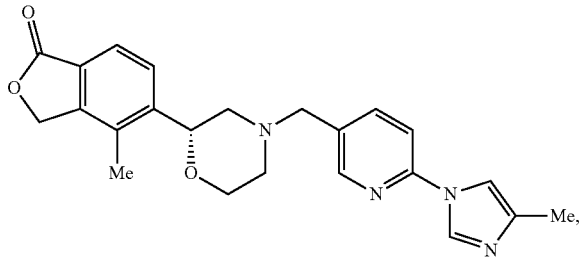

22. A pharmaceutical composition comprising one or more compounds according to claim 20, or a salt thereof; and a pharmaceutically acceptable carrier or diluent.

23. A pharmaceutical composition, which comprises a pharmaceutically acceptable carrier and a compound as defined in claim 20, or pharmaceutically acceptable salt, alone or in combination with another therapeutic agent.

24. A method for the treatment of a cardiovascular disease, which comprises administering to a patient having said disease a therapeutically affective amount of a compound of claim 20, or pharmaceutically acceptable salt thereof.

25. The method of claim 24, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

26. A method for promoting diuresis or natriuresis, which comprises administering to a patient in need thereof a therapeutically affective amount of a compound of claim 20, or pharmaceutically acceptable salt thereof.

27. A compound, wherein the compound is

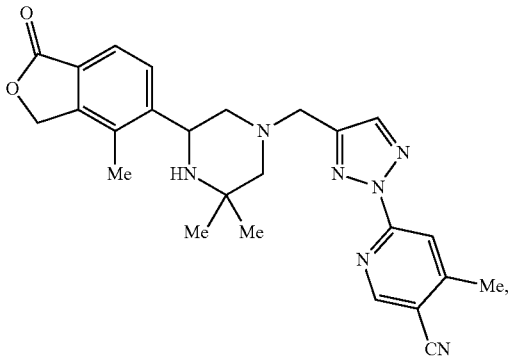

or salt thereof.

28. A compound, wherein the compound is

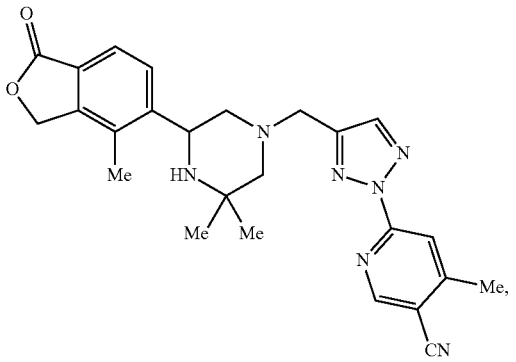

29. A pharmaceutical composition comprising one or more compounds according to claim 27, or a salt thereof; and a pharmaceutically acceptable carrier or diluent.

30. A pharmaceutical composition, which comprises a pharmaceutically acceptable carrier and a compound as defined in claim 27, or pharmaceutically acceptable salt, alone or in combination with another therapeutic agent.

31. A method for the treatment of a cardiovascular disease, which comprises administering to a patient having said disease a therapeutically affective amount of a compound of claim 27, or pharmaceutically acceptable salt thereof.

32. The method of claim 31, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

33. A method for promoting diuresis or natriuresis, which comprises administering to a patient in need thereof a therapeutically affective amount of a compound of claim 27, or pharmaceutically acceptable salt thereof.

34. A compound, wherein the compound is

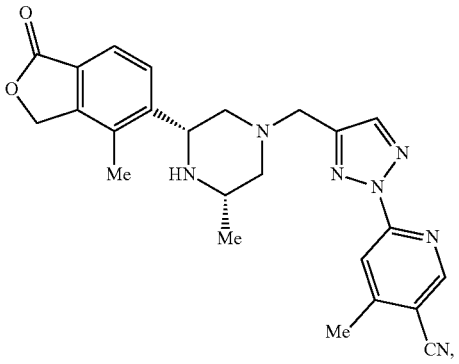

or salt thereof.

35. A compound, wherein the compound is

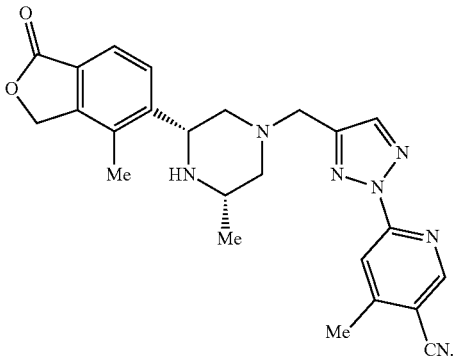

36. A pharmaceutical composition comprising one or more compounds according to claim 34, or a salt thereof and a pharmaceutically acceptable carrier or diluent.

37. A pharmaceutical composition, which comprises a pharmaceutically acceptable carrier and a compound as defined in claim 34, or pharmaceutically acceptable salt, alone or in combination with another therapeutic agent.

38. A method for the treatment of a cardiovascular disease, which comprises administering to a patient having said disease a therapeutically affective amount of a compound of claim 34, or pharmaceutically acceptable salt thereof.

39. The method of claim 38, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

40. A method for promoting diuresis or natriuresis, which comprises administering to a patient in need thereof a therapeutically affective amount of a compound of claim 34, or pharmaceutically acceptable salt thereof.

41. A compound, wherein the compound is

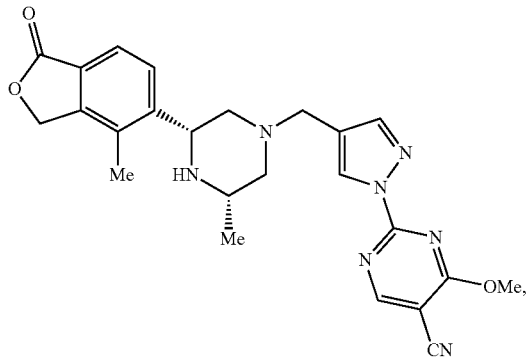

or salt thereof.

42. A compound, wherein the compound is

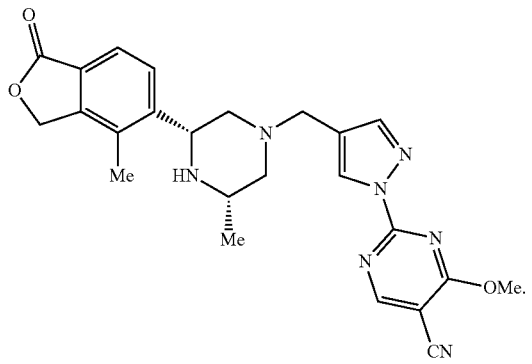

43. A pharmaceutical composition comprising one or more compounds according to claim 41, or a salt thereof; and a pharmaceutically acceptable carrier or diluent.

44. A pharmaceutical composition, which comprises a pharmaceutically acceptable carrier and a compound as defined in claim 41, or pharmaceutically acceptable salt, alone or in combination with another therapeutic agent.

45. A method for the treatment of a cardiovascular disease, which comprises administering to a patient having said disease a therapeutically affective amount of a compound of claim 41, or pharmaceutically acceptable salt thereof.

46. The method of claim 45, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

47. A method for promoting diuresis or natriuresis, which comprises administering to a patient in need thereof a therapeutically affective amount of a compound of claim 41, or pharmaceutically acceptable salt thereof.

48. A compound, wherein the compound is

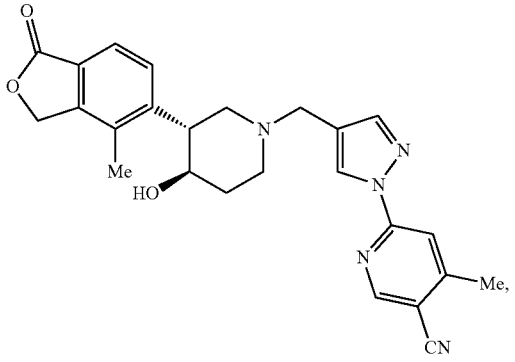

or salt thereof.

49. A compound, wherein the compound is

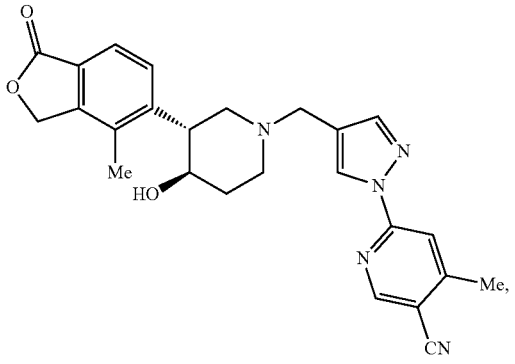

50. A pharmaceutical composition comprising one or more compounds according to claim 48, or a salt thereof; and a pharmaceutically acceptable carrier or diluent.

51. A pharmaceutical composition, which comprises a pharmaceutically acceptable carrier and a compound as defined in claim 48, or pharmaceutically acceptable salt, alone or in combination with another therapeutic agent.

52. A method for the treatment of a cardiovascular disease, which comprises administering to a patient having said disease a therapeutically affective amount of a compound of claim 48, or pharmaceutically acceptable salt thereof.

53. The method of claim 52, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

54. A method for promoting diuresis or natriuresis, which comprises administering to a patient in need thereof a therapeutically affective amount of a compound of claim 48, or pharmaceutically acceptable salt thereof.

55. A compound, wherein the compound is

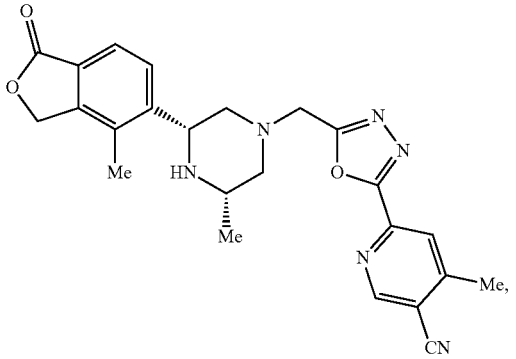

or salt thereof.

56. A compound, wherein the compound is

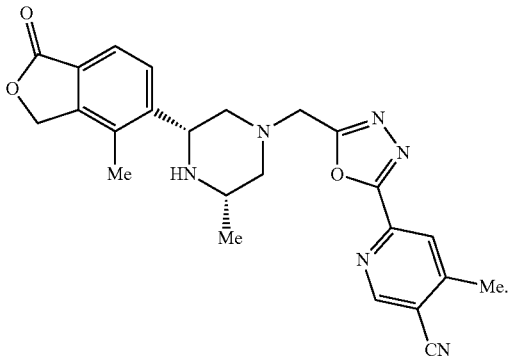

57. A pharmaceutical composition comprising one or more compounds according to claim 55, or a salt thereof; and a pharmaceutically acceptable carrier or diluent.

58. A pharmaceutical composition, which comprises a pharmaceutically acceptable carrier and a compound as defined in claim 55, or pharmaceutically acceptable salt, alone or in combination with another therapeutic agent.

59. A method for the treatment of a cardiovascular disease, which comprises administering to a patient having said disease a therapeutically affective amount of a compound of claim 55, or pharmaceutically acceptable salt thereof.

60. The method of claim 59, wherein the cardiovascular disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

61. A method for promoting diuresis or natriuresis, which comprises administering to a patient in need thereof a therapeutically affective amount of a compound of claim 55, or pharmaceutically acceptable salt thereof.

* * * * *